US007875424B2

(12) United States Patent
Türeci et al.

(10) Patent No.: US 7,875,424 B2
(45) Date of Patent: Jan. 25, 2011

(54) IDENTIFICATION OF TUMOUR-ASSOCIATED CELL SURFACE ANTIGENS FOR DIAGNOSIS AND THERAPY

(75) Inventors: Özlem Türeci, Mainz (DE); Ugur Sahin, Mainz (DE); Gerd Helftenbein, Gemünden (DE); Volker Schlüter, Munich (DE)

(73) Assignee: Ganymed Pharmaceuticals, AG (DE)

( * ) Notice: Subject to any disclaimer, the term of this patent is extended or adjusted under 35 U.S.C. 154(b) by 841 days.

(21) Appl. No.: 10/573,229

(22) PCT Filed: Sep. 23, 2004

(86) PCT No.: PCT/EP2004/010697

§ 371 (c)(1), (2), (4) Date: Jan. 16, 2007

(87) PCT Pub. No.: WO2005/030250

PCT Pub. Date: Apr. 7, 2005

(65) Prior Publication Data

US 2008/0166340 A1 Jul. 10, 2008

(30) Foreign Application Priority Data

Sep. 26, 2003 (DE) ................................ 103 44 799

(51) Int. Cl.
*C12Q 1/68* (2006.01)

(52) U.S. Cl. ........................................................ 435/6

(58) Field of Classification Search ....................... None
See application file for complete search history.

(56) References Cited

FOREIGN PATENT DOCUMENTS

WO WO 98/37094 * 8/1998

OTHER PUBLICATIONS

Tockman et al (Cancer Res., 1992, 52:2711s-2718s).*
NCBI GenBank BU183861, p. 1-2, printed Jun. 19, 2007, IDS.*
Agencourt_7964945 DNA Sequence, EBI Accession No. BU183861 (last updated Sep. 4, 2000).

* cited by examiner

*Primary Examiner*—Laura B Goddard
(74) *Attorney, Agent, or Firm*—Olson & Cepuritis, Ltd.

(57) ABSTRACT

According to the invention, tumour-associated gene products and nucleic acids coding therefor were identified. The present invention relates to the therapy and diagnosis of diseases wherein said tumour-associated gene products are expressed aberrantly. The invention also relates to proteins, polypeptides and peptides which are expressed in a tumour-associated manner and the nucleic acids coding therefor.

1 Claim, 50 Drawing Sheets

A

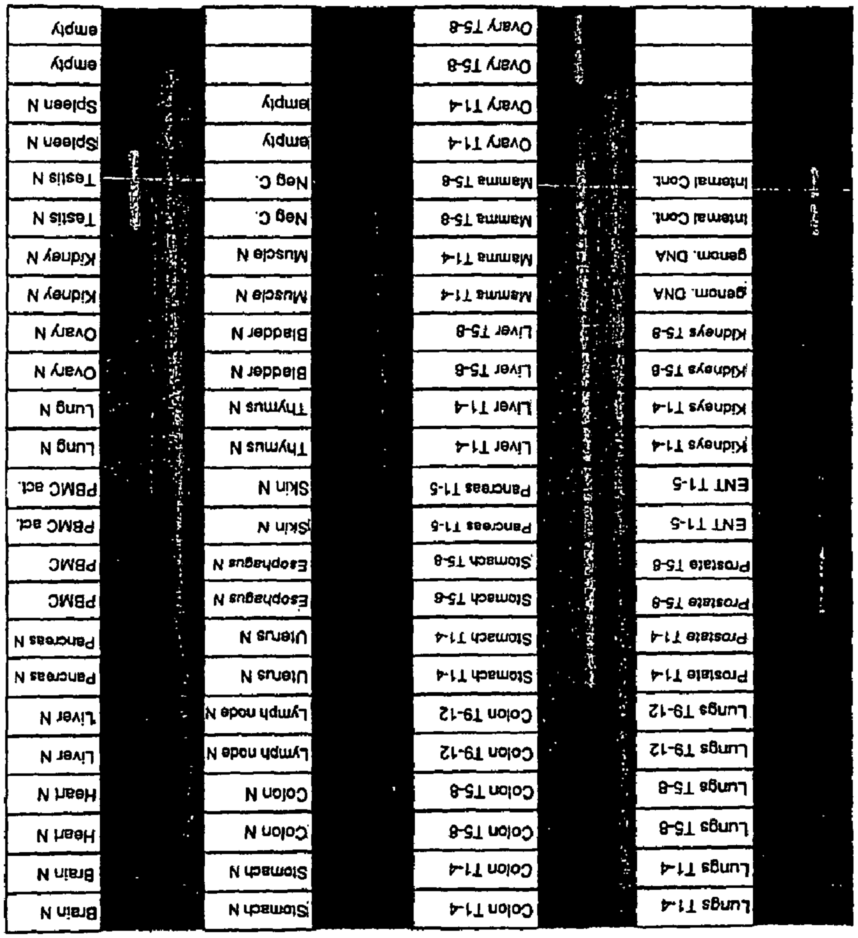

Fig. 6

B

Figure 1:
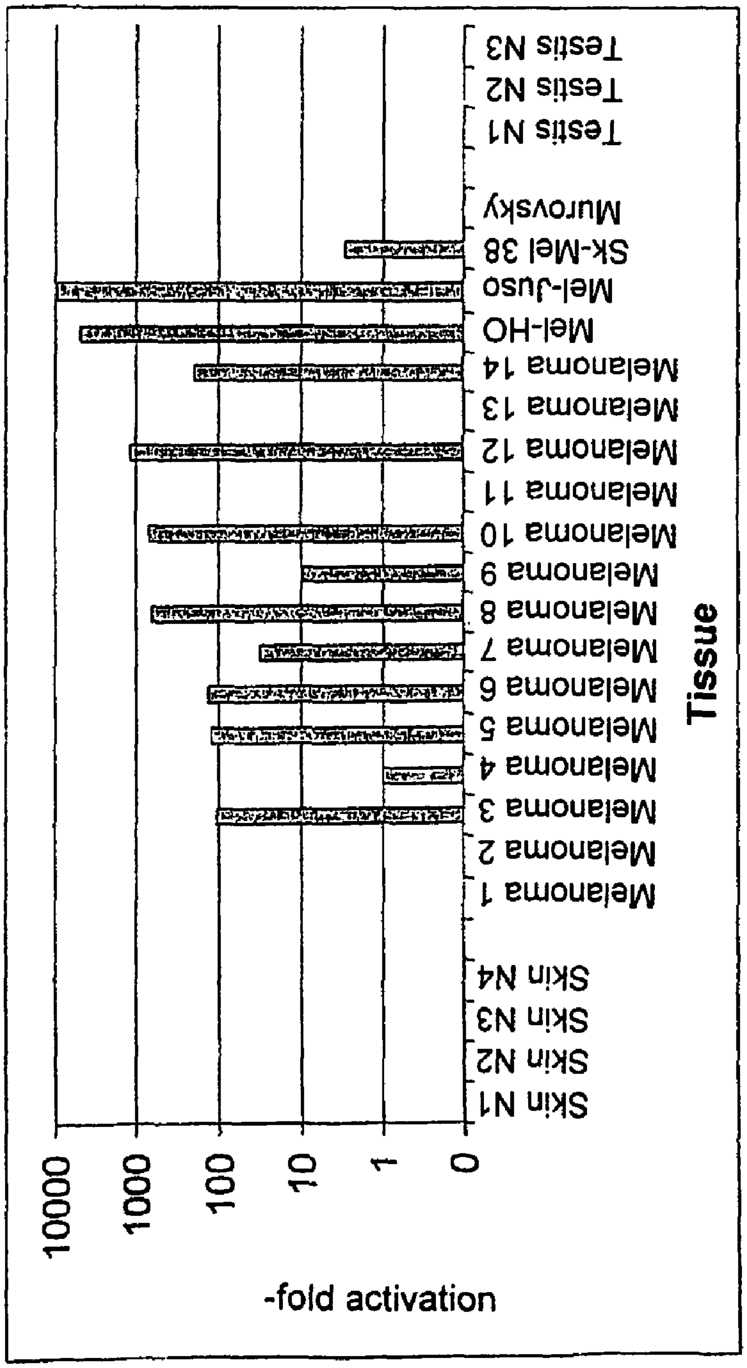

| | | | |
|---|---|---|---|
| Brain N | Stomach N | Colon T1-4 | Lungs T1-4 |
| Brain N | Stomach N | Colon T1-4 | Lungs T1-4 |
| Heart N | Colon N | Colon T5-8 | Lungs T5-8 |
| Heart N | Colon N | Colon T5-8 | Lungs T5-8 |
| Liver N | Lymph node N | Colon T9-12 | Lungs T9-12 |
| Liver N | Lymph node N | Colon T9-12 | Lungs T9-12 |
| Pancreas N | Uterus N | Stomach T1-4 | Prostate T1-4 |
| Pancreas N | Uterus N | Stomach T1-4 | Prostate T1-4 |
| PBMC | Esophagus N | Stomach T5-8 | Prostate T5-8 |
| PBMC | Esophagus N | Stomach T5-8 | Prostate T5-8 |
| PBMC act. | Skin N | Pancreas T1-5 | ENT T1-5 |
| PBMC act. | Skin N | Pancreas T1-5 | ENT T1-5 |
| Lung N | Thymus N | Liver T1-4 | Kidneys T1-4 |
| Lung N | Thymus N | Liver T1-4 | Kidneys T1-4 |
| Ovary N | Bladder N | Liver T5-8 | Kidneys T5-8 |
| Ovary N | Bladder N | Liver T5-8 | Kidneys T5-8 |
| Kidney N | Muscle N | Mamma T1-4 | genom. DNA |
| Kidney N | Muscle N | Mamma T1-4 | genom. DNA |
| Testis N | Neg C. | Mamma T5-8 | Internal Cont. |
| Testis N | Neg C. | Mamma T5-8 | Internal Cont. |
| Spleen N | empty | Ovary T1-4 | |
| Spleen N | empty | Ovary T1-4 | |
| empty | | Ovary T5-8 | |
| empty | | Ovary T5-8 | |

A 1:150

B 1:300

C 1:600

A B

A

B

A

B

SEQUENCE LISTING

```
<160> NUMBER OF SEQ ID NOS: 312

<210> SEQ ID NO 1
<211> LENGTH: 920
<212> TYPE: DNA
<213> ORGANISM: Homo sapiens

<400> SEQUENCE: 1

tctgtagagg ggaatggctg ctgtgtcatg ggggtgcatg agcagcccag tggagaggtg      60

cacttggtga gaaaccgatg cctctgccaa ccacctgcac taacctgctg ggtctgagac     120

tgagccactt tggaagctga tcttggagca ccagtcaagc ccttagctgg ctgcagccac     180

agccaacaac aagactgcaa cctcctgggg gatcctgagc cagaatcccc tggctaaatt     240

gctccttgat tcttaaccca cagaaattgt gtaagacctc catcaggtgt cgacaaggaa     300

gatcccagta gggcaggaga caggagcacc tctgctgtgg ccaatgcagg aatgctggcc     360

atcattgctt ctgctgggcg actgagaagc atcacccact tccccagaac ctttttttacg    420

tggagtgaaa actttaaggg gctgtccagc taaacctcca acctccagat cccatgccaa     480

tttctctgct tctgcaaaag gacttcaagt gaaagacatc tgcagctgtg aacgggggta     540

aaaccctccc tgccccaggc cccaagcaag gatttcccta gcggggagga aggtagaatc     600

gagagacctc taaccctggg agaggaggga gggaaatctc cgaggaccag ggttatgcaa     660

caacacaagg gaagtacctg ctgggttctg ggggttgggg aaggaaaatc cctactgccc     720

caagagccag ccccgaaccc aaggcacagc ttatactggc cccggggcct ggggggggcac    780

gaaaaccttg aaaaaggggc gccttcccag cttccccggg ggtaagggct ttacccccca     840

gaggggggggg gaaaaatccg agtgggatct ttcccaaccg ccgaagacta aaacctttaa    900

acccccaaag aaaccttcta                                                 920


<210> SEQ ID NO 2
<211> LENGTH: 88
<212> TYPE: PRT
<213> ORGANISM: Homo sapiens

<400> SEQUENCE: 2

Arg Arg Phe Leu Trp Gly Phe Lys Gly Phe Ser Leu Arg Arg Leu Gly
1               5                   10                  15

Lys Ile Pro Leu Gly Phe Phe Pro Pro Pro Leu Gly Gly Lys Ala Leu
            20                  25                  30

Thr Pro Gly Glu Ala Gly Lys Ala Pro Leu Phe Gln Gly Phe Arg Ala
        35                  40                  45
```

-continued

```
Pro Pro Gly Pro Gly Ala Ser Ile Ser Cys Ala Leu Gly Ser Gly Leu
    50                  55                  60

Ala Leu Gly Ala Val Gly Ile Phe Leu Pro Gln Pro Pro Glu Pro Ser
65                  70                  75                  80

Arg Tyr Phe Pro Cys Val Val Ala
                85


<210> SEQ ID NO 3
<211> LENGTH: 22
<212> TYPE: DNA
<213> ORGANISM: Artificial Sequence
<220> FEATURE:
<223> OTHER INFORMATION: Oligonucleotide

<400> SEQUENCE: 3

gcagccacag ccaacaacaa ga                                              22


<210> SEQ ID NO 4
<211> LENGTH: 25
<212> TYPE: DNA
<213> ORGANISM: Artificial Sequence
<220> FEATURE:
<223> OTHER INFORMATION: Oligonucleotide

<400> SEQUENCE: 4

acagcagagg tgctcctgtc tcctg                                           25


<210> SEQ ID NO 5
<211> LENGTH: 2856
<212> TYPE: DNA
<213> ORGANISM: Homo sapiens

<400> SEQUENCE: 5

atggccaaaa gaaatctcag cactgtgaca gagttcattc ttgtagtctt cacagatcac     60

cctgaactgg cagttccact cttcctagtg tttctcagtt tctatcttgt cacttttctg    120

gggaatgggg ggatgatcat tctaatccaa gtggatgccc aactccacac ccccgtgtac    180

ttcttcctga gccaccttgc tttcctggat gcctgctgtg cctcagtaat cacccctcag    240

attctggcca cactggccac agacaagaca gttatctcct atggctgccg tgctgtgcag    300

ttctctttct tcaccatatg tgcaggcaca gagtgttacc tgctgtcagt gatggcctat    360

gaccgctttg ttgccattag caatccactg cactgtaaca tgaccatgac tccaggtacc    420

tgcagggtct tttggccag tgccttcatc tgtggggtgt caggggccat tctgcatacc     480

acgtgcacct tcaccctctc cttctgttgt gacaatcaga tcaacttctt cttctgtgac    540

ctcccacccc tgctgaagct cgcctgcagc agcatgacac aaactgagat tgtcattctc    600

ctttgtgcaa aatgcatgtt cctagccaat gtcatggtta tcctgatctg ctacatgctc    660

attatcagag ccattttgag ggtgaagtcg gcaggaggcc tcctgatagc atctgctcat    720

ttcgatgcat atgtatatga gacaggcatc aactacaaca cagtttatgg ctcaggaaag    780

gcagtagggt ggtcctggag gagcctgcgg gaaaccaacc acatgagacc aggaaatact    840

tcaaaacact cagcagccca gctgcatcaa tgcctcatcc agcaagttgg caggtggccc    900

ttgcagagca tgcccttccc cgtttctgca gggccacctt ataagtcagt gcagcctctc    960

cctggagacc cccggcctct cctgtgcatc accggattat ttctgacttt gaagatgatg   1020

gggtgtgggc ccaggaggcc cagggacagg aagtctgact tcttcataaa cacagaccct   1080

ggtgcagggt caccagaaga acagaggtgt ggatgggaag ggcatccttc ccactcctat   1140
```

-continued

```
accctggggc tgtctctgcc agtcaacttc ggcctgaaat gtccatggtg gacactatct   1200

ggaccccag ctacctgcca acgtccagac ctgcagacac cttctccacc aaaggagata   1260

tgttcatccg ggctgcgacc ccttacacac agcgctggac cagacagaag tcaagttcca   1320

gcagcctccg gagcagccac tatgctgaca aaggggctgc ccgacatcac tgtgggactg   1380

cagatttatg actcctgcat ctcagggatc caggctctgg ggagcaccct ggccctgctg   1440

tccaatcagc ttccacccac aaccaactat gcttgtggct cccagcaaca tctcctgggc   1500

gtggttggag ggatgacctt cctggagtca gagcccatgt ctgagctgct ctccatctac   1560

agagtccctc agggccaaag actcaccaaa aactttgaag taaaagaact tgtctgcaca   1620

tatctggtag gacagcttcc ttatggcctg gtcagttatg acaacagcaa ctttgagtgg   1680

ctggatcagc agctgcagaa gcagatcggg ggcgagggac ttcctgttgg cgctgcgccc   1740

agccgtgtag ccaggcaaca gtctgatgag gaagctgtgg gaggagtgca gggatacagg   1800

tggtctggat taggggcttc catccaaagt gccagagaag gggcttggca tcgcacaggg   1860

ctggagaaca tgaccactgc ccacctgtct gccttcaaac ttcctgatct aactgccact   1920

taccaagcct acctggcagc caaagccctg tgggttgcct atcagaactt gatgtcctgc   1980

tctgagagag agggaccatt cctgggaggc acgtatgcca atgcatggga agccaggctt   2040

tctcaggtta acttcaccac caaagcccaa gaagaggttt tcttcgccaa agatggggaa   2100

gtgctgacaa cgtttgacat taaaaacatc tatgttctcc cagacctgtc aggacagaca   2160

gccattgttg gacactttga cttcagagca ccttctggaa aagagcttct gttggatgac   2220

agcgcaattg tctgggcaga aggaccctta aagattagag ctgagagaac cctaagaacc   2280

aagaccacac agcacctctc acatcccaag ctccaggagt cccttcctct gtctgcaacg   2340

aaaaacgtcc tgtggaaacc aggaagtcaa ccctatttga gaagtcaaaa tgctgctaca   2400

aaagccttcc ctgacccaga agagaaatcg caatgtcacc agtttctctt tctcccttca   2460

gatagtgttg catgtcagaa gtgctctgac aaccagtggc ccaatgtgca gaagggcgag   2520

tgcatcccca aaacccttga cttcttgttc tatcacaagc cccttgacac agcgttggct   2580

gtctgcacag ccctgctctt tctccttgcc ctggccatct taggcatctt ccatgttgtc   2640

tgctcctgtg tctgggtgtc cttcatacct gcccacatgc atgcccacag caaagacacc   2700

atggccatgg aggtctttgt catcttggca tcagcaggag gcctcatgtc ctccctcttc   2760

ttttccaaat gctacatcat ccttctccat cctgaaaaga acacaaaaga ccaaatgttt   2820

ggccggcatc atcgcaagtg ggaaaaactg aagtga                              2856
```

<210> SEQ ID NO 6
<211> LENGTH: 951
<212> TYPE: PRT
<213> ORGANISM: Homo sapiens

<400> SEQUENCE: 6

```
Met Ala Lys Arg Asn Leu Ser Thr Val Thr Glu Phe Ile Leu Val Val
1               5                   10                  15

Phe Thr Asp His Pro Glu Leu Ala Val Pro Leu Phe Leu Val Phe Leu
            20                  25                  30

Ser Phe Tyr Leu Val Thr Phe Leu Gly Asn Gly Gly Met Ile Ile Leu
        35                  40                  45

Ile Gln Val Asp Ala Gln Leu His Thr Pro Val Tyr Phe Phe Leu Ser
    50                  55                  60
```

-continued

```
His Leu Ala Phe Leu Asp Ala Cys Cys Ala Ser Val Ile Thr Pro Gln
65                  70                  75                  80

Ile Leu Ala Thr Leu Ala Thr Asp Lys Thr Val Ile Ser Tyr Gly Cys
                85                  90                  95

Arg Ala Val Gln Phe Ser Phe Phe Thr Ile Cys Ala Gly Thr Glu Cys
            100                 105                 110

Tyr Leu Leu Ser Val Met Ala Tyr Asp Arg Phe Val Ala Ile Ser Asn
        115                 120                 125

Pro Leu His Cys Asn Met Thr Met Thr Pro Gly Thr Cys Arg Val Phe
    130                 135                 140

Leu Ala Ser Ala Phe Ile Cys Gly Val Ser Gly Ala Ile Leu His Thr
145                 150                 155                 160

Thr Cys Thr Phe Thr Leu Ser Phe Cys Cys Asp Asn Gln Ile Asn Phe
                165                 170                 175

Phe Phe Cys Asp Leu Pro Pro Leu Leu Lys Leu Ala Cys Ser Ser Met
            180                 185                 190

Thr Gln Thr Glu Ile Val Ile Leu Leu Cys Ala Lys Cys Met Phe Leu
        195                 200                 205

Ala Asn Val Met Val Ile Leu Ile Cys Tyr Met Leu Ile Ile Arg Ala
    210                 215                 220

Ile Leu Arg Val Lys Ser Ala Gly Gly Leu Leu Ile Ala Ser Ala His
225                 230                 235                 240

Phe Asp Ala Tyr Val Tyr Glu Thr Gly Ile Asn Tyr Asn Thr Val Tyr
                245                 250                 255

Gly Ser Gly Lys Ala Val Gly Trp Ser Trp Arg Ser Leu Arg Glu Thr
            260                 265                 270

Asn His Met Arg Pro Gly Asn Thr Ser Lys His Ser Ala Ala Gln Leu
        275                 280                 285

His Gln Cys Leu Ile Gln Gln Val Gly Arg Trp Pro Leu Gln Ser Met
    290                 295                 300

Pro Phe Pro Val Ser Ala Gly Pro Pro Tyr Lys Ser Val Gln Pro Leu
305                 310                 315                 320

Pro Gly Asp Pro Arg Pro Leu Leu Cys Ile Thr Gly Leu Phe Leu Thr
                325                 330                 335

Leu Lys Met Met Gly Cys Gly Pro Arg Arg Pro Arg Asp Arg Lys Ser
            340                 345                 350

Asp Phe Phe Ile Asn Thr Asp Pro Gly Ala Gly Ser Pro Glu Glu Gln
        355                 360                 365

Arg Cys Gly Trp Glu Gly His Pro Ser His Ser Tyr Thr Leu Gly Leu
    370                 375                 380

Ser Leu Pro Val Asn Phe Gly Leu Lys Cys Pro Trp Trp Thr Leu Ser
385                 390                 395                 400

Gly Pro Pro Ala Thr Cys Gln Arg Pro Asp Leu Gln Thr Pro Ser Pro
                405                 410                 415

Pro Lys Glu Ile Cys Ser Ser Gly Leu Arg Pro Leu Thr His Ser Ala
            420                 425                 430

Gly Pro Asp Arg Ser Gln Val Pro Ala Ala Ser Gly Ala Ala Thr Met
        435                 440                 445

Leu Thr Lys Gly Leu Pro Asp Ile Thr Val Gly Leu Gln Ile Tyr Asp
    450                 455                 460

Ser Cys Ile Ser Gly Ile Gln Ala Leu Gly Ser Thr Leu Ala Leu Leu
465                 470                 475                 480
```

-continued

```
Ser Asn Gln Leu Pro Pro Thr Thr Asn Tyr Ala Cys Gly Ser Gln Gln
                485                 490                 495

His Leu Leu Gly Val Val Gly Gly Met Thr Phe Leu Glu Ser Glu Pro
            500                 505                 510

Met Ser Glu Leu Leu Ser Ile Tyr Arg Val Pro Gln Gly Gln Arg Leu
        515                 520                 525

Thr Lys Asn Phe Glu Val Lys Glu Leu Val Cys Thr Tyr Leu Val Gly
    530                 535                 540

Gln Leu Pro Tyr Gly Leu Val Ser Tyr Asp Asn Ser Asn Phe Glu Trp
545                 550                 555                 560

Leu Asp Gln Gln Leu Gln Lys Gln Ile Gly Gly Glu Gly Leu Pro Val
                565                 570                 575

Gly Ala Ala Pro Ser Arg Val Ala Arg Gln Gln Ser Asp Glu Glu Ala
            580                 585                 590

Val Gly Gly Val Gln Gly Tyr Arg Trp Ser Gly Leu Gly Ala Ser Ile
        595                 600                 605

Gln Ser Ala Arg Glu Gly Ala Trp His Arg Thr Gly Leu Glu Asn Met
    610                 615                 620

Thr Thr Ala His Leu Ser Ala Phe Lys Leu Pro Asp Leu Thr Ala Thr
625                 630                 635                 640

Tyr Gln Ala Tyr Leu Ala Ala Lys Ala Leu Trp Val Ala Tyr Gln Asn
                645                 650                 655

Leu Met Ser Cys Ser Glu Arg Glu Gly Pro Phe Leu Gly Gly Thr Tyr
            660                 665                 670

Ala Asn Ala Trp Glu Ala Arg Leu Ser Gln Val Asn Phe Thr Thr Lys
        675                 680                 685

Ala Gln Glu Glu Val Phe Phe Ala Lys Asp Gly Glu Val Leu Thr Thr
    690                 695                 700

Phe Asp Ile Lys Asn Ile Tyr Val Leu Pro Asp Leu Ser Gly Gln Thr
705                 710                 715                 720

Ala Ile Val Gly His Phe Asp Phe Arg Ala Pro Ser Gly Lys Glu Leu
                725                 730                 735

Leu Leu Asp Asp Ser Ala Ile Val Trp Ala Glu Gly Pro Leu Lys Ile
            740                 745                 750

Arg Ala Glu Arg Thr Leu Arg Thr Lys Thr Thr Gln His Leu Ser His
        755                 760                 765

Pro Lys Leu Gln Glu Ser Leu Pro Leu Ser Ala Thr Lys Asn Val Leu
    770                 775                 780

Trp Lys Pro Gly Ser Gln Pro Tyr Leu Arg Ser Gln Asn Ala Ala Thr
785                 790                 795                 800

Lys Ala Phe Pro Asp Pro Glu Glu Lys Ser Gln Cys His Gln Phe Leu
                805                 810                 815

Phe Leu Pro Ser Asp Ser Val Ala Cys Gln Lys Cys Ser Asp Asn Gln
            820                 825                 830

Trp Pro Asn Val Gln Lys Gly Glu Cys Ile Pro Lys Thr Leu Asp Phe
        835                 840                 845

Leu Phe Tyr His Lys Pro Leu Asp Thr Ala Leu Ala Val Cys Thr Ala
    850                 855                 860

Leu Leu Phe Leu Leu Ala Leu Ala Ile Leu Gly Ile Phe His Val Val
865                 870                 875                 880

Cys Ser Cys Val Trp Val Ser Phe Ile Pro Ala His Met His Ala His
                885                 890                 895
```

-continued

```
Ser Lys Asp Thr Met Ala Met Glu Val Phe Val Ile Leu Ala Ser Ala
            900                 905                 910

Gly Gly Leu Met Ser Ser Leu Phe Phe Ser Lys Cys Tyr Ile Ile Leu
        915                 920                 925

Leu His Pro Glu Lys Asn Thr Lys Asp Gln Met Phe Gly Arg His His
    930                 935                 940

Arg Lys Trp Glu Lys Leu Lys
945                 950
```

```
<210> SEQ ID NO 7
<211> LENGTH: 22
<212> TYPE: DNA
<213> ORGANISM: Artificial Sequence
<220> FEATURE:
<223> OTHER INFORMATION: Oligonucleotide

<400> SEQUENCE: 7

aggtggtgtg acgctgctgc ta                                              22


<210> SEQ ID NO 8
<211> LENGTH: 22
<212> TYPE: DNA
<213> ORGANISM: Artificial Sequence
<220> FEATURE:
<223> OTHER INFORMATION: Oligonucleotide

<400> SEQUENCE: 8

tcttcttggg ctttggtggt ga                                              22


<210> SEQ ID NO 9
<211> LENGTH: 543
<212> TYPE: DNA
<213> ORGANISM: Homo sapiens

<400> SEQUENCE: 9

ataaagcggg acaacacaga acttcccagt tacaccaggc atcctggccc aaagtttccc      60

aaatccaggc ggctagaggc ccactgcttc ccaactacca gctgaggggg tccgtcccga     120

gaagggagaa gaggccgaag aggaaacatg aacttctatt tactcctagc gagcagcatt     180

ctgtgtgcct tgattgtctt ctggaaatat cgccgctttc agagaaacac tggcgaaatg     240

tcatcaaatt caactgctct tgcactagtg agaccctctt cttctgggtt aattaacagc     300

aatacagaca acaatcttgc agtctacgac ctctctcggg atattttaaa taatttccca     360

cactcaatag ccaggcagaa gcgaatattg gtaaacctca gtatggtgga aaacaagctg     420

gttgaactgg aacatactct acttagcaag ggtttcagag gtgcatcacc tcaccggaaa     480

tccacctaaa agcgtacagg atgtaatgcc agtggtggaa atcattaaag acactttgag     540

tag                                                                   543


<210> SEQ ID NO 10
<211> LENGTH: 113
<212> TYPE: PRT
<213> ORGANISM: Homo sapiens

<400> SEQUENCE: 10

Met Asn Phe Tyr Leu Leu Leu Ala Ser Ser Ile Leu Cys Ala Leu Ile
1               5                   10                  15

Val Phe Trp Lys Tyr Arg Arg Phe Gln Arg Asn Thr Gly Glu Met Ser
            20                  25                  30
```

-continued

```
Ser Asn Ser Thr Ala Leu Ala Leu Val Arg Pro Ser Ser Gly Leu
        35                  40                  45

Ile Asn Ser Asn Thr Asp Asn Asn Leu Ala Val Tyr Asp Leu Ser Arg
    50                  55                  60

Asp Ile Leu Asn Asn Phe Pro His Ser Ile Ala Arg Gln Lys Arg Ile
65                  70                  75                  80

Leu Val Asn Leu Ser Met Val Glu Asn Lys Leu Val Glu Leu Glu His
                85                  90                  95

Thr Leu Leu Ser Lys Gly Phe Arg Gly Ala Ser Pro His Arg Lys Ser
            100                 105                 110

Thr
```

<210> SEQ ID NO 11
<211> LENGTH: 22
<212> TYPE: DNA
<213> ORGANISM: Artificial Sequence
<220> FEATURE:
<223> OTHER INFORMATION: Oligonucleotide

<400> SEQUENCE: 11

```
gtgtgccttg attgtcttct gg                                               22
```

<210> SEQ ID NO 12
<211> LENGTH: 19
<212> TYPE: DNA
<213> ORGANISM: Artificial Sequence
<220> FEATURE:
<223> OTHER INFORMATION: Oligonucleotide

<400> SEQUENCE: 12

```
cctggctatt gagtgtggg                                                   19
```

<210> SEQ ID NO 13
<211> LENGTH: 2761
<212> TYPE: DNA
<213> ORGANISM: Homo sapiens

<400> SEQUENCE: 13

```
ctaggcctca gtctgtctgc atccaggtgc ttattaaaac agtgtgttgc tccacaccgc      60

ctcgtgttgt ctgttggcgc gctctccggg ttccaaccaa tgcaagagcc ttggggctgg     120

ccctgaaacc tgcgaggggc ttccgtccac gtccccagtg gacctaccac ccctccatct     180

gggaaagcag gccacagcag ccggacaaag gaagctcctc agcctctagt cgcctctctg     240

tgcatgcaca tcggtcactg atctcgccta ctggcacaga cgtgtttatc ggccaaactg     300

accctcacaa aaagctacca ccgaagtgga caggcccta cactgtgata ctcagcacac      360

caactgcagt gagagtccga ggactcccca actggatcca tcgcaccagg gtcaagctca     420

cccccaaggc agcttcttcc tccaaaacat taacagctaa gtgtttgtct gggccaattt     480

ctcctaccaa gtttaaatta accaacattt ttttcttaaa accaaaacac aaggaagact     540

aaccacgtgc ttccaggaat ggcctgtatc tacccaacca ctttctatac ctctcttcca     600

accaaaagtc ttaatatggg aatatccctc accacgatcc taatactgtc agtagctgtc     660

ctgctgtcca cagcagcccc tccgagctgc cgtgagtgtt atcagtcttt gcactacaga     720

ggggagatgc aacaatactt tacttaccat actcatatag aaagatcctg ttatggaaac     780

ttaatcgagg aatgtgttga atcaggaaag agttattata aagtaaagaa tctaggagta     840

tgtggcagtc gtaatggggc tatttgcccc agagggaagc agtggctttg cttcaccaaa     900
```

-continued attggacaat ggggagtaaa cactcaggtg cttgaggaca taaagagaga acagattata 960
gccaaagcca aagcctcaaa accaacaact ccccctgaaa atcgcccgcg gcatttccat 1020
tcctttatac aaaaactata agcagatgca tcccttccta agccaggaaa aaatctgttt 1080
gtagatctag gagaaccatt gtgcttacca tgaatgtgtc caattgttgg gtatgcgggg 1140
gagctttatg agtgaacagt ggctgtggga cgggatagac attcccccttt acttacaggc 1200 atcccaaaac cccagactca ctttcactcc tcaggaatgc ccgcagtcct ggacacttac 1260
caacccagta tgagggacgg tgtgcatatc ccgcaagtgg actgataaaa cccatcgcgc 1320
cgtaggtgaa aacccgtcac caaaccctaa cagtcaatgc ctccatagct gagtggtggc 1380
caaggttacc ccctggagcc tggtctcctt ctaacttaag ctacctcaat tgtgtcttgt 1440
caaaaaaggc ctggtactgt acgaacacca ctaaccctta tgccgcatac ctccgcctaa 1500
gtgtactatg cgacaatcct aggaacacca gctgacaatg gactgccact gacggattcc 1560
tgtggatatg gggaacccag gcttactcac agctacctta tcactggcaa ggtacttgct 1620
tcctaggcac aattcaacct ggattctttt tacttccgaa gcaggcgggc aacaccctca 1680
gagtccctgt gtatgataac cagagaaaaa tgatccttgg aggtaggagg gagccaaaga 1740
ttgtgagagg acgagtggcc tctgcaacgg atcattgaat actatggtcc tgccacttgg 1800
gcagaggatg gttcatgggg ttatcgcact cccatatata tgccaaatag agcgattaga 1860
ctacaagctg ttctagagat aatcactaac caaactgcct cagccctaga aatgctcgcg 1920
caacaacaaa accaaatgcg cgcggcaatt tatcaaaaca ggctggccct agactactta 1980
ttagcagaag agggtgcggg ctgtggtaag tttaacatct ccaattgctg tcttaacata 2040
ggcaataatg gagaagaggt tctggaaatc gcttcaaaca tcagaaaagt agcccgtgta 2100
ccagtccaaa cctgggaggg atgggaccca gcaaaccttc taggagggtg gttctctaat 2160
ttaggaggat ttaaaatgct ggtggggaca gtcattttca tcactggggt cctcctgttt 2220
ctcccctgtg gtatcccatt aaaactcttg ttgaaactac agttaacctc ctgacaatcc 2280
agatgatgct cctgctacag cggcacgatg gataccaacc cgtctctcaa gaatacccca 2340
aaaattaagt ttttcttttt ccaaggtgcc cacgccaccc ctatgtcacg cctgaagtag 2400
ttattgagaa agtcgtccct ttccccttt ctataaccaa atagacagga atggaagatt 2460
ctcctcgggg cctgaaagct tgcgggatga ataactcctc ctcctcaggc ccagtcccaa 2520
ggtacaaact tgcaccagca gcaagatagc agaggcagga agagagctgg ctggaagaca 2580 cgtacccccct gaagatcaag agggaggtcg ccctggtact acatagcagt cacgttaggc 2640
tgggacaatt cctgtttaca gaggactata aaacccctgc cccatcctca cttggggctg 2700
atgccatttt aggcctcagc ctgtctgcat gcaggcgctc attaaaacag catgttgctc 2760
c 2761

<210> SEQ ID NO 14
<211> LENGTH: 160
<212> TYPE: PRT
<213> ORGANISM: Homo sapiens

<400> SEQUENCE: 14

Met Ala Cys Ile Tyr Pro Thr Thr Phe Tyr Thr Ser Leu Pro Thr Lys
1 5 10 15

Ser Leu Asn Met Gly Ile Ser Leu Thr Thr Ile Leu Ile Leu Ser Val
20 25 30

-continued

```
Ala Val Leu Leu Ser Thr Ala Ala Pro Pro Ser Cys Arg Glu Cys Tyr
        35                  40                  45

Gln Ser Leu His Tyr Arg Gly Glu Met Gln Gln Tyr Phe Thr Tyr His
    50                  55                  60

Thr His Ile Glu Arg Ser Cys Tyr Gly Asn Leu Ile Glu Glu Cys Val
65                  70                  75                  80

Glu Ser Gly Lys Ser Tyr Tyr Lys Val Lys Asn Leu Gly Val Cys Gly
                85                  90                  95

Ser Arg Asn Gly Ala Ile Cys Pro Arg Gly Lys Gln Trp Leu Cys Phe
            100                 105                 110

Thr Lys Ile Gly Gln Trp Gly Val Asn Thr Gln Val Leu Glu Asp Ile
        115                 120                 125

Lys Arg Glu Gln Ile Ile Ala Lys Ala Lys Ala Ser Lys Pro Thr Thr
    130                 135                 140

Pro Pro Glu Asn Arg Pro Arg His Phe His Ser Phe Ile Gln Lys Leu
145                 150                 155                 160


<210> SEQ ID NO 15
<211> LENGTH: 21
<212> TYPE: DNA
<213> ORGANISM: Artificial Sequence
<220> FEATURE:
<223> OTHER INFORMATION: Oligonucleotide

<400> SEQUENCE: 15

cctctagtcg cctctctgtg c                                                21


<210> SEQ ID NO 16
<211> LENGTH: 17
<212> TYPE: DNA
<213> ORGANISM: Artificial Sequence
<220> FEATURE:
<223> OTHER INFORMATION: Oligonucleotide

<400> SEQUENCE: 16

accctggtgc gatggat                                                     17


<210> SEQ ID NO 17
<211> LENGTH: 1635
<212> TYPE: DNA
<213> ORGANISM: Homo sapiens

<400> SEQUENCE: 17

gcctgtccct gccttaagtg cctactggat cccgggagcc tgggctgggg cctgggcact      60

gcttcctcct tggcccctca ggcccttgga agcagagaga gaacctcttg cagatcccag     120

gctcgtcccc agcacagcag acaccaggaa ggtggccaga gcctcactga gccgaaccga     180

cggccgccca cccacccagg ctggagccat ggataaattc cgcatgctct tccagcactt     240

ccagtcaagc tcggagtcgg tgatgaatgg catctgcctg ctgctggctg cggtcaccgt     300

caagctgtac tcctcctttg acttcaactg tccctgcctg gtgcactaca atgcactcta     360

cggcctgggc ctgctgctga cgccccccgct cgccctgttt ctctgcggcc tcctcgccaa     420

ccggcagtct gtggtgatgg tcgaggagtg gcgccggccc gcagggcacc ggaggaagga     480

cccaggcatc atcaggtaca tgtgctcctc tgtgctgcag agggcgctgg ccgccccccct     540

ggtctggatc ctgctggccc tccttgacgg gaagtgcttc gtgtgtgcct tcagcagctc     600

tgtggaccct gagaagtttc tggactttgc caacatgacc cccagccagg tacagctctt     660

cctggccaag gttccctgca aggaggatga gctggtcagg gatagccctg ctcggaaggc     720
```

-continued

```
agtgtctcgc tacctgcggt gcctgtcaca ggccatcggc tggagcgtca ccctgctgct    780

gatcatcgcg gccttcctgg cccgctgcct gaggccctgc ttcgaccaga cagtcttcct    840

gcagcgcaga tactggagca actacgtgga cctggagcag aagctcttcg acgagacctg    900

ctgtgagcat gcgcgggact tcgcgcaccg ctgcgtgctg cacttctttg ccagcatgcg    960

gagtgagctg caggcgcggg ggctgcgccg gggcaatgca ggcaggagac tcgagctccc   1020

cgcagtgcct gagcccccag aaggcctgga tagtggaagt gggaaggccc acctgcgcgc   1080

aatctccagc cgggagcagg tggaccgcct cctaagcacg tggtactcca gcaagccgcc   1140

gctggacctg gctgcatccc ccgggctctg cgggggtggc cttagccacc gcgcccctac   1200

cttggcactg ggcacgaggc tgtcacaaca caccgacgtg tagggtcctg gccaggcttg   1260

aagcggcagt gttcgcaggt gaaatgccgc gctgacaaag ttctggagtc tttccaggcc   1320

gtggggaccc cacggcaggc accctaagtc ttgttagcct cctttttaaa gtagcccaat   1380

ctctgcctag tttctgggtg tggcctccag cgcgcttcac aaactttaat gtggactcgg   1440

ttcaccgagg gccttgttaa atacaggttc agacagtgta gccaggaccg agtctgagat   1500

tctgcatttt aaacaagctc ctggaggctg atgtgctttt ggtcagtgaa ccaaactttg   1560

agtagcaaga atctaagtaa atctgccatg ggttctgggt tctagatgtc aattctaaat   1620

aataataatg acctt                                                    1635
```

```
<210> SEQ ID NO 18
<211> LENGTH: 344
<212> TYPE: PRT
<213> ORGANISM: Homo sapiens

<400> SEQUENCE: 18

Met Asp Lys Phe Arg Met Leu Phe Gln His Phe Gln Ser Ser Ser Glu
1               5                   10                  15

Ser Val Met Asn Gly Ile Cys Leu Leu Leu Ala Ala Val Thr Val Lys
            20                  25                  30

Leu Tyr Ser Ser Phe Asp Phe Asn Cys Pro Cys Leu Val His Tyr Asn
        35                  40                  45

Ala Leu Tyr Gly Leu Gly Leu Leu Leu Thr Pro Pro Leu Ala Leu Phe
    50                  55                  60

Leu Cys Gly Leu Leu Ala Asn Arg Gln Ser Val Val Met Val Glu Glu
65                  70                  75                  80

Trp Arg Arg Pro Ala Gly His Arg Arg Lys Asp Pro Gly Ile Ile Arg
                85                  90                  95

Tyr Met Cys Ser Ser Val Leu Gln Arg Ala Leu Ala Ala Pro Leu Val
            100                 105                 110

Trp Ile Leu Leu Ala Leu Leu Asp Gly Lys Cys Phe Val Cys Ala Phe
        115                 120                 125

Ser Ser Ser Val Asp Pro Glu Lys Phe Leu Asp Phe Ala Asn Met Thr
    130                 135                 140

Pro Ser Gln Val Gln Leu Phe Leu Ala Lys Val Pro Cys Lys Glu Asp
145                 150                 155                 160

Glu Leu Val Arg Asp Ser Pro Ala Arg Lys Ala Val Ser Arg Tyr Leu
                165                 170                 175

Arg Cys Leu Ser Gln Ala Ile Gly Trp Ser Val Thr Leu Leu Leu Ile
            180                 185                 190

Ile Ala Ala Phe Leu Ala Arg Cys Leu Arg Pro Cys Phe Asp Gln Thr
        195                 200                 205
```

-continued

```
Val Phe Leu Gln Arg Arg Tyr Trp Ser Asn Tyr Val Asp Leu Glu Gln
    210                 215                 220

Lys Leu Phe Asp Glu Thr Cys Cys Glu His Ala Arg Asp Phe Ala His
225                 230                 235                 240

Arg Cys Val Leu His Phe Phe Ala Ser Met Arg Ser Glu Leu Gln Ala
                245                 250                 255

Arg Gly Leu Arg Arg Gly Asn Ala Gly Arg Arg Leu Glu Leu Pro Ala
            260                 265                 270

Val Pro Glu Pro Pro Glu Gly Leu Asp Ser Gly Ser Gly Lys Ala His
        275                 280                 285

Leu Arg Ala Ile Ser Ser Arg Glu Gln Val Asp Arg Leu Leu Ser Thr
    290                 295                 300

Trp Tyr Ser Ser Lys Pro Pro Leu Asp Leu Ala Ala Ser Pro Gly Leu
305                 310                 315                 320

Cys Gly Gly Gly Leu Ser His Arg Ala Pro Thr Leu Ala Leu Gly Thr
                325                 330                 335

Arg Leu Ser Gln His Thr Asp Val
            340
```

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide

<400> SEQUENCE: 19
gaggaaggac ccaggcatca 20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide

<400> SEQUENCE: 20
gaaggcacac acgaagcact 20

<210> SEQ ID NO 21
<211> LENGTH: 4556
<212> TYPE: DNA
<213> ORGANISM: Homo sapiens

<400> SEQUENCE: 21
gcggccgccc cattcccaga ccggccgcca gcccatctgg ttagctcccg ccgctccgcg 60
ccgcccggga gtcgggagcc gcggggaacc gggcacctgc acccgcctct gggagtgagt 120
ggttccagct ggtgcctggc ctgtgtctct tggatgccct gtggcttcag tccgtctcct 180
gttgcccacc acctcgtccc tgggccgcct gataccccag cccaacagct aaggtgtgga 240
tggacagtag gggctggct tctctcactg gtcaggggtc ttctccccctg tctgcctccc 300 ggagctagga ctgcagaggg gcctatcatg gtgcttgcag gccccctggc tgtctcgctg 360
ttgctgccca gcctcacact gctggtgtcc cacctctcca gctcccagga tgtctccagt 420
gagcccagca gtgagcagca gctgtgcgcc cttagcaagc accccaccgt ggcctttgaa 480
gacctgcagc cgtgggtctc taacttcacc taccctggag cccgggattt ctcccagctg 540
gctttggacc cctccgggaa ccagctcatc gtgggagcca ggaactacct cttcagactc 600

-continued

```
agccttgcca atgtctctct tcttcaggcc acagagtggg cctccagtga ggacacgcgc    660
cgctcctgcc aaagcaaagg gaagactgag gaggagtgtc agaactacgt gcgagtcctg    720
atcgtcgccg gccggaaggt gttcatgtgt ggaaccaatg ccttttcccc catgtgcacc    780
agcagacagg tggggaacct cagccggact attgagaaga tcaatggtgt ggcccgctgc    840
ccctatgacc cacgccacaa ctccacagct gtcatctcct cccaggggga gctctatgca    900
gccacggtca tcgacttctc aggtcgggac cctgccatct accgcagcct gggcagtggg    960
ccaccgcttc gcactgccca atataactcc aagtggctta atgagccaaa cttcgtggca   1020
gcctatgata ttgggctgtt tgcatacttc ttcctgcggg agaacgcagt ggagcacgac   1080
tgtggacgca ccgtgtactc tcgcgtggcc cgcgtgtgca agaatgacgt gggggggccga   1140
ttcctgctgg aggacacatg gaccacattc atgaaggccc ggctcaactg ctcccgcccg   1200
ggcgaggtcc ccttctacta taacgagctg cagagtgcct tccacttgcc ggagcaggac   1260
ctcatctatg gagttttcac aaccaacgta aacagcatcg cggcttctgc tgtctgcgcc   1320
ttcaacctca gtgctatctc ccaggctttc aatggcccat ttcgctacca ggagaacccc   1380
agggctgcct ggctccccat agccaacccc atccccaatt tccagtgtgg caccctgcct   1440
gagaccggtc ccaacgagaa cctgacggag cgcagcctgc aggacgcgca gcgcctcttc   1500
ctgatgagcg aggccgtgca gccggtgaca cccgagccct gtgtcaccca ggacagcgtg   1560
cgcttctcac acctcgtggt ggacctggtg caggctaaag acacgctcta ccatgtactc   1620
tacattggca ccgagtcggg caccatcctg aaggcgctgt ccacggcgag ccgcagcctc   1680
cacggctgct acctggagga gctgcacgtg ctgcccccgg ggcgccgcga gcccctgcgc   1740
agcctgcgca tcctgcacag cgcccgcgcg ctcttcgtgg ggctgagaga cggcgtcctg   1800
cgggtcccac tggagaggtg cgccgcctac cgcagccagg gggcatgcct gggggcccgg   1860
gacccgtact gtggctggga cgggaagcag caacgttgca gcacactcga ggacagctcc   1920
aacatgagcc tctggaccca gaacatcacc gcctgtcctg tgcggaatgt gacacgggat   1980
gggggcttcg gcccatggtc accatggcaa ccatgtgagc acttggatgg ggacaactca   2040
ggctcttgcc tgtgtcgagc tcgatcctgt gattcccctc gaccccgctg tgggggcctt   2100
gactgcctgg ggccagccat ccacatcgcc aactgctcca ggaatggggc gtggaccccg   2160
tggtcatcgt gggcgctgtg cagcacgtcc tgtggcatcg gcttccaggt ccgccagcga   2220
agttgcagca accctgctcc ccgccacggg ggccgcatct gcgtgggcaa gagccgggag   2280
gaacggttct gtaatgagaa cacgccttgc ccggtgccca tcttctgggc ttcctggggc   2340
tcctggagca agtgcagcag caactgtgga gggggcatgc agtcgcggcg tcgggcctgc   2400
gagaacggca actcctgcct gggctgcggc gtggagttca agacgtgcaa ccccgagggc   2460
tgccccgaag tgcggcgcaa cacccccctgg acgccgtggc tgcccgtgaa cgtgacgcag   2520
ggcggggcac ggcaggagca gcggttccgc ttcacctgcc gcgcgcccct tgcagacccg   2580
cacggcctgc agttcggcag gagaaggacc gagacgagga cctgtcccgc ggacggctcc   2640
ggctcctgcg acaccgacgc cctggtggag gtcctcctgc gcagcgggag cacctccccg   2700
cacacggtga gcgggggctg ggccgcctgg ggcccgtggt cgtcctgctc ccgggactgc   2760
gagctgggct tccgcgtccg caagagaacg tgcactaacc cggagccccg caacgggggc   2820
ctgccctgcg tgggcgatgc tgccgagtac caggactgca acccccaggc ttgcccagtt   2880
cggggtgctt ggtcctgctg gacctcatgg tctccatgct cagcttcctg tggtgggggt   2940
```

-continued

```
cactatcaac gcacccgttc ctgcaccagc cccgcaccct ccccaggtga ggacatctgt   3000

ctcgggctgc acacggagga ggcactatgt gccacacagg cctgcccaga aggctggtcg   3060

ccctggtctg agtggagtaa gtgcactgac gacggagccc agagccgaag ccggcactgt   3120

gaggagctcc tcccagggtc cagcgcctgt gctggaaaca gcagccagag ccgcccctgc   3180

ccctacagcg agattcccgt catcctgcca gcctccagca tggaggaggc caccgactgt   3240

gcagggttca atctcatcca cttggtggcc acgggcatct cctgcttctt gggctctggg   3300

ctcctgaccc tagcagtgta cctgtcttgc cagcactgcc agcgtcagtc ccaggagtcc   3360

acactggtcc atcctgccac ccccaaccat ttgcactaca agggcggagg caccccgaag   3420

aatgaaaagt acacacccat ggaattcaag accctgaaca agaataactt gatccctgat   3480

gacagagcca acttctaccc attgcagcag accaatgtgt acacgactac ttactaccca   3540

agccccctga acaaacacag cttccggccc gaggcctcac ctggacaacg gtgcttcccc   3600

aacagctgat accgccgtcc tggggacttg ggcttcttgc cttcataagg cacagagcag   3660

atggagatgg gacagtggag ccagtttggt tttctccctc tgcactaggc caagaacttg   3720

ctgccttgcc tgtggggggt cccatccggc ttcagagagc tctggctggc attgaccatg   3780

ggggaaaggg ctggtttcag gctgacatat ggccgcaggt ccagttcagc ccaggtctct   3840

catggttatc ttccaaccca ctgtcacgct gacactatgc tgccatgcct gggctgtgga   3900

cctactgggc atttgaggaa ttggagaatg gagatggcaa gagggcaggc ttttaagttt   3960

gggttggaga caacttcctg tggcccccac aagctgagtc tggccttctc cagctggccc   4020

caaaaaaggc ctttgctaca tcctgattat ctctgaaagt aatcaatcaa gtggctccag   4080

tagctctgga ttttctgcca gggctgggcc attgtggtgc tgccccagta tgacatggga   4140

ccaaggccag cgcaggttat ccacctctgc ctggaagtct atactctacc cagggcatcc   4200

ctctggtcag aggcagtgag tactgggaac tggaggctga cctgtgctta gaagtccttt   4260

aatctgggct ggtacaggcc tcagccttgc cctcaatgca cgaaaggtgg cccaggagag   4320

aggatcaatg ccataggagg cagaagtctg gcctctgtgc ctctatggag actatcttcc   4380

agttgctgct caacagagtt gttggctgag acctgcttgg gagtctctgc tggcccttca   4440

tctgttcagg aacacacaca cacacacact cacacacgca cacacaatca caatttgcta   4500

cagcaacaaa aaagacattg ggctgtggca ttattaatta aagatgatat ccagtc        4556
```

<210> SEQ ID NO 22
<211> LENGTH: 1151
<212> TYPE: PRT
<213> ORGANISM: Homo sapiens

<400> SEQUENCE: 22

```
Met Pro Cys Gly Phe Ser Pro Ser Pro Val Ala His His Leu Val Pro
1               5                   10                  15

Gly Pro Pro Asp Thr Pro Ala Gln Gln Leu Arg Cys Gly Trp Thr Val
            20                  25                  30

Gly Gly Trp Leu Leu Ser Leu Val Arg Gly Leu Leu Pro Cys Leu Pro
        35                  40                  45

Pro Gly Ala Arg Thr Ala Glu Gly Pro Ile Met Val Leu Ala Gly Pro
    50                  55                  60

Leu Ala Val Ser Leu Leu Leu Pro Ser Leu Thr Leu Leu Val Ser His
65                  70                  75                  80

Leu Ser Ser Ser Gln Asp Val Ser Ser Glu Pro Ser Ser Glu Gln Gln
                85                  90                  95
```

-continued

```
Leu Cys Ala Leu Ser Lys His Pro Thr Val Ala Phe Glu Asp Leu Gln
            100                 105                 110

Pro Trp Val Ser Asn Phe Thr Tyr Pro Gly Ala Arg Asp Phe Ser Gln
        115                 120                 125

Leu Ala Leu Asp Pro Ser Gly Asn Gln Leu Ile Val Gly Ala Arg Asn
    130                 135                 140

Tyr Leu Phe Arg Leu Ser Leu Ala Asn Val Ser Leu Leu Gln Ala Thr
145                 150                 155                 160

Glu Trp Ala Ser Ser Glu Asp Thr Arg Arg Ser Cys Gln Ser Lys Gly
                165                 170                 175

Lys Thr Glu Glu Glu Cys Gln Asn Tyr Val Arg Val Leu Ile Val Ala
            180                 185                 190

Gly Arg Lys Val Phe Met Cys Gly Thr Asn Ala Phe Ser Pro Met Cys
        195                 200                 205

Thr Ser Arg Gln Val Gly Asn Leu Ser Arg Thr Ile Glu Lys Ile Asn
    210                 215                 220

Gly Val Ala Arg Cys Pro Tyr Asp Pro Arg His Asn Ser Thr Ala Val
225                 230                 235                 240

Ile Ser Ser Gln Gly Glu Leu Tyr Ala Ala Thr Val Ile Asp Phe Ser
                245                 250                 255

Gly Arg Asp Pro Ala Ile Tyr Arg Ser Leu Gly Ser Gly Pro Pro Leu
            260                 265                 270

Arg Thr Ala Gln Tyr Asn Ser Lys Trp Leu Asn Glu Pro Asn Phe Val
        275                 280                 285

Ala Ala Tyr Asp Ile Gly Leu Phe Ala Tyr Phe Phe Leu Arg Glu Asn
    290                 295                 300

Ala Val Glu His Asp Cys Gly Arg Thr Val Tyr Ser Arg Val Ala Arg
305                 310                 315                 320

Val Cys Lys Asn Asp Val Gly Gly Arg Phe Leu Leu Glu Asp Thr Trp
                325                 330                 335

Thr Thr Phe Met Lys Ala Arg Leu Asn Cys Ser Arg Pro Gly Glu Val
            340                 345                 350

Pro Phe Tyr Tyr Asn Glu Leu Gln Ser Ala Phe His Leu Pro Glu Gln
        355                 360                 365

Asp Leu Ile Tyr Gly Val Phe Thr Thr Asn Val Asn Ser Ile Ala Ala
    370                 375                 380

Ser Ala Val Cys Ala Phe Asn Leu Ser Ala Ile Ser Gln Ala Phe Asn
385                 390                 395                 400

Gly Pro Phe Arg Tyr Gln Glu Asn Pro Arg Ala Ala Trp Leu Pro Ile
                405                 410                 415

Ala Asn Pro Ile Pro Asn Phe Gln Cys Gly Thr Leu Pro Glu Thr Gly
            420                 425                 430

Pro Asn Glu Asn Leu Thr Glu Arg Ser Leu Gln Asp Ala Gln Arg Leu
        435                 440                 445

Phe Leu Met Ser Glu Ala Val Gln Pro Val Thr Pro Glu Pro Cys Val
    450                 455                 460

Thr Gln Asp Ser Val Arg Phe Ser His Leu Val Val Asp Leu Val Gln
465                 470                 475                 480

Ala Lys Asp Thr Leu Tyr His Val Leu Tyr Ile Gly Thr Glu Ser Gly
                485                 490                 495

Thr Ile Leu Lys Ala Leu Ser Thr Ala Ser Arg Ser Leu His Gly Cys
            500                 505                 510
```

-continued

```
Tyr Leu Glu Glu Leu His Val Leu Pro Pro Gly Arg Arg Glu Pro Leu
        515                 520                 525

Arg Ser Leu Arg Ile Leu His Ser Ala Arg Ala Leu Phe Val Gly Leu
    530                 535                 540

Arg Asp Gly Val Leu Arg Val Pro Leu Glu Arg Cys Ala Ala Tyr Arg
545                 550                 555                 560

Ser Gln Gly Ala Cys Leu Gly Ala Arg Asp Pro Tyr Cys Gly Trp Asp
                565                 570                 575

Gly Lys Gln Gln Arg Cys Ser Thr Leu Glu Asp Ser Ser Asn Met Ser
            580                 585                 590

Leu Trp Thr Gln Asn Ile Thr Ala Cys Pro Val Arg Asn Val Thr Arg
        595                 600                 605

Asp Gly Gly Phe Gly Pro Trp Ser Pro Trp Gln Pro Cys Glu His Leu
    610                 615                 620

Asp Gly Asp Asn Ser Gly Ser Cys Leu Cys Arg Ala Arg Ser Cys Asp
625                 630                 635                 640

Ser Pro Arg Pro Arg Cys Gly Gly Leu Asp Cys Leu Gly Pro Ala Ile
                645                 650                 655

His Ile Ala Asn Cys Ser Arg Asn Gly Ala Trp Thr Pro Trp Ser Ser
            660                 665                 670

Trp Ala Leu Cys Ser Thr Ser Cys Gly Ile Gly Phe Gln Val Arg Gln
        675                 680                 685

Arg Ser Cys Ser Asn Pro Ala Pro Arg His Gly Gly Arg Ile Cys Val
    690                 695                 700

Gly Lys Ser Arg Glu Glu Arg Phe Cys Asn Glu Asn Thr Pro Cys Pro
705                 710                 715                 720

Val Pro Ile Phe Trp Ala Ser Trp Gly Ser Trp Ser Lys Cys Ser Ser
                725                 730                 735

Asn Cys Gly Gly Gly Met Gln Ser Arg Arg Arg Ala Cys Glu Asn Gly
            740                 745                 750

Asn Ser Cys Leu Gly Cys Gly Val Glu Phe Lys Thr Cys Asn Pro Glu
        755                 760                 765

Gly Cys Pro Glu Val Arg Arg Asn Thr Pro Trp Thr Pro Trp Leu Pro
    770                 775                 780

Val Asn Val Thr Gln Gly Gly Ala Arg Gln Glu Gln Arg Phe Arg Phe
785                 790                 795                 800

Thr Cys Arg Ala Pro Leu Ala Asp Pro His Gly Leu Gln Phe Gly Arg
                805                 810                 815

Arg Arg Thr Glu Thr Arg Thr Cys Pro Ala Asp Gly Ser Gly Ser Cys
            820                 825                 830

Asp Thr Asp Ala Leu Val Glu Val Leu Leu Arg Ser Gly Ser Thr Ser
        835                 840                 845

Pro His Thr Val Ser Gly Gly Trp Ala Ala Trp Gly Pro Trp Ser Ser
    850                 855                 860

Cys Ser Arg Asp Cys Glu Leu Gly Phe Arg Val Arg Lys Arg Thr Cys
865                 870                 875                 880

Thr Asn Pro Glu Pro Arg Asn Gly Gly Leu Pro Cys Val Gly Asp Ala
                885                 890                 895

Ala Glu Tyr Gln Asp Cys Asn Pro Gln Ala Cys Pro Val Arg Gly Ala
            900                 905                 910

Trp Ser Cys Trp Thr Ser Trp Ser Pro Cys Ser Ala Ser Cys Gly Gly
        915                 920                 925
```

-continued

```
Gly His Tyr Gln Arg Thr Arg Ser Cys Thr Ser Pro Ala Pro Ser Pro
    930                 935                 940

Gly Glu Asp Ile Cys Leu Gly Leu His Thr Glu Glu Ala Leu Cys Ala
945                 950                 955                 960

Thr Gln Ala Cys Pro Glu Gly Trp Ser Pro Trp Ser Glu Trp Ser Lys
                965                 970                 975

Cys Thr Asp Asp Gly Ala Gln Ser Arg Ser Arg His Cys Glu Glu Leu
            980                 985                 990

Leu Pro Gly Ser Ser Ala Cys Ala  Gly Asn Ser Ser Gln  Ser Arg Pro
        995                 1000                 1005

Cys Pro  Tyr Ser Glu Ile Pro  Val Ile Leu Pro Ala  Ser Ser Met
    1010                 1015                 1020

Glu Glu  Ala Thr Asp Cys Ala  Gly Phe Asn Leu Ile  His Leu Val
    1025                 1030                 1035

Ala Thr  Gly Ile Ser Cys Phe  Leu Gly Ser Gly Leu  Leu Thr Leu
    1040                 1045                 1050

Ala Val  Tyr Leu Ser Cys Gln  His Cys Gln Arg Gln  Ser Gln Glu
    1055                 1060                 1065

Ser Thr  Leu Val His Pro Ala  Thr Pro Asn His Leu  His Tyr Lys
    1070                 1075                 1080

Gly Gly  Gly Thr Pro Lys Asn  Glu Lys Tyr Thr Pro  Met Glu Phe
    1085                 1090                 1095

Lys Thr  Leu Asn Lys Asn Asn  Leu Ile Pro Asp Asp  Arg Ala Asn
    1100                 1105                 1110

Phe Tyr  Pro Leu Gln Gln Thr  Asn Val Tyr Thr Thr  Thr Tyr Tyr
    1115                 1120                 1125

Pro Ser  Pro Leu Asn Lys His  Ser Phe Arg Pro Glu  Ala Ser Pro
    1130                 1135                 1140

Gly Gln  Arg Cys Phe Pro Asn  Ser
    1145                 1150


<210> SEQ ID NO 23
<211> LENGTH: 21
<212> TYPE: DNA
<213> ORGANISM: Artificial Sequence
<220> FEATURE:
<223> OTHER INFORMATION: Oligonucleotide

<400> SEQUENCE: 23

tgcagcacgt cctgtggcat c                                              21


<210> SEQ ID NO 24
<211> LENGTH: 21
<212> TYPE: DNA
<213> ORGANISM: Artificial Sequence
<220> FEATURE:
<223> OTHER INFORMATION: Oligonucleotide

<400> SEQUENCE: 24

gttgcacgtc ttgaactcca c                                              21


<210> SEQ ID NO 25
<211> LENGTH: 1299
<212> TYPE: DNA
<213> ORGANISM: Homo sapiens

<400> SEQUENCE: 25

atgaaattca agctgcttgc tgagtcctat tgccggctgc tgggagccag gagagccctg     60
```

-continued

```
aggagtagtc actcagtagc agctgacgcg tgggtccacc atgaactgga gtatctttga    120

gggactcctg agtggggtca acaagtactc cacagccttt gggcgcatct ggctgtctct    180

ggtcttcatc ttccgcgtgc tggtgtacct ggtgacggcc gagcgtgtgt ggagtgatga    240

ccacaaggac ttcgactgca atactcgcca gcccggctgc tccaacgtct gctttgatga    300

gttcttccct gtgtcccatg tgcgcctctg ggccctgcag cttatcctgg tgacatgccc    360

ctcactgctc gtggtcatgc acgtggccta ccgggaggtt caggagaaga ggcaccgaga    420

agcccatggg gagaacagtg ggcgcctcta cctgaacccc ggcaagaagc ggggtgggct    480

ctggtggaca tatgtctgca gcctagtgtt caaggcgagc gtggacatcg cctttctcta    540

tgtgttccac tcattctacc ccaaatatat cctccctcct gtggtcaagt gccacgcaga    600

tccatgtccc aatatagtgg actgcttcat ctccaagccc tcagagaaga acattttcac    660

cctcttcatg gtggccacag ctgccatctg catcctgctc aacctcgtgg agctcatcta    720

cctggtgagc aagagatgcc acgagtgcct ggcagcaagg aaagctcaag ccatgtgcac    780

aggtcatcac cccccacggta ccacctcttc ctgcaaacaa gacgacctcc tttcgggtga    840

cctcatcttt ctgggctcag acagtcatcc tcctctctta ccagaccgcc cccgagacca    900

tgtgaagaaa accatcttgt gaggggctgc ctggactggt ctggcaggtt gggcctggat    960

ggggaggctc tagcatctct cataggtgca acctgagagt gggggagcta agccatgagg   1020

taggggcagg caagagagag gattcagacg ctctgggagc cagttcctag tcctcaactc   1080

cagccacctg ccccagctcg acggcactgg gccagttccc cctctgctct gcagctcggt   1140

ttccttttct agaatggaaa tagtgagggc caatgcccag ggttggaggg aggagggcgt   1200

tcatagaaga acacacatgc gggcaccttc atcgtgtgtg gcccactgtc agaacttaat   1260

aaaagtcaac tcatttgctg gaaaaaaaaa aaaaaaaaa                          1299
```

<210> SEQ ID NO 26
<211> LENGTH: 273
<212> TYPE: PRT
<213> ORGANISM: Homo sapiens

<400> SEQUENCE: 26

```
Met Asn Trp Ser Ile Phe Glu Gly Leu Leu Ser Gly Val Asn Lys Tyr
1               5                   10                  15

Ser Thr Ala Phe Gly Arg Ile Trp Leu Ser Leu Val Phe Ile Phe Arg
            20                  25                  30

Val Leu Val Tyr Leu Val Thr Ala Glu Arg Val Trp Ser Asp Asp His
        35                  40                  45

Lys Asp Phe Asp Cys Asn Thr Arg Gln Pro Gly Cys Ser Asn Val Cys
    50                  55                  60

Phe Asp Glu Phe Phe Pro Val Ser His Val Arg Leu Trp Ala Leu Gln
65                  70                  75                  80

Leu Ile Leu Val Thr Cys Pro Ser Leu Leu Val Val Met His Val Ala
                85                  90                  95

Tyr Arg Glu Val Gln Glu Lys Arg His Arg Glu Ala His Gly Glu Asn
            100                 105                 110

Ser Gly Arg Leu Tyr Leu Asn Pro Gly Lys Lys Arg Gly Gly Leu Trp
        115                 120                 125

Trp Thr Tyr Val Cys Ser Leu Val Phe Lys Ala Ser Val Asp Ile Ala
    130                 135                 140

Phe Leu Tyr Val Phe His Ser Phe Tyr Pro Lys Tyr Ile Leu Pro Pro
145                 150                 155                 160
```

-continued

Val Val Lys Cys His Ala Asp Pro Cys Pro Asn Ile Val Asp Cys Phe
165 170 175

Ile Ser Lys Pro Ser Glu Lys Asn Ile Phe Thr Leu Phe Met Val Ala
180 185 190

Thr Ala Ala Ile Cys Ile Leu Leu Asn Leu Val Glu Leu Ile Tyr Leu
195 200 205

Val Ser Lys Arg Cys His Glu Cys Leu Ala Ala Arg Lys Ala Gln Ala
210 215 220

Met Cys Thr Gly His His Pro His Gly Thr Thr Ser Ser Cys Lys Gln
225 230 235 240

Asp Asp Leu Leu Ser Gly Asp Leu Ile Phe Leu Gly Ser Asp Ser His
245 250 255

Pro Pro Leu Leu Pro Asp Arg Pro Arg Asp His Val Lys Lys Thr Ile
260 265 270

Leu

<210> SEQ ID NO 27
<211> LENGTH: 22
<212> TYPE: DNA
<213> ORGANISM: Artificial Sequence
<220> FEATURE:
<223> OTHER INFORMATION: Oligonucleotide

<400> SEQUENCE: 27
ggagtagtca ctcagtagca gc 22

<210> SEQ ID NO 28
<211> LENGTH: 19
<212> TYPE: DNA
<213> ORGANISM: Artificial Sequence
<220> FEATURE:
<223> OTHER INFORMATION: Oligonucleotide

<400> SEQUENCE: 28
gaactcatca aagcagacg 19

<210> SEQ ID NO 29
<211> LENGTH: 1528
<212> TYPE: DNA
<213> ORGANISM: Homo sapiens

<400> SEQUENCE: 29
ggaaggcaca ggcctgagaa gtctgcggct gagctgggag caaatccccc accccctacc 60
tgggggacag ggcaagtgag acctggtgag ggtggctcag caggaaggga aggagaggtg 120
tctgtgcgtc ctgcacccac atctttctct gtcccctcct tgccctgtct ggaggctgct 180
agactcctat cttctgaatt ctatagtgcc tgggtctcag cgcagtgccg atggtggccc 240
gtccttgtgg ttcctctcta cctggggaaa taaggtgcag cggccatggc tacagcaaga 300 ccccccctgga tgtgggtgct ctgtgctctg atcacagcct tgcttctggg ggtcacagag 360
catgttctcg ccaacaatga tgtttcctgt gaccacccct ctaacaccgt gccctctggg 420
agcaaccagg acctgggagc tggggccggg gaagacgccc ggtcggatga cagcagcagc 480
cgcatcatca atggatccga ctgcgatatg cacacccagc cgtggcaggc cgcgctgttg 540
ctaaggccca accagctcta ctgcggggcg gtgttggtgc atccacagtg gctgctcacg 600
gccgcccact gcaggaagaa agttttcaga gtccgtctcg gccactactc cctgtcacca 660
gtttatgaat ctgggcagca gatgttccag gggtcaaat ccatccccca ccctggctac 720

-continued

```
tcccaccctg gccactctaa cgacctcatg ctcatcaaac tgaacagaag aattcgtccc    780

actaaagatg tcagacccat caacgtctcc tctcattgtc cctctgctgg gacaaagtgc    840

ttggtgtctg gctgggggac aaccaagagc cccaagtgc  acttccctaa ggtcctccag    900

tgcttgaata tcagcgtgct aagtcagaaa aggtgcgagg atgcttaccc gagacagata    960

gatgacacca tgttctgcgc cggtgacaaa gcaggtagag actcctgcca gggtgattct   1020

ggggggcctg tggtctgcaa tggctccctg cagggactcg tgtcctgggg agattaccct   1080

tgtgcccggc ccaacagacc gggtgtctac acgaacctct gcaagttcac caagtggatc   1140

caggaaacca tccaggccaa ctcctgagtc atcccaggac tcagcacacc ggcatcccca   1200

cctgctgcag ggacagccct gacactcctt tcagaccctc attccttccc agagatgttg   1260

agaatgttca tctctccagc ccctgacccc atgtctcctg gactcagggt ctgcttcccc   1320

cacattgggc tgaccgtgtc tctctagttg aaccctggga acaatttcca aaactgtcca   1380

gggcgggggt tgcgtctcaa tctccctggg gcactttcat cctcaagctc agggcccatc   1440

ccttctctgc agctctgacc caaatttagt cccagaaata aactgagaag tggaaaaaaa   1500

aaaaaaaaaa aaaaaaaaaa aaaaaaaa                                       1528


<210> SEQ ID NO 30
<211> LENGTH: 293
<212> TYPE: PRT
<213> ORGANISM: Homo sapiens

<400> SEQUENCE: 30

Met Ala Thr Ala Arg Pro Pro Trp Met Trp Val Leu Cys Ala Leu Ile
1               5                   10                  15

Thr Ala Leu Leu Leu Gly Val Thr Glu His Val Leu Ala Asn Asn Asp
            20                  25                  30

Val Ser Cys Asp His Pro Ser Asn Thr Val Pro Ser Gly Ser Asn Gln
        35                  40                  45

Asp Leu Gly Ala Gly Ala Gly Glu Asp Ala Arg Ser Asp Asp Ser Ser
    50                  55                  60

Ser Arg Ile Ile Asn Gly Ser Asp Cys Asp Met His Thr Gln Pro Trp
65                  70                  75                  80

Gln Ala Ala Leu Leu Leu Arg Pro Asn Gln Leu Tyr Cys Gly Ala Val
                85                  90                  95

Leu Val His Pro Gln Trp Leu Leu Thr Ala Ala His Cys Arg Lys Lys
            100                 105                 110

Val Phe Arg Val Arg Leu Gly His Tyr Ser Leu Ser Pro Val Tyr Glu
        115                 120                 125

Ser Gly Gln Gln Met Phe Gln Gly Val Lys Ser Ile Pro His Pro Gly
    130                 135                 140

Tyr Ser His Pro Gly His Ser Asn Asp Leu Met Leu Ile Lys Leu Asn
145                 150                 155                 160

Arg Arg Ile Arg Pro Thr Lys Asp Val Arg Pro Ile Asn Val Ser Ser
                165                 170                 175

His Cys Pro Ser Ala Gly Thr Lys Cys Leu Val Ser Gly Trp Gly Thr
            180                 185                 190

Thr Lys Ser Pro Gln Val His Phe Pro Lys Val Leu Gln Cys Leu Asn
        195                 200                 205

Ile Ser Val Leu Ser Gln Lys Arg Cys Glu Asp Ala Tyr Pro Arg Gln
    210                 215                 220
```

-continued

```
Ile Asp Asp Thr Met Phe Cys Ala Gly Asp Lys Ala Gly Arg Asp Ser
225                 230                 235                 240

Cys Gln Gly Asp Ser Gly Gly Pro Val Val Cys Asn Gly Ser Leu Gln
                245                 250                 255

Gly Leu Val Ser Trp Gly Asp Tyr Pro Cys Ala Arg Pro Asn Arg Pro
            260                 265                 270

Gly Val Tyr Thr Asn Leu Cys Lys Phe Thr Lys Trp Ile Gln Glu Thr
        275                 280                 285

Ile Gln Ala Asn Ser
    290


<210> SEQ ID NO 31
<211> LENGTH: 19
<212> TYPE: DNA
<213> ORGANISM: Artificial Sequence
<220> FEATURE:
<223> OTHER INFORMATION: Oligonucleotide

<400> SEQUENCE: 31

cagaaaaggt gcgaggatg                                                  19


<210> SEQ ID NO 32
<211> LENGTH: 21
<212> TYPE: DNA
<213> ORGANISM: Artificial Sequence
<220> FEATURE:
<223> OTHER INFORMATION: Oligonucleotide

<400> SEQUENCE: 32

ctgggatgac tcaggagttg g                                               21


<210> SEQ ID NO 33
<211> LENGTH: 636
<212> TYPE: DNA
<213> ORGANISM: Homo sapiens

<400> SEQUENCE: 33

atgacagaag cagcatcgct tgtccctaag aggccaagga ggctcagagg cagccacaag     60

ctgcgagttc tggcatggcc agtggtcgtg gtggtgaact ttgtttggca gtgcaacggc    120

agcattgctc acaccttcct ggagctaagc ttcgcctgcc ctggaggaag gtacgcaggc    180

agtcgcccag ccccggttgc agggatggac cgcgaccagc agagggcaga aagtgcctgt    240

gtcccccatt ctcgatcccg gggccccaac ctcccatcgg ctcagtcccc cgcccaatct    300

ctgccaggcc cggagctttc ccagacccct cacccacact ccaggctcac tccccgttcc    360

tgggcctggg cccccccttgc acgagtccag ggccagccgt cctcgccttc tgcccgcccc    420

cgtccttcgt tcctgggagc cggccctctc cgcggaccaa gcggccccga gcaggcgccg    480

ccgcccgggg gactccgact cagcccccgc gacctacctc ggccgacagt cgggggttcc    540

caagcggcca ctcccggccg gcgccgtccc ctggcggagc cgccgcgctc cctgccgtcc    600

gcgcagtctg gcctcgctcg gggccactcc tcgtag                              636


<210> SEQ ID NO 34
<211> LENGTH: 211
<212> TYPE: PRT
<213> ORGANISM: Homo sapiens

<400> SEQUENCE: 34

Met Thr Glu Ala Ala Ser Leu Val Pro Lys Arg Pro Arg Arg Leu Arg
1               5                   10                  15
```

-continued

```
Gly Ser His Lys Leu Arg Val Leu Ala Trp Pro Val Val Val Val Val
            20                  25                  30

Asn Phe Val Trp Gln Cys Asn Gly Ser Ile Ala His Thr Phe Leu Glu
        35                  40                  45

Leu Ser Phe Ala Cys Pro Gly Gly Arg Tyr Ala Gly Ser Arg Pro Ala
    50                  55                  60

Pro Val Ala Gly Met Asp Arg Asp Gln Gln Arg Ala Glu Ser Ala Cys
65                  70                  75                  80

Val Pro His Ser Arg Ser Arg Gly Pro Asn Leu Pro Ser Ala Gln Ser
                85                  90                  95

Pro Ala Gln Ser Leu Pro Gly Pro Glu Leu Ser Gln Thr Pro His Pro
            100                 105                 110

His Ser Arg Leu Thr Pro Arg Ser Trp Ala Trp Ala Pro Leu Ala Arg
        115                 120                 125

Val Gln Gly Gln Pro Ser Ser Pro Ser Ala Arg Pro Arg Pro Ser Phe
    130                 135                 140

Leu Gly Ala Gly Pro Leu Arg Gly Pro Ser Gly Pro Glu Gln Ala Pro
145                 150                 155                 160

Pro Pro Gly Gly Leu Arg Leu Ser Pro Arg Asp Leu Pro Arg Pro Thr
                165                 170                 175

Val Gly Gly Ser Gln Ala Ala Thr Pro Gly Arg Arg Arg Pro Leu Ala
            180                 185                 190

Glu Pro Pro Arg Ser Leu Pro Ser Ala Gln Ser Gly Leu Ala Arg Gly
        195                 200                 205

His Ser Ser
    210
```

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide

<400> SEQUENCE: 35
tgctctcact gtggtcctca g 21

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide

<400> SEQUENCE: 36
tttgtaaagc tccagcgcta c 21

<210> SEQ ID NO 37
<211> LENGTH: 969
<212> TYPE: DNA
<213> ORGANISM: Homo sapiens

<400> SEQUENCE: 37
atgaaggact gtaggaacaa tggcaaggat tgtcaaagtg cccctgcaac acgtaggcac 60
ctcttctctg aagctgccct gcccccttat cgtctttccc aagggcactt cctcacagcc 120
ctggggggcc tcatggcggt gccattcatc ctggccaagg acctgtgcct gcagcaggac 180
cccctgacac agagctacct catcagcacc atttctttg ctccagcatc tgcatgctcc 240

-continued

```
tgcaagctgc ccattcccca gggaggtacg tttgcttttg tggtaatttc tctggccatg    300

ctctcccttc cctcctggaa ttgccctgag tggacactca gtgccagcca ggtgaacacc    360

aactttccag aattcactca gaaatggcag aagaggatcc aagagggtgc tatcatggtc    420

acttcctgtg tccggatgct ggtgggcttc tcaggcctga ctggctttct catgggtttc    480

atctgctcct tggccgttgc tccaactaac tgcctagtgg ccctgcccct cttggattct    540

gcaggcaata atgccgggat ccagtggggg atttctgcca tgtattgctt cgtgttgcgt    600

cttcgcaagg atgagctctg gccatttggt tctccacggc tgcgtttgcc accatcccca    660

ccccgtgatc ggaggcatgt ccccaccccc gtgatcggag gcatgaccct gtttggggtc    720

atcactgccg tggggatctc caatctgcag tacgtggaca tgaacttgtc caggagcctc    780

ttcgcctttg gcttctccat ctactgtggg ctcaccattc ccaaccgggt gagcaaaaac    840

cccgagatgc tccagacagg gattctccag ccggaccagg ttgttcagat gctgctgacc    900

atgggcatgt tcatcagtgg atttctgggt tttcttctag acaacaccat ccccgagctc    960

cttcaataa                                                            969
```

```
<210> SEQ ID NO 38
<211> LENGTH: 322
<212> TYPE: PRT
<213> ORGANISM: Homo sapiens

<400> SEQUENCE: 38

Met Lys Asp Cys Arg Asn Asn Gly Lys Asp Cys Gln Ser Ala Pro Ala
1               5                   10                  15

Thr Arg Arg His Leu Phe Ser Glu Ala Ala Leu Pro Pro Tyr Arg Leu
            20                  25                  30

Ser Gln Gly His Phe Leu Thr Ala Leu Gly Gly Leu Met Ala Val Pro
        35                  40                  45

Phe Ile Leu Ala Lys Asp Leu Cys Leu Gln Gln Asp Pro Leu Thr Gln
    50                  55                  60

Ser Tyr Leu Ile Ser Thr Ile Phe Phe Ala Pro Ala Ser Ala Cys Ser
65                  70                  75                  80

Cys Lys Leu Pro Ile Pro Gln Gly Gly Thr Phe Ala Phe Val Val Ile
                85                  90                  95

Ser Leu Ala Met Leu Ser Leu Pro Ser Trp Asn Cys Pro Glu Trp Thr
            100                 105                 110

Leu Ser Ala Ser Gln Val Asn Thr Asn Phe Pro Glu Phe Thr Gln Lys
        115                 120                 125

Trp Gln Lys Arg Ile Gln Glu Gly Ala Ile Met Val Thr Ser Cys Val
    130                 135                 140

Arg Met Leu Val Gly Phe Ser Gly Leu Thr Gly Phe Leu Met Gly Phe
145                 150                 155                 160

Ile Cys Ser Leu Ala Val Ala Pro Thr Asn Cys Leu Val Ala Leu Pro
                165                 170                 175

Leu Leu Asp Ser Ala Gly Asn Asn Ala Gly Ile Gln Trp Gly Ile Ser
            180                 185                 190

Ala Met Tyr Cys Phe Val Leu Arg Leu Arg Lys Asp Glu Leu Trp Pro
        195                 200                 205

Phe Gly Ser Pro Arg Leu Arg Leu Pro Pro Ser Pro Pro Arg Asp Arg
    210                 215                 220

Arg His Val Pro Thr Pro Val Ile Gly Gly Met Thr Leu Phe Gly Val
225                 230                 235                 240
```

-continued

```
Ile Thr Ala Val Gly Ile Ser Asn Leu Gln Tyr Val Asp Met Asn Leu
                245                 250                 255

Ser Arg Ser Leu Phe Ala Phe Gly Phe Ser Ile Tyr Cys Gly Leu Thr
            260                 265                 270

Ile Pro Asn Arg Val Ser Lys Asn Pro Glu Met Leu Gln Thr Gly Ile
        275                 280                 285

Leu Gln Pro Asp Gln Val Val Gln Met Leu Leu Thr Met Gly Met Phe
    290                 295                 300

Ile Ser Gly Phe Leu Gly Phe Leu Leu Asp Asn Thr Ile Pro Glu Leu
305                 310                 315                 320

Leu Gln


<210> SEQ ID NO 39
<211> LENGTH: 20
<212> TYPE: DNA
<213> ORGANISM: Artificial Sequence
<220> FEATURE:
<223> OTHER INFORMATION: Oligonucleotide

<400> SEQUENCE: 39

atggcggtgc cattcatcct                                                    20


<210> SEQ ID NO 40
<211> LENGTH: 20
<212> TYPE: DNA
<213> ORGANISM: Artificial Sequence
<220> FEATURE:
<223> OTHER INFORMATION: Oligonucleotide

<400> SEQUENCE: 40

caggagggaa gggagagcat                                                    20


<210> SEQ ID NO 41
<211> LENGTH: 1679
<212> TYPE: DNA
<213> ORGANISM: Homo sapiens

<400> SEQUENCE: 41

gaggaggcgc gcgtcgccgc cccgcgtccc gcctgcggcc cgcgcccccg gcgtcaccgc      60

ctcctgcccg cctgcccgcc tgcccgcctg cccgcctacc cgcctacccg cctacccgcc     120

taccccccctg ccggcctgcc gtccttccac gcggagagcc atggagggag tgagcgcgct    180

gctggcccgc tgccccacgg ccggcctggc cggcggcctg ggggtcacgg cgtgcgccgc     240

ggccggcgtg ttgctctacc ggatcgcgcg gaggatgaag ccaacgcaca cgatggtcaa     300

ctgctggttc tgcaaccagg atacgctggt gccctatggg aaccgcaact gctgggactg     360

tccccactgc gagcagtaca acggcttcca ggagaacggc gactacaaca agccgatccc     420

cgcccagtac ttggagcacc tgaaccacgt ggtgagcagc gcgcccagcc tgcgcgaccc     480

ttcgcagccg cagcagtggg tgagcagcca agtcctgctg tgcaagaggt gcaaccacca     540

ccagaccacc aagatcaagc agctggccgc cttcgctccc cgcgaggagg gcaggtatga     600

cgaggaggtc gaggtgtacc ggcatcacct ggagcagatg tacaagctgt gccggccgtg     660

ccaagcggct gtggagtact acatcaagca ccagaaccgc cagctgcgcg ccctgttgct     720

cagccaccag ttcaagcgcc gggaggccga ccagacccac gcacagaact tctcctccgc     780

cgtgaagtcc ccggtccagg tcatcctgct ccgtgccctc gccttcctgg cctgcgcctt     840

cctactgacc accgcgctgt atggggccag cggacacttc gccccaggca ccactgtgcc     900
```

-continued

```
cctggccctg ccacctggtg gcaatggctc agccacacct gacaatggca ccacccctgg    960

ggccgagggc tggcggcagt tgctgggcct actccccgag cacatggcgg agaagctgtg   1020

tgaggcctgg gcctttgggc agagccacca gacgggcgtc gtggcactgg gcctactcac   1080

ctgcctgctg gcaatgctgc tggctggccg catcaggctc cggaggatcg atgccttctg   1140

cacctgcctg tgggccctgc tgctggggct gcacctggct gagcagcacc tgcaggccgc   1200

ctcgcctagc tggctagaca cgctcaagtt cagcaccaca tctttgtgct gcctggttgg   1260

cttcacggcg gctgtggcca caaggaaggc aacgggccca cggaggttcc ggccccgaag   1320

gtcagagaag cagccatgac tgcgggggga ggacacacgg atgctcaggc ccaggctttg   1380

ccaggtccga agcgggcccc tctctgtcct gcctcttttc acctgctcac gccctcccac   1440

ccccacccta cagccccagg tcctggccca gtccctccac tgcctcgaag agtcagtctg   1500

ccctgccttt tcctttcggg caccaccagc catccccgag tgccctgtag ccactcacca   1560

ctgctgccac ctctctggcc aatggccctt tcactggcct ggtgactgga atgtgggcag   1620

cgcccacaca ggctctggcc catggcttcc tactggcagc tccaggcacc cccctctca    1679
```

<210> SEQ ID NO 42
<211> LENGTH: 392
<212> TYPE: PRT
<213> ORGANISM: Homo sapiens

<400> SEQUENCE: 42

```
Met Glu Gly Val Ser Ala Leu Leu Ala Arg Cys Pro Thr Ala Gly Leu
1               5                   10                  15

Ala Gly Gly Leu Gly Val Thr Ala Cys Ala Ala Ala Gly Val Leu Leu
            20                  25                  30

Tyr Arg Ile Ala Arg Arg Met Lys Pro Thr His Thr Met Val Asn Cys
        35                  40                  45

Trp Phe Cys Asn Gln Asp Thr Leu Val Pro Tyr Gly Asn Arg Asn Cys
    50                  55                  60

Trp Asp Cys Pro His Cys Glu Gln Tyr Asn Gly Phe Gln Glu Asn Gly
65                  70                  75                  80

Asp Tyr Asn Lys Pro Ile Pro Ala Gln Tyr Leu Glu His Leu Asn His
                85                  90                  95

Val Val Ser Ser Ala Pro Ser Leu Arg Asp Pro Ser Gln Pro Gln Gln
            100                 105                 110

Trp Val Ser Ser Gln Val Leu Leu Cys Lys Arg Cys Asn His His Gln
        115                 120                 125

Thr Thr Lys Ile Lys Gln Leu Ala Ala Phe Ala Pro Arg Glu Glu Gly
    130                 135                 140

Arg Tyr Asp Glu Glu Val Glu Val Tyr Arg His His Leu Glu Gln Met
145                 150                 155                 160

Tyr Lys Leu Cys Arg Pro Cys Gln Ala Ala Val Glu Tyr Tyr Ile Lys
                165                 170                 175

His Gln Asn Arg Gln Leu Arg Ala Leu Leu Leu Ser His Gln Phe Lys
            180                 185                 190

Arg Arg Glu Ala Asp Gln Thr His Ala Gln Asn Phe Ser Ser Ala Val
        195                 200                 205

Lys Ser Pro Val Gln Val Ile Leu Leu Arg Ala Leu Ala Phe Leu Ala
    210                 215                 220

Cys Ala Phe Leu Leu Thr Thr Ala Leu Tyr Gly Ala Ser Gly His Phe
225                 230                 235                 240
```

-continued

```
Ala Pro Gly Thr Thr Val Pro Leu Ala Leu Pro Pro Gly Gly Asn Gly
            245                 250                 255

Ser Ala Thr Pro Asp Asn Gly Thr Thr Pro Gly Ala Glu Gly Trp Arg
        260                 265                 270

Gln Leu Leu Gly Leu Leu Pro Glu His Met Ala Glu Lys Leu Cys Glu
    275                 280                 285

Ala Trp Ala Phe Gly Gln Ser His Gln Thr Gly Val Val Ala Leu Gly
    290                 295                 300

Leu Leu Thr Cys Leu Leu Ala Met Leu Leu Ala Gly Arg Ile Arg Leu
305                 310                 315                 320

Arg Arg Ile Asp Ala Phe Cys Thr Cys Leu Trp Ala Leu Leu Leu Gly
            325                 330                 335

Leu His Leu Ala Glu Gln His Leu Gln Ala Ala Ser Pro Ser Trp Leu
        340                 345                 350

Asp Thr Leu Lys Phe Ser Thr Thr Ser Leu Cys Cys Leu Val Gly Phe
    355                 360                 365

Thr Ala Ala Val Ala Thr Arg Lys Ala Thr Gly Pro Arg Arg Phe Arg
    370                 375                 380

Pro Arg Arg Ser Glu Lys Gln Pro
385                 390
```

<210> SEQ ID NO 43
<211> LENGTH: 23
<212> TYPE: DNA
<213> ORGANISM: Artificial Sequence
<220> FEATURE:
<223> OTHER INFORMATION: Oligonucleotide

<400> SEQUENCE: 43
ctacatcaag caccagaacc gcc 23

<210> SEQ ID NO 44
<211> LENGTH: 19
<212> TYPE: DNA
<213> ORGANISM: Artificial Sequence
<220> FEATURE:
<223> OTHER INFORMATION: Oligonucleotide

<400> SEQUENCE: 44
ggacttcacg gcggaggag 19

<210> SEQ ID NO 45
<211> LENGTH: 727
<212> TYPE: DNA
<213> ORGANISM: Homo sapiens

<400> SEQUENCE: 45
aggcagttgc gggttgcagg agttcaggaa aggaggtggg actagagtca acctggaata 60
gctctacagt aacaatggca gcctttttgt tgctgggaca tccatacagg caacttagct 120
ggtgaaagga ctctggattg gttggcagtc tgcttttttt tttccaaggt gatcacttta 180
ctgtagaaga aatgaggtta acagaaaaga gtgagggaga acaacaactc aagcccaaca 240
actctaatgc acccaatgaa gatcaagaag aagaaatcca acagtcagaa cagcatactc 300
cagcaaggca gcgaacacaa agagcagaca cacagccatc cagatgtcga ttgccttcac 360
gtaggacacc tacaacatcc agcgacagaa cgatcaacct tcttgaagtc cttccgtggc 420
ctactgagtg gattttcaac ccctatcgat tgcctgctct ttttgagctt tatcctgaat 480

-continued

```
ttcttctggt gtttaaagaa gccttccatg acatatccca ttgtctgaaa gcccagatgg    540

aaaagatcgg actgcccatc atactccacc tcttcgcact ctccaccctc tacttctaca    600

agtttttcct tcctacaatt ctttcccttt ctttctttat tcttcttgta cttctgcttc    660

tgctttttat tattgtcttc attctgatct tcttctgatt cttttgtttc aataaacagc    720

aatgagc                                                              727


<210> SEQ ID NO 46
<211> LENGTH: 168
<212> TYPE: PRT
<213> ORGANISM: Homo sapiens

<400> SEQUENCE: 46

Met Arg Leu Thr Glu Lys Ser Glu Gly Glu Gln Gln Leu Lys Pro Asn
1               5                   10                  15

Asn Ser Asn Ala Pro Asn Glu Asp Gln Glu Glu Glu Ile Gln Gln Ser
            20                  25                  30

Glu Gln His Thr Pro Ala Arg Gln Arg Thr Gln Arg Ala Asp Thr Gln
        35                  40                  45

Pro Ser Arg Cys Arg Leu Pro Ser Arg Arg Thr Pro Thr Thr Ser Ser
    50                  55                  60

Asp Arg Thr Ile Asn Leu Leu Glu Val Leu Pro Trp Pro Thr Glu Trp
65                  70                  75                  80

Ile Phe Asn Pro Tyr Arg Leu Pro Ala Leu Phe Glu Leu Tyr Pro Glu
                85                  90                  95

Phe Leu Leu Val Phe Lys Glu Ala Phe His Asp Ile Ser His Cys Leu
            100                 105                 110

Lys Ala Gln Met Glu Lys Ile Gly Leu Pro Ile Ile Leu His Leu Phe
        115                 120                 125

Ala Leu Ser Thr Leu Tyr Phe Tyr Lys Phe Phe Leu Pro Thr Ile Leu
    130                 135                 140

Ser Leu Ser Phe Phe Ile Leu Leu Val Leu Leu Leu Leu Leu Phe Ile
145                 150                 155                 160

Ile Val Phe Ile Leu Ile Phe Phe
                165


<210> SEQ ID NO 47
<211> LENGTH: 20
<212> TYPE: DNA
<213> ORGANISM: Artificial Sequence
<220> FEATURE:
<223> OTHER INFORMATION: Oligonucleotide

<400> SEQUENCE: 47

gctggtgaaa ggactctgga                                                 20


<210> SEQ ID NO 48
<211> LENGTH: 20
<212> TYPE: DNA
<213> ORGANISM: Artificial Sequence
<220> FEATURE:
<223> OTHER INFORMATION: Oligonucleotide

<400> SEQUENCE: 48

tcgctggatg ttgtaggtgt                                                 20


<210> SEQ ID NO 49
<211> LENGTH: 950
<212> TYPE: DNA
```

<213> ORGANISM: Homo sapiens

<400> SEQUENCE: 49

```
gcgagcccga gcaggcagac gcgcggccgg cggtctgggg gcgcgccgcc tcccggtccc    60
caaaatgtga agcggggagg gcggagacgc agagacggcc cggccgggcg ccctcgccgc   120
cctccggcag ccgcgccgct ccctccgctg cacgcccagg cctgagcagc gaggccaccg   180
ggccgcgcgc tcccagcttc gctcggacgc ggcttcggcc cgcagagggt tcgtggcccg   240
gacgcggcga gagctgggcc caggacggtg cgtccggcct cgcccgcggc tgctcgcacc   300
aacaagtttg aacaatgatc accgtcaacc ccgatgggaa gataatggtc agaagatgcc   360
tggtcaccct gagacccttt cggcttttt g tcctgggcat cggcttcttc actctctgct   420
tcctgatgac gtctctggga ggccagttct cggcccggcg cctgggggac tcgccattca   480
ccatccgcac agaagtgatg gggggccccg agtcccgcgg cgtcctgcgc aagatgagcg   540
acctgctgga gctgatggtg aagcgcatgg acgcactggc caggctggag aacagcagtg   600
agctgcaccg ggccggcggc gacctgcact ttcccgcaga caggatgccc cctggggccg   660
gcctcatgga gcggatccag gctattgccc agaacgtctc cgacatcgct gtgaaggtgg   720
accagatcct gcgccacagt ctgctcctgc acagcaaggt gtcagaaggc cggcgggacc   780
agtgtgaggc acccagtgac cccaagttcc ctgactgctc agggaaggtg gcagtggatg   840
cgtgcccgct ggacctctga cccctgctac gccttctttg gggtggacgg caccgagtgc   900
tccttcctca tctacctcag tgaggtcgag tggttctgcc cccgctgcc              950
```

<210> SEQ ID NO 50
<211> LENGTH: 181
<212> TYPE: PRT
<213> ORGANISM: Homo sapiens

<400> SEQUENCE: 50

```
Met Ile Thr Val Asn Pro Asp Gly Lys Ile Met Val Arg Arg Cys Leu
  1               5                  10                  15

Val Thr Leu Arg Pro Phe Arg Leu Phe Val Leu Gly Ile Gly Phe Phe
             20                  25                  30

Thr Leu Cys Phe Leu Met Thr Ser Leu Gly Gly Gln Phe Ser Ala Arg
         35                  40                  45

Arg Leu Gly Asp Ser Pro Phe Thr Ile Arg Thr Glu Val Met Gly Gly
     50                  55                  60

Pro Glu Ser Arg Gly Val Leu Arg Lys Met Ser Asp Leu Leu Glu Leu
 65                  70                  75                  80

Met Val Lys Arg Met Asp Ala Leu Ala Arg Leu Glu Asn Ser Ser Glu
                 85                  90                  95

Leu His Arg Ala Gly Gly Asp Leu His Phe Pro Ala Asp Arg Met Pro
            100                 105                 110

Pro Gly Ala Gly Leu Met Glu Arg Ile Gln Ala Ile Ala Gln Asn Val
        115                 120                 125

Ser Asp Ile Ala Val Lys Val Asp Gln Ile Leu Arg His Ser Leu Leu
    130                 135                 140

Leu His Ser Lys Val Ser Glu Gly Arg Arg Asp Gln Cys Glu Ala Pro
145                 150                 155                 160

Ser Asp Pro Lys Phe Pro Asp Cys Ser Gly Lys Val Ala Val Asp Ala
                165                 170                 175

Cys Pro Leu Asp Leu
            180
```

-continued

<210> SEQ ID NO 51
<211> LENGTH: 21
<212> TYPE: DNA
<213> ORGANISM: Artificial Sequence
<220> FEATURE:
<223> OTHER INFORMATION: Oligonucleotide

<400> SEQUENCE: 51
agatgcctgg tcaccctgag a 21

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide

<400> SEQUENCE: 52
ggccccccat cacttctgtg 20

<210> SEQ ID NO 53
<211> LENGTH: 396
<212> TYPE: DNA
<213> ORGANISM: Homo sapiens

<400> SEQUENCE: 53
ctgcaagacc gcatcgccac gttcttcttc ccaaaaggca tgatgctcac cacggctgcg 60
ctgatgctct tcttcttaca cctgggcatc ttcatcagag acgtgcacaa cttctgcatc 120
acctaccact atgaccacat gagctttcac tacacggtcg tcctgatgtt ctcccaggtg 180
atcagcatct gctgggctgc catggggtca ctctatgctg agatgacaga aaacaatgct 240
caacggagcc atgttcttca accgcctgtc cttggagttt ctggccatcg agtaccggga 300
ggagcaccac tgaggcctgg ggagtcggaa cagggctaag gagggggaag caaaaggctg 360
cctcgggtgt tttaataaag ttgttgttta tttcca 396

<210> SEQ ID NO 54
<211> LENGTH: 99
<212> TYPE: PRT
<213> ORGANISM: Homo sapiens

<400> SEQUENCE: 54

Met Met Leu Thr Thr Ala Ala Leu Met Leu Phe Phe Leu His Leu Gly
1 5 10 15

Ile Phe Ile Arg Asp Val His Asn Phe Cys Ile Thr Tyr His Tyr Asp
20 25 30

His Met Ser Phe His Tyr Thr Val Val Leu Met Phe Ser Gln Val Ile
35 40 45

Ser Ile Cys Trp Ala Ala Met Gly Ser Leu Tyr Ala Glu Met Thr Glu
50 55 60

Asn Asn Ala Gln Arg Ser His Val Leu Gln Pro Pro Val Leu Gly Val
65 70 75 80

Ser Gly His Arg Val Pro Gly Gly Ala Pro Leu Arg Pro Gly Glu Ser
85 90 95

Glu Gln Gly

<210> SEQ ID NO 55
<211> LENGTH: 22
<212> TYPE: DNA

-continued

<213> ORGANISM: Artificial Sequence
<220> FEATURE:
<223> OTHER INFORMATION: Oligonucleotide

<400> SEQUENCE: 55
ccgttgagca ttgttttctg tc 22

<210> SEQ ID NO 56
<211> LENGTH: 22
<212> TYPE: DNA
<213> ORGANISM: Artificial Sequence
<220> FEATURE:
<223> OTHER INFORMATION: Oligonucleotide

<400> SEQUENCE: 56
tgctcttctt cttacacctg gg 22

<210> SEQ ID NO 57
<211> LENGTH: 539
<212> TYPE: DNA
<213> ORGANISM: Homo sapiens

<400> SEQUENCE: 57
ggtgccttaa tgtttgtggc atggatgact actgttagca taggtgtact ggttgcccgg 60
ttcttcaagc cagtttggtc aaaagctttc ttgcttggtg aagcagcttg gtttcaggtg 120
catcggatgc tcatgttcac cacaactgtc ctcacctgca ttgcttttgt tatgccgttt 180
atatacaggg gaggctggag taggcatgca ggttaccacc catacctcgg ctgtatagtg 240
atgactttgg cagttcttca gcctcttctg gcagtcttca ggccaccttt acatgaccca 300
agaaggcaaa tgtttaactg gactcattgg agtatgggaa cagctgctag aataatagca 360
gacttaaaac aatctggaaa atgtgggtgc atctctttta aggattggta gattacgcag 420
ccataaaaaa gaatgaagtc atgtcttttg tagcaacatg gatgctgctg gaagtgatta 480
tcctacatga attaatgcag aaacagaaaa tcacatacca catgttctca cttataaat 539

<210> SEQ ID NO 58
<211> LENGTH: 133
<212> TYPE: PRT
<213> ORGANISM: Homo sapiens

<400> SEQUENCE: 58

```
Met Phe Val Ala Trp Met Thr Thr Val Ser Ile Gly Val Leu Val Ala
1               5                   10                  15

Arg Phe Phe Lys Pro Val Trp Ser Lys Ala Phe Leu Leu Gly Glu Ala
            20                  25                  30

Ala Trp Phe Gln Val His Arg Met Leu Met Phe Thr Thr Thr Val Leu
        35                  40                  45

Thr Cys Ile Ala Phe Val Met Pro Phe Ile Tyr Arg Gly Gly Trp Ser
    50                  55                  60

Arg His Ala Gly Tyr His Pro Tyr Leu Gly Cys Ile Val Met Thr Leu
65                  70                  75                  80

Ala Val Leu Gln Pro Leu Leu Ala Val Phe Arg Pro Pro Leu His Asp
                85                  90                  95

Pro Arg Arg Gln Met Phe Asn Trp Thr His Trp Ser Met Gly Thr Ala
            100                 105                 110

Ala Arg Ile Ile Ala Asp Leu Lys Gln Ser Gly Lys Cys Gly Cys Ile
        115                 120                 125
```

-continued

```
Ser Phe Lys Asp Trp
    130


<210> SEQ ID NO 59
<211> LENGTH: 20
<212> TYPE: DNA
<213> ORGANISM: Artificial Sequence
<220> FEATURE:
<223> OTHER INFORMATION: Oligonucleotide

<400> SEQUENCE: 59

ttgtggcatg gatgactact                                                20


<210> SEQ ID NO 60
<211> LENGTH: 20
<212> TYPE: DNA
<213> ORGANISM: Artificial Sequence
<220> FEATURE:
<223> OTHER INFORMATION: Oligonucleotide

<400> SEQUENCE: 60

catcactata cagccgaggt                                                20


<210> SEQ ID NO 61
<211> LENGTH: 3317
<212> TYPE: DNA
<213> ORGANISM: Homo sapiens

<400> SEQUENCE: 61

acactgcgtc cccatcagct caaagaatac gcatggggac aagcctgggg ggccgtctga      60

gagtccccca accctggatc cccacggcag cccccactgt tgggtttttc agtggctggt     120

gtgccctggg ctggtcacct ctgcattttg ctctgctggg agtttgctcc tggccctcca     180

acagcgcctc ctctgtgagg aggaactcct gttcccgtgg ctctgctggc tctggaggct     240

ggagttcccg tgctgggccc tcctgggcgg gttctctctt gctgccgcca gtaccctgcc     300

cctctcgtcc tcctgggtag cctgggagga atggcagaag aaagcagtga agccaggtag     360

cagtagcccg gccaccccac caggctctgc tgtaggctgg gctctcaagg cagctgctcc     420

aggaggggcc ccctaggaag ggactgccac actcctggga gcgttcctgg ccccctccag     480

tgcaaatgac cctgggcccc aaggctccga acacccgccc ctctgctcca ggctagcttg     540

gctgagcccg atgcttctca aggtgaggag ggcgtccttg aagcctccgg ccaccccaca     600

ccaaggagct ttcagggcag gaaatgtgat cgggcagctg atttatctcc ttacctggtc     660

tttgttcaca gcctggctcc ggccccccac cctgctgcag ggcccgagga cgtctcccca     720

ggggtcccca cctcggtctc cttgggggga ctgtgctgag cccagctgcc tctgtgagat     780

gaagataaga aggcgaagac atgaagggcc tgcctggggg cagtctggct ttcttgcagg     840

ggggctgcac ctggttccct cctccctctc gctggcagcc tgcggggtgg tgaggatgaa     900

ggggctgtgg ggccggggtg cagggattag agggaggtga ctgccatctc ttcctcctca     960

tcgtgttttt cacctcttaa gtcaacttta gattctcgga ctcagagttc tctcctgacg    1020

gtggcagggt cctcagatca ccggtgcaga cagggccaga cagggccaat gtggggaccc    1080

actcagcctg tggcctctgc aggagggagg tcggaggcct cagcagccac cccggccacc    1140

tcctgaaaca gtgaatgtcc ttcattttca gctggcaagc tctgatctta caacgaggta    1200

tggaactgtt cagaaaactt tcagcagacg ttcgagggaa aacagctcag cttcccatgc    1260

cccccacctc tgccaggagc gaccccatat cccccaaaca gaattctggt agcccgggac    1320
```

-continued

```
cacagggtct tcctgtgcct cccctgccag ctctgcatga ctttgtcacg tacttgagtg   1380

ctggctgaga tgatgctacc gctaccaaac aggtgggagg ccagccccag ccccagcccc   1440

agccccaccg gggccggagc tcccggtgaa gaagcgtctg cctggttcgc aggtgtccag   1500

gacacaccag tcgcctgact cccggtcagg caaacgcaca catcaagttc ttgcaagcca   1560

gggctctgct ggcatcttca agaggaggga gggtcctggc cctgaccaca gggctccctt   1620

aacaggagga gttacaaact cggcttcctg gggggcatcg tggggtgtgc tgcctgccag   1680

gagaccccac tcctggtcac ggggttccgt cccacacagt ggcaggagcc atgcatgatt   1740

cttggctgaa gaagaacccg cacagctatg tggtctgccg cccagcaggg aagcccccac   1800

atcagcccta agggaacttc ccaaagctca gcaggtgcct cttcctgcca tccgctaggt   1860

cttctcttgg cccctctccc aagccttgac ccatagctga cacttctaga aaagtcttta   1920

ccgagaaacg gaccggctgc atgggtggtg aggagggcag ttgcccaggg cctggcatca   1980

gaggggcctg tggctaaggc tgtcctgaaa ttcttaatca ttttacctct gaacttgcgg   2040

gtttttgttg ttgtttttg aggcagagtc ttgctctgtc acccaggctg gagtgcagtg   2100

gtgcgatctt ggcttactgc aacttccgac tcccaggttc aagcgattct cctgcctcag   2160

cctcccgagt agctgggact acagaagtgc accaccacac ccggttaatt tttgtatttt   2220

tagtagagac ggggtttcac catgttggcc aggctgatct caaactcctg atacacccgc   2280

ctcggcctct caaagcactg ggattacagg tgtgagccac cgcgcccggc cctttttcctg   2340

cctcctaaac aagtggccag gaattctcct cctgcaccgg gtccccagat tgtgtggcaa   2400

gccctgcaga tggcacaggg gactggttct tcctcgtgga aagccaggcc cggacacctc   2460

tcgggcatcg cctgttgggg tgaccctccc acacccagcc tggaacccta gccagctcag   2520

cctccgtccg ctgagaaatc aaggtgacct tgtggctcag ccctcagggg gcactcacca   2580

cacaagagtt ccctttcaag accccctgtt cggggctggg gcccccagga acggttgggg   2640

caccttcctg gggccctgtt tttccccagg agcggggcct gggagctgag ggcgtctcat   2700

ctccccacag gcatctgctg ctgctcctgg ctgccactca cccctgtgag atgctgaggg   2760

caggatacct gtctgtgcgg ggcgtgggaa aaagggagaa agcctggcag agggttgggg   2820

gctaagaagc aaagggcgtg gaagggccac cgtgcacttt tgaagtctct acttgccagt   2880

ggccacccca cctctccctg ccctcatcca aggacggaca ggcctggcag gtggaccgga   2940

gctgtggggc agaagcatcc caggcctggc ctcagaggag ggaggccatg gtgaaagtgg   3000

aggctgtctg catccacctc cccagccttt gtcaccggga cctcagcctg accccaggcc   3060

caccccaggc tgctcaccga ggtgggtacc ctgcccaccg ccagctcaga tgcggtgtgt   3120

ggactccctt ctctctgggg gtgagcggga gttccctccc ctccacatca ggagctgggg   3180

gagagctgga gggccctggg atccccttga ccctggtcat cagccccagc cctgacaggc   3240

cctgcgtgtg ccatgtgtgg cctgggtttg gagctcagca ccctgcggga attctattaa   3300

atctccgatt ttatctg                                                  3317
```

<210> SEQ ID NO 62
<211> LENGTH: 129
<212> TYPE: PRT
<213> ORGANISM: Homo sapiens

<400> SEQUENCE: 62

```
Met Leu Leu Lys Val Arg Arg Ala Ser Leu Lys Pro Pro Ala Thr Pro
1               5                   10                  15
```

-continued

His Gln Gly Ala Phe Arg Ala Gly Asn Val Ile Gly Gln Leu Ile Tyr
20 25 30

Leu Leu Thr Trp Ser Leu Phe Thr Ala Trp Leu Arg Pro Pro Thr Leu
35 40 45

Leu Gln Gly Pro Arg Thr Ser Pro Gln Gly Ser Pro Pro Arg Ser Pro
50 55 60

Trp Gly Asp Cys Ala Glu Pro Ser Cys Leu Cys Glu Met Lys Ile Arg
65 70 75 80

Arg Arg Arg His Glu Gly Pro Ala Trp Gly Gln Ser Gly Phe Leu Ala
85 90 95

Gly Gly Leu His Leu Val Pro Ser Ser Leu Ser Leu Ala Ala Cys Gly
100 105 110

Val Val Arg Met Lys Gly Leu Trp Gly Arg Gly Ala Gly Ile Arg Gly
115 120 125

Arg

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide

<400> SEQUENCE: 63
ccccaaggct ccgaacaccc 20

<210> SEQ ID NO 64
<211> LENGTH: 20
<212> TYPE: DNA
<213> ORGANISM: Artificial Sequence
<220> FEATURE:
<223> OTHER INFORMATION: Oligonucleotide

<400> SEQUENCE: 64
cccgatcaca tttcctgccc 20

<210> SEQ ID NO 65
<211> LENGTH: 3338
<212> TYPE: DNA
<213> ORGANISM: Homo sapiens

<400> SEQUENCE: 65
gtaggaagta tatgggtagg gtcagataat atttctgaaa ggaaacaccc aggagtatcc 60
caagttaatg acattttaga ccctccaaca accacacaag tcagctcctt ggaaagactc 120
tggttacttt tacaaagcaa accaggagaa ttttcataat acctgataac tatgtaagac 180
ttggaatatt tgaatttcta ggacatggga ttgtgcaacc attcatttta tcccataata 240
ttgaaatctc cctcagataa gcctctcggc acctaataga gttttcttag tgaagggcta 300
cctttctgtg ggtaacaggg aagggcaaaa taaacaacca aataatatca taatcacgag 360
tgtcaatgat tgctggaaca ggtgggggtt ggtcattaaa ttctagttgt ttccactatt 420
ccagtaggag ttgtgtgaat gttagcaaaa gaccagggtg ttacgatctg actgtgtttc 480
atcaattgcc ttgacttttg gatgaaatgc gatttgagga catatcatta ttagatttgc 540
cacagattcc aattttttttc tctaatatga ggctaaccat gatgtccttt cccaggaagg 600
acaatctctc ctttatcagg gaaaaatcag taggggcttc ctcaattttc tccttcatcc 660
ccaccacaga gtcatagagg tcaagtcctt ttcttgtgaa acctaaaaaa tgcaaattcc 720

-continued

```
aaggttgctg ctatggtgta ctaattttgt cacagtgaca tgccctgtca cagggcgtat    780
gtgttctgtt atacagttga aatattggtt atactattga aatgtttttg tactattgaa    840
atcccaaata aacttaattc taaaagaagc atgacctcaa cagcctcaca cctacttata    900
tcttgtagtt ctttctgtct aatgctggca atctaagcat gttccaggca agcaacattc    960
aatagcgttt tactgctcca ataagttggt tcaattagca atgtcaaagg cagtcactaa   1020
atagatagtg tataaccttc atacaatctc gtattatttt ccactaatta ctatagaaaa   1080
atcgatgaag tttcattaca atggaataac ttcaatcaca cttcaaaaac tacatacgga   1140
agatagccac aacttgctgc tctcaaaaaa cacagagatg gcatctttac tttgtttcaa   1200
atccccaacc ctggtggcgg tccaaagtta tggcagttat aaccccttat gtcattataa   1260
ggaggaaggg taaatattaa gtcaacatcc tttaaagcta agagtatgac tacagtgggg   1320
tggaatttgg gacttcatgc ccactccctg tttctgttct attttacctt tcctgacctc   1380
taagccaaca ggagaggggg aagggccaca cttttgtgac ccttgttaaa gaattgtgag   1440
tttaggaaac aaagatggac ttctgagggg gtagttgagg atgggctgaa ggcacagaag   1500
aaaccagctg gtgtgcccct ctccccacta gcagaccctt cttcctcatt ggttcagggc   1560
aaacaatccc ccaaaaattc aagaaaacta acttagagtt attttctgtt atttctcttt   1620
tccttgatct ggagccaatg cagaaagaaa tctaaaggtg aaggaaaggc agcgttcagc   1680
actgagcaag tccatgttgg agaaagttca cagggaattg gaaatccttg tcttcgtggt   1740
tcctggctca gcaggacccc tgtggggcct ctccctctct tgggaaagag attgctctag   1800
aaggtttact acaccagtga ggagaagatg agcgcaaggg ggattggccg gctgagggcg   1860
aaatcaagac tggagccaag tgcgctgagc tctcacatga ggtcctttgc tcctgttccc   1920
tggaggcata agtggctggg gtagagagaa gcaggggtat ttcttctgtc ctttcttgct   1980
tagggattgg gggtggaaat ctccccgcat ctaaggaaat ttgaaaagac aaactatggc   2040
tgcttcttca agcaaaccac ctcaccacac tatccagggg ataaaacccg cttgctgctg   2100
ctaaattatg ccaagagaga acattctgat atttctcctc aattctaggc atgacagcgt   2160
gacttggtgc ttaaaggcat ggagttttga gttgcagacc taggtttgag tgctgaatct   2220
actagcttca gggtgttaaa aaagtttctt aatctctcta aaccttattt ttctcaaaga   2280
taaaaaactg ggtgtagttg tgagtatagt gaatgcacat agtatgtgcc tttggcatgt   2340
taattcacta ttattctgga cataatttct cctaagaaaa aggatgaact aattgcaggg   2400
cctagcctaa gctctgagaa gtcattcgtt atagcatttc agtccatagt aaacaagaag   2460
aaatgaggta aagagtttaa accagggaag gcatagctgt ggtcaccaaa caacctgtta   2520
aaggcgagct gtaggcacca aaaaacctat tatggactga attgtgttcc tcaaattcat   2580
atgttgaagt gctaacccca agtaccaaat gtgactgtat ttggggatag ggtccctgaa   2640
gaagtcactc agctggaagg agtcatattg gattaggtgt tgggaattgg ctggccaagg   2700
gagaaatcaa ggctggaacc aagtgctgaa ctctcacatc aggtcctttg ctcctgttcc   2760
ctggacccta atccaatatg actggcatct ttatatgaag aggaagaggc accagagggt   2820
acacacgcag agaaaaggcc atgtgtggac acagtaagat gacggacatc tgtaagccaa   2880
ggagggaaac ctcagaagaa accagccttg cctgcacctt gatcttggag gtccagtctc   2940
cagaactgtg aaaaaaatga actggtgttg tttaaatccc ccagtcgtgg tattttgtca   3000
tggtggccct agaagacaat atacaaccca aaggaatatt ctttccactt tctccctctt   3060
ccactttata gttttttctc cttcgtttct ttctttttct cttttacttt cctttcttc   3120
```

-continued

```
tcttctcttt cctctggttt ttaattttaa ttttaatttt tggccttcct atacctccat   3180

ttgcctctcc aggaagctga attccagaca attaatcatt catctcatca gttcagcaaa   3240

gcaaatgccc tcaatggttt cttttgtgat tcgattatta tgggatcaga atgtatctta   3300

ttcctctggg aaaaatgaaa cataaaaatt tcagaaat                           3338


<210> SEQ ID NO 66
<211> LENGTH: 122
<212> TYPE: PRT
<213> ORGANISM: Homo sapiens

<400> SEQUENCE: 66

Met Asn Trp Cys Cys Leu Asn Pro Pro Val Val Val Phe Cys His Gly
1               5                   10                  15

Gly Pro Arg Arg Gln Tyr Thr Thr Gln Arg Asn Ile Leu Ser Thr Phe
            20                  25                  30

Ser Leu Phe His Phe Ile Val Phe Ser Pro Ser Phe Leu Ser Phe Ser
        35                  40                  45

Leu Leu Leu Ser Phe Ser Ser Leu Leu Phe Pro Leu Val Phe Asn Phe
    50                  55                  60

Asn Phe Asn Phe Trp Pro Ser Tyr Thr Ser Ile Cys Leu Ser Arg Lys
65                  70                  75                  80

Leu Asn Ser Arg Gln Leu Ile Ile His Leu Ile Ser Ser Ala Lys Gln
                85                  90                  95

Met Pro Ser Met Val Ser Phe Val Ile Arg Leu Leu Trp Asp Gln Asn
            100                 105                 110

Val Ser Tyr Ser Ser Gly Lys Asn Glu Thr
        115                 120


<210> SEQ ID NO 67
<211> LENGTH: 19
<212> TYPE: DNA
<213> ORGANISM: Artificial Sequence
<220> FEATURE:
<223> OTHER INFORMATION: Oligonucleotide

<400> SEQUENCE: 67

ctaaaggtga aggaaaggc                                                  19


<210> SEQ ID NO 68
<211> LENGTH: 17
<212> TYPE: DNA
<213> ORGANISM: Artificial Sequence
<220> FEATURE:
<223> OTHER INFORMATION: Oligonucleotide

<400> SEQUENCE: 68

cgctcatctt ctcctca                                                    17


<210> SEQ ID NO 69
<211> LENGTH: 1119
<212> TYPE: DNA
<213> ORGANISM: Homo sapiens

<400> SEQUENCE: 69

tcaccctcct ggccaattgt gttgcacctt gggcactgaa tcacatgagc cgtcgactaa      60

gccagatgct tctcatgttc ctactggcaa cctgccttct ggccatcata tttgtgcctc     120

aagaaatgca gaccctgcgt gtggttttgg caaccctggg tgtgggagct gcttctcttg     180
```

-continued

```
gcattacctg ttctactgcc caagaaaatg aactaattcc ttccataatc aggtacaaaa    240

gtttatgtgt gctctgtcat tctcaaaatg gacctgtctc aaccaattga cacttaacaa    300

gggaaaaaaa tccaagacaa gttagttaaa aaacaatcaa atgtaatagt cataaaaaca    360

acaaattaca gcccaagttt atatcaagct gactttgttc cagacgctgc attaagtctt    420

ttaatgcagt atcccatgta ccttctgaac cacctgaaag gttgatgtta aggaaaatag    480

cattttgtaa atgataaaaa tgtgtctaat tcacttgtga atctaaaata aattgctagc    540

aaataagaga aaatttcaaa agcaagagta tgttatcacc tccatgtgtt taagtgctca    600

tccataatca cagcaaaatg ataaatcaca aattatatgt atgattttta acaacttttc    660

ctctgttgct gtttttactc caaggggaag agctactgga atcactggaa actttgctaa    720

tattggggga gccctggctt ccctcatgat gatcctaagc atatattctc gacccctgcc    780

ctggatcatc tatggagtct ttgccatcct ctctggcctt gttgtcctcc tccttcctga    840

aaccaggaac cagcctcttc ttgacagcat ccaggatgtg gaaaatgagg gagtaaatag    900

cctagctgcc cctcagagga gctctgtgct ataggtctgt gctgaggaaa gcaaaacacc    960

atttagggct accatccccc aaaaaggctt agatctgggc tattcccatg tagtcagtgc   1020

ctttgccttt ggtgtatcct catcccttcc acagtgacct catacatccc ctgagcctca   1080

ctagatcaca cagaccatct ctgcccagcc tgtccagga                          1119
```

<210> SEQ ID NO 70
<211> LENGTH: 97
<212> TYPE: PRT
<213> ORGANISM: Homo sapiens

<400> SEQUENCE: 70

```
Met Ile Phe Asn Asn Phe Ser Ser Val Ala Val Phe Thr Pro Arg Gly
1               5                   10                  15

Arg Ala Thr Gly Ile Thr Gly Asn Phe Ala Asn Ile Gly Gly Ala Leu
            20                  25                  30

Ala Ser Leu Met Met Ile Leu Ser Ile Tyr Ser Arg Pro Leu Pro Trp
        35                  40                  45

Ile Ile Tyr Gly Val Phe Ala Ile Leu Ser Gly Leu Val Val Leu Leu
    50                  55                  60

Leu Pro Glu Thr Arg Asn Gln Pro Leu Leu Asp Ser Ile Gln Asp Val
65                  70                  75                  80

Glu Asn Glu Gly Val Asn Ser Leu Ala Ala Pro Gln Arg Ser Ser Val
                85                  90                  95

Leu
```

<210> SEQ ID NO 71
<211> LENGTH: 21
<212> TYPE: DNA
<213> ORGANISM: Artificial Sequence
<220> FEATURE:
<223> OTHER INFORMATION: Oligonucleotide

<400> SEQUENCE: 71

```
ttctggccat catatttgtg c                                               21
```

<210> SEQ ID NO 72
<211> LENGTH: 21
<212> TYPE: DNA
<213> ORGANISM: Artificial Sequence
<220> FEATURE:
<223> OTHER INFORMATION: Oligonucleotide -continued

<400> SEQUENCE: 72
agtgattccc agtagctctt c 21

<210> SEQ ID NO 73
<211> LENGTH: 2837
<212> TYPE: DNA
<213> ORGANISM: Homo sapiens

<400> SEQUENCE: 73
atatcacctc ctaggaaata tgcagtaaga tggattgtgt gtctaaaggt taaactcttt 60
ttccaacaga tggatctagg ccgtatggag gattcactgc ttctcatacc tccagtgaag 120
atgcagataa agtgggatgt tgtaaatgta cttcatttta atcaggaaga agctgctatg 180
gtgaatttaa aacttgtaat gccattagat gagcttctag cacagtttca gtcatgttac 240
catgaggatt ggtgtgacct gttccatatt ccgtggtcca ttatttggtg ctgaaagaga 300
ccatctacct cctagaagtg tgtggtgggt ctcttccaaa tactcctgaa ggaaacttta 360
cttctcctgg ctatgatgga gtcaggaatt actcgagaaa cctaaactgt gaatggactc 420
tcagcaatcc aaatcaggga aattcatcta tttatattca ttttgaagat ttttacctag 480
aaagtcacca agactgtcaa tttgatgtcc ttgagtttcg agtgggtttg ttaagagcct 540
ggtaagaagt gcaagattga caaaggtaag gttagtagcg gaggtaagtg aaagcttgaa 600
tataggaaac cttggaccac ttgccattgc agtggataaa attttcaaga tttcgttgaa 660
tttgaaagtc aaagattcca ttttaaagcc attgactacc attgtccagt cgctattggg 720
gccaggccat gttacaaagg atattgaacg tttgggctta atgtgagggc ttgtgaccta 780
gagtctggag gttgcaaggg agacagccaa gtgatgtgtc atggggaaac cttcttcagg 840
tggattttga ggcttcactg caatactagc ttcctgttgc tgctgcaaca aattattatt 900
attattatta ttattattat tattattatt ttcagatgga gtctcgctct gtcactcagg 960
ctggagtgca gtggtgcgat ctcagctcgt tgcaagctcc gccttgtggg ttcatgccat 1020
tctcgtgcct cagcctccca agtagctggg actacaggaa cccgccacca cacctggcta 1080
atgtttcgta tttttagtag aggtggggtt tcatcgtgtt agccaggatg gtctcggtct 1140
cctgacctag tgattcacct gtcttggcct cccaaagttc tgggattaca ggcgtgagcc 1200
acacacttag tgtctttaaa caacatatat gtattctctc acagttctgg aggccagaat 1260
tctaaattcc ctcccactga gtcaaggtgg gagcagggca agtgccttcg gaggctctgt 1320
gggagaatcc atttcctggc tctggaggca gcctgcactc ctcgactttt gatgccctcc 1380
ttgaatgact ccaatttctc gcttccatca ctacacctcc caccactctc ccatcacctg 1440
ctctgctctt acaaggatca gtgagtacat caacttgcca cctaaagaag ccgggataat 1500
cttccctgcc aaaggtcctt aacttcatta catctgcaaa gcttctttta ccatataagg 1560
tgcaccgggt acttcttgag cattgggatg atctgcttca cctccagtca cacagcttcc 1620
aggcactggg agtggtcctc ctgcaggatg ttcagcttcg acttggccag agaaatggaa 1680
tggttgcatc acttatctac gtaaacaatt gaagaattgt ctgaaagaaa agcagaagga 1740
acatctgaag gaacacctga tgaggctgca ccccttggcgg aaagaacacc tgacatggct 1800
gaaagcttgg tggaaaaacc acctgatgag gctgcaccct tggtggaggg aacagctgac 1860
aaaattcaat gtttggggaa agcaacatct ggaaagtttg aacagtcagc agaagaaaca 1920
cctaagaaaa ttatgaggac tgcaaaagaa acatctaaga aatttgcatg gccagcaaaa 1980

-continued

```
gaaagaccta ggaagatcac atgggaggaa aaataaacat ctgtaaagac tgaatgcgtg   2040

gcaggagtaa tacctaataa aactgaagtt ttggaaaaag gaacatctaa gatgctcacg   2100

tgtcctacaa aagaaacatc tacaaaagca agtacaaatg tggatgtgag ttctgtagag   2160

tctatattca gagtctcacc ctgtcaccca ggctggaatg caatggcacg atctcggctc   2220

actgcaacct ccacctccca gaaggaagca acaaagacag caactgaaca acaagaaaat   2280

gatattggaa ttattgaatg agcgccataa gatctaacaa ataagatgcc cacatcagag   2340

tcaggacaaa aagaagatac gaaatcacct tcagtttctg aggtcacagc tatggatgtg   2400

gaagagatag gaaaggcctc accacttaag atagaagcag cagctgcata gtggtaacag   2460

caatgagtgg atgtcaaaag acagattcaa ctagcctatc aatattcttg ggtgcagttc   2520

cttctcatga aagagcaagg gaacttaaaa aatatcactg tgaacaactt acagcaaaaa   2580

taaaacaaat gaaaaataag ttttgggtac tacaaaagga actatcagaa gcaaaaaataa   2640

aattgcagta agtgaatcaa aaggttaaat gggaacaaga gctctgcagt gtgagcttgg   2700

aatgaagttg ataatagtga gaccttgttg gtacaagact atgtaacaca acctgcactt   2760

ctcaacaaaa aattgctttt ctgacttctg cactcagtag gtatctttgg aaaataatct   2820

cctattggta ctgaggc                                                  2837
```

<210> SEQ ID NO 74
<211> LENGTH: 102
<212> TYPE: PRT
<213> ORGANISM: Homo sapiens

<400> SEQUENCE: 74

```
Met Cys His Gly Glu Thr Phe Phe Arg Trp Ile Leu Arg Leu His Cys
1               5                   10                  15

Asn Thr Ser Phe Leu Leu Leu Leu Gln Gln Ile Ile Ile Ile Ile Ile
            20                  25                  30

Ile Ile Ile Ile Ile Ile Ile Phe Arg Trp Ser Leu Ala Leu Ser Leu
        35                  40                  45

Arg Leu Glu Cys Ser Gly Ala Ile Ser Ala Arg Cys Lys Leu Arg Leu
    50                  55                  60

Val Gly Ser Cys His Ser Arg Ala Ser Ala Ser Gln Val Ala Gly Thr
65                  70                  75                  80

Thr Gly Thr Arg His His Thr Trp Leu Met Phe Arg Ile Phe Ser Arg
                85                  90                  95

Gly Gly Val Ser Ser Cys
            100
```

<210> SEQ ID NO 75
<211> LENGTH: 21
<212> TYPE: DNA
<213> ORGANISM: Artificial Sequence
<220> FEATURE:
<223> OTHER INFORMATION: Oligonucleotide

<400> SEQUENCE: 75

```
catctacctc ctagaagtgt g                                               21
```

<210> SEQ ID NO 76
<211> LENGTH: 21
<212> TYPE: DNA
<213> ORGANISM: Artificial Sequence
<220> FEATURE:
<223> OTHER INFORMATION: Oligonucleotide -continued

<400> SEQUENCE: 76
cactcgaaac tcaaggacat c 21

<210> SEQ ID NO 77
<211> LENGTH: 5868
<212> TYPE: DNA
<213> ORGANISM: Homo sapiens

<400> SEQUENCE: 77
gatctctccc atgaagtgac caggatagag aagcaccaga accgccaaaa gtatgggctg 60
tgcgtcatct tcctttcctg taccatgatg cccaacttta aagagctgat ccatttcgag 120
gtcagcatcg gtcactatgg gaacaagatg gacctgaatt acaagcctct agtctcaagc 180
acaccgtaca gcccagtgat atatgatggg aacatctacc attatgtgcc ctggtacaac 240
accaagcctg tcgtggccgt gacctccaac tgggaggacg tcagcttccg catgaactgc 300
ctcaacctcc tccacttcac tcgggaccgc ctgaaagcca acctggacac cctgaaatcc 360
acgcggaatc cgaaggatcc agctctcctc taccagtggg agaaactgct gagggagctg 420
gcagaggact gcaagcgccc tctgccctgc atgacctatc agcccaaagc caccagcctg 480
gacaggaaga ggtggcagct ccgcagcctc ctcctgcagg aactggccca aaaggccaag 540
caagccaagc ccaaggacat ggtggccaca gcggaggact ggctgtaccg cctcaacacc 600
gtgctccctg agccccagat gggcctccct gacgtgatga tttggctggt ggccaaggag 660
cagcgagtgg cctatgcaca gtacccagag ggtgaaggac agaaggatgt gctcccagct 720
cacctccggg tctgcatgtg gcttggcaat gtcacagaca gcaaggacct gcagctgctc 780
cgccagggtg acacagcggt gtacgccgag atggtgagtg tatgagaatc aggccaagta 840
taaagaccag tgggggcagc aggggctgta tcactgcccc aacttctcgg atgtcatggg 900
gaacaagacc ctccccatga cggatttcca accacccctg ggatggcact ggcaggacag 960
ctggacagtg gaacctcaga gaaggctcct cctggacata gacatcaaca agagccaggt 1020
gctggaggag gtatatgaga accagggccg tgacaccaga ggggcctggg ggcctgccgc 1080
catcccaaac acagacgtga atggacagcc catggaggcc cgggagaacg tgaagtgccc 1140
ccaaggctgg cactttaaga aggactgggt ggtggagctg aaccacgcag tggacagtaa 1200
gggctgggag tatggagtgg ggatcccacc gtcgggcctg ccccaggtct ggagcccggt 1260
ggagaagacc taccactcgt gccgccgccg gcgctgggcg cgtgtgcgct tcaggaacca 1320
tggggagctg agccacgagc aggagaccct ctccttcctg cagctgggcc tggccaaggg 1380
cgaggaggag ggctgggagt atgacacctt cggctccaag ttccacctca accctcagcc 1440
ccagagccgg ttccgccgcc gctgctggcg ccgcaggctg gcccccaaca aggacaaggg 1500
catcgcgccc atattcctcc tggaggggtc cttggctatg gatctgaaat accacgctgg 1560
gaaggaagag gacagcaaga catggccatg gggtctggac agacagttca gggacccccca 1620 gaggcaggac acccggcccc ccaacttgcc cttcatctac tgcaccttca ataagcccca 1680
ctactaccag ctcttctgct acatctacca ggcccggaac ctggtgtcca atcagatcct 1740
gacattccaa gggcccttca ttcgggtggt cttcctgaac cacagccagt gcacccaaac 1800
cctgaggagc tctgcaggcc ccacatgggc ccagacactc atcttccagc acctccttct 1860
gtacgagaac ccacaggaca ccaaagagag cccaccgctt gtggtgctgg agctgtggca 1920
gcgtgacttc tggggcaagg agagcttgtg gggacggagc gtgtggcccc caatggtctg 1980
gctggatctc caggaccgga tcctgccccc catgaggtgg catccccttg taaaggagtt 2040

-continued

```
ggggaaggaa gagggcgaga tcttggcatc ctgtgagctg atcctccaga ctgagaagct   2100
tggagagaag cagctgccta tcttaagcgt tccctggaag aatggggcat acacactccc   2160
caagagcatc cagcccacga taaagaggat ggccattgag gtgctggcga tgtgggatgg   2220
ggacggtggg caggacaggc gggggtggtc tggagtgcgc tgcagccttc tgctggtcct   2280
ccctgactac tggatccaaa gctcacaccc cgaaaaagac tacctgggag gtggagggag   2340
acaggagaga aacgaagagg ttctggtgta acactggaaa tcattttacc acaaacctct   2400
gcagtgagga gtaggcaaag ggctgtagca tgcatgatca cttgtgggac tcacgctgcc   2460
cctgcgcagt agcaactact ttgcagagaa ggaaatagag gctccaagag ataacacatt   2520
ccacgcacag tgatgcaggg actaactgac agggccattt aggcccagcc ctgtctgact   2580
gcagatgcca ggatgttgct cacctctctt ctgagagtag catgagggtc ctcattcaga   2640
agctgtgtgc cctgccgcaa atgtggcaaa gagcacaaga cggtcaggcc tctgggactg   2700
aaggcttccc caagatcagg caacttggct ggttcccgct ttaggccccg aggaggccca   2760
aagtcagggt gcagctattt cctggcagga tgccaggtca ctgaatggcc atggggtcct   2820
caatgagcta gacggcacag gggccctgag aaatccaggc acttcctgct tcttcaggcc   2880
tcagaggcag tcggcttcag gaactcctac ctgagaactg atgaggccag acaaggcagc   2940
gggtgaggag gggcaatgcc tgcgggctat ggaggtcagt ggaggatgca gccagtggcc   3000
agaggtcacc tccctcatgg gttgggggac agcgtcccag ccccgagggc aagcactgat   3060
ccctcacagg acggggaagc ctgtccttgt gcgccttcag acactggctc ctctgcagcc   3120
ccattccctg gccctgcagg ctcctgctgc accgctattg cccctcagcc cccttctctg   3180
gccaggaccc cattacagag gcgctgcctg ccccttgtcc tgccctcctt ctttgttctg   3240
gtagatcctg gcctggggcc ttcggaacat gaagaaggcg agctcccccc agctcctggt   3300
ggaattcggg gaagagtccc tgaggacaga acccatcagg gactttcaga ccaaccccaa   3360
cttccccgag tctgagtctg tcctagtcct cacagtgctc atgccgacgg aggaggccta   3420
tgcactgccc ctcgtggtga aggtggtaga caactgggcc ttcggccagc agaccgtgac   3480
gggccaggcc aacatcgact tcctccagcc ctacttctgt gacccctggg ctcaagacta   3540
tatgcaccca aagcttccaa cgctgtctga gaagaagcac caagacttcc taggctacct   3600
ctacagaaag ttctggttca agtccagtaa agcagaggat gagtatgagc atgaggtgga   3660
ctggtggagc aagctgttct gggccacaga tgagcacaag tccctgaagt acaagtacaa   3720
agactaccac accctcaagg tgtatgagtg tgagctggag gccgtgccag ccttccaggg   3780
cctgcaggac ttctgccaga ccttcaaact ctaccaggag cagcccaagt tggacagccc   3840
cgtggtaggg gagttcaagg gccttttccg catctacccc tttcctgaga atccagaagc   3900
cccaaagccc ccgctgcagt tcttggtttg gccagagaga gaggacttcc cccagccgtg   3960
cttggtgcgg gtgtacatgg tacgagccat caacctgcag ccccaggact acaatggcct   4020
gtgtgaccct tatgtgatcc tgaaactggg caagacagag cttggcaacc gggacatgta   4080
ccagcccaac actctggatc ccatctttgg catgatgttt gaactcacct gcaacatacc   4140
cctggagaag gacctagaga tccagctcta tgacttcgac ctattttcac ctgatgataa   4200
gataggaacc acagtcatcg accttgaaaa ccgactccta tctggctttg gagctcattg   4260
tgggctctcc aaatcctact gccagtcagg gccctttaga tggcgggatc agatgccccc   4320
aagctacctc ctagaacgct atgccaagcg gaaagggcta cctccgcctc tgttcagtcc   4380
```

-continued

```
tgaggaagat gctgttttct ataatgggaa aaagttcaag ctgcaaagct ttgagcccaa   4440

aacccctact gttcatggtt tgggacccaa gaaggaacgc cttgcactgt acctcctgca   4500

cacccagggg ctggtacctg agcacgtgga gacccgcaca ctgtacagcc acagccagcc   4560

aggcatcgac cagggaaagg tgcaaatgtg ggtggacatc ttccccaaga agctggggcc   4620

tcctggcccc caagtcaaca tcaaccccag aaagcctaaa cggtatgagc tgcgatgcat   4680

catctggaag actgccaatg tggacctggt ggatgacaat ttaagtagag agaagacgag   4740

cgacatctac atcaaagggt ggttatacgg gctggagaag gacatgcaga agacagacat   4800

ccactaccac tcgctgactg gggaggccga cttcaactgg cggttcatct ttaccatgga   4860

ctacctggcg gcggagcgca cgtgtgtcca gagccagaag gattacatat ggagcctgga   4920

tgccacgtcc atgaagttcc cagcccgact tatcatccag gtctgggaca atgacatctt   4980

ctcccccgac gacttcctag ggtcctggaa gctggatttg tctgacatgc cctcccggc    5040

tcggcacgcc aagcagtgct ccatcaggat gatggacgcc gaccccaagt ggccctattt   5100

catccaatac aagcacttct ccctctttaa gaagaagact gtgactggct ggtggccttg   5160

ccaggtcctc gatggtggca aatggcgctt gtcgggcaag gtgaagatga gcctggagat   5220

tctgtcagag aaggaagcct taatcaagcc agccgggcga ggccagtcgg aacccaacca   5280

gtaccccaca cttcatcctc ccctacgcac caacacctct ttcacgtggc tgcggtcacc   5340

agttcaaaac ttctgctata ttttctggaa acgctatcgc ttcaaactca tagcctttat   5400

ggtcatatcg attatagcac ttatgctgtt taacttcatc tattcagctc cgcactattt   5460

ggccatgagc tggatcaaac ctcaacttca gctgtatcct cccattaaaa tattcaatat   5520

catcaattca ctaaacacca gcaacgccag ctcttccatc cttcccaccc aggatccaaa   5580

cctaaagcct acaatagacc atgagtggaa actccaccca ggacccacaa atcacctgag   5640

tgatattttc ccagaacttc cagccccagg agactaatta gtccatgctg cctggctttc   5700

ctcctgctac caacagccct ccccttgggc tggctaccag ttctttgttt ctatcttcta   5760

gaatatatgc aagatgctag gaatattctg gctattgtgt tcagaaatca ctttcaacaa   5820

gacgagcaga gctgtaattt tccactgaaa taaacaagtt ctataaca                5868
```

<210> SEQ ID NO 78
<211> LENGTH: 802
<212> TYPE: PRT
<213> ORGANISM: Homo sapiens

<400> SEQUENCE: 78

```
Met Lys Lys Ala Ser Ser Pro Gln Leu Leu Val Glu Phe Gly Glu Glu
1               5                   10                  15

Ser Leu Arg Thr Glu Pro Ile Arg Asp Phe Gln Thr Asn Pro Asn Phe
            20                  25                  30

Pro Glu Ser Glu Ser Val Leu Val Leu Thr Val Leu Met Pro Thr Glu
        35                  40                  45

Glu Ala Tyr Ala Leu Pro Leu Val Val Lys Val Val Asp Asn Trp Ala
    50                  55                  60

Phe Gly Gln Gln Thr Val Thr Gly Gln Ala Asn Ile Asp Phe Leu Gln
65                  70                  75                  80

Pro Tyr Phe Cys Asp Pro Trp Ala Gln Asp Tyr Met His Pro Lys Leu
                85                  90                  95

Pro Thr Leu Ser Glu Lys Lys His Gln Asp Phe Leu Gly Tyr Leu Tyr
            100                 105                 110
```

-continued

```
Arg Lys Phe Trp Phe Lys Ser Ser Lys Ala Glu Asp Glu Tyr Glu His
        115                 120                 125

Glu Val Asp Trp Trp Ser Lys Leu Phe Trp Ala Thr Asp Glu His Lys
    130                 135                 140

Ser Leu Lys Tyr Lys Tyr Lys Asp Tyr His Thr Leu Lys Val Tyr Glu
145                 150                 155                 160

Cys Glu Leu Glu Ala Val Pro Ala Phe Gln Gly Leu Gln Asp Phe Cys
                165                 170                 175

Gln Thr Phe Lys Leu Tyr Gln Glu Gln Pro Lys Leu Asp Ser Pro Val
            180                 185                 190

Val Gly Glu Phe Lys Gly Leu Phe Arg Ile Tyr Pro Phe Pro Glu Asn
        195                 200                 205

Pro Glu Ala Pro Lys Pro Pro Leu Gln Phe Leu Val Trp Pro Glu Arg
    210                 215                 220

Glu Asp Phe Pro Gln Pro Cys Leu Val Arg Val Tyr Met Val Arg Ala
225                 230                 235                 240

Ile Asn Leu Gln Pro Gln Asp Tyr Asn Gly Leu Cys Asp Pro Tyr Val
                245                 250                 255

Ile Leu Lys Leu Gly Lys Thr Glu Leu Gly Asn Arg Asp Met Tyr Gln
            260                 265                 270

Pro Asn Thr Leu Asp Pro Ile Phe Gly Met Met Phe Glu Leu Thr Cys
        275                 280                 285

Asn Ile Pro Leu Glu Lys Asp Leu Glu Ile Gln Leu Tyr Asp Phe Asp
    290                 295                 300

Leu Phe Ser Pro Asp Asp Lys Ile Gly Thr Thr Val Ile Asp Leu Glu
305                 310                 315                 320

Asn Arg Leu Leu Ser Gly Phe Gly Ala His Cys Gly Leu Ser Lys Ser
                325                 330                 335

Tyr Cys Gln Ser Gly Pro Phe Arg Trp Arg Asp Gln Met Pro Pro Ser
            340                 345                 350

Tyr Leu Leu Glu Arg Tyr Ala Lys Arg Lys Gly Leu Pro Pro Pro Leu
        355                 360                 365

Phe Ser Pro Glu Glu Asp Ala Val Phe Tyr Asn Gly Lys Lys Phe Lys
    370                 375                 380

Leu Gln Ser Phe Glu Pro Lys Thr Pro Thr Val His Gly Leu Gly Pro
385                 390                 395                 400

Lys Lys Glu Arg Leu Ala Leu Tyr Leu Leu His Thr Gln Gly Leu Val
                405                 410                 415

Pro Glu His Val Glu Thr Arg Thr Leu Tyr Ser His Ser Gln Pro Gly
            420                 425                 430

Ile Asp Gln Gly Lys Val Gln Met Trp Val Asp Ile Phe Pro Lys Lys
        435                 440                 445

Leu Gly Pro Pro Gly Pro Gln Val Asn Ile Asn Pro Arg Lys Pro Lys
    450                 455                 460

Arg Tyr Glu Leu Arg Cys Ile Ile Trp Lys Thr Ala Asn Val Asp Leu
465                 470                 475                 480

Val Asp Asp Asn Leu Ser Arg Glu Lys Thr Ser Asp Ile Tyr Ile Lys
                485                 490                 495

Gly Trp Leu Tyr Gly Leu Glu Lys Asp Met Gln Lys Thr Asp Ile His
            500                 505                 510

Tyr His Ser Leu Thr Gly Glu Ala Asp Phe Asn Trp Arg Phe Ile Phe
        515                 520                 525
```

-continued

```
Thr Met Asp Tyr Leu Ala Ala Glu Arg Thr Cys Val Gln Ser Gln Lys
    530                 535                 540

Asp Tyr Ile Trp Ser Leu Asp Ala Thr Ser Met Lys Phe Pro Ala Arg
545                 550                 555                 560

Leu Ile Ile Gln Val Trp Asp Asn Asp Ile Phe Ser Pro Asp Asp Phe
                565                 570                 575

Leu Gly Val Leu Glu Leu Asp Leu Ser Asp Met Pro Leu Pro Ala Arg
            580                 585                 590

His Ala Lys Gln Cys Ser Ile Arg Met Met Asp Ala Asp Pro Lys Trp
        595                 600                 605

Pro Tyr Phe Ile Gln Tyr Lys His Phe Ser Leu Phe Lys Lys Lys Thr
    610                 615                 620

Val Thr Gly Trp Trp Pro Cys Gln Val Leu Asp Gly Gly Lys Trp Arg
625                 630                 635                 640

Leu Ser Gly Lys Val Lys Met Ser Leu Glu Ile Leu Ser Glu Lys Glu
                645                 650                 655

Ala Leu Ile Lys Pro Ala Gly Arg Gly Gln Ser Glu Pro Asn Gln Tyr
            660                 665                 670

Pro Thr Leu His Pro Pro Leu Arg Thr Asn Thr Ser Phe Thr Trp Leu
        675                 680                 685

Arg Ser Pro Val Gln Asn Phe Cys Tyr Ile Phe Trp Lys Arg Tyr Arg
    690                 695                 700

Phe Lys Leu Ile Ala Phe Met Val Ile Ser Ile Ile Ala Leu Met Leu
705                 710                 715                 720

Phe Asn Phe Ile Tyr Ser Ala Pro His Tyr Leu Ala Met Ser Trp Ile
                725                 730                 735

Lys Pro Gln Leu Gln Leu Tyr Pro Pro Ile Lys Ile Phe Asn Ile Ile
            740                 745                 750

Asn Ser Leu Asn Thr Ser Asn Ala Ser Ser Ser Ile Leu Pro Thr Gln
        755                 760                 765

Asp Pro Asn Leu Lys Pro Thr Ile Asp His Glu Trp Lys Leu His Pro
    770                 775                 780

Gly Pro Thr Asn His Leu Ser Asp Ile Phe Pro Glu Leu Pro Ala Pro
785                 790                 795                 800

Gly Asp


<210> SEQ ID NO 79
<211> LENGTH: 21
<212> TYPE: DNA
<213> ORGANISM: Artificial Sequence
<220> FEATURE:
<223> OTHER INFORMATION: Oligonucleotide

<400> SEQUENCE: 79

tgttcagtcc tgaggaagat g                                                21


<210> SEQ ID NO 80
<211> LENGTH: 21
<212> TYPE: DNA
<213> ORGANISM: Artificial Sequence
<220> FEATURE:
<223> OTHER INFORMATION: Oligonucleotide

<400> SEQUENCE: 80

atgatgcatc gcagctcata c                                                21


<210> SEQ ID NO 81
```

-continued

<211> LENGTH: 3170
<212> TYPE: DNA
<213> ORGANISM: Homo sapiens

<400> SEQUENCE: 81
ggctcaccga caacttcatc gccgccgtgc gccgccgaga cttcgccaac atgaccagcc 60
tggtgcacct cactctctcc cggaacacca tcggccaggt ggcagctggc gccttcgccg 120
acctgcgtgc cctccgggcc ctgcacctgg acagcaaccg cctggcggag gtgcgcggcg 180
accagctccg cggcctgggc aacctccgcc acctgatcct tggaaacaac cagatccgcc 240
gggtggagtc ggcggccttt gacgccttcc tgtccaccgt ggaggacctg gatctgtcct 300
acaacaacct ggaggccctg ccgtgggagg cggtgggcca gatggtgaac ctaaacaccc 360
tcacgctgga ccacaacctc atcgaccaca tcgcggaggg gaccttcgtg cagcttcaca 420
agctggtccg tctggacatg acctccaacc gcctgcataa actcccgccc gacgggctct 480
tcctgaggtc gcagggcacc gggcccaagc cgcccaccc gctgaccgtc agcttcggcg 540 gcaacccct gcactgcaac tgcgagctgc tctggctgcg gcggctgacc cgcgaggacg 600
acttagagac ctgcgccacg cccgaacacc tcaccgaccg ctacttctgg tccatccccg 660
aggaggagtt cctgtgtgag cccccgctga tcacacggca ggcgggggc cgggccctgg 720 tggtggaagg ccaggcggtg agcctgcgct gccgagcggt gggtgacccc gagccggtgg 780
tgcactgggt ggcacctgat gggcggctgc tggggaactc cagccggacc cgggtccggg 840
gggacgggac gctggatgtg accatcacca ccttgaggga cagtggcacc ttcacttgta 900
tcgcctccaa tgctgctggg gaagcgacgg cgcccgtgga ggtgtgcgtg gtacctctgc 960
ctctgatggc accccgccg gctgccccgc cgcctctcac cgagcccggc tcctctgaca 1020
tcgccacgcc gggcagacca ggtgccaacg attctgcggc tgagcgtcgg ctcgtggcag 1080
ccgagctcac ctcgaactcc gtgctcatcc gctggccagc ccagaggcct gtgcccggaa 1140
tacgcatgta ccaggttcag tacaacagtt ccgttgatga ctccctcgtc tacaggatga 1200
tcccgtccac cagtcagacc ttcctggtga atgacctggc ggcgggccgt gcctacgact 1260
tgtgcgtgct ggcggtctac gacgacgggg ccacagcgct gccggcaacg cgagtggtgg 1320
gctgtgtaca gttcaccacc gctggggatc cggcgccctg ccgcccgctg agggcccatt 1380
tcttgggcgg caccatgatc atcgccatcg gggcgtcat cgtcgcctcg gtcctcgtct 1440
tcatcgttct gctcatgatc cgctataagg tgtatggcga cggggacagc cgccgcgtca 1500
agggctccag gtcgctcccg cgggtcagcc acgtgtgctc gcagaccaac ggcgcaggca 1560
caggcgcggc acaggccccg gccctgccgg cccaggacca ctacgaggcg ctgcgcgagg 1620
tggagtccca ggctgccccc gccgtcgccg tcgaggccaa ggccatggag gccgagacgg 1680
catccgcgga gccggaggtg gtccttggac gttctctggg cggctcggcc acctcgctgt 1740
gcctgctgcc atccgaggaa acttccgggg aggagtctcg ggccgcggtg ggccctcgaa 1800
ggagccgatc cggcgccctg gagccaccaa cctcggcgcc ccctactcta gctctagttc 1860
ctgggggagc cgcggcccgg ccgaggccgc agcagcgcta ttcgttcgac ggggactacg 1920
gggcactatt ccagagccac agttacccgc gccgcgcccg gcggacaaag cgccaccggt 1980
ccacgccgca cctggacggg gctggagggg gcgcggccgg ggaggatgga gacctggggc 2040
tgggctccgc cagggcgtgc ctggctttca ccagcaccga gtggatgctg gagagtaccg 2100
tgtgagcggc gggcgggcgc cgggacgcct gggtgccgca gaccaaacgc ccagccgcac 2160
ggacgctggg gcgggactgg gagaaagcgc agcgccaaga cattggacca gagtggagac 2220

-continued

```
gcgcccttgt ccccgggagg gggcggggca gcctcgggct gcggctcgag gccacgcccc   2280

cgtgcccagg gcggggttcg gggaccggct gccggcctcc cttcccctat ggactcctcg   2340

acccccctcc taccccctccc ctcgcgcgct cgcggacctc gctggagccg gtgccttaca   2400

cagcgaagcg cggggagggg cagggccccc tgacactgca gcactgagac acgagccccc   2460

tcccccagcc cgtcacccgg ggccggggcg aggggcccat ttcttgtatc tggctggact   2520

agatcctatt ctgtcccgcg gcggcctcca aagcctccca ccccacccca cgcacattcc   2580

tggtccggtc gggtctggct tggggtcccc ctttctctgt ttccctcgtt tgtctctatc   2640

ccgccctctt gtcgtctctc tgtagtgcct gtctttccct atttgcctct cctttctctc   2700

tgtcctgtcg tctcttgtcc ctcggccctc cctggttttg tctagtctcc ctgtctctcc   2760

tgatttcttc tctttactca ttctcccggg caggtcccac tggaaggacc agactctccc   2820

aaataaatcc ccacacgaac aaaatccaaa accaaatccc cctccctacc ggagccggga   2880

ccctccgccg cagcagaatt aaactttttt ctgtgtctga ggccctgctg acctgtgtgt   2940

gtgtctgtat gtgtgtccgc gtgtagtgtg tgtgtgtgtg tgtgtgtgtg tgtgtgtgtg   3000

tgtgtgttgg gggagggtga cctagattgc agcataagga ctctaagtga gactgaagga   3060

agatgggaag atgactaact ggggccggag gagactggca gacaggcttt tatcctctga   3120

gagacttaga ggtggggaat aatcacaaaa ataaaatgat cataatagct              3170
```

<210> SEQ ID NO 82
<211> LENGTH: 684
<212> TYPE: PRT
<213> ORGANISM: Homo sapiens

<400> SEQUENCE: 82

```
Met Thr Ser Leu Val His Leu Thr Leu Ser Arg Asn Thr Ile Gly Gln
1               5                   10                  15

Val Ala Ala Gly Ala Phe Ala Asp Leu Arg Ala Leu Arg Ala Leu His
            20                  25                  30

Leu Asp Ser Asn Arg Leu Ala Glu Val Arg Gly Asp Gln Leu Arg Gly
        35                  40                  45

Leu Gly Asn Leu Arg His Leu Ile Leu Gly Asn Asn Gln Ile Arg Arg
    50                  55                  60

Val Glu Ser Ala Ala Phe Asp Ala Phe Leu Ser Thr Val Glu Asp Leu
65                  70                  75                  80

Asp Leu Ser Tyr Asn Asn Leu Glu Ala Leu Pro Trp Glu Ala Val Gly
                85                  90                  95

Gln Met Val Asn Leu Asn Thr Leu Thr Leu Asp His Asn Leu Ile Asp
            100                 105                 110

His Ile Ala Glu Gly Thr Phe Val Gln Leu His Lys Leu Val Arg Leu
        115                 120                 125

Asp Met Thr Ser Asn Arg Leu His Lys Leu Pro Pro Asp Gly Leu Phe
    130                 135                 140

Leu Arg Ser Gln Gly Thr Gly Pro Lys Pro Pro Thr Pro Leu Thr Val
145                 150                 155                 160

Ser Phe Gly Gly Asn Pro Leu His Cys Asn Cys Glu Leu Leu Trp Leu
                165                 170                 175

Arg Arg Leu Thr Arg Glu Asp Asp Leu Glu Thr Cys Ala Thr Pro Glu
            180                 185                 190

His Leu Thr Asp Arg Tyr Phe Trp Ser Ile Pro Glu Glu Glu Phe Leu
        195                 200                 205
```

-continued

```
Cys Glu Pro Pro Leu Ile Thr Arg Gln Ala Gly Gly Arg Ala Leu Val
    210                 215                 220

Val Glu Gly Gln Ala Val Ser Leu Arg Cys Arg Ala Val Gly Asp Pro
225                 230                 235                 240

Glu Pro Val Val His Trp Val Ala Pro Asp Gly Arg Leu Leu Gly Asn
                245                 250                 255

Ser Ser Arg Thr Arg Val Arg Gly Asp Gly Thr Leu Asp Val Thr Ile
            260                 265                 270

Thr Thr Leu Arg Asp Ser Gly Thr Phe Thr Cys Ile Ala Ser Asn Ala
        275                 280                 285

Ala Gly Glu Ala Thr Ala Pro Val Glu Val Cys Val Val Pro Leu Pro
    290                 295                 300

Leu Met Ala Pro Pro Pro Ala Ala Pro Pro Pro Leu Thr Glu Pro Gly
305                 310                 315                 320

Ser Ser Asp Ile Ala Thr Pro Gly Arg Pro Gly Ala Asn Asp Ser Ala
                325                 330                 335

Ala Glu Arg Arg Leu Val Ala Ala Glu Leu Thr Ser Asn Ser Val Leu
            340                 345                 350

Ile Arg Trp Pro Ala Gln Arg Pro Val Pro Gly Ile Arg Met Tyr Gln
        355                 360                 365

Val Gln Tyr Asn Ser Ser Val Asp Asp Ser Leu Val Tyr Arg Met Ile
    370                 375                 380

Pro Ser Thr Ser Gln Thr Phe Leu Val Asn Asp Leu Ala Ala Gly Arg
385                 390                 395                 400

Ala Tyr Asp Leu Cys Val Leu Ala Val Tyr Asp Asp Gly Ala Thr Ala
                405                 410                 415

Leu Pro Ala Thr Arg Val Val Gly Cys Val Gln Phe Thr Thr Ala Gly
            420                 425                 430

Asp Pro Ala Pro Cys Arg Pro Leu Arg Ala His Phe Leu Gly Gly Thr
        435                 440                 445

Met Ile Ile Ala Ile Gly Gly Val Ile Val Ala Ser Val Leu Val Phe
    450                 455                 460

Ile Val Leu Leu Met Ile Arg Tyr Lys Val Tyr Gly Asp Gly Asp Ser
465                 470                 475                 480

Arg Arg Val Lys Gly Ser Arg Ser Leu Pro Arg Val Ser His Val Cys
                485                 490                 495

Ser Gln Thr Asn Gly Ala Gly Thr Gly Ala Ala Gln Ala Pro Ala Leu
            500                 505                 510

Pro Ala Gln Asp His Tyr Glu Ala Leu Arg Glu Val Glu Ser Gln Ala
        515                 520                 525

Ala Pro Ala Val Ala Val Glu Ala Lys Ala Met Glu Ala Glu Thr Ala
    530                 535                 540

Ser Ala Glu Pro Glu Val Val Leu Gly Arg Ser Leu Gly Gly Ser Ala
545                 550                 555                 560

Thr Ser Leu Cys Leu Leu Pro Ser Glu Glu Thr Ser Gly Glu Glu Ser
                565                 570                 575

Arg Ala Ala Val Gly Pro Arg Arg Ser Arg Ser Gly Ala Leu Glu Pro
            580                 585                 590

Pro Thr Ser Ala Pro Pro Thr Leu Ala Leu Val Pro Gly Gly Ala Ala
        595                 600                 605

Ala Arg Pro Arg Pro Gln Gln Arg Tyr Ser Phe Asp Gly Asp Tyr Gly
    610                 615                 620
```

-continued

```
Ala Leu Phe Gln Ser His Ser Tyr Pro Arg Arg Ala Arg Arg Thr Lys
625                 630                 635                 640

Arg His Arg Ser Thr Pro His Leu Asp Gly Ala Gly Gly Gly Ala Ala
                645                 650                 655

Gly Glu Asp Gly Asp Leu Gly Leu Gly Ser Ala Arg Ala Cys Leu Ala
            660                 665                 670

Phe Thr Ser Thr Glu Trp Met Leu Glu Ser Thr Val
        675                 680


<210> SEQ ID NO 83
<211> LENGTH: 17
<212> TYPE: DNA
<213> ORGANISM: Artificial Sequence
<220> FEATURE:
<223> OTHER INFORMATION: Oligonucleotide

<400> SEQUENCE: 83

cgaactccgt gctcatc                                                    17


<210> SEQ ID NO 84
<211> LENGTH: 17
<212> TYPE: DNA
<213> ORGANISM: Artificial Sequence
<220> FEATURE:
<223> OTHER INFORMATION: Oligonucleotide

<400> SEQUENCE: 84

cgcacaagtc gtaggca                                                    17


<210> SEQ ID NO 85
<211> LENGTH: 2206
<212> TYPE: DNA
<213> ORGANISM: Homo sapiens

<400> SEQUENCE: 85

cgacaacgtc acccgcagac cggccaatcc cgccaggccg cggcccagtg gcgccggcgc     60

acaccgaaga cgacaccagc catccggcca atcccgcccc gccgcgcccc gcaggcccgc    120

ccactcctcg cttctccact tcccttctcg aagtgtccgg tcgcttctcg caggcggcgc    180

gcttgctggg tcacagtgag gcggctccgc gcaggcgcag ccgggcgggc gaggagcggg    240

gaagctgact cagggctgcg gccggggtcc tgcggggtag gagcgcgagg ccggcctgag    300

ggaggaggcc tagcgaccca tccggcgcct cccgccccgg gcacccgccc gcggccgcgc    360

atcctgcggg ccccaggagg cctccatctc aaaacaacgt gtttttagga tctcatccac    420

tatcacagtt tcagctttcc ccaaactgga atgtgtcttt gcagacgccc atccttatta    480

aagggcaaag acttctcata cacctaggat ggatcttata ttcttggcgg gactgcagag    540

aaggtgccgt gtcctgagtc ctcatgtcag ggcacaggct tccagccagt tctacctggg    600

ttatgtttat ctcaattccc tggtggtatt ggtgtctgct gggttttgcc agaatgaaga    660

caccgtgttt tcatttgtca gttgattcgt attttccagg aagacattct gagattacag    720

cattgtctta gtcaaggtgc tgcagaagga cagaactaat aggatatatg tacatatgaa    780

agaaagttta tgaagaactg gctcacacca tcacaaggca aagtcccatg acaggccatc    840

tgcaagctga ggagcgagga agccagcagt ggctcagccg gagtccaaca gcctcaaacg    900

gaatccaaca gttcaggctt cagtctgtgg ccaaatgccc agagaccccg gaaagctact    960

ggtgttagtc ccagagccgg aaggccaaag aacctggagt gtgatgtcca agggcaggag   1020

gaatggacag aagcatccag catggggtaa agacgaaagc cagaagactc agcaagctag   1080
```

-continued cttacctact ttcttctgcc tgccttgttc tagccgcgct ggcagccggt tggagggtgc 1140 ccaccccac tgagggtgga tcttcctctc ctagtccact gactcaaatt tcagtctctc 1200
tgggagcacc atcacaccag aaacaatacc agccatctag ccacccttca gttcaccatc 1260
acaaccattg tcttattcat gaaacttctg cagacccacc ttaacctcca tcggtgactt 1320
ctacctgaag ccctctgatt gttgcccagt ggtgcttttt aaaataattt ccatagtttc 1380
ttctacacct ttagttggca ttctactgta aaggagagat tttattttct tactcattta 1440
tttgttagtt tatagtcacc accatatgga tgcagagttc tgtctcattc actgggaagt 1500
attctattgc agtcatgatt tattttgatg ttcacatccc agagttggtg agtgagcgcc 1560
ccttcacgct ggctcccgag tgctgacgtg tccccgtcct tctctgcact tttccttacc 1620
tcctggcctc agatattcca gggtcatttg ttctctccct gctccaaccc tgcagtcagc 1680
catctcccta gggacgttgg ttcctttatg gaaggtggca tttagaagcc aggatttggg 1740
ctgagcactg tggctcatgc ttgtaatccc agcacttggg gaggccgaag tgggcggatc 1800
gctggaggcc aagagtctga gaccagcctg gctaacatgg tgaaaccctt ccccgtctct 1860
actacaaata aaaaattagc tgggtgtgtt ggcacgtgcc tgtaatccca gttactcagg 1920
aggctgaagc accagaatct cttgaaccca ggaggccgag gttgcagtga gccaagattg 1980
caccactgca ctacagcttg ggtgacagcg cgagacaccg tctcaaaaag gataataatt 2040
taaaaaacag caggatttgg gtgagcagtg cgctcattgc ttctgggctc tctcggtgga 2100
cataggctag gaatgtaaga tgtatgtgcc tgtgtatata cacacgtctg tagctatgtc 2160
tatgttgcat acatgtgttt ttccaaaaac caaatccata accatg 2206

<210> SEQ ID NO 86
<211> LENGTH: 93
<212> TYPE: PRT
<213> ORGANISM: Homo sapiens

<400> SEQUENCE: 86

Met Asp Arg Ser Ile Gln His Gly Val Lys Thr Lys Ala Arg Arg Leu
1 5 10 15

Ser Lys Leu Ala Tyr Leu Leu Ser Ser Ala Cys Leu Val Leu Ala Ala
20 25 30

Leu Ala Ala Gly Trp Arg Val Pro Thr Pro Thr Glu Gly Gly Ser Ser
35 40 45

Ser Pro Ser Pro Leu Thr Gln Ile Ser Val Ser Leu Gly Ala Pro Ser
50 55 60

His Gln Lys Gln Tyr Gln Pro Ser Ser His Pro Ser Val His His His
65 70 75 80

Asn His Cys Leu Ile His Glu Thr Ser Ala Asp Pro Pro
85 90

<210> SEQ ID NO 87
<211> LENGTH: 21
<212> TYPE: DNA
<213> ORGANISM: Artificial Sequence
<220> FEATURE:
<223> OTHER INFORMATION: Oligonucleotide

<400> SEQUENCE: 87
aaactacgtg tggccaggat c 21

<210> SEQ ID NO 88

-continued

<211> LENGTH: 21
<212> TYPE: DNA
<213> ORGANISM: Artificial Sequence
<220> FEATURE:
<223> OTHER INFORMATION: Oligonucleotide

<400> SEQUENCE: 88
cgacatgagg actcaggaca c 21

<210> SEQ ID NO 89
<211> LENGTH: 455
<212> TYPE: DNA
<213> ORGANISM: Homo sapiens

<400> SEQUENCE: 89
gtgaagacag ggagctcaag tgacctcctc cagggtatat agctgtggtg tgggaagcat 60
catgagaaca cggtctttga tggggataat tactctgaat ctaccaggct gattaagcca 120
cagcagatca gcaggtgaga attcaactgt ccagatagaa aggtggacat ggaaaaattg 180
ggctttgcaa atggtcaccc aattcttgcc ttcctggtct ccagatcacc cttcctatac 240
cgccactctg gagaaagaag tacagaacgc taacaaggat ggcttggagt tgcagtggtc 300
acctcagatc ttaaggtcac tttggagatg gaacccctgt gactaggaat ggcagaagag 360
aaaggtagaa agagattgag tcctggggat gtggcagagc accatcctag ccccgtactg 420
cgtacttctg gacttccttt aaattgagag aaaca 455

<210> SEQ ID NO 90
<211> LENGTH: 61
<212> TYPE: PRT
<213> ORGANISM: Homo sapiens

<400> SEQUENCE: 90

Cys Phe Ser Gln Phe Lys Gly Ser Pro Glu Val Arg Ser Thr Gly Leu
1               5                   10                  15

Gly Trp Cys Ser Ala Thr Ser Pro Gly Leu Asn Leu Phe Leu Pro Phe
            20                  25                  30

Ser Ser Ala Ile Pro Ser His Arg Gly Ser Ile Ser Lys Val Thr Leu
        35                  40                  45

Arg Ser Glu Val Thr Thr Ala Thr Pro Ser His Pro Cys
    50                  55                  60

<210> SEQ ID NO 91
<211> LENGTH: 20
<212> TYPE: DNA
<213> ORGANISM: Artificial Sequence
<220> FEATURE:
<223> OTHER INFORMATION: Oligonucleotide

<400> SEQUENCE: 91
gaacacggtc tttgatgggg 20

<210> SEQ ID NO 92
<211> LENGTH: 21
<212> TYPE: DNA
<213> ORGANISM: Artificial Sequence
<220> FEATURE:
<223> OTHER INFORMATION: Oligonucleotide

<400> SEQUENCE: 92
gccatccttg ttagcgttct g 21

-continued

<210> SEQ ID NO 93
<211> LENGTH: 1230
<212> TYPE: DNA
<213> ORGANISM: Homo sapiens

<400> SEQUENCE: 93
aggggcagag gggtcttccc aaccctaccc ctattttcgg tgatttttgt gtgagaatat 60
taatattaaa aataaacgga gaaaaaaaat cctgtttcgc taacggctgg tggtagcagg 120
ttgagtaccg ggagggctgc aagaccgtga ttgatgggga ggactgcgca gaccctggcg 180
agggtgagcc cctccccgga ggcgcctgtg gaatgtccag ggctctggtc cgctcctcgg 240
gatggggggt gcctaatcct agagccgcat tccaggataa ggggggtggg gagaggctgg 300
gccgggggag gggcaggaaa gagggctata agggcagcgg cccaggcggg cgggatccag 360
gcgggccatg gcggatgtcc ccggggcaca gcgagcggtt cctggtgacg gcccagagcc 420
ccgggacccc ctggactgtt gggcctgcgc tgttcttgta acagcccaga atctgctggt 480
ggctgccttc aatcttctcc tgctggtgct ggtgctaggg accatcttgc tacccgctgt 540
caccatgctg ggcttcggct tcctctgcca ctctcagttc ctgcgctccc aggcaccccc 600
ttgcaccgcg cacctgcggg accccggttt cacggcccta ctggtcaccg gattcctgct 660
cctcgtgccg ctgctcgtgc ttgctctggc cagctaccgc cgcctctgcc tgcgcctccg 720
cctagccgat tgcctcgtgc cctacagccg agccctttat cggcgtcggc gcgccccgca 780
gccgcggcaa atccgggcct caccagggtc ccaggccgtt cccacatcag gaaaggtctg 840
ggtctaatga ccctcgagtc aagaacaacc ctgacggctg ccctccctct tattcggccc 900
aaggacttga agcccggcat cttccgacct gccctgcccc cacccctgcc tgagcggagt 960
cctagcatcc ccttgggagc agcagcgtca gtggacccag tgctgagaaa agcccccaca 1020
tcccggaaaa cccactttcc tttcacgacc cacatctcaa tcctgaacat ctaggctgga 1080
acctgcacac ctccccctca gctccgtcgt gaatgggaca acaatctcgt gccctcgttt 1140
tatggtgcag cttctctagt atttctgggg ctgggggcg gggctggagg ggaaggagtg 1200
tccacgcatc aataaagatt taacgaactg 1230

<210> SEQ ID NO 94
<211> LENGTH: 159
<212> TYPE: PRT
<213> ORGANISM: Homo sapiens

<400> SEQUENCE: 94

Met Ala Asp Val Pro Gly Ala Gln Arg Ala Val Pro Gly Asp Gly Pro
1 5 10 15

Glu Pro Arg Asp Pro Leu Asp Cys Trp Ala Cys Ala Val Leu Val Thr
20 25 30

Ala Gln Asn Leu Leu Val Ala Ala Phe Asn Leu Leu Leu Leu Val Leu
35 40 45

Val Leu Gly Thr Ile Leu Leu Pro Ala Val Thr Met Leu Gly Phe Gly
50 55 60

Phe Leu Cys His Ser Gln Phe Leu Arg Ser Gln Ala Pro Pro Cys Thr
65 70 75 80

Ala His Leu Arg Asp Pro Gly Phe Thr Ala Leu Leu Val Thr Gly Phe
85 90 95

Leu Leu Leu Val Pro Leu Leu Val Leu Ala Leu Ala Ser Tyr Arg Arg
100 105 110

-continued

```
Leu Cys Leu Arg Leu Arg Leu Ala Asp Cys Leu Val Pro Tyr Ser Arg
        115                 120                 125

Ala Leu Tyr Arg Arg Arg Arg Ala Pro Gln Pro Arg Gln Ile Arg Ala
    130                 135                 140

Ser Pro Gly Ser Gln Ala Val Pro Thr Ser Gly Lys Val Trp Val
145                 150                 155
```

<210> SEQ ID NO 95
<211> LENGTH: 21
<212> TYPE: DNA
<213> ORGANISM: Artificial Sequence
<220> FEATURE:
<223> OTHER INFORMATION: Oligonucleotide

<400> SEQUENCE: 95

```
ttcctctgcc actctcagtt c                                              21
```

<210> SEQ ID NO 96
<211> LENGTH: 21
<212> TYPE: DNA
<213> ORGANISM: Artificial Sequence
<220> FEATURE:
<223> OTHER INFORMATION: Oligonucleotide

<400> SEQUENCE: 96

```
cgataaaggg ctcggctgta g                                              21
```

<210> SEQ ID NO 97
<211> LENGTH: 1020
<212> TYPE: DNA
<213> ORGANISM: Homo sapiens

<400> SEQUENCE: 97

```
atggaggagg aggaggagga tgatgactat gagaactcaa cacctcccta caaggacctt     60

cctcccaagc cagggaccat ggaggaggag gaggaggatg atgactatga gaactcaaca    120

cctccctaca aggaccttcc tcccaagcca gggaccatgg aggaggagga ggaggatgat    180

gactatgaga actcaacacc tccctacaag gaccttcctc ccaagccagg ttcaagtgct    240

ccaccaagac ctccaagggc agcaaaggaa acagagaaac ccccacttcc ttgcaagccc    300

cggaacatga caggcctgga cctcgccgct gtcacctgtc cacctcctca actggctgtg    360

aatcttgagc cttctccatt gcagccatcc ctggccgcaa ctccagtccc ctggctcaat    420

cagaggtctg gaggtcctgg ctgctgccag aagaggtgga tggtgtacct gtgtctgctg    480

gtggtgactt ccctgttcct gggctgcctt ggtctcactg tgaccctgat taagttgact    540

ggcatggcag ggctagctgg cctgaagcat gacattgccc gtgtaagagc tgacaccaac    600

cagtccctgg tggaactttg ggcttatta gactgccgcc gaattacctg tcctgaaggc    660

tggctgccct ttgagggcaa gtgttactac ttctccccaa gcaccaagtc atgggatgag    720

gcccggatgt tctgccagga gaattactct cacttggtca tcatcaatag ctttgctgag    780

cacaattttg tggccaaggc ccatggctct ccacgggtgt actggctggg gctgaatgac    840

agggcccagg aaggggactg gaggtggctg gatgggtctc ctgtgacatt aaggcaacca    900

gaggaaccca ataacatcca cgatgaggac tgtgctacca tgaacaaagg tggcacctgg    960

aatgatctct cttgctacaa aactacgtat tggatttgtg agcggaaatg ttcctgttga   1020
```

<210> SEQ ID NO 98
<211> LENGTH: 339
<212> TYPE: PRT

-continued

<213> ORGANISM: Homo sapiens

<400> SEQUENCE: 98

Met Glu Glu Glu Glu Glu Asp Asp Asp Tyr Glu Asn Ser Thr Pro Pro
1 5 10 15

Tyr Lys Asp Leu Pro Pro Lys Pro Gly Thr Met Glu Glu Glu Glu Glu
20 25 30

Asp Asp Asp Tyr Glu Asn Ser Thr Pro Pro Tyr Lys Asp Leu Pro Pro
35 40 45

Lys Pro Gly Thr Met Glu Glu Glu Glu Glu Asp Asp Asp Tyr Glu Asn
50 55 60

Ser Thr Pro Pro Tyr Lys Asp Leu Pro Pro Lys Pro Gly Ser Ser Ala
65 70 75 80

Pro Pro Arg Pro Pro Arg Ala Ala Lys Glu Thr Glu Lys Pro Pro Leu
85 90 95

Pro Cys Lys Pro Arg Asn Met Thr Gly Leu Asp Leu Ala Ala Val Thr
100 105 110

Cys Pro Pro Pro Gln Leu Ala Val Asn Leu Glu Pro Ser Pro Leu Gln
115 120 125

Pro Ser Leu Ala Ala Thr Pro Val Pro Trp Leu Asn Gln Arg Ser Gly
130 135 140

Gly Pro Gly Cys Cys Gln Lys Arg Trp Met Val Tyr Leu Cys Leu Leu
145 150 155 160

Val Val Thr Ser Leu Phe Leu Gly Cys Leu Gly Leu Thr Val Thr Leu
165 170 175

Ile Lys Leu Thr Gly Met Ala Gly Leu Ala Gly Leu Lys His Asp Ile
180 185 190

Ala Arg Val Arg Ala Asp Thr Asn Gln Ser Leu Val Glu Leu Trp Gly
195 200 205

Leu Leu Asp Cys Arg Arg Ile Thr Cys Pro Glu Gly Trp Leu Pro Phe
210 215 220

Glu Gly Lys Cys Tyr Tyr Phe Ser Pro Ser Thr Lys Ser Trp Asp Glu
225 230 235 240

Ala Arg Met Phe Cys Gln Glu Asn Tyr Ser His Leu Val Ile Ile Asn
245 250 255

Ser Phe Ala Glu His Asn Phe Val Ala Lys Ala His Gly Ser Pro Arg
260 265 270

Val Tyr Trp Leu Gly Leu Asn Asp Arg Ala Gln Glu Gly Asp Trp Arg
275 280 285

Trp Leu Asp Gly Ser Pro Val Thr Leu Arg Gln Pro Glu Glu Pro Asn
290 295 300

Asn Ile His Asp Glu Asp Cys Ala Thr Met Asn Lys Gly Gly Thr Trp
305 310 315 320

Asn Asp Leu Ser Cys Tyr Lys Thr Thr Tyr Trp Ile Cys Glu Arg Lys
325 330 335

Cys Ser Cys

<210> SEQ ID NO 99
<211> LENGTH: 21
<212> TYPE: DNA
<213> ORGANISM: Artificial Sequence
<220> FEATURE:
<223> OTHER INFORMATION: Oligonucleotide

<400> SEQUENCE: 99

-continued

```
atagctttgc tgagcacctt c                                              21


<210> SEQ ID NO 100
<211> LENGTH: 21
<212> TYPE: DNA
<213> ORGANISM: Artificial Sequence
<220> FEATURE:
<223> OTHER INFORMATION: Oligonucleotide

<400> SEQUENCE: 100

aagagacact cagatatgga c                                              21


<210> SEQ ID NO 101
<211> LENGTH: 1680
<212> TYPE: DNA
<213> ORGANISM: Homo sapiens

<400> SEQUENCE: 101

atggccaatg tcaccttggt gacaggattt cttcttatgg ggttttctaa tatccagaag     60

ctgcggattt tatatggtgt gctcttccta ctgatttacc tggcagccct aatgagtaac    120

cttctcatca ttactctcat taccctggac gtaaagctcc aaacacccat gtacttcttc    180

ctgaagaact tatccttttt ggatgtcttc ctggtgtctg ttccaatccc aaaattcatt    240

gtcaacaacc taacccacaa caattccatt tccattctag gatgtgcctt ccagctactt    300

ttaatgactt ccttctcagc aggagagata tttatcctca ctgccatgtc ctatgaccgc    360

tatgtagcca tctgctgtcc cctgaactac gaggtaatca tgaatactgg agtctgtgtg    420

ttaatggcaa gtgtttcctg ggccattgga gggctctttg gtactgcgta cacagctggc    480

acattttcca tgcctttctg tggctccagt gtgattccac agtttttctg tgatgttcct    540

tcattactaa ggatttcctg ttctgaaaca ctaatggtaa tttatgcagg tattggagtt    600

ggtgcatgtt taagcatttc ttgtttcatc tgtattgtga tctcttacat ttatatcttc    660

tccactgtac tgaagatccc taccactaaa ggactgtgtg attgggttaa agggctcagt    720

gcggggactc tgtttttctgg tttcagtacc acaatggaca caggcaacaa aactctgccc    780

caggactttc tcttactggg ctttcctggt tctcaaactc ttcagctctc tctctttatg    840

ctttttctgg tgatgtacat cctcacagtt agtggtaatg tggctatctt gatgttggtg    900

agcacctccc atcagttgca tacccccatg tacttctttc tgagcaacct ctccttcctg    960

gagatttggt ataccacagc agcagtgccc aaagcactgg ccatcctact ggggagaagt   1020

cagaccatat catttacaag ctgtcttttg cagatgtact ttgttttctc attaggctgc   1080

acagagtact tcctcctggc agccatggct tatgaccgct gtcttgccat ctgctatcct   1140

ttacactacg gagccatcat gagtagcctg ctctcagcgc agctggccct gggctcctgg   1200

gtgtgtggtt tcgtggccat tgcagtgccc acagccctca tcagtggcct gtccttctgt   1260

ggcccccgtg ccatcaacca cttcttctgt gacattgcac cctggattgc cctggcctgc   1320

accaacacac aggcagtaga gcttgtggcc tttgtgattg ctgttgtggt tatcctgagt   1380

tcatgcctca tcacctttgt ctcctatgtg tacatcatca gcaccatcct caggatcccc   1440

tctgccagtg gccggagcaa agccttctcc acgtgctcct cgcatctcac cgtggtgctc   1500

atttggtatg ggtccacagt tttccttcac gtccgcacct ctatcaaaga tgccttggat   1560

ctgatcaaag ctgtccacgt cctgaacact gtggtgactc cagttttaaa ccccttcatc   1620

tatacgcttc gtaataagga agtaagagag actctgctga agaaatggaa gggaaaataa   1680
```

-continued

<210> SEQ ID NO 102
<211> LENGTH: 559
<212> TYPE: PRT
<213> ORGANISM: Homo sapiens

<400> SEQUENCE: 102

```
Met Ala Asn Val Thr Leu Val Thr Gly Phe Leu Leu Met Gly Phe Ser
1               5                   10                  15

Asn Ile Gln Lys Leu Arg Ile Leu Tyr Gly Val Leu Phe Leu Leu Ile
            20                  25                  30

Tyr Leu Ala Ala Leu Met Ser Asn Leu Leu Ile Ile Thr Leu Ile Thr
        35                  40                  45

Leu Asp Val Lys Leu Gln Thr Pro Met Tyr Phe Phe Leu Lys Asn Leu
    50                  55                  60

Ser Phe Leu Asp Val Phe Leu Val Ser Val Pro Ile Pro Lys Phe Ile
65                  70                  75                  80

Val Asn Asn Leu Thr His Asn Asn Ser Ile Ser Ile Leu Gly Cys Ala
                85                  90                  95

Phe Gln Leu Leu Leu Met Thr Ser Phe Ser Ala Gly Glu Ile Phe Ile
            100                 105                 110

Leu Thr Ala Met Ser Tyr Asp Arg Tyr Val Ala Ile Cys Cys Pro Leu
        115                 120                 125

Asn Tyr Glu Val Ile Met Asn Thr Gly Val Cys Val Leu Met Ala Ser
    130                 135                 140

Val Ser Trp Ala Ile Gly Gly Leu Phe Gly Thr Ala Tyr Thr Ala Gly
145                 150                 155                 160

Thr Phe Ser Met Pro Phe Cys Gly Ser Ser Val Ile Pro Gln Phe Phe
                165                 170                 175

Cys Asp Val Pro Ser Leu Leu Arg Ile Ser Cys Ser Glu Thr Leu Met
            180                 185                 190

Val Ile Tyr Ala Gly Ile Gly Val Gly Ala Cys Leu Ser Ile Ser Cys
        195                 200                 205

Phe Ile Cys Ile Val Ile Ser Tyr Ile Tyr Ile Phe Ser Thr Val Leu
    210                 215                 220

Lys Ile Pro Thr Thr Lys Gly Leu Cys Asp Trp Val Lys Gly Leu Ser
225                 230                 235                 240

Ala Gly Thr Leu Phe Ser Gly Phe Ser Thr Thr Met Asp Thr Gly Asn
                245                 250                 255

Lys Thr Leu Pro Gln Asp Phe Leu Leu Leu Gly Phe Pro Gly Ser Gln
            260                 265                 270

Thr Leu Gln Leu Ser Leu Phe Met Leu Phe Leu Val Met Tyr Ile Leu
        275                 280                 285

Thr Val Ser Gly Asn Val Ala Ile Leu Met Leu Val Ser Thr Ser His
    290                 295                 300

Gln Leu His Thr Pro Met Tyr Phe Phe Leu Ser Asn Leu Ser Phe Leu
305                 310                 315                 320

Glu Ile Trp Tyr Thr Thr Ala Ala Val Pro Lys Ala Leu Ala Ile Leu
                325                 330                 335

Leu Gly Arg Ser Gln Thr Ile Ser Phe Thr Ser Cys Leu Leu Gln Met
            340                 345                 350

Tyr Phe Val Phe Ser Leu Gly Cys Thr Glu Tyr Phe Leu Leu Ala Ala
        355                 360                 365

Met Ala Tyr Asp Arg Cys Leu Ala Ile Cys Tyr Pro Leu His Tyr Gly
    370                 375                 380
```

-continued

```
Ala Ile Met Ser Ser Leu Leu Ser Ala Gln Leu Ala Leu Gly Ser Trp
385                 390                 395                 400

Val Cys Gly Phe Val Ala Ile Ala Val Pro Thr Ala Leu Ile Ser Gly
                405                 410                 415

Leu Ser Phe Cys Gly Pro Arg Ala Ile Asn His Phe Phe Cys Asp Ile
            420                 425                 430

Ala Pro Trp Ile Ala Leu Ala Cys Thr Asn Thr Gln Ala Val Glu Leu
        435                 440                 445

Val Ala Phe Val Ile Ala Val Val Val Ile Leu Ser Ser Cys Leu Ile
    450                 455                 460

Thr Phe Val Ser Tyr Val Tyr Ile Ile Ser Thr Ile Leu Arg Ile Pro
465                 470                 475                 480

Ser Ala Ser Gly Arg Ser Lys Ala Phe Ser Thr Cys Ser Ser His Leu
                485                 490                 495

Thr Val Val Leu Ile Trp Tyr Gly Ser Thr Val Phe Leu His Val Arg
            500                 505                 510

Thr Ser Ile Lys Asp Ala Leu Asp Leu Ile Lys Ala Val His Val Leu
        515                 520                 525

Asn Thr Val Val Thr Pro Val Leu Asn Pro Phe Ile Tyr Thr Leu Arg
    530                 535                 540

Asn Lys Glu Val Arg Glu Thr Leu Leu Lys Lys Trp Lys Gly Lys
545                 550                 555
```

<210> SEQ ID NO 103
<211> LENGTH: 25
<212> TYPE: DNA
<213> ORGANISM: Artificial Sequence
<220> FEATURE:
<223> OTHER INFORMATION: Oligonucleotide

<400> SEQUENCE: 103

```
catttcttgt ttcatctgta ttgtg                                             25
```

<210> SEQ ID NO 104
<211> LENGTH: 20
<212> TYPE: DNA
<213> ORGANISM: Artificial Sequence
<220> FEATURE:
<223> OTHER INFORMATION: Oligonucleotide

<400> SEQUENCE: 104

```
tgttgcctgt gtccattgtg                                                   20
```

<210> SEQ ID NO 105
<211> LENGTH: 499
<212> TYPE: DNA
<213> ORGANISM: Homo sapiens

<400> SEQUENCE: 105

```
acacccacat ggtcggcgtg caggatattt cgctggaccc tagaaaagcc accacgacct      60

gtgggccatg atgctacccc aatggctgct gctgctgttc cttctcttct tctttctctt     120

cctcctcacc aggggctcac tttctccaac aaaatacaac cttttggagc tcaaggagtc     180

ttgcatccgg aaccaggact gcgagactgg ctgctgccaa cgtgctccag acaattgcga     240

gtcgcactgc gcggagaagg ggtccgaggg cagtctgtgt caaacgcagg tgttctttgg     300

ccaatataga gcgtgtccct gcctgcggaa cctgacttgt atatattcaa agaatgagaa     360

atggcttagc atcgcctatg gccgttgtca gaaaattgga aggcagaagt tggctaagaa     420
```

-continued

```
aatgttcttc tagtgctccc tccttcttgc tgcctcctcc tcctccacct gctctcctcc    480

ctacccagag ctctgtgtt                                                 499


<210> SEQ ID NO 106
<211> LENGTH: 121
<212> TYPE: PRT
<213> ORGANISM: Homo sapiens

<400> SEQUENCE: 106

Met Met Leu Pro Gln Trp Leu Leu Leu Leu Phe Leu Leu Phe Phe Phe
1               5                   10                  15

Leu Phe Leu Leu Thr Arg Gly Ser Leu Ser Pro Thr Lys Tyr Asn Leu
            20                  25                  30

Leu Glu Leu Lys Glu Ser Cys Ile Arg Asn Gln Asp Cys Glu Thr Gly
        35                  40                  45

Cys Cys Gln Arg Ala Pro Asp Asn Cys Glu Ser His Cys Ala Glu Lys
    50                  55                  60

Gly Ser Glu Gly Ser Leu Cys Gln Thr Gln Val Phe Phe Gly Gln Tyr
65                  70                  75                  80

Arg Ala Cys Pro Cys Leu Arg Asn Leu Thr Cys Ile Tyr Ser Lys Asn
                85                  90                  95

Glu Lys Trp Leu Ser Ile Ala Tyr Gly Arg Cys Gln Lys Ile Gly Arg
            100                 105                 110

Gln Lys Leu Ala Lys Lys Met Phe Phe
        115                 120


<210> SEQ ID NO 107
<211> LENGTH: 17
<212> TYPE: DNA
<213> ORGANISM: Artificial Sequence
<220> FEATURE:
<223> OTHER INFORMATION: Oligonucleotide

<400> SEQUENCE: 107

tgtgtcaaac gcaggtg                                                    17


<210> SEQ ID NO 108
<211> LENGTH: 20
<212> TYPE: DNA
<213> ORGANISM: Artificial Sequence
<220> FEATURE:
<223> OTHER INFORMATION: Oligonucleotide

<400> SEQUENCE: 108

ggagggagca ctagaagaac                                                 20


<210> SEQ ID NO 109
<211> LENGTH: 659
<212> TYPE: DNA
<213> ORGANISM: Homo sapiens

<400> SEQUENCE: 109

agcaaattac accattaatg tcatcctggc gaatgaaaca agagaatagt atttatcaga     60

gaaagtctgg tgagttgaag tccaagaccc caggaaacaa ctagccctgc tgggctgccc    120

ctccttcgga gtgggactat atgatcctca tcaggccaat ccacgtcaca gaatggtcta    180

ggcattggat gagtgcctca atctgagcca atgaaggtca ttgctgagac attttactgg    240

ttgccaggct gcaggcatcc caggcttcct gctgccctca tgtctacaac ctgtcgtctg    300

gaacattcca ggagccactt ttatcacttg cagcaatctt cttcagtgag ttccccagga    360
```

-continued

```
cttgatttca tcttacaatc tgattccatg tgtctcccat attttaagga ttctttatta    420

tttctggctt acagagaaca aacattattt tttgctttcc tggtctgttc tagattttca    480

aaaataactc tgtcacttct gttatatggt atcattgctt gtaattatct atttacttat    540

ctgtctctgg actggactct ttacagacag gcaataacta attatctgtc tgtctggcat    600

ttggtagtca ctcataaatc gtttattgca ttactaacta aataaaaaag ttgaccttg     659
```

<210> SEQ ID NO 110
<211> LENGTH: 144
<212> TYPE: PRT
<213> ORGANISM: Homo sapiens

<400> SEQUENCE: 110

```
Met Lys Val Ile Ala Glu Thr Phe Tyr Trp Leu Pro Gly Cys Arg His
1               5                   10                  15

Pro Arg Leu Pro Ala Ala Leu Met Ser Thr Thr Cys Arg Leu Glu His
            20                  25                  30

Ser Arg Ser His Phe Tyr His Leu Gln Gln Ser Ser Ser Val Ser Ser
        35                  40                  45

Pro Gly Leu Asp Phe Ile Leu Gln Ser Asp Ser Met Cys Leu Pro Tyr
    50                  55                  60

Phe Lys Asp Ser Leu Leu Phe Leu Ala Tyr Arg Glu Gln Thr Leu Phe
65                  70                  75                  80

Phe Ala Phe Leu Val Cys Ser Arg Phe Ser Lys Ile Thr Leu Ser Leu
                85                  90                  95

Leu Leu Tyr Gly Ile Ile Ala Cys Asn Tyr Leu Phe Thr Tyr Leu Ser
            100                 105                 110

Leu Asp Trp Thr Leu Tyr Arg Gln Ala Ile Thr Asn Tyr Leu Ser Val
        115                 120                 125

Trp His Leu Val Val Thr His Lys Ser Phe Ile Ala Leu Leu Thr Lys
    130                 135                 140
```

<210> SEQ ID NO 111
<211> LENGTH: 25
<212> TYPE: DNA
<213> ORGANISM: Artificial Sequence
<220> FEATURE:
<223> OTHER INFORMATION: Oligonucleotide

<400> SEQUENCE: 111

```
atcctggcga atgaaacaag agaat                                           25
```

<210> SEQ ID NO 112
<211> LENGTH: 26
<212> TYPE: DNA
<213> ORGANISM: Artificial Sequence
<220> FEATURE:
<223> OTHER INFORMATION: Oligonucleotide

<400> SEQUENCE: 112

```
gcaaccagta aaatgtctca gcaatg                                          26
```

<210> SEQ ID NO 113
<211> LENGTH: 831
<212> TYPE: DNA
<213> ORGANISM: Homo sapiens

<400> SEQUENCE: 113

```
atgcgaagaa agaacctcac agaggtaaca gagtttgttt tcctgggatt ctccagattc     60
```

-continued

```
cacaaacatc acatcactct ctttgtggtt tttctcatcc tgtacacatt aactgtggct    120
ggcaatgcca tcatcatgac catcatctgc attgaccgtc acctccacac tcccatgtac    180
ttcttcctga gcatgctggc tagctcaaag acagtgtaca cactgttcat cattccacag    240
atgctctcca gcttcgtaac ccagacccag ccaatctccc tagcaggttg taccacccaa    300
acgttcttct ttgttacctt ggccatcaac aattgcttct tgctcacagt gatgggctat    360
gaccactata tggccatctg caatcccttg agatacaggg tcattacgag caagaaggtg    420
tgtgtccagc tggtgtgtgg agcctttagc attggcctgg ccatggcagc tgtccaggta    480
acatccatat ttaccttacc tttttgtcac acggtggttg gtcatttctt ctgtgacatc    540
ctccctgtca tgaaactctc ctgtattaat accactatca atgagataat caattttgtt    600
gtcaggttat ttgtcatcct ggtccccatg ggtctggtct tcatctccta tgtcctcatc    660
atctccactg tcctcaagat tgcctcagct gagggttgga agaagacctt tgccacctgt    720
gccttccacc tcactgtggt cattgtccat tatggctgtg cttccattgc ctacctcatg    780
cccaagtcag aaaactctat agaacaagac ctccttctct cagtgaccta a             831
```

```
<210> SEQ ID NO 114
<211> LENGTH: 276
<212> TYPE: PRT
<213> ORGANISM: Homo sapiens

<400> SEQUENCE: 114

Met Arg Arg Lys Asn Leu Thr Glu Val Thr Glu Phe Val Phe Leu Gly
1               5                   10                  15

Phe Ser Arg Phe His Lys His His Ile Thr Leu Phe Val Val Phe Leu
            20                  25                  30

Ile Leu Tyr Thr Leu Thr Val Ala Gly Asn Ala Ile Ile Met Thr Ile
        35                  40                  45

Ile Cys Ile Asp Arg His Leu His Thr Pro Met Tyr Phe Phe Leu Ser
    50                  55                  60

Met Leu Ala Ser Ser Lys Thr Val Tyr Thr Leu Phe Ile Ile Pro Gln
65                  70                  75                  80

Met Leu Ser Ser Phe Val Thr Gln Thr Gln Pro Ile Ser Leu Ala Gly
                85                  90                  95

Cys Thr Thr Gln Thr Phe Phe Phe Val Thr Leu Ala Ile Asn Asn Cys
            100                 105                 110

Phe Leu Leu Thr Val Met Gly Tyr Asp His Tyr Met Ala Ile Cys Asn
        115                 120                 125

Pro Leu Arg Tyr Arg Val Ile Thr Ser Lys Lys Val Cys Val Gln Leu
    130                 135                 140

Val Cys Gly Ala Phe Ser Ile Gly Leu Ala Met Ala Ala Val Gln Val
145                 150                 155                 160

Thr Ser Ile Phe Thr Leu Pro Phe Cys His Thr Val Val Gly His Phe
                165                 170                 175

Phe Cys Asp Ile Leu Pro Val Met Lys Leu Ser Cys Ile Asn Thr Thr
            180                 185                 190

Ile Asn Glu Ile Ile Asn Phe Val Val Arg Leu Phe Val Ile Leu Val
        195                 200                 205

Pro Met Gly Leu Val Phe Ile Ser Tyr Val Leu Ile Ile Ser Thr Val
    210                 215                 220

Leu Lys Ile Ala Ser Ala Glu Gly Trp Lys Lys Thr Phe Ala Thr Cys
225                 230                 235                 240
```

-continued

```
Ala Phe His Leu Thr Val Val Ile Val His Tyr Gly Cys Ala Ser Ile
                245                 250                 255

Ala Tyr Leu Met Pro Lys Ser Glu Asn Ser Ile Glu Gln Asp Leu Leu
            260                 265                 270

Leu Ser Val Thr
        275
```

<210> SEQ ID NO 115
<211> LENGTH: 18
<212> TYPE: DNA
<213> ORGANISM: Artificial Sequence
<220> FEATURE:
<223> OTHER INFORMATION: Oligonucleotide

<400> SEQUENCE: 115
cttcgtaacc cagaccca 18

<210> SEQ ID NO 116
<211> LENGTH: 18
<212> TYPE: DNA
<213> ORGANISM: Artificial Sequence
<220> FEATURE:
<223> OTHER INFORMATION: Oligonucleotide

<400> SEQUENCE: 116
cttgctcgta atgaccct 18

<210> SEQ ID NO 117
<211> LENGTH: 1233
<212> TYPE: DNA
<213> ORGANISM: Homo sapiens

<400> SEQUENCE: 117
gaagcagcca ccaccatctt gggagctctg ggagcaagga cccctgtaac acattcatcc 60
ttgaatgaca aaatgtctgg tccagcatgg tattataaca taaacatgaa gaggaagaga 120
catgagagat acgcacagtg aagagaccaa gctgggacac agtacgaagg tggcatctgc 180
acgccaagca gagggacctc agaagaaact gagccagcca gcaccccacc ttcgtctttg 240
acctccagcc tccagaacta aggatagagc tcttcatctc tgttagaaac gaccatcaaa 300
aagatacatc aattcattag aatcaaaagg acatgagtta tcagaattct ttctcctgaa 360
agaaagtgga gatcaaaggt aaaacttcta gagaatgaga tgaaggcaga tgaaagaagt 420
taacaagaca ttacatgact tgataatatt gcatgtatgc aaaaacctta tgaaatcaac 480
tgtgttctag cgaccacttg tttttctttt tgtcataata ctttttattc tcttgcaatg 540
atattgattc atctgcacct gacatcaact ctgcatttgt agaaggtgat aagaatacag 600
ggaaatggaa taagtggctt tgcctgcaat cccgcagcag cagaaatgtc catttcctct 660
ctcctgaata atactacatt ctccactggg ttccacaagt ttcgaggtaa aagcatgaac 720
atacacgaag tcaccatcac taccctcacc accaccacca ttatttccac catattcacc 780
cttttaatac gcaaacttcc tccaaggctt cctgaagtca cccagaaatg catttcccca 840
agagtgagtt gtgctaacat tgtatcctat ggaactctgg gaagctaccc agatcctcaa 900
ctcttggagt cttgctgact gcatgttcca ggctccacat ttaagctcca gtgactgctg 960
atgactgcat gacctaacac atgtcctcaa tcctttcttg gcctcagttt cttcaccagt 1020
gaattctgaa tgctggaatt ggcaatattt caggttcttt ccaactggaa atacccatgc 1080
taataatttt agtaagtcaa tagccataga aacctactga caaaatgagt attttaacag 1140

-continued agacagttgt actttcttaa tttttagcag aagggaatgc atatgtataa tatctatgtt 1200
gccttctatg tgtaaaaata aatacacaga cac 1233

<210> SEQ ID NO 118
<211> LENGTH: 90
<212> TYPE: PRT
<213> ORGANISM: Homo sapiens

<400> SEQUENCE: 118

Met Ser Ile Ser Ser Leu Leu Asn Asn Thr Thr Phe Ser Thr Gly Phe
1 5 10 15

His Lys Phe Arg Gly Lys Ser Met Asn Ile His Glu Val Thr Ile Thr
20 25 30

Thr Leu Thr Thr Thr Thr Ile Ile Ser Thr Ile Phe Thr Leu Leu Ile
35 40 45

Arg Lys Leu Pro Pro Arg Leu Pro Glu Val Thr Gln Lys Cys Ile Ser
50 55 60

Pro Arg Val Ser Cys Ala Asn Ile Val Ser Tyr Gly Thr Leu Gly Ser
65 70 75 80

Tyr Pro Asp Pro Gln Leu Leu Glu Ser Cys
85 90

<210> SEQ ID NO 119
<211> LENGTH: 19
<212> TYPE: DNA
<213> ORGANISM: Artificial Sequence
<220> FEATURE:
<223> OTHER INFORMATION: Oligonucleotide

<400> SEQUENCE: 119
caccccacct tcgtctttg 19

<210> SEQ ID NO 120
<211> LENGTH: 24
<212> TYPE: DNA
<213> ORGANISM: Artificial Sequence
<220> FEATURE:
<223> OTHER INFORMATION: Oligonucleotide

<400> SEQUENCE: 120
gttttacctt tgatctccac tttc 24

<210> SEQ ID NO 121
<211> LENGTH: 4209
<212> TYPE: DNA
<213> ORGANISM: Homo sapiens

<400> SEQUENCE: 121
agttgcttga aagcaacgtg cctattcaca tggagaatct tccctttcct ttaaaattac 60
ttagtgcctc atcgctaaac gcccccagct ccacaccatg ggtgttggat atcttcctca 120
ccttggtgtt tgccctgggg ttcttcttcc tattactccc ctacttatct tacttccatt 180
gtgatgaccc accctcacca tcgcctggga agagaaagtg tccagtaggg cggaggcgga 240
ggcccagagg caggatgaaa aaccacagtc tgagagctgg tagagagtgc ccgagaggcc 300
tggaggagac ttcggacctt ctttcacaac tgcagagcct cctggggcca caccttgaca 360
aaggtgactt tggtcagctc tccggtccag accccccagg tgaggtgggc gaaagagcac 420
ctgatggagc ctcccagtcc tctcatgagc ctatggaaga tgctgctccc attctctccc 480

-continued

```
cgttagcttc cccggatcct caagccaagc atcctcagga tctggcctcc accccatcac     540
caggcccaat gaccacctca gtctcctccc taagtgcctc ccagccacca gaaccttccc     600
ttcccctaga acacccctca cccgagccac ctgcactttt ccctcaccca ccacacaccc     660
ctgatcctct ggcctgctct ccgcctcctc caaaaggctt cactgctcct cccctgcggg     720
actccacact gataactcca tctcactgtg actcagtggc acttccactg ggcaccgtcc     780
ctcaaagctt gtctccacat gaggatttgg tggcttctgt cccagccatc tcaggccttg     840
gtggctcaaa cagtcatgtt tctgcctcct cccggtggca ggagactgcc agaacctcgt     900
gcgcctttaa ctcatcagtc cagcaagatc ctctttcccg ccacccacca gagacctgtc     960
agatggaagc tggtagcctg tttttgctca gctctgatgg ccagaatgtc gtggggatac    1020
aagtcacaga aacagccaag gtcaacattt gggaagaaaa agaaaatgtt ggatcattta    1080
caaatcaaat gaccccagaa aagcacttaa attctttggg gaatttggct aaatcattgg    1140
atgctgagca ggacaccaca aacccaaaac ccttctggaa catgggagag aactcgaaac    1200
agctgcccgg acctcagaag tgctcagatc ctaggctctt gcaggaaagt tttggaaga    1260
attatagcca gcttttctgg ggcctcccct ctctgcacag cgagtccctg gtggctaacg    1320
cctgggtaac tgacaggtct tatactttac agtctcctcc tttcttgttc aatgaaatgt    1380
ccaatgtctg cccaattcaa agggagacta caatgtcccc actgcttttc caggcccagc    1440
ccctgtccca ccgccaaccc tttatttcat ccacacccca attcctgccc acacctatgg    1500
ctcaggccga ggctcaggcc catcttcagt cttctttccc agtcctatct cctgcttttc    1560
catccctgat taagaacact ggagtagctt gccctgcatc gcagaataaa gtgcaagctc    1620
tctccctacc tgaaactcag caccctgaat ggcctttgtt gaggaaacaa ctagaaggta    1680
ggttggcttt accctctagg gtccaaaaat ctcaggacgt ctttagtgtc tccactccta    1740
accttcccca ggaaagtttg acatccattc tgcctgagaa ctttccagtc agtcctgaac    1800
tccggagaca actggagcaa cacataaaaa agtggatcat ccaacactgg ggcaacctgg    1860
gaaggatcca agagtctctg gatctgatgc agcttcggga cgaatcacca gggacaagtc    1920
aggccaaggg caaacccagt ccctggcagt cctccacgtc cacaggtgaa agcagcaagg    1980
aggcacagaa ggtgaagttc cagctagaga gggacctgtg cccacatctg ggcaaattc    2040
tgggtgagac cccacaaaat ctatccaggg acatgaaaag cttcccacgg aaggttctgg    2100
gggtgacttc tgaggagtcg gaaaggaact tgaggaagcc cttgaggagt gactcgggaa    2160
gtgatttatt aagatgcaca gagaggactc atatagaaaa catcctgaaa gcccacatgg    2220
gcaggaactt gggccagacc aacgagggct tgatccccgt gcgtgtgcgt cgatcctggc    2280
ttgctgtcaa ccaggctctt cccgtgtcca acacccatgt gaaaaccagc aatctagcag    2340
ccccgaaaag tgggaaagcc tgtgtgaaca cagcccaggt gctttccttc ctcgagccgt    2400
gtactcagca ggggttggga gcccatattg tgaggttttg ggccaaacac aggtggggtc    2460
taccccctcag ggtcctcaag cccattcagt gctttaaact ggaaaaggtt tcatccttgt    2520
cccttacgca gcttgctggt ccctcctcag ccacctgtga atctggggct ggctcagaag    2580
ttgaggtgga catgttcctt agaaagccac caatggcaag tctgagaaag caggtgctga    2640
ccaaagcatc tgatcacatg ccagagagtc ttctggcctc ctcacctgca tggaagcagt    2700
tccagagggc accgcgagga atcccatctt ggaatgatca tgggcccttg aagcctcctc    2760
cagctggaca ggagggcagg tggccatcta agcccctcac gtacagcctc acaggcagca    2820
cccagcagag caggagctta ggagcccaat cttcaaaggc tggagagaca agggaggcag    2880
```

-continued

```
tgccacaatg cagagtcccc ttggaaacct gtatgctggc aaacctccaa gccacaagtg   2940
aggatgtgca tggtttcgag gctccaggga ccagcaaaag ctctctacac cctagagtgt   3000
ctgtctccca agatccaaga aagctgtgtc ttatggagga ggttgttagt gaatttgagc   3060
ctggaatggc cacaaagtca gagacccagc ctcaagtttg tgccgctgtt gtgctccttc   3120
cagatgggca agcatctgtt gtgccccacg cttcagagaa tttggtttct caagtgcccc   3180
agggccatct ccagagcatg cctactggga acatgcgggc ttcccaggag ctacatgacc   3240
tcatggcagc cagaaggagc aaactggtgc aagaggagcc cagaaaccca aactgtcaag   3300
gctcatgcaa gagccaaagg ccaatgtttc cccctattca caagagtgag aagtctagga   3360
agcccaactt agaaaaacat gaagaaaggc ttgaaggatt gaggactcct caacttaccc   3420
cagtcaggaa aacagaagac acccatcagg atgaaggcgt ccagctactg ccatcaaaga   3480
aacagcctcc ttcagtaagc cactttggag aaaacatcaa gcaatttttt cagtggattt   3540
tttcaaagaa aaaaagcaag ccagcaccag tcactgctga gagccaaaaa acagtaaaaa   3600
acagatcatg tgtgtacagc agcagtgctg aagctcaggg tctcatgacg gcagttggac   3660
aaatgctgga caagaaaatg tcactttgcc atgcgcacca tgcctcgaag gtaaatcagc   3720
acaaacagaa gtttcaagcc ccagtctgtg ggtttccctg caaccacagg cacctcttct   3780
actcagaaca tggcagaata ctgagctatg cagccagcag tcaacaagcc actctcaaga   3840
gccagggttg tcccaacaga gacaggcaaa tcagaaatca acagcccttg aaaagtgtgc   3900
ggtgcaacaa tgagcaatgg ggcctgcgac atccccaaat cttgcacccc aagaaagctg   3960
tatccccagt cagtccccct cagcactggc cgaagacatc cggtgcctct agccaccatc   4020
accactgtcc aaggcactgt cttctttggg aaggtatctg atttggtcag tcacaaattc   4080
tttttagcc ttccctggag aaaaacaagt ccccaagaaa aaattcactc tatgtagaga    4140
aaaaatattt tctctcatgt tagtaaatgc agaacattta atattccaca atatatatgg   4200
tttttatt                                                            4209
```

<210> SEQ ID NO 122
<211> LENGTH: 1343
<212> TYPE: PRT
<213> ORGANISM: Homo sapiens

<400> SEQUENCE: 122

```
Met Glu Asn Leu Pro Phe Pro Leu Lys Leu Leu Ser Ala Ser Ser Leu
1               5                   10                  15

Asn Ala Pro Ser Ser Thr Pro Trp Val Leu Asp Ile Phe Leu Thr Leu
            20                  25                  30

Val Phe Ala Leu Gly Phe Phe Phe Leu Leu Leu Pro Tyr Leu Ser Tyr
        35                  40                  45

Phe His Cys Asp Asp Pro Pro Ser Pro Ser Pro Gly Lys Arg Lys Cys
    50                  55                  60

Pro Val Gly Arg Arg Arg Arg Pro Arg Gly Arg Met Lys Asn His Ser
65                  70                  75                  80

Leu Arg Ala Gly Arg Glu Cys Pro Arg Gly Leu Glu Glu Thr Ser Asp
                85                  90                  95

Leu Leu Ser Gln Leu Gln Ser Leu Leu Gly Pro His Leu Asp Lys Gly
            100                 105                 110

Asp Phe Gly Gln Leu Ser Gly Pro Asp Pro Pro Gly Glu Val Gly Glu
        115                 120                 125
```

-continued

```
Arg Ala Pro Asp Gly Ala Ser Gln Ser Ser His Glu Pro Met Glu Asp
    130                 135                 140

Ala Ala Pro Ile Leu Ser Pro Leu Ala Ser Pro Asp Pro Gln Ala Lys
145                 150                 155                 160

His Pro Gln Asp Leu Ala Ser Thr Pro Ser Pro Gly Pro Met Thr Thr
                165                 170                 175

Ser Val Ser Ser Leu Ser Ala Ser Gln Pro Pro Glu Pro Ser Leu Pro
            180                 185                 190

Leu Glu His Pro Ser Pro Glu Pro Pro Ala Leu Phe Pro His Pro Pro
        195                 200                 205

His Thr Pro Asp Pro Leu Ala Cys Ser Pro Pro Pro Pro Lys Gly Phe
    210                 215                 220

Thr Ala Pro Pro Leu Arg Asp Ser Thr Leu Ile Thr Pro Ser His Cys
225                 230                 235                 240

Asp Ser Val Ala Leu Pro Leu Gly Thr Val Pro Gln Ser Leu Ser Pro
                245                 250                 255

His Glu Asp Leu Val Ala Ser Val Pro Ala Ile Ser Gly Leu Gly Gly
            260                 265                 270

Ser Asn Ser His Val Ser Ala Ser Ser Arg Trp Gln Glu Thr Ala Arg
        275                 280                 285

Thr Ser Cys Ala Phe Asn Ser Ser Val Gln Gln Asp Pro Leu Ser Arg
    290                 295                 300

His Pro Pro Glu Thr Cys Gln Met Glu Ala Gly Ser Leu Phe Leu Leu
305                 310                 315                 320

Ser Ser Asp Gly Gln Asn Val Val Gly Ile Gln Val Thr Glu Thr Ala
                325                 330                 335

Lys Val Asn Ile Trp Glu Glu Lys Glu Asn Val Gly Ser Phe Thr Asn
            340                 345                 350

Gln Met Thr Pro Glu Lys His Leu Asn Ser Leu Gly Asn Leu Ala Lys
        355                 360                 365

Ser Leu Asp Ala Glu Gln Asp Thr Thr Asn Pro Lys Pro Phe Trp Asn
    370                 375                 380

Met Gly Glu Asn Ser Lys Gln Leu Pro Gly Pro Gln Lys Cys Ser Asp
385                 390                 395                 400

Pro Arg Leu Leu Gln Glu Ser Phe Trp Lys Asn Tyr Ser Gln Leu Phe
                405                 410                 415

Trp Gly Leu Pro Ser Leu His Ser Glu Ser Leu Val Ala Asn Ala Trp
            420                 425                 430

Val Thr Asp Arg Ser Tyr Thr Leu Gln Ser Pro Pro Phe Leu Phe Asn
        435                 440                 445

Glu Met Ser Asn Val Cys Pro Ile Gln Arg Glu Thr Thr Met Ser Pro
    450                 455                 460

Leu Leu Phe Gln Ala Gln Pro Leu Ser His Arg Gln Pro Phe Ile Ser
465                 470                 475                 480

Ser Thr Pro Gln Phe Leu Pro Thr Pro Met Ala Gln Ala Glu Ala Gln
                485                 490                 495

Ala His Leu Gln Ser Ser Phe Pro Val Leu Ser Pro Ala Phe Pro Ser
            500                 505                 510

Leu Ile Lys Asn Thr Gly Val Ala Cys Pro Ala Ser Gln Asn Lys Val
        515                 520                 525

Gln Ala Leu Ser Leu Pro Glu Thr Gln His Pro Glu Trp Pro Leu Leu
    530                 535                 540
```

-continued

```
Arg Lys Gln Leu Glu Gly Arg Leu Ala Leu Pro Ser Arg Val Gln Lys
545                 550                 555                 560

Ser Gln Asp Val Phe Ser Val Ser Thr Pro Asn Leu Pro Gln Glu Ser
                565                 570                 575

Leu Thr Ser Ile Leu Pro Glu Asn Phe Pro Val Ser Pro Glu Leu Arg
            580                 585                 590

Arg Gln Leu Glu Gln His Ile Lys Lys Trp Ile Ile Gln His Trp Gly
        595                 600                 605

Asn Leu Gly Arg Ile Gln Glu Ser Leu Asp Leu Met Gln Leu Arg Asp
    610                 615                 620

Glu Ser Pro Gly Thr Ser Gln Ala Lys Gly Lys Pro Ser Pro Trp Gln
625                 630                 635                 640

Ser Ser Thr Ser Thr Gly Glu Ser Ser Lys Glu Ala Gln Lys Val Lys
                645                 650                 655

Phe Gln Leu Glu Arg Asp Leu Cys Pro His Leu Gly Gln Ile Leu Gly
            660                 665                 670

Glu Thr Pro Gln Asn Leu Ser Arg Asp Met Lys Ser Phe Pro Arg Lys
        675                 680                 685

Val Leu Gly Val Thr Ser Glu Glu Ser Glu Arg Asn Leu Arg Lys Pro
    690                 695                 700

Leu Arg Ser Asp Ser Gly Ser Asp Leu Leu Arg Cys Thr Glu Arg Thr
705                 710                 715                 720

His Ile Glu Asn Ile Leu Lys Ala His Met Gly Arg Asn Leu Gly Gln
                725                 730                 735

Thr Asn Glu Gly Leu Ile Pro Val Arg Val Arg Arg Ser Trp Leu Ala
            740                 745                 750

Val Asn Gln Ala Leu Pro Val Ser Asn Thr His Val Lys Thr Ser Asn
        755                 760                 765

Leu Ala Ala Pro Lys Ser Gly Lys Ala Cys Val Asn Thr Ala Gln Val
    770                 775                 780

Leu Ser Phe Leu Glu Pro Cys Thr Gln Gln Gly Leu Gly Ala His Ile
785                 790                 795                 800

Val Arg Phe Trp Ala Lys His Arg Trp Gly Leu Pro Leu Arg Val Leu
                805                 810                 815

Lys Pro Ile Gln Cys Phe Lys Leu Glu Lys Val Ser Ser Leu Ser Leu
            820                 825                 830

Thr Gln Leu Ala Gly Pro Ser Ser Ala Thr Cys Glu Ser Gly Ala Gly
        835                 840                 845

Ser Glu Val Glu Val Asp Met Phe Leu Arg Lys Pro Pro Met Ala Ser
    850                 855                 860

Leu Arg Lys Gln Val Leu Thr Lys Ala Ser Asp His Met Pro Glu Ser
865                 870                 875                 880

Leu Leu Ala Ser Ser Pro Ala Trp Lys Gln Phe Gln Arg Ala Pro Arg
                885                 890                 895

Gly Ile Pro Ser Trp Asn Asp His Gly Pro Leu Lys Pro Pro Pro Ala
            900                 905                 910

Gly Gln Glu Gly Arg Trp Pro Ser Lys Pro Leu Thr Tyr Ser Leu Thr
        915                 920                 925

Gly Ser Thr Gln Gln Ser Arg Ser Leu Gly Ala Gln Ser Ser Lys Ala
    930                 935                 940

Gly Glu Thr Arg Glu Ala Val Pro Gln Cys Arg Val Pro Leu Glu Thr
945                 950                 955                 960
```

-continued

```
Cys Met Leu Ala Asn Leu Gln Ala Thr Ser Glu Asp Val His Gly Phe
                965                 970                 975

Glu Ala Pro Gly Thr Ser Lys Ser Ser Leu His Pro Arg Val Ser Val
            980                 985                 990

Ser Gln Asp Pro Arg Lys Leu Cys  Leu Met Glu Glu Val  Val Ser Glu
        995                 1000                1005

Phe Glu  Pro Gly Met Ala Thr  Lys Ser Glu Thr Gln  Pro Gln Val
    1010                 1015                 1020

Cys Ala  Ala Val Val Leu Leu  Pro Asp Gly Gln Ala  Ser Val Val
    1025                 1030                 1035

Pro His  Ala Ser Glu Asn Leu  Val Ser Gln Val Pro  Gln Gly His
    1040                 1045                 1050

Leu Gln  Ser Met Pro Thr Gly  Asn Met Arg Ala Ser  Gln Glu Leu
    1055                 1060                 1065

His Asp  Leu Met Ala Ala Arg  Arg Ser Lys Leu Val  Gln Glu Glu
    1070                 1075                 1080

Pro Arg  Asn Pro Asn Cys Gln  Gly Ser Cys Lys Ser  Gln Arg Pro
    1085                 1090                 1095

Met Phe  Pro Pro Ile His Lys  Ser Glu Lys Ser Arg  Lys Pro Asn
    1100                 1105                 1110

Leu Glu  Lys His Glu Glu Arg  Leu Glu Gly Leu Arg  Thr Pro Gln
    1115                 1120                 1125

Leu Thr  Pro Val Arg Lys Thr  Glu Asp Thr His Gln  Asp Glu Gly
    1130                 1135                 1140

Val Gln  Leu Leu Pro Ser Lys  Lys Gln Pro Pro Ser  Val Ser His
    1145                 1150                 1155

Phe Gly  Glu Asn Ile Lys Gln  Phe Phe Gln Trp Ile  Phe Ser Lys
    1160                 1165                 1170

Lys Lys  Ser Lys Pro Ala Pro  Val Thr Ala Glu Ser  Gln Lys Thr
    1175                 1180                 1185

Val Lys  Asn Arg Ser Cys Val  Tyr Ser Ser Ser Ala  Glu Ala Gln
    1190                 1195                 1200

Gly Leu  Met Thr Ala Val Gly  Gln Met Leu Asp Lys  Lys Met Ser
    1205                 1210                 1215

Leu Cys  His Ala His His Ala  Ser Lys Val Asn Gln  His Lys Gln
    1220                 1225                 1230

Lys Phe  Gln Ala Pro Val Cys  Gly Phe Pro Cys Asn  His Arg His
    1235                 1240                 1245

Leu Phe  Tyr Ser Glu His Gly  Arg Ile Leu Ser Tyr  Ala Ala Ser
    1250                 1255                 1260

Ser Gln  Gln Ala Thr Leu Lys  Ser Gln Gly Cys Pro  Asn Arg Asp
    1265                 1270                 1275

Arg Gln  Ile Arg Asn Gln Gln  Pro Leu Lys Ser Val  Arg Cys Asn
    1280                 1285                 1290

Asn Glu  Gln Trp Gly Leu Arg  His Pro Gln Ile Leu  His Pro Lys
    1295                 1300                 1305

Lys Ala  Val Ser Pro Val Ser  Pro Pro Gln His Trp  Pro Lys Thr
    1310                 1315                 1320

Ser Gly  Ala Ser Ser His His  His His Cys Pro Arg  His Cys Leu
    1325                 1330                 1335

Leu Trp  Glu Gly Ile
    1340
```

-continued

<210> SEQ ID NO 123
<211> LENGTH: 24
<212> TYPE: DNA
<213> ORGANISM: Artificial Sequence
<220> FEATURE:
<223> OTHER INFORMATION: Oligonucleotide

<400> SEQUENCE: 123
ctattactcc cctacttatc ttac 24

<210> SEQ ID NO 124
<211> LENGTH: 18
<212> TYPE: DNA
<213> ORGANISM: Artificial Sequence
<220> FEATURE:
<223> OTHER INFORMATION: Oligonucleotide

<400> SEQUENCE: 124
tttcgcccac ctcacctg 18

<210> SEQ ID NO 125
<211> LENGTH: 3136
<212> TYPE: DNA
<213> ORGANISM: Homo sapiens

<400> SEQUENCE: 125
gtcgccgccg ctaccgccgc cgccgccgca gggcccgccg ctgggatgcc gagcgcccgc 60
gccgccgctg cctctgtcct ccgcgcgctg ctcagctgaa ggcgcacagg attcaattac 120
tggacttgtc aactctgcca gtgtacgtgc catttctctt ccactatgag aggaccgatt 180
gtattgcaca tttgtctggc tttctgtagc cttctgcttt tcagcgttgc cacacaatgt 240
ctggccttcc ccaaaataga aaggaggagg gagatagcac atgttcatgc ggaaaaaggg 300
cagtccgata agatgaacac cgatgaccta gaaaatagct ctgttacctc aaagcagact 360
ccccaactgg tggtctctga agatccaatg atgatgtcag cagtaccatc ggcaacatca 420
ttaaataaag cattctcgat taacaaagaa acccagcctg gacaagctgg gctcatgcaa 480
acagaacgcc ctggtgtttc cacacctact gagtcaggtg tcccctcagc tgaagaagta 540
tttggttcca gccagccaga gagaatatct cctgaaagtg gacttgccaa ggccatgtta 600
accattgcta tcactgcgac tccttctctg actgttgatg aaaaggagga actccttaca 660
agcactaact ttcagcccat tgtagaagag atcacagaaa ccacaaaagg ttttctgaag 720
tatatggata atcaatcatt tgcaactgaa agtcaggaag gagttggttt gggacattca 780
ccttcatcct atgtgaatac taaggaaatg ctaaccacca atccaaagac tgagaaattt 840
gaagcagaca cagaccacag gacaacttct tttcctggtg ctgagtccac agcaggcagt 900
gagcctggaa gcctcacccc tgataaggag aagccttcgc agatgacagc tgataacacc 960
caggctgctg ccaccaagca accactcgaa acttccgagt acaccctgag tgttgagcca 1020
gaaactgata gtctgctggg agccccagaa gtcacagtga gtgtcagcac agctgttcca 1080
gctgcctctg ccttaagtga tgagtgggat gacaccaaat tagagagtgt aagccggata 1140 aggacccccca agcttggaga caatgaagag actcaggtga gaacggagat gtctcagaca 1200
gcacaagtaa gccatgaggg tatggaagga ggccagcctt ggacagaggc tgcacaggtg 1260
gctctggggc tgcctgaagg ggaaacacac acgggcacag ccctgctaat agcgcatggg 1320
aatgagagat cacctgcttt cactgatcaa agttccttta cccccacaag tctgatggaa 1380
gacatgaaag tttccattgt gaacttgctc caaagtacgg gagacttcac ggaatccacc 1440

-continued

```
aaggaaaacg atgccctgtt tttcttagaa accactgttt ctgtctctgt atatgagtct   1500

gaggcagacc aactgttggg aaatacaatg aaagacatca tcactcaaga gatgacaaca   1560

gctgttcaag agccagatgc cactttatcc atggtgacac aagagcaggt tgctaccctc   1620

gagcttatca gagacagtgg caagactgag gaagaaaagg aggacccctc tcctgtgtct   1680

gacgttcctg gtgttactca gctgtcaaga agatgggagc ctctggccac tacaatttca   1740

actacagtcg tccctttgtc ttttgaagtt actcccactg tggaagaaca aatggacaca   1800

gtcacagggc caaatgagga gttcacacca gttctgggat ctccagtgac acctcctgga   1860

ataatggtgg gggaacccag catttcccct gcacttcctg ctttggaggc atcctctgag   1920

agaagaactg ttgttccatc tattactcgt gttaatacag ctgcctcata tggcctggac   1980

caacttgaat ctgaagaggg acaagaagat gaggatgaag aggatgaaga agatgaagat   2040

gaagaagagg aagatgagga agaagatgag gaagataaag atgcagactc gctggatgag   2100

ggcttggatg gtgacactga gctgccaggt tttaccctcc ctggtatcac atcccaggaa   2160

ccaggcttag aggagggaaa catggacctg ttggagggag ctacctacca ggtgccagat   2220

gccctcgagt gggaacagca gaatcaaggc ctggtgagaa gctggatgga aaaattaaaa   2280

gacaaggctg gttacatgtc tgggatgctg gtgcctgtag ggttgggat agctggagcc    2340

ttgttcatct tgggagccct ctacagcatt aaggttatga atcgccgaag gagaaatggc   2400

ttcaaaaggc ataaaagaaa gcagagagaa ttcaacagca tgcaagatcg agtaatgctc   2460

ttagccgaca gctctgaaga tgaattttga attggactgg gttttaattg ggatattcaa   2520

cgatgctact attctaattt ttattttgga gcagaaaaaa aaaaagaaca acctgccaca   2580

ttgctgctat caggccgtta gtcctagtgt ctgctgggtg ctgggtagta gatttttctt   2640

gtactgagca gaaatggcat gttgtatact aaacgtatca tgcagtattt ggttttattc   2700

tgtagtgaat tttccacaac cgtgggctac aactcataaa tatgcaacat atatgttttt   2760

cagtaggagt tgctacatta ggcagagtaa atattttgta gttttccaca gtgtcttttc   2820

cttggtttga attacctgca ttgagaataa tgattgttgc caccaaggca tgcttgactc   2880

tgagatataa atcttaacaa agaataactt ctcaagatat actctaccta cttgaaacca   2940

cagggttgtg ggccatggta catactgcat ttgcatcaaa ctagcagtaa ctcagaatga   3000

aatcattttc attaagaagc tctctcagca tattaggatt atatgtagat ttgtatgtat   3060

tttgcattat gtacttcagt ctcctagttt tattattctc accttccgtt ttattcttgg   3120

cgaggaaaaa aatgca                                                     3136
```

<210> SEQ ID NO 126
<211> LENGTH: 774
<212> TYPE: PRT
<213> ORGANISM: Homo sapiens

<400> SEQUENCE: 126

```
Met Arg Gly Pro Ile Val Leu His Ile Cys Leu Ala Phe Cys Ser Leu
1               5                   10                  15

Leu Leu Phe Ser Val Ala Thr Gln Cys Leu Ala Phe Pro Lys Ile Glu
            20                  25                  30

Arg Arg Arg Glu Ile Ala His Val His Ala Glu Lys Gly Gln Ser Asp
        35                  40                  45

Lys Met Asn Thr Asp Asp Leu Glu Asn Ser Ser Val Thr Ser Lys Gln
    50                  55                  60
```

-continued

```
Thr Pro Gln Leu Val Val Ser Glu Asp Pro Met Met Met Ser Ala Val
65                  70                  75                  80

Pro Ser Ala Thr Ser Leu Asn Lys Ala Phe Ser Ile Asn Lys Glu Thr
                85                  90                  95

Gln Pro Gly Gln Ala Gly Leu Met Gln Thr Glu Arg Pro Gly Val Ser
            100                 105                 110

Thr Pro Thr Glu Ser Gly Val Pro Ser Ala Glu Glu Val Phe Gly Ser
        115                 120                 125

Ser Gln Pro Glu Arg Ile Ser Pro Glu Ser Gly Leu Ala Lys Ala Met
    130                 135                 140

Leu Thr Ile Ala Ile Thr Ala Thr Pro Ser Leu Thr Val Asp Glu Lys
145                 150                 155                 160

Glu Glu Leu Leu Thr Ser Thr Asn Phe Gln Pro Ile Val Glu Glu Ile
                165                 170                 175

Thr Glu Thr Thr Lys Gly Phe Leu Lys Tyr Met Asp Asn Gln Ser Phe
            180                 185                 190

Ala Thr Glu Ser Gln Glu Gly Val Gly Leu Gly His Ser Pro Ser Ser
        195                 200                 205

Tyr Val Asn Thr Lys Glu Met Leu Thr Thr Asn Pro Lys Thr Glu Lys
    210                 215                 220

Phe Glu Ala Asp Thr Asp His Arg Thr Thr Ser Phe Pro Gly Ala Glu
225                 230                 235                 240

Ser Thr Ala Gly Ser Glu Pro Gly Ser Leu Thr Pro Asp Lys Glu Lys
                245                 250                 255

Pro Ser Gln Met Thr Ala Asp Asn Thr Gln Ala Ala Ala Thr Lys Gln
            260                 265                 270

Pro Leu Glu Thr Ser Glu Tyr Thr Leu Ser Val Glu Pro Glu Thr Asp
        275                 280                 285

Ser Leu Leu Gly Ala Pro Glu Val Thr Val Ser Val Ser Thr Ala Val
    290                 295                 300

Pro Ala Ala Ser Ala Leu Ser Asp Glu Trp Asp Asp Thr Lys Leu Glu
305                 310                 315                 320

Ser Val Ser Arg Ile Arg Thr Pro Lys Leu Gly Asp Asn Glu Glu Thr
                325                 330                 335

Gln Val Arg Thr Glu Met Ser Gln Thr Ala Gln Val Ser His Glu Gly
            340                 345                 350

Met Glu Gly Gly Gln Pro Trp Thr Glu Ala Ala Gln Val Ala Leu Gly
        355                 360                 365

Leu Pro Glu Gly Glu Thr His Thr Gly Thr Ala Leu Leu Ile Ala His
    370                 375                 380

Gly Asn Glu Arg Ser Pro Ala Phe Thr Asp Gln Ser Ser Phe Thr Pro
385                 390                 395                 400

Thr Ser Leu Met Glu Asp Met Lys Val Ser Ile Val Asn Leu Leu Gln
                405                 410                 415

Ser Thr Gly Asp Phe Thr Glu Ser Thr Lys Glu Asn Asp Ala Leu Phe
            420                 425                 430

Phe Leu Glu Thr Thr Val Ser Val Ser Val Tyr Glu Ser Glu Ala Asp
        435                 440                 445

Gln Leu Leu Gly Asn Thr Met Lys Asp Ile Ile Thr Gln Glu Met Thr
    450                 455                 460

Thr Ala Val Gln Glu Pro Asp Ala Thr Leu Ser Met Val Thr Gln Glu
465                 470                 475                 480
```

-continued

```
Gln Val Ala Thr Leu Glu Leu Ile Arg Asp Ser Gly Lys Thr Glu Glu
                485                 490                 495

Glu Lys Glu Asp Pro Ser Pro Val Ser Asp Val Pro Gly Val Thr Gln
            500                 505                 510

Leu Ser Arg Arg Trp Glu Pro Leu Ala Thr Thr Ile Ser Thr Thr Val
        515                 520                 525

Val Pro Leu Ser Phe Glu Val Thr Pro Thr Val Glu Glu Gln Met Asp
    530                 535                 540

Thr Val Thr Gly Pro Asn Glu Glu Phe Thr Pro Val Leu Gly Ser Pro
545                 550                 555                 560

Val Thr Pro Pro Gly Ile Met Val Gly Glu Pro Ser Ile Ser Pro Ala
                565                 570                 575

Leu Pro Ala Leu Glu Ala Ser Ser Glu Arg Arg Thr Val Val Pro Ser
            580                 585                 590

Ile Thr Arg Val Asn Thr Ala Ala Ser Tyr Gly Leu Asp Gln Leu Glu
        595                 600                 605

Ser Glu Glu Gly Gln Glu Asp Glu Asp Glu Glu Asp Glu Glu Asp Glu
    610                 615                 620

Asp Glu Glu Glu Glu Asp Glu Glu Glu Asp Glu Glu Asp Lys Asp Ala
625                 630                 635                 640

Asp Ser Leu Asp Glu Gly Leu Asp Gly Asp Thr Glu Leu Pro Gly Phe
                645                 650                 655

Thr Leu Pro Gly Ile Thr Ser Gln Glu Pro Gly Leu Glu Glu Gly Asn
            660                 665                 670

Met Asp Leu Leu Glu Gly Ala Thr Tyr Gln Val Pro Asp Ala Leu Glu
        675                 680                 685

Trp Glu Gln Gln Asn Gln Gly Leu Val Arg Ser Trp Met Glu Lys Leu
    690                 695                 700

Lys Asp Lys Ala Gly Tyr Met Ser Gly Met Leu Val Pro Val Gly Val
705                 710                 715                 720

Gly Ile Ala Gly Ala Leu Phe Ile Leu Gly Ala Leu Tyr Ser Ile Lys
                725                 730                 735

Val Met Asn Arg Arg Arg Arg Asn Gly Phe Lys Arg His Lys Arg Lys
            740                 745                 750

Gln Arg Glu Phe Asn Ser Met Gln Asp Arg Val Met Leu Leu Ala Asp
        755                 760                 765

Ser Ser Glu Asp Glu Phe
    770
```

```
<210> SEQ ID NO 127
<211> LENGTH: 18
<212> TYPE: DNA
<213> ORGANISM: Artificial Sequence
<220> FEATURE:
<223> OTHER INFORMATION: Oligonucleotide

<400> SEQUENCE: 127

ccctccctgg tatcacat                                                   18


<210> SEQ ID NO 128
<211> LENGTH: 18
<212> TYPE: DNA
<213> ORGANISM: Artificial Sequence
<220> FEATURE:
<223> OTHER INFORMATION: Oligonucleotide

<400> SEQUENCE: 128
```

-continued

```
caccagcatc ccagacat                                                  18


<210> SEQ ID NO 129
<211> LENGTH: 3627
<212> TYPE: DNA
<213> ORGANISM: Homo sapiens

<400> SEQUENCE: 129

gggactgggg ggttcccaga tccttgaagc tcactccgcc tcctcactct cactgcattt     60

cccaccttcc tgtgggcctt gcggcatctt catcactgag gcacctggtt acgcttcacc    120

tcttgtttcc tgccctcact gcattccctc acctctacct ttttatcctt ccaccctagg    180

cttctctcct ccctcttccc tcactcctga ctcttcctct tcccagcgga cggctggagg    240

accgctcagt ctctcctctc tcacttccct tcctctctct caccttcacc acccaacacc    300

tccctccctg cctctttctt tctgctccct cattctctcc ccaccactct cttctcgtgg    360

ccccctgcc cgcgcgccct cttcccttcc ccttgcctca ctctctcagc tttcttccca    420

cagttgagct cgggcagctc tttctgggga tagctatggg gctttggggg aagaaaggga    480

cagtggctcc ccatgaccag agtccaagac gaagacctaa aaaagggctt atcaagaaaa    540

aaatggtgaa gagggaaaaa cagaagcgca atatggagga actgaagaag gaagtggtca    600

tggatgatca caaattaacc ttggaagagc tgagcaccaa gtactccgtg gacctgacaa    660

agggccatag ccaccaaagg gcaaaggaaa tcctgactcg aggtggaccc aatactgtta    720

ccccaccccc caccactcca gaatgggtca aattctgtaa gcaactgttc ggaggcttct    780

ccctcctact atggactggg gccattctct gctttgtggc ctacagcatc cagatatatt    840

tcaatgagga gcctaccaaa gacaacctct acctgagcat cgtactgtcc gtcgtggtca    900

tcgtcactgg ctgcttctcc tattatcagg aggccaagag ctccaagatc atggagtctt    960

ttaagaacat ggtgcctcag caagctctgg taattcgagg aggagagaag atgcaaatta   1020

atgtacaaga ggtggtgttg ggagacctgg tggaaatcaa gggtggagac cgagtccctg   1080

ctgacctccg gcttatctct gcacaaggat gtaaggtgga caactcatcc ttgactgggg   1140

agtcagaacc ccagagccgc tcccctgact tcacccatga gaaccctctg gagacccgaa   1200

acatctgctt cttttccacc aactgtgtgg aaggaaccgc ccggggtatt gtgattgcta   1260

cgggagactc cacagtgatg ggcagaattg cctccctgac gtcaggcctg gcggttggcc   1320

agacacctat cgctgctgag atcgaacact tcatccatct gatcactgtg gtggccgtct   1380

tccttggtgt cacttttttt gcgctctcac ttctcttggg ctatggttgg ctggaggcta   1440

tcatttttct cattggcatc attgtggcca atgtgcctga ggggctgttg gccacagtca   1500

ctgtgtgcct gaccctcaca gccaagcgca tggcgcggaa gaactgcctg gtgaagaacc   1560

tggaggcggt ggagacgctg ggctccacgt ccaccatctg ctcagacaag acgggcaccc   1620

tcacccagaa ccgcatgacc gtcgcccaca tgtggtttga tatgaccgtg tatgaggccg   1680

acaccactga agaacagact ggaaaaacat ttaccaagag ctctgatacc tggtttatgc   1740

tggcccgaat cgctggcctc tgcaaccggg ctgactttaa ggctaatcag gagatcctgc   1800

ccattgctaa gagggccaca acaggtgatg cttccgagtc agccctcctc aagttcatcg   1860

agcagtctta cagctctgtg gcggagatga gagagaaaaa ccccaaggtg gcagagattc   1920

cctttaattc taccaacaag taccagatgt ccatccacct tcgggaggac agctcccaga   1980

cccacgtact gatgatgaag ggtgctccgg agaggatctt ggagttttgt tctacctttc   2040

ttctgaatgg gcaggagtac tcaatgaacg atgaaatgaa ggaagccttc caaaatgcct   2100
```

-continued

```
acttagaact gggaggtctg ggggaacgtg tgctaggctt ctgcttcttg aatctgccta   2160
gcagcttctc caagggattc ccatttaata cagatgaaat aaatttcccc atggacaacc   2220
tttgttttgt gggcctcata tccatgattg accctccccg agctgcagtg cctgatgctg   2280
tgagcaagtg tcgcagtgca ggaattaagg tgatcatggt aacaggagat catcccatta   2340
cagctaaggc cattgccaag ggtgtgggca tcatctcaga aggcactgag acggcagagg   2400
aagtcgctgc ccggcttaag atccctatca gcaaggtcga tgccagtgct gccaaagcca   2460
ttgtggtgca tggtgcagaa ctgaaggaca tacagtccaa gcagcttgat cagatcctcc   2520
agaaccaccc tgagatcgtg tttgctcgga cctcccctca gcagaagctc atcattgtcg   2580
agggatgtca gaggctggga gccgttgtgg ccgtgacagg tgacggggtg aacgactccc   2640
ctgcgctgaa gaaggctgac attggcattg ccatgggcat ctctggctct gacgtctcta   2700
agcaggcagc cgacatgatc ctgctggatg acaactttgc ctccatcgtc acgggggtgg   2760
aggagggccg cctgatcttt gacaacctga agaaatccat catgtacacc ctgaccagca   2820
acatccccga gatcacgccc ttcctgatgt tcatcatcct cggtataccc ctgcctctgg   2880
gaaccataac catcctctgc attgatctcg gcactgacat ggtccctgcc atctccttgg   2940
cttatgagtc agctgaaagc gacatcatga agaggcttcc aaggaaccca aagacggata   3000
atctggtgaa ccaccgtctc attggcatgg cctatggaca gattgggatg atccaggctc   3060
tggctggatt ctttacctac tttgtaatcc tggctgagaa tggttttagg cctgttgatc   3120
tgctgggcat ccgcctccac tgggaagata aatacttgaa tgacctggag gacagctacg   3180
gacagcagtg gacctatgag caacgaaaag ttgtggagtt cacatgccaa acggcctttt   3240
ttgtcaccat cgtggttgtg cagtgggcgg atctcatcat ctccaagact cgccgcaact   3300
cacttttcca gcagggcatg agaaacaaag tcttaatatt tgggatcctg gaggagacac   3360
tcttggctgc atttctgtcc tacactccag gcatggacgt ggccctgcga atgtacccac   3420
tcaagataac ctggtggctc tgtgccattc cctacagtat tctcatcttc gtctatgatg   3480
aaatcagaaa actcctcatc cgtcagcacc cggatggctg ggtggaaagg gagacgtact   3540
actaaactca gcagatgaag agcttcatgt gacacagggg tgttgtgaga gctgggatgg   3600
ggccagagat tataagtttg acacaac                                       3627
```

<210> SEQ ID NO 130
<211> LENGTH: 1029
<212> TYPE: PRT
<213> ORGANISM: Homo sapiens

<400> SEQUENCE: 130

```
Met Gly Leu Trp Gly Lys Lys Gly Thr Val Ala Pro His Asp Gln Ser
1               5                   10                  15

Pro Arg Arg Arg Pro Lys Lys Gly Leu Ile Lys Lys Lys Met Val Lys
            20                  25                  30

Arg Glu Lys Gln Lys Arg Asn Met Glu Glu Leu Lys Lys Glu Val Val
        35                  40                  45

Met Asp Asp His Lys Leu Thr Leu Glu Glu Leu Ser Thr Lys Tyr Ser
    50                  55                  60

Val Asp Leu Thr Lys Gly His Ser His Gln Arg Ala Lys Glu Ile Leu
65                  70                  75                  80

Thr Arg Gly Gly Pro Asn Thr Val Thr Pro Pro Pro Thr Thr Pro Glu
                85                  90                  95
```

-continued

```
Trp Val Lys Phe Cys Lys Gln Leu Phe Gly Gly Phe Ser Leu Leu Leu
            100                 105                 110

Trp Thr Gly Ala Ile Leu Cys Phe Val Ala Tyr Ser Ile Gln Ile Tyr
        115                 120                 125

Phe Asn Glu Glu Pro Thr Lys Asp Asn Leu Tyr Leu Ser Ile Val Leu
    130                 135                 140

Ser Val Val Val Ile Val Thr Gly Cys Phe Ser Tyr Tyr Gln Glu Ala
145                 150                 155                 160

Lys Ser Ser Lys Ile Met Glu Ser Phe Lys Asn Met Val Pro Gln Gln
                165                 170                 175

Ala Leu Val Ile Arg Gly Gly Glu Lys Met Gln Ile Asn Val Gln Glu
            180                 185                 190

Val Val Leu Gly Asp Leu Val Glu Ile Lys Gly Gly Asp Arg Val Pro
        195                 200                 205

Ala Asp Leu Arg Leu Ile Ser Ala Gln Gly Cys Lys Val Asp Asn Ser
    210                 215                 220

Ser Leu Thr Gly Glu Ser Glu Pro Gln Ser Arg Ser Pro Asp Phe Thr
225                 230                 235                 240

His Glu Asn Pro Leu Glu Thr Arg Asn Ile Cys Phe Phe Ser Thr Asn
                245                 250                 255

Cys Val Glu Gly Thr Ala Arg Gly Ile Val Ile Ala Thr Gly Asp Ser
            260                 265                 270

Thr Val Met Gly Arg Ile Ala Ser Leu Thr Ser Gly Leu Ala Val Gly
        275                 280                 285

Gln Thr Pro Ile Ala Ala Glu Ile Glu His Phe Ile His Leu Ile Thr
    290                 295                 300

Val Val Ala Val Phe Leu Gly Val Thr Phe Phe Ala Leu Ser Leu Leu
305                 310                 315                 320

Leu Gly Tyr Gly Trp Leu Glu Ala Ile Ile Phe Leu Ile Gly Ile Ile
                325                 330                 335

Val Ala Asn Val Pro Glu Gly Leu Leu Ala Thr Val Thr Val Cys Leu
            340                 345                 350

Thr Leu Thr Ala Lys Arg Met Ala Arg Lys Asn Cys Leu Val Lys Asn
        355                 360                 365

Leu Glu Ala Val Glu Thr Leu Gly Ser Thr Ser Thr Ile Cys Ser Asp
    370                 375                 380

Lys Thr Gly Thr Leu Thr Gln Asn Arg Met Thr Val Ala His Met Trp
385                 390                 395                 400

Phe Asp Met Thr Val Tyr Glu Ala Asp Thr Thr Glu Glu Gln Thr Gly
                405                 410                 415

Lys Thr Phe Thr Lys Ser Ser Asp Thr Trp Phe Met Leu Ala Arg Ile
            420                 425                 430

Ala Gly Leu Cys Asn Arg Ala Asp Phe Lys Ala Asn Gln Glu Ile Leu
        435                 440                 445

Pro Ile Ala Lys Arg Ala Thr Thr Gly Asp Ala Ser Glu Ser Ala Leu
    450                 455                 460

Leu Lys Phe Ile Glu Gln Ser Tyr Ser Ser Val Ala Glu Met Arg Glu
465                 470                 475                 480

Lys Asn Pro Lys Val Ala Glu Ile Pro Phe Asn Ser Thr Asn Lys Tyr
                485                 490                 495

Gln Met Ser Ile His Leu Arg Glu Asp Ser Ser Gln Thr His Val Leu
            500                 505                 510
```

-continued

```
Met Met Lys Gly Ala Pro Glu Arg Ile Leu Glu Phe Cys Ser Thr Phe
        515                 520                 525

Leu Leu Asn Gly Gln Glu Tyr Ser Met Asn Asp Glu Met Lys Glu Ala
    530                 535                 540

Phe Gln Asn Ala Tyr Leu Glu Leu Gly Gly Leu Gly Glu Arg Val Leu
545                 550                 555                 560

Gly Phe Cys Phe Leu Asn Leu Pro Ser Ser Phe Ser Lys Gly Phe Pro
                565                 570                 575

Phe Asn Thr Asp Glu Ile Asn Phe Pro Met Asp Asn Leu Cys Phe Val
            580                 585                 590

Gly Leu Ile Ser Met Ile Asp Pro Pro Arg Ala Ala Val Pro Asp Ala
        595                 600                 605

Val Ser Lys Cys Arg Ser Ala Gly Ile Lys Val Ile Met Val Thr Gly
    610                 615                 620

Asp His Pro Ile Thr Ala Lys Ala Ile Ala Lys Gly Val Gly Ile Ile
625                 630                 635                 640

Ser Glu Gly Thr Glu Thr Ala Glu Glu Val Ala Ala Arg Leu Lys Ile
                645                 650                 655

Pro Ile Ser Lys Val Asp Ala Ser Ala Ala Lys Ala Ile Val Val His
            660                 665                 670

Gly Ala Glu Leu Lys Asp Ile Gln Ser Lys Gln Leu Asp Gln Ile Leu
        675                 680                 685

Gln Asn His Pro Glu Ile Val Phe Ala Arg Thr Ser Pro Gln Gln Lys
    690                 695                 700

Leu Ile Ile Val Glu Gly Cys Gln Arg Leu Gly Ala Val Val Ala Val
705                 710                 715                 720

Thr Gly Asp Gly Val Asn Asp Ser Pro Ala Leu Lys Lys Ala Asp Ile
                725                 730                 735

Gly Ile Ala Met Gly Ile Ser Gly Ser Asp Val Ser Lys Gln Ala Ala
            740                 745                 750

Asp Met Ile Leu Leu Asp Asp Asn Phe Ala Ser Ile Val Thr Gly Val
        755                 760                 765

Glu Glu Gly Arg Leu Ile Phe Asp Asn Leu Lys Lys Ser Ile Met Tyr
    770                 775                 780

Thr Leu Thr Ser Asn Ile Pro Glu Ile Thr Pro Phe Leu Met Phe Ile
785                 790                 795                 800

Ile Leu Gly Ile Pro Leu Pro Leu Gly Thr Ile Thr Ile Leu Cys Ile
                805                 810                 815

Asp Leu Gly Thr Asp Met Val Pro Ala Ile Ser Leu Ala Tyr Glu Ser
            820                 825                 830

Ala Glu Ser Asp Ile Met Lys Arg Leu Pro Arg Asn Pro Lys Thr Asp
        835                 840                 845

Asn Leu Val Asn His Arg Leu Ile Gly Met Ala Tyr Gly Gln Ile Gly
    850                 855                 860

Met Ile Gln Ala Leu Ala Gly Phe Phe Thr Tyr Phe Val Ile Leu Ala
865                 870                 875                 880

Glu Asn Gly Phe Arg Pro Val Asp Leu Leu Gly Ile Arg Leu His Trp
                885                 890                 895

Glu Asp Lys Tyr Leu Asn Asp Leu Glu Asp Ser Tyr Gly Gln Gln Trp
            900                 905                 910

Thr Tyr Glu Gln Arg Lys Val Val Glu Phe Thr Cys Gln Thr Ala Phe
        915                 920                 925
```

-continued

```
Phe Val Thr Ile Val Val Val Gln Trp Ala Asp Leu Ile Ile Ser Lys
    930                 935                 940

Thr Arg Arg Asn Ser Leu Phe Gln Gln Gly Met Arg Asn Lys Val Leu
945                 950                 955                 960

Ile Phe Gly Ile Leu Glu Glu Thr Leu Leu Ala Ala Phe Leu Ser Tyr
                965                 970                 975

Thr Pro Gly Met Asp Val Ala Leu Arg Met Tyr Pro Leu Lys Ile Thr
            980                 985                 990

Trp Trp Leu Cys Ala Ile Pro Tyr  Ser Ile Leu Ile Phe  Val Tyr Asp
        995                 1000                1005

Glu Ile  Arg Lys Leu Leu Ile  Arg Gln His Pro Asp  Gly Trp Val
    1010                1015                1020

Glu Arg  Glu Thr Tyr Tyr
    1025
```

<210> SEQ ID NO 131
<211> LENGTH: 21
<212> TYPE: DNA
<213> ORGANISM: Artificial Sequence
<220> FEATURE:
<223> OTHER INFORMATION: Oligonucleotide

<400> SEQUENCE: 131
tgtaatcctg gctgagaatg g 21

<210> SEQ ID NO 132
<211> LENGTH: 18
<212> TYPE: DNA
<213> ORGANISM: Artificial Sequence
<220> FEATURE:
<223> OTHER INFORMATION: Oligonucleotide

<400> SEQUENCE: 132
aagtgagttg cggcgagt 18

<210> SEQ ID NO 133
<211> LENGTH: 279
<212> TYPE: DNA
<213> ORGANISM: Homo sapiens

<400> SEQUENCE: 133

```
atgtatgtaa aaattgcaaa acatctcaat gatgtttatg ccccccagaa ggtactgtgt     60

cacgggatct catatattct ggctgtcatt gtcataataa gccactcttg gtcatatgga    120

aaagcattca gctgctccct gcctttgctc acagcgtgtg gtactctctt agaagctatt    180

cctgtcctat ttaggcagtt attcctgctt cttgtgttgg acctgaagtc aacagggcca    240

gcaatagaga agaaagatga tgtgaaggag agcaactga                           279
```

<210> SEQ ID NO 134
<211> LENGTH: 92
<212> TYPE: PRT
<213> ORGANISM: Homo sapiens

<400> SEQUENCE: 134

```
Met Tyr Val Lys Ile Ala Lys His Leu Asn Asp Val Tyr Ala Pro Gln
1               5                   10                  15

Lys Val Leu Cys His Gly Ile Ser Tyr Ile Leu Ala Val Ile Val Ile
            20                  25                  30

Ile Ser His Ser Trp Ser Tyr Gly Lys Ala Phe Ser Cys Ser Leu Pro
        35                  40                  45
```

-continued

```
Leu Leu Thr Ala Cys Gly Thr Leu Leu Glu Ala Ile Pro Val Leu Phe
    50                  55                  60

Arg Gln Leu Phe Leu Leu Leu Val Leu Asp Leu Lys Ser Thr Gly Pro
65                  70                  75                  80

Ala Ile Glu Lys Lys Asp Asp Val Lys Glu Ser Asn
                85                  90


<210> SEQ ID NO 135
<211> LENGTH: 20
<212> TYPE: DNA
<213> ORGANISM: Artificial Sequence
<220> FEATURE:
<223> OTHER INFORMATION: Oligonucleotide

<400> SEQUENCE: 135

tgctccctgc ctttgctcac                                                20


<210> SEQ ID NO 136
<211> LENGTH: 24
<212> TYPE: DNA
<213> ORGANISM: Artificial Sequence
<220> FEATURE:
<223> OTHER INFORMATION: Oligonucleotide

<400> SEQUENCE: 136

ggtacttggt ctcgaacgat gatc                                           24


<210> SEQ ID NO 137
<211> LENGTH: 1569
<212> TYPE: DNA
<213> ORGANISM: Homo sapiens

<400> SEQUENCE: 137

atgcctgtag gggtggccc tgagagtgtg ggcaggtgca atggctgtca atgccacata      60

aagggcaagg ggatctacat cctaaacagt gaaagaccag tgcccggaga ctacatctac    120

atcaggaaga agaagcagca aaattctgac ccacagccca agaggggtcg gggcagcaga    180

acctcagcca cagccaatca cagcggggtc cttcggggag gggcgtggcc tgacaacttc    240

ggcgacgcgg ctggaccaat ccggacggag gagagcgaag ctcctctgca ctgggcccag    300

gtgcgctcct cagcgtctcc gggtggcggg gcgcgcggga tggaggagtc ttgggaggct    360

gcgcccggag gccaagccgg ggcagagctc ccaatggagc ccgtgggaag cctggtcccc    420

acgctggagc agccgcaggt gcccgcgaag gtgcgacaac ctgaaggtcc cgaaagcagc    480

ccaagtccgg ccggggccgt ggagaaggcg gcgggcgcag gcctggagcc ctcgagcaag    540

aaaaagccgc cttcgcctcg ccccgggtcc ccgcgcgtgc cgccgctcag cctgggctac    600

ggggtctgcc ccgagccgcc gtcaccgggc cctgccttgg tcaagctgcc ccggaatggc    660

gaggcgcccg gggctgagcc tgcgcccagc gcctgggcgc ccatggagct gcaggtagat    720

gtgcgcgtga agcccgtggg cgcggccggt ggcagcagca cgccatcgcc caggccctcc    780

acgcgcttcc tcaaggtgcc ggtgcccgag tcccctgcct tctcccgcca cgcggacccg    840

gcgcaccagc tcctgctgcg cgcaccatcc cagggcggca cgtggggccg ccgctcgccg    900

ctggctgcag cccggacgga gagcggctgc gacgcagagg gccgggccag ccccgcggaa    960

ggaagcgccg gctccccggg ctcccccacg tgctgccgct gcaaggagct ggggctggag   1020

aaggaggatg cggcgctgtt gccccgcgcg gggttggacg gcgacgagaa gctgccccgg   1080

gccgtaacgc ttacggggct acccatgtac gtgaagtccc tgtactgggc cctggcgttc   1140
```

-continued

```
atggctgtgc tcctggcagt ctctggggtt gtcattgtgg tcctggcctc aagagcagga   1200

gccagatgcc agcagtgccc cccaggctgg gtgttgtccg aggagcactg ttactacttc   1260

tctgcagaag cgcaggcctg ggaagccagc caggctttct gctcagccta ccacgctacc   1320

ctcccccctgc taagccacac ccaggacttc ctgggcagat acccagtctc caggcactcc   1380

tgggtggggg cctggcgagg cccccagggc tggcactgga tcgacgaggc cccactcccg   1440

ccccagctac tccctgagga cggcgaggac aatctggata tcaactgtgg ggccctggag   1500

gaaggcacgc tggtggctgc aaactgcagc actccaagac cctgggtctg tgccaagggg   1560

acccagtga                                                            1569
```

<210> SEQ ID NO 138
<211> LENGTH: 522
<212> TYPE: PRT
<213> ORGANISM: Homo sapiens

<400> SEQUENCE: 138

```
Met Pro Val Gly Gly Gly Pro Glu Ser Val Gly Arg Cys Asn Gly Cys
1               5                   10                  15

Gln Cys His Ile Lys Gly Lys Gly Ile Tyr Ile Leu Asn Ser Glu Arg
            20                  25                  30

Pro Val Pro Gly Asp Tyr Ile Tyr Ile Arg Lys Lys Lys Gln Gln Asn
        35                  40                  45

Ser Asp Pro Gln Pro Lys Arg Gly Arg Gly Ser Arg Thr Ser Ala Thr
    50                  55                  60

Ala Asn His Ser Gly Val Leu Arg Gly Gly Ala Trp Pro Asp Asn Phe
65                  70                  75                  80

Gly Asp Ala Ala Gly Pro Ile Arg Thr Glu Glu Ser Glu Ala Pro Leu
                85                  90                  95

His Trp Ala Gln Val Arg Ser Ser Ala Ser Pro Gly Gly Gly Ala Arg
            100                 105                 110

Gly Met Glu Glu Ser Trp Glu Ala Ala Pro Gly Gly Gln Ala Gly Ala
        115                 120                 125

Glu Leu Pro Met Glu Pro Val Gly Ser Leu Val Pro Thr Leu Glu Gln
    130                 135                 140

Pro Gln Val Pro Ala Lys Val Arg Gln Pro Glu Gly Pro Glu Ser Ser
145                 150                 155                 160

Pro Ser Pro Ala Gly Ala Val Glu Lys Ala Ala Gly Ala Gly Leu Glu
                165                 170                 175

Pro Ser Ser Lys Lys Lys Pro Pro Ser Pro Arg Pro Gly Ser Pro Arg
            180                 185                 190

Val Pro Pro Leu Ser Leu Gly Tyr Gly Val Cys Pro Glu Pro Pro Ser
        195                 200                 205

Pro Gly Pro Ala Leu Val Lys Leu Pro Arg Asn Gly Glu Ala Pro Gly
    210                 215                 220

Ala Glu Pro Ala Pro Ser Ala Trp Ala Pro Met Glu Leu Gln Val Asp
225                 230                 235                 240

Val Arg Val Lys Pro Val Gly Ala Ala Gly Gly Ser Ser Thr Pro Ser
                245                 250                 255

Pro Arg Pro Ser Thr Arg Phe Leu Lys Val Pro Val Pro Glu Ser Pro
            260                 265                 270

Ala Phe Ser Arg His Ala Asp Pro Ala His Gln Leu Leu Leu Arg Ala
        275                 280                 285
```

-continued

```
Pro Ser Gln Gly Gly Thr Trp Gly Arg Arg Ser Pro Leu Ala Ala Ala
    290                 295                 300

Arg Thr Glu Ser Gly Cys Asp Ala Glu Gly Arg Ala Ser Pro Ala Glu
305                 310                 315                 320

Gly Ser Ala Gly Ser Pro Gly Ser Pro Thr Cys Cys Arg Cys Lys Glu
                325                 330                 335

Leu Gly Leu Glu Lys Glu Asp Ala Ala Leu Leu Pro Arg Ala Gly Leu
            340                 345                 350

Asp Gly Asp Glu Lys Leu Pro Arg Ala Val Thr Leu Thr Gly Leu Pro
        355                 360                 365

Met Tyr Val Lys Ser Leu Tyr Trp Ala Leu Ala Phe Met Ala Val Leu
    370                 375                 380

Leu Ala Val Ser Gly Val Val Ile Val Val Leu Ala Ser Arg Ala Gly
385                 390                 395                 400

Ala Arg Cys Gln Gln Cys Pro Pro Gly Trp Val Leu Ser Glu Glu His
                405                 410                 415

Cys Tyr Tyr Phe Ser Ala Glu Ala Gln Ala Trp Glu Ala Ser Gln Ala
            420                 425                 430

Phe Cys Ser Ala Tyr His Ala Thr Leu Pro Leu Leu Ser His Thr Gln
        435                 440                 445

Asp Phe Leu Gly Arg Tyr Pro Val Ser Arg His Ser Trp Val Gly Ala
    450                 455                 460

Trp Arg Gly Pro Gln Gly Trp His Trp Ile Asp Glu Ala Pro Leu Pro
465                 470                 475                 480

Pro Gln Leu Leu Pro Glu Asp Gly Glu Asp Asn Leu Asp Ile Asn Cys
                485                 490                 495

Gly Ala Leu Glu Glu Gly Thr Leu Val Ala Ala Asn Cys Ser Thr Pro
            500                 505                 510

Arg Pro Trp Val Cys Ala Lys Gly Thr Gln
        515                 520


<210> SEQ ID NO 139
<211> LENGTH: 18
<212> TYPE: DNA
<213> ORGANISM: Artificial Sequence
<220> FEATURE:
<223> OTHER INFORMATION: Oligonucleotide

<400> SEQUENCE: 139

gagaaggagg atgcggcg                                                  18


<210> SEQ ID NO 140
<211> LENGTH: 21
<212> TYPE: DNA
<213> ORGANISM: Artificial Sequence
<220> FEATURE:
<223> OTHER INFORMATION: Oligonucleotide

<400> SEQUENCE: 140

ggaccacaat gacaacccca g                                              21


<210> SEQ ID NO 141
<211> LENGTH: 2217
<212> TYPE: DNA
<213> ORGANISM: Homo sapiens

<400> SEQUENCE: 141

atggtttgca cgttcgattc tgagcttctg aattgtcaaa ggaaagatga atataatcag     60
```

-continued

```
ttccagactt atcgggccca taaaataaaa gccaaaagaa gcatagccac tcctgaaaac    120
ctgaagaaat tattgccacg tgttcccaaa aacagtgccc tgagtgatga aatgacaaag    180
cttcacaaag gagctaagcc atgcaaatca aatacatttg gatgttttcc tattcatcag    240
gctgtacttt caggttccaa agaatgcatg gaaataatat tgaagtttgg tgaagagcac    300
gggtacagca gacagtgtca catcaacttt gtggataacg ggaaagccag ccctctccat    360
ctggctgtgc aaaatggtga cttggaaatg atgaaaatgt gcctggacaa tggtgtacaa    420
atagacctag tggagatgca acagatcaaa gagctggtaa tggatgaaga caacgatggg    480
tgtactcctc tacattatgc atgtagacag gggggccctg gttctgtaaa taacctactt    540
ggctttaatg tgtccattca ttccaaaagc aaagataaga aatcacctct gcattttgca    600
gccagttatg ggcgtatcaa tacctgtcag aggctcctac aagacataag tgatacgagg    660
cttctgaatg aaggggacct tcatggaatg actcctctcc atctggcagc aaagaatgga    720
catgataaag tagttcagct tcttctgaaa aaaggtgcat tgtttctcag atgggatgaa    780
tgtcttaagg tttttagtca ttattctcca aacaataaat gtccaatttt ggaaatgatc    840
gaatacctcc ctgaatgcat gaagaaagtt ctacccttct tttctaatgt tcacgtaaga    900
cctgctccaa accagaatca aataaaccat ggagaacaca ggttggctta cggatttata    960
gcccatatga taaatctagg attttactgt cttggtctca taccaatgac ctttcttgtt   1020
gtcagaataa aaccaggaat ggctttcaac tctgctggaa tcatcaataa aactagtgat   1080
cattcagaaa tactagataa catgaattca agtctaataa caatttgtat gattttagtt   1140
ttttgctcaa gtatattagg gtatgtcaaa gaagtggttc aaatttttcca acagaaaagg   1200
aattacttta tggatattag cagtagtact gaatggatta tcaacacgat gggccccatt   1260
ttagtgctgc ccttgttcac tgaaatagca gcccatctgc aatttgagaa ttgtggaatt   1320
ttcattgtta tattggaggt aatttttaaa actttgttga ggtctgcagt tgtatttttc   1380
ttccttcttt tggcttttgg actcagcttt tacgtcctcc tgaatttaca gtccttccta   1440
gaaccatttc tgaagaataa attggcacat ccagttctgt cctttgcaca gcttatttcc   1500
ttcacagtat ttgccccaat tgtcctcatg aatttactta ttggtttggc agttggtgac   1560
attgctgagg tccagaaaca tgcatcattg aagaggatag ctatgcagaa gctgccatgc   1620
tgttgcatac gcaaagtgga tcggaaatcc accgccgtat gtcccaacaa acccagatgt   1680
gatgggacat tatttcaagt cctactcgct ctaggccccc taccccctaga agaaaataga   1740
aacataaaaa gttttcttcc tactgagatc actgttaaga ggactcacga acaccttcct   1800
tctgcaggtt ttggtcatca tgggaaacat accttgtcct tgcttttggt agaagagtgg   1860
cttcctctga atgtagtaca ctcctcttgc tctgccttca gagtggttgg ccagatcttt   1920
cccattagac attttcagtg gattcatgtg aatgagccgc acactggcaa tttaaaagag   1980
aaattggctg ctccatacat cactcaccag atcaagccat tcttgcgagc agctggtttt   2040
tgcacagtga aggtggtcca gagagatgac atctctgtgt ggagtgtgga tttcaggtgg   2100
ctcaatgcat gggaagcagc gattcgaaag cagtctctca gacaatctga gatggaggaa   2160
ctgagctgct cgctgctgct gcgtgtcact gatgtgcaca caagaagctt gtattag      2217
```

<210> SEQ ID NO 142
<211> LENGTH: 738
<212> TYPE: PRT
<213> ORGANISM: Homo sapiens

<400> SEQUENCE: 142

-continued

```
Met Val Cys Thr Phe Asp Ser Glu Leu Leu Asn Cys Gln Arg Lys Asp
1               5                   10                  15

Glu Tyr Asn Gln Phe Gln Thr Tyr Arg Ala His Lys Ile Lys Ala Lys
            20                  25                  30

Arg Ser Ile Ala Thr Pro Glu Asn Leu Lys Lys Leu Leu Pro Arg Val
        35                  40                  45

Pro Lys Asn Ser Ala Leu Ser Asp Glu Met Thr Lys Leu His Lys Gly
    50                  55                  60

Ala Lys Pro Cys Lys Ser Asn Thr Phe Gly Cys Phe Pro Ile His Gln
65                  70                  75                  80

Ala Val Leu Ser Gly Ser Lys Glu Cys Met Glu Ile Ile Leu Lys Phe
                85                  90                  95

Gly Glu Glu His Gly Tyr Ser Arg Gln Cys His Ile Asn Phe Val Asp
            100                 105                 110

Asn Gly Lys Ala Ser Pro Leu His Leu Ala Val Gln Asn Gly Asp Leu
        115                 120                 125

Glu Met Met Lys Met Cys Leu Asp Asn Gly Val Gln Ile Asp Leu Val
    130                 135                 140

Glu Met Gln Gln Ile Lys Glu Leu Val Met Asp Glu Asp Asn Asp Gly
145                 150                 155                 160

Cys Thr Pro Leu His Tyr Ala Cys Arg Gln Gly Gly Pro Gly Ser Val
                165                 170                 175

Asn Asn Leu Leu Gly Phe Asn Val Ser Ile His Ser Lys Ser Lys Asp
            180                 185                 190

Lys Lys Ser Pro Leu His Phe Ala Ala Ser Tyr Gly Arg Ile Asn Thr
        195                 200                 205

Cys Gln Arg Leu Leu Gln Asp Ile Ser Asp Thr Arg Leu Leu Asn Glu
    210                 215                 220

Gly Asp Leu His Gly Met Thr Pro Leu His Leu Ala Ala Lys Asn Gly
225                 230                 235                 240

His Asp Lys Val Val Gln Leu Leu Leu Lys Lys Gly Ala Leu Phe Leu
                245                 250                 255

Arg Trp Asp Glu Cys Leu Lys Val Phe Ser His Tyr Ser Pro Asn Asn
            260                 265                 270

Lys Cys Pro Ile Leu Glu Met Ile Glu Tyr Leu Pro Glu Cys Met Lys
        275                 280                 285

Lys Val Leu Pro Phe Phe Ser Asn Val His Val Arg Pro Ala Pro Asn
    290                 295                 300

Gln Asn Gln Ile Asn His Gly Glu His Arg Leu Ala Tyr Gly Phe Ile
305                 310                 315                 320

Ala His Met Ile Asn Leu Gly Phe Tyr Cys Leu Gly Leu Ile Pro Met
                325                 330                 335

Thr Phe Leu Val Val Arg Ile Lys Pro Gly Met Ala Phe Asn Ser Ala
            340                 345                 350

Gly Ile Ile Asn Lys Thr Ser Asp His Ser Glu Ile Leu Asp Asn Met
        355                 360                 365

Asn Ser Ser Leu Ile Thr Ile Cys Met Ile Leu Val Phe Cys Ser Ser
    370                 375                 380

Ile Leu Gly Tyr Val Lys Glu Val Val Gln Ile Phe Gln Gln Lys Arg
385                 390                 395                 400

Asn Tyr Phe Met Asp Ile Ser Ser Ser Thr Glu Trp Ile Ile Asn Thr
                405                 410                 415
```

-continued

```
Met Gly Pro Ile Leu Val Leu Pro Leu Phe Thr Glu Ile Ala Ala His
            420                 425                 430

Leu Gln Phe Glu Asn Cys Gly Ile Phe Ile Val Ile Leu Glu Val Ile
        435                 440                 445

Phe Lys Thr Leu Leu Arg Ser Ala Val Val Phe Phe Phe Leu Leu Leu
    450                 455                 460

Ala Phe Gly Leu Ser Phe Tyr Val Leu Leu Asn Leu Gln Ser Phe Leu
465                 470                 475                 480

Glu Pro Phe Leu Lys Asn Lys Leu Ala His Pro Val Leu Ser Phe Ala
                485                 490                 495

Gln Leu Ile Ser Phe Thr Val Phe Ala Pro Ile Val Leu Met Asn Leu
            500                 505                 510

Leu Ile Gly Leu Ala Val Gly Asp Ile Ala Glu Val Gln Lys His Ala
        515                 520                 525

Ser Leu Lys Arg Ile Ala Met Gln Lys Leu Pro Cys Cys Cys Ile Arg
    530                 535                 540

Lys Val Asp Arg Lys Ser Thr Ala Val Cys Pro Asn Lys Pro Arg Cys
545                 550                 555                 560

Asp Gly Thr Leu Phe Gln Val Leu Leu Ala Leu Gly Pro Leu Pro Leu
                565                 570                 575

Glu Glu Asn Arg Asn Ile Lys Ser Phe Leu Pro Thr Glu Ile Thr Val
            580                 585                 590

Lys Arg Thr His Glu His Leu Pro Ser Ala Gly Phe Gly His His Gly
        595                 600                 605

Lys His Thr Leu Ser Leu Leu Leu Val Glu Glu Trp Leu Pro Leu Asn
    610                 615                 620

Val Val His Ser Ser Cys Ser Ala Phe Arg Val Val Gly Gln Ile Phe
625                 630                 635                 640

Pro Ile Arg His Phe Gln Trp Ile His Val Asn Glu Pro His Thr Gly
                645                 650                 655

Asn Leu Lys Glu Lys Leu Ala Ala Pro Tyr Ile Thr His Gln Ile Lys
            660                 665                 670

Pro Phe Leu Arg Ala Ala Gly Phe Cys Thr Val Lys Val Val Gln Arg
        675                 680                 685

Asp Asp Ile Ser Val Trp Ser Val Asp Phe Arg Trp Leu Asn Ala Trp
    690                 695                 700

Glu Ala Ala Ile Arg Lys Gln Ser Leu Arg Gln Ser Glu Met Glu Glu
705                 710                 715                 720

Leu Ser Cys Ser Leu Leu Leu Arg Val Thr Asp Val His Thr Arg Ser
                725                 730                 735

Leu Tyr
```

```
<210> SEQ ID NO 143
<211> LENGTH: 20
<212> TYPE: DNA
<213> ORGANISM: Artificial Sequence
<220> FEATURE:
<223> OTHER INFORMATION: Oligonucleotide

<400> SEQUENCE: 143

ttccttactc tccgctttcc                                                   20


<210> SEQ ID NO 144
<211> LENGTH: 20
<212> TYPE: DNA
<213> ORGANISM: Artificial Sequence
```

-continued

<220> FEATURE:
<223> OTHER INFORMATION: Oligonucleotide

<400> SEQUENCE: 144
aactttgtgg ataacgggaa 20

<210> SEQ ID NO 145
<211> LENGTH: 1155
<212> TYPE: DNA
<213> ORGANISM: Homo sapiens

<400> SEQUENCE: 145
atgcagtctc tcatctcgcc ggtgaccaag gcgatcctgg tggccctctt catcttcgcc 60
atcctcctca tcctctacgt gatcctctgg gacgcaccgg ggagagcggg tgagtgcgct 120
cgtgcgggcg ctttgggggg ccacggttgg ggagccccaa cttcggggag gacgcggaat 180
ccggacgcgg gactgaaccc gaggattcac ggagcccggg gctcccctat ggggcacggg 240
aagcggcaga tgcgcgtgca gagaggtccg tcccacccac cccctgggcg ccttgggtcc 300
aaggcgcata ggcgctcccg cctgtggccg ccaccggtgc agcagaacgc gggctctcgg 360
gtgggtccaa tgcgctatgg cacaccaggc gctatcgggt ccctagccct ctgctccggc 420
ggtggggacc ccgcactcaa gttccctata acctccatgg acaaacacgg aaaaatcatg 480
tcttggaaga acagcatcgc cctacagata cagactaggc actttgcaca tgaaacaaga 540
gtcccagaaa tttctagaag caaatctcgc attcgtgacc gccagaccta cgggatgtac 600
cactttggga attttggaga agaaagaata aaggcagaaa tgaggataca gaaagcatgt 660
cacttgaaga tcaagaagtc aagcttggat gccaatggta aagtggatga tggtgaggat 720
gatgatggtg aggatgatga tggtgaggat gatgatggtg atgatgatgg tgaggatgat 780
gatggtgagg atgatgatgg tgaggatgat gatggtgagg atgatggtga ggatgatgat 840
ggtgatgatg atggtgagga tgatgatggt gatgatgatg gtgatgatga tggtgaggat 900
gatgatggtg aggatgatga tggtgacagt gaggatgatg gtgaggatgg tgatgatgat 960
ggtgaggatg atgatggtga cagtgaggat gatggcgatg atggtgatga tgatggtgag 1020
gatgatgatc atggtgatga tgtgaggatg atgatgatga tggtgatgac agtgacgatg 1080
atgaagaatg ttgttggtaa ttacagactt cctgagctac caacttggac atctgtacaa 1140
cgatacaaat tttga 1155

<210> SEQ ID NO 146
<211> LENGTH: 384
<212> TYPE: PRT
<213> ORGANISM: Homo sapiens

<400> SEQUENCE: 146

Met Gln Ser Leu Ile Ser Pro Val Thr Lys Ala Ile Leu Val Ala Leu
1 5 10 15

Phe Ile Phe Ala Ile Leu Leu Ile Leu Tyr Val Ile Leu Trp Asp Ala
20 25 30

Pro Gly Arg Ala Gly Glu Cys Ala Arg Ala Gly Ala Leu Gly Gly His
35 40 45

Gly Trp Gly Ala Pro Thr Ser Gly Arg Thr Arg Asn Pro Asp Ala Gly
50 55 60

Leu Asn Pro Arg Ile His Gly Ala Arg Gly Ser Pro Met Gly His Gly
65 70 75 80

-continued

```
Lys Arg Gln Met Arg Val Gln Arg Gly Pro Ser His Pro Pro Pro Gly
                85                  90                  95

Arg Leu Gly Ser Lys Ala His Arg Arg Ser Arg Leu Trp Pro Pro Pro
            100                 105                 110

Val Gln Gln Asn Ala Gly Ser Arg Val Gly Pro Met Arg Tyr Gly Thr
        115                 120                 125

Pro Gly Ala Ile Gly Ser Leu Ala Leu Cys Ser Gly Gly Gly Asp Pro
    130                 135                 140

Ala Leu Lys Phe Pro Ile Thr Ser Met Asp Lys His Gly Lys Ile Met
145                 150                 155                 160

Ser Trp Lys Asn Ser Ile Ala Leu Gln Ile Gln Thr Arg His Phe Ala
                165                 170                 175

His Glu Thr Arg Val Pro Glu Ile Ser Arg Ser Lys Ser Arg Ile Arg
            180                 185                 190

Asp Arg Gln Thr Tyr Gly Met Tyr His Phe Gly Asn Phe Gly Glu Glu
        195                 200                 205

Arg Ile Lys Ala Glu Met Arg Ile Gln Lys Ala Cys His Leu Lys Ile
    210                 215                 220

Lys Lys Ser Ser Leu Asp Ala Asn Gly Lys Val Asp Asp Gly Glu Asp
225                 230                 235                 240

Asp Asp Gly Glu Asp Asp Asp Gly Glu Asp Asp Asp Gly Asp Asp Asp
                245                 250                 255

Gly Glu Asp Asp Asp Gly Glu Asp Asp Asp Gly Glu Asp Asp Asp Gly
            260                 265                 270

Glu Asp Asp Gly Glu Asp Asp Asp Gly Asp Asp Asp Gly Glu Asp Asp
        275                 280                 285

Asp Gly Asp Asp Asp Gly Asp Asp Asp Gly Glu Asp Asp Asp Gly Glu
    290                 295                 300

Asp Asp Asp Gly Asp Ser Glu Asp Asp Gly Glu Asp Gly Asp Asp Asp
305                 310                 315                 320

Gly Glu Asp Asp Asp Gly Asp Ser Glu Asp Asp Gly Asp Asp Gly Asp
                325                 330                 335

Asp Asp Gly Glu Asp Asp Asp His Gly Asp Asp Val Arg Met Met Met
            340                 345                 350

Met Met Val Met Thr Val Thr Met Met Lys Asn Val Val Gly Asn Tyr
        355                 360                 365

Arg Leu Pro Glu Leu Pro Thr Trp Thr Ser Val Gln Arg Tyr Lys Phe
    370                 375                 380
```

<210> SEQ ID NO 147
<211> LENGTH: 21
<212> TYPE: DNA
<213> ORGANISM: Artificial Sequence
<220> FEATURE:
<223> OTHER INFORMATION: Oligonucleotide

<400> SEQUENCE: 147
tccatgctgc cagcttcata c 21

<210> SEQ ID NO 148
<211> LENGTH: 21
<212> TYPE: DNA
<213> ORGANISM: Artificial Sequence
<220> FEATURE:
<223> OTHER INFORMATION: Oligonucleotide

<400> SEQUENCE: 148

-continued

```
ctcacaagtg atgagattga g                                              21


<210> SEQ ID NO 149
<211> LENGTH: 4384
<212> TYPE: DNA
<213> ORGANISM: Homo sapiens

<400> SEQUENCE: 149

aaacagacgc ataactgtgc attgttcttt gggattttga gagccttcat ctcaatttca     60

actttaaagc agcttaatct ttaaggaaca tatctctgat ctgggtaatt tgtagaactt    120

aatttgaggg tcattacatg tgaggatagc aggagttgaa gatgccaagg acctgaaggg    180

ctactggagg gacaggtgaa gtgatttgaa gatgtagcat tttgaatctc tttctggccc    240

atcctctgct tcacaccaga atcattgtga cctgtagacc tgcaaaacaa aggaccaaag    300

gttagcatgc agaagtgaaa gtgtcaataa taaccaaacc actccatcaa gttaggtctg    360

gggaaaagca gcagcaaaaa tgagttctta cttctgggca caaaatgaaa gtaacagacc    420

tgatttactc tgcgggcagc cagctgacta ccttgttgaa gagaaacatt tcacaacgct    480

tgtatgcttc attgttgttt tgggagggct tttgaagatg tgtttaaaga attgtgaagt    540

cattgttttg acgattcttt ctctatcagg attcgtgata ggacacatgg cctacaattc    600

tgttgaggtg caccaaattg tctaccctct tctaagaaca tcaagttttt cactttattc    660

ttacttttca cctttaatta tatttatggt tgctttggat gtagaatttt atacactcaa    720

gaaaatgttt tggcaggtct tgttaactgg attaattagc ttttctacag caagcatcat    780

aattggatat gtcgttataa aattcaataa agattcatgg gatttgcaat cttgcctact    840

ctttagcatc acccttggca ttatagatcc tcttcgttct gtgaattcac taaaaactat    900

tggcatttct aaaatataca ttgatctcat tagaggagaa tcattgatca tttgtagcat    960

cgcatcaatt ttttttggaa attttcgggg caacagaatc cacttttcta tttttagaga   1020

tttacatgta ggcattgaac tcagctatga catttttggga agcataatat ttggatattg   1080

gtgtgcaaaa atcattcagt gtatattggc tgacgttttt agcaatatgc tgactaatat   1140

cattctctgc ttttcaatgg tgtacatgac tttctatatt gtggaatttt taggaatgtc   1200

aggcactctt gccttagccg ctgtaggact gaatttagat tctttaactt ttaaaccgaa   1260

gatcgaactt gtaattacta agttcttaag aatttttttca tctgtatatg aacatttaat   1320

atatgctttc tttggcattg tgattggatg tggagaactc agccactatg aatttcacac   1380

tatacctttc atattcattt tatttacaac agtgaatttg gtaaggttgc ttactatttt   1440

gttagtgagc cctattttga tgcattcaaa ttatgaatat aattggcgat ggggagttgt   1500

aatcacgtgg tctggaatta aaggagtttt taatttactc tgggctcctg atgtttataa   1560

tctcgctgaa cgaaaagtgg aagtaccaca aatgtttata ctctatgtac aagtaatatc   1620

attattgaca atgggaataa attcatacgt gatgactcag tcagccagga agttagattt   1680

gtgtgttctt tccctcccaa gacaaatgat cttgcaaaat gccactcagc acatacagga   1740

gatagtacag aacacaataa ctttatttaa aacagaaaaa attttgacaa atgttaactg   1800

gaccttagta gaagataaaa cgaggatcga atacattcct ttttcccacg tttcacataa   1860

tgatatgaag acagaatcca caacagatga agctttaatg gaggaagcca gattgcatgt   1920

agctgcaata caaatgagta gctttgaaaa acagcgtaac aatggaattc ttgaaataga   1980

ggcagcccgg atattaattg gtgcagcaaa atgctattac tccatccaag gaaaattcat   2040

gagtatttat gatgtttcaa cttatatgag aactagaagt tggcttataa agtttaaaaa   2100
```

-continued

```
tgttttaact ttcttggaat attgtataga aaagatacat tttattccac ctgagagtaa   2160
tacatttctg acttttatat ttcacatagt attttctgaa gaatttgaat atacaggaca   2220
gattataaat ttgatatata tttatcctat gataatacat ctgtggccaa tggcaagagg   2280
tttaaatgta tcagcactga tatcaataaa ctactatttt atgtttttat atgtattaga   2340
atcaacattg aagataataa ttttgaaaag gaaatatttt caacaatgtt ggaatacttt   2400
ggaatttttt atcctggtta ttggaatcat tgatatcttt tgtgtatact ttgtgaaatt   2460
gagaccagac aacttggctc ttatacagct tacagtaata atgggatatt taagaataat   2520
taggtttctt cctctcttca agataatagt accaatactg ataagaattg cagatgtgca   2580
gatcaaaaag cgcctcagct tgatgtatag tattacaaaa ggctatatca aaagtcaaga   2640
agatgccaaa cttctaataa aacaaatagc tgtctgtgaa tcaatatatc agaaactatg   2700
tgaaattttg gaaaccaaca aacaggatgc tgtcaaagaa ttagtactca tggagcatga   2760
gggtcgtgat gttgtcattg ctttgaagac taaacaggca atccggaatg tgattgctaa   2820
agctctaaaa aatctcacct tcctttgttc aagaggcatt attgataagc atgaagtcat   2880
tgagataaat aaggtacttc ttaaaaaatt aaaagcacta aataactttc caaaggcaat   2940
cccaccccca actcctgaca tataccttca caacatcatt tggctggaag gtaaagatgt   3000
tctcattgac ttcttcaagg aaagagccaa acttgcctgt tttgactctg gagataccat   3060
ttgtaaagga ggtgaaatgc cacaaggaat ctacttaatt atttcaggaa tggcaatttt   3120
gcatagttta tctcctacct ttggaataga gagtaatcaa aggtgtgata gagggtccag   3180
agacatgttt acagagttct gtactactgg ggacataatt ggagagctaa gctgtctgct   3240
taagcgtgaa attgaatata ccgtcatctg tgaaactagt ttacaggcct gctttatctc   3300
cctggaggat ttatatgaag gctttgatgc cttctggcca tctctggaat ataaaatatg   3360
gctaaagctt gctctcagta ctgcctatca gtattttgaa tcaagtctta ttgatgagga   3420
cttaaggttt cagaactgtg tgatgttcaa tcaagcatat gtggaaactt tatcaagcta   3480
tagtgacatg attattgata atatgaccat gaaatttgtt atcattgtgt atggcagtgt   3540
aattgatact aagacagagg aaccatattt tgcaccttgc attataccta caacctgtga   3600
gcaggttcag ggaacttctg atttaagcaa gctgctgata atccaagcat ctgagcttac   3660
ccaaagaaat agtaacacca atgtcatggc ctcagtcaac acggtctttg aacaaccagg   3720
aaagaatata aatggaagac aaaagatgag ttgaaaactg gataccattt tagaaaaggg   3780
tattaatgat acaaatatga tgtgtggagt caggttaaag accaaactac tttcctcgct   3840
caaatactaa aggattatct gcaaggagtt tacttagaag ctactgaaac aggttactgc   3900
tgcatttagt ttataagcaa tggatggact tctgtaaaac ttcttaattt taagtagttg   3960
cattatattt gggatgttaa aaaagtcttc aggataatat aaaatacact gaaacatatg   4020
tcctaccaaa tgaaaccctg tttccagcta agagcaaatt ttaacatagt gcattataaa   4080
aagtgttgta taactgatat gttactctct aaagcataga acctgtaatt ttcatttgtg   4140
aaattgttat aattagtgcc tccctaatat tttcccgagt atagctattc tccccttccc   4200
agtttggtaa atattgaaaa acagaattat attccacaat cttagtaact ttcagtaagt   4260
aagtaacttt tgctttcagt gaaatttagg agaaattaat attctcatat tgcatagtac   4320
tgtttgatgt cacctttcat tttattttta aaaatcaaat aaagttgagt tttatggttg   4380
tcta                                                                4384
```

-continued

<210> SEQ ID NO 150
<211> LENGTH: 1124
<212> TYPE: PRT
<213> ORGANISM: Homo sapiens

<400> SEQUENCE: 150

```
Met Ser Ser Tyr Phe Trp Ala Gln Asn Glu Ser Asn Arg Pro Asp Leu
1               5                   10                  15

Leu Cys Gly Gln Pro Ala Asp Tyr Leu Val Glu Glu Lys His Phe Thr
            20                  25                  30

Thr Leu Val Cys Phe Ile Val Val Leu Gly Gly Leu Leu Lys Met Cys
        35                  40                  45

Leu Lys Asn Cys Glu Val Ile Val Leu Thr Ile Leu Ser Leu Ser Gly
    50                  55                  60

Phe Val Ile Gly His Met Ala Tyr Asn Ser Val Glu Val His Gln Ile
65                  70                  75                  80

Val Tyr Pro Leu Leu Arg Thr Ser Ser Phe Ser Leu Tyr Ser Tyr Phe
                85                  90                  95

Ser Pro Leu Ile Ile Phe Met Val Ala Leu Asp Val Glu Phe Tyr Thr
            100                 105                 110

Leu Lys Lys Met Phe Trp Gln Val Leu Leu Thr Gly Leu Ile Ser Phe
        115                 120                 125

Ser Thr Ala Ser Ile Ile Ile Gly Tyr Val Val Ile Lys Phe Asn Lys
    130                 135                 140

Asp Ser Trp Asp Leu Gln Ser Cys Leu Leu Phe Ser Ile Thr Leu Gly
145                 150                 155                 160

Ile Ile Asp Pro Leu Arg Ser Val Asn Ser Leu Lys Thr Ile Gly Ile
                165                 170                 175

Ser Lys Ile Tyr Ile Asp Leu Ile Arg Gly Glu Ser Leu Ile Ile Cys
            180                 185                 190

Ser Ile Ala Ser Ile Phe Phe Gly Asn Phe Arg Gly Asn Arg Ile His
        195                 200                 205

Phe Ser Ile Phe Arg Asp Leu His Val Gly Ile Glu Leu Ser Tyr Asp
    210                 215                 220

Ile Leu Gly Ser Ile Ile Phe Gly Tyr Trp Cys Ala Lys Ile Ile Gln
225                 230                 235                 240

Cys Ile Leu Ala Asp Val Phe Ser Asn Met Leu Thr Asn Ile Ile Leu
                245                 250                 255

Cys Phe Ser Met Val Tyr Met Thr Phe Tyr Ile Val Glu Phe Leu Gly
            260                 265                 270

Met Ser Gly Thr Leu Ala Leu Ala Ala Val Gly Leu Asn Leu Asp Ser
        275                 280                 285

Leu Thr Phe Lys Pro Lys Ile Glu Leu Val Ile Thr Lys Phe Leu Arg
    290                 295                 300

Ile Phe Ser Ser Val Tyr Glu His Leu Ile Tyr Ala Phe Phe Gly Ile
305                 310                 315                 320

Val Ile Gly Cys Gly Glu Leu Ser His Tyr Glu Phe His Thr Ile Pro
                325                 330                 335

Phe Ile Phe Ile Leu Phe Thr Thr Val Asn Leu Val Arg Leu Leu Thr
            340                 345                 350

Ile Leu Leu Val Ser Pro Ile Leu Met His Ser Asn Tyr Glu Tyr Asn
        355                 360                 365

Trp Arg Trp Gly Val Val Ile Thr Trp Ser Gly Ile Lys Gly Val Phe
    370                 375                 380
```

-continued

```
Asn Leu Leu Trp Ala Pro Asp Val Tyr Asn Leu Ala Glu Arg Lys Val
385                 390                 395                 400

Glu Val Pro Gln Met Phe Ile Leu Tyr Val Gln Val Ile Ser Leu Leu
                405                 410                 415

Thr Met Gly Ile Asn Ser Tyr Val Met Thr Gln Ser Ala Arg Lys Leu
            420                 425                 430

Asp Leu Cys Val Leu Ser Leu Pro Arg Gln Met Ile Leu Gln Asn Ala
        435                 440                 445

Thr Gln His Ile Gln Glu Ile Val Gln Asn Thr Ile Thr Leu Phe Lys
    450                 455                 460

Thr Glu Lys Ile Leu Thr Asn Val Asn Trp Thr Leu Val Glu Asp Lys
465                 470                 475                 480

Thr Arg Ile Glu Tyr Ile Pro Phe Ser His Val Ser His Asn Asp Met
                485                 490                 495

Lys Thr Glu Ser Thr Thr Asp Glu Ala Leu Met Glu Glu Ala Arg Leu
            500                 505                 510

His Val Ala Ala Ile Gln Met Ser Ser Phe Glu Lys Gln Arg Asn Asn
        515                 520                 525

Gly Ile Leu Glu Ile Glu Ala Ala Arg Ile Leu Ile Gly Ala Ala Lys
    530                 535                 540

Cys Tyr Tyr Ser Ile Gln Gly Lys Phe Met Ser Ile Tyr Asp Val Ser
545                 550                 555                 560

Thr Tyr Met Arg Thr Arg Ser Trp Leu Ile Lys Phe Lys Asn Val Leu
                565                 570                 575

Thr Phe Leu Glu Tyr Cys Ile Glu Lys Ile His Phe Ile Pro Pro Glu
            580                 585                 590

Ser Asn Thr Phe Leu Thr Phe Ile Phe His Ile Val Phe Ser Glu Glu
        595                 600                 605

Phe Glu Tyr Thr Gly Gln Ile Ile Asn Leu Ile Tyr Ile Tyr Pro Met
    610                 615                 620

Ile Ile His Leu Trp Pro Met Ala Arg Gly Leu Asn Val Ser Ala Leu
625                 630                 635                 640

Ile Ser Ile Asn Tyr Tyr Phe Met Phe Leu Tyr Val Leu Glu Ser Thr
                645                 650                 655

Leu Lys Ile Ile Ile Leu Lys Arg Lys Tyr Phe Gln Gln Cys Trp Asn
            660                 665                 670

Thr Leu Glu Phe Phe Ile Leu Val Ile Gly Ile Ile Asp Ile Phe Cys
        675                 680                 685

Val Tyr Phe Val Lys Leu Arg Pro Asp Asn Leu Ala Leu Ile Gln Leu
    690                 695                 700

Thr Val Ile Met Gly Tyr Leu Arg Ile Ile Arg Phe Leu Pro Leu Phe
705                 710                 715                 720

Lys Ile Ile Val Pro Ile Leu Ile Arg Ile Ala Asp Val Gln Ile Lys
                725                 730                 735

Lys Arg Leu Ser Leu Met Tyr Ser Ile Thr Lys Gly Tyr Ile Lys Ser
            740                 745                 750

Gln Glu Asp Ala Lys Leu Leu Ile Lys Gln Ile Ala Val Cys Glu Ser
        755                 760                 765

Ile Tyr Gln Lys Leu Cys Glu Ile Leu Glu Thr Asn Lys Gln Asp Ala
    770                 775                 780

Val Lys Glu Leu Val Leu Met Glu His Glu Gly Arg Asp Val Val Ile
785                 790                 795                 800
```

-continued

```
Ala Leu Lys Thr Lys Gln Ala Ile Arg Asn Val Ile Ala Lys Ala Leu
                805                 810                 815

Lys Asn Leu Thr Phe Leu Cys Ser Arg Gly Ile Ile Asp Lys His Glu
            820                 825                 830

Val Ile Glu Ile Asn Lys Val Leu Leu Lys Lys Leu Lys Ala Leu Asn
        835                 840                 845

Asn Phe Pro Lys Ala Ile Pro Pro Pro Thr Pro Asp Ile Tyr Leu His
    850                 855                 860

Asn Ile Ile Trp Leu Glu Gly Lys Asp Val Leu Ile Asp Phe Phe Lys
865                 870                 875                 880

Glu Arg Ala Lys Leu Ala Cys Phe Asp Ser Gly Asp Thr Ile Cys Lys
                885                 890                 895

Gly Gly Glu Met Pro Gln Gly Ile Tyr Leu Ile Ile Ser Gly Met Ala
            900                 905                 910

Ile Leu His Ser Leu Ser Pro Thr Phe Gly Ile Glu Ser Asn Gln Arg
        915                 920                 925

Cys Asp Arg Gly Ser Arg Asp Met Phe Thr Glu Phe Cys Thr Thr Gly
    930                 935                 940

Asp Ile Ile Gly Glu Leu Ser Cys Leu Leu Lys Arg Glu Ile Glu Tyr
945                 950                 955                 960

Thr Val Ile Cys Glu Thr Ser Leu Gln Ala Cys Phe Ile Ser Leu Glu
                965                 970                 975

Asp Leu Tyr Glu Gly Phe Asp Ala Phe Trp Pro Ser Leu Glu Tyr Lys
            980                 985                 990

Ile Trp Leu Lys Leu Ala Leu Ser  Thr Ala Tyr Gln Tyr  Phe Glu Ser
        995                 1000                1005

Ser Leu  Ile Asp Glu Asp Leu  Arg Phe Gln Asn Cys  Val Met Phe
    1010                 1015                 1020

Asn Gln  Ala Tyr Val Glu Thr  Leu Ser Ser Tyr Ser  Asp Met Ile
    1025                 1030                 1035

Ile Asp  Asn Met Thr Met Lys  Phe Val Ile Ile Val  Tyr Gly Ser
    1040                 1045                 1050

Val Ile  Asp Thr Lys Thr Glu  Glu Pro Tyr Phe Ala  Pro Cys Ile
    1055                 1060                 1065

Ile Pro  Thr Thr Cys Glu Gln  Val Gln Gly Thr Ser  Asp Leu Ser
    1070                 1075                 1080

Lys Leu  Leu Ile Ile Gln Ala  Ser Glu Leu Thr Gln  Arg Asn Ser
    1085                 1090                 1095

Asn Thr  Asn Val Met Ala Ser  Val Asn Thr Val Phe  Glu Gln Pro
    1100                 1105                 1110

Gly Lys  Asn Ile Asn Gly Arg  Gln Lys Met Ser
    1115                 1120
```

<210> SEQ ID NO 151
<211> LENGTH: 21
<212> TYPE: DNA
<213> ORGANISM: Artificial Sequence
<220> FEATURE:
<223> OTHER INFORMATION: Oligonucleotide

<400> SEQUENCE: 151
ctacaacctg tgagcaggtt c 21

<210> SEQ ID NO 152
<211> LENGTH: 21
<212> TYPE: DNA

-continued

<213> ORGANISM: Artificial Sequence
<220> FEATURE:
<223> OTHER INFORMATION: Oligonucleotide

<400> SEQUENCE: 152
cctgtttcag tggcttctaa g 21

<210> SEQ ID NO 153
<211> LENGTH: 1189
<212> TYPE: DNA
<213> ORGANISM: Homo sapiens

<400> SEQUENCE: 153
ctatgccttc tgaccccgtc ttggacttca actgggagaa tgtggagcca tttgaacagg 60
ctcctcttct ggagcatatt ttcttctgtc acttgtagaa aagctgtatt ggattgtgag 120
gcaatgaaaa caaatgaatt cccttctcca tgtttggact caaagactaa ggtggttatg 180
aagggtcaaa atgtatctat gttttgttcc cataagaaca aatcactgca gatcacctat 240
tcattgtttc gacgtaagac acacctggga acccaggatg gaaaaggtga acctgcgatt 300
tttaacctaa gcatcacaga agcccatgaa tcaggcccct acaaatgcaa agcccaagtt 360
accagctgtt caaaatacag tcgtgacttc agcttcacga ttgtcgaccc ggtgacttcc 420
ccagtgctga acattatggt cattcaaaca gaaacagacc gacatataac attacattgc 480
ctctcagtca atggctcgct gcccatcaat tacactttct ttgaaaacca tgttgccata 540
tcaccagcta tttccaagta tgacagggag cctgctgaat ttaacttaac caagaagaat 600
cctggagaag aggaagagta taggtgtgaa gctaaaaaca gattgcctaa ctatgcaaca 660
tacagtcacc ctgtcaccat gccctcaaca ggcggagaca gctgtccttt ctgtctgaag 720
ctactacttc cagggttatt actgttgctg gtggtgataa tcctaattct ggctttttgg 780
gtactgccca aatacaaaac aagaaaagct atgagaaata atgtgcccag ggaccgtgga 840
gacacagcca tggaagttgg aatctatgca aatatccttg aaaaacaagc aaaggaggaa 900
tctgtgccag aagtgggatc caggccgtgt gtttccacag cccaagatga ggccaaacac 960
tcccaggagc tacagtatgc caccccccgtg ttccaggagg tggcaccaag agagcaagaa 1020
gcctgtgatt cttataaatc tggatatgtc tattctgaat cctgacctca gatgatctgc 1080
ctgcctcggc ctcccaaagt gctggaacta caagcctgag ccaccgtgcc cggccctgaa 1140
tcgctttagt aaataaaggg tctccaagaa taaattcatc cgaacatgc 1189

<210> SEQ ID NO 154
<211> LENGTH: 341
<212> TYPE: PRT
<213> ORGANISM: Homo sapiens

<400> SEQUENCE: 154

Met Trp Ser His Leu Asn Arg Leu Leu Phe Trp Ser Ile Phe Ser Ser
1 5 10 15

Val Thr Cys Arg Lys Ala Val Leu Asp Cys Glu Ala Met Lys Thr Asn
20 25 30

Glu Phe Pro Ser Pro Cys Leu Asp Ser Lys Thr Lys Val Val Met Lys
35 40 45

Gly Gln Asn Val Ser Met Phe Cys Ser His Lys Asn Lys Ser Leu Gln
50 55 60

Ile Thr Tyr Ser Leu Phe Arg Arg Lys Thr His Leu Gly Thr Gln Asp
65 70 75 80

-continued

```
Gly Lys Gly Glu Pro Ala Ile Phe Asn Leu Ser Ile Thr Glu Ala His
                85                  90                  95

Glu Ser Gly Pro Tyr Lys Cys Lys Ala Gln Val Thr Ser Cys Ser Lys
            100                 105                 110

Tyr Ser Arg Asp Phe Ser Phe Thr Ile Val Asp Pro Val Thr Ser Pro
        115                 120                 125

Val Leu Asn Ile Met Val Ile Gln Thr Glu Thr Asp Arg His Ile Thr
    130                 135                 140

Leu His Cys Leu Ser Val Asn Gly Ser Leu Pro Ile Asn Tyr Thr Phe
145                 150                 155                 160

Phe Glu Asn His Val Ala Ile Ser Pro Ala Ile Ser Lys Tyr Asp Arg
                165                 170                 175

Glu Pro Ala Glu Phe Asn Leu Thr Lys Lys Asn Pro Gly Glu Glu Glu
            180                 185                 190

Glu Tyr Arg Cys Glu Ala Lys Asn Arg Leu Pro Asn Tyr Ala Thr Tyr
        195                 200                 205

Ser His Pro Val Thr Met Pro Ser Thr Gly Gly Asp Ser Cys Pro Phe
    210                 215                 220

Cys Leu Lys Leu Leu Leu Pro Gly Leu Leu Leu Leu Leu Val Val Ile
225                 230                 235                 240

Ile Leu Ile Leu Ala Phe Trp Val Leu Pro Lys Tyr Lys Thr Arg Lys
                245                 250                 255

Ala Met Arg Asn Asn Val Pro Arg Asp Arg Gly Asp Thr Ala Met Glu
            260                 265                 270

Val Gly Ile Tyr Ala Asn Ile Leu Glu Lys Gln Ala Lys Glu Glu Ser
        275                 280                 285

Val Pro Glu Val Gly Ser Arg Pro Cys Val Ser Thr Ala Gln Asp Glu
    290                 295                 300

Ala Lys His Ser Gln Glu Leu Gln Tyr Ala Thr Pro Val Phe Gln Glu
305                 310                 315                 320

Val Ala Pro Arg Glu Gln Glu Ala Cys Asp Ser Tyr Lys Ser Gly Tyr
                325                 330                 335

Val Tyr Ser Glu Ser
            340


<210> SEQ ID NO 155
<211> LENGTH: 21
<212> TYPE: DNA
<213> ORGANISM: Artificial Sequence
<220> FEATURE:
<223> OTHER INFORMATION: Oligonucleotide

<400> SEQUENCE: 155

gaggaatctg tgccagaagt g                                                21


<210> SEQ ID NO 156
<211> LENGTH: 21
<212> TYPE: DNA
<213> ORGANISM: Artificial Sequence
<220> FEATURE:
<223> OTHER INFORMATION: Oligonucleotide

<400> SEQUENCE: 156

acagagtgag actccatcct g                                                21


<210> SEQ ID NO 157
<211> LENGTH: 2713
<212> TYPE: DNA
```

-continued

<213> ORGANISM: Homo sapiens

<400> SEQUENCE: 157
gggcttggct ggggtgctca gcccaatttt ccgtgtaggg agcgggcggc ggcgggggag 60
gcagaggcgg aggcggagtc aagagcgcac cgccgcgccc gccgtgccgg gcctgagctg 120
gagccgggcg tgagtcgcag caggagccgc agccggagtc acagccgcag ccagagccgc 180
agccaaagcc tcagagagca ggagttggag cgcaggccct gctggatccg cgcctagctc 240
gccgccaggc accggccgga ggacgggccg tggtgtcagc tcactgcccg ggcgctgtgg 300
gaggcagcga gcccgcgacc ccccgggccg ggcaccgcca ggcgcggagc ccagatcgcc 360
cccctgccag gcctggtcac ggccagagca cgcaggagtt cccagggtct ggatctgcgc 420
gcaccctaat gacctgggga ctgaagagaa aaaaggaacg aggatttcat ctaaaagcat 480
aacgtgggca ctaggcgagg aggaaagtgg agaccacctg gcacggggca gaggtgcctg 540
gagcccacgc ttgagcatcg gagaccctgg catcctagca gccgcgacct tggctctgcc 600
ctgtctgagc tggaaacaca gcttagcttc tagacatcgc tggcacaggc ctggcacaag 660
taagcagtgt cctcacctgt ctgaaacggg acacggggtc ggaggaacca ggatctagcc 720
tggccccaag cggaactctc tggtggccca gaggtcgtca ctggggagcc cgcctcctgc 780
cctagcctca ctggtgcgga tgtgccgctg cccgccggag caccatgatg gcaggatgac 840
ctcagccgaa gtaggagcag cagctggtgg tgctcaggcg gctgggcccc ccgagtggcc 900
ccctggcagc cctcaggccc tccggcagcc tggccgggcc cgagtggcca tggcagcact 960
ggtgtggctg ctggcgggag ccagcatgtc aagcctcaac aagtggatct tcacagtgca 1020
cggctttggg cggcccctgc tgctgtcggc cctgcacatg ctggtggcag ccctggcatg 1080
ccaccggggg gcacggcgcc ccatgccagg cggcactcgc tgccgagtcc tactgctcag 1140
tctcaccttt ggcacgtcca tggcctgcgg caacgtgggc ctaagggctg tgcccctgga 1200
cctggcacaa ctggttacta ccaccacacc tctgttcacc ctggccctgt cggcgctgct 1260
gctgggccgc cgccaccacc cacttcagtt ggccgccatg ggtccgctct gcctgggggc 1320
cgcctgcagc ctggctggag agttccggac accccctacc ggctgtggct tcctgctcgc 1380
agccacctgc ctccgcggac tcaagtcggt tcagcaaagt gccctgctgc aggaggagag 1440
gctggacgcg gtgaccctgc tttacgccac ctcgctgccc agcttctgcc tgctggcggg 1500
tgcagccctg gtgctggagg ctggcgttgc cccaccgccc actgctggcg actctcgcct 1560
ctgggcctgc atcctgctca gctgcctcct gtctgttctc tataacctgg ccagcttctc 1620
cctgctggcc ctcacctctg ccctcaccgt ccacgtcctg ggcaacctca ccgtggtggg 1680
caacctcatc ctgtcccggc tgttgtttgg cagccgcctc agtgccctca gctacgtggg 1740
catcgcactc actctttcag gaatgttcct ttaccacaac tgcgagttcg tggcctcctg 1800
ggctgcccgt cgggggctgt ggcggaggga ccagcccagc aagggtcttt gagacctggg 1860
ggatctcagg agccacctgg gatggccctg gcctgaatcc agcctccgct gtggccatag 1920
aaggaatgga gaacagggct gggcatggtg gctcacgcct ataatcccag cacttccaga 1980
gtccgaggtg ggtggatcac ctgaggccag gagttcgaga ccagcctggc taacatggca 2040
aaacctcatc tctactaaaa atagaaaaat tagctgggca tggtggcgcg tgcctatagt 2100
cccagctaca tgggaggcta aggtgggagg atcacttgag ccctggagat cgaggctgca 2160
gtaagccaag atcgcatgct actgcactcc agcctgggag acagagcgag acgctgtctc 2220
aattaaaaaa aaaaaaaagt ggagaactgg cagtgacctc tactgggggc catggcaggg 2280

```
aggggagcct tctggaaggg ctgccttgga gattggaatg gggactccca gggagacctg   2340

cgttccatcc ctgcctgcct cacccctgcc acagactctg cacaccactg gatggtgggt   2400

ccaagcctgg cacagtccct gtgcttgtca gagtcattat tatgattaat atcaattacg   2460

atgccaaaaa ttgctgggca aactttgaag acctcaactt gttacaatga cgatgatgat   2520

gattcttggc ggttacacaa tccttcctcc tggggggggag gcagctagga ggcccagcag   2580

gggggcttct atgctgctgg gctcccctag ggagttgggg tagtctgtgc caactccagg   2640

cagctgctgt ggcctcaccc ctgggccccc caattttggg tcatccatcc tcaaatacac   2700

tatttttgct tgt                                                      2713


<210> SEQ ID NO 158
<211> LENGTH: 350
<212> TYPE: PRT
<213> ORGANISM: Homo sapiens

<400> SEQUENCE: 158

Met Cys Arg Cys Pro Pro Glu His His Asp Gly Arg Met Thr Ser Ala
1               5                   10                  15

Glu Val Gly Ala Ala Ala Gly Gly Ala Gln Ala Ala Gly Pro Pro Glu
            20                  25                  30

Trp Pro Pro Gly Ser Pro Gln Ala Leu Arg Gln Pro Gly Arg Ala Arg
        35                  40                  45

Val Ala Met Ala Ala Leu Val Trp Leu Leu Ala Gly Ala Ser Met Ser
    50                  55                  60

Ser Leu Asn Lys Trp Ile Phe Thr Val His Gly Phe Gly Arg Pro Leu
65                  70                  75                  80

Leu Leu Ser Ala Leu His Met Leu Val Ala Ala Leu Ala Cys His Arg
                85                  90                  95

Gly Ala Arg Arg Pro Met Pro Gly Gly Thr Arg Cys Arg Val Leu Leu
            100                 105                 110

Leu Ser Leu Thr Phe Gly Thr Ser Met Ala Cys Gly Asn Val Gly Leu
        115                 120                 125

Arg Ala Val Pro Leu Asp Leu Ala Gln Leu Val Thr Thr Thr Thr Pro
    130                 135                 140

Leu Phe Thr Leu Ala Leu Ser Ala Leu Leu Leu Gly Arg Arg His His
145                 150                 155                 160

Pro Leu Gln Leu Ala Ala Met Gly Pro Leu Cys Leu Gly Ala Ala Cys
                165                 170                 175

Ser Leu Ala Gly Glu Phe Arg Thr Pro Pro Thr Gly Cys Gly Phe Leu
            180                 185                 190

Leu Ala Ala Thr Cys Leu Arg Gly Leu Lys Ser Val Gln Gln Ser Ala
        195                 200                 205

Leu Leu Gln Glu Glu Arg Leu Asp Ala Val Thr Leu Leu Tyr Ala Thr
    210                 215                 220

Ser Leu Pro Ser Phe Cys Leu Leu Ala Gly Ala Ala Leu Val Leu Glu
225                 230                 235                 240

Ala Gly Val Ala Pro Pro Pro Thr Ala Gly Asp Ser Arg Leu Trp Ala
                245                 250                 255

Cys Ile Leu Leu Ser Cys Leu Leu Ser Val Leu Tyr Asn Leu Ala Ser
            260                 265                 270

Phe Ser Leu Leu Ala Leu Thr Ser Ala Leu Thr Val His Val Leu Gly
        275                 280                 285
```

-continued

```
Asn Leu Thr Val Val Gly Asn Leu Ile Leu Ser Arg Leu Leu Phe Gly
    290                 295                 300

Ser Arg Leu Ser Ala Leu Ser Tyr Val Gly Ile Ala Leu Thr Leu Ser
305                 310                 315                 320

Gly Met Phe Leu Tyr His Asn Cys Glu Phe Val Ala Ser Trp Ala Ala
                325                 330                 335

Arg Arg Gly Leu Trp Arg Arg Asp Gln Pro Ser Lys Gly Leu
            340                 345                 350
```

<210> SEQ ID NO 159
<211> LENGTH: 21
<212> TYPE: DNA
<213> ORGANISM: Artificial Sequence
<220> FEATURE:
<223> OTHER INFORMATION: Oligonucleotide

<400> SEQUENCE: 159
caagtcggtt cagcaaagtg c 21

<210> SEQ ID NO 160
<211> LENGTH: 21
<212> TYPE: DNA
<213> ORGANISM: Artificial Sequence
<220> FEATURE:
<223> OTHER INFORMATION: Oligonucleotide

<400> SEQUENCE: 160
cctgaaagag tgagtgcgat g 21

<210> SEQ ID NO 161
<211> LENGTH: 963
<212> TYPE: DNA
<213> ORGANISM: Homo sapiens

<400> SEQUENCE: 161

```
gactacacaa ggactgaacc agaaggaaga ggacagagca aagccatgaa catcatccta      60

gaaatccttc tgcttctgat caccatcatc tactcctact tggagtcgtt ggtgaagttt     120

ttcattcctc agaggagaaa atctgtggct ggggagattg ttctcattac tggagctggg     180

catggaatag gcaggcagac tacttatgaa tttgcaaaac gacagagcat attggttctg     240

tgggatatta ataagcgcgg tgtggaggaa actgcagctg agtgccgaaa actaggcgtc     300

actgcgcatg cgtatgtggt agactgcagc aacagagaag agatctatcg ctctctaaat     360

caggtgaaga aagaagtggg tgatgtaaca atcgtggtga ataatgctgg gacagtatat     420

ccagccgatc ttctcagcac caaggatgaa gagattacca agacatttga ggtcaacatc     480

ctaggacatt tttggatcac aaaagcactt cttccatcga tgatggagag aaatcatggc     540

cacatcgtca cagtggcttc agtgtgcggc cacgaaggga ttccttacct catcccatat     600

tgttccagca aatttgccgc tgttggcttt cacagaggtc tgacatcaga acttcaggcc     660

ttgggaaaaa ctggtatcaa aacctcatgt ctctgcccag tttttgtgaa tactgggttc     720

accaaaaatc caagcacaag attatggcct gtattggaga cagatgaagt cgtaagaagt     780

ctgatagatg gaatacttac caataagaaa atgatttttg ttccatcgta tatcaatatc     840

tttctgagac tacagaatcc tgataatatt aaaaacattg gtttggcact agcagcagtc     900

aaacgaacaa gattaattac ctgtcttcct gtttctcaag aatatttacg tagtttttca     960

tag                                                                   963
```

-continued

<210> SEQ ID NO 162
<211> LENGTH: 305
<212> TYPE: PRT
<213> ORGANISM: Homo sapiens

<400> SEQUENCE: 162

```
Met Asn Ile Ile Leu Glu Ile Leu Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Asn Pro
            260                 265                 270

Asp Asn Ile Lys Asn Ile Gly Leu Ala Leu Ala Ala Val Lys Arg Thr
        275                 280                 285

Arg Leu Ile Thr Cys Leu Pro Val Ser Gln Glu Tyr Leu Arg Ser Phe
    290                 295                 300

Ser
305
```

<210> SEQ ID NO 163
<211> LENGTH: 21
<212> TYPE: DNA
<213> ORGANISM: Artificial Sequence
<220> FEATURE:
<223> OTHER INFORMATION: Oligonucleotide

<400> SEQUENCE: 163
ggtctgacat cagaacttca g 21

-continued

<210> SEQ ID NO 164
<211> LENGTH: 21
<212> TYPE: DNA
<213> ORGANISM: Artificial Sequence
<220> FEATURE:
<223> OTHER INFORMATION: Oligonucleotide

<400> SEQUENCE: 164
tgcatacatc tctggctgga g 21

<210> SEQ ID NO 165
<211> LENGTH: 6014
<212> TYPE: DNA
<213> ORGANISM: Homo sapiens

<400> SEQUENCE: 165
cacccggaag gagcggtgtg agcggtccaa ggagccccgc aggtttgcct cggagatgaa 60
gcagtgtgtc cggctgacgg tccatcccaa caatatctcc gtctctcagt acaacgtgct 120
gctggtcctg gagacgtaca atgtcccgga gctgtcagct ggcgtcaact gcacctttga 180
ggacctgtca gagatggatg ggctggtcgt gggcaatcag atccagtgct actcccctgc 240
agccaaggag gtgccccgga tcatcacaga gaatggggac caccatgtcg tacagcttca 300
gctcaaatca aaggagaccg gcatgacctt cgccagcacc agctttgtct tctacaattg 360
cagcgtccac aattcgtgcc tgtcctgcgt ggagagtcca taccgctgcc actggtgtaa 420
ataccggcat gtctgcaccc atgaccccaa gacctgctcc ttccaggaag gccgagtgaa 480
gctgcccgag gactgccccc agctgctgcg agtggacaag atcctggtgc ccgtggaggt 540
gatcaagcct atcacgctga aggccaagaa cctcccccag ccccagtctg ggcagcgtgg 600
ctacgaatgc atcctcaaca ttcagggcag cgagcagcga gtgcccgccc tgcgcttcaa 660
cagctccagc gtacagtgcc agaacacctc ttattcctat gaagggatgg agatcaacaa 720
cctgcccgtg gagttgacag tcgtgtggaa tgggcacttc aacattgaca acccagctca 780
gaataaagtt cacctctaca agtgtggagc catgcgtgag agctgcgggc tgtgcctcaa 840
ggctgaccca gacttcgcat gtggctggtg ccagggccca ggccagtgca ccctgcgcca 900
gcactgccct gcccaggaga gccagtggct ggagctgtct ggtgccaaaa gcaagtgcac 960
aaacccccgc atcacagaga taatcccggt gacaggcccc cgggaagggg gcaccaaggt 1020
cactatccga ggggagaacc tgggcctgga atttcgcgac atcgcctccc atgtcaaggt 1080
tgctggcgtg gagtgcagcc ctttagtgga tggttacatc cctgcagaac agatcgtgtg 1140
tgagatgggg gaggccaagc ccagccagca tgcaggcttc gtggagatct gcgtggctgt 1200
gtgtcggcct gaattcatgg cccggtcctc acagctctat tacttcatga cactgactct 1260
ctcagatctg aagcccagcc gggggcccat gtccggaggg acccaagtga ccatcacagg 1320
caccaacctg aatgccggaa gcaacgtggt ggtgatgttt ggaaagcagc cctgtctctt 1380
ccacaggcga tctccatcct acattgtctg caacaccaca tcctcagatg aggtgctaga 1440
gatgaaggtg tcggtgcagg tggacagggc caagatccac caggacctgg tctttcagta 1500
tgtggaagac cccaccatcg tgcggattga gccagaatgg agcattgtca gtggaaacac 1560
acccatcgcc gtatgggga cccacctgga cctcatacag aacccccaga tccgtgccaa 1620
gcatggaggg aaggagcaca tcaatatctg tgaggttctg aacgctactg agatgacctg 1680
tcaggcgccc gccctcgctc tgggtcctga ccaccagtca gacctgaccg agaggcccga 1740
ggagtttggc ttcatcctgg acaacgtcca gtccctgctc atcctcaaca agaccaactt 1800

-continued

```
cacctactat cccaacccgg tgtttgaggc ctttggtccc tcaggaatcc tggagctcaa   1860
gcctggcacg cccatcatcc taaagggcaa gaacctgatc ccgcctgtgg ctgggggcaa   1920
cgtgaagctg aactacactg tgctggttgg ggagaagccg tgcaccgtga ccgtgtcaga   1980
tgtccagctg ctctgcgagt cccccaacct catcggcagg cacaaagtga tggcccgtgt   2040
cggtggcatg gagtactccc cggggatggt gtacattgcc ccggacagcc cgctcagcct   2100
gcccgccatc gtcagcatcg cagtggctgg cggcctcctc atcattttca tcgtggccgt   2160
gctcattgcc tataaacgca agtcccgcga aagtgacctc acgctgaagc ggctgcagat   2220
gcagatggac aacctggagt cccgtgtggc cctggagtgc aaggaaggta ctgagtggcc   2280
ccatgctgga ggccatgtgt gtgtgcgtgt gtgcatatgt gtgtgcatgc acatctgtgt   2340
atgtgtatgc atatgtttca tatacaaaca agcaggctgg gcagcagtgg gcagtgctgg   2400
aggctggcgg tgtgtgtgtc tgtgcgaatg tgtgtgtgtg catgtgtgtg tgtgcacatc   2460
tgtatgtata tatgtttcat atacaagcaa gcaggccggg cagcagtgag cagtgctgga   2520
ggctgtatat gtgtctgtgt gcgtgcgcat ctgtgtatgt gtatatgttt catgtacaag   2580
caagcaggcc gggcagcagt gggcagtgct ggaggctctg tgtgtgcgtg tgcatgtgtg   2640
tgtatgtatg tgtatgtgtt ccatttacaa gcaagcaggc caggcaactg tgagcagtgc   2700
tggaggctgt gtgcgcgtgt gtgtgtgtat gtgtatgtgt ttcatttaca agcaagcagg   2760
ccaggcagct gtgagcagtg ctggaggctg tgtgtgtgtg tgtgtgagca cgcacgtgtg   2820
tgagcacgca cgtgtatgtg tatgtgtgtc atttacaagc aagcaggcca ggcagctgtg   2880
agcagtgctg gaggccgtgt gtgtgtgtgt gtgtgtgtgt gcgcgcgcgc ctgtatatgt   2940
gtatgtgttt catttacaag caagcaggcc aggcagctgt gggcagtgct ggaggctgtg   3000
tgtgtgtgca cgtgtgtgta tgcgtatgtg tttcatttac aagcaagcag gccaggcagc   3060
tgtgggcagt gctggaggct gtgtgtgtgt gtgtgtgtgt gtgtgtgtat atatgtgtat   3120
gtgtatgtgt ttcatttaca agcaagcagc ccaggcagct gtgggcagtg ctggaggctg   3180
tgtgtgtgtg tgtgtgtgtg tgtgtatgtg tttcatttac aagtgtgtgt gtgtgtgtgt   3240
atgtgtatgt gtatgtgttt catttacaag caagcaggcc aggcagctgt gggcaatgct   3300
ggaggctgtg catcctacct gcatacctgc aaagcctctc actctatagt ccctatgcct   3360
gtgtcccaga ccacacccat acccaagcag gccccaccct ggcaacacca gagaggccaa   3420
ggtctccttg ccctctcctt gaaggtgtag tgattagaat ctcttttatg tgtggcaggc   3480
acacagcttt gaatgttgga ggcgcttggt gacttaaagg aaagctgcag actgataaaa   3540
agccaactcc ctccttctgc tccctgtggg ccgagcaccc caactgggag gggcagccg    3600
aggggagctc ccacccagga ttgtcacctt caccccacta gagcaccttc accccactag   3660
agcagcctcc atacctggaa tcctggttga gtgggttttg cactctactc gaggggaggt   3720
ctgggggtgt cttaacatga cgcatttcag caatctccag ctttcttcct ctagcaggaa   3780
ggtaaggctg tagggctgat ctgtgattta gaaggaaggg tgtttcaaag cttgtattaa   3840
aaaaattaca aacaccacca taaagtgaaa tcagctgcac taaatccaag aaggaaattt   3900
aggagtcaga ctcttgtaac ccccaggata tcattttgtg actcatcctg ggaggatctg   3960
agctggttct ttgctgtaga tttgtacatg gagtaaatcc ggccccatac ctggggctct   4020
cacttcacac cgattcccac cagggcagcc acggctcttt ttgatgggga agtggatcca   4080
ttccatcccc tctctacatc cttcagctgt caacacagca tccgccttgt gggactgtta   4140
```

-continued

```
attactgcct tttattatat ttacgctgct taattttttt ctccgcaatg tactctttcc   4200

tctaattagg tgtagtgatt agaatctctt ttatgtgtgg caggcacgca gctttgaatg   4260

ttggaggcgc ttggtgactt aaaggaaagc tgcagactga taaaaagcca acaccctcct   4320

tctgctccct gtgggccgag caccccaact gggagggagc agccgatggg agctcccacc   4380

caggattgtc agctgaggcc ccaggaggaa accttggctt cagactttag gggcgagcta   4440

tgctgtgcac gtaggaagaa ggggtcttac agcaaaggac ttgtcagact agccacagag   4500

gcactttgca gcttgcccag agccagccac tgaacgttta cagggctgca ctggcccaag   4560

ccaaggggtc tccttgaaga cttcacagca agccaggacg tcctctacac aaactcagaa   4620

gacacccagc tgggcccttc atgggcctaa gcttctgata tataaacata cccgtgtatt   4680

tacaaacact cccacacagg cccacacacc ctcactgaca tacactcatg gactcacaca   4740

tacactcaca tgcacacatg catgcacact cacatacact cactcgtgca ctcacacata   4800

catgcccaca catagtgaca tgctcacaca ctcatgcttt cacatacata cactcactga   4860

catacactca tgtgctcaca cgctcatgta ctcacattcg tacacacaca ctgacatata   4920

cttacacact cacacttgca catgcataca catgcactca catgcacaca tgcatgcaca   4980

ctcatacact cacgcactca acttgcaggc gtgcacacac atgcccacat actcatgcac   5040

tcacattcac acatgcgtgc acacatagac gcatgcactc acacatgcat acacacagac   5100

atacacatgc actcacattc gtacttgcat acacaccaac acacatatgc acactcacac   5160

tgacaagcat acacacacac tcatgcactc acacccacgc aggcactcac attcacacac   5220

atacacactc attgacatac attcattcac atccatgcac tcacattcac acatgcatac   5280

acactgacat tcacacttgc acatgcctac acactcactg acatacacac acacatgcag   5340

tcatacacac tccctgacat gctcacacac tgtcatactc acacactccc tgacatgctc   5400

acacactgtc acactcacac actcacatac actccctgac atacacactc agacaagtgc   5460

ccatgcaccc acacctatgc tcatgcacat gttcccacac tctcttataa gcatacacac   5520

ccatgttcct cactcaggac acacatgaat gttccccagg gcatcatgtg acatcgcaga   5580

ggacagatgg tggaaaagac atgagcaacc taatgggaag aggaaaatgg gaaacaatgc   5640

attggaagag gaagaaaaaa aataaataac caaaggtttt ggcaagtgca gtaccaggtg   5700

gagaagcttg acttttctat ccttgatcat tttattccct cccaagaagt cagtcacagg   5760

acctggaagg ccagaaaggg tacatgtggg agacggtctg aggaagtacc tcggtcacta   5820

caatattttt gcacatataa agggttgggg aggaaagaga cacaaacgta tttaacacag   5880

atttgctgga tggaagctgc gtgtgtgaac gtgtgtatga gtgagtgcat tttgattttt   5940

tttttttttt tttgcacagt taagagaaaa aatcaaacaa gcagaaaaaa aaaagaaaaa   6000

agacttatca cggt                                                      6014
```

<210> SEQ ID NO 166
<211> LENGTH: 817
<212> TYPE: PRT
<213> ORGANISM: Homo sapiens

<400> SEQUENCE: 166

```
Met Lys Gln Cys Val Arg Leu Thr Val His Pro Asn Asn Ile Ser Val
1               5                   10                  15

Ser Gln Tyr Asn Val Leu Leu Val Leu Glu Thr Tyr Asn Val Pro Glu
            20                  25                  30
```

-continued

```
Leu Ser Ala Gly Val Asn Cys Thr Phe Glu Asp Leu Ser Glu Met Asp
        35                  40                  45

Gly Leu Val Val Gly Asn Gln Ile Gln Cys Tyr Ser Pro Ala Ala Lys
    50                  55                  60

Glu Val Pro Arg Ile Ile Thr Glu Asn Gly Asp His His Val Val Gln
65                  70                  75                  80

Leu Gln Leu Lys Ser Lys Glu Thr Gly Met Thr Phe Ala Ser Thr Ser
                85                  90                  95

Phe Val Phe Tyr Asn Cys Ser Val His Asn Ser Cys Leu Ser Cys Val
            100                 105                 110

Glu Ser Pro Tyr Arg Cys His Trp Cys Lys Tyr Arg His Val Cys Thr
        115                 120                 125

His Asp Pro Lys Thr Cys Ser Phe Gln Glu Gly Arg Val Lys Leu Pro
    130                 135                 140

Glu Asp Cys Pro Gln Leu Leu Arg Val Asp Lys Ile Leu Val Pro Val
145                 150                 155                 160

Glu Val Ile Lys Pro Ile Thr Leu Lys Ala Lys Asn Leu Pro Gln Pro
                165                 170                 175

Gln Ser Gly Gln Arg Gly Tyr Glu Cys Ile Leu Asn Ile Gln Gly Ser
            180                 185                 190

Glu Gln Arg Val Pro Ala Leu Arg Phe Asn Ser Ser Ser Val Gln Cys
        195                 200                 205

Gln Asn Thr Ser Tyr Ser Tyr Glu Gly Met Glu Ile Asn Asn Leu Pro
    210                 215                 220

Val Glu Leu Thr Val Val Trp Asn Gly His Phe Asn Ile Asp Asn Pro
225                 230                 235                 240

Ala Gln Asn Lys Val His Leu Tyr Lys Cys Gly Ala Met Arg Glu Ser
                245                 250                 255

Cys Gly Leu Cys Leu Lys Ala Asp Pro Asp Phe Ala Cys Gly Trp Cys
            260                 265                 270

Gln Gly Pro Gly Gln Cys Thr Leu Arg Gln His Cys Pro Ala Gln Glu
        275                 280                 285

Ser Gln Trp Leu Glu Leu Ser Gly Ala Lys Ser Lys Cys Thr Asn Pro
    290                 295                 300

Arg Ile Thr Glu Ile Ile Pro Val Thr Gly Pro Arg Glu Gly Gly Thr
305                 310                 315                 320

Lys Val Thr Ile Arg Gly Glu Asn Leu Gly Leu Glu Phe Arg Asp Ile
                325                 330                 335

Ala Ser His Val Lys Val Ala Gly Val Glu Cys Ser Pro Leu Val Asp
            340                 345                 350

Gly Tyr Ile Pro Ala Glu Gln Ile Val Cys Glu Met Gly Glu Ala Lys
        355                 360                 365

Pro Ser Gln His Ala Gly Phe Val Glu Ile Cys Val Ala Val Cys Arg
    370                 375                 380

Pro Glu Phe Met Ala Arg Ser Ser Gln Leu Tyr Tyr Phe Met Thr Leu
385                 390                 395                 400

Thr Leu Ser Asp Leu Lys Pro Ser Arg Gly Pro Met Ser Gly Gly Thr
                405                 410                 415

Gln Val Thr Ile Thr Gly Thr Asn Leu Asn Ala Gly Ser Asn Val Val
            420                 425                 430

Val Met Phe Gly Lys Gln Pro Cys Leu Phe His Arg Arg Ser Pro Ser
        435                 440                 445
```

-continued

```
Tyr Ile Val Cys Asn Thr Thr Ser Ser Asp Glu Val Leu Glu Met Lys
    450                 455                 460

Val Ser Val Gln Val Asp Arg Ala Lys Ile His Gln Asp Leu Val Phe
465                 470                 475                 480

Gln Tyr Val Glu Asp Pro Thr Ile Val Arg Ile Glu Pro Glu Trp Ser
                485                 490                 495

Ile Val Ser Gly Asn Thr Pro Ile Ala Val Trp Gly Thr His Leu Asp
            500                 505                 510

Leu Ile Gln Asn Pro Gln Ile Arg Ala Lys His Gly Gly Lys Glu His
        515                 520                 525

Ile Asn Ile Cys Glu Val Leu Asn Ala Thr Glu Met Thr Cys Gln Ala
    530                 535                 540

Pro Ala Leu Ala Leu Gly Pro Asp His Gln Ser Asp Leu Thr Glu Arg
545                 550                 555                 560

Pro Glu Glu Phe Gly Phe Ile Leu Asp Asn Val Gln Ser Leu Leu Ile
                565                 570                 575

Leu Asn Lys Thr Asn Phe Thr Tyr Tyr Pro Asn Pro Val Phe Glu Ala
            580                 585                 590

Phe Gly Pro Ser Gly Ile Leu Glu Leu Lys Pro Gly Thr Pro Ile Ile
        595                 600                 605

Leu Lys Gly Lys Asn Leu Ile Pro Pro Val Ala Gly Gly Asn Val Lys
    610                 615                 620

Leu Asn Tyr Thr Val Leu Val Gly Glu Lys Pro Cys Thr Val Thr Val
625                 630                 635                 640

Ser Asp Val Gln Leu Leu Cys Glu Ser Pro Asn Leu Ile Gly Arg His
                645                 650                 655

Lys Val Met Ala Arg Val Gly Gly Met Glu Tyr Ser Pro Gly Met Val
            660                 665                 670

Tyr Ile Ala Pro Asp Ser Pro Leu Ser Leu Pro Ala Ile Val Ser Ile
        675                 680                 685

Ala Val Ala Gly Gly Leu Leu Ile Ile Phe Ile Val Ala Val Leu Ile
    690                 695                 700

Ala Tyr Lys Arg Lys Ser Arg Glu Ser Asp Leu Thr Leu Lys Arg Leu
705                 710                 715                 720

Gln Met Gln Met Asp Asn Leu Glu Ser Arg Val Ala Leu Glu Cys Lys
                725                 730                 735

Glu Gly Thr Glu Trp Pro His Ala Gly Gly His Val Cys Val Arg Val
            740                 745                 750

Cys Ile Cys Val Cys Met His Ile Cys Val Cys Val Cys Ile Cys Phe
        755                 760                 765

Ile Tyr Lys Gln Ala Gly Trp Ala Ala Val Gly Ser Ala Gly Gly Trp
    770                 775                 780

Arg Cys Val Cys Leu Cys Glu Cys Val Cys Val His Val Cys Val Cys
785                 790                 795                 800

Thr Ser Val Cys Ile Tyr Val Ser Tyr Thr Ser Lys Gln Ala Gly Gln
                805                 810                 815

Gln
```

<210> SEQ ID NO 167
<211> LENGTH: 21
<212> TYPE: DNA
<213> ORGANISM: Artificial Sequence
<220> FEATURE:
<223> OTHER INFORMATION: Oligonucleotide -continued

<400> SEQUENCE: 167
gcaccaaggt cactatccga g 21

<210> SEQ ID NO 168
<211> LENGTH: 21
<212> TYPE: DNA
<213> ORGANISM: Artificial Sequence
<220> FEATURE:
<223> OTHER INFORMATION: Oligonucleotide

<400> SEQUENCE: 168
tctgagagag tcagtgtcat g 21

<210> SEQ ID NO 169
<211> LENGTH: 2565
<212> TYPE: DNA
<213> ORGANISM: Homo sapiens

<400> SEQUENCE: 169
actgcgacgg taccggggcg gcggggaagg accgagaggc gggaggagca gcggctcagg 60
cgcctgcaaa ctggtggcct gaacgaggta gaccatgact gtggtttcag tggcgtcact 120
cgctgggctg ctcttcctga ggttttccta agccatcccc tggcggaacc gcccccagta 180
tggactccaa ttgccttgac agtgttttta gtggctgttg caacattatg taaagaacaa 240
ggaataacag ttgtaggaat ttgctgtgtg tatgaagtgt ttattgccca ggggtatact 300
ttgccattac tatgtactac tgctggacag tttctccgtg gaaagggtag cattccattt 360
tctatgctgc agacactagt aaaactcatt gtcttgatgt tcagtacatt attacttgtt 420
gtgattagag tccaggttat tcaatcccaa cttccagtat tcaccaggtt tgataaccca 480
gctgctgtaa gcccaactcc tacaaggcaa ctaactttta actacctcct tcctgtgaat 540
gcttggttgt tattaaatcc ttcagagctc tgctgtgatt ggaccatggg aacaatacca 600
cttatagagt cattactaga tattcgaaat ctggccacat ttactttctt ttgttttctg 660
gggatgttgg gagtattcag tatcagatac tctggtgatt cctccaagac tgttttaatg 720
ttgcctgcta aaactgacat gggtcaaaaa tttgagaaaa gtagtgaaga ttcaaagcag 780
tcaagaagag tggaaggaac tttccagaga aacctagaaa tcccaaacag tcttaaggat 840
aaatttgaac ttggtgctca tgcttttatg acagtattaa tctgttcagc tttgggactt 900
tctctagcag tgcgttgcca ctctgttgga tttgttgttg ccgagcgagt attatatgtt 960
cccagcatgg ggttctgtat tttggtagcc catggatggc agaaaatatc aacaaaaagt 1020
gtatttaaaa agctatcctg gatttgtctg tctatggtga tactcactca ttccttaaaa 1080
acattccaca gaaattggga ttgggagtct gaatatacat tgtttatgtc agccttgaag 1140
gtaaataaaa ataatgccaa actttggaat aatgtgggtc atgctctgga aaatgaaaag 1200
aactttgaga gagctttgaa atacttctta caggctaccc atgttcagcc agatgatatt 1260
ggtgcccata tgaatgtagg aagaacttat aaaaatttaa atagaaccaa agaagctgaa 1320
gaatcttaca tgatggctaa atcactgatg cctcaaatta ttcctggtaa aaaatatgca 1380
gccagaattg cccctaacca cctaaatgtt tatatcaatc tggctaacct gatccgagca 1440
aatgagtccc gactggaaga agcagatcag ctgtaccgtc aagcaataag catgaggccc 1500
gacttcaagc aggcttacat tagcagagga gaattgcttt taaaaatgaa taaacctctt 1560
aaagcaaagg aagcatatct taaagcacta gagctggaca gaaataatgc agatctttgg 1620
tacaacttgg caattgtaca tattgaactt aaagaaccaa atgaagccct aaaaaacttt 1680

-continued

```
aatcgtgctc tggaactaaa tccaaagcat aaactagcat tattcaactc tgctatagta   1740

atgcaagaat caggtgaggt taaactcaga cctgaagcta gaaaacgact tctaagttat   1800

ataaatgaag agccactaga tgctaatggg tatttcaatt tgggaatgct tgccatggat   1860

gacaaaaagg acaatgaagc agagatttgg atgaagaaag ccataaagtt acaagccgac   1920

ttccgaagtg ctttgtttaa tctggctctc ctgtattccc agactgcaaa ggaattaaag   1980

gctttgccaa ttttggagga gttactcaga tactaccctg atcatatcaa gggcctcatt   2040

ttaaaaggag acattctgat gaatcaaaag aaagatatac taggagcaaa aaaatgtttt   2100

gaaaggattt tggagatgga tccaagcaat gtgcaaggaa aacacaatct ttgtgttgtt   2160

tattttgaag aaaaagactt attaaaagct gaaagatgcc ttcttgaaac actggcatta   2220

gcaccacatg aagaatatat tcagcgccat ttgaatatag tcagggataa gatttcctca   2280

tctagtttta tagagccaat attcccaacc agtaagattt caagtgtgga aggaaagaaa   2340

attccaactg aaagtgtaaa agaaattaga ggtgaatcca gacaaacaca aatagtaaaa   2400

acaagtgata ataaaagtca gtctaaatcc aacaaacaat taggaaaaaa tggagacgaa   2460

gagacacccc acaaaacaac aaaagacatc aaagaaattg agaagaaaag agttgctgct   2520

ttaaaaagac tagaagagat tgaacgtatt ttaaatggtg aataa                    2565
```

<210> SEQ ID NO 170
<211> LENGTH: 733
<212> TYPE: PRT
<213> ORGANISM: Homo sapiens

<400> SEQUENCE: 170

```
Met Leu Gln Thr Leu Val Lys Leu Ile Val Leu Met Phe Ser Thr Leu
1               5                   10                  15

Leu Leu Val Val Ile Arg Val Gln Val Ile Gln Ser Gln Leu Pro Val
            20                  25                  30

Phe Thr Arg Phe Asp Asn Pro Ala Ala Val Ser Pro Thr Pro Thr Arg
        35                  40                  45

Gln Leu Thr Phe Asn Tyr Leu Leu Pro Val Asn Ala Trp Leu Leu Leu
    50                  55                  60

Asn Pro Ser Glu Leu Cys Cys Asp Trp Thr Met Gly Thr Ile Pro Leu
65                  70                  75                  80

Ile Glu Ser Leu Leu Asp Ile Arg Asn Leu Ala Thr Phe Thr Phe Phe
                85                  90                  95

Cys Phe Leu Gly Met Leu Gly Val Phe Ser Ile Arg Tyr Ser Gly Asp
            100                 105                 110

Ser Ser Lys Thr Val Leu Met Leu Pro Ala Lys Thr Asp Met Gly Gln
        115                 120                 125

Lys Phe Glu Lys Ser Ser Glu Asp Ser Lys Gln Ser Arg Arg Val Glu
    130                 135                 140

Gly Thr Phe Gln Arg Asn Leu Glu Ile Pro Asn Ser Leu Lys Asp Lys
145                 150                 155                 160

Phe Glu Leu Gly Ala His Ala Phe Met Thr Val Leu Ile Cys Ser Ala
                165                 170                 175

Leu Gly Leu Ser Leu Ala Val Arg Cys His Ser Val Gly Phe Val Val
            180                 185                 190

Ala Glu Arg Val Leu Tyr Val Pro Ser Met Gly Phe Cys Ile Leu Val
        195                 200                 205
```

-continued

```
Ala His Gly Trp Gln Lys Ile Ser Thr Lys Ser Val Phe Lys Lys Leu
    210                 215                 220

Ser Trp Ile Cys Leu Ser Met Val Ile Leu Thr His Ser Leu Lys Thr
225                 230                 235                 240

Phe His Arg Asn Trp Asp Trp Glu Ser Glu Tyr Thr Leu Phe Met Ser
                245                 250                 255

Ala Leu Lys Val Asn Lys Asn Asn Ala Lys Leu Trp Asn Asn Val Gly
            260                 265                 270

His Ala Leu Glu Asn Glu Lys Asn Phe Glu Arg Ala Leu Lys Tyr Phe
        275                 280                 285

Leu Gln Ala Thr His Val Gln Pro Asp Asp Ile Gly Ala His Met Asn
    290                 295                 300

Val Gly Arg Thr Tyr Lys Asn Leu Asn Arg Thr Lys Glu Ala Glu Glu
305                 310                 315                 320

Ser Tyr Met Met Ala Lys Ser Leu Met Pro Gln Ile Ile Pro Gly Lys
                325                 330                 335

Lys Tyr Ala Ala Arg Ile Ala Pro Asn His Leu Asn Val Tyr Ile Asn
            340                 345                 350

Leu Ala Asn Leu Ile Arg Ala Asn Glu Ser Arg Leu Glu Glu Ala Asp
        355                 360                 365

Gln Leu Tyr Arg Gln Ala Ile Ser Met Arg Pro Asp Phe Lys Gln Ala
    370                 375                 380

Tyr Ile Ser Arg Gly Glu Leu Leu Leu Lys Met Asn Lys Pro Leu Lys
385                 390                 395                 400

Ala Lys Glu Ala Tyr Leu Lys Ala Leu Glu Leu Asp Arg Asn Asn Ala
                405                 410                 415

Asp Leu Trp Tyr Asn Leu Ala Ile Val His Ile Glu Leu Lys Glu Pro
            420                 425                 430

Asn Glu Ala Leu Lys Asn Phe Asn Arg Ala Leu Glu Leu Asn Pro Lys
        435                 440                 445

His Lys Leu Ala Leu Phe Asn Ser Ala Ile Val Met Gln Glu Ser Gly
    450                 455                 460

Glu Val Lys Leu Arg Pro Glu Ala Arg Lys Arg Leu Leu Ser Tyr Ile
465                 470                 475                 480

Asn Glu Glu Pro Leu Asp Ala Asn Gly Tyr Phe Asn Leu Gly Met Leu
                485                 490                 495

Ala Met Asp Asp Lys Lys Asp Asn Glu Ala Glu Ile Trp Met Lys Lys
            500                 505                 510

Ala Ile Lys Leu Gln Ala Asp Phe Arg Ser Ala Leu Phe Asn Leu Ala
        515                 520                 525

Leu Leu Tyr Ser Gln Thr Ala Lys Glu Leu Lys Ala Leu Pro Ile Leu
    530                 535                 540

Glu Glu Leu Leu Arg Tyr Tyr Pro Asp His Ile Lys Gly Leu Ile Leu
545                 550                 555                 560

Lys Gly Asp Ile Leu Met Asn Gln Lys Lys Asp Ile Leu Gly Ala Lys
                565                 570                 575

Lys Cys Phe Glu Arg Ile Leu Glu Met Asp Pro Ser Asn Val Gln Gly
            580                 585                 590

Lys His Asn Leu Cys Val Val Tyr Phe Glu Glu Lys Asp Leu Leu Lys
        595                 600                 605

Ala Glu Arg Cys Leu Leu Glu Thr Leu Ala Leu Ala Pro His Glu Glu
    610                 615                 620
```

-continued

```
Tyr Ile Gln Arg His Leu Asn Ile Val Arg Asp Lys Ile Ser Ser Ser
625                 630                 635                 640

Ser Phe Ile Glu Pro Ile Phe Pro Thr Ser Lys Ile Ser Ser Val Glu
                645                 650                 655

Gly Lys Lys Ile Pro Thr Glu Ser Val Lys Glu Ile Arg Gly Glu Ser
            660                 665                 670

Arg Gln Thr Gln Ile Val Lys Thr Ser Asp Asn Lys Ser Gln Ser Lys
        675                 680                 685

Ser Asn Lys Gln Leu Gly Lys Asn Gly Asp Glu Glu Thr Pro His Lys
    690                 695                 700

Thr Thr Lys Asp Ile Lys Glu Ile Glu Lys Lys Arg Val Ala Ala Leu
705                 710                 715                 720

Lys Arg Leu Glu Glu Ile Glu Arg Ile Leu Asn Gly Glu
                725                 730
```

<210> SEQ ID NO 171
<211> LENGTH: 21
<212> TYPE: DNA
<213> ORGANISM: Artificial Sequence
<220> FEATURE:
<223> OTHER INFORMATION: Oligonucleotide

<400> SEQUENCE: 171
aggcttacat tagcagagga g 21

<210> SEQ ID NO 172
<211> LENGTH: 21
<212> TYPE: DNA
<213> ORGANISM: Artificial Sequence
<220> FEATURE:
<223> OTHER INFORMATION: Oligonucleotide

<400> SEQUENCE: 172
cgttttctag cttcaggtct g 21

<210> SEQ ID NO 173
<211> LENGTH: 3296
<212> TYPE: DNA
<213> ORGANISM: Homo sapiens

<400> SEQUENCE: 173
tgaattcaaa acagttactc tgaatggtct ttgctaagaa caatttaatg attaagtaag 60
gtcagtgtcc ttggaagtcc aaactctagc cagatttccc tggtctacac ccctagggat 120
aaggtaaatg tttaagcaca cagtgaactt cctgaggccc ccaaatctaa tggaactagc 180
tattgagggc taaaagagga tggttttttt agaaaactcg aagcaaatct ctcaggctgg 240
ggatatttca aagactacta ctattattat taataacaat tgcaatattt gttgagtccc 300
taaatgaagc taaaactttg ttctaataaa tttaatcttt acagcaacct atgaggtaga 360
taatattgtc attcccatga gggagctaag gatcagagaa ggtaagtcac ttgtctaagg 420
tcacatagct agcatgttat gcaatcagga gtcaaacctg gtttgtctga atctgaagtc 480
catctgctct gtgcactttt ataccgtctg ctttttcctt tattcctaac cttcttccat 540
tctgattccc actgagtagt ggacaggaac cactgaagtt tgcctgacac catcaaccag 600
gccctagtca cctggctttg cctttgccct gctgtgtgat cttagctccc tgcccaggcc 660
cacagccatg gccatggccc agaaactcag ccacctcctg ccgagtctgc ggcaggtcat 720
ccaggagcct cagctatctc tgcagccaga gcctgtcttc acggtggatc gagctgaggt 780

-continued

```
gccgccgctc ttctggaagc cgtacatcta tgcgggctac cggccgctgc atcagacctg    840
gcgcttctat ttccgcacgc tgttccagca gcacaacgag gccgtgaatg tctggaccca    900
cctgctggcg gccctggtac tgctgctgcg gctggccctc tttgtggaga ccgtggactt    960
ctggggagac ccacacgccc tgcccctctt catcattgtc cttgcctctt tcacctacct   1020
ctccttcagt gccttggctc acctcctgca ggccaagtct gagttctggc attacagctt   1080
cttcttcctg gactatgtgg gggtggccgt gtaccagttt ggcagtgcct tggcacactt   1140
ctactatgct atcgagcccg cctggcatgc ccaggtgcag gctgtttttc tgcccatggc   1200
tgcctttctc gcctggcttt cctgcattgg ctcctgctat aacaagtaca tccagaaacc   1260
aggcctgctg ggccgcacat gccaggaggt gccctccgtc ctggcctacg cactggacat   1320
tagtcctgtg gtgcatcgta tcttcgtgtc ctccgacccc accacggatg atccagctct   1380
tctctaccac aagtgccagg tggtcttctt tctgctggct gctgccttct tctctacctt   1440
catgcccgag cgctggttcc ctggcagctg ccatgtcttc gggcagggcc accaactttt   1500
ccacatcttc ttggtgctgt gcacgctggc tcagctggag gctgtggcac tggactatga   1560
ggcccgacgg cccatctatg agcctctgca cacgcactgg cctcacaact tttctggcct   1620
cttcctgctc acggtgggca gcagcatcct cactgcattc ctcctgagcc agctggtaca   1680
gcgcaaactt gatcagaaga ccaagtgaag gggatggca tctggtaggg agggaggtat   1740
agttggggga caggggtctg ggtttggctc caggtgggaa caaggcctgg taaagttgtt   1800
tgtgtctggc ccacagtgac tctctgtgca cgactcaact gccaagggca tcactggcca   1860
attcttggat ttagggattg gctaggagtt gctggggtcc actcctgggc ctgccccagc   1920
tccttgccca gggagaggga aagagttaac ggtgtgggcc actccagctt gcccttccac   1980
tgccactcac tggggtgagg ctgggggtca gcttggtgag gattggggct tctagattgt   2040
ctaggcagga ggtgaaactt aggccagagt cagatttgag ctgagccagg ggaggccttg   2100
gcaacctact tctactcaga tttcattgct ggatgcggaa ggggtaggcc caaaatatat   2160
acaggatctt actgtccctt gaagcccagc cacaagtgtt ggagctgcag agagacccca   2220
aaggtagtag attgtgccag atacaaatgg gtcccatcca gtgcttcata ctccttcagt   2280
cactatccca gacagtgagc cccagatctc ctagctctgg cttctgtgtc ccacacggcc   2340
tgttcccagc ttctctcctg gttcccttgt tacggattca tttatccatt cagtgtttcc   2400
tgggcctctg ctcagaggca ggtcaccact gggccctgtg gatcaatgca agatgacaaa   2460
ggcttttttt ttttttttt ttttttttt ttttgaggag tttcgctctt gttggctagg   2520
ctggagtaaa atggtgcgat ctcggctcac tgcacctccg cctcccaggt tcaagcgatt   2580
ttcctgcctc agcctcccga gtagctgggg ttacaggcat gcaccaccat gcctggctaa   2640
ttttctgtat ttttagtaga gacggggttt ctccatgttg gtcaggctgg tcttgaactc   2700
ctgacctcag gtgatctgcc cgtctcggcc tcccaaagtg ctgggattac cggcatgagc   2760
cactgcgcct ggccgacaaa ggctttgata tcagaatgaa ctgtcaaggg aggtgctgga   2820
gagggattaa cctgtgctgc ctgggaccct cagggtctta ggttggggag tgtgaatagg   2880
agtttgcaga tggagaatag gaagggcatt ccaggcagag ggaaacctgt gcagagacca   2940
agaggtgtgg aaggaaaagt ggggttgggg ctgggtggtc tggattatgg cctggatgca   3000
ataaagtact gtgacagtag ccacctcttt gttttttgtc tcctgtttcc gggaggggcc   3060
cctgctcaca ttactggagg ttttccggag gaagctgggg cccctgggag tggacacagg   3120
gtgcagggag cagttcttgt tttatctttg ctgggggatg gggttggggc cttatatacc   3180
```

-continued

```
atatctatat atacaaaatt tgtttggcaa gggagtgggc ggcagtttta ttactaaagt   3240

tttataagta gttaaaataa tgtgtttaaa atatgataat cccactttat gatctg       3296


<210> SEQ ID NO 174
<211> LENGTH: 346
<212> TYPE: PRT
<213> ORGANISM: Homo sapiens

<400> SEQUENCE: 174

Met Ala Met Ala Gln Lys Leu Ser His Leu Leu Pro Ser Leu Arg Gln
1               5                   10                  15

Val Ile Gln Glu Pro Gln Leu Ser Leu Gln Pro Glu Pro Val Phe Thr
            20                  25                  30

Val Asp Arg Ala Glu Val Pro Pro Leu Phe Trp Lys Pro Tyr Ile Tyr
        35                  40                  45

Ala Gly Tyr Arg Pro Leu His Gln Thr Trp Arg Phe Tyr Phe Arg Thr
    50                  55                  60

Leu Phe Gln Gln His Asn Glu Ala Val Asn Val Trp Thr His Leu Leu
65                  70                  75                  80

Ala Ala Leu Val Leu Leu Leu Arg Leu Ala Leu Phe Val Glu Thr Val
                85                  90                  95

Asp Phe Trp Gly Asp Pro His Ala Leu Pro Leu Phe Ile Ile Val Leu
            100                 105                 110

Ala Ser Phe Thr Tyr Leu Ser Phe Ser Ala Leu Ala His Leu Leu Gln
        115                 120                 125

Ala Lys Ser Glu Phe Trp His Tyr Ser Phe Phe Phe Leu Asp Tyr Val
    130                 135                 140

Gly Val Ala Val Tyr Gln Phe Gly Ser Ala Leu Ala His Phe Tyr Tyr
145                 150                 155                 160

Ala Ile Glu Pro Ala Trp His Ala Gln Val Gln Ala Val Phe Leu Pro
                165                 170                 175

Met Ala Ala Phe Leu Ala Trp Leu Ser Cys Ile Gly Ser Cys Tyr Asn
            180                 185                 190

Lys Tyr Ile Gln Lys Pro Gly Leu Leu Gly Arg Thr Cys Gln Glu Val
        195                 200                 205

Pro Ser Val Leu Ala Tyr Ala Leu Asp Ile Ser Pro Val Val His Arg
    210                 215                 220

Ile Phe Val Ser Ser Asp Pro Thr Thr Asp Asp Pro Ala Leu Leu Tyr
225                 230                 235                 240

His Lys Cys Gln Val Val Phe Phe Leu Leu Ala Ala Ala Phe Phe Ser
                245                 250                 255

Thr Phe Met Pro Glu Arg Trp Phe Pro Gly Ser Cys His Val Phe Gly
            260                 265                 270

Gln Gly His Gln Leu Phe His Ile Phe Leu Val Leu Cys Thr Leu Ala
        275                 280                 285

Gln Leu Glu Ala Val Ala Leu Asp Tyr Glu Ala Arg Arg Pro Ile Tyr
    290                 295                 300

Glu Pro Leu His Thr His Trp Pro His Asn Phe Ser Gly Leu Phe Leu
305                 310                 315                 320

Leu Thr Val Gly Ser Ser Ile Leu Thr Ala Phe Leu Leu Ser Gln Leu
                325                 330                 335

Val Gln Arg Lys Leu Asp Gln Lys Thr Lys
            340                 345
```

-continued

<210> SEQ ID NO 175
<211> LENGTH: 2858
<212> TYPE: DNA
<213> ORGANISM: Homo sapiens

<400> SEQUENCE: 175
agtggcgggg aagcaaagca caggagcgct gtggtgccag cggccgggct agggacgact 60
ggcgggtttg cgctggaccc gaccccgagg gcgggcgcaa gggggcgggc gctgccgtac 120
tcaggccgcg gggccagggc gggccggccg gcggggcatt taaaccccgc tgacagccag 180
tccagcccgg gacacgcgcc cagctctgta gcctcctccg tcgactcagc cttaggtacc 240
ggtcaggcaa aatgcggtcc tccctggctc cgggagtctg gttcttccgg gccttctcca 300
gggacagctg gttccgaggc ctcatcctgc tgctgacctt cctaatttac gcctgctatc 360
acatgtccag gaagcctatc agtatcgtca agagccgtct gcaccagaac tgctcggagc 420
agatcaaacc catcaatgat actcacagtc tcaatgacac catgtggtgc agctgggccc 480
catttgacaa ggacaactat aaggagttac taggggggcgt ggacaacgcc ttcctcatcg 540
cctatgccat cggcatgttc atcagtgggg tttttgggga gcggcttccg ctccgttact 600
acctctcagc tggaatgctg ctcagtggcc ttttcacctc gctctttggc ctgggatatt 660
tctggaacat ccacgagctc tggtactttg tggtcatcca ggtctgtaat ggactcgtcc 720
agaccacagg ctggccctct gtggtgacct gtgttggcaa ctggttcggg aaggggaagc 780
gggggttcat catgggcatc tggaattccc acacatctgt gggcaacatc ctgggctccc 840
tgatcgccgg catctgggtg aacgggcagt ggggcctgtc gttcatcgtg cctggcatca 900
ttactgccgt catgggcgtc atcaccttcc tcttcctcat cgaacaccca gaagatgtgg 960
actgcgcccc tcctcagcac cacggtgagc cagctgagaa ccaggacaac cctgaggacc 1020
ctgggaacag tccctgctct atcagggaga gcggccttga gactgtggcc aaatgctcca 1080
aggggccatg cgaagagcct gctgccatca gcttctttgg ggcgctccgg atcccaggcg 1140
tggtcgagtt ctctctgtgt ctgctgtttg ccaagctggt cagttacacc ttcctctact 1200
ggctgcccct ctacatcgcc aatgtggctc actttagtgc caaggaggct ggggacctgt 1260
ctacactctt cgatgttggt ggcatcatag gcggcatcgt ggcagggctc gtctctgact 1320
acaccaatgg cagggccacc acttgctgtg tcatgctcat cttggctgcc cccatgatgt 1380
tcctgtacaa ctacattggc caggacggga ttgccagctc catagtgatg ctgatcatct 1440
gtgggggcct ggtcaatggc ccatacgcgc tcatcaccac tgctgtctct gctgatctgg 1500
ggactcacaa gagcctgaag ggcaacgcca aagccctgtc cacggtcacg gccatcattg 1560
acggcaccgg ctccataggt gcggctctgg ggcctctgct ggctgggctc atctccccca 1620
cgggctggaa caatgtcttc tacatgctca tctctgccga cgtcctagcc tgcttgctcc 1680
tttgccggtt agtatacaaa gagatcttgg cctggaaggt gtccctgagc agaggcagcg 1740
ggtataaaga aatatgaggc cccaattgga acagcagcat ggagggtccc agttgggtcc 1800
ccaacgtgct ccccatgggc aagacaatgg aaacttccac aagcagggaa ggcaaaccct 1860
ctttattgaa cattagccag cccagcccag accccagggc tgcctaagga cacagagatt 1920
ctccatggga aggggactgc caagcatgag gaaatagaag attcaggggc ctgagctctg 1980
gaagctgcaa gcaaaaggga tgggactagg gctgagttgt gtctccattt tgataaggaa 2040
aggatatgct cagactcttg cttgttcaga ttccaagaca gaaggcttca caaggccaac 2100
gcctggaaaa tgggcatctc tccttcccat gttaagcttt aacctctgta atctgcctgt 2160

-continued

```
atctataggt gggcatctca ctccaccaaa ggagcccagc ctctctttgt ccctctatcc   2220

atgcaacagt cttctctgtg catttcccca agctgggccc tcttctactc tccatttagg   2280

cctgttgata actccattac ccgcccatca ctgctgttcc tccagggcca gcactcgggc   2340

gaggcagggg agctgccttc ggtacataat ttgaaggggc actccctctt gggcacatgc   2400

cggccctgag tgcctccctt gcctcactct gatcctggcc ccataatgtc ctcagtggaa   2460

ggtgatgggg gccggtgctg tggggagagt agaaagaggg gttggcatga ctaaaaatac   2520

cagtatgtgt attaagtatt ttgagaatga aatgccaagg agtgcctact atatgccagc   2580

tctaggaatg gagtagacag tggacacaag aaggacttac gccctgagca caggtgccaa   2640

tggtgacaag actggcaaga cgtgagggca tgaatggttc attcaggcag ctgctgcaga   2700

tgtggtcacc tggtgccatc tgctgctccc ttttccactt ttctatgtcc tccttccacc   2760

ccaagtcccg gatcactcgc tgttttctgg ctagctcttg gcatctccat ctgagcctaa   2820

agttgcccac tggcaccaat agattctgtt tgacctgc                           2858


<210> SEQ ID NO 176
<211> LENGTH: 501
<212> TYPE: PRT
<213> ORGANISM: Homo sapiens

<400> SEQUENCE: 176

Met Arg Ser Ser Leu Ala Pro Gly Val Trp Phe Phe Arg Ala Phe Ser
1               5                   10                  15

Arg Asp Ser Trp Phe Arg Gly Leu Ile Leu Leu Leu Thr Phe Leu Ile
            20                  25                  30

Tyr Ala Cys Tyr His Met Ser Arg Lys Pro Ile Ser Ile Val Lys Ser
        35                  40                  45

Arg Leu His Gln Asn Cys Ser Glu Gln Ile Lys Pro Ile Asn Asp Thr
    50                  55                  60

His Ser Leu Asn Asp Thr Met Trp Cys Ser Trp Ala Pro Phe Asp Lys
65                  70                  75                  80

Asp Asn Tyr Lys Glu Leu Leu Gly Gly Val Asp Asn Ala Phe Leu Ile
                85                  90                  95

Ala Tyr Ala Ile Gly Met Phe Ile Ser Gly Val Phe Gly Glu Arg Leu
            100                 105                 110

Pro Leu Arg Tyr Tyr Leu Ser Ala Gly Met Leu Leu Ser Gly Leu Phe
        115                 120                 125

Thr Ser Leu Phe Gly Leu Gly Tyr Phe Trp Asn Ile His Glu Leu Trp
    130                 135                 140

Tyr Phe Val Val Ile Gln Val Cys Asn Gly Leu Val Gln Thr Thr Gly
145                 150                 155                 160

Trp Pro Ser Val Val Thr Cys Val Gly Asn Trp Phe Gly Lys Gly Lys
                165                 170                 175

Arg Gly Phe Ile Met Gly Ile Trp Asn Ser His Thr Ser Val Gly Asn
            180                 185                 190

Ile Leu Gly Ser Leu Ile Ala Gly Ile Trp Val Asn Gly Gln Trp Gly
        195                 200                 205

Leu Ser Phe Ile Val Pro Gly Ile Ile Thr Ala Val Met Gly Val Ile
    210                 215                 220

Thr Phe Leu Phe Leu Ile Glu His Pro Glu Asp Val Asp Cys Ala Pro
225                 230                 235                 240
```

-continued

```
Pro Gln His His Gly Glu Pro Ala Glu Asn Gln Asp Asn Pro Glu Asp
                245                 250                 255

Pro Gly Asn Ser Pro Cys Ser Ile Arg Glu Ser Gly Leu Glu Thr Val
            260                 265                 270

Ala Lys Cys Ser Lys Gly Pro Cys Glu Glu Pro Ala Ala Ile Ser Phe
        275                 280                 285

Phe Gly Ala Leu Arg Ile Pro Gly Val Val Glu Phe Ser Leu Cys Leu
    290                 295                 300

Leu Phe Ala Lys Leu Val Ser Tyr Thr Phe Leu Tyr Trp Leu Pro Leu
305                 310                 315                 320

Tyr Ile Ala Asn Val Ala His Phe Ser Ala Lys Glu Ala Gly Asp Leu
                325                 330                 335

Ser Thr Leu Phe Asp Val Gly Gly Ile Ile Gly Gly Ile Val Ala Gly
            340                 345                 350

Leu Val Ser Asp Tyr Thr Asn Gly Arg Ala Thr Thr Cys Cys Val Met
        355                 360                 365

Leu Ile Leu Ala Ala Pro Met Met Phe Leu Tyr Asn Tyr Ile Gly Gln
    370                 375                 380

Asp Gly Ile Ala Ser Ser Ile Val Met Leu Ile Ile Cys Gly Gly Leu
385                 390                 395                 400

Val Asn Gly Pro Tyr Ala Leu Ile Thr Thr Ala Val Ser Ala Asp Leu
                405                 410                 415

Gly Thr His Lys Ser Leu Lys Gly Asn Ala Lys Ala Leu Ser Thr Val
            420                 425                 430

Thr Ala Ile Ile Asp Gly Thr Gly Ser Ile Gly Ala Ala Leu Gly Pro
        435                 440                 445

Leu Leu Ala Gly Leu Ile Ser Pro Thr Gly Trp Asn Asn Val Phe Tyr
    450                 455                 460

Met Leu Ile Ser Ala Asp Val Leu Ala Cys Leu Leu Leu Cys Arg Leu
465                 470                 475                 480

Val Tyr Lys Glu Ile Leu Ala Trp Lys Val Ser Leu Ser Arg Gly Ser
                485                 490                 495

Gly Tyr Lys Glu Ile
            500


<210> SEQ ID NO 177
<211> LENGTH: 21
<212> TYPE: DNA
<213> ORGANISM: Artificial Sequence
<220> FEATURE:
<223> OTHER INFORMATION: Oligonucleotide

<400> SEQUENCE: 177

tctacatcgc caatgtggct c                                                21


<210> SEQ ID NO 178
<211> LENGTH: 21
<212> TYPE: DNA
<213> ORGANISM: Artificial Sequence
<220> FEATURE:
<223> OTHER INFORMATION: Oligonucleotide

<400> SEQUENCE: 178

cagatgatca gcatcactat g                                                21


<210> SEQ ID NO 179
<211> LENGTH: 4892
<212> TYPE: DNA
```

-continued

<213> ORGANISM: Homo sapiens

<400> SEQUENCE: 179
atagaaacct taaaagggca acacaaagtt ttgaatagaa gaggccaagc agcctcgccc 60
agaagctgat gtttgtgaat gtactgggcc ttctaaagcg gcgcttcaca caccttttca 120
cttcttggca caggtaggaa aggatgatat tacaagggtc aaaatggggg taaacagaag 180
aggctgctcc tgcagaaggc ttcctgcaga agcccttgca cttggagggc tgggaagacc 240
catgctgtat ctgcatccct gtcattcgtt tcacggcatc cagttgggaa gctctgctta 300
aagctttgtc tggcacgttt tcttagctac atttttccac tccagctgag actgcctcac 360
tgagttgtca acacttggtc ttcttcagca gtgaggaacc aacaagacag gaggctgggt 420
caatactcaa cttggcaaac tccaggaaat ggtgcttaaa acgtttggct tcttgaatgg 480
aattcatggt actgctccca gcctgcacct gggttctcca acttgagaca atttctcccc 540
gcatcccccc acccttccct ggctttcact cactagcaag tgggctgctt ctactttctt 600
tctcacattc atttcttagg tccattctca gagcggttag gattactgtt taattagcct 660
cataatcata tctatgatgg caaaatcaag aaacaattta aacatgattc ttaaaagtaa 720
ggagataaat accagagaca tagaaggtga aagaatttgc ctctaggaag caggaattta 780
aatttgggga agacagggtg gagcaaggga tataaatcta gtccattttt cttttctttt 840
cttttctttt ttttttattt ttaagataga gtctcactct gtcgcccagg ctggagtgca 900
gtggcatgat cttggctcac tgcaacctct gcctccttcg ttcaagcgat tctcccacct 960
cagcctccct agtaactggg attacaagtg actgccacta tgcccagcta attttgtatt 1020
tttagtagag acgaggtttc accatgttgg ccaggctggt ctcgaactcc tgacctcagg 1080
ggatccgccc agctcagcct cccaaagtgc taggattcca ggcgtgagcc actgcacctg 1140
gcggaatcta gtccattttc cactttgcta ccacacatct gcagggtttc ttgcttgctt 1200
aaaagctttc attggctccc aatctctgat aatatcaaga gcaagttcct gaacaactca 1260
ttcaagaccc atcacccctc gcatctgtca actctgcccc ttgaatatta cacctcattt 1320
tactacacca catctagttc cctgaatatg caaacagatt tcatacattt gcacctttat 1380
acatgttatt gcttttgcct gggagagtat tctcttgctg ctataataat agctaatgac 1440
actgtgctaa gtactttctg tgatttataa ctgttaattc ttacatcaac cctatggtaa 1500
atgttactgt tatctccatt ttataaacaa gaaaactaag acttaaagag tttaagtgat 1560
ttgcagaaat atgtagtatt tggtgaggct aaatttgaac ccagcaatct gactccagga 1620
ctaacataat attacctatt catccttcta aaatgtttcc cagacactaa atttgaacag 1680
gattaaaaga tttaaatgtt tttaagtctt aaaagggcaa ggagaaaata caagtgaatt 1740
gcttttaatc tcaaactaag catgaaacaa cggctgaaat tacaaaggaa aagtgacaga 1800
tctgactgtt gaacttttaa cttcttttat ccaaaaaaaa accccataga ataaaattta 1860
aaaacaagta aaaattacaa aaaatttgca atatacatga cagataagca taacattaaa 1920
gagaacttag aaagaaaaaa tagcctacta aaaatgagca aaatgcaaat tcgtcatcat 1980
gagagaaaaa tgtaaatggc caaacatttt taagagaagt aaaaacttaa aacgataatg 2040
caccatcaaa ttgagaataa aataatactc agagctagta atttgggcca gtgacccttg 2100
gagtaggatg tatagcaact aaagaaactc atacattact gagaagggtg taaattggct 2160
caacgattct ggagagcaat ttgacagaat gtagtgaaag cgtcaaaaat gttcacacac 2220
tttgacttaa aaattacatt cctggaaatt tataatacaa acattttcta taaaaggtca 2280

-continued

```
gatggcaaat actttgggct ttgaaggcca catatgtctc tgtggctttt cttttgtgtg   2340
tgtgtttaaa aaaaaaaaaa actgcccccc ctccccccac ccttgttagg ccattcttgc   2400
attactataa agaaatacct gaggctggtt aatttatatg aaaagaggtt taactggctc   2460
atggttctgc aggctgtaca ggaagcataa tgccatctgc ttctgggggg gcctcaggaa   2520
gcttccaatc atgctggaag gtgatgggga gcagatgtct cacatggtga gaacgggagc   2580
aagaaggagt tggggggggag gagccacata aacaatgaga tccctgtgag ctcagagtga   2640
gagcacactt atcaccaagg agatggccca agctattcat gagggatccg cccctatgat   2700
ccaaacacct cccaccaggc tccacctcca acactggaga ttatatctca acatgaaatt   2760
tgaatgggac atccaaactg tatcaccccc aaaatgtaaa gtctcatcac agtacatttg   2820
gtaatggcca aaagagaaac caaactaaat gtccgagaat aaaaattagt tacaactaga   2880
tacacggagg caagttttta aaaagtgtta aaattttaaa atgttgcaga atggtatcta   2940
ttggataaaa tagtatttat gatttattaa gtggaaaata cagtttacaa aataatatgg   3000
tgtgatcccg aaaacaacat aatcatgtgt gtataaatgc atagaaaaaa atctggaaag   3060
atataaacag atatttatag tggtctaggg caggggatgg aattgtagat atttgctttt   3120
tgttttatgt atatgtttcc cataatgaaa tgtattgttt atataattaa aaaatatacg   3180
aaactttgct tgggggacaa caaagcacct catttgttaa tttgggaaaa tcttttatta   3240
caatctctgt aaggagttgg ttgctctctc ttctgtactc cctgattaca taatgctctt   3300
ctgagcactt ttatttaata gcagaatggt tgatatcatt atttagttaa ggtttcctct   3360
attatcgaac atctgagttc ccagtacact agtctcccct tatctgtggt tttgcttcca   3420
aggtttcagt tatgatcaac caagatctga aaatattaaa tgaaaaattc cagaaataaa   3480
acaattcata agttttacat tgtgcaccat cctgctgtat cctgtccagg ccatgggtca   3540
tccctcttgt tcagtgtgtc cacactgtag atgctcccct gtctgttagt cactttgtag   3600
ttggcttggt tgtcagacct actgtcaagg tattgcagta cttatgtcca agtaacactt   3660
atttaactta ataatggccc ctaaacacaa gagtagtaat gttggcaatt tgggtatgcc   3720
aaagaaaagt cataaagtgc ttcttttaag tgaaaaccca aaagtttttg aattagtaag   3780
gaaagaaaaa aatccatatg ctgaggtcgc taagatctat gataagaatg aatcttctac   3840
ctgtgaaatt gtgaaggaaa aagaaattca cgttagtttt gctgttgtac ctcaaactgc   3900
aaaagttatg gccacagtgt ataactttta ttaaaatata tttgtataac tgttcttatt   3960
ttacttttct gttttatttt tagagacagg gcttcattct gtcacccagg ctggagtgca   4020
aaggtgcaat catagctcac tgcagcctca aactctttgg ctcaagtgat cttcctgcct   4080
cagcctccca agtagctggg actgcaggtg tgcatcacta cgcccagcta attttttaat   4140
tttttgtgca gatggagtct gactctgttg cccaggaact cctggcctca agtaatcctc   4200
ccgcctcggt tttccaaaga gctgggatta caggcatgag ccactgtgcc tggctattct   4260
attttattag cagtaattgt tgttaatctc ttattgtgcc ttatttatat taataactta   4320
atcatagata gatatgtata ggaaaaaaca ttgtatataa agggttcagt actatctgca   4380
gtttcagata tccatgaggg gtcttgaaac gtatccccca caggtaaggg gggacttgta   4440
tttctctgtt ataaatatgc tggttattct ccacttgttg tgttttagtg ccatcttctg   4500
ctcttctctg ctagactctg tgcctcagaa ggtggaattt ttcataaact attccagctg   4560
gggtctcatg ccagttggtt ttgaccaatg ggtaacacca tcagtagatt ggaggatgga   4620
```

-continued aaaggaaaaa aggttaggat atgtttcacc acctcttttc ctgcttctgg ctgggttctg 4680
atggtggctt tgtcccttga aggctcctcc tgcaaggcag ccctgctcca ctgtgccagc 4740
cttcactggg ctctactaac gtgattccct ccccttattt cttcaggcct agctgtgcta 4800
actcctaggt acctccatgt ttcttgtttc ctttcatcca accctaaccc taacttctat 4860
aaatagttcc cgcaataaag tctcttcagc tg 4892

<210> SEQ ID NO 180
<211> LENGTH: 95
<212> TYPE: PRT
<213> ORGANISM: Homo sapiens

<400> SEQUENCE: 180

Met Arg Gly Leu Glu Thr Tyr Pro Pro Gln Val Arg Gly Asp Leu Tyr
1 5 10 15

Phe Ser Val Ile Asn Met Leu Val Ile Leu His Leu Leu Cys Phe Ser
20 25 30

Ala Ile Phe Cys Ser Ser Leu Leu Asp Ser Val Pro Gln Lys Val Glu
35 40 45

Phe Phe Ile Asn Tyr Ser Ser Trp Gly Leu Met Pro Val Gly Phe Asp
50 55 60

Gln Trp Val Thr Pro Ser Val Asp Trp Arg Met Glu Lys Glu Lys Arg
65 70 75 80

Leu Gly Tyr Val Ser Pro Pro Leu Phe Leu Leu Leu Ala Gly Phe
85 90 95

<210> SEQ ID NO 181
<211> LENGTH: 15
<212> TYPE: DNA
<213> ORGANISM: Artificial Sequence
<220> FEATURE:
<223> OTHER INFORMATION: Oligonucleotide

<400> SEQUENCE: 181
gctcaacgat tctgg 15

<210> SEQ ID NO 182
<211> LENGTH: 15
<212> TYPE: DNA
<213> ORGANISM: Artificial Sequence
<220> FEATURE:
<223> OTHER INFORMATION: Oligonucleotide

<400> SEQUENCE: 182
atgtggcctt caaag 15

<210> SEQ ID NO 183
<211> LENGTH: 501
<212> TYPE: DNA
<213> ORGANISM: Homo sapiens

<400> SEQUENCE: 183
atgaacagaa gcatctatga ccgacagttg ctctgtgtcc ttctagcctc gcaggagttt 60
ccagctcatg agggcagagg agatgaagag aggccgatcg acgtgagggt tgtgcaggcg 120
gcccctctga ggtgtgactc cactcctcct gagggtgctg taggagacat ctgcaaaaaa 180
gaagatgctg gcaatatgcc atcaacctca gaggggagta tttaccctga aatggctcac 240
ttcctgagga acaaacttgc tggatctagt gtacggaaac ctgattctgg gttcctttgg 300
gaaggagcat tacgggcctg gttatttctc atcctaatag ttctcaccca catcatgtgg 360

-continued

```
gtcccattag tacaggtatc tccgaatgct ccactcttcc attacattga gtcaattgct    420

catgaccttg ggcctccaat tggggctatt ttcctgctat ccatctcctg gtctatagta    480

aaagagccaa tgagcagata a                                               501


<210> SEQ ID NO 184
<211> LENGTH: 166
<212> TYPE: PRT
<213> ORGANISM: Homo sapiens

<400> SEQUENCE: 184

Met Asn Arg Ser Ile Tyr Asp Arg Gln Leu Leu Cys Val Leu Leu Ala
1               5                   10                  15

Ser Gln Glu Phe Pro Ala His Glu Gly Arg Gly Asp Glu Glu Arg Pro
            20                  25                  30

Ile Asp Val Arg Val Val Gln Ala Ala Pro Leu Arg Cys Asp Ser Thr
        35                  40                  45

Pro Pro Glu Gly Ala Val Gly Asp Ile Cys Lys Lys Glu Asp Ala Gly
    50                  55                  60

Asn Met Pro Ser Thr Ser Glu Gly Ser Ile Tyr Pro Glu Met Ala His
65                  70                  75                  80

Phe Leu Arg Asn Lys Leu Ala Gly Ser Ser Val Arg Lys Pro Asp Ser
                85                  90                  95

Gly Phe Leu Trp Glu Gly Ala Leu Arg Ala Trp Leu Phe Leu Ile Leu
            100                 105                 110

Ile Val Leu Thr His Ile Met Trp Val Pro Leu Val Gln Val Ser Pro
        115                 120                 125

Asn Ala Pro Leu Phe His Tyr Ile Glu Ser Ile Ala His Asp Leu Gly
    130                 135                 140

Pro Pro Ile Gly Ala Ile Phe Leu Leu Ser Ile Ser Trp Ser Ile Val
145                 150                 155                 160

Lys Glu Pro Met Ser Arg
                165


<210> SEQ ID NO 185
<211> LENGTH: 20
<212> TYPE: DNA
<213> ORGANISM: Artificial Sequence
<220> FEATURE:
<223> OTHER INFORMATION: Oligonucleotide

<400> SEQUENCE: 185

ctgagggtgc tgtaggagac                                                  20


<210> SEQ ID NO 186
<211> LENGTH: 15
<212> TYPE: DNA
<213> ORGANISM: Artificial Sequence
<220> FEATURE:
<223> OTHER INFORMATION: Oligonucleotide

<400> SEQUENCE: 186

ggcccgtaat gctcc                                                       15


<210> SEQ ID NO 187
<211> LENGTH: 3978
<212> TYPE: DNA
<213> ORGANISM: Homo sapiens

<400> SEQUENCE: 187
```

-continued

```
agactagggg cgagtttgga gcaagtaact gtcagtgagg ttgcagttgg tctgggctgt     60
ttggctgtga gcgaaatagc tgccccccac ttctcacttg cacaccacgg gatactcctc    120
ctgaggctcc ggatgattca gatggactgt gaaaaacaac aagatggatg atcatatgga    180
gattgcttct aacataaatc tgcataaaaa tttttctgaa acatggctgg aatatttaag    240
gagttttttt tcagtactga ggacctccct gaagtcattc taacattgtc tttgatcagc    300
tccattggag catttttgaa ccggcacttg gaagactttc caattcctgt ccctgtgata    360
ttatttttac ttggatgcag ttttgaagta ttaagcttta catcttcaca ggtccaaaga    420
tacgcaaacg ccatacaatg gatgagtcca gacttatttt ttcgtatatt tacaccagta    480
gttttcttta ctactgcatt tgacatggat acgtacatgc ttcaaaagtt attttggcag    540
atacttttaa tttcaattcc cggctttttg gttaattata tcttagttct ttggcatctg    600
gcatctgtaa atcaattact tttgaagcct acccaatggt tattattttc agctatcctt    660
gtgagttcag atcccatgct aaccgcagct gctataagag accttgggct ttctagaagc    720
ctcatcagtt taattaatgg agaaagtctg atgacctctg ttatatcatt aattacattt    780
actagtatta tggattttga ccaaagacta caaagtaaaa gaaaccatac cttagctgaa    840
gagatcgtgg gtggaatttg ttcatatatt atagcaagtt tcttgtttgg aattctaagt    900
tcaaaactga ttcaattttg gatgtcaact gtttttggtg atgatgtcaa tcatataagt    960
ctcatctttt caattctgta tctcatcttt tatatttgtg agttagttgg aatgtcagga   1020
atatttactc tggccattgt gggacttctt ttaaattcta caagttttaa agcagcaatt   1080
gaagaaacac ttcttcttga atttctgacc cttcttttaa taagccctgt tttgtctcga   1140
gttggtcatg agttcagttg gcgctggata ttcataatgg tctgtagtga aatgaagggg   1200
atgcctaata taaacatggc ccttctgctt gcctactctg atctttattt tggatctgac   1260
aaagaaaaat ctcaaatatt atttcatgga gtgttagtat gcctaataac ccttgttgtc   1320
aatagattta ttttgccagt ggcagttact atactaggtc ttcgtgatgc cacatcaaca   1380
aaatataaat cggtttgttg cacatttcaa cactttcaag agctaaccaa gtctgcagcc   1440
tctgccctta aatttgacaa agatcttgct aatgctgatt ggaacatgat tgagaaagca   1500
attacacttg aaaacccata catgttgaac gaagaagaaa caacagaaca tcagaaggtg   1560
aaatgtccac actgtaacaa ggaaatagat gagatcttta acactgaagc aatggagctg   1620
gccaacaggc gtctcttgtc agcacaaata gcaagctacc agagacaata caggaatgag   1680
attctgtccc agagtgctgt ccaggtgttg gttggtgcag cagaaagttt tggtgagaag   1740
aagggaaaat gtatgagtct tgatacaata aagaattatt ctgaaagcca aaaaacagtt   1800
acctttgcta gaaaactact acttaattgg gtgtataata ccagaaagga aaaagagggc   1860
ccatcaaaat acttcttttt tcgtatatgc catacaatag tatttactga ggaatttgaa   1920
catgttggat accttgtgat attaatgaat atatttccct ttataatctc ttggatatcc   1980
cagttaaatg taatctacca cagcgaatta aaacacacta actactgttt tcttacactt   2040
tatattctag aggcactact taagatagca gcaatgagga aggacttttt ttcacatgcc   2100
tggaacatat tcgagttagc aattacatta attggcatct tacatgtaat acttattgaa   2160
atagacacca ttaagtatat ttttaatgag actgaagtaa tagtctttat aaaagttgtt   2220
caatttttc gtatactacg cattttcaag ctcatagcac caaagttgct gcaaataata   2280
gataaaagaa tgagtcatca gaagaccttt tggtatggaa tactaaaagg ctatgtccaa   2340
```

-continued ggcgaagcag acataatgac cataattgat cagattacaa gttctaaaca gattaaacag 2400
atgttattaa agcaagtgat aaggaatatg gaacatgcta taaaagagct aggctactta 2460
gagtatgatc acccagaaat tgctgtcact gtgaaaacaa aggaagaaat taatgttatg 2520
ctcaatatgg ctacagaaat tcttaaggct tttggcttaa aaggaattat tagtaaaact 2580
gaaggtgctg gaattaataa gttaatcatg gccaaaaaga aagaggtgct tgattctcaa 2640
tctattatca ggcctcttac tgttgaagaa gttctatatc atattccgtg gctagataaa 2700
aacaaagatt atataaactt cattcaggaa aaagccaaag ttgtaacatt tgattgtgga 2760
aatgatatat ttgaagaagg tgatgagccc aaaggaatct atatcattat ttcaggcatg 2820
gtaaagcttg aaaaatcaaa gccaggttta gggattgatc aaatggtgga gtcaaaggag 2880
aaagattttc cgataattga cacagactat atgctcagtg gagaaataat aggagagata 2940
aactgcttaa ctaatgaacc tatgaaatat tctgccacct gcaaaactgt agtggagaca 3000
tgttttattc ccaaaactca cttgtatgat gcttttgagc aatgctctcc tctcattaaa 3060
caaaaaatgt ggctaaaact tggactcgct attacagcca gaaaaatcag agaacactta 3120
tcttatgagg attggaacta caatatgcaa ctaaagctct ctaatattta tgtagtagat 3180
ataccaatga gtaccaaaac tgatatttat gatgaaaatc taatctatgt tatcctcata 3240
catggagctg tagaagattg tctgttacga aaaacttata gagcaccttt cttaattcct 3300
ataacatgcc atcagataca aagtattgaa gatttcacaa aagtagtgat tattcaaact 3360
ccgattaaca tgaaaacatt cagaaggaat attagaaagt ttgttcctaa acataaaagt 3420
tatcttacac caggattaat aggttcagtt ggaacattgg aagaaggcat tcaagaagaa 3480
agaaatgtta aggaggatgg agcacacagt gccgccactg ccaggagtcc ccagccttgc 3540
tccctgctgg ggacaaagtt caactgtaag gagtccccta gaataaacct aaggaaagtc 3600
aggaaagagt aagactgtta agaagaccga agcatgtatt aatgctgtgg ctatgagagg 3660
cctcctgctg cagaaacaca cttccctaca tcaagaagga gtaacttcag gttggatcct 3720
gtgtggatga tcttggtgct aagcagaaaa gaaatttgga ccttgaaacc agcagttcaa 3780
catatatact ttttgcaaaa tttccttgat ttaaaatatt tgttatttta aatatacaaa 3840
acattttaga aaatcttaga gtaaatttta gtcttaaagc cagaaaataa gtttatagcc 3900
atctagatat tttgcatatt gctcttacag caataatggt ttggttcact ttatgaaaaa 3960
taaaatgtat taaaatat 3978

<210> SEQ ID NO 188
<211> LENGTH: 1129
<212> TYPE: PRT
<213> ORGANISM: Homo sapiens

<400> SEQUENCE: 188

Met Ala Gly Ile Phe Lys Glu Phe Phe Phe Ser Thr Glu Asp Leu Pro
1 5 10 15

Glu Val Ile Leu Thr Leu Ser Leu Ile Ser Ser Ile Gly Ala Phe Leu
20 25 30

Asn Arg His Leu Glu Asp Phe Pro Ile Pro Val Pro Val Ile Leu Phe
35 40 45

Leu Leu Gly Cys Ser Phe Glu Val Leu Ser Phe Thr Ser Ser Gln Val
50 55 60

Gln Arg Tyr Ala Asn Ala Ile Gln Trp Met Ser Pro Asp Leu Phe Phe
65 70 75 80

-continued

```
Arg Ile Phe Thr Pro Val Val Phe Phe Thr Thr Ala Phe Asp Met Asp
                85                  90                  95

Thr Tyr Met Leu Gln Lys Leu Phe Trp Gln Ile Leu Leu Ile Ser Ile
            100                 105                 110

Pro Gly Phe Leu Val Asn Tyr Ile Leu Val Leu Trp His Leu Ala Ser
        115                 120                 125

Val Asn Gln Leu Leu Leu Lys Pro Thr Gln Trp Leu Leu Phe Ser Ala
    130                 135                 140

Ile Leu Val Ser Ser Asp Pro Met Leu Thr Ala Ala Ala Ile Arg Asp
145                 150                 155                 160

Leu Gly Leu Ser Arg Ser Leu Ile Ser Leu Ile Asn Gly Glu Ser Leu
                165                 170                 175

Met Thr Ser Val Ile Ser Leu Ile Thr Phe Thr Ser Ile Met Asp Phe
            180                 185                 190

Asp Gln Arg Leu Gln Ser Lys Arg Asn His Thr Leu Ala Glu Glu Ile
        195                 200                 205

Val Gly Gly Ile Cys Ser Tyr Ile Ile Ala Ser Phe Leu Phe Gly Ile
    210                 215                 220

Leu Ser Ser Lys Leu Ile Gln Phe Trp Met Ser Thr Val Phe Gly Asp
225                 230                 235                 240

Asp Val Asn His Ile Ser Leu Ile Phe Ser Ile Leu Tyr Leu Ile Phe
                245                 250                 255

Tyr Ile Cys Glu Leu Val Gly Met Ser Gly Ile Phe Thr Leu Ala Ile
            260                 265                 270

Val Gly Leu Leu Leu Asn Ser Thr Ser Phe Lys Ala Ala Ile Glu Glu
        275                 280                 285

Thr Leu Leu Leu Glu Phe Leu Thr Leu Leu Leu Ile Ser Pro Val Leu
    290                 295                 300

Ser Arg Val Gly His Glu Phe Ser Trp Arg Trp Ile Phe Ile Met Val
305                 310                 315                 320

Cys Ser Glu Met Lys Gly Met Pro Asn Ile Asn Met Ala Leu Leu Leu
                325                 330                 335

Ala Tyr Ser Asp Leu Tyr Phe Gly Ser Asp Lys Glu Lys Ser Gln Ile
            340                 345                 350

Leu Phe His Gly Val Leu Val Cys Leu Ile Thr Leu Val Val Asn Arg
        355                 360                 365

Phe Ile Leu Pro Val Ala Val Thr Ile Leu Gly Leu Arg Asp Ala Thr
    370                 375                 380

Ser Thr Lys Tyr Lys Ser Val Cys Cys Thr Phe Gln His Phe Gln Glu
385                 390                 395                 400

Leu Thr Lys Ser Ala Ala Ser Ala Leu Lys Phe Asp Lys Asp Leu Ala
                405                 410                 415

Asn Ala Asp Trp Asn Met Ile Glu Lys Ala Ile Thr Leu Glu Asn Pro
            420                 425                 430

Tyr Met Leu Asn Glu Glu Glu Thr Thr Glu His Gln Lys Val Lys Cys
        435                 440                 445

Pro His Cys Asn Lys Glu Ile Asp Glu Ile Phe Asn Thr Glu Ala Met
    450                 455                 460

Glu Leu Ala Asn Arg Arg Leu Leu Ser Ala Gln Ile Ala Ser Tyr Gln
465                 470                 475                 480

Arg Gln Tyr Arg Asn Glu Ile Leu Ser Gln Ser Ala Val Gln Val Leu
                485                 490                 495
```

-continued

```
Val Gly Ala Ala Glu Ser Phe Gly Glu Lys Lys Gly Lys Cys Met Ser
            500                 505                 510

Leu Asp Thr Ile Lys Asn Tyr Ser Glu Ser Gln Lys Thr Val Thr Phe
        515                 520                 525

Ala Arg Lys Leu Leu Leu Asn Trp Val Tyr Asn Thr Arg Lys Glu Lys
    530                 535                 540

Glu Gly Pro Ser Lys Tyr Phe Phe Phe Arg Ile Cys His Thr Ile Val
545                 550                 555                 560

Phe Thr Glu Glu Phe Glu His Val Gly Tyr Leu Val Ile Leu Met Asn
                565                 570                 575

Ile Phe Pro Phe Ile Ile Ser Trp Ile Ser Gln Leu Asn Val Ile Tyr
            580                 585                 590

His Ser Glu Leu Lys His Thr Asn Tyr Cys Phe Leu Thr Leu Tyr Ile
        595                 600                 605

Leu Glu Ala Leu Leu Lys Ile Ala Ala Met Arg Lys Asp Phe Phe Ser
    610                 615                 620

His Ala Trp Asn Ile Phe Glu Leu Ala Ile Thr Leu Ile Gly Ile Leu
625                 630                 635                 640

His Val Ile Leu Ile Glu Ile Asp Thr Ile Lys Tyr Ile Phe Asn Glu
                645                 650                 655

Thr Glu Val Ile Val Phe Ile Lys Val Val Gln Phe Phe Arg Ile Leu
            660                 665                 670

Arg Ile Phe Lys Leu Ile Ala Pro Lys Leu Leu Gln Ile Ile Asp Lys
        675                 680                 685

Arg Met Ser His Gln Lys Thr Phe Trp Tyr Gly Ile Leu Lys Gly Tyr
    690                 695                 700

Val Gln Gly Glu Ala Asp Ile Met Thr Ile Ile Asp Gln Ile Thr Ser
705                 710                 715                 720

Ser Lys Gln Ile Lys Gln Met Leu Leu Lys Gln Val Ile Arg Asn Met
                725                 730                 735

Glu His Ala Ile Lys Glu Leu Gly Tyr Leu Glu Tyr Asp His Pro Glu
            740                 745                 750

Ile Ala Val Thr Val Lys Thr Lys Glu Glu Ile Asn Val Met Leu Asn
        755                 760                 765

Met Ala Thr Glu Ile Leu Lys Ala Phe Gly Leu Lys Gly Ile Ile Ser
    770                 775                 780

Lys Thr Glu Gly Ala Gly Ile Asn Lys Leu Ile Met Ala Lys Lys Lys
785                 790                 795                 800

Glu Val Leu Asp Ser Gln Ser Ile Ile Arg Pro Leu Thr Val Glu Glu
                805                 810                 815

Val Leu Tyr His Ile Pro Trp Leu Asp Lys Asn Lys Asp Tyr Ile Asn
            820                 825                 830

Phe Ile Gln Glu Lys Ala Lys Val Val Thr Phe Asp Cys Gly Asn Asp
        835                 840                 845

Ile Phe Glu Glu Gly Asp Glu Pro Lys Gly Ile Tyr Ile Ile Ile Ser
    850                 855                 860

Gly Met Val Lys Leu Glu Lys Ser Lys Pro Gly Leu Gly Ile Asp Gln
865                 870                 875                 880

Met Val Glu Ser Lys Glu Lys Asp Phe Pro Ile Ile Asp Thr Asp Tyr
                885                 890                 895

Met Leu Ser Gly Glu Ile Ile Gly Glu Ile Asn Cys Leu Thr Asn Glu
            900                 905                 910
```

-continued

```
Pro Met Lys Tyr Ser Ala Thr Cys Lys Thr Val Val Glu Thr Cys Phe
        915                 920                 925

Ile Pro Lys Thr His Leu Tyr Asp Ala Phe Glu Gln Cys Ser Pro Leu
    930                 935                 940

Ile Lys Gln Lys Met Trp Leu Lys Leu Gly Leu Ala Ile Thr Ala Arg
945                 950                 955                 960

Lys Ile Arg Glu His Leu Ser Tyr Glu Asp Trp Asn Tyr Asn Met Gln
                965                 970                 975

Leu Lys Leu Ser Asn Ile Tyr Val Val Asp Ile Pro Met Ser Thr Lys
            980                 985                 990

Thr Asp Ile Tyr Asp Glu Asn Leu  Ile Tyr Val Ile Leu  Ile His Gly
        995                 1000                1005

Ala Val  Glu Asp Cys Leu Leu  Arg Lys Thr Tyr Arg  Ala Pro Phe
    1010                 1015                1020

Leu Ile  Pro Ile Thr Cys His  Gln Ile Gln Ser Ile  Glu Asp Phe
    1025                 1030                1035

Thr Lys  Val Val Ile Ile Gln  Thr Pro Ile Asn Met  Lys Thr Phe
    1040                 1045                1050

Arg Arg  Asn Ile Arg Lys Phe  Val Pro Lys His Lys  Ser Tyr Leu
    1055                 1060                1065

Thr Pro  Gly Leu Ile Gly Ser  Val Gly Thr Leu Glu  Glu Gly Ile
    1070                 1075                1080

Gln Glu  Glu Arg Asn Val Lys  Glu Asp Gly Ala His  Ser Ala Ala
    1085                 1090                1095

Thr Ala  Arg Ser Pro Gln Pro  Cys Ser Leu Leu Gly  Thr Lys Phe
    1100                 1105                1110

Asn Cys  Lys Glu Ser Pro Arg  Ile Asn Leu Arg Lys  Val Arg Lys
    1115                 1120                1125

Glu
```

<210> SEQ ID NO 189
<211> LENGTH: 17
<212> TYPE: DNA
<213> ORGANISM: Artificial Sequence
<220> FEATURE:
<223> OTHER INFORMATION: Oligonucleotide

<400> SEQUENCE: 189
tttgaaccgg cacttgg 17

<210> SEQ ID NO 190
<211> LENGTH: 23
<212> TYPE: DNA
<213> ORGANISM: Artificial Sequence
<220> FEATURE:
<223> OTHER INFORMATION: Oligonucleotide

<400> SEQUENCE: 190
tcaaatgcag tagtaaagaa aac 23

<210> SEQ ID NO 191
<211> LENGTH: 2898
<212> TYPE: DNA
<213> ORGANISM: Homo sapiens

<400> SEQUENCE: 191
atgtgggtgc ggtgtgcact cctggttgca cgcgactgtg gctgtgctga gcgcgtgtgc 60
ccgtctgtgg tgcgtgaccg cgtgtgtgtt gtgggggcgg ggaaaattca tacaaaagaa 120

-continued

```
aaaaatatag cacatctctt ggaaatgaaa tacttcaagt ttaatatctc tcttgctaat    180
gcagaattta tcagccaaga cagctggctg gcctgggtgg ggtttgttaa agttgtcaag    240
tataaggcct actgtaagag ataccaagtg acttttagaa gacagtgtga gggtaaaact    300
gattactatg cttggaaaca cttagtggta caggataaaa ataagtctaa cacacacaaa    360
tacagaatga ttatttgtgt gataaataca gataccattt gtgagatggc ttatgcccat    420
atagaatggg acatgatagt ctgtgcagct tatgcacacg aacttccaaa atacggtgta    480
aaggttggcc tgacaaatga tgctgcagca tgttgtactg gcctgctgct ggcatgcagg    540
cttctcagta ggtttggcat ggacaagatc tataaaggcc aagtggaggt aaccagagat    600
gaatacaacg tgggaagcac tgatggtcag ccaggtgcct ttacctgctg tttggatgca    660
ggccttgcca gaaccaccac tgacaataaa gtttttgggg ctctgagagt gctgtggatg    720
gaggtttctc tatccctcac agtgcctaac gattccctga gtaaagggaa gcctggcccc    780
aggaaggagc agctgcctgc aagagggagc ctgagccgtg gagtcctggg agcctttgag    840
gtgggcagcc agggcgtgga ggcagcagca agcccaaacg gtcaatacgg gcccagctgg    900
ggcctggcgg cggagggcac ggagggagct aggccacagg caccaaagcg ggatttgtcc    960
tatagcagga ctgactctca cagagactgt tctcctgtct gtcacaacat gtccctgagg   1020
ggtcaccttg tccccaagaa gccctcaaag gagaagcagg gacagcagaa actggacagc   1080
aagttttatg agagctgggc cacagccttg ctcacagcta tattcccggt gcttggcatc   1140
ttggtgcttg ttgaatcttt gctgatgaat gacccaatgc gtgaatgcat cctcagcacc   1200
tctggcttct cagggcctcg cgccaggctc ctgggggtcc tggccctggg cgggcttcct   1260
ctccatcttg gtgcacctgt tattgtaatg gcgtggattg tccttgcttt gctattcaca   1320
cggagcagga ccagggctga tcctgcagac gtgctgcccc ctggtgcatt tgagaagact   1380
cgcatgcatg cactgccccc gcctcttggt ttgactttag atgacggtga agtgatcacc   1440
acaagattgc tcactgatgc ttctgtgcaa aaagtcgtgg tccggatatc tgaatcctcc   1500
tcctgcctcc acaatgggct gctatccggt aacggctgtg aggtccatta ccgcagggcg   1560
aggctcttcc aggacgctca gatgcctgct cagagcccag cttatcgggg ggatctgcga   1620
gctcctgtca acgccctgag aattcagaac cggagtcagc tcagcccagg tggaaagatc   1680
aagtggcggc agcacaggca gctggaaggt acccacagaa agaaatcgag cactatgttc   1740
agaaagatcc actccatctt taactccagc ccacagagaa agacggcggc cgagagcccc   1800
ttctacgaag gagccagccc cgcagtgaag ctgattcgaa gcagttccat gtatgtggtc   1860
ggggaccacg gggagaaatt cagcgagtcc ttaaagaagt acaaaaagcac cagtagcatg   1920
gacaccagcc tgtactacct gcggcaggag gaggaccggg cgtggatgta ttcgcgcacc   1980
caggactgcc tgcagtacct gcaggagctg ctggccttgc gcaaaaaata tctcagcagc   2040
ttcagtgatc tgaagcccca ccgcacccag gggatttcct caacctcctc caaatcctcc   2100
aagggaggga aaaagactcc tgtccggtct actcccaaag aaataaagaa agcaacccca   2160
aagaaatact cgcagttcag tgctgatgtg gccgaggcca ttgccttctt tgactccatc   2220
attgcagagc tggatacaga gagacgaccc cgggctgctg aggccagcct gccaaatgaa   2280
gatgtggact ttgacgtggc caccagctcc agggagcaca gcttgcattc taactggatc   2340
ctgcgggcac cgcgcagaca ctccgaggat atcgctgccc acactgtgca tactgtagac   2400
ggccagtttc gaaggagcac cgagcacagg accgtgggca ctcagaggag actcgagagg   2460
```

-continued

```
caccccattt atttgcccaa ggctgtggaa ggggccttca acacctggaa atttaagccc   2520

aaagcctgca aaaaagacct ggggagctcc agacagatcc ttttcaactt ctcaggagaa   2580

gatatggagt gggatgcaga gctctttgcg ttggagcccc agttgtctcc tggggaggac   2640

tactatgaga cagagaaccc caaaggacag tggctgcttc gagaaagact ttgggagcgg   2700

acgactgggt ccctgagaag ctgtccgctt tcagcgcagc atgaggtatt tggtagagtt   2760

gaaaatgcca attgtaacac agtcaaccca ctcagcacac tgcctgctgg tgccgtgcca   2820

gtgccaaaca gacctgtggc ttcccagggg acaggtctca ggacactctc agagcttgag   2880

tttctctgcg tgggctga                                                 2898


<210> SEQ ID NO 192
<211> LENGTH: 965
<212> TYPE: PRT
<213> ORGANISM: Homo sapiens

<400> SEQUENCE: 192

Met Trp Val Arg Cys Ala Leu Leu Val Ala Arg Asp Cys Gly Cys Ala
1               5                   10                  15

Glu Arg Val Cys Pro Ser Val Val Arg Asp Arg Val Cys Val Val Gly
            20                  25                  30

Ala Gly Lys Ile His Thr Lys Glu Lys Asn Ile Ala His Leu Leu Glu
        35                  40                  45

Met Lys Tyr Phe Lys Phe Asn Ile Ser Leu Ala Asn Ala Glu Phe Ile
    50                  55                  60

Ser Gln Asp Ser Trp Leu Ala Trp Val Gly Phe Val Lys Val Val Lys
65                  70                  75                  80

Tyr Lys Ala Tyr Cys Lys Arg Tyr Gln Val Thr Phe Arg Arg Gln Cys
                85                  90                  95

Glu Gly Lys Thr Asp Tyr Tyr Ala Trp Lys His Leu Val Val Gln Asp
            100                 105                 110

Lys Asn Lys Ser Asn Thr His Lys Tyr Arg Met Ile Ile Cys Val Ile
        115                 120                 125

Asn Thr Asp Thr Ile Cys Glu Met Ala Tyr Ala His Ile Glu Trp Asp
    130                 135                 140

Met Ile Val Cys Ala Ala Tyr Ala His Glu Leu Pro Lys Tyr Gly Val
145                 150                 155                 160

Lys Val Gly Leu Thr Asn Asp Ala Ala Ala Cys Cys Thr Gly Leu Leu
                165                 170                 175

Leu Ala Cys Arg Leu Leu Ser Arg Phe Gly Met Asp Lys Ile Tyr Lys
            180                 185                 190

Gly Gln Val Glu Val Thr Arg Asp Glu Tyr Asn Val Gly Ser Thr Asp
        195                 200                 205

Gly Gln Pro Gly Ala Phe Thr Cys Cys Leu Asp Ala Gly Leu Ala Arg
    210                 215                 220

Thr Thr Thr Asp Asn Lys Val Phe Gly Ala Leu Arg Val Leu Trp Met
225                 230                 235                 240

Glu Val Ser Leu Ser Leu Thr Val Pro Asn Asp Ser Leu Ser Lys Gly
                245                 250                 255

Lys Pro Gly Pro Arg Lys Glu Gln Leu Pro Ala Arg Gly Ser Leu Ser
            260                 265                 270

Arg Gly Val Leu Gly Ala Phe Glu Val Gly Ser Gln Gly Val Glu Ala
        275                 280                 285
```

-continued

```
Ala Ala Ser Pro Asn Gly Gln Tyr Gly Pro Ser Trp Gly Leu Ala Ala
    290                 295                 300

Glu Gly Thr Glu Gly Ala Arg Pro Gln Ala Pro Lys Arg Asp Leu Ser
305                 310                 315                 320

Tyr Ser Arg Thr Asp Ser His Arg Asp Cys Ser Pro Val Cys His Asn
                325                 330                 335

Met Ser Leu Arg Gly His Leu Val Pro Lys Lys Pro Ser Lys Glu Lys
            340                 345                 350

Gln Gly Gln Gln Lys Leu Asp Ser Lys Phe Tyr Glu Ser Trp Ala Thr
        355                 360                 365

Ala Leu Leu Thr Ala Ile Phe Pro Val Leu Gly Ile Leu Val Leu Val
    370                 375                 380

Glu Ser Leu Leu Met Asn Asp Pro Met Arg Glu Cys Ile Leu Ser Thr
385                 390                 395                 400

Ser Gly Phe Ser Gly Pro Arg Ala Arg Leu Leu Gly Val Leu Ala Leu
                405                 410                 415

Gly Gly Leu Pro Leu His Leu Gly Ala Pro Val Ile Val Met Ala Trp
            420                 425                 430

Ile Val Leu Ala Leu Leu Phe Thr Arg Ser Arg Thr Arg Ala Asp Pro
        435                 440                 445

Ala Asp Val Leu Pro Pro Gly Ala Phe Glu Lys Thr Arg Met His Ala
    450                 455                 460

Leu Pro Pro Pro Leu Gly Leu Thr Leu Asp Asp Gly Glu Val Ile Thr
465                 470                 475                 480

Thr Arg Leu Leu Thr Asp Ala Ser Val Gln Lys Val Val Val Arg Ile
                485                 490                 495

Ser Glu Ser Ser Ser Cys Leu His Asn Gly Leu Leu Ser Gly Asn Gly
            500                 505                 510

Cys Glu Val His Tyr Arg Arg Ala Arg Leu Phe Gln Asp Ala Gln Met
        515                 520                 525

Pro Ala Gln Ser Pro Ala Tyr Arg Gly Asp Leu Arg Ala Pro Val Asn
    530                 535                 540

Ala Leu Arg Ile Gln Asn Arg Ser Gln Leu Ser Pro Gly Gly Lys Ile
545                 550                 555                 560

Lys Trp Arg Gln His Arg Gln Leu Glu Gly Thr His Arg Lys Lys Ser
                565                 570                 575

Ser Thr Met Phe Arg Lys Ile His Ser Ile Phe Asn Ser Ser Pro Gln
            580                 585                 590

Arg Lys Thr Ala Ala Glu Ser Pro Phe Tyr Glu Gly Ala Ser Pro Ala
        595                 600                 605

Val Lys Leu Ile Arg Ser Ser Ser Met Tyr Val Val Gly Asp His Gly
    610                 615                 620

Glu Lys Phe Ser Glu Ser Leu Lys Lys Tyr Lys Ser Thr Ser Ser Met
625                 630                 635                 640

Asp Thr Ser Leu Tyr Tyr Leu Arg Gln Glu Glu Asp Arg Ala Trp Met
                645                 650                 655

Tyr Ser Arg Thr Gln Asp Cys Leu Gln Tyr Leu Gln Glu Leu Leu Ala
            660                 665                 670

Leu Arg Lys Lys Tyr Leu Ser Ser Phe Ser Asp Leu Lys Pro His Arg
        675                 680                 685

Thr Gln Gly Ile Ser Ser Thr Ser Ser Lys Ser Ser Lys Gly Gly Lys
    690                 695                 700
```

-continued

```
Lys Thr Pro Val Arg Ser Thr Pro Lys Glu Ile Lys Lys Ala Thr Pro
705                 710                 715                 720

Lys Lys Tyr Ser Gln Phe Ser Ala Asp Val Ala Glu Ala Ile Ala Phe
                725                 730                 735

Phe Asp Ser Ile Ile Ala Glu Leu Asp Thr Glu Arg Arg Pro Arg Ala
            740                 745                 750

Ala Glu Ala Ser Leu Pro Asn Glu Asp Val Asp Phe Asp Val Ala Thr
        755                 760                 765

Ser Ser Arg Glu His Ser Leu His Ser Asn Trp Ile Leu Arg Ala Pro
    770                 775                 780

Arg Arg His Ser Glu Asp Ile Ala Ala His Thr Val His Thr Val Asp
785                 790                 795                 800

Gly Gln Phe Arg Arg Ser Thr Glu His Arg Thr Val Gly Thr Gln Arg
                805                 810                 815

Arg Leu Glu Arg His Pro Ile Tyr Leu Pro Lys Ala Val Glu Gly Ala
            820                 825                 830

Phe Asn Thr Trp Lys Phe Lys Pro Lys Ala Cys Lys Lys Asp Leu Gly
        835                 840                 845

Ser Ser Arg Gln Ile Leu Phe Asn Phe Ser Gly Glu Asp Met Glu Trp
    850                 855                 860

Asp Ala Glu Leu Phe Ala Leu Glu Pro Gln Leu Ser Pro Gly Glu Asp
865                 870                 875                 880

Tyr Tyr Glu Thr Glu Asn Pro Lys Gly Gln Trp Leu Leu Arg Glu Arg
                885                 890                 895

Leu Trp Glu Arg Thr Thr Gly Ser Leu Arg Ser Cys Pro Leu Ser Ala
            900                 905                 910

Gln His Glu Val Phe Gly Arg Val Glu Asn Ala Asn Cys Asn Thr Val
        915                 920                 925

Asn Pro Leu Ser Thr Leu Pro Ala Gly Ala Val Pro Val Pro Asn Arg
    930                 935                 940

Pro Val Ala Ser Gln Gly Thr Gly Leu Arg Thr Leu Ser Glu Leu Glu
945                 950                 955                 960

Phe Leu Cys Val Gly
                965
```

<210> SEQ ID NO 193
<211> LENGTH: 22
<212> TYPE: DNA
<213> ORGANISM: Artificial Sequence
<220> FEATURE:
<223> OTHER INFORMATION: Oligonucleotide

<400> SEQUENCE: 193
cgagaggcac cccatttatt tg 22

<210> SEQ ID NO 194
<211> LENGTH: 26
<212> TYPE: DNA
<213> ORGANISM: Artificial Sequence
<220> FEATURE:
<223> OTHER INFORMATION: Oligonucleotide

<400> SEQUENCE: 194
ttctctgtct catagtagtc ctcccc 26

<210> SEQ ID NO 195
<211> LENGTH: 1363
<212> TYPE: DNA

<213> ORGANISM: Homo sapiens

<400> SEQUENCE: 195

```
aacaggcccc atgctgctct ggacggctgt gctgctcttt ggtaagtcaa cgagcatggg     60
catcccctct tggagcacta aggaccttcc ctgtgttggg aaaactgtct ggctgtacct    120
ccaagcctgg ccaaaccctg tgtttgaagg agatgccctg actctgcgat gtcagggatg    180
gaagaataca ccactgtctc aggtgaagtt ctacagagat ggaaaattcc ttcatttctc    240
taaggaaaac cagactctgt ccatgggagc agcaacagtg cagagccgtg gccagtacag    300
ctgctctggg caggtgatgt atattccaca gacattcaca caaacttcag agactgccat    360
ggttcaagtc caagagctgt ttccacctcc tgtgctgagt gccatcccct ctcctgagcc    420
ccgagagggt agcctggtga ccctgagatg tcagacaaag ctgcaccccc tgaggtcagc    480
cttgaggctc cttttctcct tccacaagga cggccacacc ttgcaggaca ggggccctca    540
cccagaactc tgcatcccgg gagccaagga gggagactct gggctttact ggtgtgaggt    600
ggcccctgag ggtggccagg tccagaagca gagcccccag ctggaggtca gagtgcaggc    660
tcctgtatcc cgtcctgtgc tcactctgca ccacgggcct gctgaccctg ctgtggggga    720
catggtgcag ctcctctgtg aggcacagag gggctcccct ccgatcctgt attccttcta    780
ccttgatgag aagattgtgg ggaaccactc agctccctgt ggtggaacca cctccctcct    840
cttcccagtg aagtcagaac aggatgctgg gaactactcc tgcgaggctg agaacagtgt    900
ctccagagag aggagtgagc ccaagaagct gtctctgaag ggttctcaag tcttgttcac    960
tcccgccagc aactggctgg ttccttggct tcctgcgagc ctgcttggcc tgatggttat   1020
tgctgctgca cttctggttt atgtgagatc ctggagaaaa gctgggcccc ttccatccca   1080
gataccaccc acagctccag gtggagagca gtgcccacta tatgccaacg tgcatcacca   1140
gaaagggaaa gatgaaggtg ttgtctactc tgtggtgcat agaacctcaa agaggagtga   1200
agccaggtct gctgagttca ccgtggggag aaagcacaaa gcttcaccca aattccaccc   1260
caccctggat ctccacacca agcggctcag ggttaatggt cgagttcagg aagcttatgt   1320
ggccttggtc aacacctgct ccctcacccc cagcctgaag tga                     1363
```

<210> SEQ ID NO 196
<211> LENGTH: 450
<212> TYPE: PRT
<213> ORGANISM: Homo sapiens

<400> SEQUENCE: 196

```
Met Leu Leu Trp Thr Ala Val Leu Leu Phe Gly Lys Ser Thr Ser Met
1               5                   10                  15

Gly Ile Pro Ser Trp Ser Thr Lys Asp Leu Pro Cys Val Gly Lys Thr
            20                  25                  30

Val Trp Leu Tyr Leu Gln Ala Trp Pro Asn Pro Val Phe Glu Gly Asp
        35                  40                  45

Ala Leu Thr Leu Arg Cys Gln Gly Trp Lys Asn Thr Pro Leu Ser Gln
    50                  55                  60

Val Lys Phe Tyr Arg Asp Gly Lys Phe Leu His Phe Ser Lys Glu Asn
65                  70                  75                  80

Gln Thr Leu Ser Met Gly Ala Ala Thr Val Gln Ser Arg Gly Gln Tyr
                85                  90                  95

Ser Cys Ser Gly Gln Val Met Tyr Ile Pro Gln Thr Phe Thr Gln Thr
            100                 105                 110
```

-continued

```
Ser Glu Thr Ala Met Val Gln Val Gln Glu Leu Phe Pro Pro Pro Val
        115                 120                 125

Leu Ser Ala Ile Pro Ser Pro Glu Pro Arg Glu Gly Ser Leu Val Thr
    130                 135                 140

Leu Arg Cys Gln Thr Lys Leu His Pro Leu Arg Ser Ala Leu Arg Leu
145                 150                 155                 160

Leu Phe Ser Phe His Lys Asp Gly His Thr Leu Gln Asp Arg Gly Pro
                165                 170                 175

His Pro Glu Leu Cys Ile Pro Gly Ala Lys Glu Gly Asp Ser Gly Leu
            180                 185                 190

Tyr Trp Cys Glu Val Ala Pro Glu Gly Gly Gln Val Gln Lys Gln Ser
        195                 200                 205

Pro Gln Leu Glu Val Arg Val Gln Ala Pro Val Ser Arg Pro Val Leu
    210                 215                 220

Thr Leu His His Gly Pro Ala Asp Pro Ala Val Gly Asp Met Val Gln
225                 230                 235                 240

Leu Leu Cys Glu Ala Gln Arg Gly Ser Pro Pro Ile Leu Tyr Ser Phe
                245                 250                 255

Tyr Leu Asp Glu Lys Ile Val Gly Asn His Ser Ala Pro Cys Gly Gly
            260                 265                 270

Thr Thr Ser Leu Leu Phe Pro Val Lys Ser Glu Gln Asp Ala Gly Asn
        275                 280                 285

Tyr Ser Cys Glu Ala Glu Asn Ser Val Ser Arg Glu Arg Ser Glu Pro
    290                 295                 300

Lys Lys Leu Ser Leu Lys Gly Ser Gln Val Leu Phe Thr Pro Ala Ser
305                 310                 315                 320

Asn Trp Leu Val Pro Trp Leu Pro Ala Ser Leu Leu Gly Leu Met Val
                325                 330                 335

Ile Ala Ala Ala Leu Leu Val Tyr Val Arg Ser Trp Arg Lys Ala Gly
            340                 345                 350

Pro Leu Pro Ser Gln Ile Pro Pro Thr Ala Pro Gly Gly Glu Gln Cys
        355                 360                 365

Pro Leu Tyr Ala Asn Val His His Gln Lys Gly Lys Asp Glu Gly Val
    370                 375                 380

Val Tyr Ser Val Val His Arg Thr Ser Lys Arg Ser Glu Ala Arg Ser
385                 390                 395                 400

Ala Glu Phe Thr Val Gly Arg Lys His Lys Ala Ser Pro Lys Phe His
                405                 410                 415

Pro Thr Leu Asp Leu His Thr Lys Arg Leu Arg Val Asn Gly Arg Val
            420                 425                 430

Gln Glu Ala Tyr Val Ala Leu Val Asn Thr Cys Ser Leu Thr Pro Ser
        435                 440                 445

Leu Lys
    450
```

<210> SEQ ID NO 197
<211> LENGTH: 19
<212> TYPE: DNA
<213> ORGANISM: Artificial Sequence
<220> FEATURE:
<223> OTHER INFORMATION: Oligonucleotide

<400> SEQUENCE: 197
gtcagggatg gaagaatac 19

<210> SEQ ID NO 198
<211> LENGTH: 18
<212> TYPE: DNA
<213> ORGANISM: Artificial Sequence
<220> FEATURE:
<223> OTHER INFORMATION: Oligonucleotide

<400> SEQUENCE: 198
acaggaggtg gaaacagc                                                   18

<210> SEQ ID NO 199
<211> LENGTH: 534
<212> TYPE: DNA
<213> ORGANISM: Homo sapiens

<400> SEQUENCE: 199
acaattgtgt cttcttccag atgtcatcgc tataaggagt ggggctttca tcacctcctt    60
gacgtaggat gtgtacatgg ctctccaggt cagagttgct ccaagcaagg ttgttttgca   120
gaagtttctt ctatgtgtca ttcttttcta cactgtgtac tatgtgtccc tgagcatggg   180
ctgcgtgatg tttgaggtgc atgagttgaa tgtcctggct ccatttgatt tcaaaacaaa   240
tccctcatgg ctcaacataa actataaagt tcttttagtt tcaacagagg tcacctactt   300
tgtttgtgga ttgttttttg ttccagttgt ggaagaatgg gtttgggatt atgctatttc   360
agtcactatt cttcatgttg ccatcacttc aactgttatg ttggaattcc ccttgacatc   420
acattggtgg gctgctttag gtatatcaaa attgcttgtt tagattctct aatgcacaga   480
aataatgtta aatagaataa ctgtggaaat atattttatt ttctcataga tttt          534

<210> SEQ ID NO 200
<211> LENGTH: 128
<212> TYPE: PRT
<213> ORGANISM: Homo sapiens

<400> SEQUENCE: 200

Met Ala Leu Gln Val Arg Val Ala Pro Ser Lys Val Val Leu Gln Lys
1               5                   10                  15

Phe Leu Leu Cys Val Ile Leu Phe Tyr Thr Val Tyr Tyr Val Ser Leu
            20                  25                  30

Ser Met Gly Cys Val Met Phe Glu Val His Glu Leu Asn Val Leu Ala
        35                  40                  45

Pro Phe Asp Phe Lys Thr Asn Pro Ser Trp Leu Asn Ile Asn Tyr Lys
    50                  55                  60

Val Leu Leu Val Ser Thr Glu Val Thr Tyr Phe Val Cys Gly Leu Phe
65                  70                  75                  80

Phe Val Pro Val Val Glu Glu Trp Val Trp Asp Tyr Ala Ile Ser Val
                85                  90                  95

Thr Ile Leu His Val Ala Ile Thr Ser Thr Val Met Leu Glu Phe Pro
            100                 105                 110

Leu Thr Ser His Trp Trp Ala Ala Leu Gly Ile Ser Lys Leu Leu Val
        115                 120                 125

<210> SEQ ID NO 201
<211> LENGTH: 20
<212> TYPE: DNA
<213> ORGANISM: Artificial Sequence
<220> FEATURE:
<223> OTHER INFORMATION: Oligonucleotide

<400> SEQUENCE: 201

-continued

```
tcaaacatca cgcagcccat                                                   20


<210> SEQ ID NO 202
<211> LENGTH: 22
<212> TYPE: DNA
<213> ORGANISM: Artificial Sequence
<220> FEATURE:
<223> OTHER INFORMATION: Oligonucleotide

<400> SEQUENCE: 202

tggggctttc atcacctcct tg                                                22


<210> SEQ ID NO 203
<211> LENGTH: 615
<212> TYPE: DNA
<213> ORGANISM: Homo sapiens

<400> SEQUENCE: 203

ggggatgtga tgtcaggctt gattgtgggc atattattgg tgccccagtc cattgcttat      60

tccctgctgg ctggccaaga acctgtctat ggtctgtaca catctttttt tgccagcatc     120

atttattttc tcttgggtac ctcccgtcac atctctgtgg gcatttttgg agtactgtgc     180

cttatgattg gtgagacagt tgaccgagaa ctacagaaag ctggctatga caatgcccat     240

agtgctcctt ccttaggaat ggtttcaaat gggagcacat tattaaatca tacatcagac     300

aggatatgtg acaaaagttg ctatgcaatt atggttggca gcactgtaac ctttatagct     360

ggagtttatc agtgattgtt ttgttaatgt ggaagcaaca ttttctatga ttaatctgct     420

gttacctgtt ttgactgagc tactacaaaa agaaaaatca ctgaattgct atgggtttct     480

gaaatatcca aaaaattaac ctgaagcagg gggaaaaatg acatcacacc attagcaggt     540

attgtgtgaa acttctaaaa atgaaactga catttatctg acttattagg aataaatact     600

ctctaatgaa ctctc                                                       615


<210> SEQ ID NO 204
<211> LENGTH: 121
<212> TYPE: PRT
<213> ORGANISM: Homo sapiens

<400> SEQUENCE: 204

Met Ser Gly Leu Ile Val Gly Ile Leu Leu Val Pro Gln Ser Ile Ala
1               5                   10                  15

Tyr Ser Leu Leu Ala Gly Gln Glu Pro Val Tyr Gly Leu Tyr Thr Ser
            20                  25                  30

Phe Phe Ala Ser Ile Ile Tyr Phe Leu Leu Gly Thr Ser Arg His Ile
        35                  40                  45

Ser Val Gly Ile Phe Gly Val Leu Cys Leu Met Ile Gly Glu Thr Val
    50                  55                  60

Asp Arg Glu Leu Gln Lys Ala Gly Tyr Asp Asn Ala His Ser Ala Pro
65                  70                  75                  80

Ser Leu Gly Met Val Ser Asn Gly Ser Thr Leu Leu Asn His Thr Ser
                85                  90                  95

Asp Arg Ile Cys Asp Lys Ser Cys Tyr Ala Ile Met Val Gly Ser Thr
            100                 105                 110

Val Thr Phe Ile Ala Gly Val Tyr Gln
        115                 120


<210> SEQ ID NO 205
<211> LENGTH: 20
```

-continued

<212> TYPE: DNA
<213> ORGANISM: Artificial Sequence
<220> FEATURE:
<223> OTHER INFORMATION: Oligonucleotide

<400> SEQUENCE: 205
taaatcatac atcagacagg 20

<210> SEQ ID NO 206
<211> LENGTH: 20
<212> TYPE: DNA
<213> ORGANISM: Artificial Sequence
<220> FEATURE:
<223> OTHER INFORMATION: Oligonucleotide

<400> SEQUENCE: 206
aaaacaggta acagcagatt 20

<210> SEQ ID NO 207
<211> LENGTH: 513
<212> TYPE: DNA
<213> ORGANISM: Homo sapiens

<400> SEQUENCE: 207
atggcggcgg ccgctctcgc gagaattcgg cccgtcgggc tccaagcccg gcgcctggcg 60
tcggagggaa agactcgagc cgaaagcccc atctctgacc ctagcaactc ataccettct 120 ggcttccctt tagcaaagcg cctggacgtc atcccctctt cagatacccc aggcctcgtc 180
ctggccactg gcttgactat tgcaggagag cctgataaga tgggacacgg ctccaccttg 240
cattcagcaa gtcgttatcc tgcaactacg atgcaccagg aagaggatgt ggtgaggcca 300
gcttttccat atgcagttag gcatcgaagg gaagatctgc tgtacctaag tggggtgggc 360
atttcatttt tagggaccgt ctttgttaaa ataatttggg acctcataaa gcctccagcc 420
attcctgatc aggacatagc ttacaacagc agcctggtgc ccataacctg gacagcctgg 480
agtgaagtca cactcccaga cttgatgttc taa 513

<210> SEQ ID NO 208
<211> LENGTH: 170
<212> TYPE: PRT
<213> ORGANISM: Homo sapiens

<400> SEQUENCE: 208

Met Ala Ala Ala Ala Leu Ala Arg Ile Arg Pro Val Gly Leu Gln Ala
1 5 10 15

Arg Arg Leu Ala Ser Glu Gly Lys Thr Arg Ala Glu Ser Pro Ile Ser
20 25 30

Asp Pro Ser Asn Ser Tyr Pro Ser Gly Phe Pro Leu Ala Lys Arg Leu
35 40 45

Asp Val Ile Pro Ser Ser Asp Thr Pro Gly Leu Val Leu Ala Thr Gly
50 55 60

Leu Thr Ile Ala Gly Glu Pro Asp Lys Met Gly His Gly Ser Thr Leu
65 70 75 80

His Ser Ala Ser Arg Tyr Pro Ala Thr Thr Met His Gln Glu Glu Asp
85 90 95

Val Val Arg Pro Ala Phe Pro Tyr Ala Val Arg His Arg Arg Glu Asp
100 105 110

Leu Leu Tyr Leu Ser Gly Val Gly Ile Ser Phe Leu Gly Thr Val Phe
115 120 125

-continued

```
Val Lys Ile Ile Trp Asp Leu Ile Lys Pro Pro Ala Ile Pro Asp Gln
    130                 135                 140

Asp Ile Ala Tyr Asn Ser Ser Leu Val Pro Ile Thr Trp Thr Ala Trp
145                 150                 155                 160

Ser Glu Val Thr Leu Pro Asp Leu Met Phe
                165                 170


<210> SEQ ID NO 209
<211> LENGTH: 20
<212> TYPE: DNA
<213> ORGANISM: Artificial Sequence
<220> FEATURE:
<223> OTHER INFORMATION: Oligonucleotide

<400> SEQUENCE: 209

tgagccctag atatacttgg                                                 20


<210> SEQ ID NO 210
<211> LENGTH: 18
<212> TYPE: DNA
<213> ORGANISM: Artificial Sequence
<220> FEATURE:
<223> OTHER INFORMATION: Oligonucleotide

<400> SEQUENCE: 210

cagtcagcct ccatttct                                                   18


<210> SEQ ID NO 211
<211> LENGTH: 508
<212> TYPE: DNA
<213> ORGANISM: Homo sapiens

<400> SEQUENCE: 211

tgagccctag atatacttgg cttgcattta ggggccatga tgtttagaga tgaataatgc     60

cttacatgct ggagtcaccc tcagtttgtc aaagtgttca cactgtgaga ggctcacaga    120

aatggaggct gactgaagga agagcagatt cacatctttc atcccttctt tatgctcatg    180

cttctaattt ttgttcccat gttttcttgc ccctcctctt cttagcattt attttgtctg    240

tttctctttc ccctcttctg gctccctctc catctctcct gagcacagaa atgcggctac    300

tgtatttaat ccacagtggc cccctctggc cccctctttg tgtctcctga gcacaggccc    360

tggccccctc tccatctctc ctgacctcct gatccgccca cctcggccag ttattgctgt    420

tttataagga aaatgttttc tagtaccaca cttgtctccc tggaagggat agaagaagga    480

gggaaggaag tagggaggca gggaagag                                       508


<210> SEQ ID NO 212
<211> LENGTH: 97
<212> TYPE: PRT
<213> ORGANISM: Homo sapiens

<400> SEQUENCE: 212

Met Pro Tyr Met Leu Glu Ser Pro Ser Val Cys Gln Ser Val His Thr
1               5                   10                  15

Val Arg Gly Ser Gln Lys Trp Arg Leu Thr Glu Gly Arg Ala Asp Ser
            20                  25                  30

His Leu Ser Ser Leu Leu Tyr Ala His Ala Ser Asn Phe Cys Ser His
        35                  40                  45

Val Phe Leu Pro Leu Leu Phe Leu Ala Phe Ile Leu Ser Val Ser Leu
    50                  55                  60
```

-continued

```
Ser Pro Leu Leu Ala Pro Ser Pro Ser Leu Leu Ser Thr Glu Met Arg
65                  70                  75                  80

Leu Leu Tyr Leu Ile His Ser Gly Pro Leu Trp Pro Pro Leu Cys Val
                85                  90                  95

Ser


<210> SEQ ID NO 213
<211> LENGTH: 25
<212> TYPE: DNA
<213> ORGANISM: Artificial Sequence
<220> FEATURE:
<223> OTHER INFORMATION: Oligonucleotide

<400> SEQUENCE: 213

ctgtatttaa tccacagtgg ccccc                                            25


<210> SEQ ID NO 214
<211> LENGTH: 27
<212> TYPE: DNA
<213> ORGANISM: Artificial Sequence
<220> FEATURE:
<223> OTHER INFORMATION: Oligonucleotide

<400> SEQUENCE: 214

tccctacttc cttccctcct tcttcta                                          27


<210> SEQ ID NO 215
<211> LENGTH: 1321
<212> TYPE: DNA
<213> ORGANISM: Homo sapiens

<400> SEQUENCE: 215

cagtgcccag gcaagcccag gagttgacat ttctctgccc agccatgggc ctcaccctgc      60

tcttgctgct gctcctggga ctagaaggtc agggcatagt tggcagcctc cctgaggtgc     120

tgcaggcacc cgtgggaagc tccattctgg tgcagtgcca ctacaggctc caggatgtca     180

aagctcagaa ggtgtggtgc cggttcttgc cggaggggtg ccagcccctg gtgtcctcag     240

ctgtggatcg cagagctcca gcgggcaggc gtacgtttct cacagacctg ggtgggggcc     300

tgctgcaggt ggaaatggtt accctgcagg aagaggatgc tggcgagtat ggctgcatgg     360

tggatggggc cagggggccc cagattttgc acagagtctc tctgaacata ctgcccccag     420

aggaagaaga agagacccat aagattggca gtctggctga gaacgcattc tcagaccctg     480

caggcagtgc caaccctttg gaacccagcc aggatgagaa gagcatcccc ttgatctggg     540

gtgctgtgct cctggtaggt ctgctggtgg cagcggtggt gctgtttgct gtgatggcca     600

agaggaaaca agggaacagg cttggtgtct gtggccgatt cctgagcagc agagtttcag     660

gcatgaatcc ctcctcagtg gtccaccacg tcagtgactc tggaccggct gctgaattgc     720

ctttggatgt accacacatt aggcttgact caccaccttc atttgacaat accacctaca     780

ccagcctacc tcttgattcc ccatcaggaa aaccttcact cccagctcca tcctcattgc     840

cccctctacc tcctaaggtc ctggtctgct ccaagcctgt gacatatgcc acagtaatct     900

tcccgggagg gaacaagggt ggagggacct cgtgtgggcc agcccagaat ccacctaaca     960

atcagactcc atccagctaa gctgctcatc acactttaaa ctcatgagga ccatccctag    1020

gggttctgtg catccatcca gccagctcat gccctaggat ccttaggata tctgagcaac    1080

cagggacttt aagatctaat ccaatgtcct aactttacta gggaaagtga cgctcagaca    1140

tgactgagat gtcttgggga agacctccct gcacccaact cccccactgg ttcttctacc    1200
```

attacacact gggctaaata aaccctaata atgatgtgca aactcttaat ggctgaatgg 1260
gaaaggaaac tgcccaagtt tgactaattg cttggcctgt gaatggaaaa gactctggtc 1320
t 1321

<210> SEQ ID NO 216
<211> LENGTH: 311
<212> TYPE: PRT
<213> ORGANISM: Homo sapiens

<400> SEQUENCE: 216

Met Gly Leu Thr Leu Leu Leu Leu Leu Leu Leu Gly Leu Glu Gly Gln
1 5 10 15

Gly Ile Val Gly Ser Leu Pro Glu Val Leu Gln Ala Pro Val Gly Ser
20 25 30

Ser Ile Leu Val Gln Cys His Tyr Arg Leu Gln Asp Val Lys Ala Gln
35 40 45

Lys Val Trp Cys Arg Phe Leu Pro Glu Gly Cys Gln Pro Leu Val Ser
50 55 60

Ser Ala Val Asp Arg Arg Ala Pro Ala Gly Arg Arg Thr Phe Leu Thr
65 70 75 80

Asp Leu Gly Gly Gly Leu Leu Gln Val Glu Met Val Thr Leu Gln Glu
85 90 95

Glu Asp Ala Gly Glu Tyr Gly Cys Met Val Asp Gly Ala Arg Gly Pro
100 105 110

Gln Ile Leu His Arg Val Ser Leu Asn Ile Leu Pro Pro Glu Glu Glu
115 120 125

Glu Glu Thr His Lys Ile Gly Ser Leu Ala Glu Asn Ala Phe Ser Asp
130 135 140

Pro Ala Gly Ser Ala Asn Pro Leu Glu Pro Ser Gln Asp Glu Lys Ser
145 150 155 160

Ile Pro Leu Ile Trp Gly Ala Val Leu Leu Val Gly Leu Leu Val Ala
165 170 175

Ala Val Val Leu Phe Ala Val Met Ala Lys Arg Lys Gln Gly Asn Arg
180 185 190

Leu Gly Val Cys Gly Arg Phe Leu Ser Ser Arg Val Ser Gly Met Asn
195 200 205

Pro Ser Ser Val Val His His Val Ser Asp Ser Gly Pro Ala Ala Glu
210 215 220

Leu Pro Leu Asp Val Pro His Ile Arg Leu Asp Ser Pro Pro Ser Phe
225 230 235 240

Asp Asn Thr Thr Tyr Thr Ser Leu Pro Leu Asp Ser Pro Ser Gly Lys
245 250 255

Pro Ser Leu Pro Ala Pro Ser Ser Leu Pro Pro Leu Pro Pro Lys Val
260 265 270

Leu Val Cys Ser Lys Pro Val Thr Tyr Ala Thr Val Ile Phe Pro Gly
275 280 285

Gly Asn Lys Gly Gly Gly Thr Ser Cys Gly Pro Ala Gln Asn Pro Pro
290 295 300

Asn Asn Gln Thr Pro Ser Ser
305 310

<210> SEQ ID NO 217
<211> LENGTH: 18
<212> TYPE: DNA

-continued

<213> ORGANISM: Artificial Sequence
<220> FEATURE:
<223> OTHER INFORMATION: Oligonucleotide

<400> SEQUENCE: 217
aggaagaaga agagaccc 18

<210> SEQ ID NO 218
<211> LENGTH: 18
<212> TYPE: DNA
<213> ORGANISM: Artificial Sequence
<220> FEATURE:
<223> OTHER INFORMATION: Oligonucleotide

<400> SEQUENCE: 218
catcacagca aacagcac 18

<210> SEQ ID NO 219
<211> LENGTH: 3874
<212> TYPE: DNA
<213> ORGANISM: Homo sapiens

<400> SEQUENCE: 219
gagaactggg gcggcgcggc gcggcgcggt gcatttccag gcgctgctct ccgtcgcaga 60
gaaccctgag ctcggcgcgc cgagagtccc agcagggcaa gggggcgcgg cgtcctggtc 120
ctcgagcttg ggagacagat gcgcatgggc gtgggggcat gcggacctaa gctcgggtga 180
agctctcggg aagggcaaga ctgcggcgac gagatgcgag cagaggagcc ctgcgccccc 240
ggggccccca gcgccctggg agcccagcgc acgccgggcc ccgagctgcg cctgtccagc 300
cagctgctgc ccgagctctg taccttcgtg gtgcgcgtgc tgttctacct ggggcctgtc 360
tacctagctg gctacctggg gctcagcata acctggttgc tgctcggcgc cctgctgtgg 420
atgtggtggc gcaggaaccg ccgcgggaag cttgggcgcc tggccgccgc cttcgaattc 480
cttgacaatg aacgcgagtt catcagccgc gagctgcggg gccagcacct gccagcctgg 540
atccacttcc cggacgtgga gcgggtcgag tgggccaaca agatcatctc tcagacctgg 600
ccctacctaa gcatgatcat ggaaagcaag ttccgggaga aacttgagcc caagatccga 660
gagaagagca tccacctgag gacctttacc tttaccaagc tctactttgg acagaagtgt 720
cccagggtca acggtgtcaa ggcacacact aatacgtgca accgaagacg tgtgactgtg 780
gacctgcaga tctgctacat cggggactgt gagatcagtg tggagctgca gaagattcag 840
gctggtgtga acgggatcca gttgcagggc accctgcggg tcatcctgga gcccctccta 900
gtggacaagc cctttgtggg agccgtgact gtgttcttcc ttcagaagca gcacctacag 960
atcaactgga ctggcctgac caacctgctg gatgcgccgg gaatcaatga tgtgtcagac 1020
agcttactgg aggacctcat tgccacccac ctggtgctgc ccaaccgtgt gactgtgcct 1080
gtgaagaagg ggctggatct gaccaacctg cgcttccctc tgccctgtgg ggtgatcaga 1140
gtgcacttgc tggaggcaga gcagctggcc cagaaggaca actttctggg gctccgaggc 1200
aagtcagatc cctacgccaa ggtgagcatc ggcctacagc atttccggag taggaccatc 1260
tacaggaacc tgaaccccac ctggaacgaa gtgtttgagt tcatggtgta cgaagtccct 1320
ggacaggacc tggaggtaga cctgtatgat gaggataccg acagggatga cttcctgggc 1380
agcctgcaga tctgccttgg agatgtcatg accaacagag tggtggatga gtggtttgtc 1440
ctgaatgaca caaccagcgg gcggctgcac ctgcggctgg agtggctttc attgcttact 1500
gaccaagaag ttctgactga ggaccatggt ggcctttcca ctgccattct cgtggtcttc 1560

-continued

```
ttggagagtg cctgcaactt gccgagaaac ccttttgact acctgaatgg tgaatatcga   1620
gccaaaaaac tctccaggtt tgccagagtg aaacaaggtc agcaaagacc cttcttccta   1680
tgtcaaacta tctgtaggca agaagacaca tacaagtaag acctgtcccc acaacaagga   1740
ccctgtgtgg agccaggtgt tctccttctt tgtgcacaat gtggccactg agcggctcca   1800
tctgaaggtt tgatggaaga agggctcttg aaacagagtt aagaggtttt taagccaggc   1860
gggctgggaa gcttgaagtg caccttgagc aggttctcct ggcagcgttt aaagtcagcc   1920
ccttgtatgt aagagaggac actgaggccc cacaaggcct catctcctta aggctagtgc   1980
ctgaggtcac tgtatagggg gatgtgggag gataaatcct caagtccctt gactttccct   2040
gcaaaagggt ctttatattt gctacacagt acccagagca gcctatctac acaggacatt   2100
aataatggtg tactttaaaa aatatatgtt tcatttaatc ttcacaaaag atctgtagag   2160
taagcaaaga gaggcaaaaa caatgtcttg tccaagatct catgaccaac aagtggtgga   2220
gctgggatct tttagggccc tgagccctgc ctggagagca gcacagctca tcagtcccca   2280
aagccccctg gctctgggca tttgacagac tagctcatac agatcataat tgcctctact   2340
ctgagtcact atcttccctg acagaagaca aggaccaggt ctggcctgat cccattctag   2400
ttttcagaat aggaccagat gcccatagaa gcacagtaca gactgaagta aacccaaact   2460
tggctggggc tcagatacta gtagtggagt ggtggggctt ggttatcctc ttgttttgtg   2520
actggaccac tgcccaggtg cttgatgatg accaggagtg tgctctggga atgctggagg   2580
tccccctgtg ccagatcctc ccctatgctg acctcactct tgagcagcgc tttcagctgg   2640
accactcagg cctggacagc ctcatctcca tgaggctggt gcttgcagtt cctgcaagtg   2700
gaggaacgag agctggggag cccatacaca ggacctgaag ccctaaagaa aggccctctg   2760
ctcatcaaga aagtggctac caaccagggt cccaaagccc aacctcagga agaaggccct   2820
acagatttgc catgtccccc agaccctgct tctgatacta aggacgtatc caggagtacc   2880
acaaccacca ccagtgctac caccgttgcc actgagccca catcccaaga gacaggccca   2940
gagcctaaag gcaaggacag tgccaaaagg ttctgtgagc ccatcgggga gaagaagagt   3000
ccagccacca tcttcctgac tgtcccaggt ccccactctc cagggcccat caagtcaccc   3060
agacccatga aatgccctgc ctccccattc gcatggccgc ccaagaggct ggctcccagc   3120
atgtcctcgc tcaactcctt ggcctcttct tgctttgacc tggcagatat cagcctcaac   3180
attgagtatg cacctctctg cttaatcttt tctaaaatcg cctgtatgaa aaatacctcg   3240
ctggatggaa aagtagatat gaacttacat ttctgtgcaa gttgtttttt cacaaaatat   3300
cttcctaaga ggcagcatgg tgtggtagaa agaacacagg acaagggaga gagagccaaa   3360
caggctgttt atggctctag ctgcgtactg actataaaat agatgctgga ctctggttga   3420
ggtggggacc tcaggcgacg gcagctgggt gagattcagc tcacagtgcg ctatgtgtgt   3480
ctgcggcgct gcctcagcgt gctaatcaat ggctgcagaa acctaacacc atgtaccagc   3540
agtggagctg atccctacgt ccgtgtctac ttgttgccag aaaggaagtg ggcatgtcgt   3600
aagaagactt cagtgaagcg gaagaccttg gaacccctgt ttgatgagac atttgaattt   3660
tttgttccca tggaagaagt aaagaagagg tcactagatg ttgcagtgaa aaatagtagg   3720
ccacttggct cacacagaag aaaggagtta ggaaaagtac tgattgactt atcaaaagaa   3780
gatctgatta agggcttttc acaatggtaa gtgtgccctt tcattttatc actgttatcc   3840
tgctattcaa gacagttttc ccttttcagt actg                               3874
```

-continued

<210> SEQ ID NO 220
<211> LENGTH: 501
<212> TYPE: PRT
<213> ORGANISM: Homo sapiens

<400> SEQUENCE: 220

```
Met Arg Ala Glu Glu Pro Cys Ala Pro Gly Ala Pro Ser Ala Leu Gly
1               5                   10                  15

Ala Gln Arg Thr Pro Gly Pro Glu Leu Arg Leu Ser Ser Gln Leu Leu
            20                  25                  30

Pro Glu Leu Cys Thr Phe Val Val Arg Val Leu Phe Tyr Leu Gly Pro
        35                  40                  45

Val Tyr Leu Ala Gly Tyr Leu Gly Leu Ser Ile Thr Trp Leu Leu Leu
    50                  55                  60

Gly Ala Leu Leu Trp Met Trp Trp Arg Arg Asn Arg Arg Gly Lys Leu
65                  70                  75                  80

Gly Arg Leu Ala Ala Ala Phe Glu Phe Leu Asp Asn Glu Arg Glu Phe
                85                  90                  95

Ile Ser Arg Glu Leu Arg Gly Gln His Leu Pro Ala Trp Ile His Phe
            100                 105                 110

Pro Asp Val Glu Arg Val Glu Trp Ala Asn Lys Ile Ile Ser Gln Thr
        115                 120                 125

Trp Pro Tyr Leu Ser Met Ile Met Glu Ser Lys Phe Arg Glu Lys Leu
    130                 135                 140

Glu Pro Lys Ile Arg Glu Lys Ser Ile His Leu Arg Thr Phe Thr Phe
145                 150                 155                 160

Thr Lys Leu Tyr Phe Gly Gln Lys Cys Pro Arg Val Asn Gly Val Lys
                165                 170                 175

Ala His Thr Asn Thr Cys Asn Arg Arg Arg Val Thr Val Asp Leu Gln
            180                 185                 190

Ile Cys Tyr Ile Gly Asp Cys Glu Ile Ser Val Glu Leu Gln Lys Ile
        195                 200                 205

Gln Ala Gly Val Asn Gly Ile Gln Leu Gln Gly Thr Leu Arg Val Ile
    210                 215                 220

Leu Glu Pro Leu Leu Val Asp Lys Pro Phe Val Gly Ala Val Thr Val
225                 230                 235                 240

Phe Phe Leu Gln Lys Gln His Leu Gln Ile Asn Trp Thr Gly Leu Thr
                245                 250                 255

Asn Leu Leu Asp Ala Pro Gly Ile Asn Asp Val Ser Asp Ser Leu Leu
            260                 265                 270

Glu Asp Leu Ile Ala Thr His Leu Val Leu Pro Asn Arg Val Thr Val
        275                 280                 285

Pro Val Lys Lys Gly Leu Asp Leu Thr Asn Leu Arg Phe Pro Leu Pro
    290                 295                 300

Cys Gly Val Ile Arg Val His Leu Leu Glu Ala Glu Gln Leu Ala Gln
305                 310                 315                 320

Lys Asp Asn Phe Leu Gly Leu Arg Gly Lys Ser Asp Pro Tyr Ala Lys
                325                 330                 335

Val Ser Ile Gly Leu Gln His Phe Arg Ser Arg Thr Ile Tyr Arg Asn
            340                 345                 350

Leu Asn Pro Thr Trp Asn Glu Val Phe Glu Phe Met Val Tyr Glu Val
        355                 360                 365

Pro Gly Gln Asp Leu Glu Val Asp Leu Tyr Asp Glu Asp Thr Asp Arg
    370                 375                 380
```

-continued

Asp Asp Phe Leu Gly Ser Leu Gln Ile Cys Leu Gly Asp Val Met Thr
385 390 395 400

Asn Arg Val Val Asp Glu Trp Phe Val Leu Asn Asp Thr Thr Ser Gly
405 410 415

Arg Leu His Leu Arg Leu Glu Trp Leu Ser Leu Leu Thr Asp Gln Glu
420 425 430

Val Leu Thr Glu Asp His Gly Gly Leu Ser Thr Ala Ile Leu Val Val
435 440 445

Phe Leu Glu Ser Ala Cys Asn Leu Pro Arg Asn Pro Phe Asp Tyr Leu
450 455 460

Asn Gly Glu Tyr Arg Ala Lys Lys Leu Ser Arg Phe Ala Arg Val Lys
465 470 475 480

Gln Gly Gln Gln Arg Pro Phe Phe Leu Cys Gln Thr Ile Cys Arg Gln
485 490 495

Glu Asp Thr Tyr Lys
500

<210> SEQ ID NO 221
<211> LENGTH: 20
<212> TYPE: DNA
<213> ORGANISM: Artificial Sequence
<220> FEATURE:
<223> OTHER INFORMATION: Oligonucleotide

<400> SEQUENCE: 221
tggggcctgt ctacctagct 20

<210> SEQ ID NO 222
<211> LENGTH: 19
<212> TYPE: DNA
<213> ORGANISM: Artificial Sequence
<220> FEATURE:
<223> OTHER INFORMATION: Oligonucleotide

<400> SEQUENCE: 222
tcttgttggc ccactcgac 19

<210> SEQ ID NO 223
<211> LENGTH: 1020
<212> TYPE: DNA
<213> ORGANISM: Homo sapiens

<400> SEQUENCE: 223
agacacagga cctgctgggc cacagaaagg aggctctggg tagacgcact agattactgg 60
ataaatcact tcaatttccc aatgaatttt atattgttta tttttatacc tggagttttt 120
tccttaaaaa gtagcacttt gaagcctact attgaagcat tgcctaatgt gctaccttta 180
aatgaagatg ttaataagca ggaagaaaag aatgaagatc atactcccaa ttatgctcct 240
gctaatgaga aaaatggcaa ttattataaa gatataaaac aatatgtgtt cacaacacaa 300
aatccaaatg gcactgagtc tgaaatatct gtgagagcca caactgacct gaattttgct 360
ctaaaaaacg ataaaactgt caatgcaact acatatgaaa aatccaccat tgaagaagaa 420
acaactacta gcgaaccctc tcataaaaat attcaaagat caaccccaaa cgtgcctgca 480
ttttggacaa tgttagctaa agctataaat ggaacagcag tggtcatgga tgataaagat 540
caattatttc acccaattcc agagtctgat gtgaatgcta cacagggaga aaatcagcca 600
gatctagagg atctgaagat caaaataatg ctgggaatct cgttgatgac cctcctcctc 660

-continued

```
tttgtggtcc tcttggcatt ctgtagtgct acactgtaca aactgaggca tctgagttat    720

aaaagttgtg agagtcagta ctctgtcaac ccagagctgg ccacgatgtc ttactttcat    780

ccatcagaag gtgtttcaga tacatccttt tccaagagtg cagagagcag cacatttttg    840

ggtaccactt cttcagatat gagaagatca ggcacaagaa catcagaatc taagataatg    900

acggatatca tttccatagg ctcagataat gagatgcatg aaaacgatga gtcggttacc    960

cggtgaagaa atcaaggaac ccggtgaaga aatcttattg atgaataaat aactttaatt   1020
```

<210> SEQ ID NO 224
<211> LENGTH: 294
<212> TYPE: PRT
<213> ORGANISM: Homo sapiens

<400> SEQUENCE: 224

```
Met Asn Phe Ile Leu Phe Ile Phe Ile Pro Gly Val Phe Ser Leu Lys
1               5                   10                  15

Ser Ser Thr Leu Lys Pro Thr Ile Glu Ala Leu Pro Asn Val Leu Pro
            20                  25                  30

Leu Asn Glu Asp Val Asn Lys Gln Glu Glu Lys Asn Glu Asp His Thr
        35                  40                  45

Pro Asn Tyr Ala Pro Ala Asn Glu Lys Asn Gly Asn Tyr Tyr Lys Asp
    50                  55                  60

Ile Lys Gln Tyr Val Phe Thr Thr Gln Asn Pro Asn Gly Thr Glu Ser
65                  70                  75                  80

Glu Ile Ser Val Arg Ala Thr Thr Asp Leu Asn Phe Ala Leu Lys Asn
                85                  90                  95

Asp Lys Thr Val Asn Ala Thr Thr Tyr Glu Lys Ser Thr Ile Glu Glu
            100                 105                 110

Glu Thr Thr Thr Ser Glu Pro Ser His Lys Asn Ile Gln Arg Ser Thr
        115                 120                 125

Pro Asn Val Pro Ala Phe Trp Thr Met Leu Ala Lys Ala Ile Asn Gly
    130                 135                 140

Thr Ala Val Val Met Asp Asp Lys Asp Gln Leu Phe His Pro Ile Pro
145                 150                 155                 160

Glu Ser Asp Val Asn Ala Thr Gln Gly Glu Asn Gln Pro Asp Leu Glu
                165                 170                 175

Asp Leu Lys Ile Lys Ile Met Leu Gly Ile Ser Leu Met Thr Leu Leu
            180                 185                 190

Leu Phe Val Val Leu Leu Ala Phe Cys Ser Ala Thr Leu Tyr Lys Leu
        195                 200                 205

Arg His Leu Ser Tyr Lys Ser Cys Glu Ser Gln Tyr Ser Val Asn Pro
    210                 215                 220

Glu Leu Ala Thr Met Ser Tyr Phe His Pro Ser Glu Gly Val Ser Asp
225                 230                 235                 240

Thr Ser Phe Ser Lys Ser Ala Glu Ser Ser Thr Phe Leu Gly Thr Thr
                245                 250                 255

Ser Ser Asp Met Arg Arg Ser Gly Thr Arg Thr Ser Glu Ser Lys Ile
            260                 265                 270

Met Thr Asp Ile Ile Ser Ile Gly Ser Asp Asn Glu Met His Glu Asn
        275                 280                 285

Asp Glu Ser Val Thr Arg
    290
```

<210> SEQ ID NO 225

-continued

<211> LENGTH: 24
<212> TYPE: DNA
<213> ORGANISM: Artificial Sequence
<220> FEATURE:
<223> OTHER INFORMATION: Oligonucleotide

<400> SEQUENCE: 225
tgaatgctac acagggagaa aatc 24

<210> SEQ ID NO 226
<211> LENGTH: 21
<212> TYPE: DNA
<213> ORGANISM: Artificial Sequence
<220> FEATURE:
<223> OTHER INFORMATION: Oligonucleotide

<400> SEQUENCE: 226
tgaaagtaag acatcgtggc c 21

<210> SEQ ID NO 227
<211> LENGTH: 309
<212> TYPE: DNA
<213> ORGANISM: Homo sapiens

<400> SEQUENCE: 227
atgaccacag ccacccctct gggggatacc accttcttct cactgaacat gaccaccagg 60
ggagaagact tcctgtataa gagttctgga gccattgttg ctgccgttgt ggtggttgtc 120
atcatcatct tcaccgtggt tctgatcctg ctgaagatgt acaacaggaa aatgaggacg 180
aggcgggaac tagagcccaa gggccccaag ccaaccgccc cttctgccgt gggcccaaac 240
agcaacggca gccaacaccc agcaactgtg accttcagtc ctgttgacgt ccaggtggag 300
acgcgatga 309

<210> SEQ ID NO 228
<211> LENGTH: 102
<212> TYPE: PRT
<213> ORGANISM: Homo sapiens

<400> SEQUENCE: 228

Met Thr Thr Ala Thr Pro Leu Gly Asp Thr Thr Phe Phe Ser Leu Asn
1 5 10 15

Met Thr Thr Arg Gly Glu Asp Phe Leu Tyr Lys Ser Ser Gly Ala Ile
20 25 30

Val Ala Ala Val Val Val Val Val Ile Ile Ile Phe Thr Val Val Leu
35 40 45

Ile Leu Leu Lys Met Tyr Asn Arg Lys Met Arg Thr Arg Arg Glu Leu
50 55 60

Glu Pro Lys Gly Pro Lys Pro Thr Ala Pro Ser Ala Val Gly Pro Asn
65 70 75 80

Ser Asn Gly Ser Gln His Pro Ala Thr Val Thr Phe Ser Pro Val Asp
85 90 95

Val Gln Val Glu Thr Arg
100

<210> SEQ ID NO 229
<211> LENGTH: 19
<212> TYPE: DNA
<213> ORGANISM: Artificial Sequence
<220> FEATURE:
<223> OTHER INFORMATION: Oligonucleotide -continued

<400> SEQUENCE: 229
ggggatacca ccttcttct 19

<210> SEQ ID NO 230
<211> LENGTH: 18
<212> TYPE: DNA
<213> ORGANISM: Artificial Sequence
<220> FEATURE:
<223> OTHER INFORMATION: Oligonucleotide

<400> SEQUENCE: 230
agttgctggg tgttggct 18

<210> SEQ ID NO 231
<211> LENGTH: 2510
<212> TYPE: DNA
<213> ORGANISM: Homo sapiens

<400> SEQUENCE: 231
gactttttaa taatagtcgt tctgactgat gtgaaatgga gtctctttgt ggttctgatt 60
tgcatctctg atgatgcatg atgttgacca gtttttaata tgtttgttga ctgcttgtat 120
gtcttctttt aagaagtgtc tgttcatatc ctttgccctt tcgcttctat gcaccaataa 180
cacccaggct gagagtcaaa ccaagaacac aatcctgact acagtagcca taaagaaaat 240
gaaatacctg ggaatacacc taatcaaaaa catgaaagca ctctctagag ggagaactac 300
aaaacattgc tgaaagaaat cagagatgat tctctgaaaa agaagtcaga ttagaaatga 360
ttctctgaaa aagaaatcat ctctgatttc tttcagcagt gtgtttttttg tttgtttgtt 420 tgttttgaga cagagtcttg ctctgtcgcc aaggctggag ggcaatggca tgatttcagc 480
tcactacaac ctcctgctcc tgggttcgag cgattctcct acctcagcct cccgagtagc 540
tgggattaca ggaggctgag aaaatgttag aaattggggg agacaagttt cccttagaga 600
gcaggaagtt actaagtagt cctggaaaga acatcagttg cagatgtgac ccctctgaga 660
ttaatatatc tgatgaaatg cctaaaacta cagtttggaa agctctcagt atgaattctg 720
gaaatgcaaa ggaaaagagt ctcttcaact aagagtcttt gctgggatgg aagatttggg 780
ccgtgtggtg cctcagggaa gttctggtta cagagaaaat ggcgagtctc tcagagaaga 840
agcaagacca agtctggccc tgtccttggt catctcaaag ccatgccgaa gcattcagtt 900
attcttggtg tgcattggaa ggcatccagc tatccccata ccagcagcca gtcaccagat 960
gtgaatgtgg aagcagaaga ccacctcctg ttggttcttc tcctcttcct tctttttctc 1020
tttagaacgg ccaccattga agacctagct tcccattttc cagacgtttt ctctgaaatt 1080
ctctgctggc ctgccaagcc atatggattc attctgccac tgaggagtcc ttcagtgagg 1140
tccctcttcc taaaggacag agtggggagt aggaggggaa cagagaggac atcctctctg 1200
gctctccagt gctcttagtg tctacaggct cctaggcagc cctgggcctt ggtttgatta 1260
cctcccctgg gggatgctgg tcagacccag aggttgtcag gaggtcagct accaggaaga 1320
tccatgatct gggcattggc agtgcctgcc accacagcca ggaagatgcc tctgacctgg 1380
gtgcatctcc atcactcctt agcagcagcc tgcataactg gcaagaatct tggatgatac 1440
aagagccaag aagggacatt tgagttgtgt cgcttagata ggaaagggat ccagggaaaa 1500
tcaacagtaa gtgaggatga gcagtgtctc ttggttttca ttgaggatag agtaagagat 1560
tgagtttaga ttgcaacaga aggaattagt ttagatacca ggaagaactt cctagcctga 1620
agatttgtca tagtgtctgc tttctagata tctgggaaag atttgataat agttgtttgt 1680

-continued

```
gaatagaaag gaggatatga tgtttttatt ggccattttg cgggactctt cgacttcttg   1740

ctgctgtctc ttgaggatac attccaattc catcctggcg agatccaagt gcttacgtac   1800

tgtctcctta gctgccttag agtaaacgat catcagttca atggaccaaa atcaccttca   1860

gccatgtggt ttcttcatca tcatggattt cttttggttg acaaacattc tggctctcag   1920

atgcaaaaag tcacactggg aaatgaactg taagtggtga aattagtttt ggtatttaat   1980

ttaaaactac atttatagtt tttctcttct cttctatgtt gcaatgaatg taaagtattt   2040

gggatccagt gcttataaac ctttccttcc tttgtgcaca gaatgtaact agcaagccca   2100

ttagcaccca gataattcta tcatgttagt ttcccatcct ggaaaatctt tgtacagtgg   2160

gaagttcccc gatgtgtttt tctttcttag gtgaagggtt ggctatatca ctttattgaa   2220

ttttgcattc cttagacttt taaaatatac taatgtattc tagtcttact ctaaagacct   2280

ttgatgttaa aggaatcctt catttatttc atattcccta tctcataggg ccacaattat   2340

tttaatacag agatgatttt caaaatattt taacaactgg tacaggacag atgccagcca   2400

ctcagaaggg atgcctgctg taaacaagca gtatgtatgg ttgtaccaat gcctattggc   2460

tgaacattat gctactttca gatattaaaa tggtgttcct ttgaatcgtg              2510
```

```
<210> SEQ ID NO 232
<211> LENGTH: 164
<212> TYPE: PRT
<213> ORGANISM: Homo sapiens

<400> SEQUENCE: 232

Met Gln Arg Lys Arg Val Ser Ser Thr Lys Ser Leu Cys Trp Asp Gly
1               5                   10                  15

Arg Phe Gly Pro Cys Gly Ala Ser Gly Lys Phe Trp Leu Gln Arg Lys
            20                  25                  30

Trp Arg Val Ser Gln Arg Arg Ser Lys Thr Lys Ser Gly Pro Val Leu
        35                  40                  45

Gly His Leu Lys Ala Met Pro Lys His Ser Val Ile Leu Gly Val His
    50                  55                  60

Trp Lys Ala Ser Ser Tyr Pro His Thr Ser Ser Gln Ser Pro Asp Val
65                  70                  75                  80

Asn Val Glu Ala Glu Asp His Leu Leu Leu Val Leu Leu Leu Phe Leu
                85                  90                  95

Leu Phe Leu Phe Arg Thr Ala Thr Ile Glu Asp Leu Ala Ser His Phe
            100                 105                 110

Pro Asp Val Phe Ser Glu Ile Leu Cys Trp Pro Ala Lys Pro Tyr Gly
        115                 120                 125

Phe Ile Leu Pro Leu Arg Ser Pro Ser Val Arg Ser Leu Phe Leu Lys
    130                 135                 140

Asp Arg Val Gly Ser Arg Arg Gly Thr Glu Arg Thr Ser Ser Leu Ala
145                 150                 155                 160

Leu Gln Cys Ser


<210> SEQ ID NO 233
<211> LENGTH: 20
<212> TYPE: DNA
<213> ORGANISM: Artificial Sequence
<220> FEATURE:
<223> OTHER INFORMATION: Oligonucleotide

<400> SEQUENCE: 233
```

-continued gaggctgaga aaatgttaga 20

<210> SEQ ID NO 234
<211> LENGTH: 18
<212> TYPE: DNA
<213> ORGANISM: Artificial Sequence
<220> FEATURE:
<223> OTHER INFORMATION: Oligonucleotide

<400> SEQUENCE: 234
tccatcccag caaagact 18

<210> SEQ ID NO 235
<211> LENGTH: 1977
<212> TYPE: DNA
<213> ORGANISM: Homo sapiens

<400> SEQUENCE: 235
cgtgggcttg aggacctgga gagagtagat cctgaagaac tttttcagtc tgctgaagag 60
cttggaagac tggagacaga aggcagagtc tcaggctctg aaggtataag gagtgtgagt 120
tcctgtgaga aacactcatt tgattgtgaa aagacttgaa ttctatgcta agcagggttc 180
caagtagcta aatgaatgat ctcagcaagt ctctcttgct gctgctgcta ctcgtttaca 240
tttattgatt acttacgatg attcaggtac tgttgtaagt gctttacatg ctgttatacg 300
agactcttgg gagaaatcac tttaatgaag cttgagacac atggcattgc catgcaatga 360
tttttccccc ctcttcacgg gatcagaggg aactaataga atgtgacaat gattctttag 420
cagggactgc tgaggcttct ggttcctttt taagatctgc agtgaaagaa gatgagaaac 480
atggatatgc ccttcttttg gtccccctct tcctttattt gatctctact tccttctata 540
aatatattag ggctacattg tccctttgta tttcaaacaa ggcaaaaaga ggttgtaatt 600
acactttact gcaatcctca gtttctccag ggaacaggaa tgcaaaggct ttgaaggcct 660
ctctatttgc tgacatggtc agctgggtgc catgggccaa gtccttctgt tgccctcctc 720
tgtcaccaag taagctaggt cctttctgag gctcaggttt gctgtgatga tgatcacttt 780
taggcagaag gttagaggcc tcatgagtgc tatatggact ttattaggct ttagatttga 840
tggggaataa gggatgtgat ttgtcttttg ggaactcatc tttgattcat cattgtctct 900
tggtatcttg gaatttccat gtcattacag tctacagaat gaaagagtaa cctgtcccag 960
aggagaggca ggtgaaagac tccacagcat gctcattctc attctgtctt ctcagtgaca 1020
ccgaggttta ctgagtgccc actatgtgcc aagcactgtg ctcagggctt tctttgtatg 1080
catgatctca gtgaatctca ccaagcctca tctggaaaac ggggacaaat taacaacagg 1140
atggcaaatt gaaaaacacg taaccatgtt ctacagatgg aaaggggtgc ttggttatta 1200
tgaaggcccc ctcgcaagcg tgtgggacat gggtgtgttc tctgggttgt actgatcaga 1260
tcaaggacct cccccaccct tctcacactc tgcccacttc cgccctttgc ttatcagacc 1320
cttagccagt gactcattcc agaaccagaa ccttggtgaa atctcaaccg acaccagaga 1380
tcggtgtctt cagtcctaga ctgatggaga aaatccagaa tatatactag aagctccaaa 1440
tgctctgggt ttcagctcct ctgtgctgtg gacactgact ttggctcaga actccgattt 1500
agtacaaaag gctcattttt atttcagggg cactcttcct aaagcaaacc taataaatga 1560
aatatggaat tcacagatac acacacacat taaaaaatta acctagtgta tctgtgagga 1620
gtaggcagaa attcactgta taaaagaatg cttcatttca tagagaattt gtgttaagat 1680
tccattagat agtacatttc tcaaagattt ttgaggttgt atttgcttta ccaaaacttg 1740

-continued

```
gtttatgtaa gtggaaaaag catgttgcaa aataacttgg tgtctatgat tcagtttatg   1800

taaaataata aatgtatgta ggaatacgtg tgttgaaaga tgtacatcaa tttgctaaca   1860

atggttatct ctgacgtggt gggatttgag atgtgttttt ctttttggtt gtatttttct   1920

ctattgtttg acttaacaca gaacatgttt ggttacaaca ataaagttat tgaagac      1977
```

<210> SEQ ID NO 236
<211> LENGTH: 130
<212> TYPE: PRT
<213> ORGANISM: Homo sapiens

<400> SEQUENCE: 236

```
Met Ile Phe Pro Pro Ser Ser Arg Asp Gln Arg Glu Leu Ile Glu Cys
1               5                   10                  15

Asp Asn Asp Ser Leu Ala Gly Thr Ala Glu Ala Ser Gly Ser Phe Leu
            20                  25                  30

Arg Ser Ala Val Lys Glu Asp Glu Lys His Gly Tyr Ala Leu Leu Leu
        35                  40                  45

Val Pro Leu Phe Leu Tyr Leu Ile Ser Thr Ser Phe Tyr Lys Tyr Ile
    50                  55                  60

Arg Ala Thr Leu Ser Leu Cys Ile Ser Asn Lys Ala Lys Arg Gly Cys
65                  70                  75                  80

Asn Tyr Thr Leu Leu Gln Ser Ser Val Ser Pro Gly Asn Arg Asn Ala
                85                  90                  95

Lys Ala Leu Lys Ala Ser Leu Phe Ala Asp Met Val Ser Trp Val Pro
            100                 105                 110

Trp Ala Lys Ser Phe Cys Cys Pro Pro Leu Ser Pro Ser Lys Leu Gly
        115                 120                 125

Pro Phe
    130
```

<210> SEQ ID NO 237
<211> LENGTH: 18
<212> TYPE: DNA
<213> ORGANISM: Artificial Sequence
<220> FEATURE:
<223> OTHER INFORMATION: Oligonucleotide

<400> SEQUENCE: 237

```
atgattcttt agcaggga                                                   18
```

<210> SEQ ID NO 238
<211> LENGTH: 18
<212> TYPE: DNA
<213> ORGANISM: Artificial Sequence
<220> FEATURE:
<223> OTHER INFORMATION: Oligonucleotide

<400> SEQUENCE: 238

```
ctctttttgc cttgtttg                                                   18
```

<210> SEQ ID NO 239
<211> LENGTH: 1293
<212> TYPE: DNA
<213> ORGANISM: Homo sapiens

<400> SEQUENCE: 239

```
aggccgaggg gttcggcgac gcggagggag ggagagtctg ggccgcgcgg gagccgcagg     60

gcgccctagc cttcgcagaa acgatggcgg aggaagaagg accacctgta gagctgcgcc    120
```

-continued

```
aaagaaaaaa gccaaagtct tcagaaaata aggaatctgc caaagaagag aaaatcagtg    180
acattccaat tcctgaaaga gctccaaaac atgtattatt tcaacgcttt gcaaagattt    240
tcattggctg tcttgcagcg gttactagtg gtatgatgta tgctctctac ttatcagcat    300
accatgaacg gaaattctgg ttttccaaca ggcaggagct tgaacgggaa atcacgtttc    360
agggtgacag tgccatttat tactcctatt ataaagatat gttaaaggca ccttcatttg    420
aaagaggtgt ttacgaactg acacacaata acaaaactgt atctctgaag actataaatg    480
cagtgcagca aatgtctctg tatccggaac ttattgctag cattttatat caagccactg    540
gtagcaatga gattattgag ccagtgtatt tctatattgg cattgttttt ggattgcaag    600
gaatatatgt tactgcttta tttgttacaa gttggcttat gagtggaaca tggctagcag    660
gaatgcttac tgttgcgtgg ttcgttatta acagttgcac agacccctgg tacagtgtgg    720
gaggtgacaa cacaggatat taataccagg aggcaggaat cattgggacc gtcttggagg    780
ctggctacca cattcaatta actttgctat taatttcatg taatccctat atctgtcttc    840
atatttgaag aggaaaagat actttctcat gtaaacataa tggttttaaa gaataagact    900
ctcttatgct acttaaacaa aagaataaga ctctctttag agatcttagt gagaattgta    960
agaaataaaa taaacagaag tctgactgcc ttatttgatg tcactgatgt atgttgtatt   1020
gctggagtag aagttaaata gaaaaattga cctggtatat tctactcaaa tgtatctttt   1080
gacaattgaa atgttcttaa tagctaagtt ttaaaaaatg cgtttgtttg ctttttgttt   1140
atattttatt ggtatgtatc ttgtactgca aaatacattt taatgccatg aaagaatatg   1200
ctgtctcttt attcatcagc tttatagctt ttatttatat atgacttctt agaaaagtat   1260
aaaaagatat taaagtcatt ccattatatt atg                                 1293
```

<210> SEQ ID NO 240
<211> LENGTH: 219
<212> TYPE: PRT
<213> ORGANISM: Homo sapiens

<400> SEQUENCE: 240

```
Met Ala Glu Glu Glu Gly Pro Pro Val Glu Leu Arg Gln Arg Lys Lys
1               5                   10                  15

Pro Lys Ser Ser Glu Asn Lys Glu Ser Ala Lys Glu Glu Lys Ile Ser
            20                  25                  30

Asp Ile Pro Ile Pro Glu Arg Ala Pro Lys His Val Leu Phe Gln Arg
        35                  40                  45

Phe Ala Lys Ile Phe Ile Gly Cys Leu Ala Ala Val Thr Ser Gly Met
    50                  55                  60

Met Tyr Ala Leu Tyr Leu Ser Ala Tyr His Glu Arg Lys Phe Trp Phe
65                  70                  75                  80

Ser Asn Arg Gln Glu Leu Glu Arg Glu Ile Thr Phe Gln Gly Asp Ser
                85                  90                  95

Ala Ile Tyr Tyr Ser Tyr Tyr Lys Asp Met Leu Lys Ala Pro Ser Phe
            100                 105                 110

Glu Arg Gly Val Tyr Glu Leu Thr His Asn Asn Lys Thr Val Ser Leu
        115                 120                 125

Lys Thr Ile Asn Ala Val Gln Gln Met Ser Leu Tyr Pro Glu Leu Ile
    130                 135                 140

Ala Ser Ile Leu Tyr Gln Ala Thr Gly Ser Asn Glu Ile Ile Glu Pro
145                 150                 155                 160
```

-continued

```
Val Tyr Phe Tyr Ile Gly Ile Val Phe Gly Leu Gln Gly Ile Tyr Val
              165                 170                 175

Thr Ala Leu Phe Val Thr Ser Trp Leu Met Ser Gly Thr Trp Leu Ala
            180                 185                 190

Gly Met Leu Thr Val Ala Trp Phe Val Ile Asn Ser Cys Thr Asp Pro
        195                 200                 205

Trp Tyr Ser Val Gly Gly Asp Asn Thr Gly Tyr
    210                 215


<210> SEQ ID NO 241
<211> LENGTH: 19
<212> TYPE: DNA
<213> ORGANISM: Artificial Sequence
<220> FEATURE:
<223> OTHER INFORMATION: Oligonucleotide

<400> SEQUENCE: 241

accgctgcaa gacagccaa                                                19


<210> SEQ ID NO 242
<211> LENGTH: 20
<212> TYPE: DNA
<213> ORGANISM: Artificial Sequence
<220> FEATURE:
<223> OTHER INFORMATION: Oligonucleotide

<400> SEQUENCE: 242

gcagaaacga tggcggagga                                               20


<210> SEQ ID NO 243
<211> LENGTH: 1291
<212> TYPE: DNA
<213> ORGANISM: Homo sapiens

<400> SEQUENCE: 243

atcatgtatt ccattgccac tggaggcttg gttttgatgg cagtgtttta tacacagaaa     60

gacagctgca tggaaaacaa aattctgctg ggagtaaatg gaggcctgtg cctgcttata    120

tcattggtag ccatctcacc ctgggtccaa aatcgacagc cacactcggg gctcttacaa    180

tcaggggtca taagctgcta tgtcacctac ctcaccttct cagctctgtc cagcaaacct    240

gcagaagtag ttctagatga acatgggaaa aatgttacaa tctgtgtgcc tgactttggt    300

caagacctgt acagagatga aaacttggtg actatactgg ggaccagcct cttaatcgga    360

tgtatcttgt attcatgttt gacatcaaca acaagatcga gttctgacgc tctgcagggg    420

cgatacgcag ctcctgaatt ggagatagct cgctgttgtt tttgcttcag tcctggtgga    480

gaggacactg aagagcagca gccggggaag gagggaccac gggtcattta tgacgagaag    540

aaaggcaccg tctacatcta ctcctacttc cacttcgtgt tcttcctagc ttccctgtat    600

gtgatgatga ccgtcaccaa ctggttcaac tacgaaagtg ccaacatcga gagcttcttc    660

agcgggagct ggtccatctt ctgggtcaag atggcctcct gctggatatg cgtgctgttg    720

tacctgtgta cgctggtcgc tcccctctgc tgccccaccc gggagttctc tgtgtgatga    780

tatcggcggt cccctgggct ttgtgggcct acagcctgga aagtgccatc ttttgaacag    840

tgtccccggg gcagggactg gcgccctgtg cctgagtggg tctgaaaaag ctttgagaga    900

gaaaaaaaaa aatctcctga ttagcttttt actttttgaaa ttcaaaaaga aactaccagt    960

ttgtcccaaa ggaattgaaa ttttcaacca aactgatcat ggttgaaata tcttacccct   1020

aggaactgga taccagttat gttgacttcc ttctgcatgt ttttgccaaa acagaatttg   1080
```

-continued

```
gggcacagca tcttttcaca gggataaaaa tatcttgtgg ggccagtcat tctcatcctc   1140

ggaatagaaa aacatgccaa aatcttgagt ccccagcgcc taacagaatc cagacccctc   1200

tcactcactt ccgcctctta gagccttgtc cccagggggc tttgaggaca ggactcagcc   1260

tgcagggccc ctggtattta tagggtccaa g                                  1291
```

<210> SEQ ID NO 244
<211> LENGTH: 257
<212> TYPE: PRT
<213> ORGANISM: Homo sapiens

<400> SEQUENCE: 244

```
Met Tyr Ser Ile Ala Thr Gly Gly Leu Val Leu Met Ala Val Phe Tyr
1               5                   10                  15

Thr Gln Lys Asp Ser Cys Met Glu Asn Lys Ile Leu Leu Gly Val Asn
            20                  25                  30

Gly Gly Leu Cys Leu Leu Ile Ser Leu Val Ala Ile Ser Pro Trp Val
        35                  40                  45

Gln Asn Arg Gln Pro His Ser Gly Leu Leu Gln Ser Gly Val Ile Ser
    50                  55                  60

Cys Tyr Val Thr Tyr Leu Thr Phe Ser Ala Leu Ser Ser Lys Pro Ala
65                  70                  75                  80

Glu Val Val Leu Asp Glu His Gly Lys Asn Val Thr Ile Cys Val Pro
                85                  90                  95

Asp Phe Gly Gln Asp Leu Tyr Arg Asp Glu Asn Leu Val Thr Ile Leu
            100                 105                 110

Gly Thr Ser Leu Leu Ile Gly Cys Ile Leu Tyr Ser Cys Leu Thr Ser
        115                 120                 125

Thr Thr Arg Ser Ser Ser Asp Ala Leu Gln Gly Arg Tyr Ala Ala Pro
    130                 135                 140

Glu Leu Glu Ile Ala Arg Cys Cys Phe Cys Phe Ser Pro Gly Gly Glu
145                 150                 155                 160

Asp Thr Glu Glu Gln Gln Pro Gly Lys Glu Gly Pro Arg Val Ile Tyr
                165                 170                 175

Asp Glu Lys Lys Gly Thr Val Tyr Ile Tyr Ser Tyr Phe His Phe Val
            180                 185                 190

Phe Phe Leu Ala Ser Leu Tyr Val Met Met Thr Val Thr Asn Trp Phe
        195                 200                 205

Asn Tyr Glu Ser Ala Asn Ile Glu Ser Phe Phe Ser Gly Ser Trp Ser
    210                 215                 220

Ile Phe Trp Val Lys Met Ala Ser Cys Trp Ile Cys Val Leu Leu Tyr
225                 230                 235                 240

Leu Cys Thr Leu Val Ala Pro Leu Cys Cys Pro Thr Arg Glu Phe Ser
                245                 250                 255

Val
```

<210> SEQ ID NO 245
<211> LENGTH: 18
<212> TYPE: DNA
<213> ORGANISM: Artificial Sequence
<220> FEATURE:
<223> OTHER INFORMATION: Oligonucleotide

<400> SEQUENCE: 245

```
agtcaggcac acagattg                                                   18
```

-continued

<210> SEQ ID NO 246
<211> LENGTH: 18
<212> TYPE: DNA
<213> ORGANISM: Artificial Sequence
<220> FEATURE:
<223> OTHER INFORMATION: Oligonucleotide

<400> SEQUENCE: 246
ttctgctggg agtaaatg 18

<210> SEQ ID NO 247
<211> LENGTH: 2412
<212> TYPE: DNA
<213> ORGANISM: Homo sapiens

<400> SEQUENCE: 247
gaacccaggc atcctgggct ccagctgaaa ccattgcatg tggctttccc catccctggc 60
cccgtgactc agtccctctg aagggagcag ccctcttttt tggcaatcac cagggaggtg 120
gggggaggag gaggggagct aggtggtgac atcacagtcg aaggttataa aagcttccag 180
ccaaacggca ttgaagttga agatacaacc tgacagcaca gcctgagatc ttggggatcc 240
ctcagcctaa cacccacaga cgtcagctgg tggattcccg ctgcatcaag gcctacccac 300
tgtctccatg ctgggctctc cctgccttct gtggctcctg gccgtgacct tcttggttcc 360
cagagctcag cccttggccc ctcaagactt tgaagaagag gaggcagatg agactgagac 420
ggcgtggccg cctttgccgg ctgtcccctg cgactacgac cactgccgac acctgcaggt 480
gccctgcaag gagctacaga gggtcgggcc ggcggcctgc ctgtgcccag gactctccag 540
ccccgcccag ccgcccgacc cgccgcgcat gggagaagtg cgcattgcgg ccgaagaggg 600
ccgcgcagtg gtccactggt gtgccccctt ctccccggtc ctccactact ggctgctgct 660
ttgggacggc agcgaggctg cgcagaaggg gcccccgctg aacgctacgg tccgcagagc 720
cgaactgaag gggctgaagc caggggggcat ttatgtcgtt tgcgtagtgg ccgctaacga 780
ggccggggca agccgcgtgc cccaggctgg aggagagggc ctcgaggggg ccgacatccc 840
tgccttcggg ccttgcagcc gccttgcggt gccgcccaac ccccgcactc tggtccacgc 900
ggccgtcggg gtgggcacgg ccctggccct gctaagctgt gccgccctgg tgtggcactt 960
ctgcctgcgc gatcgctggg gctgcccgcg ccgagccgcc gcccgagccg caggggcgct 1020
ctgaaagggg cctgggggca tctcgggcac agacagcccc acctggggcg ctcagcctgg 1080
cccccgggaa agaggaaaac ccgctgcctc cagggagggc tggacggcga gctgggagcc 1140
agccccaggc tccagggcca cggcggagtc atggttctca ggactgagcg cttgtttagg 1200
tccggtactt ggcgctttgt ttcctggctg aggtctggga aggaatagaa aggggccccc 1260
aatttttttt taagcggcca gataataaat aatgtaacct ttgcggttta agaggataaa 1320
atggaggata ttattatgtg ggtatttata tgacctttgt aaccatttaa aaatgtaaaa 1380
acgacctgac ttagtaatgc gaacctatag tagcagctac tccagaggct gaaatgggag 1440
gatctcttga gcccaggagt tggagtccag tccagccagg gcaacacagc cagacgccct 1500
tgttttttat tttgttttgt tttggttttt tgttttttga ggagtttccc tctgtcacac 1560
aagctggagg gcaatggcgc catctcagct cactgcaacg tccacctcct gggttcaagc 1620
gattctcctg cctcagcatc ctaattagtt gggattacag gcgcccacca ccatgcccgg 1680
ctaatttttg tgttttttta gtagagacgg ggtttcacca tgttgtcagg ctggtctcaa 1740
actcctgacc tcaggtactc cacccgcctt ggtctctcaa agtgctggga ttacaggcat 1800

-continued

```
aagccactgt gcccaggcag acccccttct ttaaagatgt aaaacccggc cgggcgcggt   1860

ggctcacgcc tgtaatccca gcactttggg aggctgaggc gggcagatca cgaagtcagg   1920

agatcgagac catcctggct aacacggtga aaccccgtct ctactaaaaa tacaaaaatt   1980

agccgggcat ggtggtgggt acctgtagtc ccagctactc cggaggctga ggcaggagaa   2040

tggcgtgaac ccgggaggcg gatcttgcag tgagcggaga ttgcaccact gcactccagc   2100

ctgggtgaca gagcaagact ccctctcaaa agaaaaagaa aaaagatgta aaaaccattc   2160

ttagtttgtg ggccttacaa atcaggccac tggcccattg cttgtagtta gttgatccat   2220

gtcatgcacc ctaaaaatgg ctctgtcact gtgagtggct tcagtaggat tttgagaata   2280

agtttatatt cttgctaggt aaaacaaaac aaaaacgaca gtaataccaa ggaatctccc   2340

ccccctttta ccctccattt gtgtttattg catatccact ataacaacat taaaggacct   2400

ttaaaaggaa gt                                                       2412
```

<210> SEQ ID NO 248
<211> LENGTH: 238
<212> TYPE: PRT
<213> ORGANISM: Homo sapiens

<400> SEQUENCE: 248

```
Met Leu Gly Ser Pro Cys Leu Leu Trp Leu Leu Ala Val Thr Phe Leu
1               5                   10                  15

Val Pro Arg Ala Gln Pro Leu Ala Pro Gln Asp Phe Glu Glu Glu Glu
            20                  25                  30

Ala Asp Glu Thr Glu Thr Ala Trp Pro Pro Leu Pro Ala Val Pro Cys
        35                  40                  45

Asp Tyr Asp His Cys Arg His Leu Gln Val Pro Cys Lys Glu Leu Gln
    50                  55                  60

Arg Val Gly Pro Ala Ala Cys Leu Cys Pro Gly Leu Ser Ser Pro Ala
65                  70                  75                  80

Gln Pro Pro Asp Pro Pro Arg Met Gly Glu Val Arg Ile Ala Ala Glu
                85                  90                  95

Glu Gly Arg Ala Val Val His Trp Cys Ala Pro Phe Ser Pro Val Leu
            100                 105                 110

His Tyr Trp Leu Leu Leu Trp Asp Gly Ser Glu Ala Ala Gln Lys Gly
        115                 120                 125

Pro Pro Leu Asn Ala Thr Val Arg Arg Ala Glu Leu Lys Gly Leu Lys
    130                 135                 140

Pro Gly Gly Ile Tyr Val Val Cys Val Val Ala Ala Asn Glu Ala Gly
145                 150                 155                 160

Ala Ser Arg Val Pro Gln Ala Gly Gly Glu Gly Leu Glu Gly Ala Asp
                165                 170                 175

Ile Pro Ala Phe Gly Pro Cys Ser Arg Leu Ala Val Pro Pro Asn Pro
            180                 185                 190

Arg Thr Leu Val His Ala Ala Val Gly Val Gly Thr Ala Leu Ala Leu
        195                 200                 205

Leu Ser Cys Ala Ala Leu Val Trp His Phe Cys Leu Arg Asp Arg Trp
    210                 215                 220

Gly Cys Pro Arg Arg Ala Ala Ala Arg Ala Ala Gly Ala Leu
225                 230                 235
```

<210> SEQ ID NO 249
<211> LENGTH: 18

-continued

<212> TYPE: DNA
<213> ORGANISM: Artificial Sequence
<220> FEATURE:
<223> OTHER INFORMATION: Oligonucleotide

<400> SEQUENCE: 249
atccctcagc ctaacacc 18

<210> SEQ ID NO 250
<211> LENGTH: 18
<212> TYPE: DNA
<213> ORGANISM: Artificial Sequence
<220> FEATURE:
<223> OTHER INFORMATION: Oligonucleotide

<400> SEQUENCE: 250
gccgtctcag tctcatct 18

<210> SEQ ID NO 251
<211> LENGTH: 1024
<212> TYPE: DNA
<213> ORGANISM: Homo sapiens

<400> SEQUENCE: 251
gagcgccagg ggttccagct gcacgtccca ggctctccag cgcgcggcag gccggggcgg 60
gacgaggaga gctgcgggga caacgcctgt ggctgggtcc ggaggtgcgg gtgcggcgcg 120
ggacaagcgg gcagcatgct cagggcggtc gggagcctac tgcgccttgg ccgcgggcta 180
acagtccgct gcggccccgg ggcgcctctc gaggccacgc gacggcccgc accggctctt 240
ccgccccggg gtctcccctg ctactccagc ggcggggccc ccagcaattc tgggccccaa 300
ggtcacgggg agattcaccg agtccccacg cagcgcaggc cttcgcagtt cgacaagaaa 360
atcctgctgt ggacagggcg tttcaaatcg atggaggaga tcccgcctcg gatcccgcca 420
gaaatgatag acaccgcaag aaacaaagct cgagtgaaag cttgttacat aatgattgga 480
ctcacaatta tcgcctgctt tgctgtgata gtgtcagcca aaagggctgt agaacgacat 540
gaatccttaa caagttggaa cttggcaaag aaagctaagt ggcgtgaaga agctgcattg 600
gctgcacagg ctaaagctaa atgatattct aagtgacaaa gtgttcacct gaataccatc 660
cctgtcatca gcaacagtag aagatgggaa aaatagaata tttaccaaaa tatctgccat 720
ggttttattt tggtaacaag aagcacaatg tcttttttat ttttattttt tagtaaactt 780
ttactgaagt ataccatgca ttcaaaaagt ggacaaaact gtatacagtc tgatagatat 840
ttatgtcgtg aacacctgtg taaccactgc caaagtgaag atgtagaata ttggcaacac 900
ttcacagcct cattcctgcc ttttctcagc cattacctcc caaacatagc agtttttctg 960
agtttcatca cctttgattc attttgcctg tttttgaact ttatataaat ggatttatac 1020
atta 1024

<210> SEQ ID NO 252
<211> LENGTH: 162
<212> TYPE: PRT
<213> ORGANISM: Homo sapiens

<400> SEQUENCE: 252

Met Leu Arg Ala Val Gly Ser Leu Leu Arg Leu Gly Arg Gly Leu Thr
1 5 10 15

Val Arg Cys Gly Pro Gly Ala Pro Leu Glu Ala Thr Arg Arg Pro Ala
20 25 30

-continued

```
Pro Ala Leu Pro Pro Arg Gly Leu Pro Cys Tyr Ser Ser Gly Gly Ala
        35                  40                  45

Pro Ser Asn Ser Gly Pro Gln Gly His Gly Glu Ile His Arg Val Pro
    50                  55                  60

Thr Gln Arg Arg Pro Ser Gln Phe Asp Lys Lys Ile Leu Leu Trp Thr
65                  70                  75                  80

Gly Arg Phe Lys Ser Met Glu Glu Ile Pro Pro Arg Ile Pro Pro Glu
                85                  90                  95

Met Ile Asp Thr Ala Arg Asn Lys Ala Arg Val Lys Ala Cys Tyr Ile
            100                 105                 110

Met Ile Gly Leu Thr Ile Ile Ala Cys Phe Ala Val Ile Val Ser Ala
        115                 120                 125

Lys Arg Ala Val Glu Arg His Glu Ser Leu Thr Ser Trp Asn Leu Ala
    130                 135                 140

Lys Lys Ala Lys Trp Arg Glu Glu Ala Ala Leu Ala Ala Gln Ala Lys
145                 150                 155                 160

Ala Lys


<210> SEQ ID NO 253
<211> LENGTH: 19
<212> TYPE: DNA
<213> ORGANISM: Artificial Sequence
<220> FEATURE:
<223> OTHER INFORMATION: Oligonucleotide

<400> SEQUENCE: 253

attatcgcct gctttgctg                                                    19


<210> SEQ ID NO 254
<211> LENGTH: 22
<212> TYPE: DNA
<213> ORGANISM: Artificial Sequence
<220> FEATURE:
<223> OTHER INFORMATION: Oligonucleotide

<400> SEQUENCE: 254

ttcccatctt ctactgttgc tg                                                22


<210> SEQ ID NO 255
<211> LENGTH: 852
<212> TYPE: DNA
<213> ORGANISM: Homo sapiens

<400> SEQUENCE: 255

ttagggcgag tttaaggcac tgtggcagct gtgagataaa gtctggttcc tccccagctg      60

gctcaggaaa tgttcgcgga tacaacggcg gccccctctg ggcatacctg cctgtggagc     120

ggagagtgga cggtgtgagg gggaccggga gaggcaccaa atctggcctg ggggcccgag     180

aagcttcctc tcagtgacca caatatgaat gggaacagca agatggcaaa agcttgctga     240

gtggtacagc gccagcctgg gtagtggcct ccccagcaag ttgcatgtca ctagcttcct     300

gtggctgtca ctcctgggcc caggcacctc cgaagatcag cacctcctca tgggctcaag     360

cgaggacagg agcccgtcac ccatgagctc tcaagggcag agccactgtc ctgtctcgat     420

ggctccaccg tgactccagt ggactttgga cagtggggag caggcccaac agggccactc     480

ggatgtggtc actctggatt tgggtggatc agcaccaagc tagactcatc cccagccccc     540

aggtgctgtt gctgctcctg cgtgaggccc catccacagc tgcagctgtg gcagggtggc     600

tagtggtggc cagcatggcc ctgctgcagc tccacgctgt ggggggcgtg gccctgacca     660
```

```
gcagccaccc ctccatgtgg gccacagggg aggagcttag gaagccgcct tggcaaggtt    720

ccgcaggctc tgcgtctggt gtggaagagc tcacggggaa gcactcctgc ccaggacccg    780

aggagccggc caccgttcag aaggccccag cttgaaggcc tggagagccg cccagcagca    840

caacacaggg aa                                                        852


<210> SEQ ID NO 256
<211> LENGTH: 110
<212> TYPE: PRT
<213> ORGANISM: Homo sapiens

<400> SEQUENCE: 256

Met Trp Ser Leu Trp Ile Trp Val Asp Gln His Gln Ala Arg Leu Ile
1               5                   10                  15

Pro Ser Pro Gln Val Leu Leu Leu Leu Leu Arg Glu Ala Pro Ser Thr
            20                  25                  30

Ala Ala Ala Val Ala Gly Trp Leu Val Val Ala Ser Met Ala Leu Leu
        35                  40                  45

Gln Leu His Ala Val Gly Gly Val Ala Leu Thr Ser Ser His Pro Ser
    50                  55                  60

Met Trp Ala Thr Gly Glu Glu Leu Arg Lys Pro Pro Trp Gln Gly Ser
65                  70                  75                  80

Ala Gly Ser Ala Ser Gly Val Glu Glu Leu Thr Gly Lys His Ser Cys
                85                  90                  95

Pro Gly Pro Glu Glu Pro Ala Thr Val Gln Lys Ala Pro Ala
            100                 105                 110


<210> SEQ ID NO 257
<211> LENGTH: 18
<212> TYPE: DNA
<213> ORGANISM: Artificial Sequence
<220> FEATURE:
<223> OTHER INFORMATION: Oligonucleotide

<400> SEQUENCE: 257

ttgctgttcc cattcata                                                   18


<210> SEQ ID NO 258
<211> LENGTH: 19
<212> TYPE: DNA
<213> ORGANISM: Artificial Sequence
<220> FEATURE:
<223> OTHER INFORMATION: Oligonucleotide

<400> SEQUENCE: 258

gataaagtct ggttcctcc                                                  19


<210> SEQ ID NO 259
<211> LENGTH: 4231
<212> TYPE: DNA
<213> ORGANISM: Homo sapiens

<400> SEQUENCE: 259

gcggccgcct ttgcaaggtt gctggacaga tggaactgga agggcagccg tctgccgccc     60

acgaacacct tctcaagcac tttgagtgac cacggcttgc aagctggtgg ctggcccccc    120

gagtcccggg ctctgaggca cggccgtcga cttaagcgtt gcatcctgtt acctggagac    180

cctctgagct ctcacctgct acttctgccg ctgcttctgc acagagcccg ggcgaggacc    240

cctccaggat gcaggtcccg aacagcaccg gcccggacaa cgcgacgctg cagatgctgc    300
```

-continued

```
ggaacccggc gatcgcggtg gccctgcccg tggtgtactc gctggtggcg gcggtcagca    360
tcccgggcaa cctcttctct ctgtgggtgc tgtgccggcg catggggccc agatccccgt    420
cggtcatctt catgatcaac ctgagcgtca cggacctgat gctggccagc gtgttgcctt    480
tccaaatcta ctaccattgc aaccgccacc actgggtatt cggggtgctg ctttgcaacg    540
tggtgaccgt ggccttttac gcaaacatgt attccagcat cctcaccatg acctgtatca    600
gcgtggagcg cttcctgggg gtcctgtacc cgctcagctc caagcgctgg cgccgccgtc    660
gttacgcggt ggccgcgtgt gcagggacct ggctgctgct cctgaccgcc ctgtccccgc    720
tggcgcgcac cgatctcacc tacccggtgc acgccctggg catcatcacc tgcttcgacg    780
tcctcaagtg gacgatgctc cccagcgtgg ccatgtgggc cgtgttcctc ttcaccatct    840
tcatcctgct gttcctcatc ccgttcgtga tcaccgtggc ttgttacacg gccaccatcc    900
tcaagctgtt gcgcacggag gaggcgcacg gccgggagca gcggaggcgc gcggtgggcc    960
tggccgcggt ggtcttgctg gcctttgtca cctgcttcgc ccccaacaac ttcgtgctcc   1020
tggcgcacat cgtgagccgc ctgttctacg gcaagagcta ctaccacgtg tacaagctca   1080
cgctgtgtct cagctgcctc aacaactgtc tggacccgtt tgtttattac tttgcgtccc   1140
gggaattcca gctgcgcctg cgggaatatt tgggctgccg ccgggtgccc agagacaccc   1200
tggacacgcg ccgcgagagc ctcttctccg ccaggaccac gtccgtgcgc tccgaggccg   1260
gtgcgcaccc tgaagggatg gagggagcca ccaggcccgg cctccagagg caggagagtg   1320
tgttctgagt cccgggggcg cagcttggag agccgggggc gcagcttgga gatccagggg   1380
cgcatggaga ggccacggtg ccagaggttc agggagaaca gctgcgttgc tcccaggcac   1440
tgcagaggcc cggtggggaa gggtctccag gctttattcc tcccaggcac tgcagaggca   1500
ccggtgagga agggtctcca ggcttcactc agggtagaga aacaagcaaa gcccagcagc   1560
gcacagggtg cttgttatcc tgcagagggt gcctctgcct ctctgtgtca ggggacagct   1620
tgtgtcacca cgcccggcta atttttgtat tttttttagt agagctgggc tgtcaccccc   1680
gagctcctta gacactcctc acacctgtcc atacccgagg gtggatattc aaccagcccc   1740
accgcctacc cgactcggtt tctggatatc ctccgtgggc gaactgcgag ccccattccc   1800
agctcttctc cctgctgaca tcgtccctta gttgtggttc tggccttctc cattctcctc   1860
caggggttct ggtctccgta gcccggtgca cgccgaaatt tctgtttatt tcactcaggg   1920
gcactgtggt tgctgtggtt ggaattcttc tttcagagga gcgcctgggg ctcctgcaag   1980
tcagctactc tccgtgccca cttcccccca cacacacacc ccaccctgtt gctgaccaag   2040
gtgatttttg gcacatttgt tctggcctgg cttggtggga ccccacccct attctgcttc   2100
tgtgagtccc tgatagagaa ggaggtccca tcaggcccct ggaacacact caggcttccc   2160
tgactcagga caaggaccac gggaggccca ggtgcggaaa ggaggctccg tgagatgggg   2220
tccagcccat cccaacacaa gggtgcagct tgattcggga gttccccacc tcctgcccat   2280
tctccgcgtc cttttacccc atggagagcc tcagccatgg caagtccatc tggagtccag   2340
gaagcaggca actggcctga cccatgagac cgtttggaga ccaagcagca gatgcaggtg   2400
tggaccccag gaacctacag gggtgtcagc cgctgagccc cctccctgct gtgtgggtgg   2460
tgagcaggct gggtctttgt ctgtcttctt ctacacggca tgtgcctgca ccagccccaa   2520
cacctgagct ggtttagcgc aaagaagagc tctgactctc caggggtgct gggacatcac   2580
gtggaattgg atcccaggct ctcttgggcg agaaagacca ttctggaggt gggagtggga   2640
```

-continued

```
gagctgcctg tctgcccacg ggctctgcgt ctccgcagtg ggtggccttg gatgcccggc   2700
ccctcccttt ctgtgcactg gggacgctga tggaggctga agctgctgtt cggaggccct   2760
ctattggtgc ctctctcctg ccgtcatcac tatggcagga aaacagagat ggtttagtaa   2820
tgaattatca ttcccaaacc cgtgtccacc tggaacatca ggatgggacc atgtttgaaa   2880
atcgggtctt tccaaatgta attaagtaag gcgaggccat actgcattta caatgggccc   2940
aatccagtgt ccctatgaga gacggaagag gagacacaga cacaaagcag gaggccacat   3000
aaagacagag gcagagactg aagtgatgct gccccaagcc cagggatgcc tggagtcccc   3060
aggagctggg agaggcagga aggaccctcc cctagagtct ctggagggaa ctggatacaa   3120
ttgcagagtg cactaaacag ttgccccaga aagacatgtc ttgttttaaa gcccagaacc   3180
tgaaattatt atagatttta ttcggtaata aggaactttg catgtgtaat tacttaagga   3240
tatgaagatg agattgtgct ggattattaa gcaccctaaa tgccatgaca ggtgtccttc   3300
caagagacag aagaggagac acagacacag agcaggagga cacgtggaga cagaggcaga   3360
ctggagtgat gcggccacaa gcccagggac acctggagcc cccaggagct gggagaggca   3420
ggaaggatcc tcccctagag cctccagggg gaactggagg atgcgtaaga gacccagaac   3480
ttccacagaa ggaggaaaat taacctcctg cttctctaga ctgttccaaa gctgaaccct   3540
agaaagcaaa gctgatacag aagcatccag gctgcaggag tacaggtcgc aagtgctgag   3600
cgtgggcctt gggtgtgtct catgggggaa aaaaaactgt gaaaaacctc agagtagcat   3660
cttcacagta acgcacggac gatccctaaa ctgccttgta aacaaaaatg agagcttgag   3720
tcagaggaag ccgagacaat atccttcctc gacaacgtgc gagaaccctg acgtccccca   3780
gcaaaggaag acgttgcaag caggcaaaat gcgtcgattt tttttttttg tcagtatgat   3840
gatttttgca gccacttggc tatggagagc agccgacacc ccctcttaca gccgtggatg   3900
tttcctggaa gctgactcag tctgttcact ggttgagctt tgagtgaaaa gataacacag   3960
gtctattgac tcacacacat gttttaagat ggaaaacttt acttctgttc ttggcaggac   4020
atggagagag ggagggattc caaaaagtct cagcctccat caaggcgtgg cagctcatgc   4080
cggtaatctc agcactttgg gaggctcagg cgggaggact gattgagtcc gggtgttcaa   4140
gggccaacct aggcaacaca gtgagaactc atctctgtaa aaaataaaaa taaaacatta   4200
aaaaaaaaca tgagctttga agtgcacagg g                                  4231
```

<210> SEQ ID NO 260
<211> LENGTH: 359
<212> TYPE: PRT
<213> ORGANISM: Homo sapiens

<400> SEQUENCE: 260

```
Met Gln Val Pro Asn Ser Thr Gly Pro Asp Asn Ala Thr Leu Gln Met
1               5                   10                  15

Leu Arg Asn Pro Ala Ile Ala Val Ala Leu Pro Val Val Tyr Ser Leu
            20                  25                  30

Val Ala Ala Val Ser Ile Pro Gly Asn Leu Phe Ser Leu Trp Val Leu
        35                  40                  45

Cys Arg Arg Met Gly Pro Arg Ser Pro Ser Val Ile Phe Met Ile Asn
    50                  55                  60

Leu Ser Val Thr Asp Leu Met Leu Ala Ser Val Leu Pro Phe Gln Ile
65                  70                  75                  80

Tyr Tyr His Cys Asn Arg His His Trp Val Phe Gly Val Leu Leu Cys
                85                  90                  95
```

-continued

```
Asn Val Val Thr Val Ala Phe Tyr Ala Asn Met Tyr Ser Ser Ile Leu
        100                 105                 110

Thr Met Thr Cys Ile Ser Val Glu Arg Phe Leu Gly Val Leu Tyr Pro
        115                 120                 125

Leu Ser Ser Lys Arg Trp Arg Arg Arg Arg Tyr Ala Val Ala Ala Cys
    130                 135                 140

Ala Gly Thr Trp Leu Leu Leu Leu Thr Ala Leu Ser Pro Leu Ala Arg
145                 150                 155                 160

Thr Asp Leu Thr Tyr Pro Val His Ala Leu Gly Ile Ile Thr Cys Phe
                165                 170                 175

Asp Val Leu Lys Trp Thr Met Leu Pro Ser Val Ala Met Trp Ala Val
            180                 185                 190

Phe Leu Phe Thr Ile Phe Ile Leu Leu Phe Leu Ile Pro Phe Val Ile
        195                 200                 205

Thr Val Ala Cys Tyr Thr Ala Thr Ile Leu Lys Leu Leu Arg Thr Glu
    210                 215                 220

Glu Ala His Gly Arg Glu Gln Arg Arg Arg Ala Val Gly Leu Ala Ala
225                 230                 235                 240

Val Val Leu Leu Ala Phe Val Thr Cys Phe Ala Pro Asn Asn Phe Val
                245                 250                 255

Leu Leu Ala His Ile Val Ser Arg Leu Phe Tyr Gly Lys Ser Tyr Tyr
            260                 265                 270

His Val Tyr Lys Leu Thr Leu Cys Leu Ser Cys Leu Asn Asn Cys Leu
        275                 280                 285

Asp Pro Phe Val Tyr Tyr Phe Ala Ser Arg Glu Phe Gln Leu Arg Leu
    290                 295                 300

Arg Glu Tyr Leu Gly Cys Arg Arg Val Pro Arg Asp Thr Leu Asp Thr
305                 310                 315                 320

Arg Arg Glu Ser Leu Phe Ser Ala Arg Thr Thr Ser Val Arg Ser Glu
                325                 330                 335

Ala Gly Ala His Pro Glu Gly Met Glu Gly Ala Thr Arg Pro Gly Leu
            340                 345                 350

Gln Arg Gln Glu Ser Val Phe
        355
```

<210> SEQ ID NO 261
<211> LENGTH: 19
<212> TYPE: DNA
<213> ORGANISM: Artificial Sequence
<220> FEATURE:
<223> OTHER INFORMATION: Oligonucleotide

<400> SEQUENCE: 261
cctgttacct ggagaccct 19

<210> SEQ ID NO 262
<211> LENGTH: 18
<212> TYPE: DNA
<213> ORGANISM: Artificial Sequence
<220> FEATURE:
<223> OTHER INFORMATION: Oligonucleotide

<400> SEQUENCE: 262
accagcgagt acaccacg 18

<210> SEQ ID NO 263
<211> LENGTH: 717

-continued

<212> TYPE: DNA
<213> ORGANISM: Homo sapiens

<400> SEQUENCE: 263

```
ggccgggctg gggcttcagc gggaggcagc agaggggaag tggtcagcgt ggcgaatgac     60
ggaagaaact cgcattgtct actggatcaa ggacagacag ctcaccaacc gtgacagcac    120
catactggaa cttcaaaaag ttctgaaaac atgttgtgct cagagcatga aaattttctg    180
ctgtctttgg aactttgtct acaaacagtt agaagatgca gcccaagggc tcaccatggg    240
tggcgatgtt gaagaacatg aagaccttac tgctgatagc accatcttca aatttgtgga    300
agcttataca gagtgggagg tgaagaggtg gtcagacaac aatctgataa tgaaacaaac    360
aaatgtgaag agaagacgct tagatgatgt tggccctgaa ttggaaaagg ctgtctggga    420
gctcggctgc ccacccagca ttcagtgtct gctacctcct gtctgttatg cttgtgtctg    480
gtttttcaa gttttaattt ttttttaat tcttagtttt tgtgggtaca tagtaggtgt    540
atatatttat gggttacatg agatgttttg atacaggcat gcaatatgta ataatcacct    600
catggagaat ggggtaccca tcacatcaag catttatcct ttgtgttaca aacggtccag    660
ttagactctt ttagttatta ttaaaatgta caattaaatt atttttgact atagtca       717
```

<210> SEQ ID NO 264
<211> LENGTH: 171
<212> TYPE: PRT
<213> ORGANISM: Homo sapiens

<400> SEQUENCE: 264

```
Met Thr Glu Glu Thr Arg Ile Val Tyr Trp Ile Lys Asp Arg Gln Leu
1               5                   10                  15

Thr Asn Arg Asp Ser Thr Ile Leu Glu Leu Gln Lys Val Leu Lys Thr
            20                  25                  30

Cys Cys Ala Gln Ser Met Lys Ile Phe Cys Cys Leu Trp Asn Phe Val
        35                  40                  45

Tyr Lys Gln Leu Glu Asp Ala Ala Gln Gly Leu Thr Met Gly Gly Asp
    50                  55                  60

Val Glu Glu His Glu Asp Leu Thr Ala Asp Ser Thr Ile Phe Lys Phe
65                  70                  75                  80

Val Glu Ala Tyr Thr Glu Trp Glu Val Lys Arg Trp Ser Asp Asn Asn
                85                  90                  95

Leu Ile Met Lys Gln Thr Asn Val Lys Arg Arg Arg Leu Asp Asp Val
            100                 105                 110

Gly Pro Glu Leu Glu Lys Ala Val Trp Glu Leu Gly Cys Pro Pro Ser
        115                 120                 125

Ile Gln Cys Leu Leu Pro Pro Val Cys Tyr Ala Cys Val Trp Phe Phe
    130                 135                 140

Gln Val Leu Ile Phe Phe Leu Ile Leu Ser Phe Cys Gly Tyr Ile Val
145                 150                 155                 160

Gly Val Tyr Ile Tyr Gly Leu His Glu Met Phe
                165                 170
```

<210> SEQ ID NO 265
<211> LENGTH: 18
<212> TYPE: DNA
<213> ORGANISM: Artificial Sequence
<220> FEATURE:
<223> OTHER INFORMATION: Oligonucleotide

<400> SEQUENCE: 265

-continued

```
ttcaacatcg ccacccat                                                18


<210> SEQ ID NO 266
<211> LENGTH: 20
<212> TYPE: DNA
<213> ORGANISM: Artificial Sequence
<220> FEATURE:
<223> OTHER INFORMATION: Oligonucleotide

<400> SEQUENCE: 266

cagcagaggg gaagtggtca                                              20


<210> SEQ ID NO 267
<211> LENGTH: 390
<212> TYPE: DNA
<213> ORGANISM: Homo sapiens

<400> SEQUENCE: 267

atggaagtga tattaccaga caaacctcag gtagatgcac tggcctttct agctgctgtc     60

accatgctgt ggataacgct gcccatgagt ccttttgcag aagcagagaa attggcatgg    120

gatctggagg ttggaggttt agctggacag ccccttaaag ttttcactcc acgtaaaaaa    180

ggttctgggg aagtgggtga tgcttctcag tcgcccagca gaagcaatga tggccagcat    240

tcctgcattg gccacagcag agatctctgc tgctacactg ctcagaccct cataatctcc    300

tacacatcaa atggtctttc tcctttagca actccaccct tccaccctat tcctggaaac    360

tgctacgaca gtgttgatta taaaatatag                                    390


<210> SEQ ID NO 268
<211> LENGTH: 129
<212> TYPE: PRT
<213> ORGANISM: Homo sapiens

<400> SEQUENCE: 268

Met Glu Val Ile Leu Pro Asp Lys Pro Gln Val Asp Ala Leu Ala Phe
1               5                   10                  15

Leu Ala Ala Val Thr Met Leu Trp Ile Thr Leu Pro Met Ser Pro Phe
            20                  25                  30

Ala Glu Ala Glu Lys Leu Ala Trp Asp Leu Glu Val Gly Gly Leu Ala
        35                  40                  45

Gly Gln Pro Leu Lys Val Phe Thr Pro Arg Lys Lys Gly Ser Gly Glu
    50                  55                  60

Val Gly Asp Ala Ser Gln Ser Pro Ser Arg Ser Asn Asp Gly Gln His
65                  70                  75                  80

Ser Cys Ile Gly His Ser Arg Asp Leu Cys Cys Tyr Thr Ala Gln Thr
                85                  90                  95

Leu Ile Ile Ser Tyr Thr Ser Asn Gly Leu Ser Pro Leu Ala Thr Pro
            100                 105                 110

Pro Phe His Pro Ile Pro Gly Asn Cys Tyr Asp Ser Val Asp Tyr Lys
        115                 120                 125

Ile


<210> SEQ ID NO 269
<211> LENGTH: 2856
<212> TYPE: DNA
<213> ORGANISM: Homo sapiens

<400> SEQUENCE: 269
```

-continued

```
atggccaaaa gaaatctcag cactgtgaca gagttcattc ttgtagtctt cacagatcac     60
cctgaactgg cagttccact cttcctagtg tttctcagtt tctatcttgt cacttttctg    120
gggaatgggg ggatgatcat tctaatccaa gtggatgccc aactccacac ccccgtgtac    180
ttcttcctga gccaccttgc tttcctggat gcctgctgtg cctcagtaat cacccctcag    240
attctggcca cactggccac agacaagaca gttatctcct atggctgccg tgctgtgcag    300
ttctctttct tcaccatatg tgcaggcaca gagtgttacc tgctgtcagt gatggcctat    360
gaccgctttg ttgccattag caatccactg cactgtaaca tgaccatgac tccaggtacc    420
tgcagggtct ttttggccag tgccttcatc tgtggggtgt caggggccat tctgcatacc    480
acgtgcacct tcaccctctc cttctgttgt gacaatcaga tcaacttctt cttctgtgac    540
ctcccacccc tgctgaagct cgcctgcagc agcatgacac aaactgagat tgtcattctc    600
ctttgtgcaa aatgcatgtt cctagccaat gtcatggtta tcctgatctg ctacatgctc    660
attatcagag ccattttgag ggtgaagtcg gcaggaggcc tcctgatagc atctgctcat    720
ttcgatgcat atgtatatga gacaggcatc aactacaaca cagtttatgg ctcaggaaag    780
gcagtagggt ggtcctggag gagcctgcgg gaaaccaacc acatgagacc aggaaatact    840
tcaaaacact cagcagccca gctgcatcaa tgcctcatcc agcaagttgg caggtggccc    900
ttgcagagca tgcccttccc cgtttctgca gggccacctt ataagtcagt gcagcctctc    960
cctggagacc cccggcctct cctgtgcatc accggattat ttctgacttt gaagatgatg   1020
gggtgtgggc ccaggaggcc cagggacagg aagtctgact tcttcataaa cacagaccct   1080
ggtgcagggt caccagaaga acagaggtgt ggatgggaag ggcatccttc ccactcctat   1140
accctggggc tgtctctgcc agtcaacttc ggcctgaaat gtccatggtg gacactatct   1200
ggacccccag ctacctgcca acgtccagac ctgcagacac cttctccacc aaaggagata   1260
tgttcatccg ggctgcgacc ccttacacac agcgctggac cagacagaag tcaagttcca   1320
gcagcctccg gagcagccac tatgctgaca aaggggctgc ccgacatcac tgtgggactg   1380
cagatttatg actcctgcat ctcagggatc caggctctgg ggagcaccct ggccctgctg   1440
tccaatcagc ttccacccac aaccaactat gcttgtggct cccagcaaca tctcctgggc   1500
gtggttggag ggatgacctt cctggagtca gagcccatgt ctgagctgct ctccatctac   1560
agagtccctc agggccaaag actcaccaaa aactttgaag taaaagaact tgtctgcaca   1620
tatctggtag gacagcttcc ttatggcctg gtcagttatg acaacagcaa ctttgagtgg   1680
ctggatcagc agctgcagaa gcagatcggg ggcgagggac ttcctgttgg cgctgcgccc   1740
agccgtgtag ccaggcaaca gtctgatgag gaagctgtgg gaggagtgca gggatacagg   1800
tggtctggat taggggcttc catccaaagt gccagagaag ggcttggca tcgcacaggg   1860
ctggagaaca tgaccactgc ccacctgtct gccttcaaac ttcctgatct aactgccact   1920
taccaagcct acctggcagc caaagccctg tgggttgcct atcagaactt gatgtcctgc   1980
tctgagagag agggaccatt cctgggaggc acgtatgcca atgcatggga agccaggctt   2040
tctcaggtta acttcaccac caaagcccaa gaagaggttt tcttcgccaa agatggggaa   2100
gtgctgacaa cgtttgacat taaaaacatc tatgttctcc cagacctgtc aggacagaca   2160
gccattgttg gacactttga cttcagagca ccttctggaa aagagcttct gttggatgac   2220
agcgcaattg tctgggcaga aggaccctta aagattagag ctgagagaac cctaagaacc   2280
aagaccacac agcacctctc acatcccaag ctccaggagt cccttcctct gtctgcaacg   2340
aaaaacgtcc tgtggaaacc aggaagtcaa ccctatttga gaagtcaaaa tgctgctaca   2400
```

-continued

```
aaagccttcc ctgacccaga agagaaatcg caatgtcacc agtttctctt tctcccttca   2460

gatagtgttg catgtcagaa gtgctctgac aaccagtggc ccaatgtgca gaagggcgag   2520

tgcatcccca aaacccttga cttcttgttc tatcacaagc cccttgacac agcgttggct   2580

gtctgcacag ccctgctctt tctccttgcc ctggccatct taggcatctt ccatgttgtc   2640

tgctcctgtg tctgggtgtc cttcatacct gcccacatgc atgcccacag caaagacacc   2700

atggccatgg aggtctttgt catcttggca tcagcaggag gcctcatgtc ctccctcttc   2760

ttttccaaat gctacatcat ccttctccat cctgaaaaga acacaaaaga ccaaatgttt   2820

ggccggcatc atcgcaagtg ggaaaaactg aagtga                              2856
```

<210> SEQ ID NO 270
<211> LENGTH: 951
<212> TYPE: PRT
<213> ORGANISM: Homo sapiens

<400> SEQUENCE: 270

```
Met Ala Lys Arg Asn Leu Ser Thr Val Thr Glu Phe Ile Leu Val Val
1               5                   10                  15

Phe Thr Asp His Pro Glu Leu Ala Val Pro Leu Phe Leu Val Phe Leu
            20                  25                  30

Ser Phe Tyr Leu Val Thr Phe Leu Gly Asn Gly Gly Met Ile Ile Leu
        35                  40                  45

Ile Gln Val Asp Ala Gln Leu His Thr Pro Val Tyr Phe Phe Leu Ser
    50                  55                  60

His Leu Ala Phe Leu Asp Ala Cys Cys Ala Ser Val Ile Thr Pro Gln
65                  70                  75                  80

Ile Leu Ala Thr Leu Ala Thr Asp Lys Thr Val Ile Ser Tyr Gly Cys
                85                  90                  95

Arg Ala Val Gln Phe Ser Phe Phe Thr Ile Cys Ala Gly Thr Glu Cys
            100                 105                 110

Tyr Leu Leu Ser Val Met Ala Tyr Asp Arg Phe Val Ala Ile Ser Asn
        115                 120                 125

Pro Leu His Cys Asn Met Thr Met Thr Pro Gly Thr Cys Arg Val Phe
    130                 135                 140

Leu Ala Ser Ala Phe Ile Cys Gly Val Ser Gly Ala Ile Leu His Thr
145                 150                 155                 160

Thr Cys Thr Phe Thr Leu Ser Phe Cys Cys Asp Asn Gln Ile Asn Phe
                165                 170                 175

Phe Phe Cys Asp Leu Pro Pro Leu Leu Lys Leu Ala Cys Ser Ser Met
            180                 185                 190

Thr Gln Thr Glu Ile Val Ile Leu Leu Cys Ala Lys Cys Met Phe Leu
        195                 200                 205

Ala Asn Val Met Val Ile Leu Ile Cys Tyr Met Leu Ile Ile Arg Ala
    210                 215                 220

Ile Leu Arg Val Lys Ser Ala Gly Gly Leu Leu Ile Ala Ser Ala His
225                 230                 235                 240

Phe Asp Ala Tyr Val Tyr Glu Thr Gly Ile Asn Tyr Asn Thr Val Tyr
                245                 250                 255

Gly Ser Gly Lys Ala Val Gly Trp Ser Trp Arg Ser Leu Arg Glu Thr
            260                 265                 270

Asn His Met Arg Pro Gly Asn Thr Ser Lys His Ser Ala Ala Gln Leu
        275                 280                 285
```

-continued

```
His Gln Cys Leu Ile Gln Gln Val Gly Arg Trp Pro Leu Gln Ser Met
    290                 295                 300

Pro Phe Pro Val Ser Ala Gly Pro Pro Tyr Lys Ser Val Gln Pro Leu
305                 310                 315                 320

Pro Gly Asp Pro Arg Pro Leu Leu Cys Ile Thr Gly Leu Phe Leu Thr
                325                 330                 335

Leu Lys Met Met Gly Cys Gly Pro Arg Arg Pro Arg Asp Arg Lys Ser
            340                 345                 350

Asp Phe Phe Ile Asn Thr Asp Pro Gly Ala Gly Ser Pro Glu Glu Gln
        355                 360                 365

Arg Cys Gly Trp Glu Gly His Pro Ser His Ser Tyr Thr Leu Gly Leu
    370                 375                 380

Ser Leu Pro Val Asn Phe Gly Leu Lys Cys Pro Trp Trp Thr Leu Ser
385                 390                 395                 400

Gly Pro Pro Ala Thr Cys Gln Arg Pro Asp Leu Gln Thr Pro Ser Pro
                405                 410                 415

Pro Lys Glu Ile Cys Ser Ser Gly Leu Arg Pro Leu Thr His Ser Ala
            420                 425                 430

Gly Pro Asp Arg Ser Gln Val Pro Ala Ala Ser Gly Ala Ala Thr Met
        435                 440                 445

Leu Thr Lys Gly Leu Pro Asp Ile Thr Val Gly Leu Gln Ile Tyr Asp
    450                 455                 460

Ser Cys Ile Ser Gly Ile Gln Ala Leu Gly Ser Thr Leu Ala Leu Leu
465                 470                 475                 480

Ser Asn Gln Leu Pro Pro Thr Thr Asn Tyr Ala Cys Gly Ser Gln Gln
                485                 490                 495

His Leu Leu Gly Val Val Gly Gly Met Thr Phe Leu Glu Ser Glu Pro
            500                 505                 510

Met Ser Glu Leu Leu Ser Ile Tyr Arg Val Pro Gln Gly Gln Arg Leu
        515                 520                 525

Thr Lys Asn Phe Glu Val Lys Glu Leu Val Cys Thr Tyr Leu Val Gly
    530                 535                 540

Gln Leu Pro Tyr Gly Leu Val Ser Tyr Asp Asn Ser Asn Phe Glu Trp
545                 550                 555                 560

Leu Asp Gln Gln Leu Gln Lys Gln Ile Gly Gly Glu Gly Leu Pro Val
                565                 570                 575

Gly Ala Ala Pro Ser Arg Val Ala Arg Gln Gln Ser Asp Glu Glu Ala
            580                 585                 590

Val Gly Gly Val Gln Gly Tyr Arg Trp Ser Gly Leu Gly Ala Ser Ile
        595                 600                 605

Gln Ser Ala Arg Glu Gly Ala Trp His Arg Thr Gly Leu Glu Asn Met
    610                 615                 620

Thr Thr Ala His Leu Ser Ala Phe Lys Leu Pro Asp Leu Thr Ala Thr
625                 630                 635                 640

Tyr Gln Ala Tyr Leu Ala Ala Lys Ala Leu Trp Val Ala Tyr Gln Asn
                645                 650                 655

Leu Met Ser Cys Ser Glu Arg Glu Gly Pro Phe Leu Gly Gly Thr Tyr
            660                 665                 670

Ala Asn Ala Trp Glu Ala Arg Leu Ser Gln Val Asn Phe Thr Thr Lys
        675                 680                 685

Ala Gln Glu Glu Val Phe Phe Ala Lys Asp Gly Glu Val Leu Thr Thr
    690                 695                 700
```

-continued

```
Phe Asp Ile Lys Asn Ile Tyr Val Leu Pro Asp Leu Ser Gly Gln Thr
705                 710                 715                 720

Ala Ile Val Gly His Phe Asp Phe Arg Ala Pro Ser Gly Lys Glu Leu
                725                 730                 735

Leu Leu Asp Asp Ser Ala Ile Val Trp Ala Glu Gly Pro Leu Lys Ile
            740                 745                 750

Arg Ala Glu Arg Thr Leu Arg Thr Lys Thr Thr Gln His Leu Ser His
        755                 760                 765

Pro Lys Leu Gln Glu Ser Leu Pro Leu Ser Ala Thr Lys Asn Val Leu
    770                 775                 780

Trp Lys Pro Gly Ser Gln Pro Tyr Leu Arg Ser Gln Asn Ala Ala Thr
785                 790                 795                 800

Lys Ala Phe Pro Asp Pro Glu Glu Lys Ser Gln Cys His Gln Phe Leu
                805                 810                 815

Phe Leu Pro Ser Asp Ser Val Ala Cys Gln Lys Cys Ser Asp Asn Gln
            820                 825                 830

Trp Pro Asn Val Gln Lys Gly Glu Cys Ile Pro Lys Thr Leu Asp Phe
        835                 840                 845

Leu Phe Tyr His Lys Pro Leu Asp Thr Ala Leu Ala Val Cys Thr Ala
    850                 855                 860

Leu Leu Phe Leu Leu Ala Leu Ala Ile Leu Gly Ile Phe His Val Val
865                 870                 875                 880

Cys Ser Cys Val Trp Val Ser Phe Ile Pro Ala His Met His Ala His
                885                 890                 895

Ser Lys Asp Thr Met Ala Met Glu Val Phe Val Ile Leu Ala Ser Ala
            900                 905                 910

Gly Gly Leu Met Ser Ser Leu Phe Phe Ser Lys Cys Tyr Ile Ile Leu
        915                 920                 925

Leu His Pro Glu Lys Asn Thr Lys Asp Gln Met Phe Gly Arg His His
    930                 935                 940

Arg Lys Trp Glu Lys Leu Lys
945                 950
```

<210> SEQ ID NO 271
<211> LENGTH: 956
<212> TYPE: DNA
<213> ORGANISM: Homo sapiens

<400> SEQUENCE: 271

```
gccgcgctgt atggggccag cggacacttc gccccaggca ccactgtgcc cctggccctg      60

ccacctggtg gcaatggctc agccacacct gacaatggca ccacccctgg ggccgagggc     120

tggcggcagt tgctgggcct actccccgag cacatggcgg agaagctgtg tgaggcctgg     180

gcctttgggc agagccacca gacgggcgtc gtggcactgg gcctactcac ctgcctgctg     240

gcaatgctgc tggctggccg catcaggctc cggaggatcg atgccttctg cacctgcctg     300

tgggccctgc tgctggggct gcacctggct gagcagcacc tgcaggccgc ctcgcctagc     360

tggctagaca cgctcaagtt cagcaccaca tctttgtgct gcctggttgg cttcacggcg     420

gctgtggcca caaggaaggc aacgggccca cggaggttcc ggccccgaag gttcttccca     480

ggagactctg ccggcctttt ccccaccagc cccagcttgg ccatccctca cccgagtgtc     540

ggaggctctc cagcgtctct gttcatcccc agcccgccca gcttcctgcc cctcgccaac     600

caagcagctc ttccggtctc ctcgacggac ctcaccctcc tcatttgcct ggccgcctca     660

gccgggccct ctctctggga accataccct ctctgactcg agcagactcc ggctatctgt     720
```

-continued tcagcggtag ccgcccacca tctcaggtgt ctcgatctgg gggagtttcc tgttttcaga 780
ttacttctct cttcttgtcg gggaagctgc ccctccgtcc catcctttcc cagggccttc 840
cgggggcggc tcggtgggcc tccagtccgg ctctctggcc acgggaggcc ctcatcagcc 900
tgccggtcaa cctgagggac gaagtgtgtt gtccggcacc cctggagagg cccaaa 956

<210> SEQ ID NO 272
<211> LENGTH: 231
<212> TYPE: PRT
<213> ORGANISM: Homo sapiens

<400> SEQUENCE: 272

Ala Ala Leu Tyr Gly Ala Ser Gly His Phe Ala Pro Gly Thr Thr Val
1 5 10 15

Pro Leu Ala Leu Pro Pro Gly Gly Asn Gly Ser Ala Thr Pro Asp Asn
20 25 30

Gly Thr Thr Pro Gly Ala Glu Gly Trp Arg Gln Leu Leu Gly Leu Leu
35 40 45

Pro Glu His Met Ala Glu Lys Leu Cys Glu Ala Trp Ala Phe Gly Gln
50 55 60

Ser His Gln Thr Gly Val Val Ala Leu Gly Leu Leu Thr Cys Leu Leu
65 70 75 80

Ala Met Leu Leu Ala Gly Arg Ile Arg Leu Arg Arg Ile Asp Ala Phe
85 90 95

Cys Thr Cys Leu Trp Ala Leu Leu Leu Gly Leu His Leu Ala Glu Gln
100 105 110

His Leu Gln Ala Ala Ser Pro Ser Trp Leu Asp Thr Leu Lys Phe Ser
115 120 125

Thr Thr Ser Leu Cys Cys Leu Val Gly Phe Thr Ala Ala Val Ala Thr
130 135 140

Arg Lys Ala Thr Gly Pro Arg Arg Phe Arg Pro Arg Arg Phe Phe Pro
145 150 155 160

Gly Asp Ser Ala Gly Leu Phe Pro Thr Ser Pro Ser Leu Ala Ile Pro
165 170 175

His Pro Ser Val Gly Gly Ser Pro Ala Ser Leu Phe Ile Pro Ser Pro
180 185 190

Pro Ser Phe Leu Pro Leu Ala Asn Gln Ala Ala Leu Pro Val Ser Ser
195 200 205

Thr Asp Leu Thr Leu Leu Ile Cys Leu Ala Ala Ser Ala Gly Pro Ser
210 215 220

Leu Trp Glu Pro Tyr Pro Leu
225 230

<210> SEQ ID NO 273
<211> LENGTH: 1806
<212> TYPE: DNA
<213> ORGANISM: Homo sapiens

<400> SEQUENCE: 273
gaggaggcgc gcgtcgccgc cccgcgtccc gcctgcggcc cgcgcccccg gcgtcaccgc 60
ctcctgcccg cctgcccgcc tgcccgcctg cccgcctacc cgcctacccg cctacccgcc 120
tacccccctg ccggcctgcc gtccttccac gcggagagcc atggagggag tgagcgcgct 180
gctggcccgc tgccccacgg ccggcctggc cggcggcctg ggggtcacgg cgtgcgccgc 240
ggccggcgtg ttgctctacc ggatcgcgcg gaggatgaag ccaacgcaca cgatggtcaa 300

-continued

```
ctgctggttc tgcaaccagg atacgctggt gccctatggg aaccgcaact gctgggactg    360

tccccactgc gagcagtaca acggcttcca ggagaacggc gactacaaca agccgatccc    420

cgcccagtac ttggagcacc tgaaccacgt ggtgagcagc gcgcccagcc tgcgcgaccc    480

ttcgcagccg cagcagtggg tgagcagcca agtcctgctg tgcaagaggt gcaaccacca    540

ccagaccacc aagatcaagc agctggccgc cttcgctccc cgcgaggagg gcaggtatga    600

cgaggaggtc gaggtgtacc ggcatcacct ggagcagatg tacaagctgt gccggccgtg    660

ccaagcggct gtggagtact acatcaagca ccagaaccgc cagctgcgcg ccctgttgct    720

cagccaccag ttcaagcgcc gggaggccga ccagacccac gcacagaact tctcctccgc    780

cgtgaagtcc ccggtccagg tcatcctgct ccgtgccctc gccttcctgg cctgcgcctt    840

cctactgacc accgcgctgt atggggccag cggacacttc gccccaggca ccactgtgcc    900

cctggccctg ccacctggtg gcaatggctc agccacacct gacaatggca ccacccctgg    960

ggccgagggc tggcggcagt tgctgggcct actccccgag cacatggcgg agaagctgtg   1020

tgaggcctgg gcctttgggc agagccacca gacgggcgtc gtggcactgg gcctactcac   1080

ctgcctgctg gcaatgctgc tggctggccg catcaggctc cggaggatcg atgccttctg   1140

cacctgcctg tgggccctgc tgctggggct gcacctggct gagcagcacc tgcaggccgc   1200

ctcgcctagc tggctagaca cgctcaagtt cagcaccaca tctttgtgct gcctggttgg   1260

cttcacggcg gctgtggcca caaggaaggc aacgggccca cggaggttcc ggccccgaag   1320

gttcttccca ggagactctg ccggcctttt ccccaccagc cccagcttgg ccatccctca   1380

cccgagtgtc ggaggctctc cagcgtctct gttcatcccc agcccgccca gcttcctgcc   1440

cctcgccaac caagcagctc ttccggtctc ctcgacggac ctcaccctcc tcatttgcct   1500

ggccgcctca gccgggccct ctctctggga accatacct ctctgactcg agcagactcc   1560

ggctatctgt tcagcggtag ccgcccacca tctcaggtgt ctcgatctgg gggagtttcc   1620

tgttttcaga ttacttctct cttcttgtcg gggaagctgc ccctccgtcc catcctttcc   1680

cagggccttc cgggggcggc tcggtgggcc tccagtccgg ctctctggcc acgggaggcc   1740

ctcatcagcc tgccggtcaa cctgagggac gaagtgtgtt gtccggcacc cctggagagg   1800

cccaaa                                                                1806
```

<210> SEQ ID NO 274
<211> LENGTH: 461
<212> TYPE: PRT
<213> ORGANISM: Homo sapiens

<400> SEQUENCE: 274

```
Met Glu Gly Val Ser Ala Leu Leu Ala Arg Cys Pro Thr Ala Gly Leu
1               5                   10                  15

Ala Gly Gly Leu Gly Val Thr Ala Cys Ala Ala Ala Gly Val Leu Leu
            20                  25                  30

Tyr Arg Ile Ala Arg Arg Met Lys Pro Thr His Thr Met Val Asn Cys
        35                  40                  45

Trp Phe Cys Asn Gln Asp Thr Leu Val Pro Tyr Gly Asn Arg Asn Cys
    50                  55                  60

Trp Asp Cys Pro His Cys Glu Gln Tyr Asn Gly Phe Gln Glu Asn Gly
65                  70                  75                  80

Asp Tyr Asn Lys Pro Ile Pro Ala Gln Tyr Leu Glu His Leu Asn His
                85                  90                  95
```

-continued

```
Val Val Ser Ser Ala Pro Ser Leu Arg Asp Pro Ser Gln Pro Gln Gln
            100                 105                 110

Trp Val Ser Ser Gln Val Leu Leu Cys Lys Arg Cys Asn His His Gln
        115                 120                 125

Thr Thr Lys Ile Lys Gln Leu Ala Ala Phe Ala Pro Arg Glu Glu Gly
    130                 135                 140

Arg Tyr Asp Glu Glu Val Glu Val Tyr Arg His His Leu Glu Gln Met
145                 150                 155                 160

Tyr Lys Leu Cys Arg Pro Cys Gln Ala Ala Val Glu Tyr Tyr Ile Lys
                165                 170                 175

His Gln Asn Arg Gln Leu Arg Ala Leu Leu Leu Ser His Gln Phe Lys
            180                 185                 190

Arg Arg Glu Ala Asp Gln Thr His Ala Gln Asn Phe Ser Ser Ala Val
        195                 200                 205

Lys Ser Pro Val Gln Val Ile Leu Leu Arg Ala Leu Ala Phe Leu Ala
    210                 215                 220

Cys Ala Phe Leu Leu Thr Thr Ala Leu Tyr Gly Ala Ser Gly His Phe
225                 230                 235                 240

Ala Pro Gly Thr Thr Val Pro Leu Ala Leu Pro Pro Gly Gly Asn Gly
                245                 250                 255

Ser Ala Thr Pro Asp Asn Gly Thr Thr Pro Gly Ala Glu Gly Trp Arg
            260                 265                 270

Gln Leu Leu Gly Leu Leu Pro Glu His Met Ala Glu Lys Leu Cys Glu
        275                 280                 285

Ala Trp Ala Phe Gly Gln Ser His Gln Thr Gly Val Val Ala Leu Gly
    290                 295                 300

Leu Leu Thr Cys Leu Leu Ala Met Leu Leu Ala Gly Arg Ile Arg Leu
305                 310                 315                 320

Arg Arg Ile Asp Ala Phe Cys Thr Cys Leu Trp Ala Leu Leu Leu Gly
                325                 330                 335

Leu His Leu Ala Glu Gln His Leu Gln Ala Ala Ser Pro Ser Trp Leu
            340                 345                 350

Asp Thr Leu Lys Phe Ser Thr Thr Ser Leu Cys Cys Leu Val Gly Phe
        355                 360                 365

Thr Ala Ala Val Ala Thr Arg Lys Ala Thr Gly Pro Arg Arg Phe Arg
    370                 375                 380

Pro Arg Arg Phe Phe Pro Gly Asp Ser Ala Gly Leu Phe Pro Thr Ser
385                 390                 395                 400

Pro Ser Leu Ala Ile Pro His Pro Ser Val Gly Gly Ser Pro Ala Ser
                405                 410                 415

Leu Phe Ile Pro Ser Pro Pro Ser Phe Leu Pro Leu Ala Asn Gln Ala
            420                 425                 430

Ala Leu Pro Val Ser Ser Thr Asp Leu Thr Leu Leu Ile Cys Leu Ala
        435                 440                 445

Ala Ser Ala Gly Pro Ser Leu Trp Glu Pro Tyr Pro Leu
    450                 455                 460
```

<210> SEQ ID NO 275
<211> LENGTH: 600
<212> TYPE: DNA
<213> ORGANISM: Homo sapiens
<220> FEATURE:
<221> NAME/KEY: misc_feature
<222> LOCATION: (460)..(460)
<223> OTHER INFORMATION: n is a, c, g, t or u
<220> FEATURE:

<221> NAME/KEY: misc_feature
<222> LOCATION: (530)..(530)
<223> OTHER INFORMATION: n is a, c, g, t or u
<220> FEATURE:
<221> NAME/KEY: misc_feature
<222> LOCATION: (574)..(574)
<223> OTHER INFORMATION: n is a, c, g, t or u
<220> FEATURE:
<221> NAME/KEY: misc_feature
<222> LOCATION: (577)..(577)
<223> OTHER INFORMATION: n is a, c, g, t or u

<400> SEQUENCE: 275

```
tcaagtctga cttgcatcta cactgcgggc aagatgcggc tgcaagaccg catcgccacg      60

ttcttcttcc caaaaggcat gatgctcacc acggctgcgc tgatgctctt cttcttacac     120

ctgggcatct tcatcagaga cgtgcacaac ttctgcatca cctaccacta tgaccacatg     180

agctttcact acacggtcgt cctgatgttc tcccaggtga tcagcatctg ctgggctgcc     240

atggggtcac tctatgctga gatgacagaa aacaagtacg tctgcttctc cgccctgacc     300

atcctgagtg agtggcagga gggggagggt gcaagaggga gcggggagct ttggaaccct     360

gagatgtggc aaggagtagc cagggaaggg tactggggct catgggggc tctgtccccc      420

gcccagtgct caacggagcc atgctcttca accgcctgtn cttggagttt ctggccatcg     480

agtaccggga ggagcaccac tgaggcctgg ggagtcggaa cagggctaan gagggggaag     540

caaaaggctg cctcgggtgt tttaataaag ctgntgntta tttccaaaaa aaaaaaaaaa     600
```

<210> SEQ ID NO 276
<211> LENGTH: 174
<212> TYPE: PRT
<213> ORGANISM: Homo sapiens
<220> FEATURE:
<221> NAME/KEY: UNSURE
<222> LOCATION: (128)..(128)
<223> OTHER INFORMATION: Xaa is S, P, T or A
<220> FEATURE:
<221> NAME/KEY: UNSURE
<222> LOCATION: (151)..(151)
<223> OTHER INFORMATION: Xaa is M, T, K or R
<220> FEATURE:
<221> NAME/KEY: UNSURE
<222> LOCATION: (166)..(166)
<223> OTHER INFORMATION: Xaa is L, M or V
<220> FEATURE:
<221> NAME/KEY: UNSURE
<222> LOCATION: (167)..(167)
<223> OTHER INFORMATION: Xaa is F, L, I or V

<400> SEQUENCE: 276

```
Met Met Leu Thr Thr Ala Ala Leu Met Leu Phe Phe Leu His Leu Gly
1               5                   10                  15

Ile Phe Ile Arg Asp Val His Asn Phe Cys Ile Thr Tyr His Tyr Asp
            20                  25                  30

His Met Ser Phe His Tyr Thr Val Val Leu Met Phe Ser Gln Val Ile
        35                  40                  45

Ser Ile Cys Trp Ala Ala Met Gly Ser Leu Tyr Ala Glu Met Thr Glu
    50                  55                  60

Asn Lys Tyr Val Cys Phe Ser Ala Leu Thr Ile Leu Ser Glu Trp Gln
65                  70                  75                  80

Glu Gly Glu Gly Ala Arg Gly Ser Gly Glu Leu Trp Asn Pro Glu Met
                85                  90                  95

Trp Gln Gly Val Ala Arg Glu Gly Tyr Trp Gly Ser Trp Gly Ala Leu
            100                 105                 110
```

-continued

```
Ser Pro Ala Gln Cys Ser Thr Glu Pro Cys Ser Ser Thr Ala Cys Xaa
        115                 120                 125

Trp Ser Phe Trp Pro Ser Ser Thr Gly Arg Ser Thr Thr Glu Ala Trp
    130                 135                 140

Gly Val Gly Thr Gly Leu Xaa Arg Gly Lys Gln Lys Ala Ala Ser Gly
145                 150                 155                 160

Val Leu Ile Lys Leu Xaa Xaa Ile Ser Lys Lys Lys Lys Lys
                165                 170


<210> SEQ ID NO 277
<211> LENGTH: 457
<212> TYPE: DNA
<213> ORGANISM: Homo sapiens

<400> SEQUENCE: 277

aaacactgca ggctacgaat cggtcattgc ataggttttc catgaatcag gaagattcag      60

tcctggtaaa ttcattccca ggaacatcgc tgccactgct attattctag cagctgttcc     120

catactccaa tgagtccagt taaacatttg ccttcttggg tcatgtaaag gtggcctgaa     180

gactgccaga agaggctgaa gaactgccaa agtcatcact atacagccga ggtatgggtg     240

gtaacctgca tgcctactcc agcctcccct gtatataaac ggcataacaa aagcaatgca     300

ggtgaggaca gttgtggtga acatgagcat ccgatgcacc tgaaaccaag ctgcttcacc     360

aagcaagaaa gcttttgacc aaactggctt gaagaaccgg gcaaccagta cacctatgct     420

aacagtagtc atccatgcca caaacattaa ggcacca                              457


<210> SEQ ID NO 278
<211> LENGTH: 144
<212> TYPE: PRT
<213> ORGANISM: Homo sapiens

<400> SEQUENCE: 278

Met Phe Val Ala Trp Met Thr Thr Val Ser Ile Gly Val Leu Val Ala
1               5                   10                  15

Arg Phe Phe Lys Pro Val Trp Ser Lys Ala Phe Leu Leu Gly Glu Ala
            20                  25                  30

Ala Trp Phe Gln Val His Arg Met Leu Met Phe Thr Thr Thr Val Leu
        35                  40                  45

Thr Cys Ile Ala Phe Val Met Pro Phe Ile Tyr Arg Gly Gly Trp Ser
    50                  55                  60

Arg His Ala Gly Tyr His Pro Tyr Leu Gly Cys Ile Val Met Thr Leu
65                  70                  75                  80

Ala Val Leu Gln Pro Leu Leu Ala Val Phe Arg Pro Pro Leu His Asp
                85                  90                  95

Pro Arg Arg Gln Met Phe Asn Trp Thr His Trp Ser Met Gly Thr Ala
            100                 105                 110

Ala Arg Ile Ile Ala Val Ala Ala Met Phe Leu Gly Met Asn Leu Pro
        115                 120                 125

Gly Leu Asn Leu Pro Asp Ser Trp Lys Thr Tyr Ala Met Thr Asp Ser
    130                 135                 140


<210> SEQ ID NO 279
<211> LENGTH: 293
<212> TYPE: DNA
<213> ORGANISM: Homo sapiens

<400> SEQUENCE: 279
```

-continued

```
ttttttttt tttttttaag gctgaagcaa ataggaacgt atatttctca tgaatccaaa      60

gcaaagacac aggaagtgct ggcattcttt tggtggctgg tagctcttga ccttctcttc    120

aaggttgcca catgccttag cagcagctca tgacttcacg ttctcaccgt attcgaaggc    180

aggaagcatg gagtagctgg cagctgcgtt tgacacagac tgccctcgga ccccttctcc    240

gcgcagtgcg actcgcaatt gtctggagca cgttggcagc agccctcgtg ccg           293


<210> SEQ ID NO 280
<211> LENGTH: 45
<212> TYPE: PRT
<213> ORGANISM: Homo sapiens

<400> SEQUENCE: 280

Arg His Glu Gly Cys Cys Gln Arg Ala Pro Asp Asn Cys Glu Ser His
1               5                   10                  15

Cys Ala Glu Lys Gly Ser Glu Gly Ser Leu Cys Gln Thr Gln Leu Pro
            20                  25                  30

Ala Thr Pro Cys Phe Leu Pro Ser Asn Thr Val Arg Thr
        35                  40                  45


<210> SEQ ID NO 281
<211> LENGTH: 15
<212> TYPE: PRT
<213> ORGANISM: Homo sapiens

<400> SEQUENCE: 281

Cys Gln Lys Gln Arg Asn Trp His Gly Ile Trp Arg Leu Glu Val
1               5                   10                  15


<210> SEQ ID NO 282
<211> LENGTH: 13
<212> TYPE: PRT
<213> ORGANISM: Homo sapiens

<400> SEQUENCE: 282

Met Ala Lys Gln Gly Glu Met Asn Thr Ser Thr Ser Cys
1               5                   10


<210> SEQ ID NO 283
<211> LENGTH: 13
<212> TYPE: PRT
<213> ORGANISM: Homo sapiens

<400> SEQUENCE: 283

Pro Lys Arg Gly Gly Arg Ala Gly Arg Glu His Ser Cys
1               5                   10


<210> SEQ ID NO 284
<211> LENGTH: 91
<212> TYPE: PRT
<213> ORGANISM: Homo sapiens

<400> SEQUENCE: 284

Arg Phe Gln Arg Asn Thr Gly Glu Met Ser Ser Asn Ser Thr Ala Leu
1               5                   10                  15

Ala Leu Val Arg Pro Ser Ser Ser Gly Leu Ile Asn Ser Asn Thr Asp
            20                  25                  30

Asn Asn Leu Ala Val Tyr Asp Leu Ser Arg Asp Ile Leu Asn Asn Phe
        35                  40                  45

Pro His Ser Ile Ala Arg Gln Lys Arg Ile Leu Val Asn Leu Ser Met
    50                  55                  60
```

-continued

```
Val Glu Asn Lys Leu Val Glu Leu Glu His Thr Leu Leu Ser Lys Gly
65                  70                  75                  80

Phe Arg Gly Ala Ser Pro His Arg Lys Ser Thr
                85                  90


<210> SEQ ID NO 285
<211> LENGTH: 15
<212> TYPE: PRT
<213> ORGANISM: Homo sapiens

<400> SEQUENCE: 285

Cys Lys Tyr Arg Arg Phe Gln Arg Asn Thr Gly Glu Met Ser Ser
1               5                   10                  15


<210> SEQ ID NO 286
<211> LENGTH: 14
<212> TYPE: PRT
<213> ORGANISM: Homo sapiens

<400> SEQUENCE: 286

Cys Lys Gly Phe Arg Gly Ala Ser Pro His Arg Lys Ser Thr
1               5                   10


<210> SEQ ID NO 287
<211> LENGTH: 19
<212> TYPE: PRT
<213> ORGANISM: Homo sapiens

<400> SEQUENCE: 287

Met Ala Cys Ile Tyr Pro Thr Thr Phe Tyr Thr Ser Leu Pro Thr Lys
1               5                   10                  15

Ser Leu Asn


<210> SEQ ID NO 288
<211> LENGTH: 121
<212> TYPE: PRT
<213> ORGANISM: Homo sapiens

<400> SEQUENCE: 288

Ala Pro Pro Ser Cys Arg Glu Cys Tyr Gln Ser Leu His Tyr Arg Gly
1               5                   10                  15

Glu Met Gln Gln Tyr Phe Thr Tyr His Thr His Ile Glu Arg Ser Cys
            20                  25                  30

Tyr Gly Asn Leu Ile Glu Glu Cys Val Glu Ser Gly Lys Ser Tyr Tyr
        35                  40                  45

Lys Val Lys Asn Leu Gly Val Cys Gly Ser Arg Asn Gly Ala Ile Cys
    50                  55                  60

Pro Arg Gly Lys Gln Trp Leu Cys Phe Thr Lys Ile Gly Gln Trp Gly
65                  70                  75                  80

Val Asn Thr Gln Val Leu Glu Asp Ile Lys Arg Glu Gln Ile Ile Ala
                85                  90                  95

Lys Ala Lys Ala Ser Lys Pro Thr Thr Pro Pro Glu Asn Arg Pro Arg
            100                 105                 110

His Phe His Ser Phe Ile Gln Lys Leu
        115                 120


<210> SEQ ID NO 289
<211> LENGTH: 15
<212> TYPE: PRT
<213> ORGANISM: Homo sapiens
```

<400> SEQUENCE: 289

Cys Glu Asn Arg Pro Arg His Phe His Ser Phe Ile Gln Lys Leu
1 5 10 15

<210> SEQ ID NO 290
<211> LENGTH: 13
<212> TYPE: PRT
<213> ORGANISM: Homo sapiens

<400> SEQUENCE: 290

Cys Ile Tyr Pro Thr Thr Phe Tyr Thr Ser Leu Pro Thr
1 5 10

<210> SEQ ID NO 291
<211> LENGTH: 14
<212> TYPE: PRT
<213> ORGANISM: Homo sapiens

<400> SEQUENCE: 291

Cys Lys Glu Asp Glu Leu Val Arg Asp Ser Pro Ala Arg Lys
1 5 10

<210> SEQ ID NO 292
<211> LENGTH: 12
<212> TYPE: PRT
<213> ORGANISM: Homo sapiens

<400> SEQUENCE: 292

Ala Leu Gly Thr Arg Leu Ser Gln His Thr Asp Val
1 5 10

<210> SEQ ID NO 293
<211> LENGTH: 11
<212> TYPE: PRT
<213> ORGANISM: Homo sapiens

<400> SEQUENCE: 293

Asp Phe Asn Cys Pro Cys Leu Val His Tyr Asn
1 5 10

<210> SEQ ID NO 294
<211> LENGTH: 53
<212> TYPE: PRT
<213> ORGANISM: Homo sapiens

<400> SEQUENCE: 294

Ser Ser Ser Val Asp Pro Glu Lys Phe Leu Asp Phe Ala Asn Met Thr
1 5 10 15

Pro Ser Gln Val Gln Leu Phe Leu Ala Lys Val Pro Cys Lys Glu Asp
20 25 30

Glu Leu Val Arg Asp Ser Pro Ala Arg Lys Ala Val Ser Arg Tyr Leu
35 40 45

Arg Cys Leu Ser Gln
50

<210> SEQ ID NO 295
<211> LENGTH: 146
<212> TYPE: PRT
<213> ORGANISM: Homo sapiens

<400> SEQUENCE: 295

-continued

```
Arg Cys Leu Arg Pro Cys Phe Asp Gln Thr Val Phe Leu Gln Arg Arg
1               5                   10                  15

Tyr Trp Ser Asn Tyr Val Asp Leu Glu Gln Lys Leu Phe Asp Glu Thr
            20                  25                  30

Cys Cys Glu His Ala Arg Asp Phe Ala His Arg Cys Val Leu His Phe
        35                  40                  45

Phe Ala Ser Met Arg Ser Glu Leu Gln Ala Arg Gly Leu Arg Arg Gly
    50                  55                  60

Asn Ala Gly Arg Arg Leu Glu Leu Pro Ala Val Pro Glu Pro Pro Glu
65                  70                  75                  80

Gly Leu Asp Ser Gly Ser Gly Lys Ala His Leu Arg Ala Ile Ser Ser
                85                  90                  95

Arg Glu Gln Val Asp Arg Leu Leu Ser Thr Trp Tyr Ser Ser Lys Pro
            100                 105                 110

Pro Leu Asp Leu Ala Ala Ser Pro Gly Leu Cys Gly Gly Gly Leu Ser
        115                 120                 125

His Arg Ala Pro Thr Leu Ala Leu Gly Thr Arg Leu Ser Gln His Thr
    130                 135                 140

Asp Val
145


<210> SEQ ID NO 296
<211> LENGTH: 1035
<212> TYPE: PRT
<213> ORGANISM: Homo sapiens

<400> SEQUENCE: 296

Met Pro Cys Gly Phe Ser Pro Ser Pro Val Ala His His Leu Val Pro
1               5                   10                  15

Gly Pro Pro Asp Thr Pro Ala Gln Gln Leu Arg Cys Gly Trp Thr Val
            20                  25                  30

Gly Gly Trp Leu Leu Ser Leu Val Arg Gly Leu Leu Pro Cys Leu Pro
        35                  40                  45

Pro Gly Ala Arg Thr Ala Glu Gly Pro Ile Met Val Leu Ala Gly Pro
    50                  55                  60

Leu Ala Val Ser Leu Leu Leu Pro Ser Leu Thr Leu Leu Val Ser His
65                  70                  75                  80

Leu Ser Ser Ser Gln Asp Val Ser Ser Glu Pro Ser Ser Glu Gln Gln
                85                  90                  95

Leu Cys Ala Leu Ser Lys His Pro Thr Val Ala Phe Glu Asp Leu Gln
            100                 105                 110

Pro Trp Val Ser Asn Phe Thr Tyr Pro Gly Ala Arg Asp Phe Ser Gln
        115                 120                 125

Leu Ala Leu Asp Pro Ser Gly Asn Gln Leu Ile Val Gly Ala Arg Asn
    130                 135                 140

Tyr Leu Phe Arg Leu Ser Leu Ala Asn Val Ser Leu Leu Gln Ala Thr
145                 150                 155                 160

Glu Trp Ala Ser Ser Glu Asp Thr Arg Arg Ser Cys Gln Ser Lys Gly
                165                 170                 175

Lys Thr Glu Glu Glu Cys Gln Asn Tyr Val Arg Val Leu Ile Val Ala
            180                 185                 190

Gly Arg Lys Val Phe Met Cys Gly Thr Asn Ala Phe Ser Pro Met Cys
        195                 200                 205

Thr Ser Arg Gln Val Gly Asn Leu Ser Arg Thr Ile Glu Lys Ile Asn
    210                 215                 220
```

-continued

```
Gly Val Ala Arg Cys Pro Tyr Asp Pro Arg His Asn Ser Thr Ala Val
225                 230                 235                 240

Ile Ser Ser Gln Gly Glu Leu Tyr Ala Ala Thr Val Ile Asp Phe Ser
                245                 250                 255

Gly Arg Asp Pro Ala Ile Tyr Arg Ser Leu Gly Ser Gly Pro Pro Leu
            260                 265                 270

Arg Thr Ala Gln Tyr Asn Ser Lys Trp Leu Asn Glu Pro Asn Phe Val
        275                 280                 285

Ala Ala Tyr Asp Ile Gly Leu Phe Ala Tyr Phe Phe Leu Arg Glu Asn
    290                 295                 300

Ala Val Glu His Asp Cys Gly Arg Thr Val Tyr Ser Arg Val Ala Arg
305                 310                 315                 320

Val Cys Lys Asn Asp Val Gly Gly Arg Phe Leu Leu Glu Asp Thr Trp
                325                 330                 335

Thr Thr Phe Met Lys Ala Arg Leu Asn Cys Ser Arg Pro Gly Glu Val
            340                 345                 350

Pro Phe Tyr Tyr Asn Glu Leu Gln Ser Ala Phe His Leu Pro Glu Gln
        355                 360                 365

Asp Leu Ile Tyr Gly Val Phe Thr Thr Asn Val Asn Ser Ile Ala Ala
    370                 375                 380

Ser Ala Val Cys Ala Phe Asn Leu Ser Ala Ile Ser Gln Ala Phe Asn
385                 390                 395                 400

Gly Pro Phe Arg Tyr Gln Glu Asn Pro Arg Ala Ala Trp Leu Pro Ile
                405                 410                 415

Ala Asn Pro Ile Pro Asn Phe Gln Cys Gly Thr Leu Pro Glu Thr Gly
            420                 425                 430

Pro Asn Glu Asn Leu Thr Glu Arg Ser Leu Gln Asp Ala Gln Arg Leu
        435                 440                 445

Phe Leu Met Ser Glu Ala Val Gln Pro Val Thr Pro Glu Pro Cys Val
    450                 455                 460

Thr Gln Asp Ser Val Arg Phe Ser His Leu Val Val Asp Leu Val Gln
465                 470                 475                 480

Ala Lys Asp Thr Leu Tyr His Val Leu Tyr Ile Gly Thr Glu Ser Gly
                485                 490                 495

Thr Ile Leu Lys Ala Leu Ser Thr Ala Ser Arg Ser Leu His Gly Cys
            500                 505                 510

Tyr Leu Glu Glu Leu His Val Leu Pro Pro Gly Arg Arg Glu Pro Leu
        515                 520                 525

Arg Ser Leu Arg Ile Leu His Ser Ala Arg Ala Leu Phe Val Gly Leu
    530                 535                 540

Arg Asp Gly Val Leu Arg Val Pro Leu Glu Arg Cys Ala Ala Tyr Arg
545                 550                 555                 560

Ser Gln Gly Ala Cys Leu Gly Ala Arg Asp Pro Tyr Cys Gly Trp Asp
                565                 570                 575

Gly Lys Gln Gln Arg Cys Ser Thr Leu Glu Asp Ser Ser Asn Met Ser
            580                 585                 590

Leu Trp Thr Gln Asn Ile Thr Ala Cys Pro Val Arg Asn Val Thr Arg
        595                 600                 605

Asp Gly Gly Phe Gly Pro Trp Ser Pro Trp Gln Pro Cys Glu His Leu
    610                 615                 620

Asp Gly Asp Asn Ser Gly Ser Cys Leu Cys Arg Ala Arg Ser Cys Asp
625                 630                 635                 640
```

-continued

```
Ser Pro Arg Pro Arg Cys Gly Gly Leu Asp Cys Leu Gly Pro Ala Ile
                645                 650                 655

His Ile Ala Asn Cys Ser Arg Asn Gly Ala Trp Thr Pro Trp Ser Ser
            660                 665                 670

Trp Ala Leu Cys Ser Thr Ser Cys Gly Ile Gly Phe Gln Val Arg Gln
        675                 680                 685

Arg Ser Cys Ser Asn Pro Ala Pro Arg His Gly Gly Arg Ile Cys Val
    690                 695                 700

Gly Lys Ser Arg Glu Glu Arg Phe Cys Asn Glu Asn Thr Pro Cys Pro
705                 710                 715                 720

Val Pro Ile Phe Trp Ala Ser Trp Gly Ser Trp Ser Lys Cys Ser Ser
                725                 730                 735

Asn Cys Gly Gly Gly Met Gln Ser Arg Arg Arg Ala Cys Glu Asn Gly
            740                 745                 750

Asn Ser Cys Leu Gly Cys Gly Val Glu Phe Lys Thr Cys Asn Pro Glu
        755                 760                 765

Gly Cys Pro Glu Val Arg Arg Asn Thr Pro Trp Thr Pro Trp Leu Pro
    770                 775                 780

Val Asn Val Thr Gln Gly Gly Ala Arg Gln Glu Gln Arg Phe Arg Phe
785                 790                 795                 800

Thr Cys Arg Ala Pro Leu Ala Asp Pro His Gly Leu Gln Phe Gly Arg
                805                 810                 815

Arg Arg Thr Glu Thr Arg Thr Cys Pro Ala Asp Gly Ser Gly Ser Cys
            820                 825                 830

Asp Thr Asp Ala Leu Val Glu Val Leu Leu Arg Ser Gly Ser Thr Ser
        835                 840                 845

Pro His Thr Val Ser Gly Gly Trp Ala Ala Trp Gly Pro Trp Ser Ser
    850                 855                 860

Cys Ser Arg Asp Cys Glu Leu Gly Phe Arg Val Arg Lys Arg Thr Cys
865                 870                 875                 880

Thr Asn Pro Glu Pro Arg Asn Gly Gly Leu Pro Cys Val Gly Asp Ala
                885                 890                 895

Ala Glu Tyr Gln Asp Cys Asn Pro Gln Ala Cys Pro Val Arg Gly Ala
            900                 905                 910

Trp Ser Cys Trp Thr Ser Trp Ser Pro Cys Ser Ala Ser Cys Gly Gly
        915                 920                 925

Gly His Tyr Gln Arg Thr Arg Ser Cys Thr Ser Pro Ala Pro Ser Pro
    930                 935                 940

Gly Glu Asp Ile Cys Leu Gly Leu His Thr Glu Glu Ala Leu Cys Ala
945                 950                 955                 960

Thr Gln Ala Cys Pro Glu Gly Trp Ser Pro Trp Ser Glu Trp Ser Lys
                965                 970                 975

Cys Thr Asp Asp Gly Ala Gln Ser Arg Ser Arg His Cys Glu Glu Leu
            980                 985                 990

Leu Pro Gly Ser Ser Ala Cys Ala  Gly Asn Ser Ser Gln  Ser Arg Pro
        995                 1000                 1005

Cys Pro  Tyr Ser Glu Ile Pro  Val Ile Leu Pro Ala  Ser Ser Met
    1010                 1015                 1020

Glu Glu  Ala Thr Asp Cys Ala  Gly Phe Asn Leu Ile
    1025                 1030                 1035
```

<210> SEQ ID NO 297
<211> LENGTH: 16
<212> TYPE: PRT

-continued

<213> ORGANISM: Homo sapiens

<400> SEQUENCE: 297

```
Cys Pro Tyr Asp Pro Arg His Asn Ser Thr Ala Val Ile Ser Ser Gln
1               5                   10                  15
```

<210> SEQ ID NO 298
<211> LENGTH: 11
<212> TYPE: PRT
<213> ORGANISM: Homo sapiens

<400> SEQUENCE: 298

```
Cys Pro Glu Val Arg Arg Asn Thr Pro Trp Thr
1               5                   10
```

<210> SEQ ID NO 299
<211> LENGTH: 35
<212> TYPE: PRT
<213> ORGANISM: Homo sapiens

<400> SEQUENCE: 299

```
Glu Arg Val Trp Ser Asp Asp His Lys Asp Phe Asp Cys Asn Thr Arg
1               5                   10                  15

Gln Pro Gly Cys Ser Asn Val Cys Phe Asp Glu Phe Phe Pro Val Ser
            20                  25                  30

His Val Arg
        35
```

<210> SEQ ID NO 300
<211> LENGTH: 38
<212> TYPE: PRT
<213> ORGANISM: Homo sapiens

<400> SEQUENCE: 300

```
His Ser Phe Tyr Pro Lys Tyr Ile Leu Pro Pro Val Val Lys Cys His
1               5                   10                  15

Ala Asp Pro Cys Pro Asn Ile Val Asp Cys Phe Ile Ser Lys Pro Ser
            20                  25                  30

Glu Lys Asn Ile Phe Thr
        35
```

<210> SEQ ID NO 301
<211> LENGTH: 15
<212> TYPE: PRT
<213> ORGANISM: Homo sapiens

<400> SEQUENCE: 301

```
Cys Leu Pro Asp Arg Pro Arg Asp His Val Lys Lys Thr Ile Leu
1               5                   10                  15
```

<210> SEQ ID NO 302
<211> LENGTH: 13
<212> TYPE: PRT
<213> ORGANISM: Homo sapiens

<400> SEQUENCE: 302

```
Glu Arg Val Trp Ser Asp Asp His Lys Asp Phe Asp Cys
1               5                   10
```

<210> SEQ ID NO 303
<211> LENGTH: 38
<212> TYPE: PRT
<213> ORGANISM: Homo sapiens -continued

<400> SEQUENCE: 303

Asn Asn Asp Val Ser Cys Asp His Pro Ser Asn Thr Val Pro Ser Gly
1               5                   10                  15

Ser Asn Gln Asp Leu Gly Ala Gly Ala Gly Glu Asp Ala Arg Ser Asp
            20                  25                  30

Asp Ser Ser Ser Arg Ile
        35

<210> SEQ ID NO 304
<211> LENGTH: 15
<212> TYPE: PRT
<213> ORGANISM: Homo sapiens

<400> SEQUENCE: 304

Cys Asp His Pro Ser Asn Thr Val Pro Ser Gly Ser Asn Gln Asp
1               5                   10                  15

<210> SEQ ID NO 305
<211> LENGTH: 12
<212> TYPE: PRT
<213> ORGANISM: Homo sapiens

<400> SEQUENCE: 305

Cys Val Pro His Ser Arg Ser Arg Gly Pro Asn Leu
1               5                   10

<210> SEQ ID NO 306
<211> LENGTH: 12
<212> TYPE: PRT
<213> ORGANISM: Homo sapiens

<400> SEQUENCE: 306

Cys Glu Leu Ser Gln Thr Pro His Pro His Ser Arg
1               5                   10

<210> SEQ ID NO 307
<211> LENGTH: 14
<212> TYPE: PRT
<213> ORGANISM: Homo sapiens

<400> SEQUENCE: 307

Cys Leu Asp Ser Ala Gly Asn Asn Ala Gly Ile Gln Trp Gly
1               5                   10

<210> SEQ ID NO 308
<211> LENGTH: 14
<212> TYPE: PRT
<213> ORGANISM: Homo sapiens

<400> SEQUENCE: 308

Cys Asn Arg Val Ser Lys Asn Pro Glu Met Leu Gln Thr Gly
1               5                   10

<210> SEQ ID NO 309
<211> LENGTH: 2115
<212> TYPE: DNA
<213> ORGANISM: Homo sapiens

<400> SEQUENCE: 309
atgcgtatat gttatgaatg ccaaaatgaa agaacattgt ggcgatgtgt ttcccaggat      60
ggggctgact acagtgtggg cgtgtgtgtc cctgattctt gtgctgaaga ggatgtgact     120

-continued

```
ctgatgtctc ggctggatac tttaagattc agaaatactt catttttggc cccttccctc    180

tttcttttta caataaattc ttcctccttg tctggtggga gtgtgaccag atgtgctgct    240

ggaaagatcc ccctggacac atttgctgcc gtatgtctgt tcatcacctt gctgggtctc    300

atcctccctc cggctggaac agtctgcgtg gcagctaggg aatgggggtc agcctgcagg    360

acatcgcggg aacacgggga acctctggcc acttacggga gtctgccact gagcgaggcg    420

gagagcaatg aacaaagaag cagaatccca cggacacact gccgggcaca tctcctcctg    480

tcagcagcct ccagcagagg aaaaaggttt ctaggagccg tggctcatgc tctggagtgc    540

ttttcttggc agaagaatgt gccagccatc tggactacaa aggcaccagg tggcacctgc    600

tctgcactga atggcattcg tgtcttgagt cttctttgga tcatctcggg acacaccagt    660

cagatgactg catggctgtc tttgggatgg aaagatggag ggcacgaaag gccactggtc    720

atgtctgggc catcagtggg aatcggagac accagagaag ccacgagtgg ttggttaagt    780

gcaagttcgt ttttaaagat gcatcagaat tcagacaaag gaataacccc caaaggcata    840

ctcagatact ttctcagtca cctggtaagg ttgcagcctc ttcacctgta ttcaatgtgc    900

ttgttggttg gactgttctc tcttgttccc tggggacctg tctgggaaat gcccaaattc    960

cactgggata actgccggca agcatggtgg acgaatctgc tgttgctaaa taactttgtg   1020

tcggtcaaga atgcgtgcaa tggctggacc tggtaccttg ccaatgactt ccagttccac   1080

ctcaccacac cagtgattat cttcatccat gtaaagagta cacagatcct catcctcctt   1140

ggggccatgc tgttcttggc atctttcaca gccactgctc tgatcacctt ggcatataaa   1200

cttcctgtcg tggctccatc agaaaccagg acttcccggg gagggctgct gaatgccagg   1260

ctgttcaccc tgtgcccttt ggttcatgga aaaagtgggt atgaaacttt tggtctggat   1320

gggaaagctg attgccttct tgcttccaaa cttctgaacc tttcaacctg cactggaaat   1380

gaacaagtgt gccctaaatg tacctttggg cttgctgatt attccaatgg acatctcagg   1440

gatttggatt ccctttgcca tgtccagatc aaacataaca ttttggctta tttccttgta   1500

tttttcagtg aagaggcgat tgtattgtat ttcgtggagt actacacaaa gccctactgc   1560

cgatttgggc cagttcttgt gggcctcttt ctgagcattt acatgcacca aaaccaccag   1620

gaaaacattc tcagaaccaa gctgcagctc tctaccaagc cctccaccgg accctgtggg   1680

cggcggctgt gggctgagtc ctctttgcgt gccacggagg atatggaggt atggaagcgg   1740

ctccaggctt tgctgtcggg ttcacaccct gttcctttaa aggtgacaaa tcgaacacac   1800

aggagagcca agcagataaa aggcttcaat ggaaaagaat cttctccagg tctggtgaac   1860

cgtgtgcttt cttgggacat ctggagtttc ctgtccagca tcagttatgc tcgctacttg   1920

gtgcatccga ttctgatcat cctttacaat ggccttcagg aaacacttat tcaccacact   1980

gacaccaaca tgttctatct tttctctgga caccgtgtgc tgaccttcgt cactgggctg   2040

gccctgacgc tgttcattga gaaaccatgt caggaactga agcagcacct gctgggccat   2100

gaatgttctg gttaa                                                    2115
```

<210> SEQ ID NO 310
<211> LENGTH: 704
<212> TYPE: PRT
<213> ORGANISM: Homo sapiens

<400> SEQUENCE: 310

```
Met Arg Ile Cys Tyr Glu Cys Gln Asn Glu Arg Thr Leu Trp Arg Cys
1               5                   10                  15
```

-continued

```
Val Ser Gln Asp Gly Ala Asp Tyr Ser Val Gly Val Cys Val Pro Asp
            20                  25                  30

Ser Cys Ala Glu Glu Asp Val Thr Leu Met Ser Arg Leu Asp Thr Leu
        35                  40                  45

Arg Phe Arg Asn Thr Ser Phe Leu Ala Pro Ser Leu Phe Leu Phe Thr
    50                  55                  60

Ile Asn Ser Ser Ser Leu Ser Gly Gly Ser Val Thr Arg Cys Ala Ala
65                  70                  75                  80

Gly Lys Ile Pro Leu Asp Thr Phe Ala Ala Val Cys Leu Phe Ile Thr
                85                  90                  95

Leu Leu Gly Leu Ile Leu Pro Pro Ala Gly Thr Val Cys Val Ala Ala
            100                 105                 110

Arg Glu Trp Gly Ser Ala Cys Arg Thr Ser Arg Glu His Gly Glu Pro
        115                 120                 125

Leu Ala Thr Tyr Gly Ser Leu Pro Leu Ser Glu Ala Glu Ser Asn Glu
    130                 135                 140

Gln Arg Ser Arg Ile Pro Arg Thr His Cys Arg Ala His Leu Leu Leu
145                 150                 155                 160

Ser Ala Ala Ser Ser Arg Gly Lys Arg Phe Leu Gly Ala Val Ala His
                165                 170                 175

Ala Leu Glu Cys Phe Ser Trp Gln Lys Asn Val Pro Ala Ile Trp Thr
            180                 185                 190

Thr Lys Ala Pro Gly Gly Thr Cys Ser Ala Leu Asn Gly Ile Arg Val
        195                 200                 205

Leu Ser Leu Leu Trp Ile Ile Ser Gly His Thr Ser Gln Met Thr Ala
    210                 215                 220

Trp Leu Ser Leu Gly Trp Lys Asp Gly Gly His Glu Arg Pro Leu Val
225                 230                 235                 240

Met Ser Gly Pro Ser Val Gly Ile Gly Asp Thr Arg Glu Ala Thr Ser
                245                 250                 255

Gly Trp Leu Ser Ala Ser Ser Phe Leu Lys Met His Gln Asn Ser Asp
            260                 265                 270

Lys Gly Ile Thr Pro Lys Gly Ile Leu Arg Tyr Phe Leu Ser His Leu
        275                 280                 285

Val Arg Leu Gln Pro Leu His Leu Tyr Ser Met Cys Leu Leu Val Gly
    290                 295                 300

Leu Phe Ser Leu Val Pro Trp Gly Pro Val Trp Glu Met Pro Lys Phe
305                 310                 315                 320

His Trp Asp Asn Cys Arg Gln Ala Trp Trp Thr Asn Leu Leu Leu Leu
                325                 330                 335

Asn Asn Phe Val Ser Val Lys Asn Ala Cys Asn Gly Trp Thr Trp Tyr
            340                 345                 350

Leu Ala Asn Asp Phe Gln Phe His Leu Thr Thr Pro Val Ile Ile Phe
        355                 360                 365

Ile His Val Lys Ser Thr Gln Ile Leu Ile Leu Leu Gly Ala Met Leu
    370                 375                 380

Phe Leu Ala Ser Phe Thr Ala Thr Ala Leu Ile Thr Leu Ala Tyr Lys
385                 390                 395                 400

Leu Pro Val Val Ala Pro Ser Glu Thr Arg Thr Ser Arg Gly Gly Leu
                405                 410                 415

Leu Asn Ala Arg Leu Phe Thr Leu Cys Pro Leu Val His Gly Lys Ser
            420                 425                 430
```

-continued

```
Gly Tyr Glu Thr Phe Gly Leu Asp Gly Lys Ala Asp Cys Leu Leu Ala
        435                 440                 445

Ser Lys Leu Leu Asn Leu Ser Thr Cys Thr Gly Asn Glu Gln Val Cys
    450                 455                 460

Pro Lys Cys Thr Phe Gly Leu Ala Asp Tyr Ser Asn Gly His Leu Arg
465                 470                 475                 480

Asp Leu Asp Ser Leu Cys His Val Gln Ile Lys His Asn Ile Leu Ala
                485                 490                 495

Tyr Phe Leu Val Phe Phe Ser Glu Glu Ala Ile Val Leu Tyr Phe Val
            500                 505                 510

Glu Tyr Tyr Thr Lys Pro Tyr Cys Arg Phe Gly Pro Val Leu Val Gly
        515                 520                 525

Leu Phe Leu Ser Ile Tyr Met His Gln Asn His Gln Glu Asn Ile Leu
    530                 535                 540

Arg Thr Lys Leu Gln Leu Ser Thr Lys Pro Ser Thr Gly Pro Cys Gly
545                 550                 555                 560

Arg Arg Leu Trp Ala Glu Ser Ser Leu Arg Ala Thr Glu Asp Met Glu
                565                 570                 575

Val Trp Lys Arg Leu Gln Ala Leu Leu Ser Gly Ser His Pro Val Pro
            580                 585                 590

Leu Lys Val Thr Asn Arg Thr His Arg Arg Ala Lys Gln Ile Lys Gly
        595                 600                 605

Phe Asn Gly Lys Glu Ser Ser Pro Gly Leu Val Asn Arg Val Leu Ser
    610                 615                 620

Trp Asp Ile Trp Ser Phe Leu Ser Ser Ile Ser Tyr Ala Arg Tyr Leu
625                 630                 635                 640

Val His Pro Ile Leu Ile Ile Leu Tyr Asn Gly Leu Gln Glu Thr Leu
                645                 650                 655

Ile His His Thr Asp Thr Asn Met Phe Tyr Leu Phe Ser Gly His Arg
            660                 665                 670

Val Leu Thr Phe Val Thr Gly Leu Ala Leu Thr Leu Phe Ile Glu Lys
        675                 680                 685

Pro Cys Gln Glu Leu Lys Gln His Leu Leu Gly His Glu Cys Ser Gly
    690                 695                 700


<210> SEQ ID NO 311
<211> LENGTH: 21
<212> TYPE: DNA
<213> ORGANISM: Artificial Sequence
<220> FEATURE:
<223> OTHER INFORMATION: Oligonucleotide

<400> SEQUENCE: 311

aaccgtgtgc tttcttggga c                                              21


<210> SEQ ID NO 312
<211> LENGTH: 19
<212> TYPE: DNA
<213> ORGANISM: Artificial Sequence
<220> FEATURE:
<223> OTHER INFORMATION: Oligonucleotide

<400> SEQUENCE: 312

acattcatgg cccagcagg                                                 19
```

IDENTIFICATION OF TUMOUR-ASSOCIATED CELL SURFACE ANTIGENS FOR DIAGNOSIS AND THERAPY

This application is the National Stage of International Application No. PCT/EP2004/010697, filed on Sep. 23, 2004, which is incorporated herein by reference.

Despite interdisciplinary approaches and exhaustive use of classical therapeutic procedures, cancers are still among the leading causes of death. More recent therapeutic concepts aim at incorporating the patient's immune system into the overall therapeutic concept by using recombinant tumor vaccines and other specific measures such as antibody therapy. A prerequisite for the success of such a strategy is the recognition of tumor-specific or tumor-associated antigens or epitopes by the patient's immune system whose effector functions are to be interventionally enhanced. Tumor cells biologically differ substantially from their nonmalignant cells of origin. These differences are due to genetic alterations acquired during tumor development and result, inter alia, also in the formation of qualitatively or quantitatively altered molecular structures in the cancer cells. Tumor-associated structures of this kind which are recognized by the specific immune system of the tumor-harboring host are referred to as tumor-associated antigens. The specific recognition of tumor-associated antigens involves cellular and humoral mechanisms which are two functionally interconnected units: $CD4^+$ and $CD8^+$ T lymphocytes recognize the processed antigens presented on the molecules of the MHC (major histocompatibility complex) classes II and I, respectively, while B lymphocytes produce circulating antibody molecules which bind directly to unprocessed antigens. The potential clinical-therapeutical importance of tumor-associated antigens results from the fact that the recognition of antigens on neoplastic cells by the immune system leads to the initiation of cytotoxic effector mechanisms and, in the presence of T helper cells, can cause elimination of the cancer cells (Pardoll, *Nat. Med.* 4:525-31, 1998). Accordingly, a central aim of tumor immunology is to molecularly define these structures. The molecular nature of these antigens has been enigmatic for a long time. Only after development of appropriate cloning techniques has it been possible to screen cDNA expression libraries of tumors systematically for tumor-associated antigens by analyzing the target structures of cytotoxic T lymphocytes (CTL) (van der Bruggen et al., *Science* 254:1643-7, 1991) or by using circulating autoantibodies (Sahin et al., *Curr. Opin. Immunol.* 9:709-16, 1997) as probes. To this end, cDNA expression libraries were prepared from fresh tumor tissue and recombinantly expressed as proteins in suitable systems. Immunoeffectors isolated from patients, namely CTL clones with tumor-specific lysis patterns, or circulating autoantibodies were utilized for cloning the respective antigens.

In recent years a multiplicity of antigens have been defined in various neoplasias by these approaches. The class of cancer/testis antigens (CTA) is of great interest here. CTA and genes encoding them (cancer/testis genes or CTG) are defined by their characteristic expression pattern [Tureci et al, *Mol Med. Today.* 3:342-9, 1997]. They are not found in normal tissues, except testis and germ cells, but are expressed in a number of human malignomas, not tumor type-specifically but with different frequency in tumor entities of very different origins (Chen & Old, *Cancer J. Sci. Am.* 5:16-7, 1999). Serum reactivities against CTA are also not found in healthy controls but only in tumor patients. This class of antigens, in particular owing to its tissue distribution, is particularly valuable for immunotherapeutic projects and is tested in current clinical patient studies (Marchand et al., *Int. J. Cancer* 80:219-30, 1999; Knuth et al., *Cancer Chemother. Pharmacol.* 46:p 46-51, 2000).

However, the probes utilized for antigen identification in the classical methods illustrated above are immunoeffectors (circulating autoantibodies or CTL clones) from patients usually having already advanced cancer. A number of data indicate that tumors can lead, for example, to tolerization and anergization of T cells and that, during the course of the disease, especially those specificities which could cause effective immune recognition are lost from the immunoeffector repertoire. Current patient studies have not yet produced any solid evidence of a real action of the previously found and utilized tumor-associated antigens. Accordingly, it cannot be ruled out that proteins evoking spontaneous immune responses are the wrong target structures.

It was the object of the present invention to provide target structures for a diagnosis and therapy of cancers.

According to the invention, this object is achieved by the subject matter of the claims.

According to the invention, a strategy for identifying and providing antigens expressed in association with a tumor and the nucleic acids coding therefor was pursued. This strategy is based on the evaluation of human protein and nucleic acid data bases with respect to potential cancer-specific antigens which are accessible on the cell surface. The definition of the filter criteria which are necessary for this together with a high throughput methodology for analysing all proteins, if possible, form the central part of the invention. Data mining first produces a list which is as complete as possible of all known genes which according to the basic principle "gene to mRNA to protein" are examined for the presence of one or more transmembrane domains. This is followed by a homology search, a classification of the hits in tissue specific groups (among others tumor tissue) and an inspection of the real existence of the mRNA. Finally, the proteins which are identified in this manner are evaluated for their aberrant activation in tumors, e.g. by expression analyses and protein chemical procedures.

Data mining is a known method of identifying tumor-associated genes. In the conventional strategies, however, transcriptoms of normal tissue libraries are usually subtracted electronically from tumor tissue libraries, with the assumption that the remaining genes are tumor-specific (Schmitt et al., *Nucleic Acids Res.* 27:4251-60, 1999; Vasmatzis et al., *Proc. Natl. Acad. Sci. USA.* 95:300-4, 1998; Scheurle et al., *Cancer Res.* 60:4037-43, 2000).

The concept of the invention, however, is based on utilizing data mining for electronically extracting all genes coding for cancer specific antigens which are accessible on the cell surfaces and then evaluating said genes for ectopic expression in tumors.

The invention thus relates in one aspect to a strategy for identifying genes differentially expressed in tumors. Said strategy combines data mining of public sequence libraries ("in silico") with subsequent evaluating laboratory-experimental ("wet bench") studies.

According to the invention, a combined strategy based on different bioinformatic scripts enabled new genes coding for cancer specific antigens which are accessible on the cell surfaces to be identified. According to the invention, these tumor-associated genes and the genetic products encoded thereby were identified and provided independently of an immunogenic action.

The tumor-associated antigens identified according to the invention have an amino acid sequence encoded by a nucleic acid which is selected from the group consisting of (a) a nucleic acid which comprises a nucleic acid sequence selected from the group consisting of SEQ ID NOs: 1, 5, 9, 13, 17, 21, 25, 29, 33, 37, 41, 45, 49, 53, 57, 61, 65, 69, 73, 77, 81, 85, 89, 93, 97, 101, 105, 109, 113, 117, 121, 125, 129, 133, 137, 141, 145, 149, 153, 157, 161, 165, 169, 173, 175, 179, 183, 187, 191, 195, 199, 203, 207, 211, 215, 219, 223, 227, 231, 235, 239, 243, 247, 251, 255, 259, 263, 267, 269, 271, 273, 275, 277, 279, 309 of the sequence listing, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, a tumor-associated antigen identified according to the invention has an amino acid sequence encoded by a nucleic acid which is selected from the group consisting of SEQ ID NOs: 1, 5, 9, 13, 17, 21, 25, 29, 33, 37, 41, 45, 49, 53, 57, 61, 65, 69, 73, 77, 81, 85, 89, 93, 97, 101, 105, 109, 113, 117, 121, 125, 129, 133, 137, 141, 145, 149, 153, 157, 161, 165, 169, 173, 175, 179, 183, 187, 191, 195, 199, 203, 207, 211, 215, 219, 223, 227, 231, 235, 239, 243, 247, 251, 255, 259, 263, 267, 269, 271, 273, 275, 277, 279, 309 of the sequence listing. In a further preferred embodiment, a tumor-associated antigen identified according to the invention comprises an amino acid sequence selected from the group consisting of SEQ ID NOs: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158, 162, 166, 170, 174, 176, 180, 184, 188, 192, 196, 200, 204, 208, 212, 216, 220, 224, 228, 232, 236, 240, 244, 248, 252, 256, 260, 264, 268, 270, 272, 274, 276, 278, 280 to 308, 310 of the sequence listing, a part or derivative thereof.

The present invention generally relates to the use of tumor-associated antigens identified according to the invention or of parts thereof, of nucleic acids coding therefor or of nucleic acids directed against said coding nucleic acids or of antibodies directed against the tumor-associated antigens identified according to the invention or parts thereof for therapy and diagnosis. This utilization may relate to individual but also to combinations of two or more of these antigens, functional fragments, nucleic acids, antibodies, etc., in one embodiment also in combination with other tumor-associated genes and antigens for diagnosis, therapy and progress control.

The property of the tumor-associated antigens identified according to the invention that they are localized on or at the cell surface qualifies them as suitable targets or means for therapy and diagnosis. Especially suitable for this is a part of the tumor-associated antigens identified according to the invention which corresponds to the non-transmembrane portion, in particular the extracellular portion of the antigens, or is comprised thereof. Therefore, according to the invention, a part of the tumor-associated antigens identified according to the invention which corresponds to the non-transmembrane portion of the antigens or is comprised thereof, or a corresponding part of the nucleic acids coding for the tumor-associated antigens identified according to the invention is preferred for therapy or diagnosis. Similarly, the use of antibodies is preferred which are directed against a part of the tumor-associated antigens identified according to the invention which corresponds to the non-transmembrane portion of the antigens or is comprised thereof.

Preferred diseases for a therapy and/or diagnosis are those in which one or more of the tumor-associated antigens identified according to the invention are selectively expressed or abnormally expressed.

The invention also relates to nucleic acids and genetic products which are expressed in association with a tumor cell and which are produced by altered splicing (splice variants) of genes or by altered translation with utilization of alternative open reading frames. Said nucleic acids comprise the sequences according to SEQ ID NOs: 1, 5, 9, 13, 17, 21, 25, 29, 33, 37, 41, 45, 49, 53, 57, 61, 65, 69, 73, 77, 81, 85, 89, 93, 97, 101, 105, 109, 113, 117, 121, 125, 129, 133, 137, 141, 145, 149, 153, 157, 161, 165, 169, 173, 175, 179, 183, 187, 191, 195, 199, 203, 207, 211, 215, 219, 223, 227, 231, 235, 239, 243, 247, 251, 255, 259, 263, 267, 269, 271, 273, 275, 277, 279, 309 of the sequence listing. Furthermore, the genetic products comprise all sequences according to SEQ ID NOs: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158, 162, 166, 170, 174, 176, 180, 184, 188, 192, 196, 200, 204, 208, 212, 216, 220, 224, 228, 232, 236, 240, 244, 248, 252, 256, 260, 264, 268, 270, 272, 274, 276, 278, 280 to 308, 310 of the sequence listing. The splice variants of the invention can be used according to the invention as targets for diagnosis and therapy of tumor diseases.

Very different mechanisms may cause splice variants to be produced, for example utilization of variable transcription initiation sites
utilization of additional exons
complete or incomplete splicing out of single or two or more exons,
splice regulator sequences altered via mutation (deletion or generation of new donor/acceptor sequences),
incomplete elimination of intron sequences.

Altered splicing of a gene results in an altered transcript sequence (splice variant). Translation of a splice variant in the region of its altered sequence results in an altered protein which may be distinctly different in the structure and function from the original protein. Tumor-associated splice variants may produce tumor-associated transcripts and tumor-associated proteins/antigens. These may be utilized as molecular markers both for detecting tumor cells and for therapeutic targeting of tumors. Detection of tumor cells, for example in blood, serum, bone marrow, sputum, bronchial lavage, bodily secretions and tissue biopsies, may be carried out according to the invention, for example, after extraction of nucleic acids by PCR amplification with splice variant-specific oligonucleotides. According to the invention, all sequence-dependent detection systems are suitable for detection. These are, apart from PCR, for example gene chip/microarray systems, Northern blot, RNAse protection assays (RDA) and others. All detection systems have in common that detection is based on a specific hybridization with at least one splice variant-specific nucleic acid sequence. However, tumor cells may also be detected according to the invention by antibodies which recognize a specific epitope encoded by the splice variant. Said antibodies may be prepared by using for immunization peptides which are specific for said splice variant. Suitable for immunization are particularly the amino acids whose epitopes are distinctly different from the variant(s) of the genetic product, which is (are) preferably produced in healthy cells. Detection of the tumor cells with antibodies may be carried out here on a sample isolated from the patient or as imaging with intravenously administered antibodies.

In addition to diagnostic usability, splice variants having new or altered epitopes are attractive targets for immunotherapy. The epitopes of the invention may be utilized for targeting therapeutically active monoclonal antibodies or T lymphocytes. In passive immunotherapy, antibodies or T lymphocytes which recognize splice variant-specific epitopes are adoptively transferred here. As in the case of other antigens, antibodies may be generated also by using standard technologies (immunization of animals, panning strategies for isolation of recombinant antibodies) with utilization of polypeptides which include these epitopes. Alternatively, it is possible to utilize for immunization nucleic acids coding for oligo- or polypeptides which contain said epitopes. Various techniques for in vitro or in vivo generation of epitope-specific T lymphocytes are known and have been described in detail (for example Kessler J H, et al. 2001, Sahin et al., 1997) and are likewise based on utilizing oligo- or polypeptides which contain the splice variant-specific epitopes or nucleic acids coding for said oligo- or polypeptides. Oligo- or polypeptides which contain the splice variant-specific epitopes or nucleic acids coding for said polypeptides may also be used for utilization as pharmaceutically active substances in active immunotherapy (vaccination, vaccine therapy).

The aberrant expression of genes in tumor cells also can be due to an altered methylation pattern of their promoters (De Smet C et al., Mol. Cell. Biol. 24(11):4781-90, 2004; De Smet C et al., Mol. Cell. Biol. 19(11):7327-35, 1999; De Smet C et al., Proc. Natl. Acad. Sci. USA. 93(14):7149-53, 1996). These differences in methylation can be used as indirect markers for the condition of the respective gene changed in the tumor. Accordingly, the increase or decrease of base methylations within the promoter region can be used for diagnostic purposes.

In one aspect, the invention relates to a pharmaceutical composition comprising an agent which recognizes the tumor-associated antigen identified according to the invention and which is preferably selective for cells which have expression or abnormal expression of a tumor-associated antigen identified according to the invention. In particular embodiments, said agent may cause induction of cell death, reduction in cell growth, damage to the cell membrane or secretion of cytokines and preferably have a tumor-inhibiting activity. In one embodiment, the agent is an antisense nucleic acid which hybridizes selectively with the nucleic acid coding for the tumor-associated antigen. In a further embodiment, the agent is an antibody which binds selectively to the tumor-associated antigen, in particular a complement-activated antibody which binds selectively to the tumor-associated antigen. In a further embodiment, the agent comprises two or more agents which each selectively recognize different tumor-associated antigens, at least one of which is a tumor-associated antigen identified according to the invention. Recognition needs not be accompanied directly with inhibition of activity or expression of the antigen. In this aspect of the invention, the antigen selectively limited to tumors preferably serves as a label for recruiting effector mechanisms to this specific location. In a preferred embodiment, the agent is a cytotoxic T lymphocyte which recognizes the antigen on an HLA molecule and lyses the cell labeled in this way. In a further embodiment, the agent is an antibody which binds selectively to the tumor-associated antigen and thus recruits natural or artificial effector mechanisms to said cell. In a further embodiment, the agent is a T helper lymphocyte which enhances effector functions of other cells specifically recognizing said antigen.

In one aspect, the invention relates to a pharmaceutical composition comprising an agent which inhibits expression or activity of a tumor-associated antigen identified according to the invention. In a preferred embodiment, the agent is an antisense nucleic acid which hybridizes selectively with the nucleic acid coding for the tumor-associated antigen. In a further embodiment, the agent is an antibody which binds selectively to the tumor-associated antigen. In a further embodiment, the agent comprises two or more agents which each selectively inhibit expression or activity of different tumor-associated antigens, at least one of which is a tumor-associated antigen identified according to the invention.

The activity of a tumor-associated antigen identified according to the invention can be any activity of a protein or a peptide. Thus, the therapeutic and diagnostic methods according to the invention can also aim at inhibiting or reducing this activity or testing this activity.

The invention furthermore relates to a pharmaceutical composition which comprises an agent which, when administered, selectively increases the amount of complexes between an HLA molecule and a peptide epitope from the tumor-associated antigen identified according to the invention. In one embodiment, the agent comprises one or more components selected from the group consisting of (i) the tumor-associated antigen or a part thereof, (ii) a nucleic acid which codes for said tumor-associated antigen or a part thereof, (iii) a host cell which expresses said tumor-associated antigen or a part thereof, and (iv) isolated complexes between peptide epitopes from said tumor-associated antigen and an MHC molecule. In one embodiment, the agent comprises two or more agents which each selectively increase the amount of complexes between MHC molecules and peptide epitopes of different tumor-associated antigens, at least one of which is a tumor-associated antigen identified according to the invention.

The invention furthermore relates to a pharmaceutical composition which comprises one or more components selected from the group consisting of (i) a tumor-associated antigen identified according to the invention or a part thereof, (ii) a nucleic acid which codes for a tumor-associated antigen identified according to the invention or for a part thereof, (iii) an antibody which binds to a tumor-associated antigen identified according to the invention or to a part thereof, (iv) an antisense nucleic acid which hybridizes specifically with a nucleic acid coding for a tumor-associated antigen identified according to the invention, (v) a host cell which expresses a tumor-associated antigen identified according to the invention or a part thereof, and (vi) isolated complexes between a tumor-associated antigen identified according to the invention or a part thereof and an HLA molecule.

A nucleic acid coding for a tumor-associated antigen identified according to the invention or for a part thereof may be present in the pharmaceutical composition in an expression vector and functionally linked to a promoter.

A host cell present in a pharmaceutical composition of the invention may secrete the tumor-associated antigen or the part thereof, express it on the surface or may additionally express an HLA molecule which binds to said tumor-associated antigen or said part thereof. In one embodiment, the host cell expresses the HLA molecule endogenously. In a further embodiment, the host cell expresses the HLA molecule and/or the tumor-associated antigen or the part thereof in a recombinant manner. The host cell is preferably nonproliferative. In a preferred embodiment, the host cell is an antigen-presenting cell, in particular a dendritic cell, a monocyte or a macrophage.

An antibody present in a pharmaceutical composition of the invention may be a monoclonal antibody. In further embodiments, the antibody is a chimeric or humanized antibody, a fragment of a natural antibody or a synthetic antibody, all of which may be produced by combinatory techniques. The antibody may be coupled to a therapeutically or diagnostically useful agent.

An antisense nucleic acid present in a pharmaceutical composition of the invention may comprise a sequence of 6-50, in particular 10-30, 15-30 and 20-30, contiguous nucleotides of the nucleic acid coding for the tumor-associated antigen identified according to the invention.

In further embodiments, a tumor-associated antigen, provided by a pharmaceutical composition of the invention either directly or via expression of a nucleic acid, or a part thereof binds to MHC molecules on the surface of cells, said binding preferably causing a cytolytic response and/or inducing cytokine release.

A pharmaceutical composition of the invention may comprise a pharmaceutically compatible carrier and/or an adjuvant. The adjuvant may be selected from saponin, GM-CSF, CpG oligonucleotides, RNA, a cytokine or a chemokine. A pharmaceutical composition of the invention is preferably used for the treatment of a disease characterized by selective expression or abnormal expression of a tumor-associated antigen. In a preferred embodiment, the disease is cancer.

The invention furthermore relates to methods of treating, diagnosing or monitoring, i.e. determining the regression, progression and/or onset of, a disease characterized by expression or abnormal expression of one of more tumor-associated antigens.

In one embodiment, the methods of treatment according to the invention comprise administering a pharmaceutical composition of the invention.

The methods of diagnosing and/or methods of monitoring according to the invention generally concern the use of means for the detection and/or the determination and/or the monitoring of the quantity of (i) a nucleic acid, which codes for the tumor-associated antigen, or a part thereof and/or (ii) the tumor-associated antigen or a part thereof and/or (iii) an antibody against the tumor-associated antigen or a part thereof and/or (iv) cytotoxic or T helper lymphocytes, which are specific for the tumor-associated antigen or a part thereof, in a biologic sample isolated from a patient.

In one aspect, the invention relates to a method of diagnosing a disease characterized by expression or abnormal expression of a tumor-associated antigen identified according to the invention. The method comprises (i) detection of a nucleic acid which codes for the tumor-associated antigen or of a part thereof and/or (ii) detection of the tumor-associated antigen or of a part thereof, and/or (iii) detection of an antibody to the tumor-associated antigen or to a part thereof and/or (iv) detection of cytotoxic or T helper lymphocytes which are specific for the tumor-associated antigen or for a part thereof in a biological sample isolated from a patient. In particular embodiments, detection comprises (i) contacting the biological sample with an agent which binds specifically to the nucleic acid coding for the tumor-associated antigen or to the part thereof, to said tumor-associated antigen or said part thereof, to the antibody or to cytotoxic or T helper lymphocytes specific for the tumor-associated antigen or parts thereof, and (ii) detecting the formation of a complex between the agent and the nucleic acid or the part thereof, the tumor-associated antigen or the part thereof, the antibody or the cytotoxic or T helper lymphocytes. In one embodiment, the disease is characterized by expression or abnormal expression of two or more different tumor-associated antigens and detection comprises detection of two or more nucleic acids coding for said two or more different tumor-associated antigens or of parts thereof, detection of two or more different tumor-associated antigens or of parts thereof, detection of two or more antibodies binding to said two or more different tumor-associated antigens or to parts thereof or detection of two or more cytotoxic or T helper lymphocytes specific for said two or more different tumor-associated antigens. In a further embodiment, the biological sample isolated from the patient is compared to a comparable normal biological sample.

The methods of diagnosing according to the invention may also utilize altered methylation patterns of the promoter region of the respective tumor-associated gene product. The detection of such methylation patterns can be performed by using methods on the basis of PCR, with the aid of restriction enzymes or by sequencing. A test suitable for this can be as follows: (1) extraction of DNA from tissue samples of patients, for example using paraffin embedded material, (2) treatment of the DNA with bisulfite containing reagents (i.e. as described in Clark S. J. et al., Nucleic Acids Res. 22(15): 2990-7, 1994), (3) amplification of DNA by means of PCR and (4) analysis by determining the amount of sequence specific amplification products (e.g. by means of quantitative PCR, hybridization techniques such as microarray methods).

The methods of diagnosing according to the invention can concern also the use of the tumor-associated antigens identified according to the invention as prognostic markers, in order to predict metastasis, e.g. through testing the migration behavior of cells, and therefore a worsened course of the disease, whereby among other things planning of a more aggressive therapy is made possible.

In a further aspect, the invention relates to a method for determining regression, course or onset of a disease characterized by expression or abnormal expression of a tumor-associated antigen identified according to the invention, which method comprises monitoring a sample from a patient who has said disease or is suspected of falling ill with said disease, with respect to one or more parameters selected from the group consisting of (i) the amount of nucleic acid which codes for the tumor-associated antigen or of a part thereof, (ii) the amount of the tumor-associated antigen or a part thereof, (iii) the amount of antibodies which bind to the tumor-associated antigen or to a part thereof, and (iv) the amount of cytolytic T cells or T helper cells which are specific for a complex between the tumor-associated antigen or a part thereof and an MHC molecule. The method preferably comprises determining the parameter(s) in a first sample at a first point in time and in a further sample at a second point in time and in which the course of the disease is determined by comparing the two samples. In particular embodiments, the disease is characterized by expression or abnormal expression of two or more different tumor-associated antigens and monitoring comprises monitoring (i) the amount of two or more nucleic acids which code for said two or more different tumor-associated antigens or of parts thereof, and/or (ii) the amount of said two or more different tumor-associated antigens or of parts thereof, and/or (iii) the amount of two or more antibodies which bind to said two or more different tumor-associated antigens or to parts thereof, and/or (iv) the amount of two or more cytolytic T cells or of T helper cells which are specific for complexes between said two or more different tumor-associated antigens or of parts thereof and MHC molecules.

According to the invention, detection of a nucleic acid or of a part thereof or determining or monitoring the amount of a nucleic acid or of a part thereof may be carried out using a polynucleotide probe which hybridizes specifically to said nucleic acid or said part thereof or may be carried out by selective amplification of said nucleic acid or said part thereof. In one embodiment, the polynucleotide probe comprises a sequence of 6-50, in particular 10-30, 15-30 and 20-30, contiguous nucleotides of said nucleic acid.

In certain embodiments of the methods of diagnosing of the invention, the promoter region or part thereof of a nucleic acid coding for a tumor-associated antigen identified according to the invention and being present in the form of genomic DNA is selectively amplified following treatment with a bisulfite containing reagent. The nucleic acid is preferably isolated from a sample of a patient to be examined before treatment with the bisulfite containing reagent. The oligonucleotides used in such amplification preferably have a sequence binding to the nucleic acid treated with a bisulfite containing reagent and preferably are completely complementary thereto. Preferably, the oligonucleotides are adapted to a different degree of methylation of the nucleic acid and bring about amplification products which can be differentiated.

According to the invention, detection of a tumor-associated antigen or of a part thereof or determining or monitoring the amount of a tumor-associated antigen or of a part thereof may be carried out using an antibody binding specifically to said tumor-associated antigen or said part thereof.

In certain embodiments, the tumor-associated antigen to be detected or the part thereof is present in a complex with an MHC molecule, in particular an HLA molecule.

According to the invention, detection of an antibody or determining or monitoring the amount of antibodies may be carried out using a protein or peptide binding specifically to said antibody.

According to the invention, detection of cytolytic T cells or of T helper cells or determining or monitoring the amount of cytolytic T cells or of T helper cells which are specific for complexes between an antigen or a part thereof and MHC molecules may be carried out using a cell presenting the complex between said antigen or said part thereof and an MHC molecule.

The polynucleotide probe, the antibody, the protein or peptide or the cell, which is used for detection or determining or monitoring, is preferably labeled in a detectable manner. In particular embodiments, the detectable marker is a radioactive marker or an enzymic marker. T lymphocytes may additionally be detected by detecting their proliferation, their cytokine production, and their cytotoxic activity triggered by specific stimulation with the complex of MHC and tumor-associated antigen or parts thereof. T lymphocytes may also be detected via a recombinant MHC molecule or else a complex of two or more MHC molecules which are loaded with the particular immunogenic fragment of one or more of the tumor-associated antigens and which can identify the specific T lymphocytes by contacting the specific T cell receptor.

In a further aspect, the invention relates to a method of treating, diagnosing or monitoring a disease characterized by expression or abnormal expression of a tumor-associated antigen identified according to the invention, which method comprises administering an antibody which binds to said tumor-associated antigen or to a part thereof and which is coupled to a therapeutic or diagnostic agent. The antibody may be a monoclonal antibody. In further embodiments, the antibody is a chimeric or humanized antibody or a fragment of a natural antibody.

The invention also relates to a method of treating a patient having a disease characterized by expression or abnormal expression of a tumor-associated antigen identified according to the invention, which method comprises (i) removing a sample containing immunoreactive cells from said patient, (ii) contacting said sample with a host cell expressing said tumor-associated antigen or a part thereof, under conditions which favor production of cytolytic T cells against said tumor-associated antigen or a part thereof, and (iii) introducing the cytolytic T cells into the patient in an amount suitable for lysing cells expressing the tumor-associated antigen or a part thereof. The invention likewise relates to cloning the T cell receptor of cytolytic T cells against the tumor-associated antigen. Said receptor may be transferred to other T cells which thus receive the desired specificity and, as under (iii), may be introduced into the patient.

In one embodiment, the host cell endogenously expresses an HLA molecule. In a further embodiment, the host cell recombinantly expresses an HLA molecule and/or the tumor-associated antigen or the part thereof. The host cell is preferably nonproliferative. In a preferred embodiment, the host cell is an antigen-presenting cell, in particular a dendritic cell, a monocyte or a macrophage.

In a further aspect, the invention relates to a method of treating a patient having a disease characterized by expression or abnormal expression of a tumor-associated antigen, which method comprises (i) identifying a nucleic acid which codes for a tumor-associated antigen identified according to the invention and which is expressed by cells associated with said disease, (ii) transfecting a host cell with said nucleic acid or a part thereof, (iii) culturing the transfected host cell for expression of said nucleic acid (this is not obligatory when a high rate of transfection is obtained), and (iv) introducing the host cells or an extract thereof into the patient in an amount suitable for increasing the immune response to the patient's cells associated with the disease. The method may further comprise identifying an MHC molecule presenting the tumor-associated antigen or a part thereof, with the host cell expressing the identified MHC molecule and presenting said tumor-associated antigen or a part thereof. The immune response may comprise a B cell response or a T cell response. Furthermore, a T cell response may comprise production of cytolytic T cells and/or T helper cells which are specific for the host cells presenting the tumor-associated antigen or a part thereof or specific for cells of the patient which express said tumor-associated antigen or a part thereof.

The invention also relates to a method of treating a disease characterized by expression or abnormal expression of a tumor-associated antigen identified according to the invention, which method comprises (i) identifying cells from the patient which express abnormal amounts of the tumor-associated antigen, (ii) isolating a sample of said cells, (iii) culturing said cells, and (iv) introducing said cells into the patient in an amount suitable for triggering an immune response to the cells.

Preferably, the host cells used according to the invention are nonproliferative or are rendered nonproliferative. A disease characterized by expression or abnormal expression of a tumor-associated antigen is in particular cancer.

The present invention furthermore relates to a nucleic acid selected from the group consisting of (a) a nucleic acid which comprises a nucleic acid sequence selected from the group consisting of SEQ ID NOs: 1, 5, 9, 13, 17, 21, 25, 29, 33, 37, 41, 45, 49, 53, 57, 61, 65, 69, 73, 77, 81, 85, 89, 93, 97, 101, 105, 109, 113, 117, 121, 125, 129, 133, 137, 141, 145, 149, 153, 157, 161, 165, 169, 173, 175, 179, 183, 187, 191, 195, 199, 203, 207, 211, 215, 219, 223, 227, 231, 235, 239, 243, 247, 251, 255, 259, 263, 267, 269, 271, 273, 275, 277, 279, 309 of the sequence listing, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). The invention furthermore relates to a nucleic acid, which codes for a protein or polypeptide comprising an amino acid sequence selected from the group consisting of SEQ ID NOs: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158, 162, 166, 170, 174, 176, 180, 184, 188, 192, 196, 200, 204, 208, 212, 216, 220, 224, 228, 232, 236, 240, 244, 248, 252, 256, 260, 264, 268, 270, 272, 274, 276, 278, 280 to 308, 310 of the sequence listing, a part or derivative thereof.

In a further aspect, the invention relates to promoter sequences of nucleic acids of the invention. These sequences may be functionally linked to another gene, preferably in an expression vector, and thus ensure selective expression of said gene in appropriate cells.

In a further aspect, the invention relates to a recombinant nucleic acid molecule, in particular DNA or RNA molecule, which comprises a nucleic acid of the invention.

The invention also relates to host cells which contain a nucleic acid of the invention or a recombinant nucleic acid molecule comprising a nucleic acid of the invention.

The host cell may also comprise a nucleic acid coding for a HLA molecule. In one embodiment, the host cell endogenously expresses the HLA molecule. In a further embodiment, the host cell recombinantly expresses the HLA molecule and/or the nucleic acid of the invention or a part thereof. Preferably, the host cell is nonproliferative. In a preferred embodiment, the host cell is an antigen-presenting cell, in particular a dendritic cell, a monocyte or a macrophage.

In a further embodiment, the invention relates to oligonucleotides which hybridize with a nucleic acid identified according to the invention and which may be used as genetic probes or as "antisense" molecules. Nucleic acid molecules in the form of oligonucleotide primers or competent samples, which hybridize with a nucleic acid identified according to the invention or parts thereof, may be used for finding nucleic acids which are homologous to said nucleic acid identified according to the invention. PCR amplification, Southern and Northern hybridization may be employed for finding homologous nucleic acids. Hybridization may be carried out under low stringency, more preferably under medium stringency and most preferably under high stringency conditions. The term "stringent conditions" according to the invention refers to conditions which allow specific hybridization between polynucleotides.

In a further aspect, the invention relates to a protein or polypeptide which is encoded by a nucleic acid selected from the group consisting of (a) a nucleic acid which comprises a nucleic acid sequence selected from the group consisting of SEQ ID NOs: 1, 5, 9, 13, 17, 21, 25, 29, 33, 37, 41, 45, 49, 53, 57, 61, 65, 69, 73, 77, 81, 85, 89, 93, 97, 101, 105, 109, 113, 117, 121, 125, 129, 133, 137, 141, 145, 149, 153, 157, 161, 165, 169, 173, 175, 179, 183, 187, 191, 195, 199, 203, 207, 211, 215, 219, 223, 227, 231, 235, 239, 243, 247, 251, 255, 259, 263, 267, 269, 271, 273, 275, 277, 279, 309 of the sequence listing, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). In a preferred embodiment, the invention relates to a protein or polypeptide which comprises an amino acid sequence selected from the group consisting of SEQ ID NOs: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158, 162, 166, 170, 174, 176, 180, 184, 188, 192, 196, 200, 204, 208, 212, 216, 220, 224, 228, 232, 236, 240, 244, 248, 252, 256, 260, 264, 268, 270, 272, 274, 276, 278, 280 to 308, 310 of the sequence listing, a part or derivative thereof.

In a further aspect, the invention relates to an immunogenic fragment of a tumor-associated antigen identified according to the invention. Said fragment preferably binds to a human HLA receptor or to a human antibody. A fragment of the invention preferably comprises a sequence of at least 6, in particular at least 8, at least 10, at least 12, at least 15, at least 20, at least 30 or at least 50, amino acids.

In a further aspect, the invention relates to an agent which binds to a tumor-associated antigen identified according to the invention or to a part thereof. In a preferred embodiment, the agent is an antibody. In further embodiments, the antibody is a chimeric, a humanized antibody or an antibody produced by combinatory techniques or is a fragment of an antibody. Furthermore, the invention relates to an antibody which binds selectively to a complex of (i) a tumor-associated antigen identified according to the invention or a part thereof and (ii) an MHC molecule to which said tumor-associated antigen identified according to the invention or said part thereof binds, with said antibody not binding to (i) or (ii) alone. An antibody of the invention may be a monoclonal antibody. In further embodiments, the antibody is a chimeric or humanized antibody or a fragment of a natural antibody.

The invention furthermore relates to a conjugate between an agent of the invention which binds to a tumor-associated antigen identified according to the invention or to a part thereof or an antibody of the invention and a therapeutic or diagnostic agent. In one embodiment, the therapeutic or diagnostic agent is a toxin.

In a further aspect, the invention relates to a kit for detecting expression or abnormal expression of a tumor-associated antigen identified according to the invention, which kit comprises agents for detection (i) of the nucleic acid which codes for the tumor-associated antigen or of a part thereof, (ii) of the tumor-associated antigen or of a part thereof, (iii) of antibodies which bind to the tumor-associated antigen or to a part thereof, and/or (iv) of T cells which are specific for a complex between the tumor-associated antigen or a part thereof and an MHC molecule. In one embodiment, the agents for detection of the nucleic acid or the part thereof are nucleic acid molecules for selective amplification of said nucleic acid, which comprise, in particular a sequence of 6-50, in particular 10-30, 15-30 and 20-30, contiguous nucleotides of said nucleic acid.

DETAILED DESCRIPTION OF THE INVENTION

According to the invention, genes are described which are expressed in tumor cells selectively or aberrantly and which are tumor-associated antigens.

According to the invention, these genes or their derivatives are preferred target structures for therapeutic approaches. Conceptionally, said therapeutic approaches may aim at inhibiting the activity of the selectively expressed tumor-associated genetic product. This is useful, if said aberrant respective selective expression is functionally important in tumor pathogenecity and if its ligation is accompanied by selective damage of the corresponding cells. Other therapeutic concepts contemplate tumor-associated antigens as labels which recruit effector mechanisms having cell-damaging potential selectively to tumor cells. Here, the function of the target molecule itself and its role in tumor development are totally irrelevant.

"Derivative" of a nucleic acid means according to the invention that single or multiple nucleotide substitutions, deletions and/or additions are present in said nucleic acid. Furthermore, the term "derivative" also comprises chemical derivatization of a nucleic acid on a base, on a sugar or on a phosphate of a nucleotide. The term "derivative" also comprises nucleic acids which contain nucleotides and nucleotide analogs not occurring naturally.

According to the invention, a nucleic acid is preferably deoxyribonucleic acid (DNA) or ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

A nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

According to the invention, complementary nucleic acids have at least 40%, in particular at least 50%, at least 60%, at least 70%, at least 80%, at least 90% and preferably at least 95%, at least 98% or at least 99%, identical nucleotides.

Nucleic acids coding for tumor-associated antigens may, according to the invention, be present alone or in combination with other nucleic acids, in particular heterologous nucleic acids. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the invention promoters, enhancers and other control elements which regulate expression of a gene. In particular embodiments of the invention, the expression control sequences can be regulated. The exact structure of regulatory sequences may vary as a function of the species or cell type, but generally comprises 5'untranscribed and 5'untranslated sequences which are involved in initiation of transcription and translation, respectively, such as TATA box, capping sequence, CAAT sequence, and the like. More specifically, 5'untranscribed regulatory sequences comprise a promoter region which includes a promoter sequence for transcriptional control of the functionally linked gene. Regulatory sequences may also comprise enhancer sequences or upstream activator sequences.

Thus, on the one hand, the tumor-associated antigens illustrated herein may be combined with any expression control sequences and promoters. On the other hand, however, the promoters of the tumor-associated genetic products illustrated herein may, according to the invention, be combined with any other genes. This allows the selective activity of these promoters to be utilized.

According to the invention, a nucleic acid may furthermore be present in combination with another nucleic acid which codes for a polypeptide controlling secretion of the protein or polypeptide encoded by said nucleic acid from a host cell. According to the invention, a nucleic acid may also be present in combination with another nucleic acid which codes for a polypeptide causing the encoded protein or polypeptide to be anchored on the cell membrane of the host cell or compartmentalized into particular organelles of said cell.

In a preferred embodiment, a recombinant DNA molecule is according to the invention a vector, where appropriate with a promoter, which controls expression of a nucleic acid, for example a nucleic acid coding for a tumor-associated antigen of the invention. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids, bacteriophages or viral genomes.

The nucleic acids coding for a tumor-associated antigen identified according to the invention may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application. According to the invention, the term "host cell" relates to any cell which can be transformed or transfected with an exogenous nucleic acid. The term "host cells" comprises according to the invention prokaryotic (e.g. *E. coli*) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

According to the invention, the term "expression" is used in its most general meaning and comprises the production of RNA or of RNA and protein. It also comprises partial expression of nucleic acids. Furthermore, expression may be carried out transiently or stably. Preferred expression systems in mammalian cells comprise pcDNA3.1 and pRc/CMV (Invitrogen, Carlsbad, Calif.), which contain a selective marker such as a gene imparting resistance to G418 (and thus enabling stably transfected cell lines to be selected) and the enhancer-promoter sequences of cytomegalovirus (CMV).

In those cases of the invention in which an HLA molecule presents a tumor-associated antigen or a part thereof, an expression vector may also comprise a nucleic acid sequence coding for said HLA molecule. The nucleic acid sequence coding for the HLA molecule may be present on the same expression vector as the nucleic acid coding for the tumor-associated antigen or the part thereof, or both nucleic acids may be present on different expression vectors. In the latter case, the two expression vectors may be cotransfected into a cell. If a host cell expresses neither the tumor-associated antigen or the part thereof nor the HLA molecule, both nucleic acids coding therefor are transfected into the cell either on the same expression vector or on different expression vectors. If the cell already expresses the HLA molecule, only the nucleic acid sequence coding for the tumor-associated antigen or the part thereof can be transfected into the cell.

The invention also comprises kits for amplification of a nucleic acid coding for a tumor-associated antigen. Such kits comprise, for example, a pair of amplification primers which hybridize to the nucleic acid coding for the tumor-associated antigen. The primers preferably comprise a sequence of 6-50, in particular 10-30, 15-30 and 20-30 contiguous nucleotides of the nucleic acid and are nonoverlapping, in order to avoid the formation of primer dimers. One of the primers will hybridize to one strand of the nucleic acid coding for the tumor-associated antigen, and the other primer will hybridize to the complementary strand in an arrangement which allows amplification of the nucleic acid coding for the tumor-associated antigen.

"Antisense" molecules or "antisense" nucleic acids may be used for regulating, in particular reducing, expression of a nucleic acid. The term "antisense molecule" or "antisense nucleic acid" refers according to the invention to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the invention, the "antisense molecule" also comprises a construct which contains a nucleic acid or a part thereof in reverse orientation with respect to its natural promoter. An antisense transcript of a nucleic acid or of a part thereof may form a duplex with the naturally occurring mRNA specifying the enzyme and thus prevent accumulation of or translation of the mRNA into the active enzyme. Another possibility is the use of ribozymes for inactivating a nucleic acid. Antisense oligonucleotides preferred according to the invention have a sequence of 6-50, in particular 10-30, 15-30 and 20-30, contiguous nucleotides of the target nucleic acid and preferably are fully complementary to the target nucleic acid or to a part thereof.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3'untranslated region or mRNA splicing site.

In one embodiment, an oligonucleotide of the invention consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly.

In preferred embodiments, an oligonucleotide of the invention is a "modified" oligonucleotide. Here, the oligonucleotide may be modified in very different ways, without impairing its ability to bind its target, in order to increase, for example, its stability or therapeutic efficacy. According to the invention, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having a covalently modified base and/or sugar. "Modified oligonucleotides" comprise, for example, oligonucleotides with sugar residues which are covalently bound to low molecular weight organic groups other than a hydroxyl group at the 3' position and a phosphate group at the 5' position. Modified oligonucleotides may comprise, for example, a 2'-O-alkylated ribose residue or another sugar instead of ribose, such as arabinose.

Preferably, the proteins and polypeptides described according to the invention have been isolated. The terms "isolated protein" or "isolated polypeptide" mean that the protein or polypeptide has been separated from its natural environment. An isolated protein or polypeptide may be in an essentially purified state. The term "essentially purified" means that the protein or polypeptide is essentially free of other substances with which it is associated in nature or in vivo.

Such proteins and polypeptides may be used, for example, in producing antibodies and in an immunological or diagnostic assay or as therapeutics. Proteins and polypeptides described according to the invention may be isolated from biological samples such as tissue or cell homogenates and may also be expressed recombinantly in a multiplicity of pro- or eukaryotic expression systems.

For the purposes of the present invention, "derivatives" of a protein or polypeptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid deletion variants are characterized by the removal of one or more amino acids from the sequence. Amino acid substitution variants are characterized by at least one residue in the sequence being removed and another residue being inserted in its place. Preference is given to the modifications being in positions in the amino acid sequence which are not conserved between homologous proteins or polypeptides. Preference is given to replacing amino acids with other ones having similar properties such as hydrophobicity, hydrophilicity, electronegativity, volume of the side chain and the like (conservative substitution). Conservative substitutions, for example, relate to the exchange of one amino acid with another amino acid listed below in the same group as the amino acid to be substituted:

1. small aliphatic, nonpolar or slightly polar residues: Ala, Ser, Thr (Pro, Gly)
2. negatively charged residues and their amides: Asn, Asp, Glu, Gln
3. positively charged residues: His, Arg, Lys
4. large aliphatic, nonpolar residues: Met, Leu, Ile, Val (Cys)
5. large aromatic residues: Phe, Tyr, Trp.

Owing to their particular part in protein architecture, three residues are shown in brackets. Gly is the only residue without a side chain and thus imparts flexibility to the chain. Pro has an unusual geometry which greatly restricts the chain. Cys can form a disulfide bridge.

The amino acid variants described above may be readily prepared with the aid of known peptide synthesis techniques such as, for example, by solid phase synthesis (Merrifield, 1964) and similar methods or by recombinant DNA manipulation. Techniques for introducing substitution mutations at predetermined sites into DNA which has a known or partially known sequence are well known and comprise M13 mutagenesis, for example. The manipulation of DNA sequences for preparing proteins having substitutions, insertions or deletions, is described in detail in Sambrook et al. (1989), for example.

According to the invention, "derivatives" of proteins or polypeptides also comprise single or multiple substitutions, deletions and/or additions of any molecules associated with the enzyme, such as carbohydrates, lipids and/or proteins or polypeptides. The term "derivative" also extends to all functional chemical equivalents of said proteins or polypeptides.

According to the invention, a part or fragment of a tumor-associated antigen has a functional property of the polypeptide from which it has been derived. Such functional properties comprise the interaction with antibodies, the interaction with other polypeptides or proteins, the selective binding of nucleic acids and an enzymatic activity. A particular property is the ability to form a complex with HLA and, where appropriate, generate an immune response. This immune response may be based on stimulating cytotoxic or T helper cells. A part or fragment of a tumor-associated antigen of the invention preferably comprises a sequence of at least 6, in particular at least 8, at least 10, at least 12, at least 15, at least 20, at least 30 or at least 50, consecutive amino acids of the tumor-associated antigen. A part or fragment of a tumor-associated antigen is preferably a part of the tumor-associated antigen which corresponds to the non-membrane portion, in particular the extracellular portion of the antigen or is comprised thereof.

A part or a fragment of a nucleic acid coding for a tumor-associated antigen relates according to the invention to the part of the nucleic acid, which codes at least for the tumor-associated antigen and/or for a part or a fragment of said tumor-associated antigen, as defined above. Preferably, a part or fragment of a nucleic acid coding for a tumor-associated antigen is that part which corresponds to the open reading frame, in particular as indicated in the sequence listing.

The isolation and identification of genes coding for tumor-associated antigens also make possible the diagnosis of a disease characterized by expression of one or more tumor-associated antigens. These methods comprise determining one or more nucleic acids which code for a tumor-associated antigen and/or determining the encoded tumor-associated antigens and/or peptides derived therefrom. The nucleic acids may be determined in the conventional manner, including by polymerase chain reaction or hybridization with a labeled probe. Tumor-associated antigens or peptides derived therefrom may be determined by screening patient antisera with respect to recognizing the antigen and/or the peptides. They may also be determined by screening T cells of the patient for specificities for the corresponding tumor-associated antigen.

The present invention also enables proteins binding to tumor-associated antigens described herein to be isolated, including antibodies and cellular binding partners of said tumor-associated antigens.

According to the invention, particular embodiments ought to involve providing "dominant negative" polypeptides derived from tumor-associated antigens. A dominant negative polypeptide is an inactive protein variant which, by way of interacting with the cellular machinery, displaces an active protein from its interaction with the cellular machinery or which competes with the active protein, thereby reducing the effect of said active protein. For example, a dominant negative receptor which binds to a ligand but does not generate any signal as response to binding to the ligand can reduce the biological effect of said ligand. Similarly, a dominant negative catalytically inactive kinase which usually interacts with target proteins but does not phosphorylate said target proteins may reduce phosphorylation of said target proteins as response to a cellular signal. Similarly, a dominant negative transcription factor which binds to a promoter site in the control region of a gene but does not increase transcription of said gene may reduce the effect of a normal transcription factor by occupying promoter binding sites, without increasing transcription.

The result of expression of a dominant negative polypeptide in a cell is a reduction in the function of active proteins. The skilled worker may prepare dominant negative variants of a protein, for example, by conventional mutagenesis methods and by evaluating the dominant negative effect of the variant polypeptide.

The invention also comprises substances such as polypeptides which bind to tumor-associated antigens. Such binding substances may be used, for example, in screening assays for detecting tumor-associated antigens and complexes of tumor-associated antigens with their binding partners and in a purification of said tumor-associated antigens and of complexes thereof with their binding partners. Such substances may also be used for inhibiting the activity of tumor-associated antigens, for example by binding to such antigens.

The invention therefore comprises binding substances such as, for example, antibodies or antibody fragments, which are capable of selectively binding to tumor-associated antigens. Antibodies comprise polyclonal and monoclonal antibodies which are produced in the conventional manner.

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology,* 7th Edition, Blackwell Scientific Publications, Oxford). The pFc' and Fc regions are, for example, effectors of the complement cascade but are not involved in antigen binding. An antibody from which the pFc' region has been enzymatically removed or which has been produced without the pFc' region, referred to as $F(ab')_2$ fragment, carries both antigen binding sites of a complete antibody. Similarly, an antibody from which the Fc region has been enzymatically removed or which has been produced without said Fc region, referred to Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

WO 92/04381 for example, describes production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

The invention also provides $F(ab')_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric $F(ab')_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The invention also comprises "single-chain" antibodies.

Preferably, an antibody used according to the invention is directed against one of the sequences according to SEQ ID NOs: 2, 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 130, 134, 138, 142, 146, 150, 154, 158, 162, 166, 170, 174, 176, 180, 184, 188, 192, 196, 200, 204, 208, 212, 216, 220, 224, 228, 232, 236, 240, 244, 248, 252, 256, 260, 264, 268, 270, 272, 274, 276, 278, 280 to 308, 310 of the sequence listing, a part or derivative thereof, in particular a sequence according to SEQ ID Nos: 281 to 308 of the sequence listing and/or may be obtained by immunization using these peptides.

The invention also comprises polypeptides which bind specifically to tumor-associated antigens. Polypeptide binding substances of this kind may be provided, for example, by degenerate peptide libraries which may be prepared simply in solution in an immobilized form or as phage-display libraries. It is likewise possible to prepare combinatorial libraries of peptides with one or more amino acids. Libraries of peptoids and nonpeptidic synthetic residues may also be prepared.

Phage display may be particularly effective in identifying binding peptides of the invention. In this connection, for example, a phage library is prepared (using, for example, the M13, fd or lambda phages) which presents inserts of from 4 to about 80 amino acid residues in length. Phages are then selected which carry inserts which bind to the tumor-associated antigen. This process may be repeated via two or more cycles of a reselection of phages binding to the tumor-associated antigen. Repeated rounds result in a concentration of phages carrying particular sequences. An analysis of DNA sequences may be carried out in order to identify the sequences of the expressed polypeptides. The smallest linear portion of the sequence binding to the tumor-associated antigen may be determined. The "two-hybrid system" of yeast may also be used for identifying polypeptides which bind to a tumor-associated antigen. Tumor-associated antigens described according to the invention or fragments thereof may be used for screening peptide libraries, including phage-display libraries, in order to identify and select peptide binding partners of the tumor-associated antigens. Such molecules may be used, for example, for screening assays, purification protocols, for interference with the function of the tumor-associated antigen and for other purposes known to the skilled worker.

The antibodies described above and other binding molecules may be used, for example, for identifying tissue which expresses a tumor-associated antigen. Antibodies may also be coupled to specific diagnostic substances for displaying cells and tissues expressing tumor-associated antigens. They may also be coupled to therapeutically useful substances. Diagnostic substances comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium. According to the invention, the term "therapeutically useful substance" means any therapeutic molecule which, as desired, is selectively guided to a cell which expresses one or more tumor-associated antigens, including anticancer agents, radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-$\alpha$, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

According to the invention, the term "disease" refers to any pathological state in which tumor-associated antigens are expressed or abnormally expressed. "Abnormal expression" means according to the invention that expression is altered, preferably increased, compared to the state in a healthy individual. An increase in expression refers to an increase by at least 10%, in particular at least 20%, at least 50% or at least 100%. In one embodiment, the tumor-associated antigen is expressed only in tissue of a diseased individual, while expression in a healthy individual is repressed. One example of such a disease is cancer, in particular seminomas, melanomas, teratomas, gliomas, colon cancer, rectal cancer, kidney cancer, breast cancer, prostate cancer, cancer of the uterus, ovarian cancer, endometrial cancer, cancer of the esophagus, blood cancer, liver cancer, pancreatic cancer, skin cancer, brain cancer and lung cancer, lymphomas, and neuroblastomas. Examples for this are lung tumor, breast tumor, prostate tumor, colon tumor, renal cell carcinoma, cervical carcinoma, colon carcinoma and mamma carcinoma or metastases of the above cancer types or tumors.

According to the invention, a biological sample may be a tissue sample and/or a cellular sample and may be obtained in the conventional manner such as by tissue biopsy, including punch biopsy, and by taking blood, bronchial aspirate, urine, feces or other body fluids, for use in the various methods described herein.

According to the invention, the term "immunoreactive cell" means a cell which can mature into an immune cell (such as B cell, T helper cell, or cytolytic T cell) with suitable stimulation. Immunoreactive cells comprise $CD34^+$ hematopoietic stem cells, immature and mature T cells and immature and mature B cells. If production of cytolytic or T helper cells recognizing a tumor-associated antigen is desired, the immunoreactive cell is contacted with a cell expressing a tumor-associated antigen under conditions which favor production, differentiation and/or selection of cytolytic T cells and of T helper cells. The differentiation of T cell precursors into a cytolytic T cell, when exposed to an antigen, is similar to clonal selection of the immune system.

Some therapeutic methods are based on a reaction of the immune system of a patient, which results in a lysis of antigen-presenting cells such as cancer cells which present one or more tumor-associated antigens. In this connection, for example autologous cytotoxic T lymphocytes specific for a complex of a tumor-associated antigen and an MHC molecule are administered to a patient having a cellular abnormality. The production of such cytotoxic T lymphocytes in vitro is known. An example of a method of differentiating T cells can be found in WO-A-96/33265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting antigen-specific cytotoxic T lymphocytes, fluorogenic tetramers of MHC class I molecule/peptide complexes are used for detecting specific clones of cytotoxic T lymphocytes (Altman et al., *Science* 274:94-96, 1996; Dunbar et al., *Curr. Biol.* 8:413-416, 1998). Soluble MHC class I molecules are folded in vitro in the presence of $\beta_2$ microglobulin and a peptide antigen binding to said class I molecule. The MHC/peptide complexes are purified and then labeled with biotin. Tetramers are formed by mixing the biotinylated peptide-MHC complexes with labeled avidin (e.g. phycoerythrin) in a molar ratio of 4:1. Tetramers are then contacted with cytotoxic T lymphocytes such as peripheral blood or lymph nodes. The tetramers bind to cytotoxic T lymphocytes which recognize the peptide antigen/MHC class I complex. Cells which are bound to the tetramers may be sorted by fluorescence-controlled cell sorting to isolate reactive cytotoxic T lymphocytes. The isolated cytotoxic T lymphocytes may then be propagated in vitro.

In a therapeutic method referred to as adoptive transfer (Greenberg, *J. Immunol.* 136(5):1917, 1986; Riddel et al., *Science* 257:238, 1992; Lynch et al., *Eur. J. Immunol.* 21:1403-1410, 1991; Kast et al., *Cell* 59:603-614, 1989), cells presenting the desired complex (e.g. dendritic cells) are combined with cytotoxic T lymphocytes of the patient to be treated, resulting in a propagation of specific cytotoxic T lymphocytes. The propagated cytotoxic T lymphocytes are then administered to a patient having a cellular anomaly characterized by particular abnormal cells presenting the specific complex. The cytotoxic T lymphocytes then lyse the abnormal cells, thereby achieving a desired therapeutic effect.

Often, of the T cell repertoire of a patient, only T cells with low affinity for a specific complex of this kind can be propagated, since those with high affinity have been extinguished due to development of tolerance. An alternative here may be a transfer of the T cell receptor itself. For this too, cells presenting the desired complex (e.g. dendritic cells) are combined with cytotoxic T lymphocytes of healthy individuals. This results in propagation of specific cytotoxic T lymphocytes with high affinity if the donor had no previous contact with the specific complex. The high affinity T cell receptor of these propagated specific T lymphocytes is cloned and can be transduced via gene transfer, for example using retroviral vectors, into T cells of other patients, as desired. Adoptive transfer is then carried out using these genetically altered T lymphocytes (Stanislawski et al., Nat. Immunol. 2:962-70, 2001; Kessels et al., Nat. Immunol. 2:957-61, 2001).

The therapeutic aspects above start out from the fact that at least some of the abnormal cells of the patient present a complex of a tumor-associated antigen and an HLA molecule. Such cells may be identified in a manner known per se. As soon as cells presenting the complex have been identified, they may be combined with a sample from the patient, which contains cytotoxic T lymphocytes. If the cytotoxic T lymphocytes lyse the cells presenting the complex, it can be assumed that a tumor-associated antigen is presented.

Adoptive transfer is not the only form of therapy which can be applied according to the invention. Cytotoxic T lymphocytes may also be generated in vivo in a manner known per se. One method uses nonproliferative cells expressing the complex. The cells used here will be those which usually express the complex, such as irradiated tumor cells or cells transfected with one or both genes necessary for presentation of the complex (i.e. the antigenic peptide and the presenting HLA molecule). Various cell types may be used. Furthermore, it is possible to use vectors which carry one or both of the genes of interest. Particular preference is given to viral or bacterial vectors. For example, nucleic acids coding for a tumor-associated antigen or for a part thereof may be functionally linked to promoter and enhancer sequences which control expression of said tumor-associated antigen or a fragment thereof in particular tissues or cell types. The nucleic acid may be incorporated into an expression vector. Expression vectors may be nonmodified extrachromosomal nucleic acids, plasmids or viral genomes into which exogenous nucleic acids may be inserted. Nucleic acids coding for a tumor-associated antigen may also be inserted into a retroviral genome, thereby enabling the nucleic acid to be integrated into the genome of the target tissue or target cell. In these systems, a microorganism such as vaccinia virus, pox virus, Herpes simplex virus, retrovirus or adenovirus carries the gene of interest and de facto "infects" host cells. Another preferred form is the introduction of the tumor-associated antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining the tumor-associated antigen or a fragment thereof with an adjuvant in order to make incorporation into antigen-presenting cells in vivo possible. The tumor-associated antigen or a fragment thereof may be represented as protein, as DNA (e.g. within a vector) or as RNA. The tumor-associated antigen is processed to produce a peptide partner for the HLA molecule, while a fragment thereof may be presented without the need for further processing. The latter is the case in particular, if these can bind to HLA molecules. Preference is given to administration forms in which the complete antigen is processed in vivo by a dendritic cell, since this may also produce T helper cell responses which are needed for an effective immune response (Ossendorp et al., *Immunol Lett.* 74:75-9, 2000; Ossendorp et al., *J. Exp. Med.* 187:693-702, 1998). In general, it is possible to administer an effective amount of the tumor-associated antigen to a patient by intradermal injection, for example. However, injection may also be carried out intranodally into a lymph node (Maloy et al., *Proc Natl Acad Sci USA* 98:3299-303, 2001). It may also be carried out in combination with reagents which facilitate uptake into dendritic cells. Preferred tumor-associated antigens comprise those which react with allogenic cancer antisera or with T cells of many cancer patients. Of particular interest, however, are those against which no spontaneous immune responses preexist. Evidently, it is possible to induce against these immune responses which can lyse tumors (Keogh et al., *J. Immunol.* 167:787-96, 2001; Appella et al., *Biomed Pept Proteins Nucleic Acids* 1:177-84, 1995; Wentworth et al., *Mol. Immunol.* 32:603-12, 1995).

The pharmaceutical compositions described according to the invention may also be used as vaccines for immunization. According to the invention, the terms "immunization" or "vaccination" mean an increase in or activation of an immune response to an antigen. It is possible to use animal models for testing an immunizing effect on cancer by using a tumor-associated antigen or a nucleic acid coding therefor. For example, human cancer cells may be introduced into a mouse to generate a tumor, and one or more nucleic acids coding for tumor-associated antigens may be administered. The effect on the cancer cells (for example reduction in tumor size) may be measured as a measure for the effectiveness of an immunization by the nucleic acid.

As part of the composition for an immunization, one or more tumor-associated antigens or stimulating fragments thereof are administered together with one or more adjuvants for inducing an immune response or for increasing an immune response. An adjuvant is a substance which is incorporated into the antigen or administered together with the latter and which enhances the immune response. Adjuvants may enhance the immune response by providing an antigen reservoir (extracellularly or in macrophages), activating macrophages and stimulating particular lymphocytes. Adjuvants are known and comprise in a nonlimiting way monophosphoryl lipid A (MPL, SmithKline Beecham), saponin such as QS21 (SmithKline Beecham), DQS21 (SmithKline Beecham; WO 96/33739), QS7, QS17, QS18 and QS-L1 (So et al., Mol. Cells. 7:178-186, 1997), incomplete Freund's adjuvant, complete Freund's adjuvant, vitamin E, montanide, alum, CpG oligonucleotides (cf. Krieg et al., Nature 374:546-9, 1995) and various water-in-oil emulsions prepared from biologically degradable oils such as squalene and/or tocopherol. Preferably, the peptides are administered in a mixture with DQS21/MPL. The ratio of DQS21 to MPL is typically about 1:10 to 10:1, preferably about 1:5 to 5:1 and in particular about 1:1. For administration to humans, a vaccine formulation typically contains DQS21 and MPL in a range from about 1 μg to about 100 μg.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. *Science* 268:1432-1434, 1995), GM-CSF and IL-18.

There are a number of compounds which enhance an immune response and which therefore may be used in a vaccination. Said compounds comprise costimulating molecules provided in the form of proteins or nucleic acids. Examples of such costimulating molecules are B7-1 and B7-2 (CD80 and CD86, respectively) which are expressed on dendritic cells (DC) and interact with the CD28 molecule expressed on the T cells. This interaction provides a costimulation (signal 2) for an antigen/MHC/TCR-stimulated (signal 1) T cell, thereby enhancing propagation of said T cell and the effector function. B7 also interacts with CTLA4 (CD152) on T cells, and studies involving CTLA4 and B7 ligands demonstrate that B7-CTLA4 interaction can enhance antitumor immunity and CTL propagation (Zheng, P. et al., *Proc. Natl. Acad. Sci. USA* 95(11):6284-6289 (1998)).

B7 is typically not expressed on tumor cells so that these are no effective antigen-presenting cells (APCs) for T cells. Induction of B7 expression would enable tumor cells to stimulate more effectively propagation of cytotoxic T lymphocytes and an effector function. Costimulation by a combination of B7/IL-6/IL-12 revealed induction of IFN-gamma and Th1-cytokine profile in a T cell population, resulting in further enhanced T cell activity (Gajewski et al., *J. Immunol.* 154:5637-5648 (1995)).

A complete activation of cytotoxic T lymphocytes and a complete effector function require an involvement of T helper cells via interaction between the CD40 ligand on said T helper cells and the CD40 molecule expressed by dendritic cells (Ridge et al., *Nature* 393:474 (1998), Bennett et al., *Nature* 393:478 (1998), Schönberger et al., *Nature* 393:480 (1998)). The mechanism of this costimulating signal probably relates to the increase in B7 production and associated IL-6/IL-12 production by said dendritic cells (antigen-presenting cells). CD40-CD40L interaction thus complements the interaction of signal 1 (antigen/MHC-TCR) and signal 2 (B7-CD28).

The use of anti-CD40 antibodies for stimulating dendritic cells would be expected to directly enhance a response to tumor antigens which are usually outside the range of an inflammatory response or which are presented by nonprofessional antigen-presenting cells (tumor cells). In these situations, T helper and B7-costimulating signals are not provided. This mechanism could be used in connection with therapies based on antigen-pulsed dendritic cells or in situations in which T helper epitopes have not been defined in known TRA precursors.

The invention also provides for administration of nucleic acids, polypeptides or peptides. Polypeptides and peptides may be administered in a manner known per se. In one embodiment, nucleic acids are administered by ex vivo methods, i.e. by removing cells from a patient, genetic modification of said cells in order to incorporate a tumor-associated antigen and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker. The invention also provides for administering nucleic acids in vivo by using vectors such as viruses and target-controlled liposomes.

In a preferred embodiment, a viral vector for administering a nucleic acid coding for a tumor-associated antigen is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Various methods may be used in order to introduce according to the invention nucleic acids into cells in vitro or in vivo. Methods of this kind comprise transfection of nucleic acid $CaPO_4$ precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor-associated antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutic compositions of the invention may be administered in pharmaceutically compatible preparations. Such preparations may usually contain pharmaceutically compatible concentrations of salts, buffer substances, preservatives, carriers, supplementing immunity-enhancing substances such as adjuvants (e.g. CpG oligonucleotides) and cytokines and, where appropriate, other therapeutically active compounds.

The therapeutically active compounds of the invention may be administered via any conventional route, including by injection or infusion. The administration may be carried out, for example, orally, intravenously, intraperitonealy, intramuscularly, subcutaneously or transdermally. Preferably, antibodies are therapeutically administered by way of a lung aerosol. Antisense nucleic acids are preferably administered by slow intravenous administration.

The compositions of the invention are administered in effective amounts. An "effective amount" refers to the amount which achieves a desired reaction or a desired effect alone or together with further doses. In the case of treatment of a particular disease or of a particular condition characterized by expression of one or more tumor-associated antigens, the desired reaction relates to inhibition of the course of the disease. This comprises slowing down the progress of the disease and, in particular, interrupting the progress of the disease. The desired reaction in a treatment of a disease or of a condition may also be delay of the onset or a prevention of the onset of said disease or said condition.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors.

The pharmaceutical compositions of the invention are preferably sterile and contain an effective amount of the therapeutically active substance to generate the desired reaction or the desired effect.

The doses administered of the compositions of the invention may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

Generally, doses of the tumor-associated antigen of from 1 ng to 1 mg, preferably from 10 ng to 100 μg, are formulated and administered for a treatment or for generating or increasing an immune response. If the administration of nucleic acids (DNA and RNA) coding for tumor-associated antigens is desired, doses of from 1 ng to 0.1 mg are formulated and administered.

The pharmaceutical compositions of the invention are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. According to the invention, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixir or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: qPCR analysis of SEQ ID NO: 1 in melanomas

Quantitative expression analysis of SEQ ID NO: 1 in healthy skin tissue, in testis and in melanomas. Logarithmic representation of relative expression (-fold activation).

Figure 2:
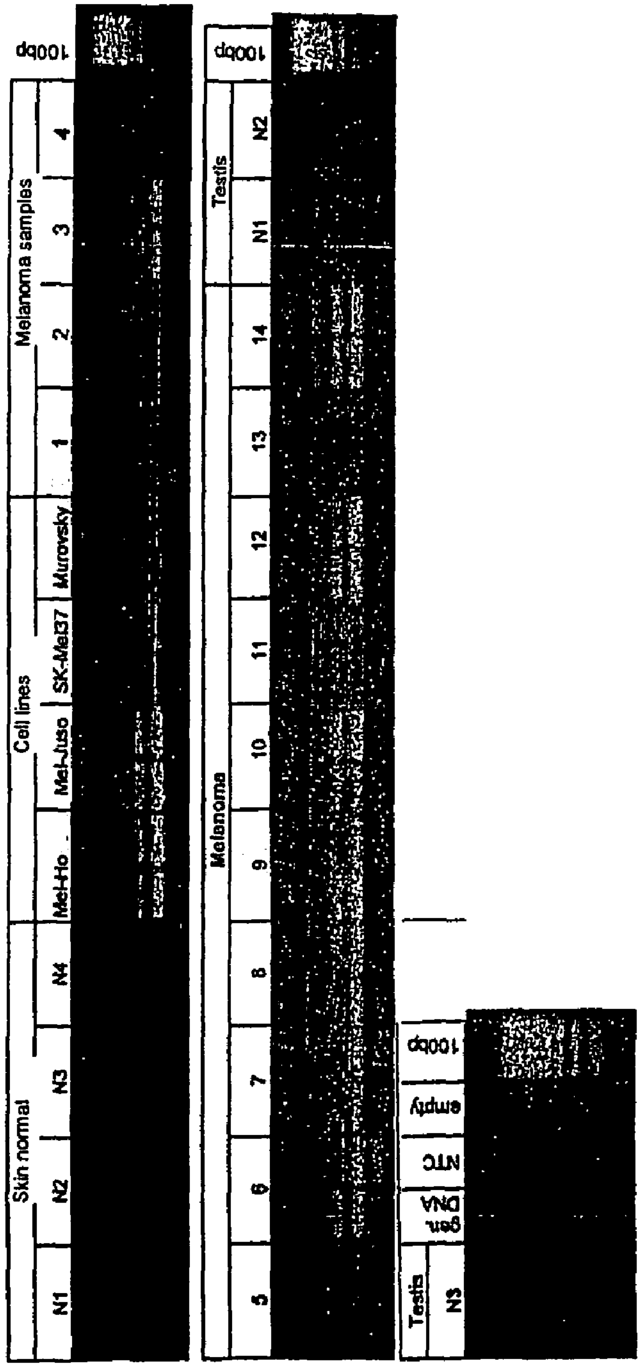

FIG. 2: Conventional RT-PCR analysis of SEQ ID NO: 1 in melanomas

RT-PCR expression analysis of SEQ ID NO: 1 in melanomas (n=14) and melanoma cell lines (n=4) in comparison with healthy skin (n=4) and with testis (n=3).

Figure 3:
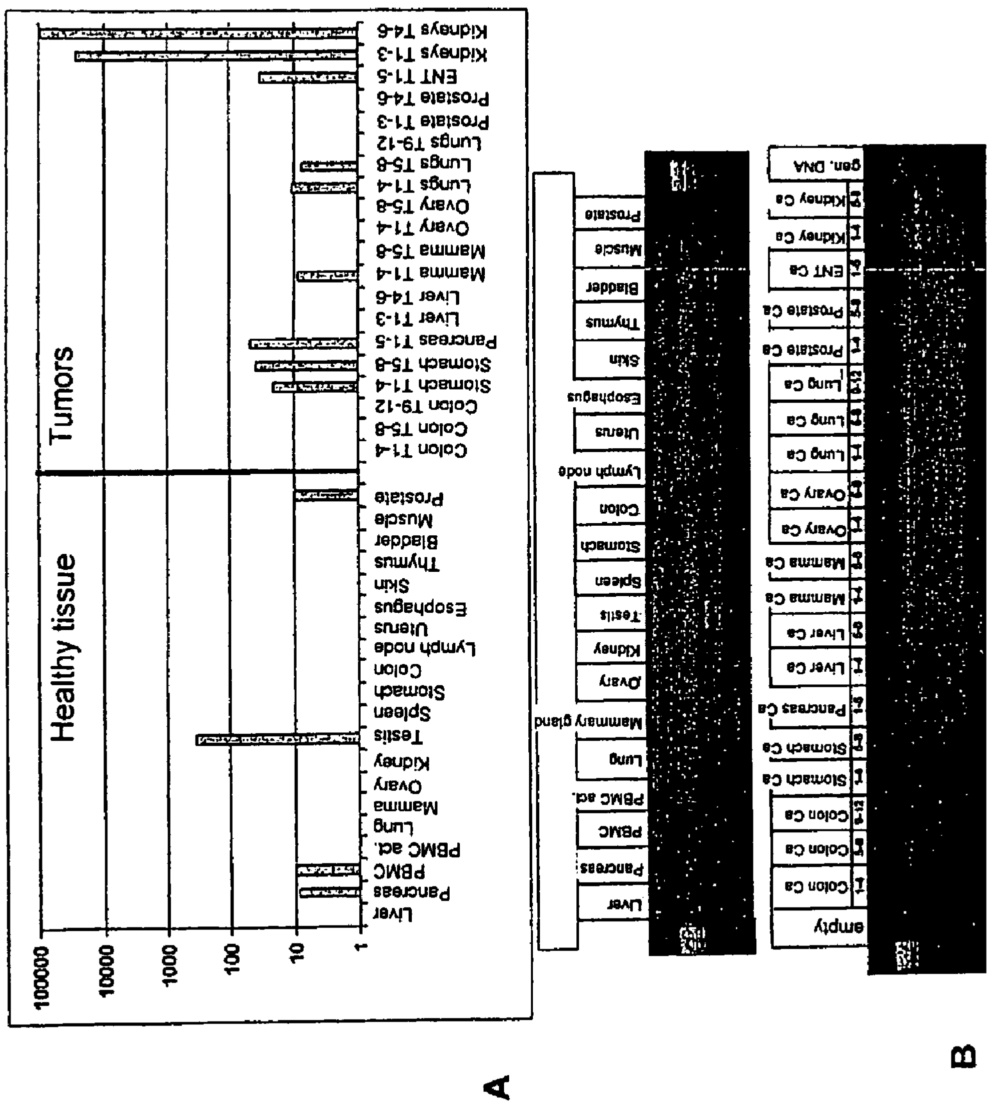

FIG. 3: qPCR analysis of SEQ ID NO: 5 in healthy tissue and in tumor samples Quantitative expression analysis of SEQ ID NO: 5 in normal tissues (left-hand side) and in various tumors (pools consisting of in each case 3-5 individual samples, right-hand side). A Logarithmic representation of relative expression (-fold activation). B Image after gel-electrophoretic fractionation of the amplified fragments.

Figure 4:
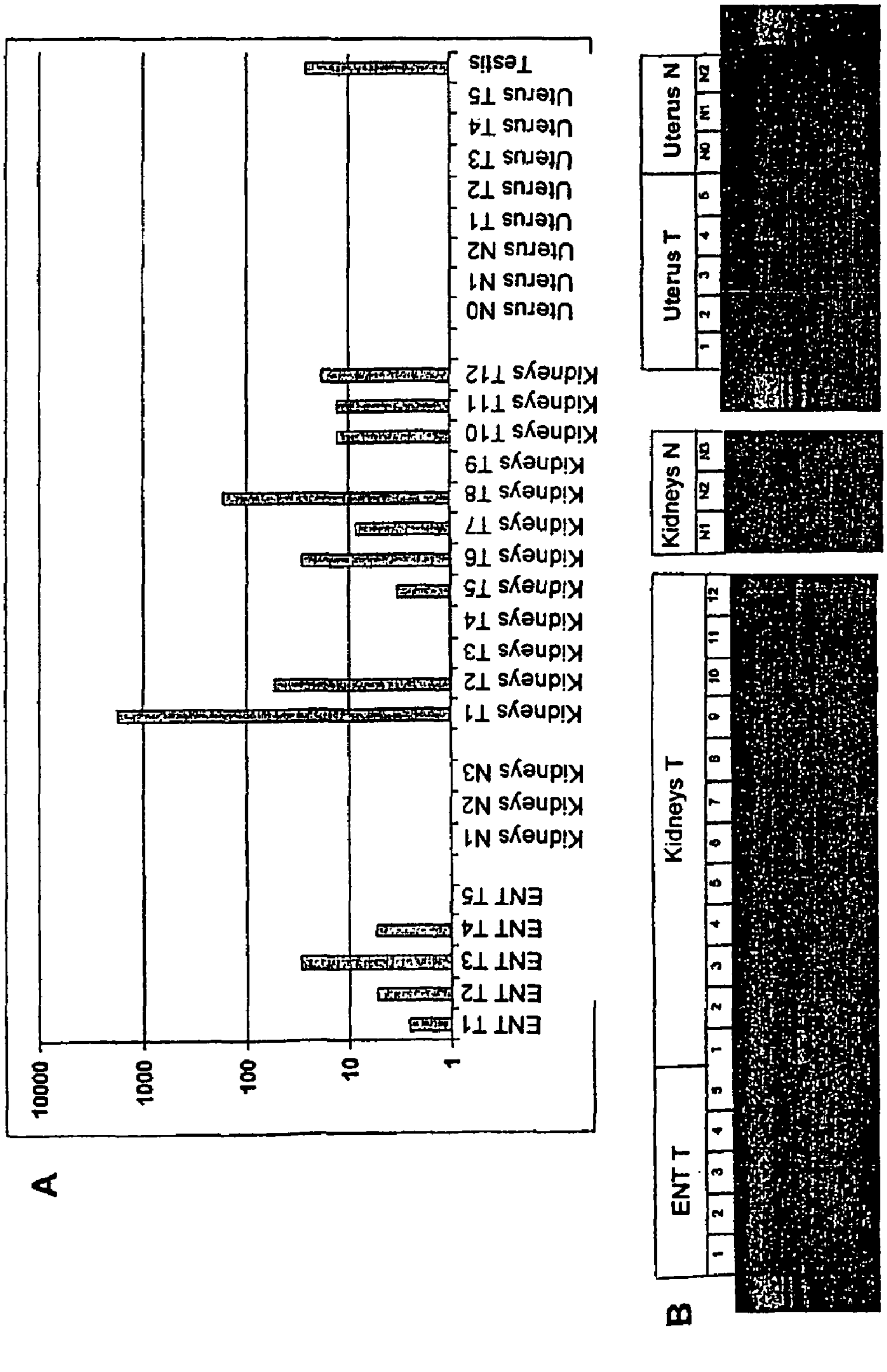

FIG. 4: Detailed analysis of SEQ ID NO: 5-specific expression

A Quantitative expression analysis of SEQ ID NO: 5 in various ENT, renal and uterine tumors in comparison with expression in the corresponding normal tissues. Logarithmic representation. B Image after gel-electrophoretic fractionation of the amplified fragments.

Figure 5:
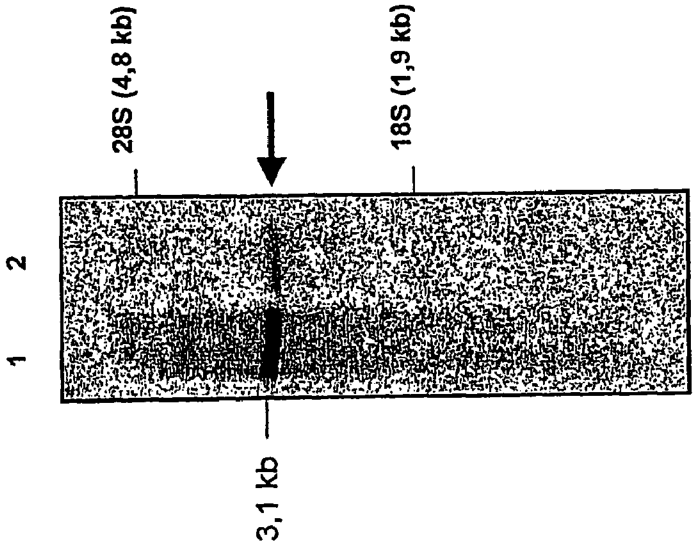

FIG. 5: Northern blot analysis with a SEQ ID NO: 5-specific sequence

Hybridization of a DIG-labeled DNA probe, prepared by PCR amplification using the primers according to SEQ ID NO: 7 and 8, with testis-specific RNA. Lane 1: 2 μg of testis-specific RNA; lane 2: 1 μg of testis-specific RNA.

Figure 6:
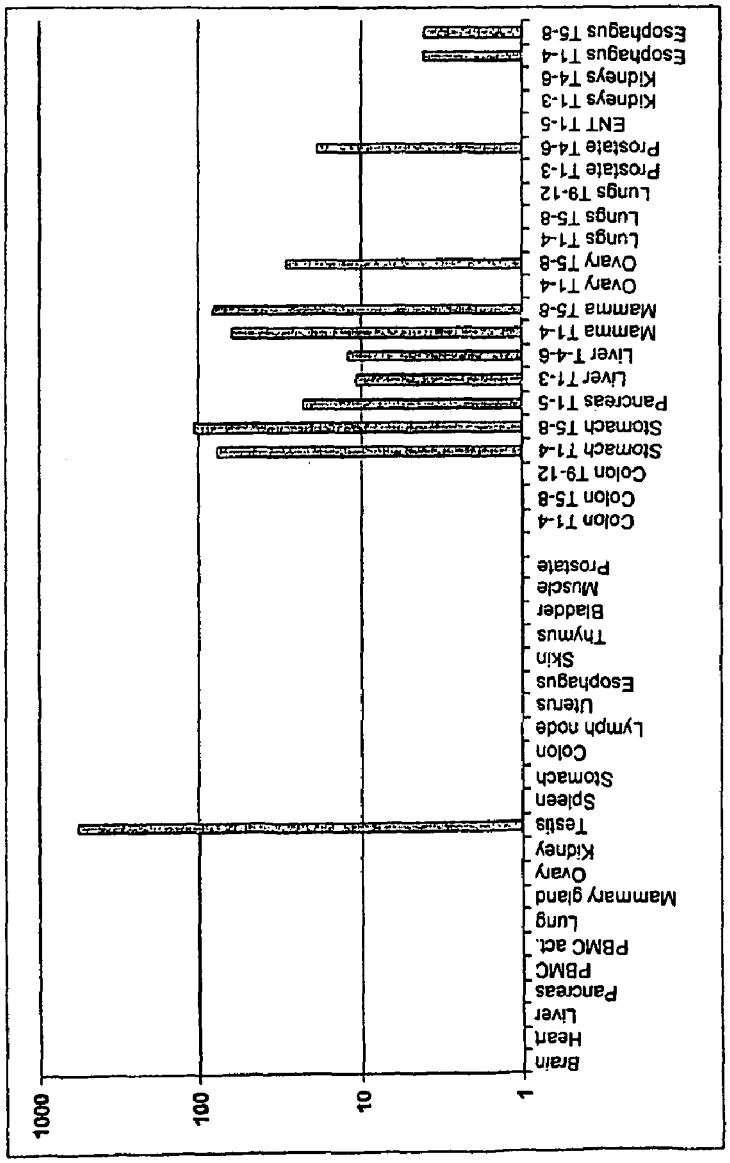

FIG. 6: qPCR analysis of LOC203413

Quantitative expression analysis of LOC203413 in healthy tissues (left) and in tumor samples (pools consisting of in each case 3-5 individual samples, right). A Logarithmic representation of expression (-fold activation). B Result after gel-electrophoretic fractionation.

Figure 7:
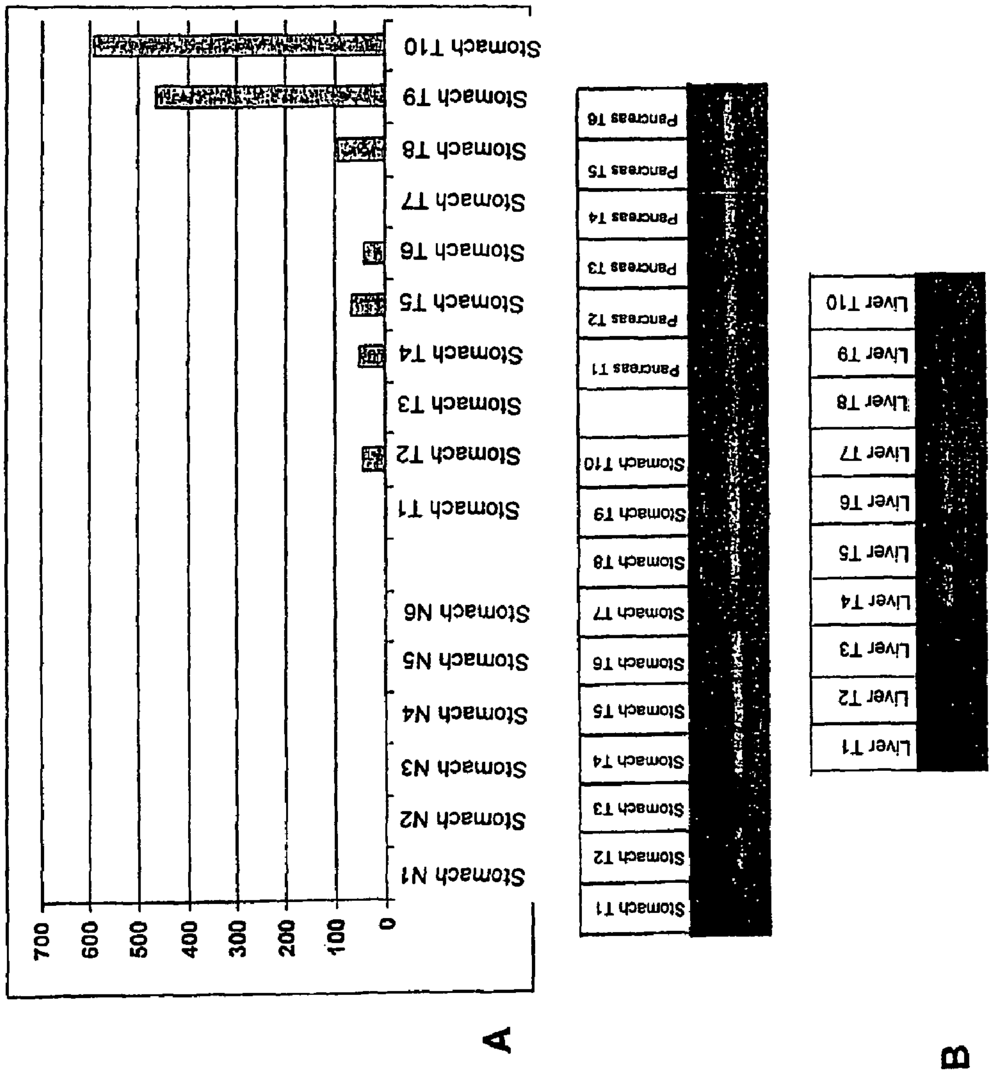

FIG. 7: Detailed analysis of LOC203413-specific expression in gastric carcinomas Quantitative expression analysis of LOC203413 in various gastric tumor samples (n=10) in comparison with expression in healthy stomach (n=6). A Linear representation of relative expression. B Image after gel-electrophoretic fractionation of the amplicons.

Figure 8:
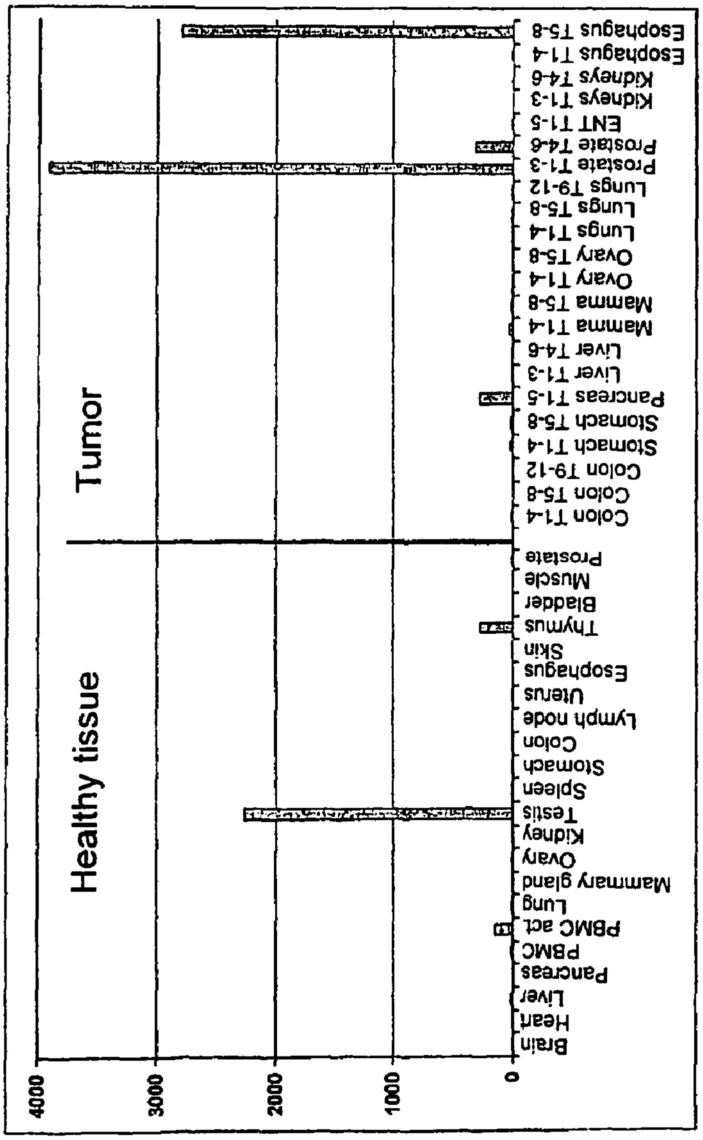

FIG. 8: qPCR analysis of LOC90625-specific expression

Quantitative expression analysis of LOC90625 in normal tissues (left) and tumor tissues (pools consisting of in each case 3-5 individual samples; right). Linear representation of relative expression (-fold activation).

Figure 9:
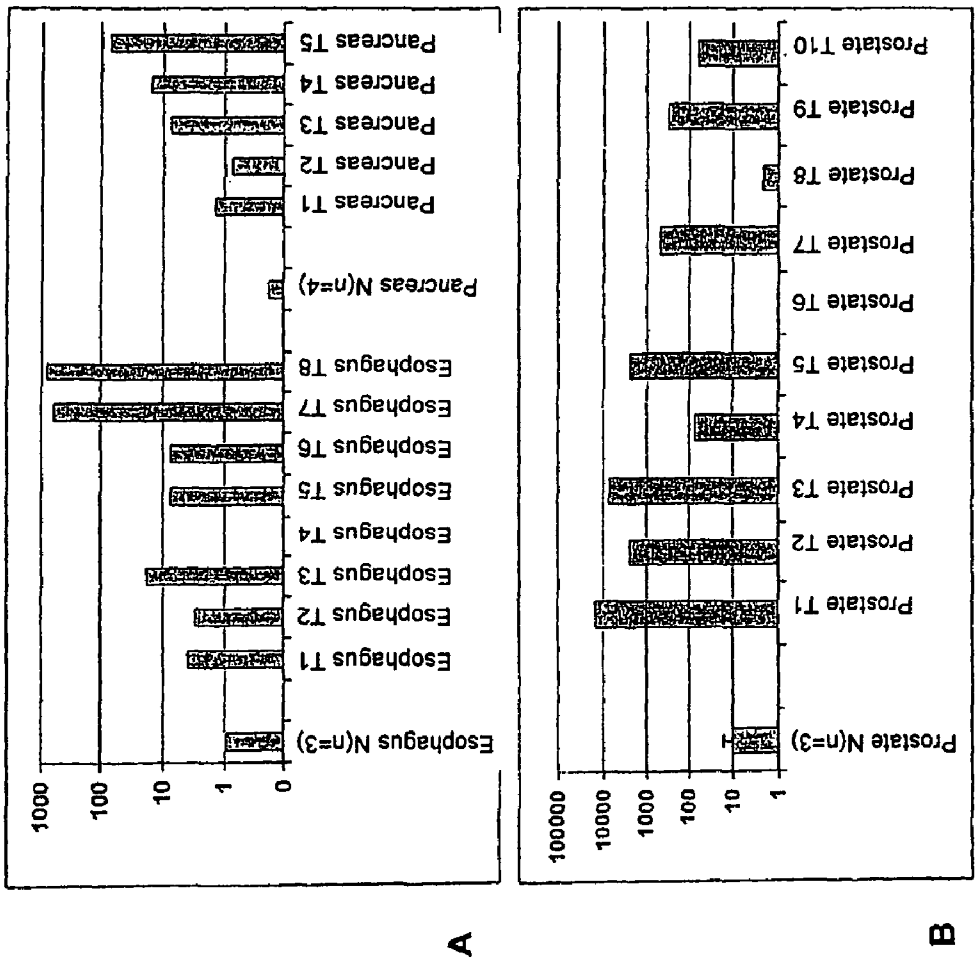

FIG. 9: Detailed analysis of LOC90652-specific expression in various types of tumors Quantitative expression analysis of LOC90625 in samples of carcinomas of the esophagus (n=8), pancreas (n=5) and prostate (n=10) in comparison with the respective healthy tissue (n=¾); logarithmic representation of relative expression (-fold activation).

Figure 10:
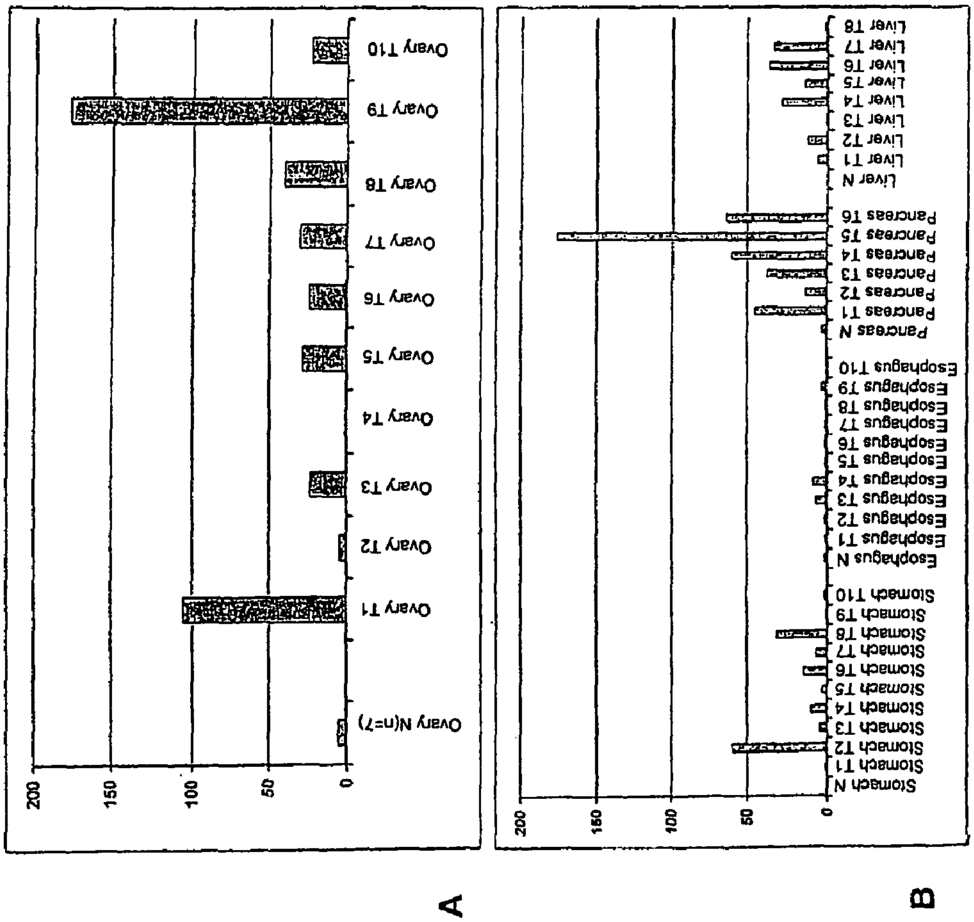

FIG. 10: qRT-PCR analysis of FAM26A in various types of tumors

Quantitative RT-PCR expression analysis of FAM26A in carcinomas of the A ovary, B stomach, esophagus, pancreas and liver, in comparison with the respective healthy tissue. Linear representation of relative expression (-fold activation).

Figure 11:
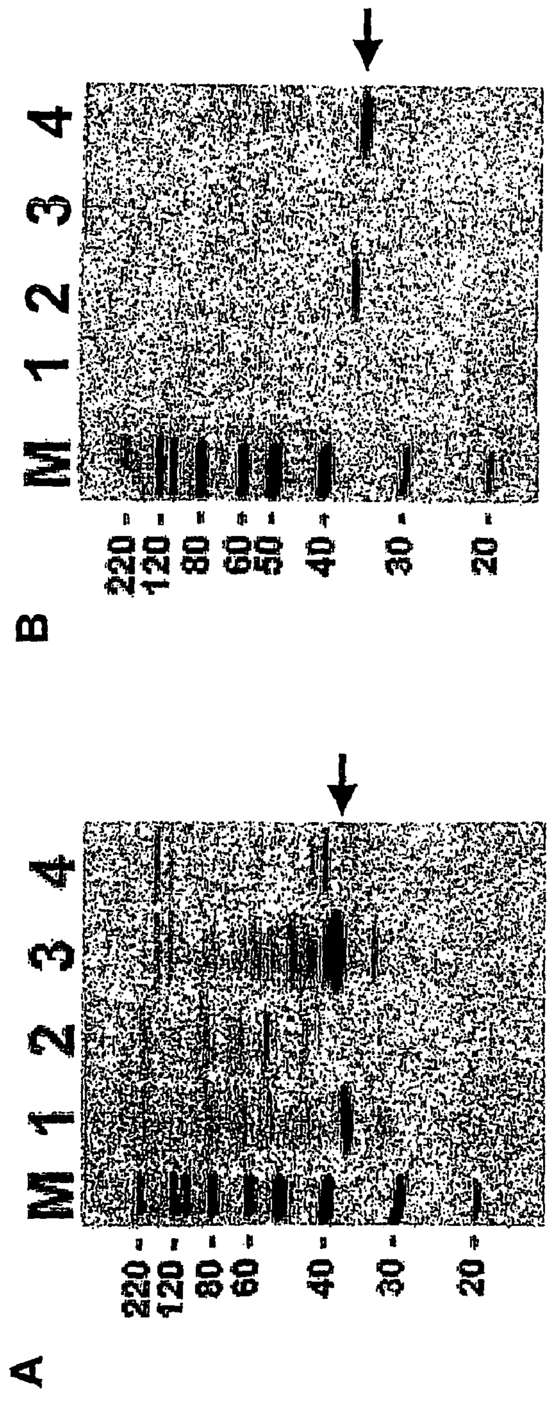

FIG. 11: Characterization of FAM26A-specific antibodies Western blot analysis of the antisera generated by immunization with a peptide of SEQ ID NO: 291 (A) and SEQ ID NO: 292 (B). Extracts of CHO cells were analyzed after transfection with in each case epitope-specific (A 1, 3; B 2, 4) or in each case epitope-unspecific (A 2, 4; B1, 3) plasmids. The arrow indicates the specific fragments.

Figure 12:
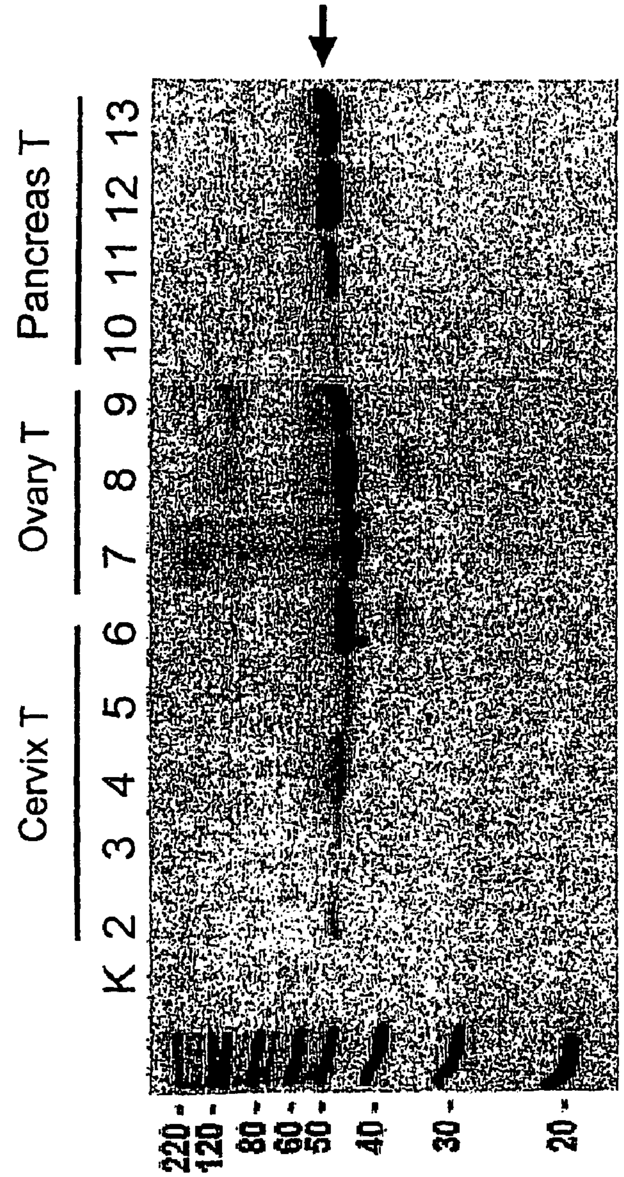

FIG. 12: Analysis of the FAM26A protein in tumors

Detection of FAM26A in cervical, ovarian and pancreatic tumors by means of FAM26A-specific antibodies (SEQ ID NO: 292).

Figure 13:
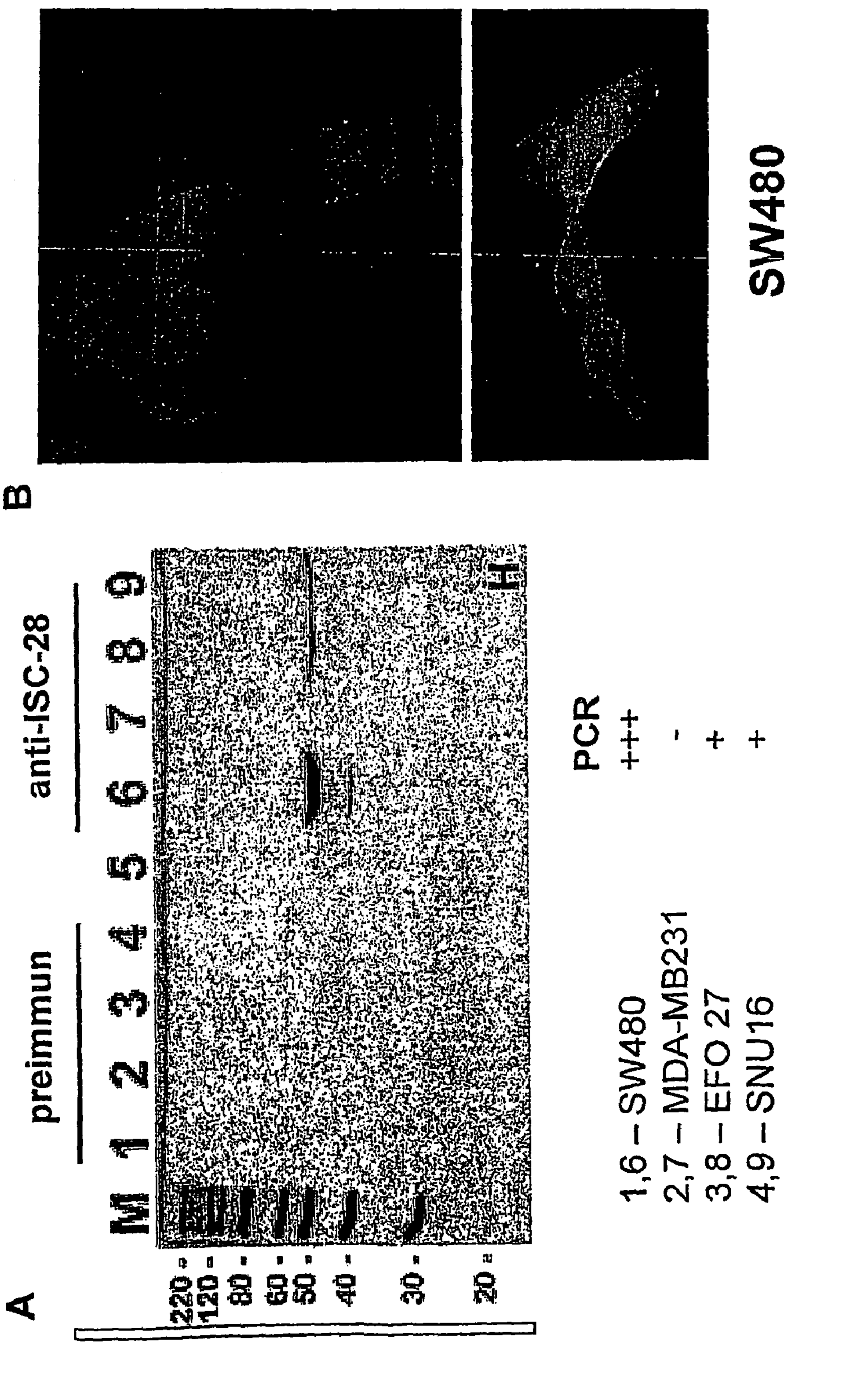

FIG. 13: Analysis of the FAM26A protein in cell lines

Analysis of the FAM26A protein in cell lines with the aid of SEQ ID NO: 291-specific antibodies. A Western blot analysis with preimmune serum as specificity control (lanes 1-5) and FAM26A-specific antibodies. B Immunofluorescence analysis of SW480 cells.

Figure 14:
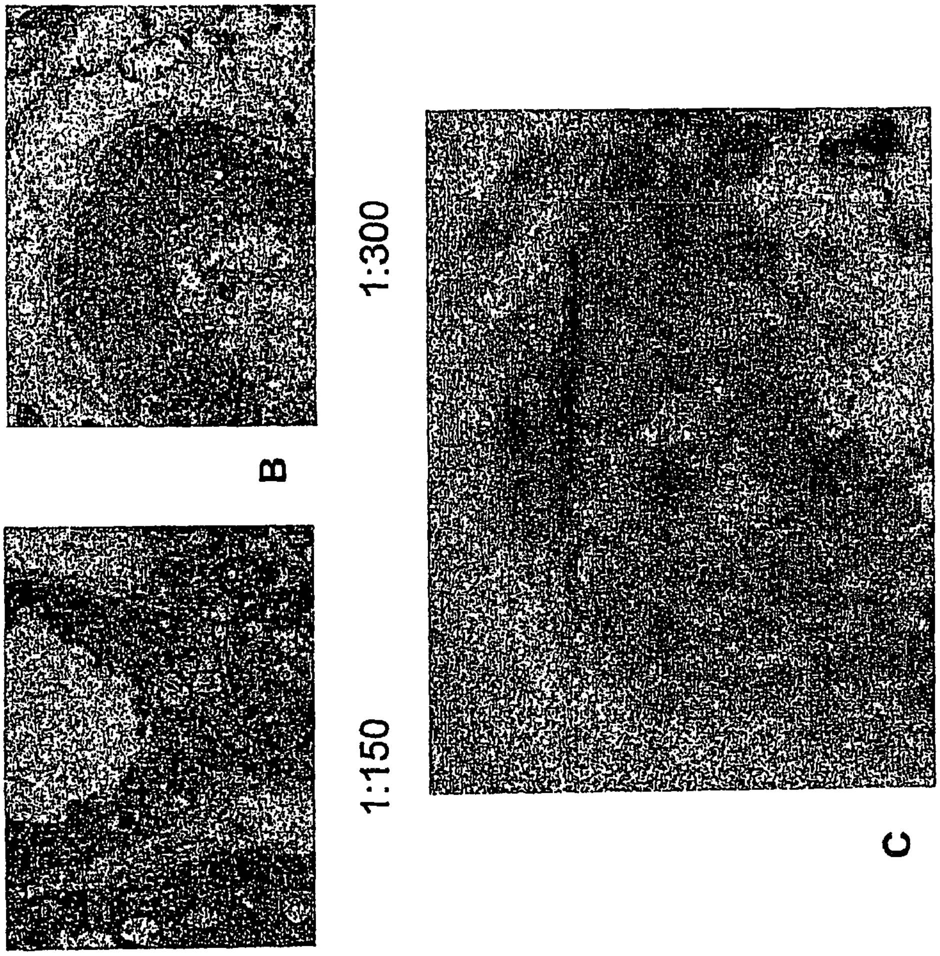

FIG. 14: Immunohistochemical detection of FAM26A in testis

Immunohistochemical analysis of the FAM26A protein in healthy testis with the aid of SEQ ID NO: 292-specific antiserum in different dilutions (A-C).

Figure 15:
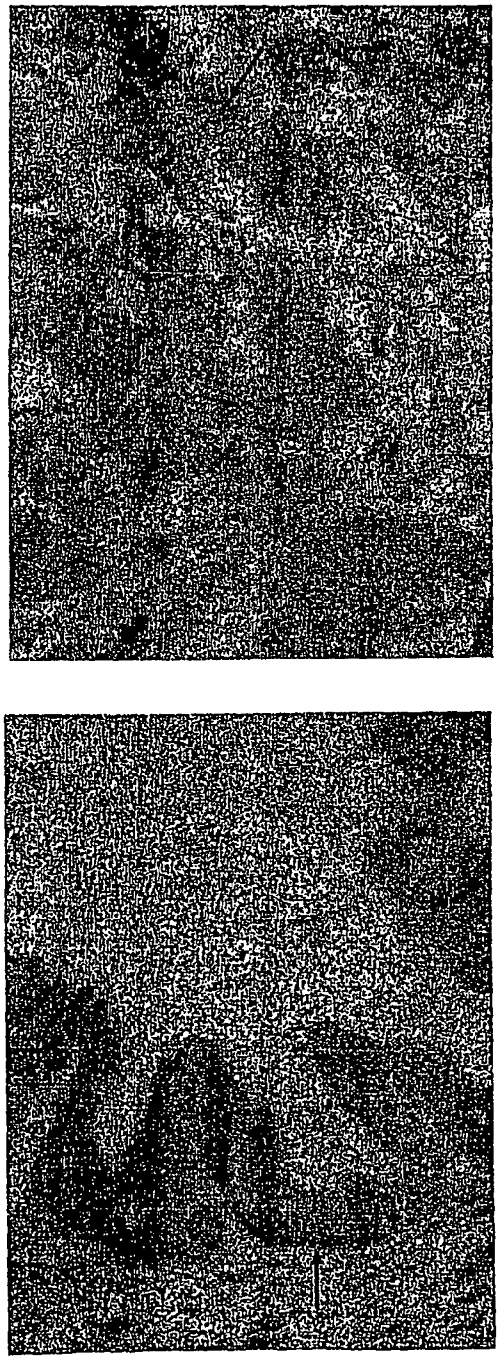

FIG. 15: Immunohistochemical analysis of FAM26A in tumors

Immunohistochemical analysis of the FAM26A protein in carcinoma samples (40-fold magnification, 1:300 dilution) with the aid of the SEQ ID NO: 292-specific antiserum. A Ovarian papillary cystadenocarcinoma. B Plate epithelial carcinoma of the cervix.

Figure 16:
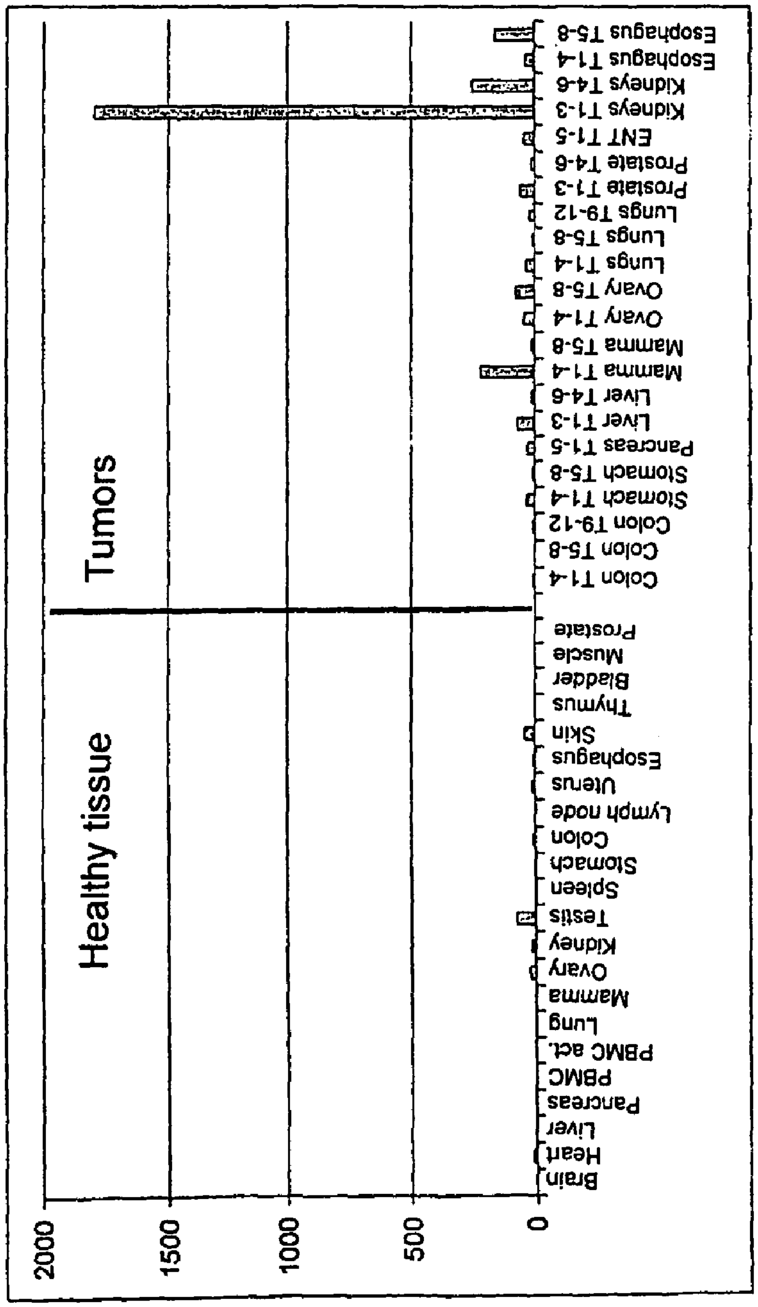

FIG. 16: qRT-PCR analysis of SEMA5B-specific expression

Quantitative expression analysis of SEMA5B in normal tissues (left) and tumor samples (pools consisting of in each case 3-5 individual samples; right). Linear representation of relative expression (-fold activation).

Figure 17:
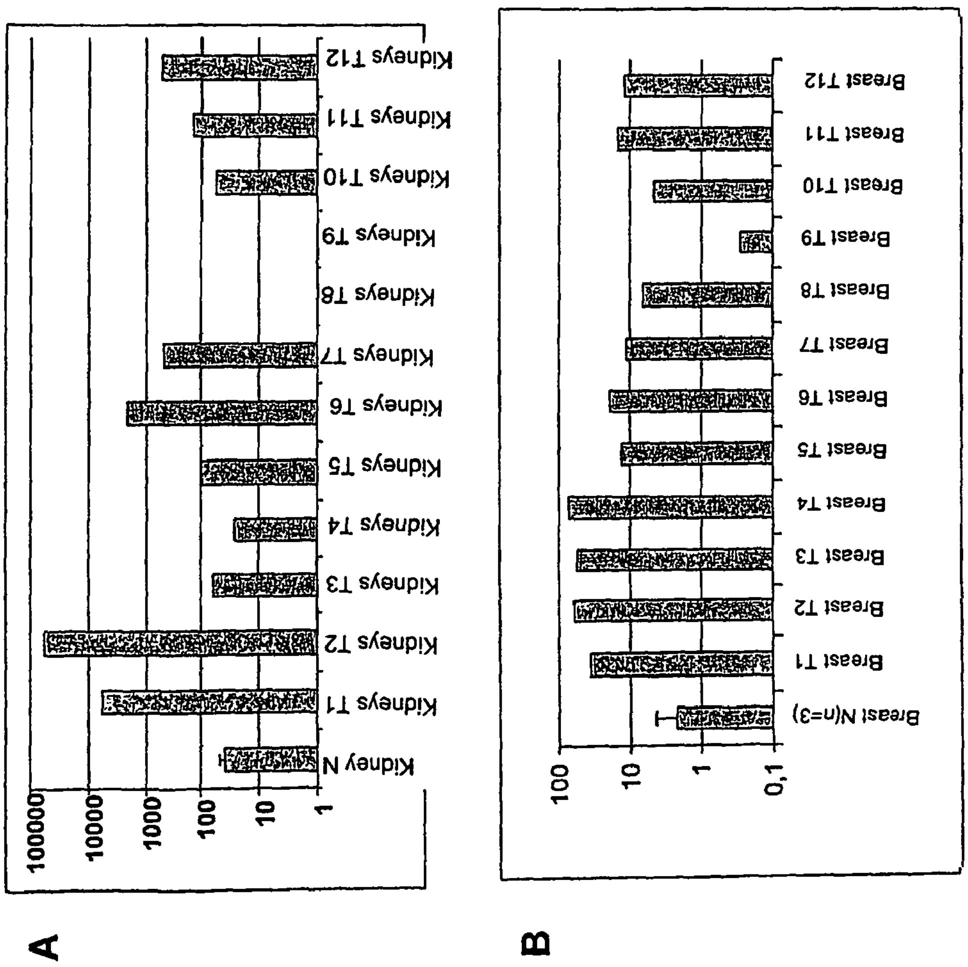

FIG. 17: Detailed analysis of SEMA5B-specific expression in renal cell carcinoma samples Quantitative expression analysis of SEMA5B in A renal cell carcinoma samples (n=12) in comparison with healthy renal tissue (N=3) and in B mammary carcinomas (N=12) in comparison with healthy breast tissue (N=3); logarithmic representation of relative expression (-fold activation).

Figure 18:
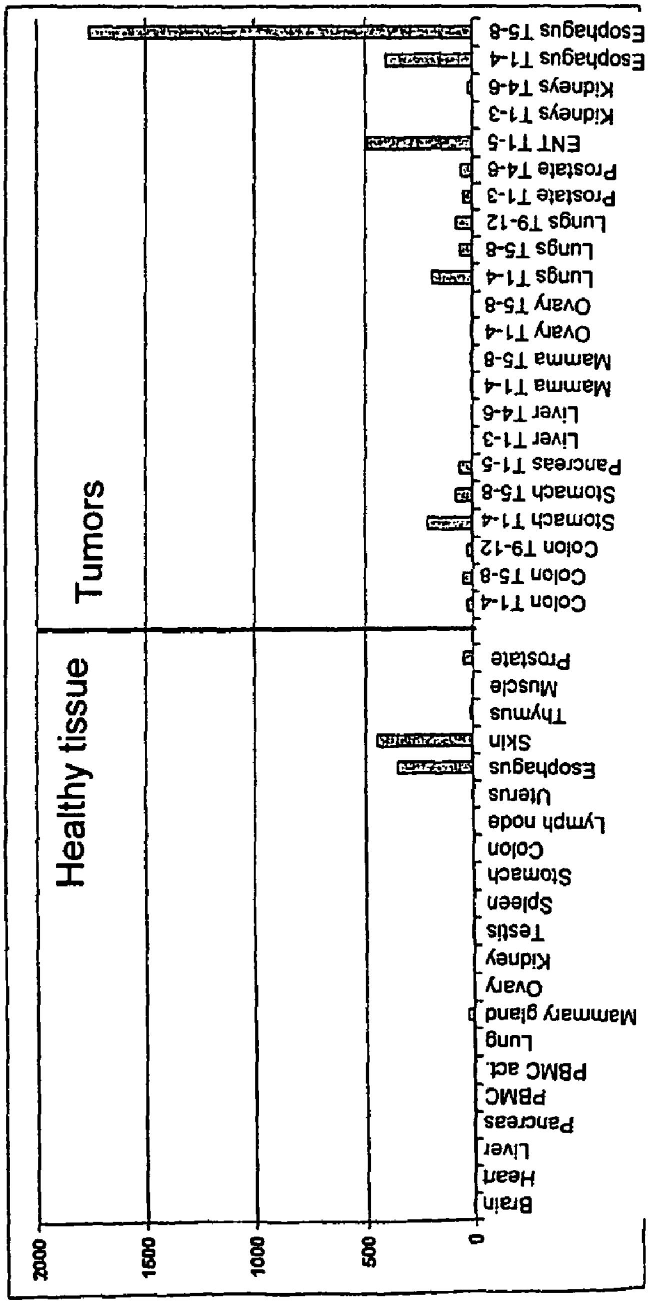

FIG. 18: qRT-PCR analysis of GJB5-specific expression

Quantitative expression analysis of GJB5 in healthy tissue samples (left) and carcinomas (pools consisting of in each case 3-5 individual samples; right). Linear representation of relative expression (-fold activation).

Figure 19:
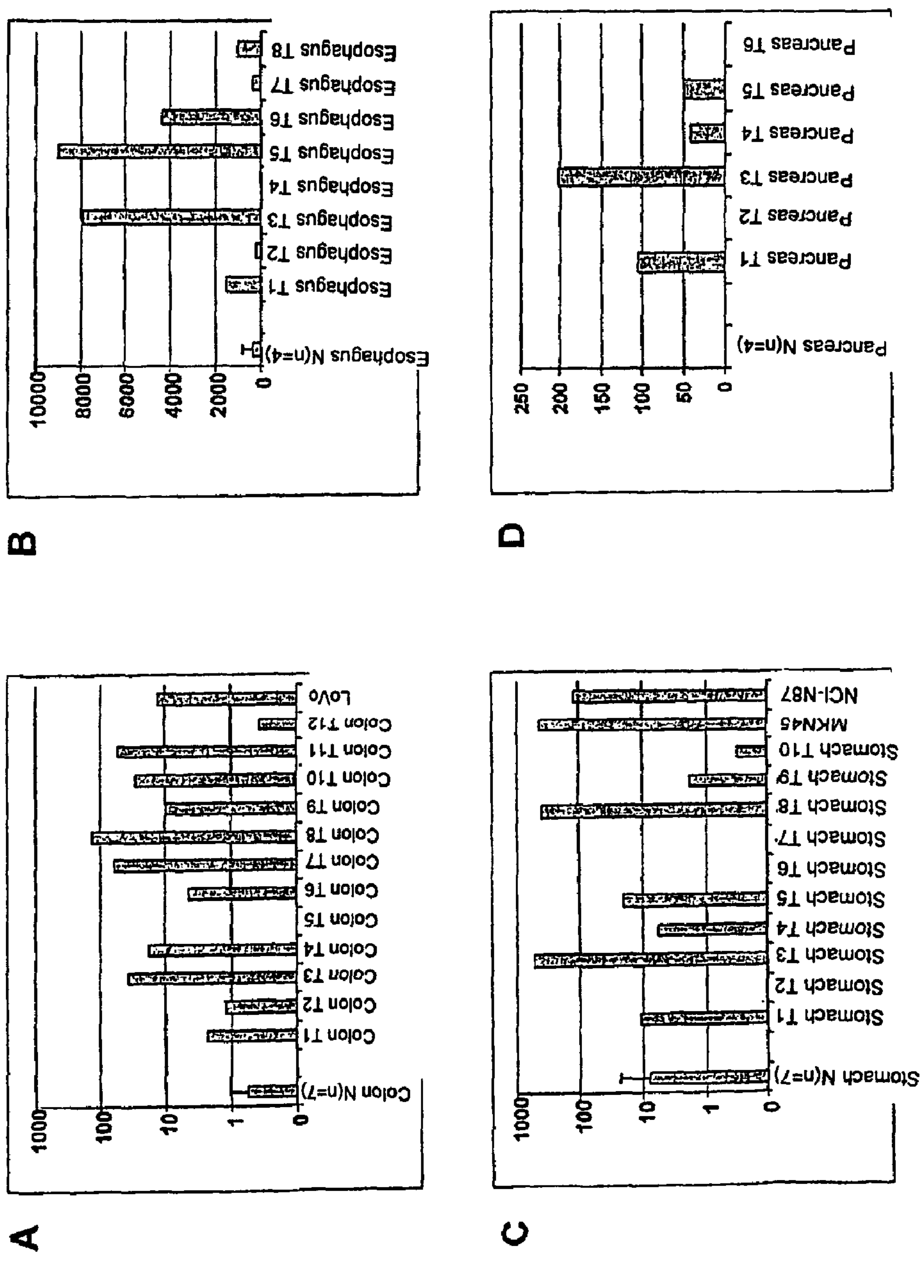

FIG. 19: Detailed analysis of GJB5-specific expression in various types of tumors Quantitative expression analysis of GJB5 in A colon carcinoma samples (n=12), B esophageal tumors (n=8), C gastric carcinomas (n=10) and D pancreatic tumors (n=5) in comparison with in each case healthy tissue samples; logarithmic (A, C) or linear (B, D) representation of relative expression (-fold activation).

Figure 20:
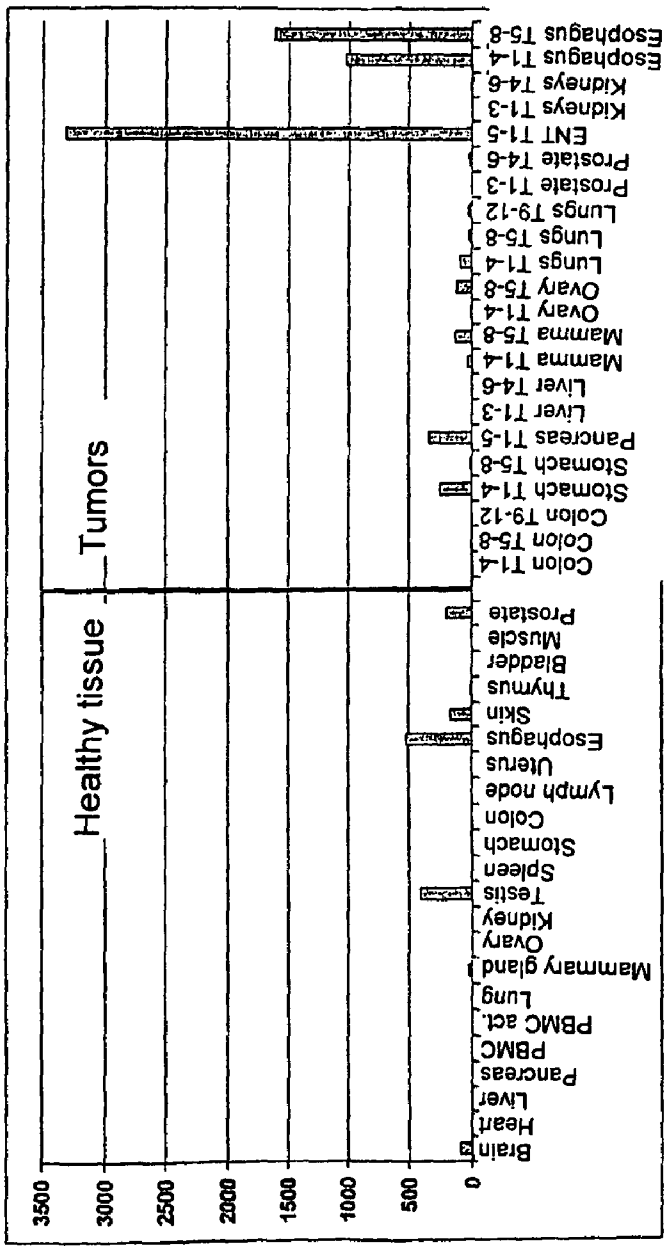

FIG. 20: qRT-PCR analysis of KLK5-specific expression

Quantitative expression analysis of KLK5 in healthy tissue samples (left) and tumors (pools consisting of in each case 3-5 individual samples; right). Linear representation of relative expression (-fold activation).

Figure 21:
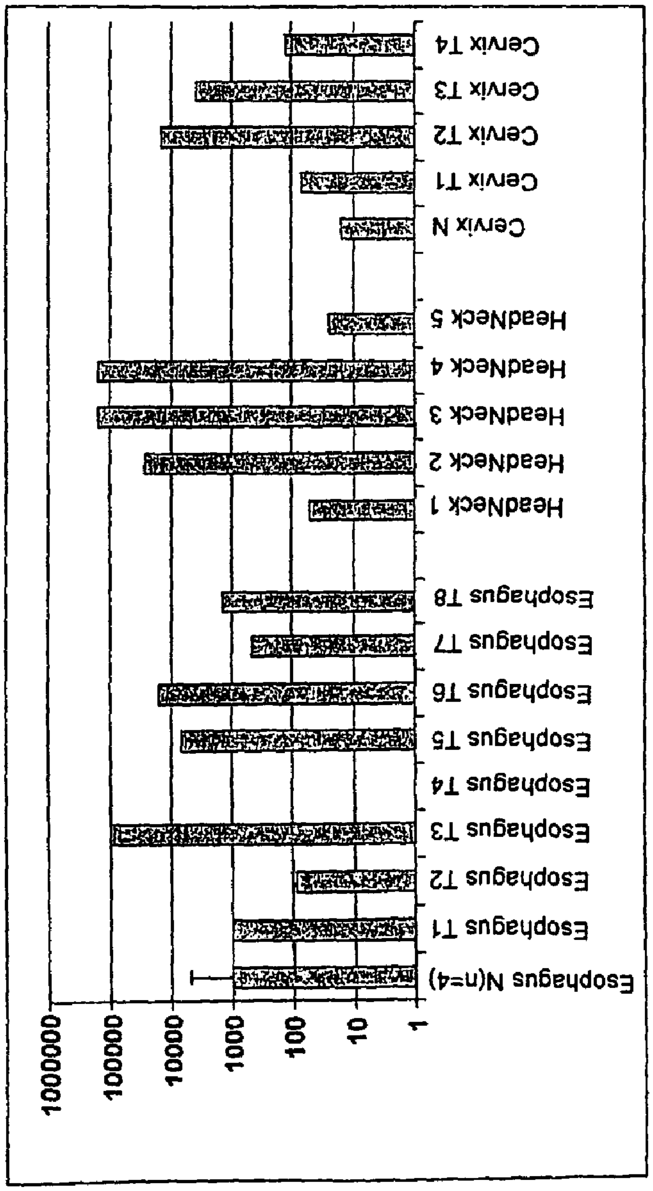

FIG. 21: Detailed analysis of KLK5-specific expression in various types of tumors Quantitative expression analysis of KLK5 in esophageal tumors (n=8), in ENT carcinomas (n=5) and in cervical tumors (n=4) in comparison with the respective healthy tissue samples; logarithmic representation of relative expression (-fold activation).

Figure 22:
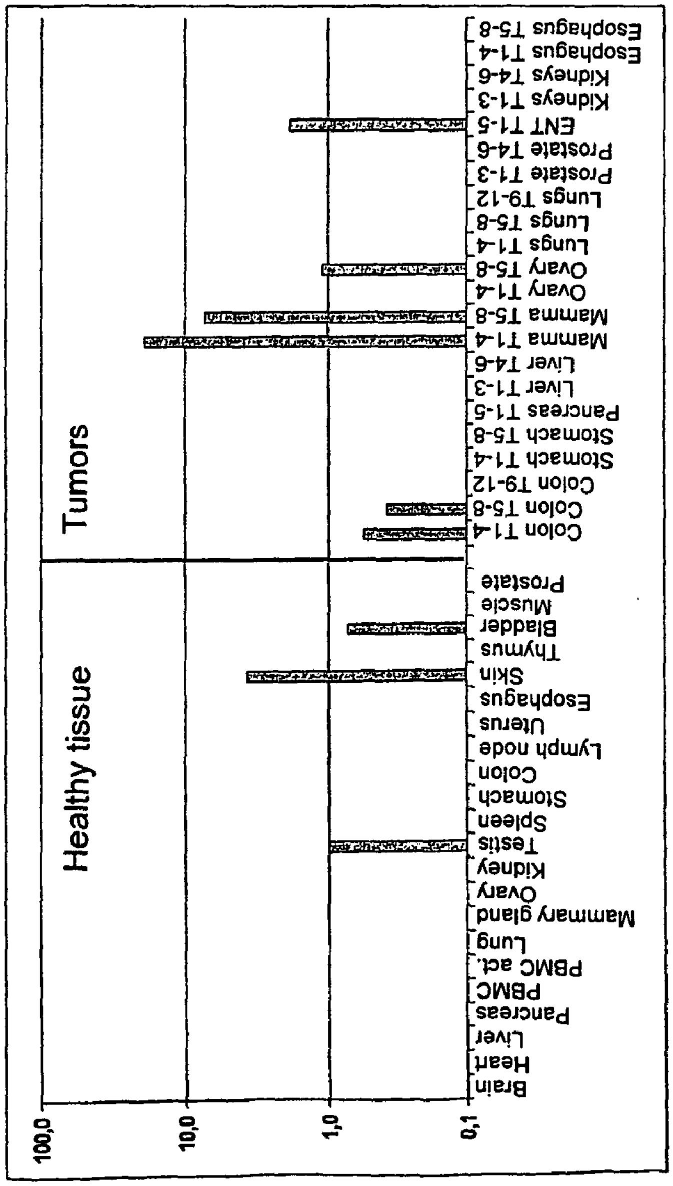

FIG. 22: qRT-PCR analysis of LOC352765-specific expression

Quantitative expression analysis of LOC352765 in healthy tissue samples (left) and tumors (pools consisting of in each case 3-5 individual samples; right). Logarithmic representation of relative expression (-fold activation).

Figure 23:
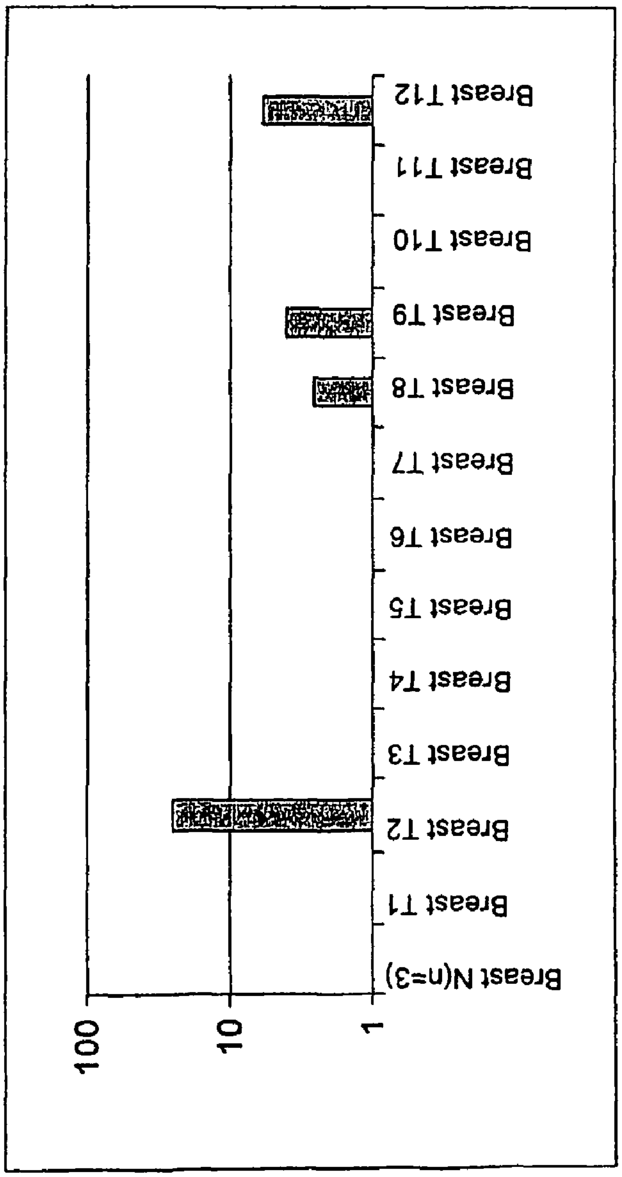

FIG. 23: Detailed analysis of LOC352765-specific expression in various types of tumors Quantitative expression analysis of LOC352765 in colon carcinomas (n=8), in mammary carcinomas (n=5) and in ENT tumors (n=4) in comparison with respective healthy tissue samples; logarithmic representation of relative expression (-fold activation).

Figure 24:
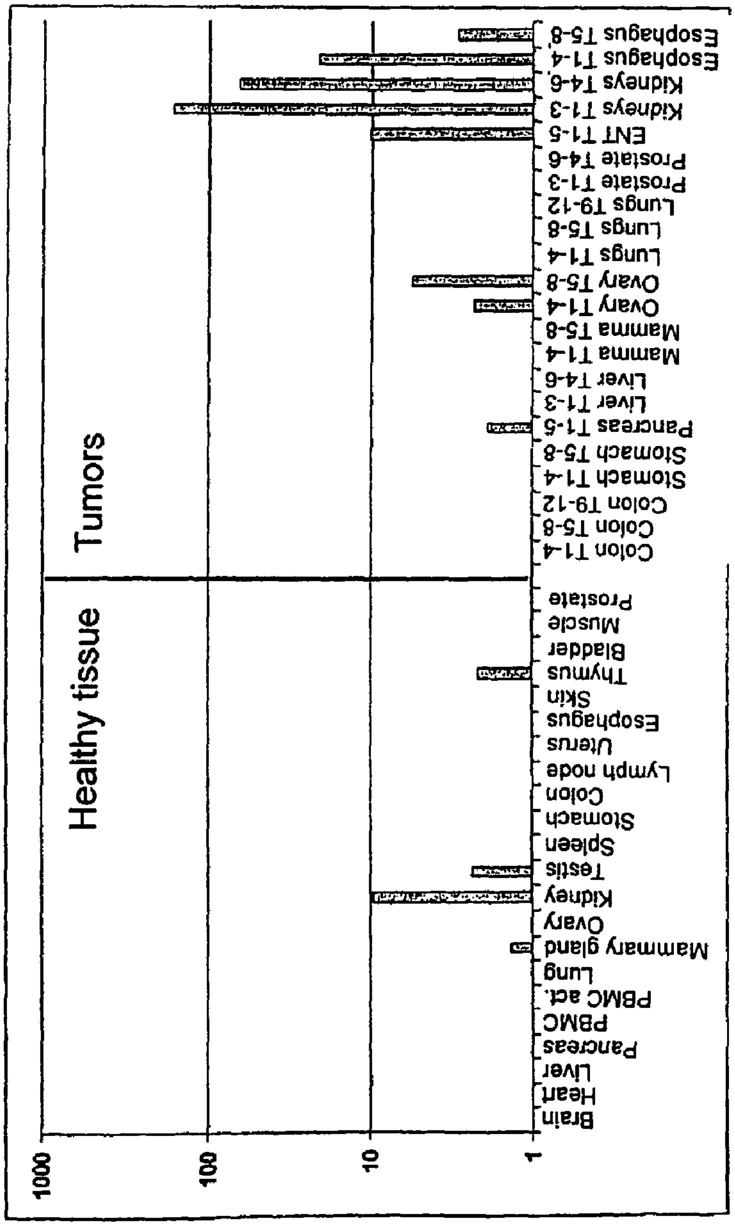

FIG. 24: qRT-PCR analysis of SVCT1-specific expression

Quantitative expression analysis of SVCT1 in healthy tissue samples (left) and tumors (pools consisting of in each case 3-5 individual samples; right). Logarithmic representation of relative expression (-fold activation).

Figure 25:
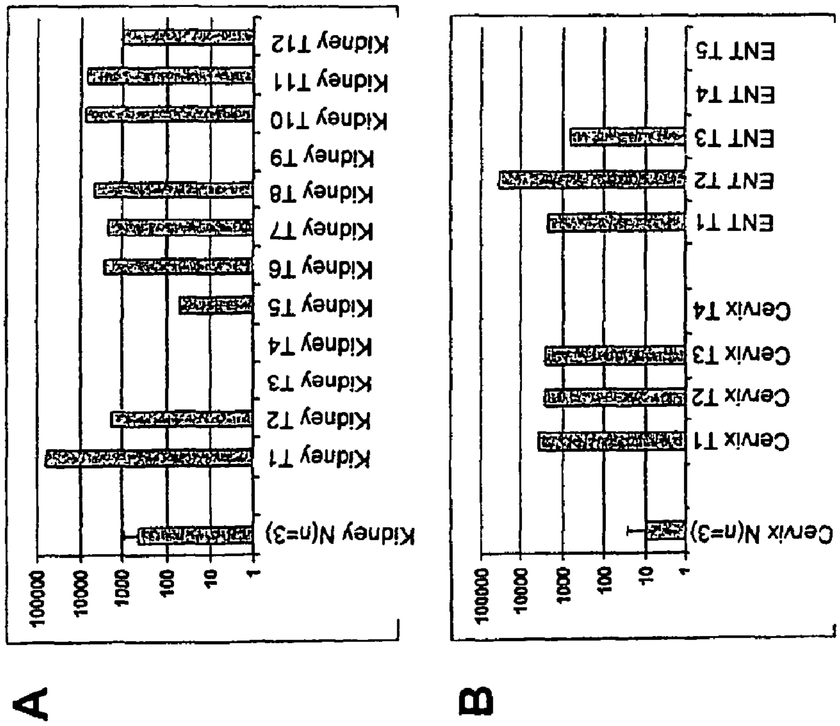

FIG. 25: Detailed analysis of SVCT1-specific expression in various types of tumors Quantitative expression analysis of SVCT1 in A kidney carcinomas (n=8), B esophageal tumors (n=5) and ENT tumors (n=4) in comparison with in each case healthy tissue samples; logarithmic representation of relative expression (-fold activation).

Figure 26:
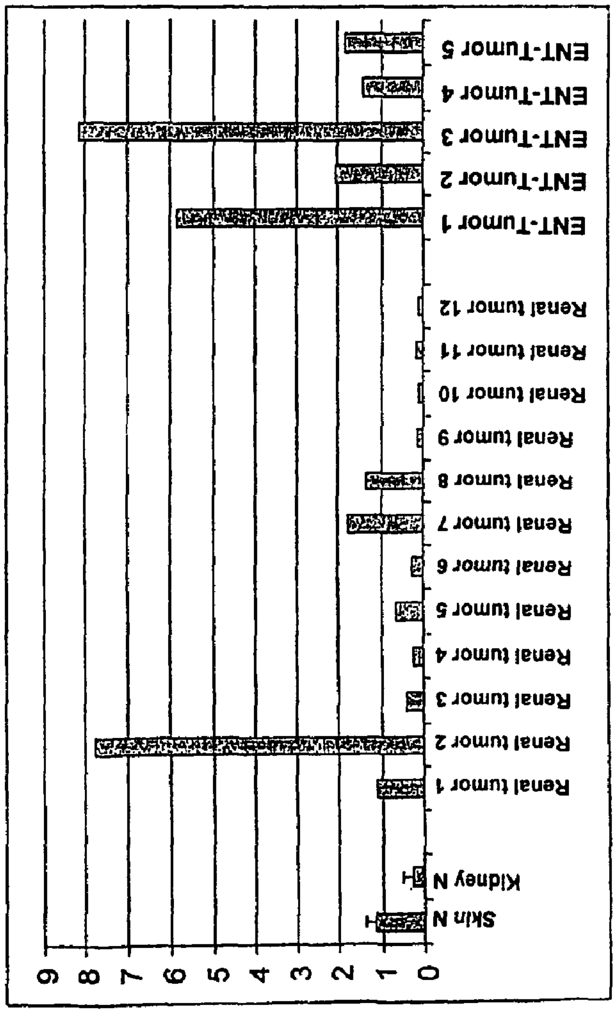

FIG. 26: qRT-PCR analysis of LOC199953-specific expression in renal cell carcinomas and in ENT tumors Quantitative expression analysis of LOC199953 in renal cell carcinomas (n=12) and ENT tumors (n=5) in comparison with healthy kidney- and skin-specific tissue samples; linear representation of relative expression (-fold activation).

Figure 27:
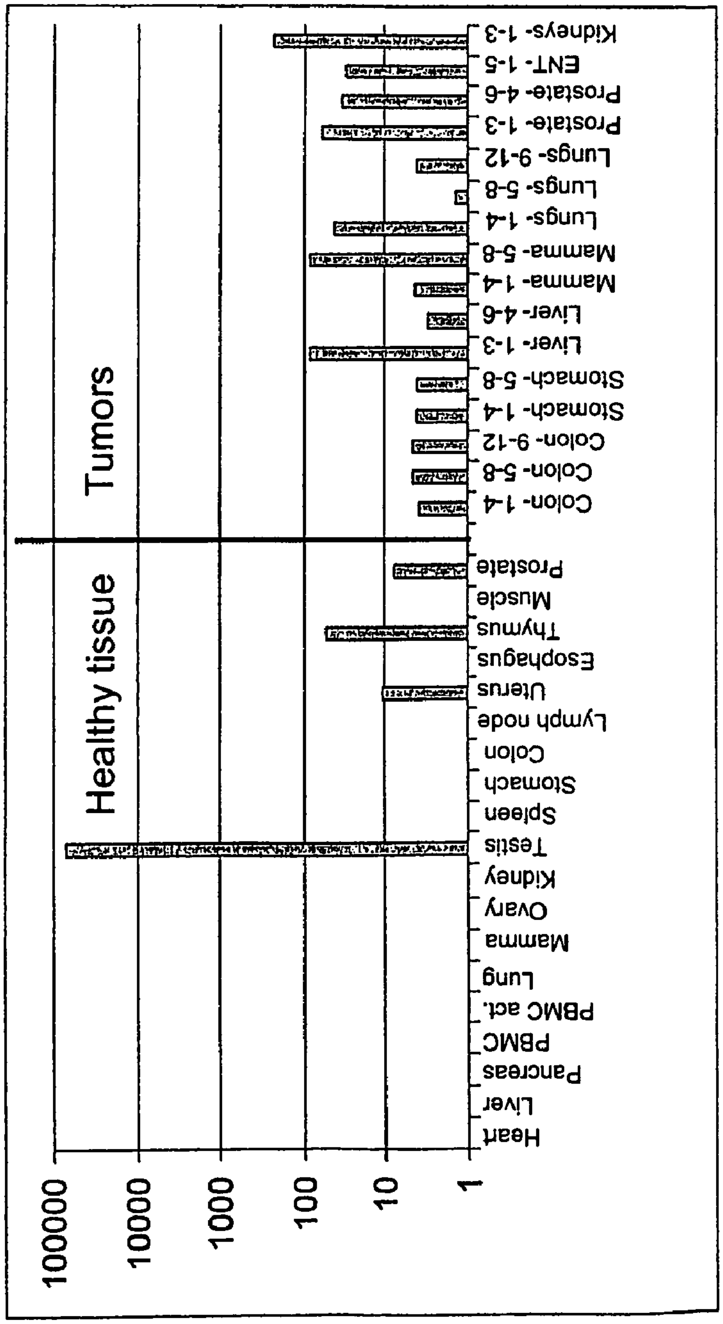

FIG. 27: qRT-PCR analysis of TMEM31-specific expression

Quantitative expression analysis of TMEM31 in healthy tissue samples (left) and tumors (pools consisting of in each case 3-5 individual samples; right). Logarithmic representation of relative expression (-fold activation).

Figure 28:
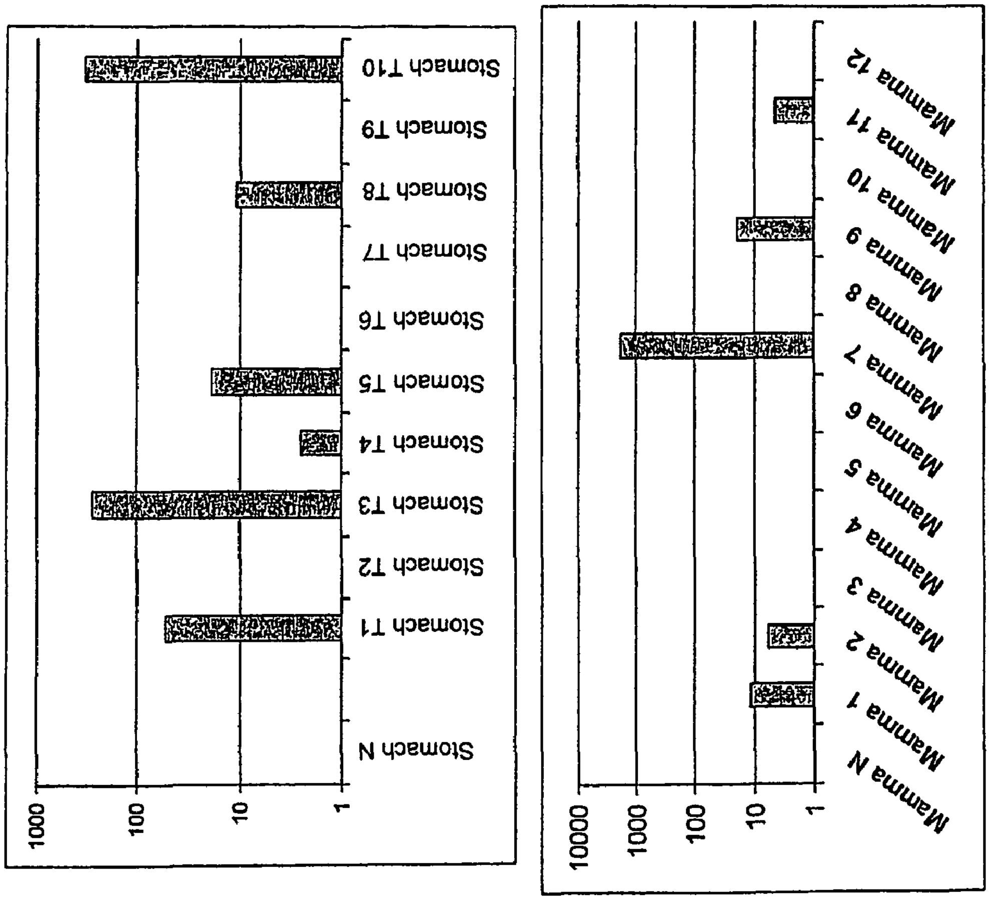

FIG. 28: Detailed analysis of TMEM31-specific expression in various types of tumors Quantitative expression analysis of TMEM31 in A gastric carcinomas (n=10) and B mammary carcinomas (n=12) in comparison with in each case healthy tissue samples; logarithmic representation of relative expression (-fold activation).

Figure 29:
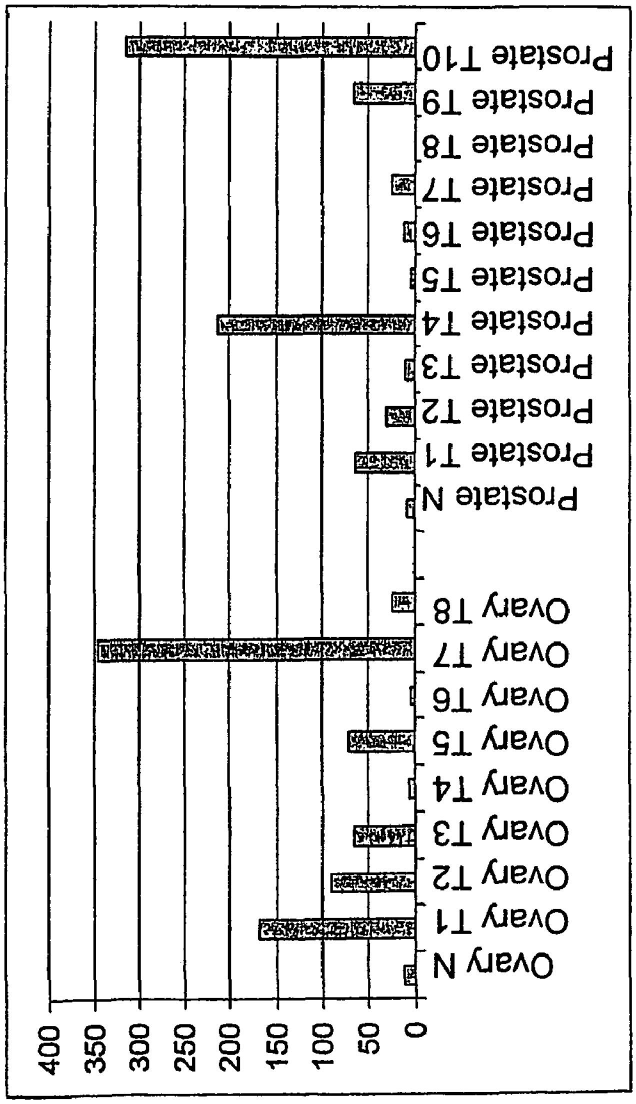

FIG. 29: qRT-PCR analysis of FLJ25132-specific expression in ovarian tumors and in prostate carcinomas Quantitative expression analysis of FLJ25132 in ovarian tumors (n=8) and in prostate carcinomas (n=10) in comparison with in each case healthy tissue samples; linear representation of relative expression (-fold activation).

Figure 30:
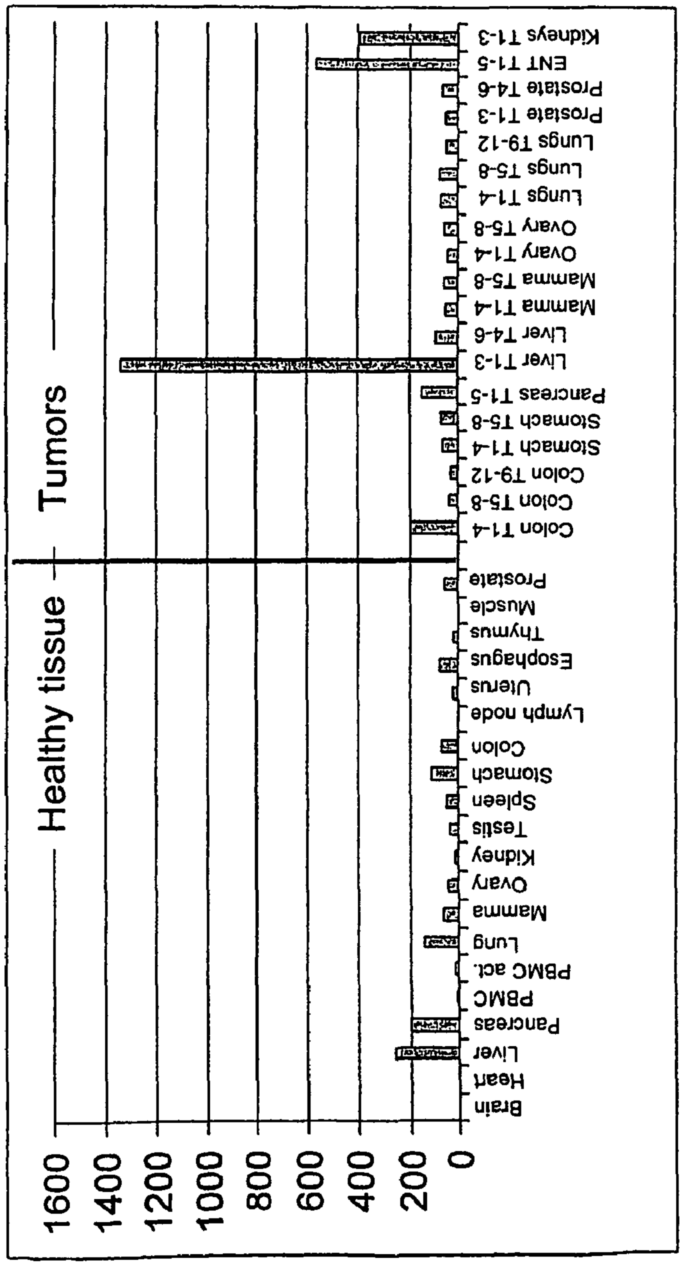

FIG. 30: qRT-PCR analysis of SEQ ID NO: 57-specific expression

Quantitative expression analysis of SEQ ID NO: 57 in healthy tissue samples (left) and in tumors (pools consisting of in each case 3-5 individual samples; right). Linear representation of relative expression (-fold activation).

Figure 31:
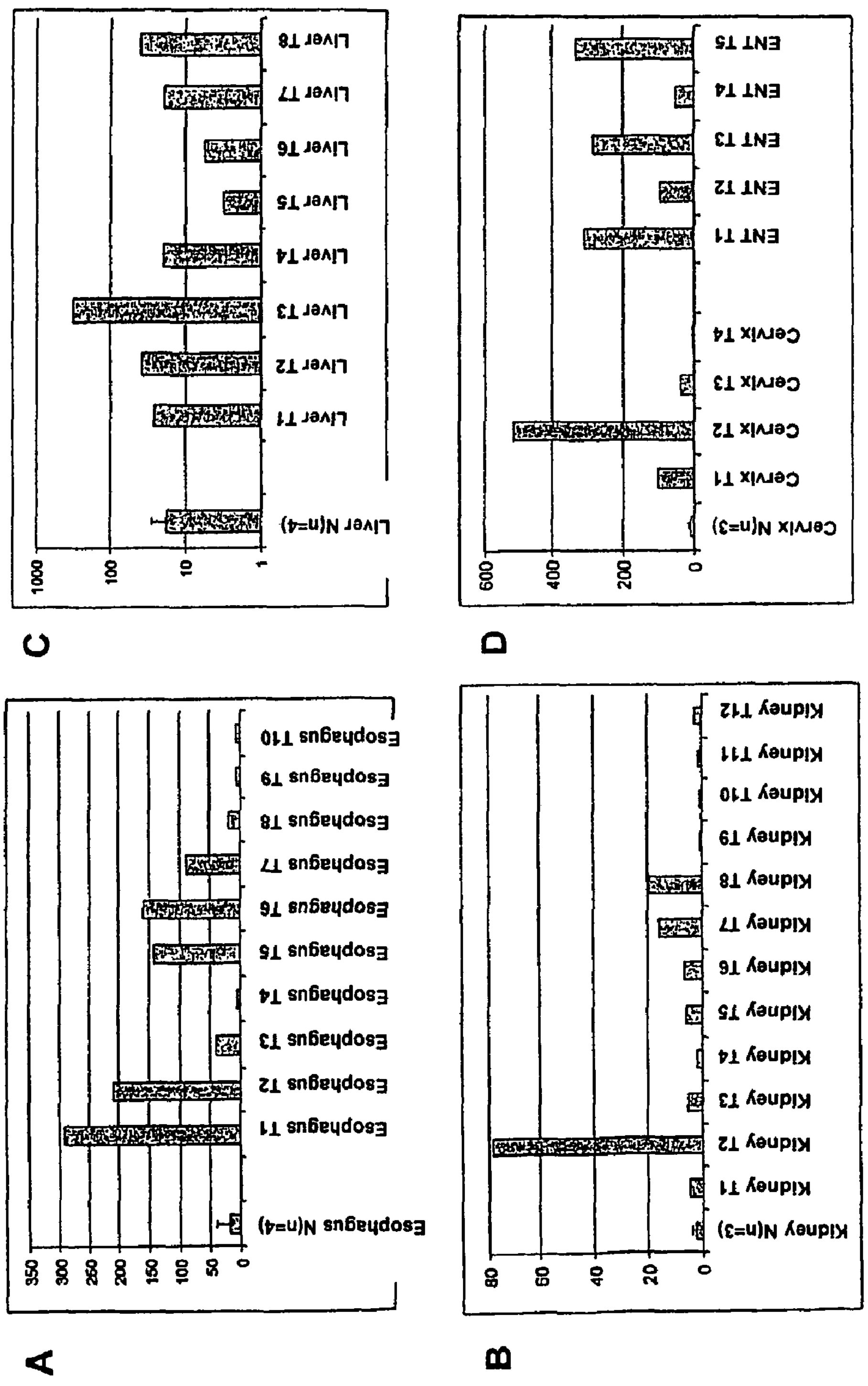

FIG. 31: Detailed analysis of SEQ ID NO: 57-specific expression in various types of tumors Quantitative expression analysis of SEQ ID NO: 57 in A esophageal tumors (n=8), B liver carcinomas (n=8), C kidney carcinomas and D cervical and ENT tumors in comparison with in each case healthy tissue samples; linear (A, C, D) or logarithmic (B) representation of relative expression (-fold activation).

Figure 32:
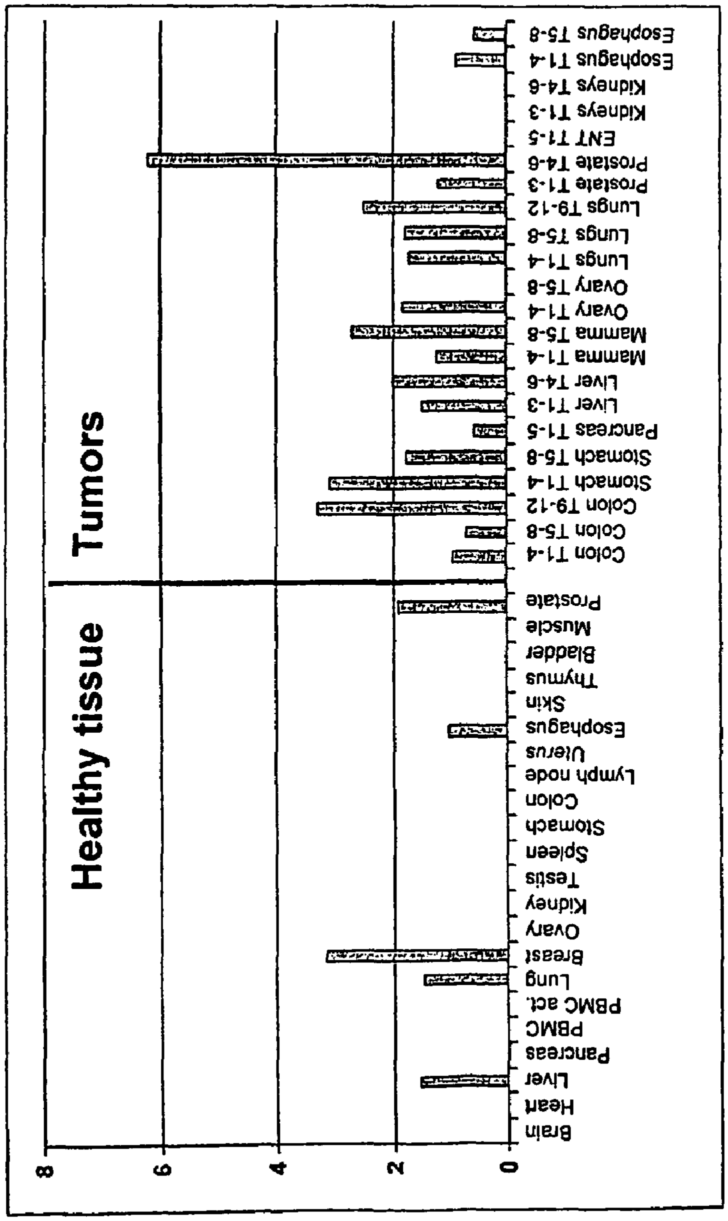

FIG. 32: qRT-PCR analysis of LOC119395-specific expression

Quantitative expression analysis of LOC119395 in healthy tissue samples (left) and in tumors (pools consisting of in each case 3-5 individual samples; right). Linear representation of relative expression (-fold activation).

Figure 33:
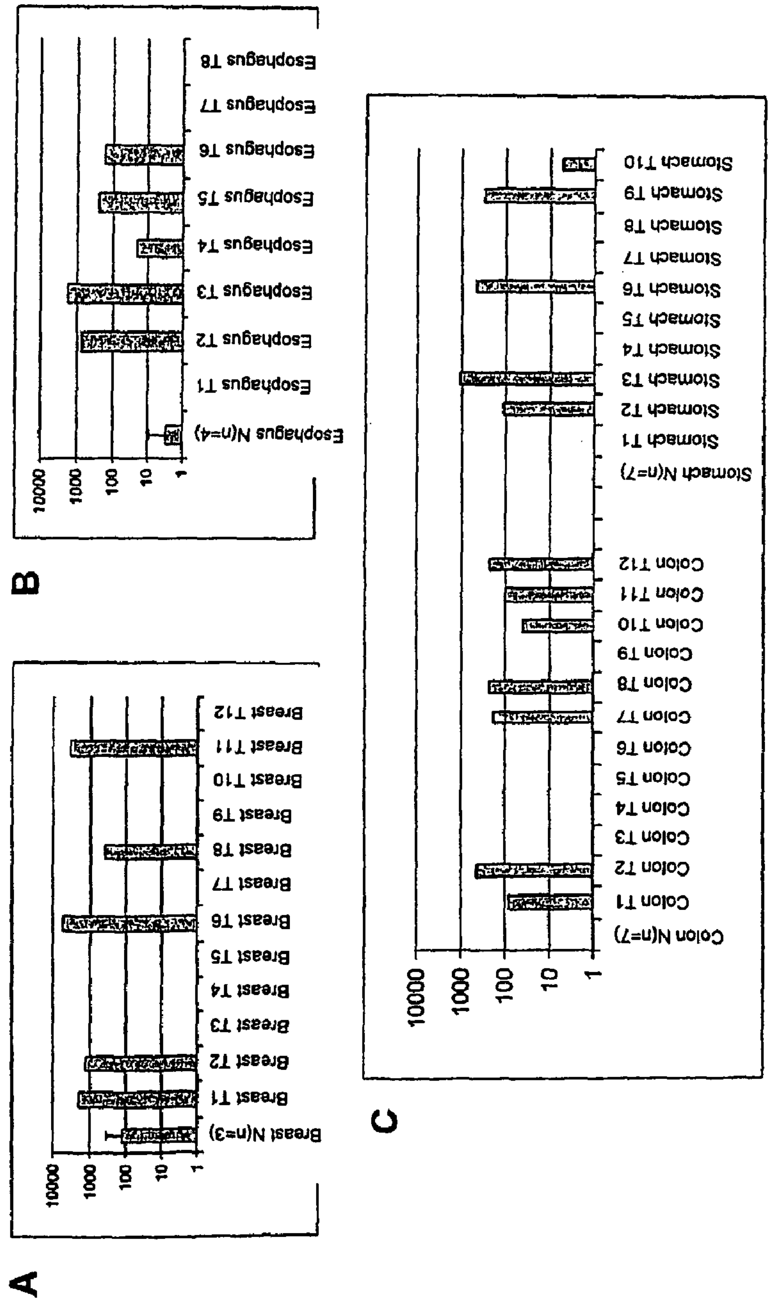

FIG. 33: Detailed analysis of LOC119395-specific expression in various types of tumors Quantitative expression analysis of LOC119395 in A breast tumors (n=12), B esophageal carcinomas (n=8) and C colon and gastric carcinomas, in comparison with in each case healthy tissue samples; logarithmic representation of relative expression (-fold activation).

Figure 34:
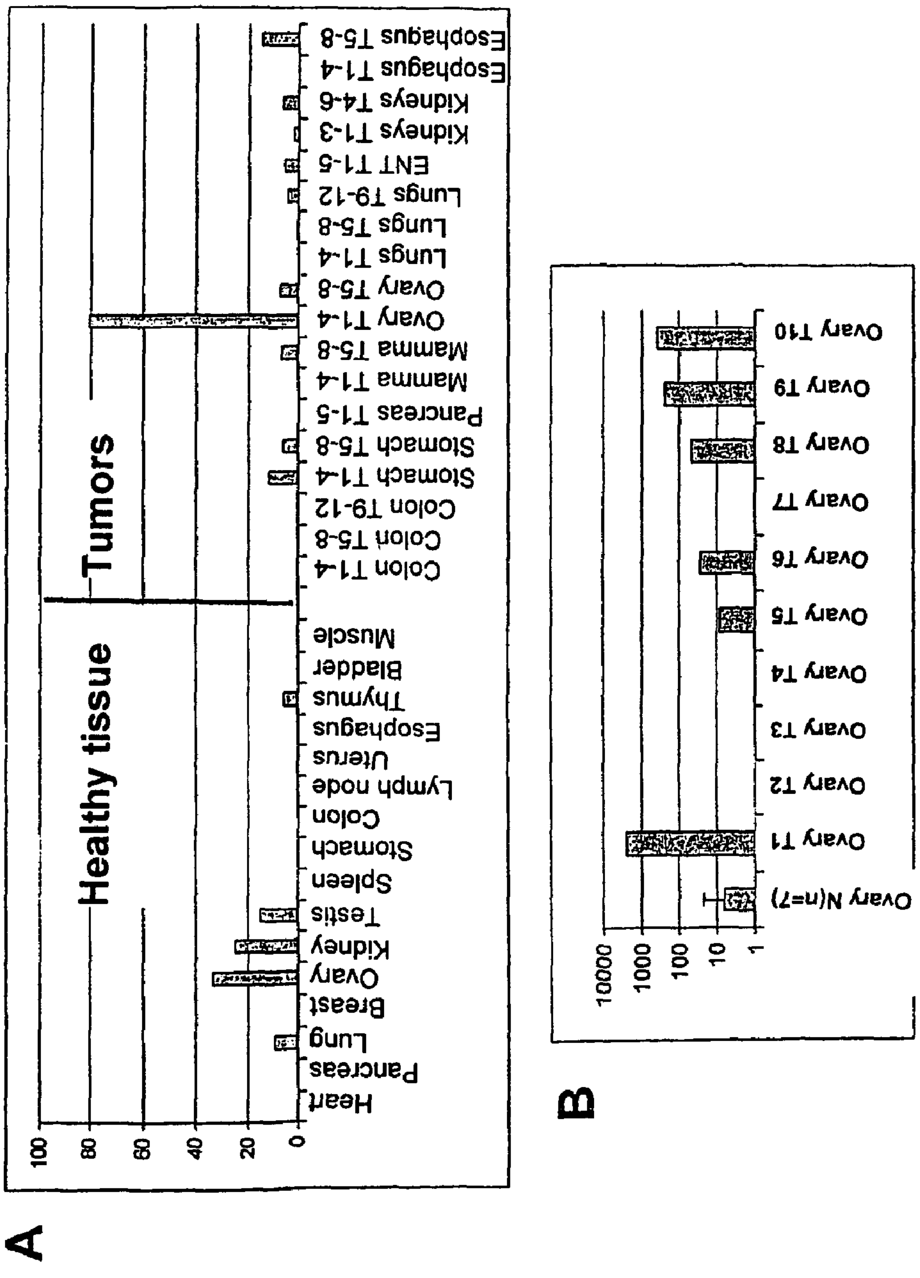

FIG. 34: qRT-PCR analysis of LOC121838-specific expression

A Quantitative analysis of LOC121838-specific expression in healthy tissue samples (left) and in tumors (pools consisting of in each case 3-5 individual samples; right). Linear representation of relative expression (-fold activation).

B Detailed analysis of LOC121838-specific RNA in ovarian tissues, logarithmic representation.

Figure 35:
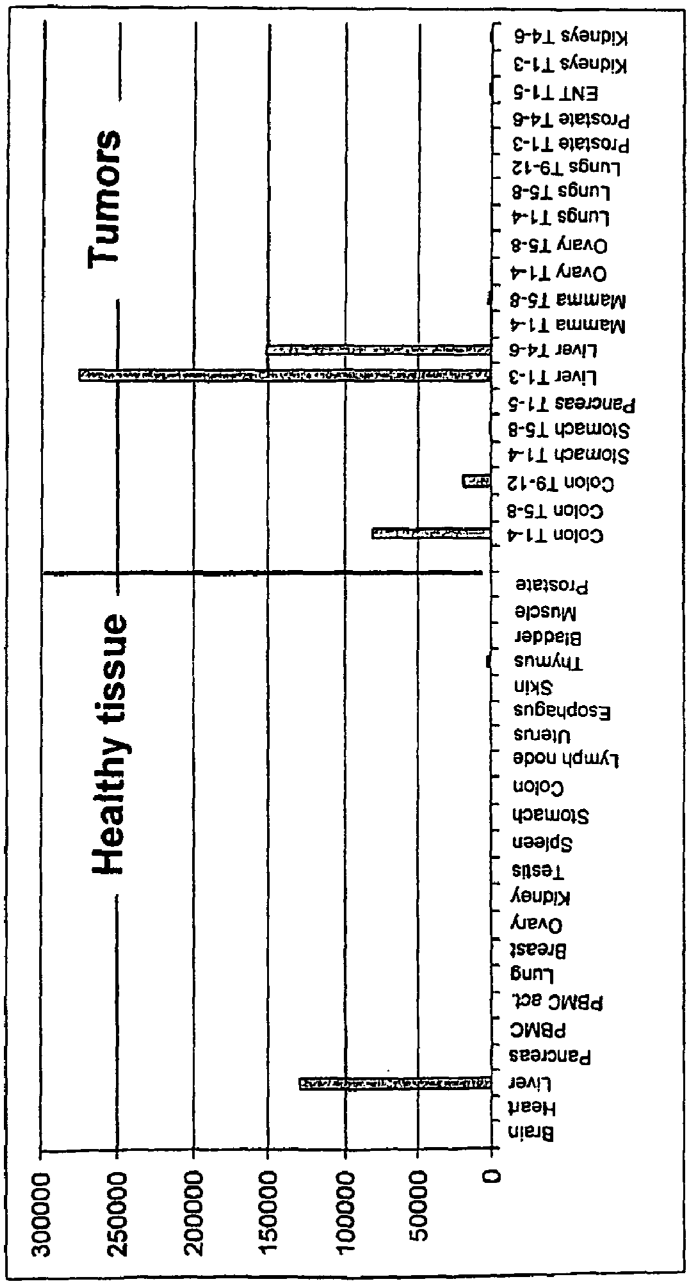

FIG. 35: qRT-PCR analysis of LOC221103-specific expression

Quantitative expression analysis of LOC221103-RNA in healthy tissue samples (left) and in tumors (pools consisting of in each case 3-5 individual samples; right). Linear representation of relative expression (-fold activation).

Figure 36:
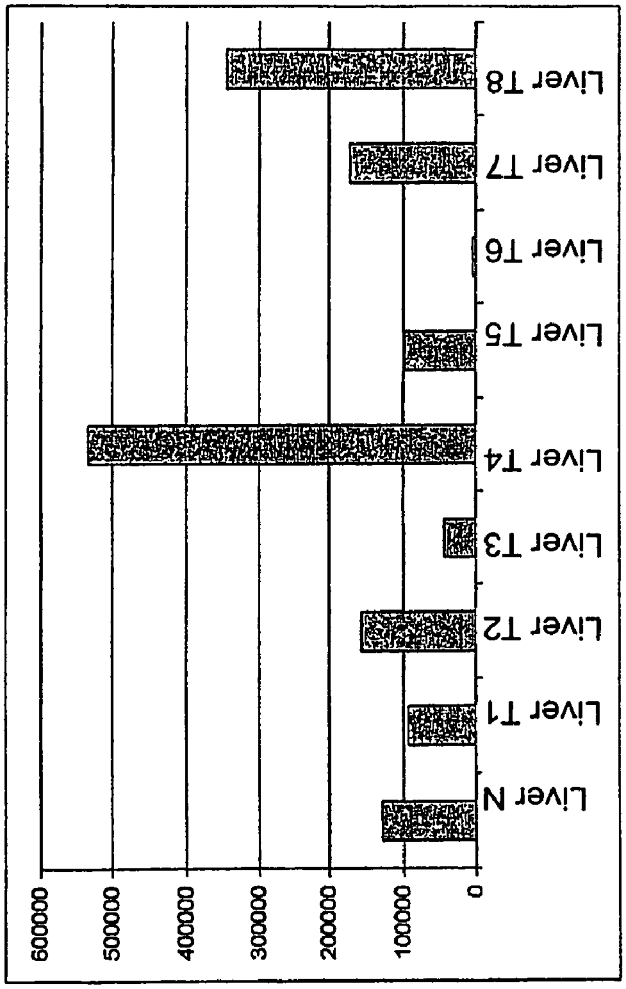

FIG. 36: Detailed qRT-PCR analysis of LOC221103-specific expression in liver samples Quantitative expression analysis of LOC221103-RNA in liver tumors (n=8) and in a healthy liver sample. Linear representation of relative expression (-fold activation).

Figure 37:
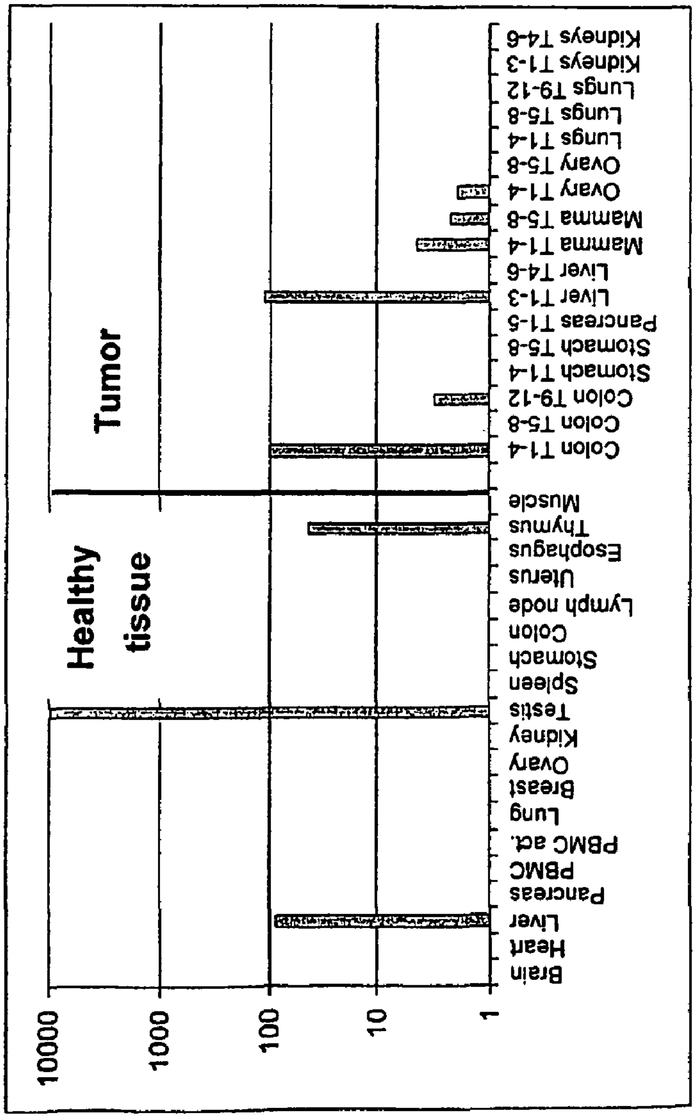

FIG. 37: qRT-PCR analysis of LOC338579-specific expression

Quantitative expression analysis of LOC338579-specific RNA in healthy tissue samples (left) and in tumors (pools consisting of in each case 3-5 individual samples; right). Logarithmic representation of relative expression (-fold activation).

Figure 38:
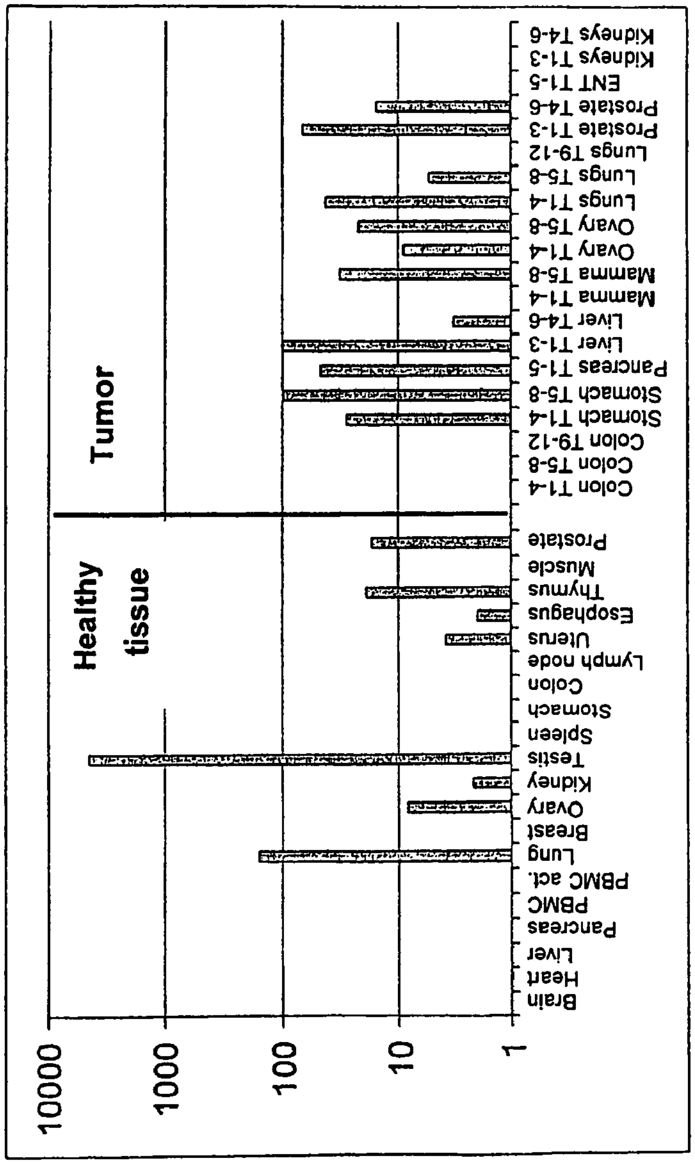

FIG. 38: qRT-PCR analysis of LOC90342-specific expression

Quantitative expression analysis of LOC90342-specific RNA in healthy tissue samples (left) and in tumors (pools consisting of in each case 3-5 individual samples; right). Logarithmic representation of relative expression (-fold activation).

Figure 39:
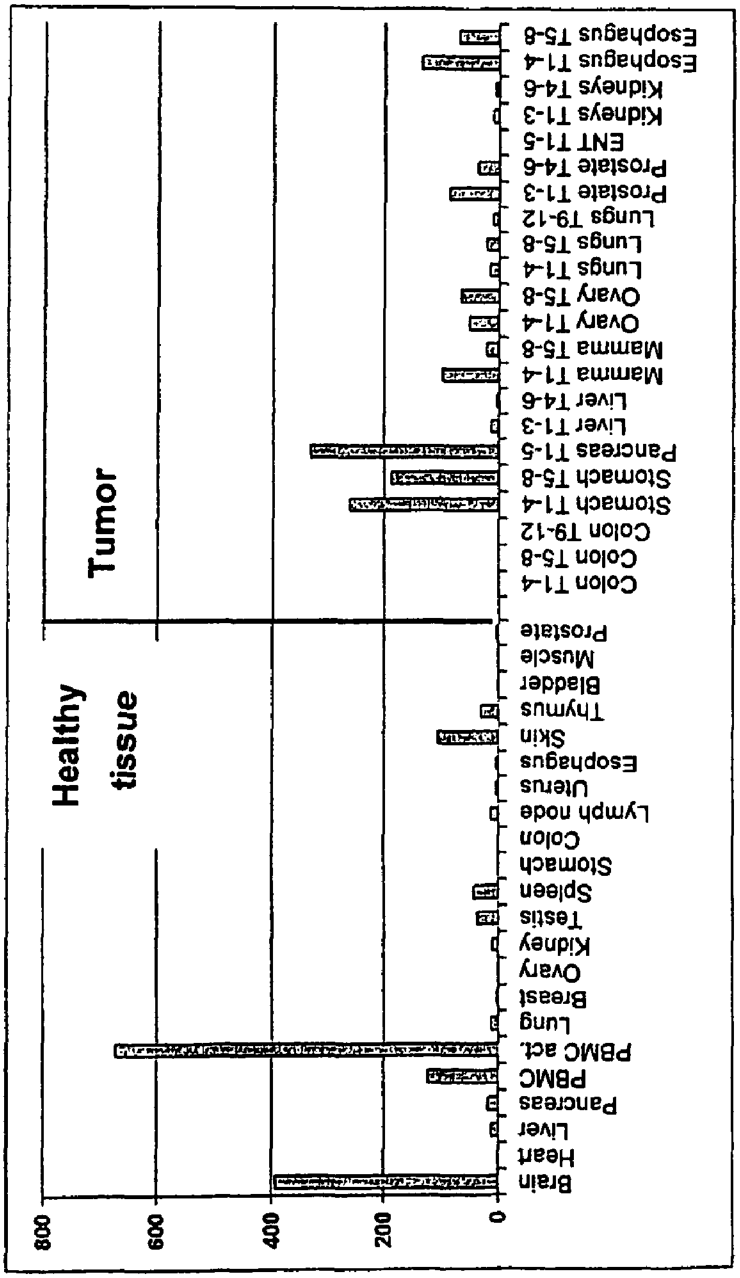

FIG. 39: qRT-PCR analysis of LRFN1-specific expression

Quantitative expression analysis of LRFN1-specific RNA in healthy tissue samples (left) and in tumors (pools consisting of in each case 3-5 individual samples; right). Logarithmic representation of relative expression (-fold activation).

Figure 40:
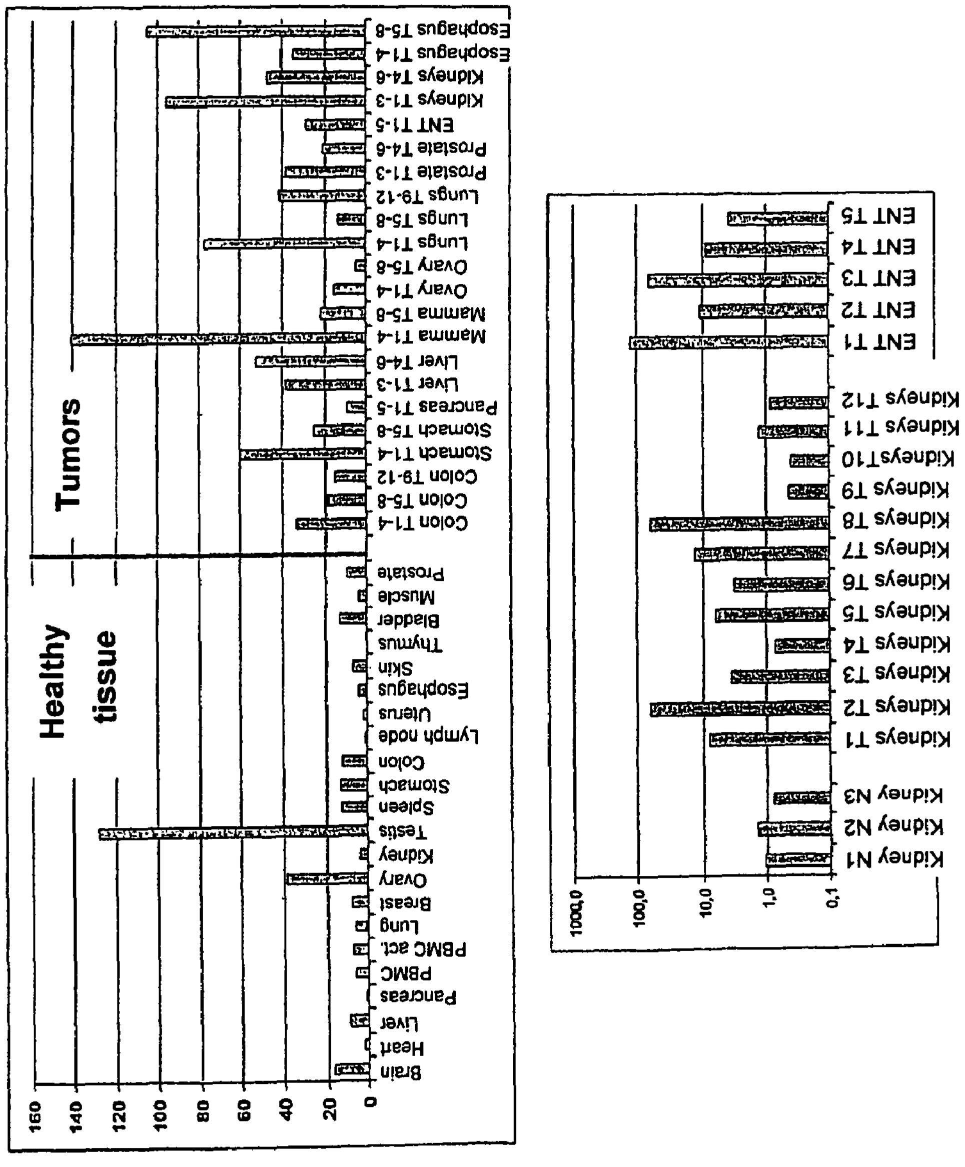

FIG. 40: qRT-PCR analysis of LOC285916-specific expression

A Quantitative analysis of LOC285916-specific expression in healthy tissue samples (left) and in tumors (pools consisting of in each case 3-5 individual samples; right). Linear representation of relative expression (-fold activation).

B Detailed analysis of LOC285916-specific RNA in kidney tissues and in ENT tumors, logarithmic representation.

Figure 41:
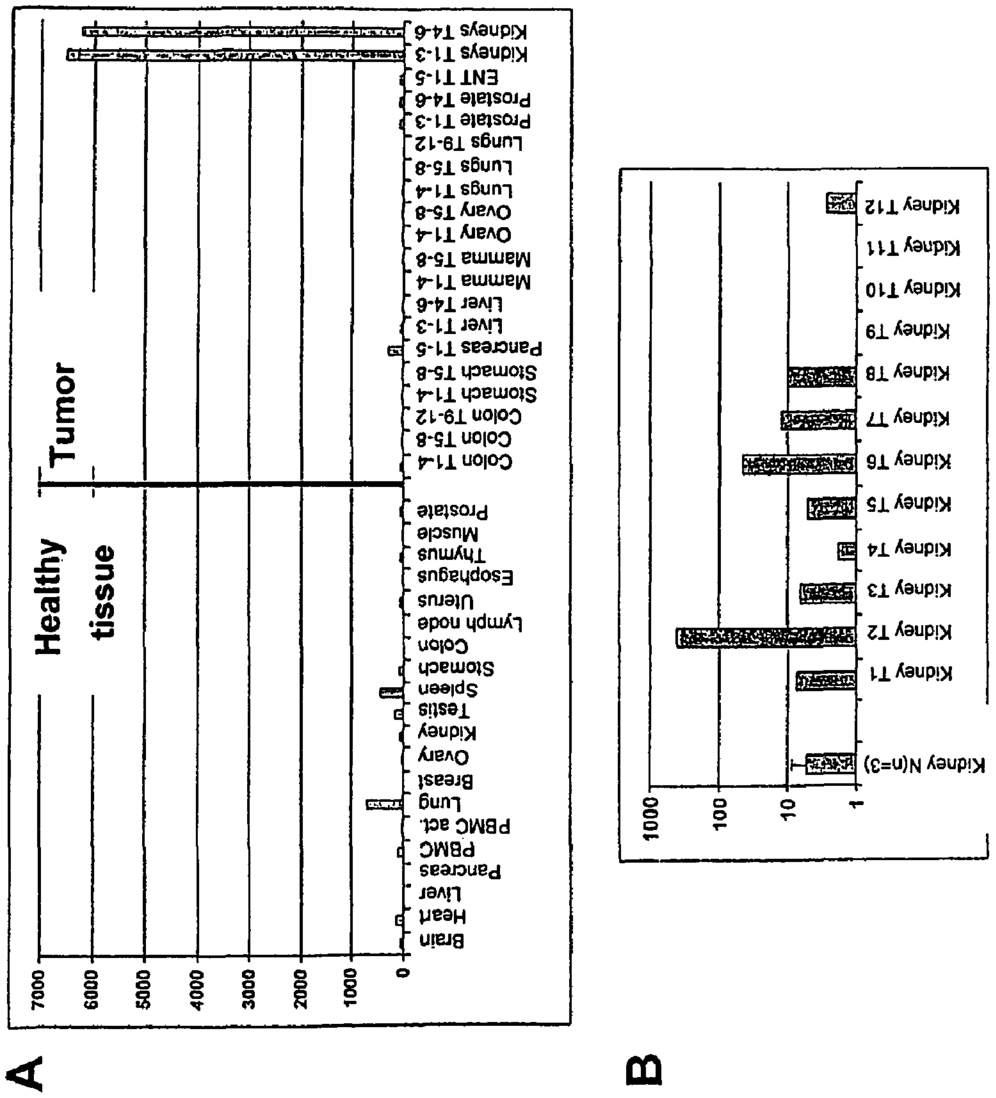

FIG. 41: qRT-PCR analysis of MGC71744-specific expression

A Quantitative analysis of MGC71744-specific expression in healthy tissue samples (left) and in tumors (pools consisting of in each case 3-5 individual samples; right). Linear representation of relative expression (-fold activation). B Detailed analysis of MGC71744-specific RNA in various kidney tissues, logarithmic representation.

Figure 42:
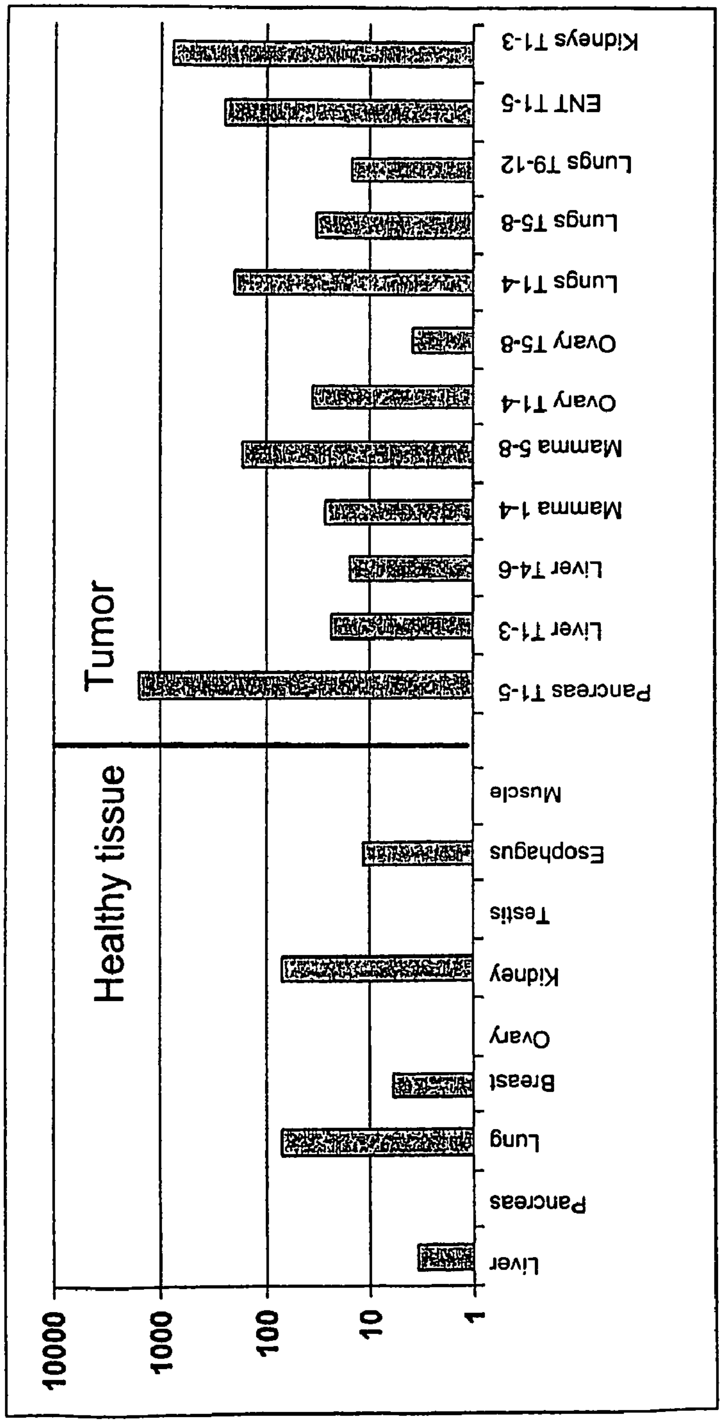

FIG. 42: qRT-PCR analysis of LOC342982-specific expression

Quantitative expression analysis of LOC342982-specific RNA in healthy tissue samples (left) and in tumors (pools consisting of in each case 3-5 individual samples; right). Logarithmic representation of relative expression (-fold activation).

Figure 43:
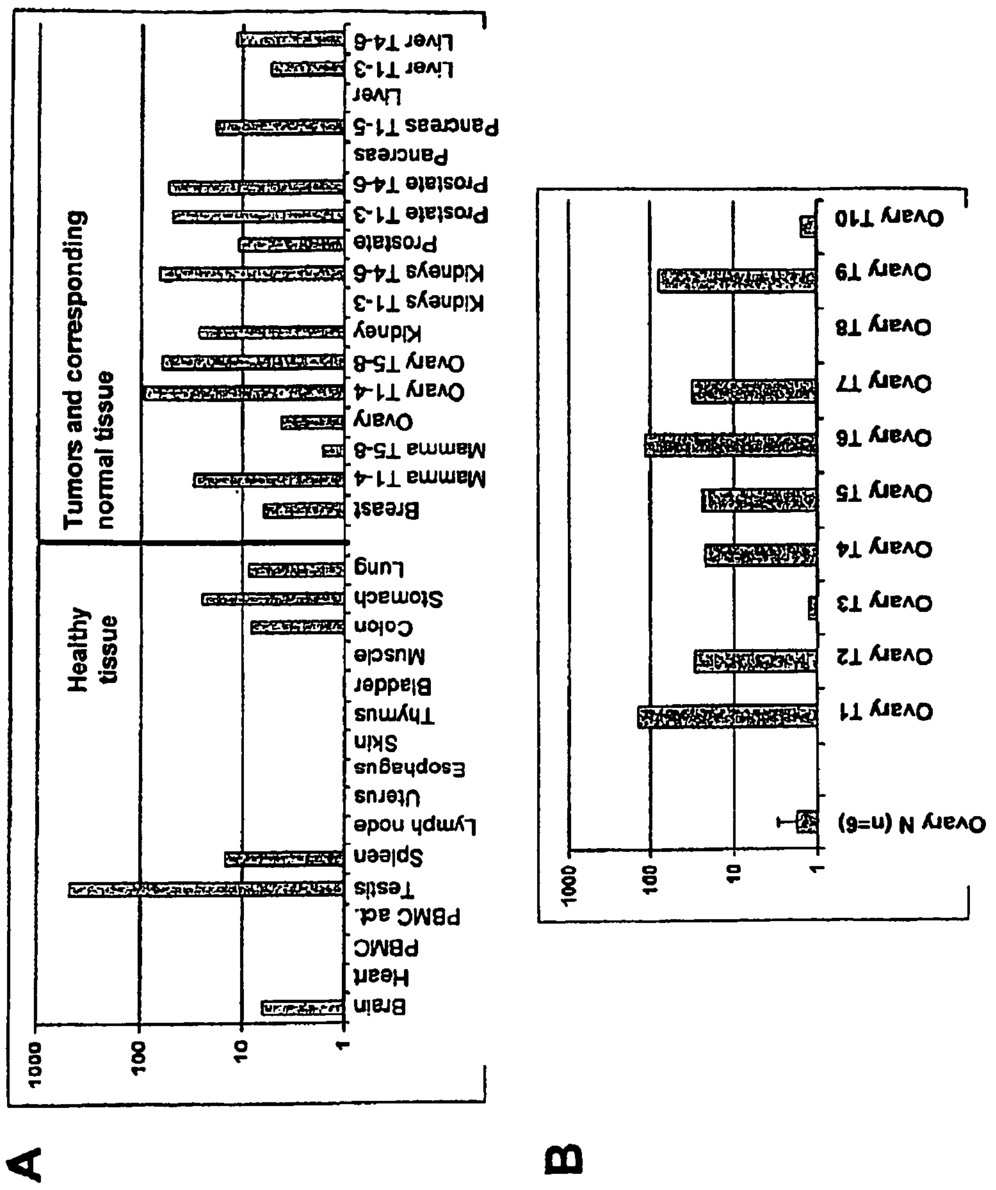

FIG. 43: qRT-PCR analysis of LOC343169-specific expression

A Quantitative analysis of LOC343169-specific expression in healthy tissue samples (left) and in tumors (pools consisting of in each case 3-5 individual samples; right). Linear representation of relative expression (-fold activation). B Detailed analysis of LOC343169-specific RNA in various ovarian tissues, logarithmic representation.

Figure 44:
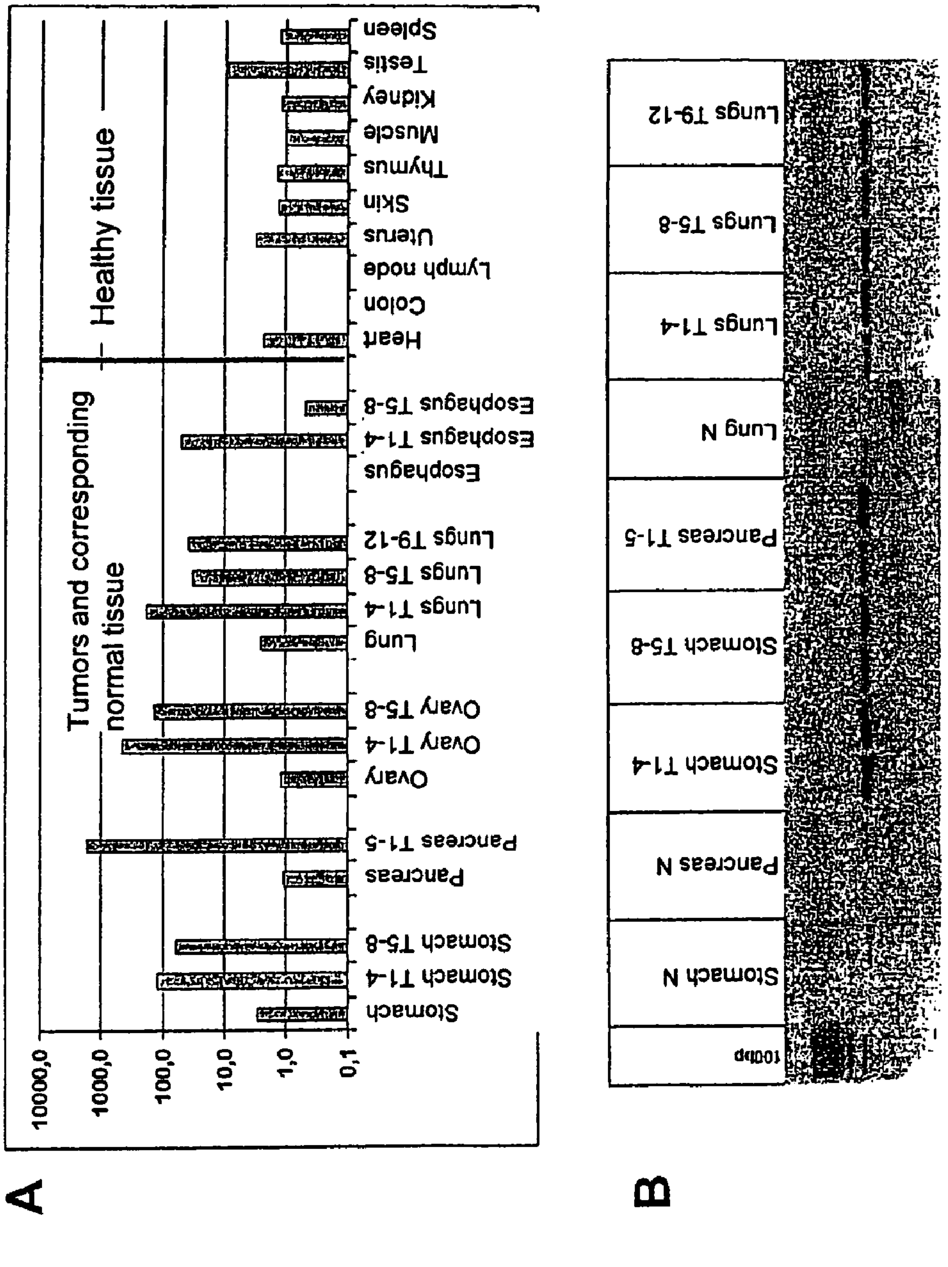

FIG. 44: qRT-PCR analysis of LOC340204-specific expression

A Quantitative analysis of LOC340204-specific expression in healthy tissue samples (left) and in tumors (pools consisting of in each case 3-5 individual samples; right). Linear representation of relative expression (-fold activation). B Gel image of selected tissue samples after gel-electrophoretic fractionation.

Figure 45:
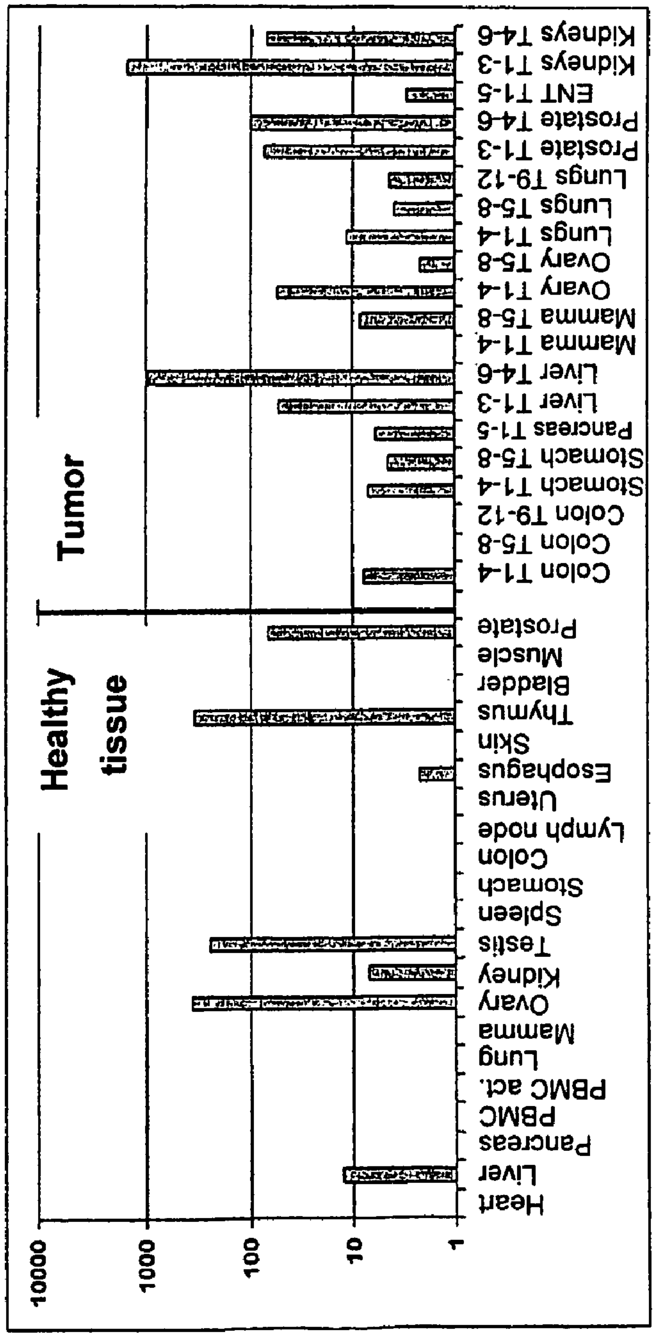

FIG. 45: qRT-PCR analysis of LOC340067-specific expression

Quantitative expression analysis of LOC340067-specific RNA in healthy tissue samples (left) and in tumors (pools consisting of in each case 3-5 individual samples; right). Logarithmic representation of relative expression (-fold activation).

Figure 46:
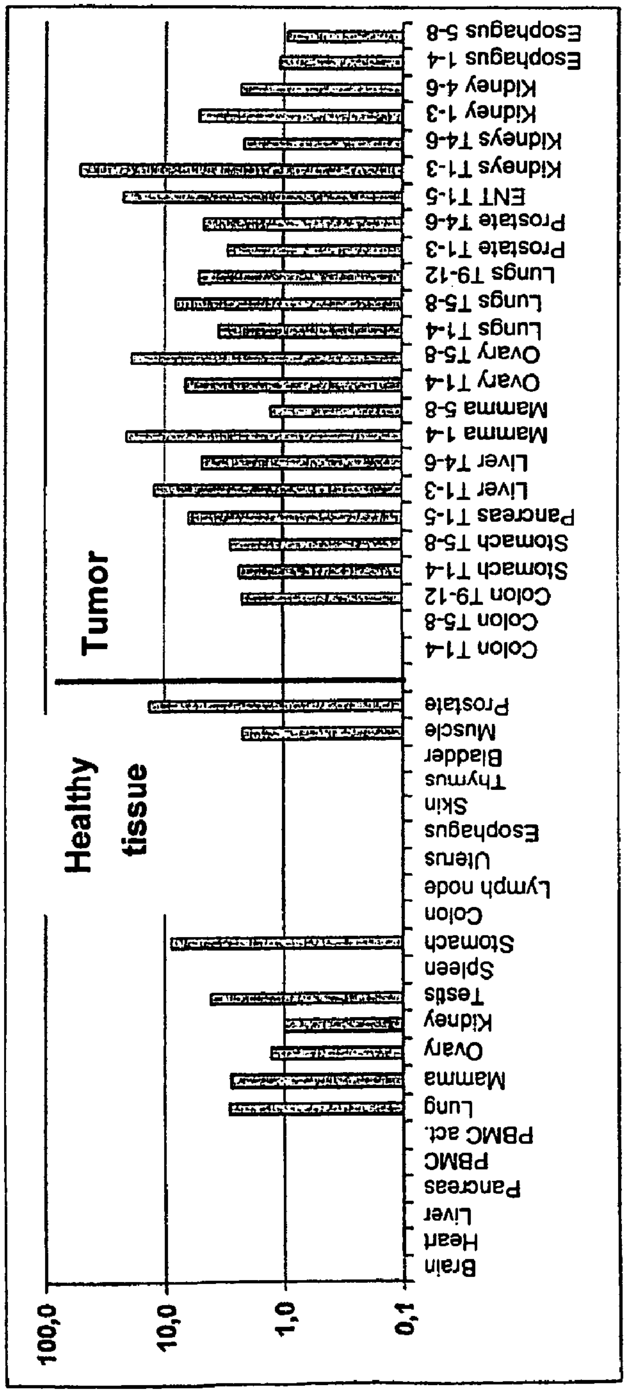

FIG. 46: qRT-PCR analysis of LOC342780-specific expression

Quantitative expression analysis of LOC342780-specific RNA in healthy tissue samples (left) and in tumors (pools consisting of in each case 3-5 individual samples; right). Logarithmic representation of relative expression (-fold activation).

Figure 47:
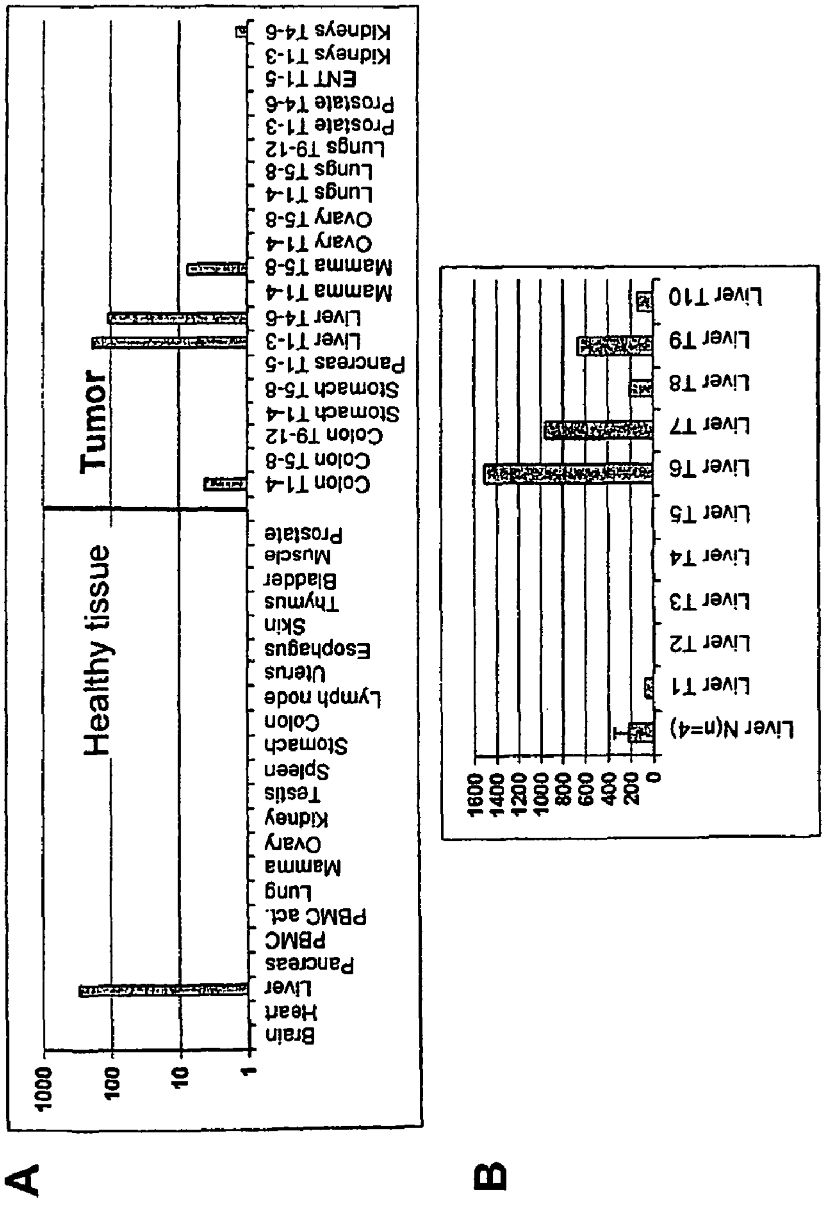

FIG. 47: qRT-PCR analysis of LOC339511-specific expression

A Quantitative analysis of LOC339511-specific expression in healthy tissue samples (left) and in tumors (pools consisting of in each case 3-5 individual samples; right). Linear representation of relative expression (-fold activation). B Detailed analysis of LOC339511-specific RNA in various liver-specific tissues; linear representation.

Figure 48:
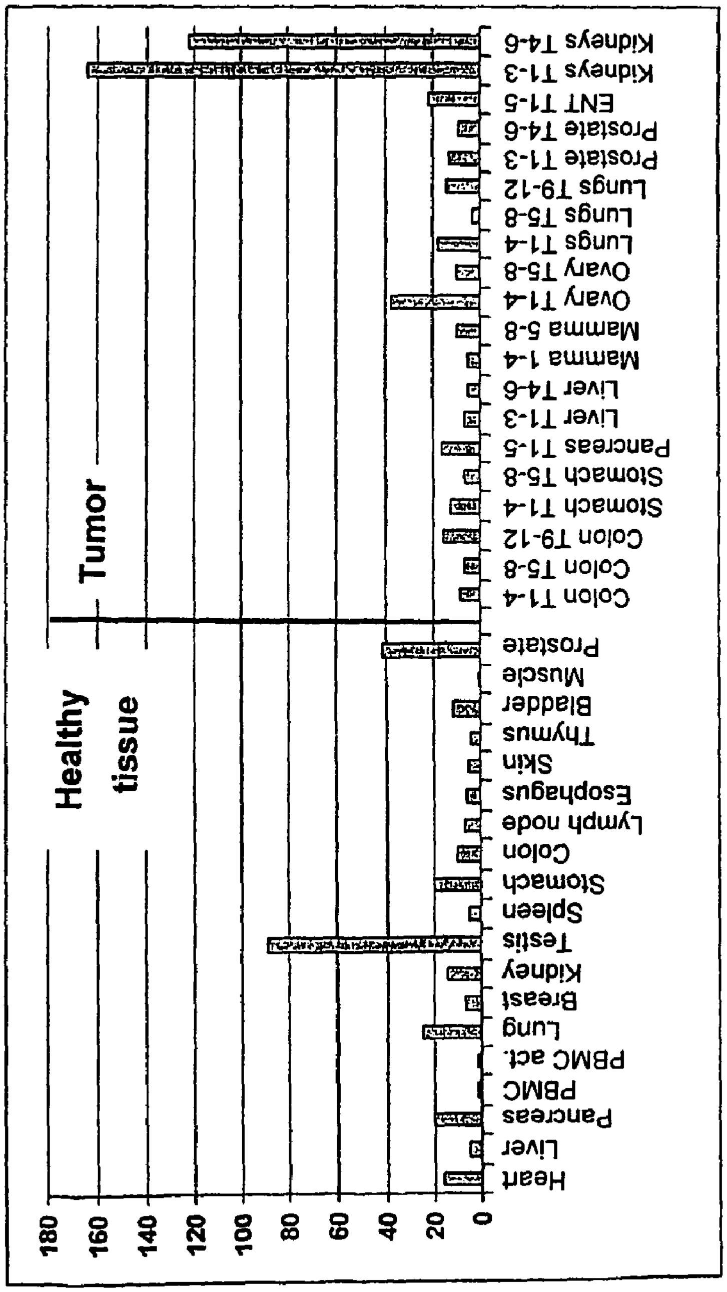

FIG. 48: qRT-PCR analysis of C14orf37-specific expression

Quantitative expression analysis of C14orf37 in healthy tissue samples (left) and in tumors (pools consisting of in each case 3-5 individual samples; right). Linear representation of relative expression (-fold activation).

Figure 49:
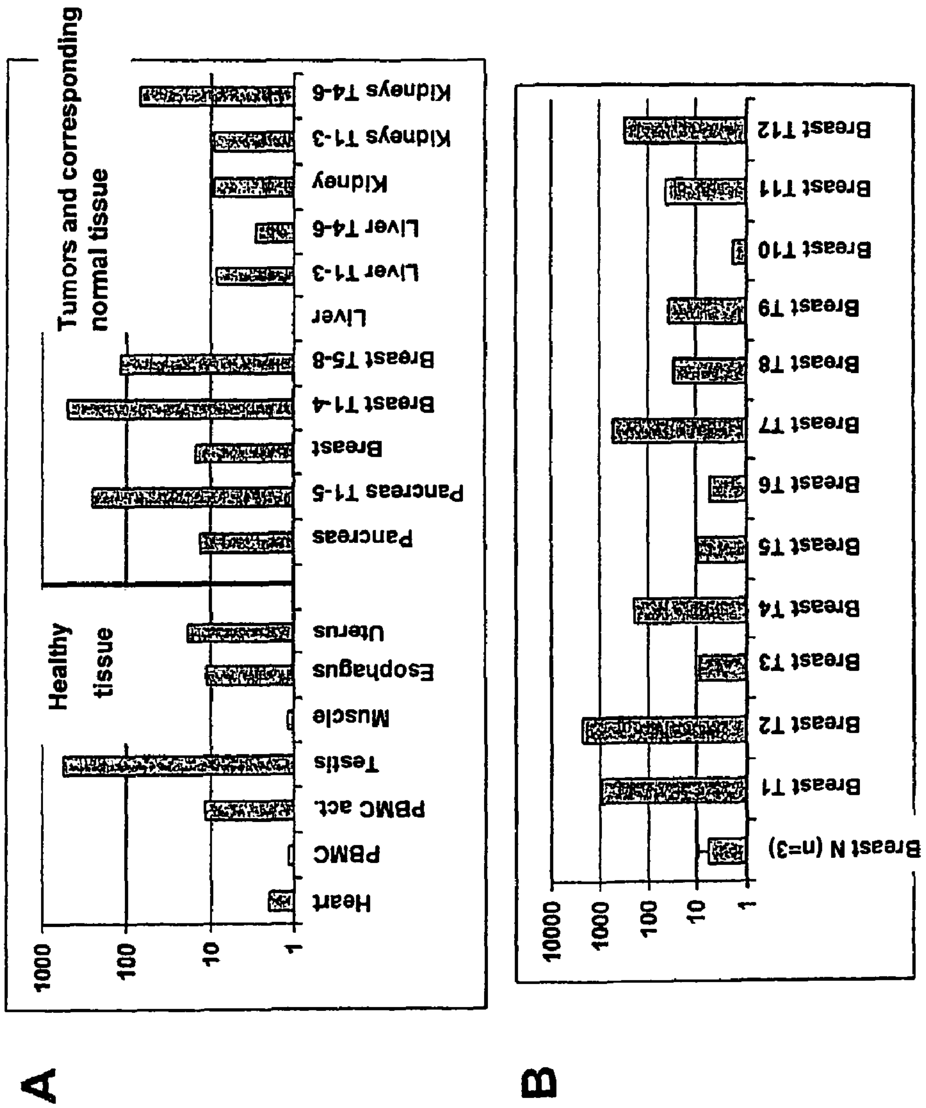

FIG. 49: qRT-PCR analysis of ATP1A4-specific expression

A Quantitative expression analysis of ATP1A4 in healthy tissue samples and in tumors (pools consisting of in each case 3-5 individual samples). Logarithmic representation of relative expression (-fold activation). B Detailed analysis of ATP1A4-specific RNA in various breast-specific tissues; logarithmic representation.

EXAMPLES

Materials and Methods

The terms "in silico" and "electronic" refer solely to the utilization of methods based on databases, which may also be used to simulate laboratory experimental processes.

Unless expressly defined otherwise, all other terms and expressions are used so as to be understood by the skilled worker. The techniques and methods mentioned are carried out in a manner known per se and are described, for example, in Sambrook et al., Molecular Cloning: A Laboratory Manual, 2nd edition (1989), Cold Spring Harbor Laboratory Press, Cold Spring Harbor, N.Y. All methods including the use of kits and reagents are carried out according to the manufacturers' information.

Example 1

Data Mining-Based Strategy for Identifying Tumor-Associated Antigens

According to the invention, public human protein and nucleic acid databases were screened with regard to cancer-specific antigens accessible on the cell surface. The definition of the screening criteria required therefor, together with high throughput methods for analyzing, if possible, all proteins, formed the central component of this strategy.

The starting point consisted of the potential genes, predicted mainly by the human genome project, which have been deposited as solely exemplary protein (XP) or mRNA (XM) entries in the RefSeq database (Pruitt et al., *Trends Genet.* January; 16(1):44-47, 2000) of the National Center for Biotechnology Information (NCBI). In another approach, the validated protein entries (NP) and, respectively, the corresponding mRNAs (NM) of the same database were also analyzed in the same manner. Following the fundamental principle of (hypothetical) gene→mRNA→protein, the proteins were first studied for the presence of transmembrane domains by combining a plurality of prediction programs for protein analysis. A total of 19 544 entries of the human XP fraction of the RefSeq database were analyzed, with 2025 hypothetical proteins satisfying said screening criteria. The human NP fraction provided a total of 19 110 entries with a proportion of 4634 filtered proteins.

The corresponding mRNA of each of these 2025 and 4634 proteins, respectively, was then subjected to a homology search in the EST database (Boguski et al., *Nat. Genet.* 4(4):332-333, 1993) of the NCBI with the aid of the BLAST algorithm (Altschul et al., *Nucleic Acids Res.* 25:3389-3402, 1997). The screening criteria in this search were set to stringent. A total of 1270 hypothetic mRNAs scored at least one hit in the EST database, with the number of hits exceeding 1000 in some cases.

Subsequently, the tissue-specific origin of the underlying cDNA library as well as the name of the library were determined for each of these valid hits. The tissues resulting therefrom were divided into 4 different groups ranging from dispensable organs (group 3) to absolutely essential organs (group 0). Another group, group 4, consisted of any samples obtained from cancer tissue. The distribution of hits to the five groups was recorded in a table which was sorted according to the best ratio of the sum of groups 3 and 4 to the sum of groups 0-2. Those mRNAs whose EST hits originated exclusively from cancer tissue reached a top position, followed by those which can additionally be found also in tissues of dispensable organs of group 3.

Since the transcripts determined in the first approach and the corresponding proteins are firstly hypothetic constructs, further screening criteria were used with the intention to prove the real existence of the mRNAs and consequently also of the proteins. For this purpose, each mRNA was compared to the predicted gene locus. Only those transcripts which have at least one splicing process, i.e. which spread over at least 2 exons, were used for more detailed analyses.

Sequential application of all the filters mentioned led to the tumor-associated antigens of the invention which can be considered extracellularly accessible, owing to a predicted transmembrane domain and the topology related thereto. The expression profile derived from the EST data indicates, in all cases, cancer-specific expression which may at most extend only to dispensable organs.

Example 2

Strategy of Validating the Tumor-Associated Antigens Identified by In Silico Analysis In order to utilize the targets for immunotherapeutic purposes (antibody therapy by means of monoclonal antibodies, vaccination, T-cell receptor-mediated therapeutic approaches; cf. EP-B-0 879 282) or other targeted approaches (small compounds, siRNA etc.) in cancer therapy as well as for diagnostic problems, the validation of the targets identified according to the invention is of central importance. In this connection, validation is carried out by expression analysis at both RNA and protein levels.

1. Examination of RNA Expression

The identified tumor antigens are first validated with the aid of RNA which is obtained from various tissues or from tissue-specific cell lines. Since the differential expression pattern of healthy tissue in comparison with tumor tissue is of decisive importance for the subsequent therapeutic application, the target genes are preferably characterized with the aid of these tissue samples.

Total RNA is isolated from native tissue samples or from tumor cell lines by standard methods of molecular biology. Said isolation may be carried out, for example, with the aid of the RNeasy Maxi kit (Qiagen, Cat. No. 75162) according to the manufacturer's instructions. This isolation method is based on the use of chaotropic reagent guanidinium isothiocyanate. Alternatively, acidic phenol can be used for isolation (Chomczynski & Sacchi, Anal. Biochem. 162: 156-159, 1987). After the tissue has been worked up by means of guanidinium isothiocyanate, RNA is extracted with acidic phenol, subsequently precipitated with isopropanol and taken up in DEPC-treated water.

2-4 μg of the RNA isolated in this way are subsequently transcribed into cDNA, for example by means of Superscript II (Invitrogen) according to the manufacturer's protocol. cDNA synthesis is primed with the aid of random hexamers (e.g. Roche Diagnostics) according to standard protocols of the relevant manufacturer. For quality control, the cDNAs are amplified over 30 cycles, using primers specific for the p53 gene which is expressed only lowly. Only p53-positive cDNA samples will be used for the subsequent reaction steps.

The targets are analyzed in detail by carrying out an expression analysis by means of PCR or quantitative PCR (qPCR) on the basis of a cDNA archive which has been isolated from various normal and tumor tissues and from tumor cell lines. For this purpose, 0.5 μl of cDNA of the above reaction mixture is amplified by a DNA polymerase (e.g. 1 U of HotStarTaq DNA polymerase, Qiagen) according to the protocols of the particular manufacturer (total volume of the reaction mixture: 25-50 μl). Aside from said polymerase, the amplification mixture comprises 0.3 mM dNTPs, reaction buffer (final concentration 1×, depending on the manufacturer of the DNA polymerase) and in each case 0.3 mM gene-specific forward and reverse primers.

The specific primers of the target gene are, as far as possible, selected in such a way that they are located in two different exons so that genomic contaminations do not lead to false-positive results. In a non-quantitative end point PCR, the cDNA is typically incubated at 95° C. for 15 minutes in order to denature the DNA and to activate the Hot-Start enzyme. Subsequently the DNA is amplified over 35 cycles (1 min at 95° C., 1 min at the primer-specific hybridization temperature (approx. 55-65° C.), 1 min at 72° C. to elongate the amplicons). Subsequently, 10 μl of the PCR mixture are applied to agarose gels and fractionated in the electric field. The DNA is made visible in the gels by staining with ethidium bromide and the PCR result is documented by way of a photograph.

As an alternative to conventional PCR, expression of a target gene may also be analyzed by quantitative real time PCR. Meanwhile various analytical systems are available for this analysis, of which the best known ones are the ABI PRISM sequence detection system (TaqMan, Applied Biosystems), the iCycler (Biorad) and the Light cycler (Roche Diagnostics). As described above, a specific PCR mixture is subjected to a run in the real time instruments. By adding a DNA-intercalating dye (e.g. ethidium bromide, CybrGreen), the newly synthesized DNA is made visible by specific light excitation (according to the dye manufacturers' information). A multiplicity of points measured during amplification enables the entire process to be monitored and the nucleic acid concentration of the target gene to be determined quantitatively. The PCR mixture is normalized by measuring a housekeeping gene (e.g. 18S RNA, β-actin). Alternative strategies via fluorescently labeled DNA probes likewise allow quantitative determination of the target gene of a specific tissue sample (see TaqMan applications from Applied Biosystems).

2. Cloning

The complete target gene which is required for further characterization of the tumor antigen is cloned according to common molecular-biological methods (e.g. in "Current Protocols in Molecular Biology", John Wiley & Sons Ltd., Wiley InterScience). In order to clone the target gene or to analyze its sequence, said gene is first amplified by a DNA polymerase having a proof reading function (e.g. pfu, Roche Diagnostics). The amplicon is then ligated by standard methods into a cloning vector. Positive clones are identified by sequence analysis and subsequently characterized with the aid of prediction programs and known algorithms.

3. Prediction of the Protein

Many of the genes found according to the invention (in particular those from the RefSeq XM domain) are newly discovered genes which require cloning of the full-length gene, determination of the open reading frame and deduction and analysis of the protein sequence. In order to clone the full-length sequence, we used common protocols for the rapid amplification of cDNA ends and the screening of cDNA expression libraries with gene-specific probes (Sambrook et al., *Molecular Cloning: A Laboratory Manual,* 2nd edition (1989), Cold Spring Harbor Laboratory Press, Cold Spring Harbor, N.Y.).

After assembling the fragments found in this way, potential open reading frames (ORF) were predicted using common prediction programs. Since the position of the PolyA tail and of polyadenylation motifs predetermines the orientation of the potential gene product, only the 3 reading frames of that particular orientation remain out of a possible 6 reading frames. The former often yield only one sufficiently large open reading frame which may code for a protein, while the other reading frames have too many stop codons and would not code for any realistic protein. In the case of alternative open reading frames, identification of the authentic ORF is assisted by taking into account the Kozak criteria for optimal transcription initiation and by analyzing the deduced protein sequences which may arise. Said ORF is further verified by generating immune sera against proteins deduced from the potential ORFs and analyzing said immune sera for recognition of a real protein in tissues and cell lines.

4. Production of Antibodies

The tumor-associated antigens identified according to the invention are characterized, for example, by using antibodies. The invention further comprises the diagnostic or therapeutic use of antibodies. Antibodies may recognize proteins in the native and/or denatured state (Anderson et al., *J. Immunol.* 143: 1899-1904, 1989; Gardsvoll, *J. Immunol. Methods* 234: 107-116, 2000; Kayyem et al., *Eur. J. Biochem.* 208: 1-8, 1992; Spiller et al., *J. Immunol. Methods* 224: 51-60, 1999).

Antisera comprising specific antibodies which specifically bind to the target protein may be prepared by various standard methods; cf., for example, "Monoclonal Antibodies: A Practical Approach" by Phillip Shepherd, Christopher Dean ISBN 0-19-963722-9, "Antibodies: A Laboratory Manual" by Ed Harlow, David Lane ISBN: 0879693142 and "Using Antibodies: A Laboratory Manual Portable Protocol NO" by Edward Harlow, David Lane, Ed Harlow ISBN: 0879695447. It is also possible here to generate affine and specific antibodies which recognize complex membrane proteins in their native form (Azorsa et al., *J. Immunol. Methods* 229: 35-48, 1999; Anderson et al., *J. Immunol.* 143: 1899-1904, 1989; Gardsvoll, *J. Immunol. Methods.* 234: 107-116, 2000). This is especially important in the preparation of antibodies which are intended to be used therapeutically but also for many diagnostic applications. For this purpose, both the complete protein and extracellular partial sequences may be used for immunization.

Immunization and Production of Polyclonal Antibodies

A species (e.g. rabbits, mice) is immunized by a first injection of the desired target protein. The immune response of the animal to the immunogen can be enhanced by a second or third immunization within a defined period of time (approx. 2-4 weeks after the previous immunization). Blood is taken from said animals and immune sera obtained, again after various defined time intervals (1st bleeding after 4 weeks, then every 2-3 weeks, up to 5 takings). The immune sera taken in this way comprise polyclonal antibodies which may be used to detect and characterize the target protein in Western blotting, by flow cytometry, immunofluorescence or immunohistochemistry.

The animals are usually immunized by any of four well-established methods, with other methods also in existence. The immunization may be carried out using peptides specific for the target protein, using the complete protein, using extracellular partial sequences of a protein which can be identified experimentally or via prediction programs. Since the prediction programs do not always work perfectly, it is also possible to employ two domains separated from one another by a transmembrane domain. In this case, one of the two domains has to be extracellular, which may then be proved experimentally (see below).

(1) In the first case, peptides (length: 8-12 amino acids) are synthesized by in vitro methods (possibly carried out by a commercial service), and said peptides are used for immunization. Normally 3 immunizations are carried out (e.g. with a concentration of 5-100 μg/immunization). The immunization may also be carried out by commercial service providers.

(2) Alternatively, immunization may be carried out using recombinant proteins. For this purpose, the cloned DNA of the target gene is cloned into an expression vector and the target protein is synthesized, for example, cell-free in vitro, in bacteria (e.g. *E. coli*), in yeast (e.g. *S. pombe*), in insect cells or in mammalian cells, according to the conditions of the particular manufacturer (e.g. Roche Diagnostics, Invitrogen, Clontech, Qiagen). It is also possible to synthesize the target protein with the aid of viral expression systems (e.g. baculovirus, vacciniavirus, adenovirus). After it has been synthesized in one of said systems, the target protein is purified, normally by employing chromatographic methods. In this context, it is also possible to use for immunization proteins which have a molecular anchor as an aid for purification (e.g. His tag, Qiagen; FLAG tag, Roche Diagnostics; GST fusion proteins). A multiplicity of protocols can be found, for example, in "Current Protocols in Molecular Biology", John Wiley & Sons Ltd., Wiley InterScience. After the target protein has been purified, an immunization is carried out as described above.

(3) If a cell line is available which synthesizes the desired protein endogenously, it is also possible to use this cell line directly for preparing the specific antiserum. In this case, immunization is carried out by 1-3 injections with in each case approx. $1\text{-}5\times10^7$ cells.

(4) The immunization may also be carried out by injecting DNA (DNA immunization). For this purpose, the target gene is first cloned into an expression vector so that the target sequence is under the control of a strong eukaryotic promoter (e.g. CMV promoter). Subsequently, DNA (e.g. 1-10 μg per injection) is transferred as immunogen using a gene gun into capillary regions with a strong blood flow in an organism (e.g. mouse, rabbit). The transferred DNA is taken up by the animal's cells, the target gene is expressed, and the animal finally develops an immune response to the target protein (Jung et al., *Mol. Cells* 12: 41-49, 2001; Kasinrerk et al., *Hybrid Hybridomics* 21: 287-293, 2002).

Production of Monoclonal Antibodies

Monoclonal antibodies are traditionally produced with the aid of the hybridoma technology (technical details: see "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142, "Using Antibodies: A Laboratory Manual Portable Protocol NO" by Edward Harlow, David Lane, Ed Harlow ISBN: 0879695447). A new method which is also used is the "SLAM" technology. Here, B cells are isolated from whole blood and the cells are made monoclonal. Subsequently the supernatant of the isolated B cell is analyzed for its antibody specificity. In contrast to the hybridoma technology, the variable region of the antibody gene is then amplified by single-cell PCR and cloned into a suitable vector. In this manner production of monoclonal antibodies is accelerated (de Wildt et al., J. Immunol. Methods 207:61-67, 1997).

5. Validation of the Targets by Protein-Chemical Methods Using Antibodies

The antibodies which can be produced as described above can be used to make a number of important statements about the target protein. Specifically the following analyses of validating the target protein are useful:

Specificity of the Antibody

Assays based on cell culture with subsequent Western blotting are most suitable for demonstrating the fact that an antibody binds specifically only to the desired target protein (various variations are described, for example, in "Current Protocols in Proteinchemistry", John Wiley & Sons Ltd., Wiley InterScience). For the demonstration, cells are transfected with a cDNA for the target protein, which is under the control of a strong eukaryotic promoter (e.g. cytomegalovirus promoter; CMV). A wide variety of methods (e.g. electroporation, liposome-based transfection, calcium phosphate precipitation) are well established for transfecting cell lines with DNA (e.g. Lemoine et al., *Methods Mol. Biol.* 75: 441-7, 1997). As an alternative, it is also possible to use cell lines which express the target gene endogenously (detection via target gene-specific RT-PCR). As a control, in the ideal case, homologous genes are cotransfected in the experiment, in order to be able to demonstrate in the following Western blot the specificity of the analyzed antibody.

In the subsequent Western blotting, cells from cell culture or tissue samples which might contain the target protein are lysed in a 1% strength SDS solution, and the proteins are denatured in the process. The lysates are fractionated according to size by electrophoresis on 8-15% strength denaturing polyacrylamide gels (contain 1% SDS) (SDS polyacrylamide gel electrophoresis, SDS-PAGE). The proteins are then transferred by one of a plurality of blotting methods (e.g. semi-dry electroblot; Biorad) to a specific membrane (e.g. nitrocellulose, Schleicher & Schüll). The desired protein can be visualized on this membrane. For this purpose, the membrane is first incubated with the antibody which recognizes the target protein (dilution approx. 1:20-1:200, depending on the specificity of said antibody), for 60 minutes. After a washing step, the membrane is incubated with a second antibody which is coupled to a marker (e.g. enzymes such as peroxidase or alkaline phosphatase) and which recognizes the first antibody. It is then possible to make the target protein visible on the membrane in a color or chemiluminescent reaction (e.g. ECL, Amersham Bioscience). An antibody with a high specificity for the target protein should in the ideal case only recognise the desired protein itself.

Localization of the Target Protein

Various methods are used to confirm the membrane localization, identified in the in silico approach, of the target protein. An important and well-established method using the antibodies described above is immunofluorescence (IF). For this purpose, cells of established cell lines which either synthesize the target protein (detection of the RNA by RT-PCR or of the protein by Western blotting) or else have been transfected with plasmid DNA are utilized. A wide variety of methods (e.g. electroporation, liposome-based transfection, calcium phosphate precipitation) are well established for transfection of cell lines with DNA (e.g. Lemoine et al., *Methods Mol. Biol.* 75: 441-7, 1997). The plasmid transfected into the cells, in immunofluorescence, may encode the unmodified protein or else couple different amino acid markers to the target protein. The principle markers are, for example, the fluorescent green fluorescent protein (GFP) in various differentially fluorescent forms, short peptide sequences of 6-12 amino acids for which high-affinity and specific antibodies are available, or the short amino acid sequence Cys-Cys-X-X-Cys-Cys which can bind via its cysteines specific fluorescent substances (Invitrogen). Cells which synthesize the target protein are fixed, for example, with paraformaldehyde or methanol. The cells may then, if required, be permeabilized by incubation with detergents (e.g. 0.2% Triton X-100). The cells are then incubated with a primary antibody which is directed against the target protein or against one of the coupled markers. After a washing step, the mixture is incubated with a second antibody coupled to a fluorescent marker (e.g. fluorescein, Texas Red, Dako), which binds to the first antibody. The cells labeled in this way are then overlaid with glycerol and analyzed with the aid of a fluorescence microscope according to the manufacturer's information. Specific fluorescence emissions are achieved in this case by specific excitation depending on the substances employed. The analysis usually permits reliable localization of the target protein, the antibody quality and the target protein being confirmed in double stainings with, in addition to the target protein, also the coupled amino acid markers or other marker proteins whose localization has already been described in the literature being stained. GFP and its derivatives represent a special case, being excitable directly and themselves fluorescing. The membrane permeability which may be controlled through the use of detergents, in immunofluorescence, allows demonstration of whether an immunogenic epitope is located inside or outside the cell. The prediction of the selected proteins can thus be supported experimentally. An alternative possibility is to detect extracellular domains by means of flow cytometry. For this purpose, cells are fixed under non-permeabilizing conditions (e.g. with PBS/Na azide/2% FCS/5 mM EDTA) and analyzed in a flow cytometer in accordance with the manufacturer's instructions. Only extracellular epitopes can be recognized by the antibody to be analyzed in this method. A difference from immunofluorescence is that it is possible to distinguish between dead and living cells by using, for example, propidium iodide or Trypan blue, and thus avoid false-positive results.

Another important detection is by immunohistochemistry (IHC) on specific tissue samples. The aim of this method is to identify the localization of a protein in a functionally intact tissue aggregate. IHC serves specifically for (1) being able to estimate the amount of target protein in tumor and normal tissues, (2) analyzing how many cells in tumor and healthy tissues synthesize the target gene, and (3) defining the cell type in a tissue (tumor, healthy cells) in which the target protein is detectable. Alternatively, the amounts of protein of a target gene may be quantified by tissue immunofluorescence using a digital camera and suitable software (e.g. Tillvision, Till-photonics, Germany). The technology has frequently been published, and details of staining and microscopy can therefore be found, for example, in "Diagnostic Immunohistochemistry" by David J., MD Dabbs ISBN: 0443065667 or in "Microscopy, Immunohistochemistry, and Antigen Retrieval Methods For Light and Electron Microscopy" ISBN: 0306467704. It should be noted that, owing to the properties of antibodies, different protocols have to be used (an example is described below) in order to obtain a meaningful result.

Normally, histologically defined tumor tissues and, as reference, comparable healthy tissues are employed in IHC. It is also possible to use as positive and negative controls cell lines in which the presence of the target gene is known through RT-PCR analyses. A background control must always be included.

Formalin-fixed (another fixation method, for example with methanol, is also possible) and paraffin-embedded tissue pieces with a thickness of 4 μm are applied to a glass support and deparaffinated with xylene, for example. The samples are washed with TBS-T and blocked in serum. This is followed by incubation with the first antibody (dilution: 1:2 to 1:2000) for 1-18 hours, with affinity-purified antibodies normally being used. A washing step is followed by incubation with a second antibody which is coupled to an alkaline phosphatase (alternative: for example peroxidase) and directed against the first antibody, for approx. 30-60 minutes. This is followed by a color reaction using said alkaline phosphatase (cf., for example, Shi et al., *J. Histochem. Cytochem.* 39: 741-748, 1991; Shin et al., *Lab. Invest.* 64: 693-702, 1991). To demonstrate antibody specificity, the reaction can be blocked by previous addition of the immunogen.

Analysis of Protein Modifications

Secondary protein modifications such as, for example, N- and O-glycosylations or myristilations may impair or even completely prevent the accessibility of immunogenic epitopes and thus call into question the efficacy of antibody therapies. Moreover, it has frequently been demonstrated that the type and amount of secondary modifications differ in normal and tumor tissues (e.g. Durand & Seta, 2000; Clin. Chem. 46: 795-805; Hakomori, 1996; Cancer Res. 56: 5309-18). The analysis of these modifications is therefore essential to the therapeutic success of an antibody. Potential binding sites can be predicted by specific algorithms.

Analysis of protein modifications usually takes place by Western blotting (see above). Glycosylations which usually have a size of several kDa, especially lead to a larger total mass of the target protein, which can be fractionated in SDS-PAGE. To detect specific O- and N-glycosidic bonds, protein lysates are incubated prior to denaturation by SDS with O- or N-glycosylases (in accordance with their respective manufacturer's instructions, e.g. PNgase, endoglycosidase F, endoglycosidase H, Roche Diagnostics). This is followed by Western blotting as described above. Thus, if there is a reduction in the size of a target protein after incubation with a glycosidase, it is possible to detect a specific glycosylation and, in this way, also analyze the tumor specificity of a modification.

Functional Analysis of the Target Gene

The function of the target molecule may be crucial for its therapeutic usefulness, so that functional analyses are an important component in the characterization of therapeutically utilizable molecules. The functional analysis may take place either in cells in cell culture experiments or else in vivo with the aid of animal models. This involves either switching off the gene of the target molecule by mutation (knockout) or inserting the target sequence into the cell or the organism (knockin). Thus it is possible to analyze functional modifications in a cellular context firstly by way of the loss of function of the gene to be analyzed (loss of function). In the second case, modifications caused by addition of the analyzed gene can be analyzed (gain of function).

a. Functional Analysis in Cells

Transfection. In order to analyze the gain of function, the gene of the target molecule must be transferred into the cell. For this purpose, cells which allow synthesis of the target molecule are transfected with a DNA. Normally, the gene of the target molecule here is under the control of a strong eukaryotic promoter (e.g. cytomegalovirus promoter; CMV). A wide variety of methods (e.g. electroporation, liposome-based transfection, calcium phosphate precipitation) are well established for transfecting cell lines with DNA (e.g. Lemoine et al., *Methods Mol. Biol.* 75: 441-7, 1997). The gene may be synthesized either transiently, without genomic integration, or else stably, with genomic integration after selection with neomycin, for example.

RNA interference (siRNA). An inhibition of expression of the target gene, which may induce a complete loss of function of the target molecule in cells, may be generated by the RNA interference (siRNA) technology in cells (Hannon, G J. 2002. RNA interference. Nature 418: 244-51; Czauderna et al. 2003. Nucl. Acid Res. 31: 670-82). For this purpose, cells are transfected with short, double-stranded RNA molecules of approx. 20-25 nucleotides in length, which are specific for the target molecule. An enzymic process then results in degradation of the specific RNA of the target gene and thus in an inhibition of the function of the target protein and consequently enables the target gene to be analyzed.

Cell lines which have been modified by means of transfection or siRNA may subsequently be analyzed in different ways. The most common examples are listed below.

1. Proliferation and Cell Cycle Behavior

A multiplicity of methods for analyzing cell proliferation are established and are commercially supplied by various companies (e.g. Roche Diagnostics, Invitrogen; details of the assay methods are described in the numerous application protocols). The number of cells in cell culture experiments can be determined by simple counting or by calorimetric assays which measure the metabolic activity of the cells (e.g. wst-1, Roche Diagnostics). Metabolic assay methods measure the number of cells in an experiment indirectly via enzymic markers. Cell proliferation may be measured directly by analyzing the rate of DNA synthesis, for example by adding bromodeoxyuridine (BrdU), with the integrated BrdU being detected calorimetrically via specific antibodies.

2. Apoptosis and Cytotoxicity

A large number of assay systems for detecting cellular apoptosis and cytotoxicity are available. A decisive characteristic is the specific, enzyme-dependent fragmentation of genomic DNA, which is irreversible and results in certain death of the cell. Methods for detecting these specific DNA fragments are commercially obtainable. An additional method available is the TUNEL assay which can detect DNA single-strand breaks also in tissue sections. Cytotoxicity is mainly detected via an altered cell permeability which serves as marker of the vitality state of cells. This involves on the one hand the analysis of markers which can typically be found intracellularly in the cell culture supernatant. On the other hand, it is also possible to analyze the absorbability of dye markers which are not absorbed by intact cells. The best-known examples of dye markers are Trypan blue and propidium iodide, a common intracellular marker is lactate dehydrogenase which can be detected enzymatically in the supernatant. Different assay systems of various commercial suppliers (e.g. Roche Diagnostics, Invitrogen) are available.

3. Migration Assay

The ability of cells to migrate is analyzed in a specific migration assay, preferably with the aid of a Boyden chamber (Corning Costar) (Cinamon G., Alon R. J. Immunol. Methods. 2003 February; 273(1-2):53-62; Stockton et al. 2001. Mol. Biol. Cell. 12: 1937-56). For this purpose, cells are cultured on a filter with a specific pore size. Cells which can migrate are capable of migrating through this filter into another culture vessel below. Subsequent microscopic analysis then permits determination of a possibly altered migration behavior induced by the gain of function or loss of function of the target molecule.

b. Functional Analysis in Animal Models

A possible alternative of cell culture experiments for the analysis of target gene function are complicated in vivo experiments in animal models. Compared to the cell-based methods, these models have the advantage of being able to detect faulty developments or diseases which are detectable only in the context of the whole organism. A multiplicity of models for human disorders are available by now (Abate-Shen & Shen. 2002. Trends in Genetics S1-5; Matsusue et al. 2003. J. Clin. Invest. 111:737-47). Various-animal models such as, for example, yeast, nematodes or zebra fish have since been characterized intensively. However, models which are preferred over other species are mammalian animal models such as, for example, mice (*Mus musculus*) because they offer the best possibility of reproducing the biological processes in a human context. For mice, on the one hand transgenic methods which integrate new genes into the mouse genome have been established in recent years (gain of function; Jegstrup I. et al. 2003. Lab Anim. 2003 January; 37(1): 1-9). On the other hand, other methodical approaches switch off genes in the mouse genome and thus induce a loss of function of a desired gene (knockout models, loss of function; Zambrowicz B P & Sands A T. 2003. Nat. Rev. Drug Discov. 2003 January; 2(1):38-51; Niwa H. 2001. Cell Struct. Funct. 2001 June; 26(3):137-48); technical details have been published in large numbers.

After the mouse models have been generated, alterations induced by the transgene or by the loss of function of a gene can be analyzed in the context of the whole organism (Balling R, 2001. Ann. Rev. Genomics Hum. Genet. 2:463-92). Thus it is possible to carry out, for example, behavior tests as well as to biochemically study established blood parameters. Histological analyses, immunohistochemistry or electron microscopy enable alterations to be characterized at the cellular level. The specific expression pattern of a gene can be detected by in-situ hybridization (Peters T. et al. 2003. Hum. Mol. Genet. 12:2109-20).

Example 3

Identification of SEQ ID NO: 1/2 as a Diagnostic and Therapeutic Cancer Target SEQ ID NO: 1 (nucleic acid sequence) is encoded by a new gene on chromosome 6 (6q26-27) and represents the deduced protein sequence (SEQ ID NO: 2). An alternative open reading frame of this gene locus is SEQ ID NO: 267 which codes for the deduced protein sequence SEQ ID NO: 268. Both protein sequences show no homologies to previously known proteins.

According to the invention, the amount of gene-specific transcripts in healthy tissue and in carcinoma samples was investigated after establishing a specific quantitative RT-PCR (primer pair SEQ ID NO: 3 and 4). The transcript was not detected in any of the normal tissues analyzed. Surprisingly, we detected very specifically substantial amounts of said transcript in almost all melanoma samples studied, although the gene is not expressed in normal skin as tissue of origin (FIG. 1). The selectivity of this marker for melanomas was confirmed by a conventional RT-PCR (FIG. 2). Surprisingly, we amplified in the process two fragments which reflect gene-specific variants (probably SEQ ID NO: 1 and SEQ ID NO: 267).

We thus demonstrate that this gene is an absolutely specific marker for melanoma cells and, due to its absence in each of the normal tissues studied, is suitable as biomarker for targeted therapeutic and diagnostic approaches.

In particular it is possible to utilize according to the invention extracellular portions of SEQ ID NO: 2 or 268 as target structure of monoclonal antibodies. This applies inter alia to the following epitopes: amino acids 1-50 based on SEQ ID NO: 2, amino acids 1-12 based on SEQ ID NO: 268, amino acids 70-88 based on SEQ ID NO: 2, amino acids 33-129 based on SEQ ID NO: 268, and SEQ ID NO: 281.

According to the invention, other target-oriented approaches such as vaccines and therapies with small compounds, which have only this gene as target structure and thus do not affect any healthy cells, are also therapeutically conceivable. Said gene may also be utilized diagnostically owing to its selectivity for tumor cells.

Example 4

Identification of SEQ ID NO: 5/6 as Diagnostic and Therapeutic Cancer Target SEQ ID NO: 5 (nucleic acid sequence) is encoded by a new gene on chromosome 11 (11q12.1) and represents the deduced protein sequence (SEQ ID NO: 6). An alternative open reading frame of this gene locus is SEQ ID NO: 269 which codes for the deduced protein sequence SEQ ID NO: 270. Both protein sequences show no homologies to previously known proteins.

According to the invention, the amount of gene-specific transcript in healthy tissue and in carcinoma samples (in each case pool of samples) was studied after establishing a gene-specific quantitative RT-PCR (primer pair SEQ ID NO: 7 and 8). We detected no specific RNA at all or else only small amounts thereof in the healthy tissues we studied, with the exception of testis (FIG. 3; A quantitative RT-PCR; B gel image). Consequently, there is a high probability of the locus expressing a germ cell-specific gene product. However, the gene is activated in many tumor samples, and specific RNA was detectable in substantial amounts (FIG. 3). The highest prevalence and level of expression were found in renal cell tumors. But specific transcripts were also detectable in gastric, pancreatic, ENT and lung tumors (FIG. 4; A quantitative RT-PCR; B gel image). Even repeated examinations of the corresponding normal tissues were unable to detect gene-specific transcripts. In order to additionally prove expression from this gene locus, a Northern blot was additionally carried out. For this purpose, a probe was prepared in a specific PCR of primers SEQ ID NO: 7 and 8 with incorporation of digoxigenin-dUTP (Roche Diagnostics) according to the manufacturer's instructions. The probe was then hybridized with 2 μg (FIG. 5, lane 1) and 1 μg (FIG. 5, lane 2), respectively, of total RNA from testis tissue and the digoxigenin of said probe was subsequently detected in a specific color reaction. An approx. 3.1 kB gene-specific fragment was detected in the experiment (FIG. 5) and thus additionally confirmed expression of this locus. Said gene locus is thus a typical representative of the class of the "cancer/testis antigens" which are expressed in normal tissues virtually exclusively in the germ cells of the testis. In tumors, however, cancer/testis antigens are frequently switched on, although they are not expressed in the underlying somatic normal tissue cells. Several members of this functionally and structurally heterogeneous class are already tested for specific immunotherapeutic approaches with cancers in phase I/II studies, owing to their attractive selective tissue distribution (e.g. Scanlan M J, Gure A O, Jungbluth A A, Old L J, Chen Y T. 2002. Immunol. Rev. 2002 October; 188:22-32).

Antibodies may be produced by utilizing the peptides according to SEQ ID NO: 282 and 283. In particular, according to the invention it is possible to utilize the extracellular domains of SEQ ID NO: 6 and SEQ ID NO: 270 as target structures of monoclonal antibodies.

Example 5

Identification of LOC203413 as Diagnostic and Therapeutic Cancer Target

The gene or protein of the gene locus LOC203413 (nucleic acid sequence: SEQ ID NO: 9; amino acid sequence: SEQ ID NO: 10) is a gene on the X chromosome (Xq24), which has not been characterized previously. Aside from a transmembrane domain, it has no further functional motifs and no homologies to previously known proteins.

According to the invention, the amount of transcript in healthy tissue and in carcinoma samples (pool of samples, number indicated in the figure) was studied after establishing an LOC203413-specific quantitative RT-PCR (primer pair SEQ ID NO: 11 and 12) (FIG. 6; A: quantitative evaluation, B: image after gel-electrophoretic fractionation). LOC203413-specific RNA cannot be detected in any of the healthy tissues we studied, with the exception of testis. Consequently, it is highly probable that LOC203413 is a germ cell-specific gene product. As FIG. 6 reveals, LOC203413-specific transcripts were detectable in gastric, pancreatic, esophageal, mammary, ovarian and prostate carcinomas, with high expression being observed in particular in gastric and mammary carcinomas. For a more detailed analysis, healthy gastric samples and gastric carcinoma samples were additionally characterized in a quantitative RT-PCR (FIG. 7A). LOC203413 was expressed in 70% of the carcinomas, whereas no significant expression was detectable in any of the healthy gastric samples. The MKN45 cell line which is derived from a gastric carcinoma also expresses LOC203413. In addition, specific expression was detected in ⅔rds of pancreatic tumors studied and in 40% of liver carcinomas (FIG. 7B).

LOC203413 is thus a typical representative of the class of cancer/testis antigens which are expressed in normal tissues exclusively in the germ cells of the testis. In tumors, however, cancer/testis antigens are frequently switched on, although they are not expressed in the underlying somatic normal tissue cells. Several members of this functionally and structurally heterogeneous class are already tested for specific immunotherapeutic approaches with cancers in phase I/II studies, owing to their attractive selective tissue distribution (e.g. Scanlan M J, Gure A O, Jungbluth A A, Old L J, Chen Y T. 2002. Immunol. Rev. 2002 October; 188:22-32).

In particular it is possible to utilize according to the invention the extracellular domain of LOC203413 as target structure of monoclonal antibodies. Thus the amino acids 22-113 (SEQ ID NO: 284) are of interest as epitopes. Conserved N-glycosylation motifs are located in the sequence at amino acid positions 34 and 83, based on SEQ ID NO: 10, which motifs may be suitable in particular for producing tumor-specific antibodies. LOC203413-specific antibodies were produced by using the peptides listed under SEQ ID NO: 285 and 286.

According to the invention, other target-oriented approaches such as vaccines and therapies with small compounds, which have only this gene as target structure and thus do not affect any healthy cells, are also therapeutically conceivable. Said gene may also be utilized diagnostically owing to its selectivity for tumor cells.

Example 6

Identification of LOC90625 as a Diagnostic and Therapeutic Cancer Target

The gene LOC90625 (nucleic acid sequence: SEQ ID NO: 13) is a gene on chromosome 21 (21q22.3), which has not been characterized previously. It encodes a protein (amino acid sequence: SEQ ID NO: 14) having a transmembrane domain but otherwise no homologies to previously known proteins.

According to the invention, the amount of gene-specific transcripts in healthy tissue and in carcinoma samples (pool of samples, the number is indicated in the figure) was investigated after establishing an LOC90625-specific quantitative RT-PCR (primer pair SEQ ID NO: 15 and 16) (FIG. 8). LOC90625 is expressed very selectively in healthy tissue, with specific transcripts being detectable especially in testis. In all other healthy tissues analyzed LOC90625-specific expression was detectable only at a low level, if at all (FIG. 8). Surprisingly, we detected LOC90625-specific overexpression in some types of tumors. LOC90625 was strongly overexpressed in particular in prostate, esophageal and pancreatic carcinomas, in comparison to the respective healthy tissue samples (FIGS. 8 and 9A).

LOC90625 is a selectively expressed antigen which is obviously increasingly expressed in proliferating tissues. Thus a selective overexpression in tumors can be observed which is therapeutically utilizable.

The extracellular domain of LOC90625 in particular can be utilized according to the invention as target structure of monoclonal antibodies. Said structure may be, for example, 1-19 (SEQ ID NO: 287) or else the amino acids 40-160 (SEQ ID NO: 288). LOC203413-specific antibodies were produced by using the peptides according to SEQ ID NO: 289 and 290.

Example 7

Identification of the FAM26A Protein as a Diagnostic and Therapeutic Cancer Target The FAM26A gene (SEQ ID NO: 17; NM_182494) which is located on chromosome 10 (10q24) encodes the gene product of SEQ ID NO: 18 (NP_872300). FAM26A has several transmembrane domains, with an N-glycosylation motif being located at amino acid position 142. The deduced protein sequence displays a distant homology to the PMP/claudin family.

According to the invention, the amount of gene-specific transcripts in healthy tissue and in tumor samples was investigated after establishing an FAM26A-specific quantitative RT-PCR (primer pair SEQ ID NO: 19 and 20) (FIG. 10). Surprisingly, we were able to detect overexpression of FAM26A in various tumors. FAM26A was expressed at a distinctly higher level in particular in ovarian, gastric, esophageal, pancreatic and liver tumors, in comparison with the corresponding healthy tissue. According to the invention, selectively high expression of FAM26A in various tumor tissues may be utilized for molecular diagnostic methods such as, for example, RT-PCR for detecting tumor cells in tissue biopsies.

In order to further verify the expression data, FAM26A-specific antibodies were produced by immunization of animals. Polyclonal antibodies were produced by using the peptides listed under SEQ ID NO: 291 and 292. The specificity of the antibodies was demonstrated by Western blot analysis (FIG. 11A: SEQ ID NO: 291; B: SEQ ID NO: 292). For this purpose, COS cells were transfected with an FAM26 fragment-encoding plasmid construct. The Western blot showed a specific signal with both antibodies, which was not detectable in the respective controls (FIG. 11). We detected FAM26A also in various cervical, ovarian and pancreatic tumors, using a SEQ ID NO: 292-specific antibody (FIG. 12), as well as in the cell lines SW480, EFO 27 and SNU 16 which were in each case RT-PCR-positive, using a SEQ ID NO: 291-specific antibody (FIG. 13A). Here we found, in addition to an approx. 50 kDa specific band, also a weaker band at approx. 40 kDa. The latter corresponds to about the expected size. The major fragment at 50 kDa represents a post-translationally modified protein. The endogenous FAM26A protein was moreover detected in SW480 cells by means of immunofluorescence using a SEQ ID NO: 292-specific antibody. The analysis reveals localization in the plasma membrane (FIG. 13B). In order to analyze localization of FAM26A in a tissue assemblage, healthy testis samples were characterized immunohistologically. In testis, the FAM26A protein was detected specifically in the membrane of spermatocytes, and due to the results, a membrane localization of FAM26A appears likely (FIG. 14). This was also confirmed in tumor samples (FIG. 15).

The extracellular domains of FAM26A in particular may be utilized according to the invention as target structures of monoclonal antibodies. These are, based on SEQ ID NO: 17, the amino acids 38-48 (SEQ ID NO: 293) and the amino acids 129-181 (SEQ ID NO: 294). Alternatively, the C-terminal amino acids 199-334 (SEQ ID NO: 295) may also be preferred epitopes for producing antibodies for diagnostic or therapeutic purposes. In addition, the N-glycosylation motif at position 142 may be an interesting point of attack for therapeutic antibodies.

Example 8

Identification of SEMA5B as Diagnostic and Therapeutic Cancer Target

The gene semaphorin 5B (SEMA5B; SEQ ID NO: 21) which encodes the protein of SEQ ID NO: 22 is located on chromosome 3 (3q21.1). SEMA5B is a type I transmembrane protein and belongs to the family of semaphorins.

According to the invention, the amount of gene-specific transcripts in healthy tissue and in carcinoma samples (pool of samples, the number is indicated in the figure) was investigated after establishing an SEMA5B-specific quantitative RT-PCR (primer pair SEQ ID NO: 23 and 24) (FIG. 16). We found that, in healthy tissue, SEMA5B is very selectively restricted to testis and skin. In all other healthy tissues analyzed SEMA5B-specific expression was detectable at low level or not at all (FIG. 16). In contrast, we surprisingly found SEMA5B-specific overexpression in some types of tumors, in particular in kidney carcinomas and breast tumors (FIGS. 17A and B), in comparison to the respective healthy tissues.

Said selective overexpression in tumors can be utilized therapeutically.

The extracellular domain of SEMA5B (aa 20-1035; SEQ ID NO: 296) in particular may be utilized according to the invention as target structure of antibodies. SEMA5B is a type I transmembrane domain protein (TM aa 1035-1057) whose C terminus is located inside the cell (aa 1058-1151). SEMA5B-specific antibodies were produced by using the peptides according to SEQ ID NO: 297 and 298.

Example 9

Identification of GJB5 as a Diagnostic and Therapeutic Cancer Target

The protein GBJ5 (nucleic acid sequence: SEQ ID NO: 25; amino acid sequence: SEQ ID NO: 26) is a member of the connexin family. The gene consists of two exons and is located on chromosome 1 (1p35.1). The deduced amino acid sequence codes for a protein of 273 amino acids. Connexins have an important function in cell-cell contacts via "gap junctions" which are used for exchanging small cytoplasmic molecules, ions and secondary transmitters and thus enable individual cells to communicate with each other. Gap junctions consist of several connexin subunits which form a membrane channel. 11 different members of the connexins have been described to date, all of which are located in a gene cluster on chromosome 1 (Richard, G.; Nature Genet. 20: 366-369, 1998). GBJ5 has four transmembrane domains, with the N and C termini of the protein being located inside the cell.

According to the invention, the amount of gene-specific transcripts in healthy tissue and in carcinoma samples was investigated (pool of samples, the number is indicated in the figure) after establishing a GBJ5-specific quantitative RT-PCR (primer pair SEQ ID NO: 27, 28). Our studies reveal differential distribution of expression in normal tissues. We found GBJ5 transcripts to be expressed virtually exclusively in the esophagus and in the skin, with transcription being very weak or not detectable in all other tissues analyzed (FIG. 18). Very strong tumor-specific overexpression was observed in esophageal, colon, gastric and pancreatic carcinomas (FIG. 18). This was confirmed by analyzing individual samples of the four carcinomas (FIG. 19 A-D). In addition, the GBJ5-specific transcript can clearly be detected in the established cell lines LoVo, MKN45 and NCI-N87 (FIG. 19 A-D).

The extracellular domains of GBJ5 in particular may be utilized according to the invention as target structure of therapeutic antibodies. Based on SEQ ID NO: 26, the amino acids 41-75 (SEQ ID NO: 299) and the region between amino acids 150 and 187 (SEQ ID NO: 300) are located extracellularly. GBJ5-specific antibodies were produced by using the peptides according to SEQ ID NO: 301 and 302.

Example 10

Identification of KLK5 as a Diagnostic and Therapeutic Cancer Target

The gene KLK5 (SEQ ID NO: 29) and its translation product (SEQ ID NO: 30) is a member of the kallikrein family, a group of serine proteases with very different physiological functions. The gene is located on chromosome 19 (19q13.3-13.4) and codes for a serine protease. KLK5 is synthesized as pro form and is activated by proteolysis in the stratum corneum (Brattsand, M et al; *J. Biol. Chem.* 274: 1999). The active protease (aa 67-293) is secreted and is involved in the process of desquamation. The propeptide (aa 30-67) remains bound to the cell surface via the transmembrane domain (aa 1-29) (Ekholm, E et al; *Jour Investigative Dermatol,* 114; 2000).

According to the invention the distribution of KLK5-specific transcripts in healthy tissue and in carcinoma samples was investigated after establishing a KLK5-specific quantitative RT-PCR (primer pair SEQ ID NO: 31, 32) (FIG. 20). In most normal tissues expression of KLK5 is at a very low to non-existent level, with moderate expression of KLK5 being found only in testis, esophagus, skin and prostate. We detected significant overexpression of KLK5 in esophageal carcinomas, cervical and in ENT tumors, in comparison with the corresponding normal tissues of origin (FIG. 20, 21). Distinctly weaker but detectable KLK5-specific expression was moreover detected in some tumors of other tissues (e.g. in gastric and pancreatic carcinomas).

The extracellular domain of KLK5 in particular may be utilized according to the invention as target structure of therapeutic antibodies (SEQ ID NO: 303). The region of the propeptide (amino acids 30 to 67) is particularly suitable for this. KLK5-specific antibodies were produced by using the peptide listed under SEQ ID NO: 304.

Example 11

Identification of LOC352765 as a Diagnostic and Therapeutic Cancer Target

The LOC352765 gene locus is located on chromosome 9 (9q34.12). The gene (SEQ ID NO: 33) encodes the gene product of SEQ ID NO: 34. The LOC352765 protein has a transmembrane domain at the N terminus. The hypothetical protein displays no homologies to previously known proteins.

According to the invention, the amount of gene-specific transcripts in healthy tissue and in carcinoma samples (pool of samples) was investigated after establishing an LOC352765-specific quantitative RT-PCR (primer pair SEQ ID NO: 35 and 36) (FIG. 22). LOC352765 is expressed very selectively in healthy tissue, and we found specific transcripts to be detectable only in testis, skin and bladder. In contrast, LOC352765-specific overexpression was detected in some types of tumors. Particularly in breast tumors, expression was higher than in the normal tissue with the highest level of expression. We also found LOC352765 to be distinctly overexpressed in colon and ovarian carcinomas and in ENT tumors (FIGS. 22, 23).

Owing to its selective overexpression in tumors, LOC352765 can be utilized therapeutically. The extracellular domain of LOC352765 (amino acids 44-211, SEQ ID NO: 34) in particular may be utilized according to the invention as target structure of antibodies and other targeted forms of therapy. Specific antibodies were produced by using the peptides according to SEQ ID NO: 305 and 306.

Example 12

Identification of SVCT1 as a Diagnostic and Therapeutic Cancer Target

The gene SVCT1 (SEQ ID NO: 37) is located on chromosome 7 (7q33) and codes for the gene product of SEQ ID NO: 38. The SVCT1 protein has four transmembrane domains and displays no homologies to previously known proteins.

According to the invention, the amount of gene-specific transcripts in healthy tissue and in carcinoma samples (pool of samples) was investigated after establishing an SVCT1-specific quantitative RT-PCR (primer pair SEQ ID NO: 39 and 40) (FIG. 24). SVCT1 in healthy tissue is restricted selectively to kidney, testis, thymus and mammary gland. In contrast, SVCT1-specific overexpression was surprisingly detected in some types of tumors. SVCT1 is strongly overexpressed in particular in carcinomas of the kidney, esophagus and pancreas and in ENT tumors (FIGS. 24, 25), and that is not only in comparison with the corresponding healthy tissue of origin but also with respect to the normal tissue with the highest level of expression over all. SVCT1 can be therapeutically utilized owing to its selective overexpression in tumors. The extracellular domains of SVCT1 in particular may be utilized according to the invention as target structures of antibodies and for other targeted forms of therapy. Specific antibodies were produced by using the peptides according to SEQ ID NO: 307 and 308.

Example 13

Identification of LOC199953 as a Diagnostic and Therapeutic Cancer Target

The gene or protein of the LOC199953 gene locus (nucleic acid sequence: SEQ ID NO: 41; amino acid sequence: SEQ ID NO: 42) is located on chromosome 1 (1q36.22). The protein has several transmembrane domains. Alternative open reading frames of this gene locus are SEQ ID NO: 271 with its gene product SEQ ID NO: 272 and SEQ ID NO: 273 with the corresponding gene product SEQ ID NO: 274. Other than that, the hypothetical protein displays no further homologies to previously known protein domains.

According to the invention, the amount of gene-specific transcripts in healthy tissue and in carcinoma samples was investigated after establishing an LOC199953-specific quantitative RT-PCR (primer pair SEQ ID NO: 43 and 44). LOC199953 is selectively expressed in healthy tissues and overexpressed in some tumors. In particular, it was possible to identify overexpression in ENT and kidney carcinomas (FIG. 26) in approx. 50% of the tumor samples, in comparison with normal tissues.

According to the invention, the extracellular domains of LOC199953 may be utilized as target structure of antibodies.

Example 14

Identification of TMEM31 as a Diagnostic and Therapeutic Cancer Target

The gene TMEM31 (SEQ ID NO: 45) of the LOC203562 gene locus is located on chromosome X (Xq22.2). The gene codes for the protein of SEQ ID NO: 46. Said protein has two transmembrane domains and otherwise displays no homologies to previously known proteins.

According to the invention, the amount of gene-specific transcripts in healthy tissue and in carcinoma samples was investigated after establishing a TMEM31-specific quantitative RT-PCR (primer pair SEQ ID NO: 47 and 48). In healthy tissues, TMEM31 is very selectively restricted especially to testis (FIG. 27). Surprisingly, we also found expression in some types of tumors, whereas no expression was detectable in the corresponding normal tissues. Said tumors are in particular carcinomas of the kidney, colon, stomach, breast, liver and lung and ENT carcinomas (FIGS. 27, 28).

TMEM31 is thus a typical representative of the class of cancer/testis antigens which are expressed in normal tissues exclusively in the germ cells of the testis. In tumors, however, cancer/testis antigens are frequently switched on, although they are not expressed in the underlying somatic normal tissue cells. Several members of this functionally and structurally heterogeneous class are already tested for specific immunotherapeutic approaches with cancers in phase I/II studies, owing to their attractive selective tissue distribution (e.g. Scanlan M J, Gure A O, Jungbluth A A, Old L J, Chen Y T. 2002. Immunol. Rev. 2002 October; 188:22-32).

The extracellular TMEM31 domains may be utilized according to the invention as target structure of antibodies.

Example 15

Identification of FLJ25132 as a Diagnostic and Therapeutic Cancer Target

The FLJ25132 gene/protein (nucleic acid sequence: SEQ ID NO: 49; amino acid sequence: SEQ ID NO: 50) is located on chromosome 17 (17q25.3). FLJ25132 has a transmembrane domain but otherwise does not display any homologies to previously known proteins.

According to the invention, the amount of gene-specific transcripts in healthy tissue and in carcinoma samples was investigated after establishing an FLJ25132-specific quantitative RT-PCR (primer pair SEQ ID NO: 51 and 52). FLJ25132 is partially overexpressed in the carcinoma samples studied by us, in comparison to healthy tissue (FIG. 29). Distinct overexpression of FLJ25132 was detected in particular in ovarian and in prostate carcinomas.

The extracellular FLJ25132 domains may be utilized according to the invention as target structure of antibodies.

Example 16

Identification of LOC143724, LOC284263, LOC283435 and LOC349260 as Diagnostic and Therapeutic Cancer Targets The gene loci (with the correspondingly encoded genes and gene products), LOC143724, LOC284263, LOC283435 and LOC349260, are combined, owing to their similar profiles.

The gene with SEQ ID NO: 53, which is present in the LOC143724 gene locus on chromosome 11 (11q13.1), encodes the gene product SEQ ID NO: 54. SEQ ID NO: 275 with its gene product SEQ ID NO: 276 represents an alternative open reading frame of this gene locus, which is either a separate transcript or a splice variant of SEQ ID NO: 53. The primers according to SEQ ID NO: 55 and 56 were used for gene-specific amplification of said gene.

The gene with SEQ ID NO: 89, which is present in the LOC284263 gene locus on chromosome 18 (18q21.1), encodes the gene product with SEQ ID NO: 90. The primers according to SEQ ID NO: 91 and 92 were used for gene-specific amplification of said gene.

The gene with SEQ ID NO: 117, which is present in the LOC283435 gene locus on chromosome 12 (12q24.32), encodes the gene product with SEQ ID NO: 118. The primers according to SEQ ID NO: 119 and 120 were used for gene-specific amplification of said gene.

The gene with SEQ ID NO: 121, which is present in the LOC349260 gene locus on chromosome 9 (9q11.2), encodes the gene product with SEQ ID NO: 122. The primers according to SEQ ID NO: 123 and 124 were used for gene-specific amplification of said gene.

All proteins have transmembrane domains and, in addition, do not display any homologies to previously known proteins.

According to the invention, the amount of gene-specific transcripts in healthy tissue and in carcinoma samples was investigated after establishing specific quantitative RT-PCR analyses. None of the four genes were detected in the healthy tissues which are investigated, with the exception of testis. Consequently, there is a high probability of said genes being germ cell-specific. However, surprisingly significant expression is found in various tumor samples.

The four genes are thus typical representatives of the class of cancer/testis antigens which are expressed in normal tissues exclusively in the germ cells of the testis. In tumors, however, cancer/testis antigens are frequently switched on, although they are not expressed in the underlying somatic normal tissue cells. Several members of this functionally and structurally heterogeneous class are already tested for specific immunotherapeutic approaches with cancers in phase I/II studies, owing to their attractive selective tissue distribution (e.g. Scanlan M J, Gure A O, Jungbluth A A, Old L J, Chen Y T. 2002. Immunol. Rev. 2002 October; 188:22-32).

The extracellular domains of the four genes may be utilized according to the invention as target structure of antibodies.

Example 17

Identification of the Sequence According to SEQ ID NO: 57 as a Diagnostic and Therapeutic Cancer Target The sequence according to SEQ ID NO: 57 is derived from a gene on chromosome 1 (1p21.3) and encodes the protein sequence according to SEQ ID NO: 58. SEQ ID NO: 277 with its gene product SEQ ID NO: 278 represents an alternative transcript of said gene locus. The transmembrane protein does not display any homologies to previously known proteins.

According to the invention, the amount of gene-specific transcripts in healthy tissue and in carcinoma samples was investigated after establishing a specific quantitative RT-PCR (primer pair SEQ ID NO: 59 and 60). SEQ ID NO: 57 is selectively expressed in the healthy tissues studied by us (FIG. 30). Specific transcripts were detectable in nearly all types of tumors analyzed and overexpressed in particular in liver, ENT and kidney tumors. This was confirmed in the analysis of individual tumor samples in comparison with healthy tissue samples (FIG. 31).

The extracellular domains of the sequence according to SEQ ID NO: 58 may be utilized according to the invention as target structure of antibodies, in particular with amino acids 20-38 and 90-133 being located extracellularly.

Example 18

Identification of LOC119395 as a Diagnostic and Therapeutic Cancer Target

The gene with SEQ ID NO: 61, which is present in the LOC119395 gene locus on chromosome 17 (17q25.3), encodes a gene product with SEQ ID NO: 62. The transmembrane protein displays no homologies to previously known proteins.

According to the invention the amount of gene-specific transcripts in healthy tissue and in carcinoma samples was investigated after establishing an LOC119395-specific quantitative RT-PCR (primer pair SEQ ID NO: 63 and 64) (FIG. 32). LOC119395 is very selectively expressed in the healthy tissues studied by us and is detectable only in a few tissues (FIG. 32). In contrast, LOC119395-specific transcripts were detectable in nearly all types of tumors analyzed. In parts distinct, tumor-selective overexpression of LOC119395 was observed in particular in gastric, ovarian and prostate carcinomas. This was confirmed in the analysis of individual tumor samples in comparison with healthy tissue samples (FIG. 33). It was possible to detect overexpression of LOC119395 in mammary carcinomas and esophageal tumors in comparison with the respective healthy tissue. Tumor-selective expression was identified in colon carcinomas and gastric carcinomas (FIG. 33).

The extracellular LOC119395 domain (amino acids 44-129) may be utilized according to the invention as target structure of antibodies.

Example 19

Identification of LOC121838 as a Diagnostic and Therapeutic Cancer Target

The gene which is located in the LOC121838 gene locus on chromosome 13 (13q14.11) and has the transcript of SEQ ID NO: 65 encodes the protein with SEQ ID NO: 66. The transmembrane protein displays no homologies to previously known proteins.

According to the invention, the amount of gene-specific transcripts in healthy tissue and in carcinoma samples was investigated after establishing an LOC121838-specific quantitative RT-PCR (primer pair SEQ ID NO: 67 and 68) (FIG. 34A). LOC121838 is very selectively expressed in the healthy tissues studied by us and is detectable only in a few tissues (FIGS. 34A and B). In contrast, LOC121838-specific transcripts were detectable in many types of tumors analyzed. We found distinct tumor-selective overexpression of LOC121838 in particular in ovarian and esophageal carcinomas.

The extracellular LOC121838 domains may be utilized according to the invention as target structure of antibodies.

Example 20

Identification of LOC221103 as a Diagnostic and Therapeutic Cancer Target

The gene which is localized in the LOC221103 gene locus on chromosome 11 (11q12.3) and has the transcript of SEQ ID NO: 69 encodes the protein with SEQ ID NO: 70. The transmembrane protein displays no homologies to previously known proteins.

According to the invention, the amount of gene-specific transcripts in healthy tissue and in carcinoma samples was investigated after establishing an LOC221103-specific quantitative RT-PCR (primer pair SEQ ID NO: 71 and 72). In the healthy tissues studied by us, LOC221103 is expressed only in the liver and otherwise not detectable (FIG. 35). Surprisingly, LOC221103-specific transcripts are overexpressed in liver carcinomas (FIG. 36).

The extracellular LOC221103 domains may be utilized according to the invention as target structure of antibodies.

Example 21

Identification of LOC338579 as a Diagnostic and Therapeutic Cancer Target

The gene which is localized in the LOC338579 gene locus on chromosome 10 (10q11.21) and has the transcript of SEQ ID NO: 73 encodes the protein with SEQ ID NO: 74. The transmembrane protein displays no homologies to previously known proteins.

According to the invention, the amount of gene-specific transcripts in healthy tissue and in carcinoma samples was investigated after establishing an LOC338579-specific quantitative RT-PCR (primer pair SEQ ID NO: 75 and 76). We found expression in healthy tissues only in testis and, at a lower level, in the liver and the thymus. Surprisingly, we found LOC338579 overexpression in colon carcinomas and liver carcinomas in comparison with the healthy tissue (FIG. 37).

The extracellular LOC338579 domains may be utilized according to the invention as target structure of antibodies.

Example 22

Identification of LOC90342 as a Diagnostic and Therapeutic Cancer Target

The gene which is located in the LOC90342 gene locus on chromosome 2 (2q11.2) and has the transcript of SEQ ID NO: 77 encodes the protein with SEQ ID NO: 78. The transmembrane protein includes a calcium-binding motif (CalB) which is conserved in protein kinase C and in various phospholipases.

According to the invention, the amount of gene-specific transcripts in healthy tissue and in carcinoma samples was investigated after establishing an LOC90342-specific quantitative RT-PCR (primer pair SEQ ID NO: 79 and 80) (FIG. 38). We found LOC90342 only in a small number of healthy tissues, most of which are of little relevance with regard to toxicity (FIG. 38). In contrast, we found LOC90342-specific transcripts in a multiplicity of the types of tumors analyzed. In parts distinctly tumor-selective overexpression of LOC90342 was observed in particular in gastric, liver, pancreatic, prostate, ovarian and lung carcinomas.

The membrane protein has a single transmembrane domain (aa 707-726). The extracellular LOC90342 domain may be utilized according to the invention as target structure of therapeutic antibodies.

Example 23

Identification of LRFN1 as a Diagnostic and Therapeutic Cancer Target

LRFN1 (SEQ ID NO: 81) is a gene which is localized on chromosome 19 (19q13.2). The gene codes for the protein of SEQ ID NO: 82. Said protein includes a transmembrane domain and displays homologies to the Myb DNA-binding domain and to a C2-type immunoglobulin domain.

According to the invention, the amount of gene-specific transcripts in healthy tissue and in carcinoma samples was investigated after establishing an LRFN1-specific quantitative RT-PCR (primer pair SEQ ID NO: 83 and 84). LRFN1 is very weakly expressed in most of the normal tissues studied, except for activated PBMC and brain (FIG. 39). In contrast, we found LRFN1-specific transcripts to be increasingly detectable in some of the types of tumors analyzed. We found distinct tumor-selective overexpression of LRFN1 in particular in gastric, pancreatic, esophageal and mammary carcinomas, in comparison with the corresponding normal tissues.

The protein includes a transmembrane domain (aa 448-470). The extracellular LFRN1 domains may be utilized according to the invention as target structure of therapeutic antibodies.

Example 24

Identification of LOC285916 as a Diagnostic and Therapeutic Cancer Target

The gene which is localized in the LOC285916 gene locus on chromosome 7 (7p22.3) and has the transcript of SEQ ID NO: 85 encodes the protein with SEQ ID NO: 86. The transmembrane protein displays no homologies to previously known proteins.

According to the invention, the amount of gene-specific transcripts in healthy tissue and in carcinoma samples was investigated after establishing an LOC285916-specific quantitative RT-PCR (primer pair SEQ ID NO: 87 and 88). In the healthy tissues studied by us, LOC285916 is expressed selectively in testis, with no or only little expression being detected by us in all other tissues studied (FIG. 40A). Surprisingly, we found LOC285916-specific transcripts in all types of tumors tested. Distinct tumor-specific overexpression was detectable in particular in mammary, esophageal, renal, ENT and lung carcinomas (FIGS. 40A and B).

The extracellular LOC285916 domains (amino acids 42 to 93) may be utilized according to the invention as target structure of antibodies.

Example 25

Identification of MGC71744 as a Diagnostic and Therapeutic Cancer Target

The MGC71744 gene with SEQ ID NO: 93 on chromosome 17 (17p13.2) encodes the protein with SEQ ID NO: 94. The transmembrane protein displays no homologies to previously known proteins.

According to the invention, the amount of gene-specific transcripts in healthy tissue and in carcinoma samples (pool of samples) was studied after establishing an MGC71744-specific quantitative RT-PCR (primer pair SEQ ID NO: 95 and 96) (FIG. 41). MGC71744 is hardly expressed in healthy tissue. We found small amounts of specific transcripts only in the lung and in the spleen. The level of MGC71744-specific expression in all other healthy tissues analyzed was low or not detectable at all (FIG. 41A). In contrast, we surprisingly found MGC71744-specific overexpression in some types of tumors, in particular in carcinomas of the kidney (FIGS. 41A & B), in comparison with healthy tissue.

The extracellular domain of MGC71744 (N terminus, aa 67-85) in particular may be utilized according to the invention as target structure of antibodies.

Example 26

Identification of LOC342982 as a Diagnostic and Therapeutic Cancer Target

The gene which is localized in the LOC342982 gene locus on chromosome 19 (19p13.13) and has the transcript of SEQ ID NO: 97 encodes the protein with SEQ ID NO: 98. The transmembrane protein displays homologies to the carbohydrate binding domain of C-type lectins.

According to the invention, the amount of gene-specific transcripts in healthy tissue and in carcinoma samples (pool of samples) was investigated after establishing an LOC342982-specific quantitative RT-PCR (primer pair SEQ ID NO: 99 and 100). LOC342982-specific RNA is selectively expressed, with only a low level of expression or no expression being detectable in many normal tissues analyzed (FIG. 42). In contrast, nearly all of the classes of tumors tested exhibited overexpression which was partly tumor-specific. Primarily pancreatic, kidney, lung and mammary carcinomas exhibit very strong expression of LOC342982-specific RNA (FIG. 42).

The extracellular domain of LOC342982 (amino acids 178-339) in particular may be utilized according to the invention as target structure of monoclonal antibodies.

Example 27

Identification of LOC343169/OR6F1 as a Diagnostic and Therapeutic Cancer Target The gene OR6F1 which is localized in the LOC343169 gene locus on chromosome 1 (1q44) and has the transcript of SEQ ID NO: 101 encodes the protein with SEQ ID NO: 102. OR6F1 has several transmembrane domains and belongs to the family of olfactory receptors and thus to the large family of G protein-coupled receptors.

According to the invention, the amount of gene-specific transcripts in healthy tissue and in carcinoma samples (pool of samples) was investigated after establishing an LOC343169/OR6F1-specific quantitative RT-PCR (primer pair SEQ ID NO: 103 and 104) (FIG. 43A). LOC343169/OR6F1 is very selectively expressed in healthy tissue, with specific transcripts being detectable especially in testis and spleen. The level of LOC343169/OR6F1-specific expression was low or not detectable at all in all other healthy tissues analyzed (FIG. 43A). In contrast, LOC343169/OR6F1-specific overexpression was surprisingly detected is some types of tumors. Tumor-specific overexpression of LOC343169/OR6F1 is seen in particular in mammary, ovarian, kidney, prostate, pancreatic and liver carcinomas (FIG. 43A). An analysis of individual samples confirmed overexpression in ovarian carcinomas. LOC343169/OR6F1 is a selectively expressed antigen which is obviously increasingly expressed in proliferating tissues. Thus selective overexpression in tumors can be observed which is therapeutically utilizable. The extracellular domains in particular may be utilized according to the invention as target structures of monoclonal antibodies.

Example 28

Identification of LOC340204 as a Diagnostic and Therapeutic Cancer Target

The gene which is localized in the LOC340204 gene locus on chromosome 6 (6p21.31) and has the transcript of SEQ ID NO: 105 encodes the protein with SEQ ID NO: 106. Said protein has a transmembrane domain. Moreover said protein displays strong homology to a "colipase" domain. A cofactor function for pancreatic lipase is attributed to colipase. SEQ ID NO: 279 with its gene product SEQ ID NO: 280 represents an alternative transcript of said gene locus, which could be both a separate transcript and a splice variant of SEQ ID NO: 105.

According to the invention, the amount of gene-specific transcripts in healthy tissue and in carcinoma samples was investigated after establishing an LOC340204-specific quantitative RT-PCR (primer pair SEQ ID NO: 107 and 108). LOC340204 is selectively expressed in healthy tissues and strongly overexpressed in some tumors. Distinct overexpression in tumor samples in comparison with various normal tissues was detected in particular in gastric, pancreatic, ovarian, lung and esophageal carcinomas (FIG. 44).

The extracellular LOC340204 domains may be utilized according to the invention as target structure of monoclonal antibodies.

Example 29

Identification of LOC340067 as a Diagnostic and Therapeutic Cancer Target

The gene which is localized in the LOC340067 gene locus on chromosome 5 (5q22.3) and has the transcript of SEQ ID NO: 109 encodes the protein with SEQ ID NO: 110. The transmembrane protein displays no homologies to other protein domains.

According to the invention, the amount of gene-specific transcripts in healthy tissue and in carcinoma samples was investigated after establishing a quantitative RT-PCR (primer pair SEQ ID NO: 111 and 112) specific for LOC340067. LOC340067 is selectively expressed in healthy tissues and strongly overexpressed in some tumors (FIG. 45). Distinct overexpression in tumor samples in comparison with various healthy tissues was detected in particular in pancreatic, mammary, liver, ovarian, lung and kidney carcinomas.

The extracellular LOC340067 domain may be utilized according to the invention as target structure of monoclonal antibodies.

Example 30

Identification of LOC342780 as a Diagnostic and Therapeutic Cancer Target

The gene which is localized in the LOC342780 gene locus on chromosome 18 (18q21.32) and has the transcript of SEQ ID NO: 309 encodes the protein with SEQ ID NO: 310. The transmembrane protein includes an acyltransferase domain which is present in many *C. elegans* proteins which have previously not been characterized in detail. According to the invention, the amount of gene-specific transcripts in healthy tissue and in carcinoma samples (pool of samples, the number is indicated in the figure) was investigated after establishing an LOC342780-specific quantitative RT-PCR (primer pair SEQ ID NO: 311 and 312). LOC342780 is very selectively expressed in healthy tissue, with specific transcripts being detectable especially in the prostate, stomach, testis, lung and the mammary gland (FIG. 46). In contrast, LOC342780-specific expression was surprisingly detected in all types of tumors analyzed. Tumor-specific overexpression of LOC342780 is seen in particular in mammary, ovarian, kidney and liver carcinomas (FIG. 46).

LOC342780 is a selectively expressed antigen which is obviously increasingly expressed in proliferating tissues. Thus selective overexpression in tumors can be observed which is therapeutically utilizable. The extracellularly located amino acids 76-89, 316-345, 399-493 and 650-665 (based on SEQ ID NO: 310) may be utilized according to the invention as target structures of monoclonal antibodies.

Example 31

Identification of LOC339511 as a Diagnostic and Therapeutic Cancer Target

The sequence according to SEQ ID NO: 113 is derived from a gene which is located on chromosome 1 (1q23.1). The gene encodes the protein of SEQ ID NO: 114. The transmembrane protein displays homologies to the group of olfactory 7-transmembrane receptors.

According to the invention, the amount of gene-specific transcripts in healthy tissue and in carcinoma samples was investigated after establishing a quantitative RT-PCR (primer pair SEQ ID NO: 115 and 116) specific for LOC339511. In healthy tissues, LOC339511 is selectively expressed in the liver (FIG. 47A). In the carcinoma samples, LOC339511-specific transcripts were identified in liver tumors, with weak expression being moreover detectable in colon carcinomas, mammary and lung carcinomas. When comparing liver-specific expression in tumor and in healthy tissue, increased expression was detected in some tumor samples (FIG. 47B).

The extracellular domains of SEQ ID NO: 113 may be utilized according to the invention as target structures of monoclonal antibodies. In particular, the extracellularly located amino acid residues 1-23, 82-100, 167-175 and 226-236 are therefore particularly suitable for producing monoclonal antibodies.

Example 32

Identification of C14orf37 as a Diagnostic and Therapeutic Cancer Target

C14orf37 (SEQ ID NO: 125) is a gene which is localized on chromosome 14 (14q22.3) and which encodes the gene product with SEQ ID NO: 126. The transmembrane protein displays no homologies to previously known proteins.

According to the invention, the amount of gene-specific transcripts in healthy tissue and in carcinoma samples was investigated after establishing a quantitative RT-PCR (primer pair SEQ ID NO: 127 and 128) specific for C14orf37. C14orf37 is expressed in various healthy tissues, and strongest in testis (FIG. 48). A distinct overexpression in comparison with various healthy tissues was detected in particular in kidney carcinomas.

The extracellular domain of SEQ ID NO: 126 may be utilized according to the invention as target structure of monoclonal antibodies.

Example 33

Identification of ATP1A4 as a Diagnostic and Therapeutic Cancer Target

The ATP1A4 gene (SEQ ID NO: 129) is located on chromosome 1 (1q21-23). The gene codes for a protein with SEQ ID NO: 130. ATP1A4 is an integral transmembrane protein with eight transmembrane domains, which is located in the plasma membrane. ATP1A4 is part of a protein complex, with the catalytical part of the sodium/potassium ATPase being present at the N terminus (Woo et al., J. 2000. Biol. Chem. 275, 20693-99). ATP1A4 displays strong homologies to numerous other representatives of the cation ATPase family.

According to the invention, the amount of gene-specific transcripts in healthy tissue and in carcinoma samples was investigated after establishing an ATP1A4-specific quantitative RT-PCR (primer pair SEQ ID NO: 131 and 132). In healthy tissues, ATP1A4 is selectively expressed especially in testis (FIG. 49). Strong overexpression of ATP1A4 was detected in some tumor samples in comparison with the respective healthy tissue. Distinct overexpression in tumor samples in comparison with healthy tissues was detected in particular in pancreatic, mammary, liver and kidney carcinomas (FIG. 49), with expression in pancreatic and mammary carcinomas being very high over all.

The extracellular domains of ATP1A4 may be utilized according to the invention as target structure of monoclonal antibodies. The following amino acid residues, based on SEQ ID NO: 130, are located extracellularly: amino acid residues 129-137, 321-329, 816-857 and 977-990.

Example 34

Identification of SEQ ID NO: 133 to 264 as a Diagnostic and Therapeutic Cancer Target The sequences according to SEQ ID NO: 133-266 are 33 genes (nucleic acid sequence, amino acid sequence), together with the respective PCR primers for specific RT-PCR reactions. All proteins have one or more transmembrane domains, but there is little information on homologies to protein domains.

According to the invention, the amount of the particular gene-specific transcripts in healthy tissue and in carcinoma samples was investigated for these genes in specific quantitative RT-PCR reactions. For all of the genes, overexpression which was partially strong in comparison with the respective healthy tissue was detected in tumor samples.

All genes of this group are therapeutically and diagnostically utilizable. The extracellular domains may be utilized here according to the invention as target structure of antibodies.

The invention claimed is:

1. A method for diagnosing melanoma in a patient, the method comprising detecting the presence of a nucleic acid comprising the nucleic acid of SEQ ID NO: 1 in a skin sample from the patient.

* * * * *